United States Patent
Persidsky et al.

(10) Patent No.: US 11,172,850 B2
(45) Date of Patent: Nov. 16, 2021

(54) SYSTEM AND METHOD TO MONITOR, GUIDE, AND EVALUATE BREATHING, UTILIZING POSTURE AND DIAPHRAGM SENSOR SIGNALS

(71) Applicant: PRANA TECH LLC, Santa Clara, CA (US)

(72) Inventors: Andre Maxim Persidsky, Santa Clara, CA (US); Robin Alexander Ahlund, Richmond, VA (US)

(73) Assignee: Prana Tech LLC, San Francisco, CA (US)

(*) Notice: Subject to any disclaimer, the term of this patent is extended or adjusted under 35 U.S.C. 154(b) by 145 days.

(21) Appl. No.: 15/972,172

(22) Filed: May 6, 2018

(65) Prior Publication Data

US 2018/0256074 A1    Sep. 13, 2018

Related U.S. Application Data

(63) Continuation-in-part of application No. 14/706,939, filed on May 7, 2015, now abandoned.
(Continued)

(51) Int. Cl.
*A61B 5/00* (2006.01)
*A61B 5/113* (2006.01)
(Continued)

(52) U.S. Cl.
CPC ............. *A61B 5/113* (2013.01); *A61B 5/1116* (2013.01); *A61B 5/6823* (2013.01);
(Continued)

(58) Field of Classification Search
CPC .................................................. A44B 11/258
See application file for complete search history.

(56) References Cited

U.S. PATENT DOCUMENTS

| | | | | |
|---|---|---|---|---|
| 4,088,138 A | * | 5/1978 | Diack | A61B 5/0408 600/484 |
| 4,161,806 A | * | 7/1979 | Hennisse | A41F 1/006 24/586.11 |

(Continued)

FOREIGN PATENT DOCUMENTS

WO    WO-0033737 A1 *  6/2000  ........... A61B 5/1135

OTHER PUBLICATIONS

Ramin Baghai, WO 00/33737 Translation, Dec. 9, 1998, pp. 1-7 (Year: 1999).*

*Primary Examiner* — Jason M Sims
*Assistant Examiner* — Sarah R Kingsley
(74) *Attorney, Agent, or Firm* — Stephen E. Zweig

(57) ABSTRACT

Device, system and method to monitor user breathing patterns utilizing posture and diaphragm (breathing) sensor signals. The user worn device comprises a housing attached to a retractable belt that is worn around the user's trunk. The housing contains both posture and breathing sensors. The device monitors the output signals of these sensors and measures the state of both the user's posture and diaphragm (e.g. changes in the belt's length or force on the belt as a function of user breathing) to analyze breathing signals. The system's processor receives, processes, and transmits sensor signal data, and can also calibrate and interpret these signals utilizing various algorithms. In a preferred embodiment, the posture sensor is an accelerometer, and the retractable belt winds around a spring tensioned spool in the device's housing. The software can produce posture adjusted user respiration data, and can also be used for breath training and other purposes.

28 Claims, 200 Drawing Sheets

Related U.S. Application Data

(60) Provisional application No. 61/989,541, filed on May 7, 2014, provisional application No. 62/044,268, filed on Aug. 31, 2014, provisional application No. 62/519,160, filed on Jun. 13, 2017.

(51) Int. Cl.
    *A61B 5/11* (2006.01)
    *G06K 9/00* (2006.01)
    *G06F 3/01* (2006.01)

(52) U.S. Cl.
    CPC ......... *G06K 9/00335* (2013.01); *A61B 5/486* (2013.01); *A61B 2562/0219* (2013.01); *G06F 3/017* (2013.01)

(56) References Cited

U.S. PATENT DOCUMENTS

| | | | | |
|---|---|---|---|---|
| 4,595,196 A | * | 6/1986 | Muchisky | A63B 23/0244 482/13 |
| 6,090,037 A | * | 7/2000 | Gavish | A61B 5/1135 600/27 |
| 2007/0293781 A1 | * | 12/2007 | Sims | A61B 5/1135 600/534 |
| 2008/0108903 A1 | * | 5/2008 | Ben-Oved | A61B 5/1135 600/484 |
| 2009/0024048 A1 | * | 1/2009 | Lang | A61B 5/1135 600/534 |
| 2010/0121216 A1 | * | 5/2010 | Hamaguchi | A61B 5/0537 600/547 |
| 2010/0286547 A1 | * | 11/2010 | Aoude | A61B 5/4818 600/534 |
| 2013/0116602 A1 | * | 5/2013 | Van Den Heuvel | A61B 5/1116 600/595 |
| 2014/0228657 A1 | | 8/2014 | Palley | |
| 2015/0374266 A1 | * | 12/2015 | Cohen | A61B 5/1116 600/594 |
| 2018/0116586 A1 | * | 5/2018 | Thompson | A61B 5/486 |

\* cited by examiner

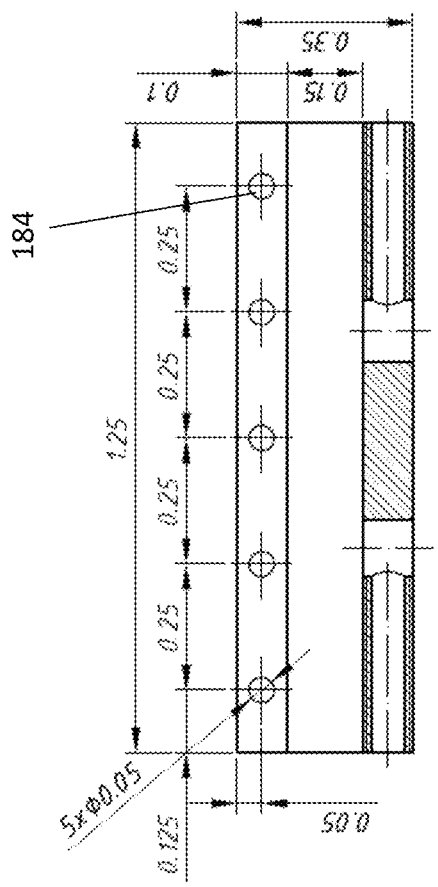
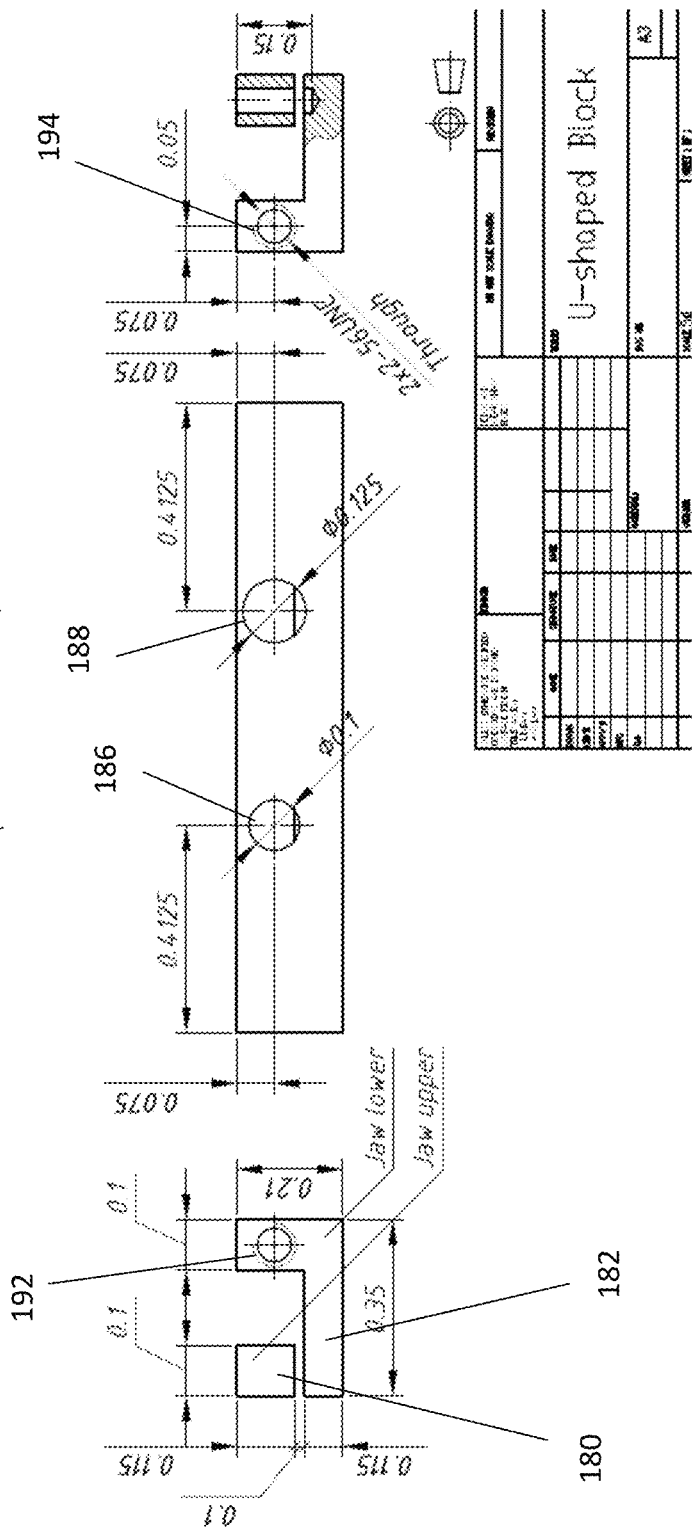
FIG. 8

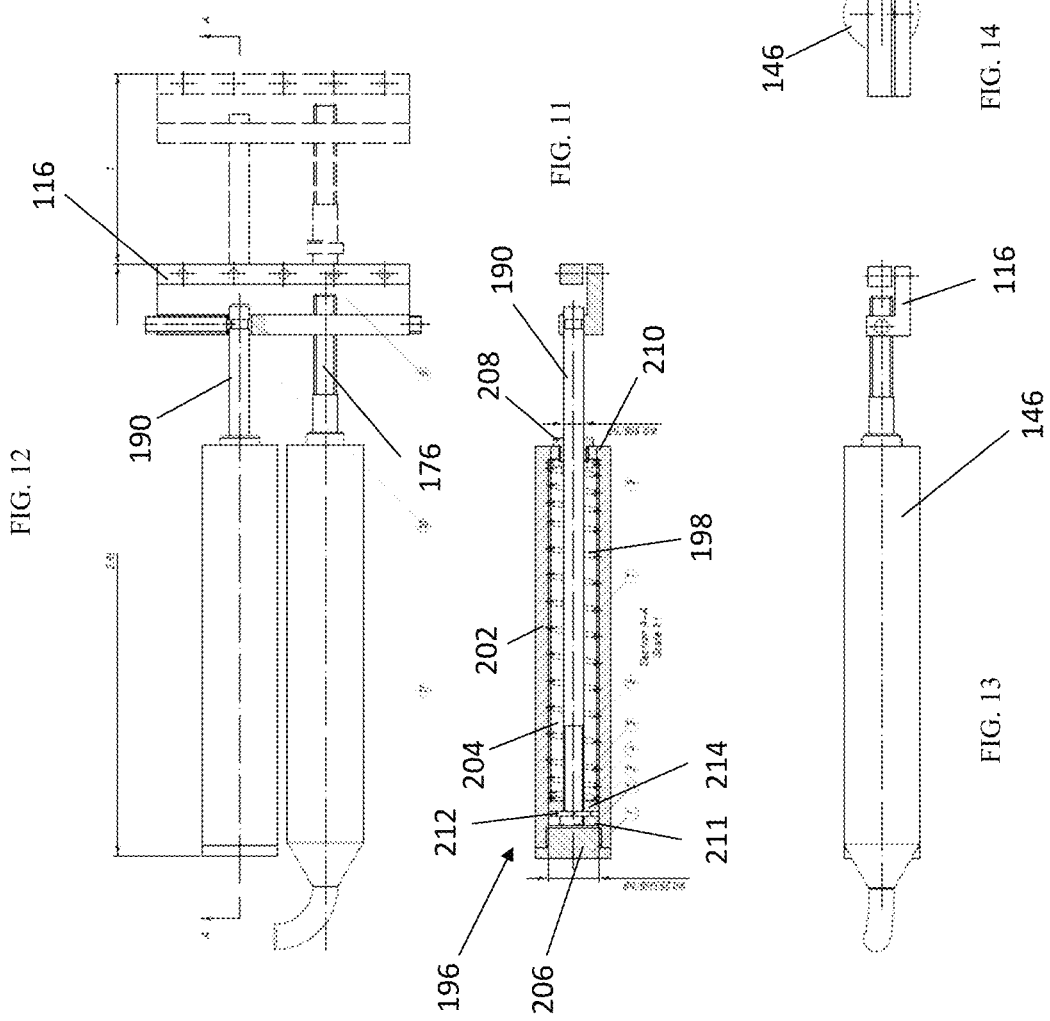

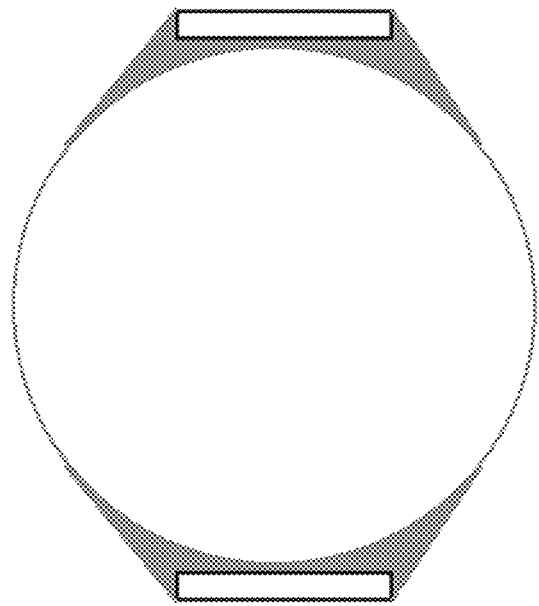
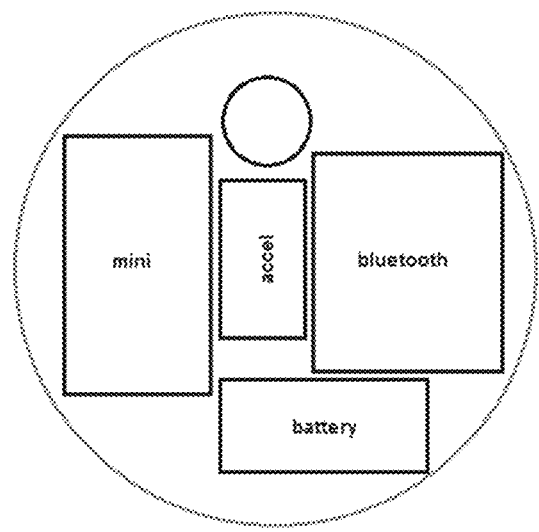
FIG.41

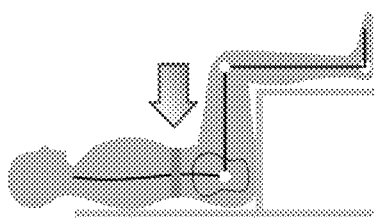
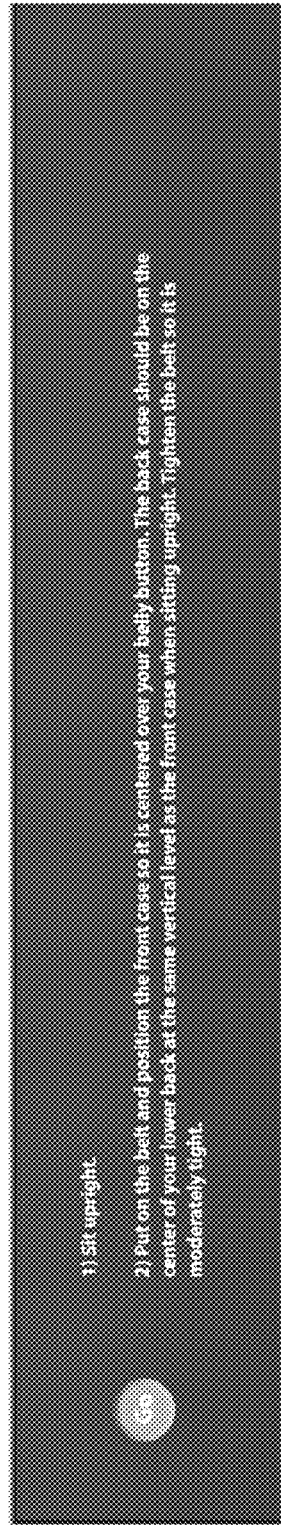
FIG. 102

FIG.108A
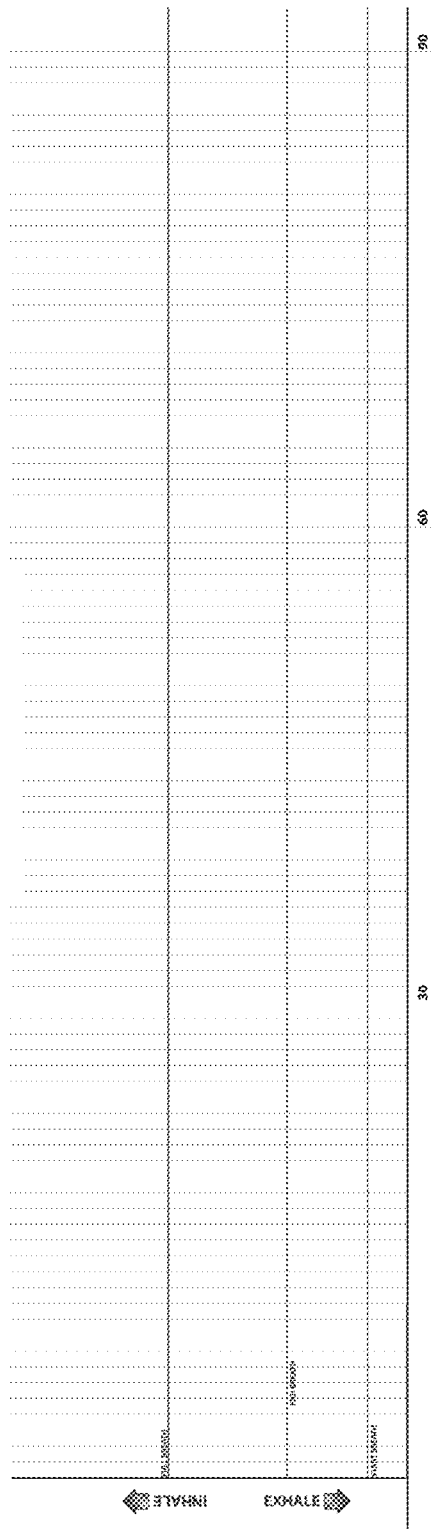
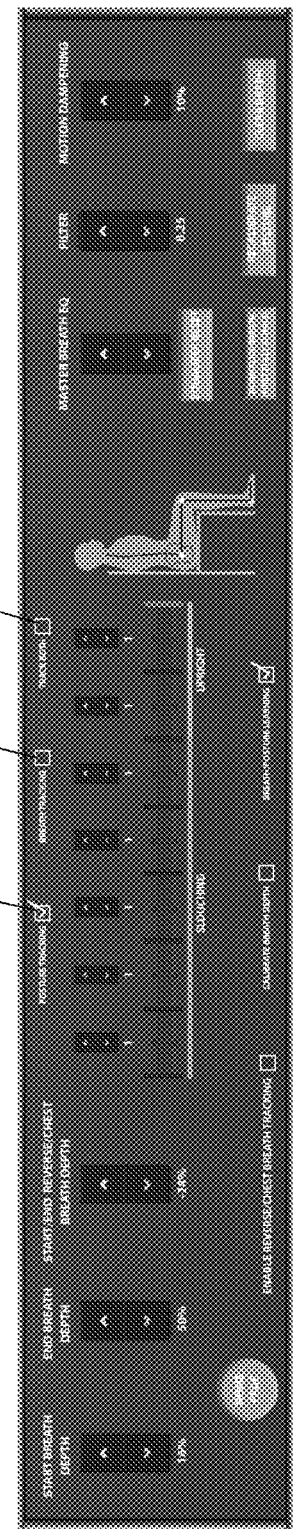

FIG.109
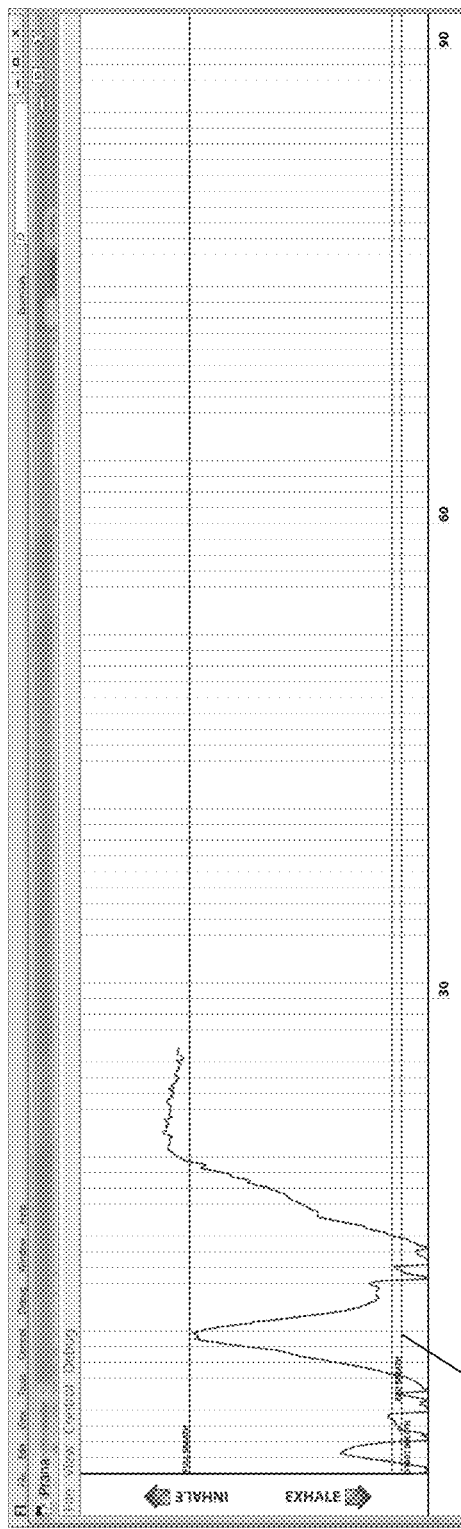
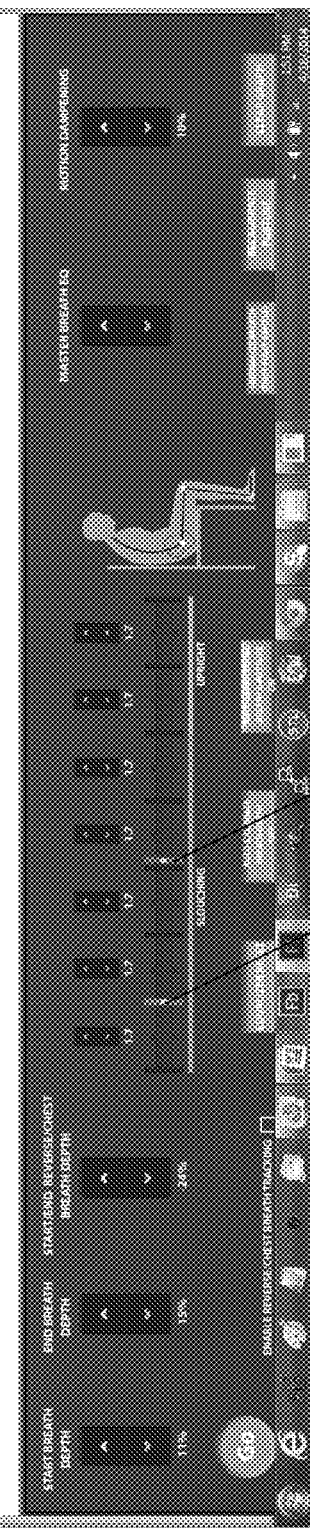

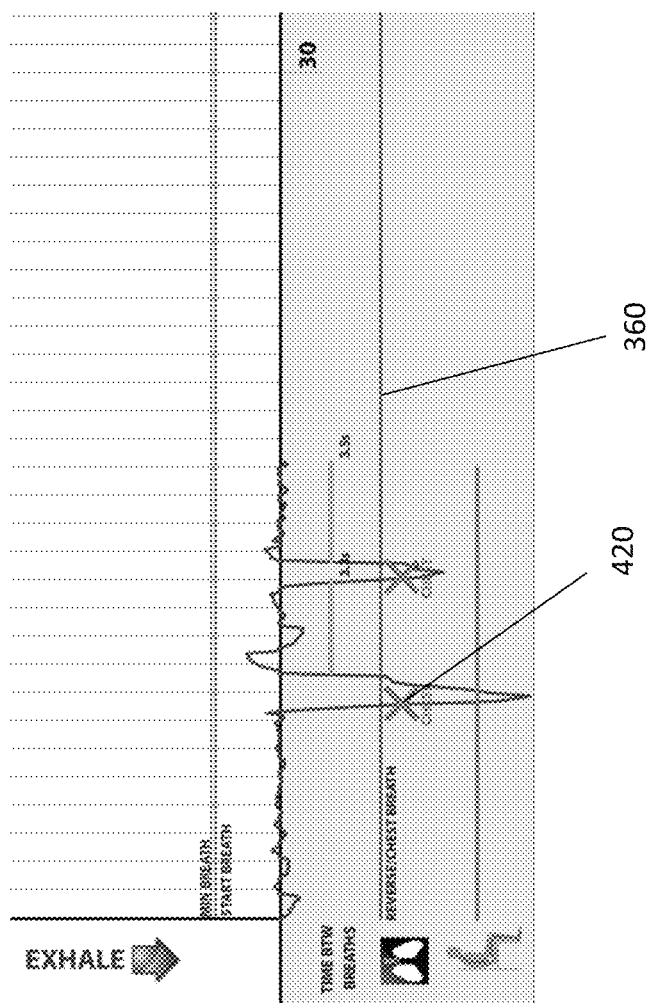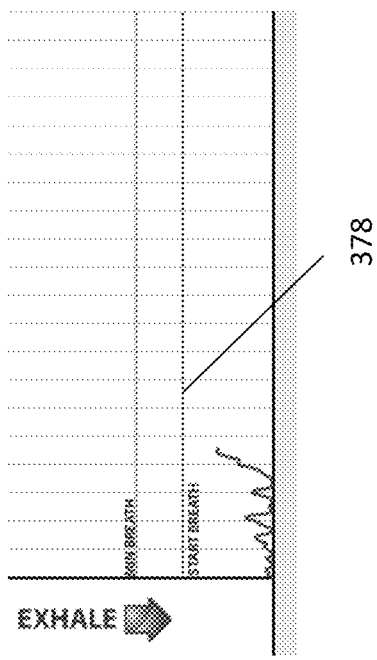

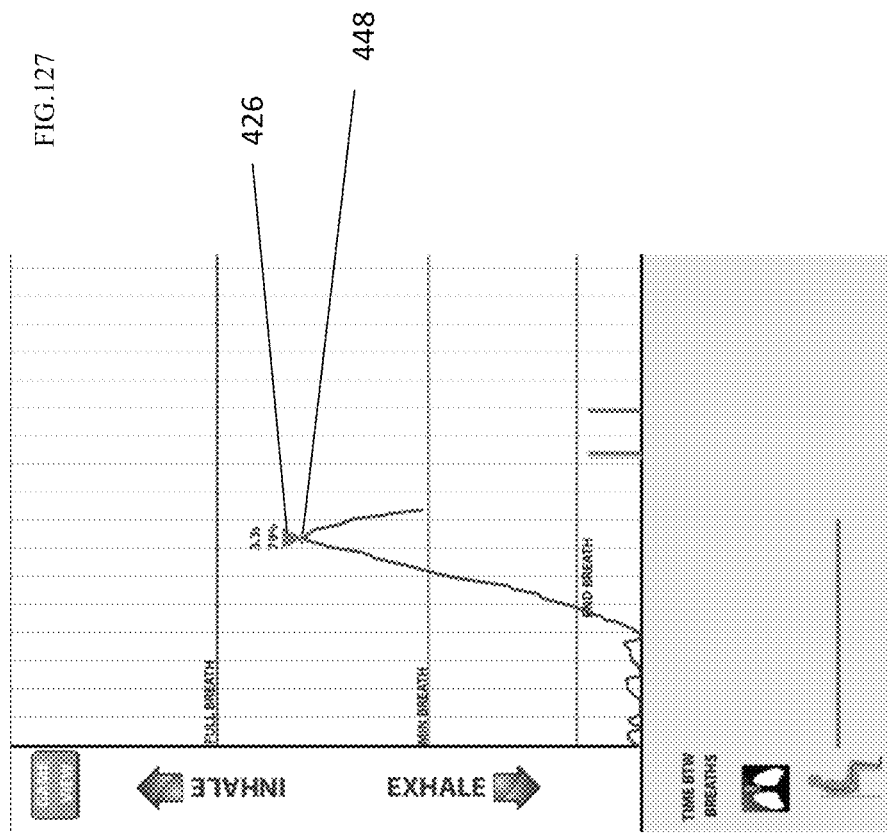

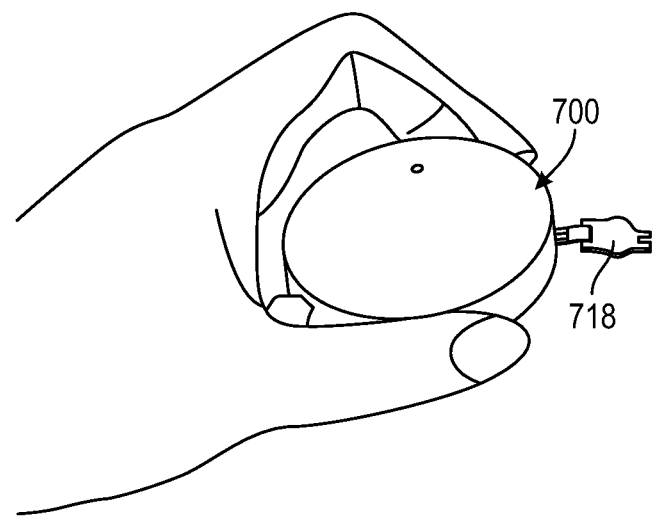
FIG. 164
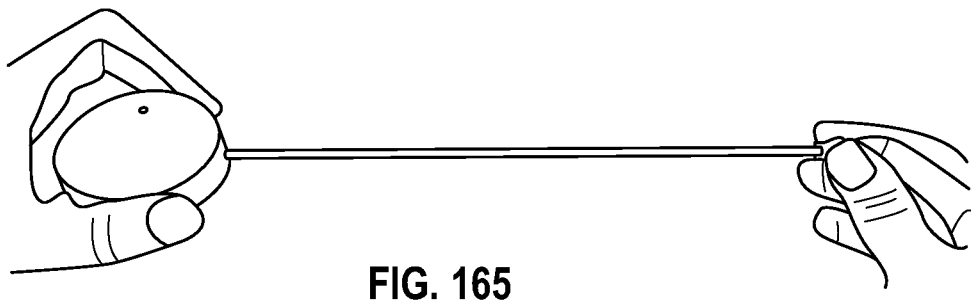
FIG. 165
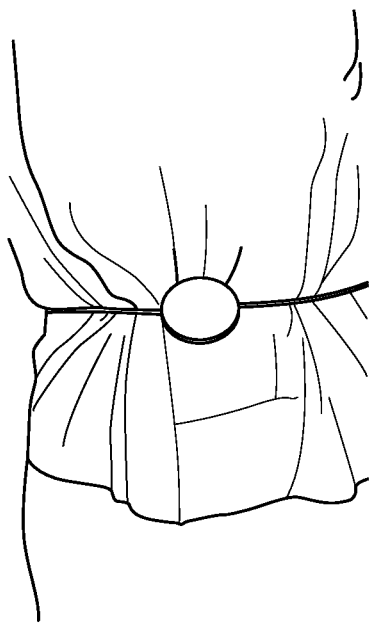 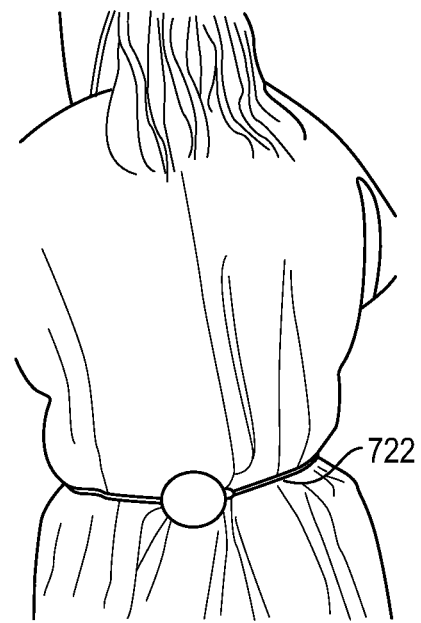
FIG. 166A  FIG. 166B

| Suppliers Part Number | Type | Part | Qty | PCB Reference |
|---|---|---|---|---|
| 1490-1052-1-ND | QFP48 | nRF52832 | 1 | IC8 |
| ADP122AUJZ-3.3-R7CT-ND | TSOT | ADP122 | 1 | IC9 |
| 1092-1055-ND | USON8 | MX25L8006EZUI-12G | 1 | IC7 |
| MCP6041T-I/OTCT-ND | SOT-23-5 | MCP6041 | 1 | IC11 |
| MMA8452QR1CT-ND | 16QFN | MMA8452 | 1 | IC3 |
| TLV493DA1B6HTSA2CT-ND | SMD | TLV493DA1B6HTSA2 | 1 | IC6 |
| 579-MCP4161-502E/MF | DFN8 | MCP4161-502E/MF | 1 | IC5 |
| AD8237ARMZ-R7CT-ND | MSOP8 | AD8237ARMZ-R7 | 1 | IC4 |
| ISL21010DFH310Z-T7ADKR- | SOT-23 | ISL21010DFH310Z-T7A | 1 | IC2 |
| MCP3425A0T-E/CHCT-ND | SOT-23-6 | MCP3425A0T-E/CH | 1 | IC1 |
| MCP73812T-420I/OTCT-ND | SOT-23-5 | MCP73812 | 1 | IC10 |
| 535-11899-1-ND | SMD Crystal | 32.768KHz 12.5pF | 1 | XT1 |
| 887-1331-1-ND | SMD Crystal | 32MHz XTAL | 1 | XT2 |
| BSS84W-FDICT-ND | SOT323 | BSS84W-7-F | 1 | TR2 |
| 568-10498-1-ND | SOT323 | BX3008NBKW,115 | 1 | TR1 |
| 712-1459-1-ND | 0402 | 3n9H Inductor | 1 | L4 |
| 490-6591-1-ND | 0402 | 3n3H Inductor | 1 | L6 |
| 490-1078-1-ND | 0402 | 2n7H Inductor | 1 | L5 |
| 445-1469-1-ND | 0402 | 15nH Inductor | 1 | L3 |
| 587-1884-1-ND | 0603 | 10uH Inductor 58mA | 1 | L2 |
| 587-1835-1-ND | 0402 | Ferrite Bead | 1 | L1 |
| 478-8151-1-ND | TantA | 10uF/6.3V Capacitor | 1 | C2 |
| 490-5915-1-ND | 0402 | 4.7uF/6.3V Capacitor | 2 | C6,8 |
| 445-8820-1-ND | 0402 | 1uF Capacitor | 1 | C18 |
| 1276-1443-1-ND | 0402 | 0.1uF Capacitor | 12 | C3,7,9,10,14,16,19,20,21,25,26,34 |
| 399-1038-1-ND | 0402 | 10nF Capacitor | 3 | C1,15,17 |
| 311-1664-1-ND | 0402 | 200pF Capacitor | 1 | C22 |
| 490-5924-1-ND | 0402 | 12pF Capacitor | 2 | C35,36 |
| 1276-1179-6-ND | 0402 | 15pF Capacitor | 2 | C11,12 |
| 478-1074-1-ND | 0402 | 22pF Capacitor | 2 | C23,24 |
| 445-9066-1-ND | 0402 | 1uF Capacitor | 4 | C5,27,32,33 |
| 311-1024-1-ND | 0402 | 100pF Capacitor | 1 | C30 |
| 478-5716-1-ND | 0402 | 0.8pF Capacitor | 1 | C28 |
| 490-5927-1-ND | 0402 | 1.2pF Capacitor | 1 | C31 |
|  | 0402 | Not Fitted | 0 | C29 |
| P0.0JCT-ND | 0402 | 0R Resistor | 2 | R3,19 |
| 311-10JRCT-ND | 0402 | 10R Resistor | 1 | R1 |
| P100JCT-ND | 0402 | 100R Resistor | 3 | R21,22,23 |
| 311-1.0KJRCT-ND | 0402 | 1K Resistor | 5 | R4,11,12,15,16 |
| 311-1.00MLRCT-ND | 0402 | 1M Resistor | 1 | R18 |
| 311-4.7KJRCT-ND | 0402 | 4K7 Resistor | 2 | R24,25 |
| 311-28.0KHRCT-ND | 0603 | 28K Resistor | 1 | R27 |
| P20.0KLCT-ND | 0402 | 20K Resistor | 1 | R6 |
| P45.3KDBCT-ND | 0603 | 45K3 0.1% Resistor | 1 | R14 |
| YAG4738CT-ND | 0603 | 499K 0.1% Resistor | 1 | R17 |
| P4.99KDBCT-ND | 0603 | 4K99 0.1% Resistor | 1 | R10 |
| P1.0KDBCT-ND | 0603 | 1K 0.1% Resistor | 2 | R9,20 |
| 311-10KJRCT-ND | 0402 | 10K Resistor | 3 | R5,7,8 |
| 311-330KJRCT-ND | 0402 | 330K Resistor | 1 | R26 |
| 311-100KLRCT-ND | 0402 | 100K Resistor | 3 | R2,13,28 |
| 712-1006-1-ND | SMD | Antenna | 1 | A1 |
| WM10922CT-ND | SMD | FPC 6 way | 1 | J5 |
| 609-4613-1-ND | SMD | Micro USB | 1 | J2 |
| 475-2506-1-ND | SMD 0603 | Red SMT LED 2mA | 1 | LD1 |

FIG. 176

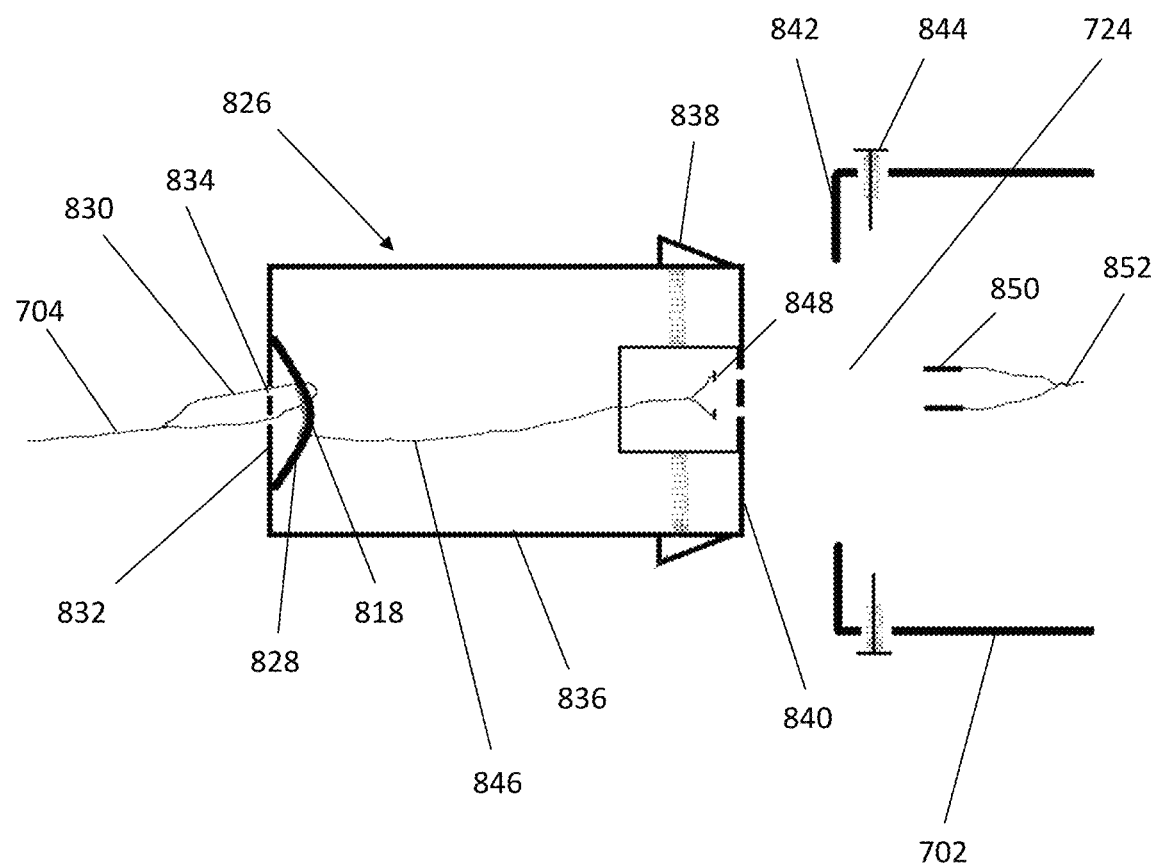

SYSTEM AND METHOD TO MONITOR, GUIDE, AND EVALUATE BREATHING, UTILIZING POSTURE AND DIAPHRAGM SENSOR SIGNALS

CROSS-REFERENCE TO RELATED APPLICATIONS

This application is a continuation in part of U.S. patent application Ser. No. 14/706,939, filed May 7, 2015; this application claims the priority benefit of U.S. provisional patent application 62/519,160, filed Jun. 13, 2017; application Ser. No. 14/706,939 claimed the benefit of provisional patent application No. 61/989,541, filed May 7, 2014, and provisional patent application No. 62/044,268, filed Aug. 31, 2014; the entire contents of all of these patents are incorporated herein by reference.

TECHNICAL FIELD

The present invention relates to a system and method to monitor, guide, and evaluate respiration with respect to one or more breathing patterns, and a method of processing one or more sensor signals related to breathing and a use thereof.

BACKGROUND OF THE INVENTION

Breathing exercises have been around for many centuries and are part of a variety of traditions such as Yoga and Tai Chi, as well as other modern techniques such as Lamaze and the Buteyko breathing method. As one example, the Pranayama are a set of Yoga breathing practices for consciously controlling and changing one's breath, including techniques such as Bhastrika, Kapalbhati, and Sama Vritti Pranayama. Aiming for specific patterns of inhalation, retention, and exhalation times are a common factor in all of these. The general goal of all such breathing practices is to improve well-being and health, such as by lowering anxiety and stress through activating the parasympathetic nervous system, inducing a more meditative relaxed state of mind, increasing energy, alertness, or by altering more concrete physiological parameters such as blood pressure and heart rate. For example, it has been shown that slow deep breathing provides an effect of decreasing blood pressure, as described in the document "Slow Breathing Improves Arterial Baroreflex Sensitivity and Decreases Blood Pressure in Essential Hypertension" by Chacko N. Joseph, et al., in "Hypertension, October 2005", Volume 46, pp. 714-718, published by the American Heart Association.

There are dozens of breathing techniques and practices available, all typically with differences in the breath pattern to follow—that is, different combinations of breathing parameters across the respiratory phases defining a breath, such as inhalation time, retention, exhalation, time between breaths, inhalation depth, and others—and with varying physiological aims. For example, in Sama Vritti Pranayama, the breather is instructed to breathe with equal inhalation and exhalation times for stress relief, and with a constant interval between breaths. More advanced levels of this technique can increase the inhalation/exhalation time. For example, a beginner might inhale and exhale for two seconds each, while a more advanced breather might do so for 5 seconds or more. Other exercises involve having varying ratios of inhalation time to exhalation time, where for example, the exhalation time could be twice as long as the inhalation time. Longer exhale times compared to inhale times have been known to help stimulate the Vagus nerve to help activate the parasympathetic nervous system. Another popular technique is called the 4-7-8 breath pattern, where the breather inhales for 4 seconds, holds breath for 7 seconds, then slowly exhales over 8 seconds, and repeats, with the aim of inducing a tranquilizing effect on the nervous system. A more advanced breathing practice may be further defined by a sequence of distinct breath patterns, changing or cycling over time. For example, a sequence could be composed of five breaths, where inhalation times steadily increase across these breaths. For example, the paper "Sudarshan Kriya yogic breathing in the treatment of stress, anxiety, and depression: part I-neurophysiologic model" by Brown R P, Gerbarg P L, in "J Altern Complement Med. 2005 February; 11(1):189-201" considers the effects of a sequence of specific breathing techniques.

A very common emphasis in breathing exercises and patterns, in addition to the pattern parameters, is to breathe from the abdomen rather than the chest, also known as diaphragmatic breathing or belly breathing. During diaphragmatic breathing, the breather is more fully contracting their diaphragm to enlarge the volume of the thoracic cavity to draw air more fully into the lungs, causing the abdomen to expand and belly to rise during inhalation. Chest breathing, on the other hand, is typically more shallow and done by expanding the chest, with much more limited diaphragmatic excursion. A number of recent studies have found evidence of health benefits for diaphragmatic breathing, including "Diaphragmatic breathing reduces exercise-induced oxidative stress" by Martarelli D. et al., in "Evidence-based complementary and alternative medicine, February 2010" and "Efficacy of diaphragmatic breathing in patients with chronic obstructive pulmonary disease" by Fernandes M. et al., in "Chronic Respiratory Disease, 2011".

Another factor affecting the quality of breath is posture. For example, the following research paper found a significant relationship between a particular seated posture and the quality of pulmonary function: "Effect of different sittings posture on pulmonary function in students" by Baghery Hojat and Esmaeilzadeh Mandi in "Journal of Physiology and Pathophysiology Vol. 2(3), pp. 29-33, July 2011". These researchers found that in slumped sitting, spirometric measurements of forced vital capacity, forced expiratory volume in 1 second, and peak expiratory flow were all significantly decreased compared to a normal upright seated posture. One explanation is that posture affects the distribution of weight of visceral organs on the diaphragm, which affects its mobility when breathing. Slumped sitting, in particular, can have an impeding effect on diaphragm mobility. The following paper found that posture does, in fact, affect diaphragmatic movement: "The effect of posture on diaphragmatic movement and vital capacity in normal subjects with a note on spirometry as an aid in determining radiological chest volumes" by O. L. Wade and J. C. Gilson, in "Thorax (1951), 6, 103." This is important to take into consideration for a system which attempts to track breath based on motions/angle changes of the abdominal wall, or girth changes of the waist, since such measurements are significantly affected by the extent of diaphragmatic excursion. For example, if such a system attempts to judge the depth of an inhalation based on the angle change of the abdominal wall or girth change of the waist, the range of such changes may be different across different postures, making it difficult to compare inhalation depths between breaths without accounting for posture.

Now discussing existing candidate technologies, in recent years, pulse oximetry has been adapted to determine respiration rate, using specialized algorithms which can extract this measure from the heart rate signal. While a pulse oximeter device can be ergonomic and convenient, unfortunately the extracted respiration data generally lags, and does not provide enough resolution to track against a breath pattern in real time. It is generally limited to summary measures such as respiration rate. Also there are no direct means of determining diaphragmatic breathing or posture.

Spirometry is a well-established technology which can provide accurate real-time measures of air flow rates and volume during inhalation and exhalation. The limitation is that breathing into a tube is required, which is not convenient for everyday settings or for use over extended periods of time. Also a spirometer has no means of distinguishing between diaphragmatic and chest breathing, or taking into account the effects of posture.

Optoelectronic Plethysmography is a recently developed method to track respiration through measurement of the chest wall motion, using a number of small reflective markers placed on the abdominal or chest wall surface, and requiring a specially designed camera to analyze motion of these markers. While the real-time data can be highly accurate and could in principle track diaphragmatic breath, this system is generally a cumbersome setup in a lab-type setting with expensive components, and not practical for everyday use.

Respiration belts, worn around the waist or chest, or individual sensors placed in those areas offer another approach. Such devices typically measure variations in girth or attempt to track movements or angle changes in the chest or abdominal wall by placing a sensor thereupon. In the former case, a stretch or displacement sensor may be used for example, and in the latter, a sensor such as an accelerometer is often employed.

Other products in the breathing monitoring field include the Spire Stone and Health Tag, produced by Spire, Inc., San Francisco, Calif.

Other work in the field includes Palley et. al., US patent application 2014/0228657.

Other products in the posture monitoring field include the Upright Go, produced by Upright Tech LTD, Yahud Israel, and Lumo Lift produced by Lumo Bodytech, based in Mountain View Calif.

SUMMARY OF THE INVENTION

There are a number of significant practical challenges to providing a system which can accurately track and evaluate a user's breathing with respect to a breathing pattern or exercise, as well as evaluate the other factors of breath quality. First, such a system must be able to accurately track all phases of respiration across the entire breath waveform and determine the times and transition points of each phase so that it can compare them to selected breath pattern parameters, such as inhalation time, breath retention, exhalation time, and time between breaths. Also important is gauging the depth of inhalation and how smooth and uniform breathing is. The sensors and methods employed must offer a high enough degree of resolution to make such determinations in real time, and not just offer summary statistical measures such as respiration rate.

Secondly, it is important that such a system and methods are able to handle and correct for a reasonable amount of body motion noise or artifacts, so that unrelated body movements are not too frequently mistaken for respiratory signals. Requiring a user to sit or stand perfectly still, especially during passive tracking, is not very practical, as it is unnatural and difficult to maintain stillness for extended periods of time. Additionally, sensor drift should be corrected for.

Thirdly, since diaphragmatic breathing is an integral part of healthy breathing patterns as discussed above, it is preferable that such a system be able to track and distinguish between diaphragmatic and non-diaphragmatic forms of breathing.

Note that in the context of the above observations, certain breathing monitoring devices presently on the market have certain disadvantages. For example, some of these devices require that the device be clipped or even permanently attached to the user's clothing, such as to the user's front waistband or bra. This can be problematic, because in addition to requiring that the user wear a particular compatible clothing configuration, if the user's clothing is too loose or bulky, or shifts position during use, this can result in an inaccurate or inconsistent breathing signal. Additionally, some devices cannot distinguish between diaphragmatic and chest breathing, in particular, those which are clipped to the bra. Thus it is useful to provide an improved device, system, and method that overcomes these disadvantages.

Fourthly, it is preferable that such a system take into account the effects of posture on breathing as described above, so that inhalation depths, for example, can be consistently measured across varying postures.

Fifthly, it is desirable that the system provides software and a user interface which clearly and intuitively tracks and identifies all phases of respiration, with a method of providing visual feedback to compare and evaluate each phase of respiration with respect to a corresponding phase of a selected breath pattern, so that a user can readily understand which phases of their breathing adhere to a pattern and which do not. Also it is preferable that such software be able to identify diaphragmatic breathing, visually tie in the effects of posture on breath, and be able to calibrate across a wide variety of body types with an intuitive visual method for such calibration. It is also preferable that such software offer both a detailed analytical view of breath data evaluation, and a more relaxed gaming mode for training against various breath patterns. Furthermore, it is desirable that such software offer both passive tracking and active training modes, allowing the user to either use the system in the background to monitor their breathing, or to consciously and proactively use the system to train with various breath exercises help induce certain physiological effects and purposely improve their breath control.

Sixthly, it is desirable that such a system be ergonomic, non-invasive, and convenient for a user to wear and use in a variety of settings.

One of the main challenges of such devices which track abdominal wall movement or angle changes, stems from the fact that various body movements, such as rocking back and forth, can mimic the angle changes and motions seen during breathing. Various mathematical and statistical techniques, with limited success, can be used in an attempt to isolate and disambiguate breathing components in the sensor signal from body movement noise, such as Principle Component Analysis and Fourier transforms. The ultimate problem is that the frequency of breathing, roughly in the 0.1 Hz to 0.4 Hz range, can largely overlap with the frequency of body movement, such as that resulting from posture changes or other natural movements. From a sensor's perspective, the difference can be practically indistinguishable. A system based on just one such sensor placed near the abdomen or chest has been typically prone to inaccuracy and noise, resulting for example in false breath starts or incorrectly judging that a breath has completed. A related difficulty in such a system is finding a fully exhaled body position baseline from which to measure the start of a breath, since this position is continuously floating with body movement. Relying on a user's abdominal or chest wall angle to return back to the same level after each exhalation, for example, is generally not practical. In addition to this, there is a certain amount of sensor drift that can influence angle and position measurement sensors, even if the body returns back to the same position or angle.

Respiration belts which track waist girth are also typically susceptible to a certain degree of body motion noise, since altering posture for example, can have the effect of momentarily stretching or displacing a sensor used in such a system, even while breath is being held, which can result in false respiratory signals.

It is, therefore, desirable to overcome the above problems of accurately tracking and evaluating a user's breathing with respect to a breathing pattern or exercise, by providing an apparatus and method for breath monitoring and training, which can accurately track all phases of respiration across the entire breath waveform, taking into account the effects of posture changes, body movement noise, and able to identify and track diaphragmatic breathing, while providing an ergonomic and convenient to wear device. It is also desirable to provide a visual feedback method to evaluate each phase of respiration in a simple clear manner, so that a user can see in real time to what degree they are adhering to a chosen breath pattern.

As will be discussed, in some embodiments, the invention may be a user-worn device with posture and diaphragm (breathing status) sensor signals. The user-worn device will typically be a unitized device (e.g. with a housing, and a retractable belt worn around the user's trunk), that often holds the housing on the user's back. The housing contains both posture and breathing sensors. The device monitors the output signals of these sensors and measures the state of both the user's posture and diaphragm (e.g. changes in the belt's length or force on the belt as a function of user breathing) to analyze breathing signals. The system's processor receives, processes, and transmits sensor signal data, and can also calibrate, and interpret these signals utilizing various algorithms. In a preferred embodiment, the posture sensor is an accelerometer, and the retractable belt winds around a spring tensioned spool in the device's housing. The software can produce posture adjusted user respiration data, and can also be used for breath training and other purposes.

The device is "unitized" in that the housing, all sensors, at least one device processor, and the belt all form a single unit, and work together as a single unit.

One embodiment of the present invention is a breath training device which measures both respiration and posture from one location on the body trunk, such as near the abdomen, or upper pubic area, utilizing a single sensor case (often referred to in the alternative as a "housing") containing an angle sensor (which can be used to measure user posture), and can include a microcontroller (e.g. a processor), memory for storing firmware and data, battery, port, and an I/O such as Bluetooth or other wired or wireless data communication device for communicating with an external computing platform such as a smart phone or laptop. A signal processing method is described which includes basic inference reasoning and assumptions to help separate and isolate the confounded variables of relative diaphragm position and relative posture position from the angle sensor output for deriving a filtered breath signal.

Thus in some embodiments, any of the device's built-in processor and/or an external computing program processor can be further configured to use current (e.g. present, real-time) breathing sensor data and current (e.g. present, real-time) angle sensor data to determine a user current diaphragm position and a user current posture position.

Another embodiment of the present invention is a breath training device which can include both an angle sensor and displacement sensor (which can be used to measure user breathing, and thus will often be referred to in the alternative as a breathing sensor) housed in a single case, which also can include a microcontroller, memory for storing firmware and data, battery, port, and an I/O such as Bluetooth for communicating with an external computing platform such as a smartphone or laptop. The case (or housing) can be mounted on a respiration belt worn around the waist area or chest portion of the user's trunk, with the case worn on a user's back, and a buckle or other fastener on the belt which can be reversibly secured and adjusted (or detached) to the housing in various places. In some embodiments, the belt can extend from both sides of the case or housing, and fastened near the user's abdomen or chest. In other embodiments, the housing may have a built-in housing fastener (which may be proximate the housing, or separated from the housing) in which case the belt fastener will attach to the housing fastener.

The displacement sensor (e.g. a breathing sensor, which as will be discussed may comprise one or more types of different sensor devices) can be used to track changes in the user's trunk circumference (during breathing) to measure inhalation and exhalation, and the angle sensor tracks posture and body movements for correcting and calibrating the displacement sensor output signal to compute a filtered breath signal used for comparing against a chosen breath pattern. An object and advantage of this embodiment of the present invention is that by placing both the angle and displacement sensors in the same case (or housing), this eliminates the need for a second sensor housing placed near the chest or abdomen. This is possible since changes in trunk circumference can be measured from the back, and thus the displacement sensor need not be placed near the abdomen or chest.

Another object of the present invention is to provide a method for computing a filtered (or posture adjusted) breath signal. This can be used, for example, to reduce the impact of varying user postures on the user respiration measurements. As a specific example, this can include the steps of computing a current posture angle of an angle sensor and a trunk circumference change of a displacement sensor, computing a relative posture position based on the relation of current posture angle to a sampled posture angle range, retrieving a learned zeroing offset from an offsets array indexed by relative posture position for dynamically setting a fully exhaled level baseline of trunk circumference, computing a relative diaphragm position based on the deviation of a current inhale level from said fully exhaled level baseline, scaling relative diaphragm position using a current posture zone coefficient to compute a signal B to account for the effect of posture, applying a motion damping filter to signal B to compute a signal C, applying a normalization test to signal C which if true, then normalizing and setting filtered breath signal to 0, and if false, setting filtered breath signal to signal C.

Another object of the present invention is to provide a dynamic normalization method which stores a zeroing offset in an offsets array indexed by relative posture position, for dynamically learning a zeroing baseline level corresponding to a fully exhaled position of relative diaphragm position at a given current relative posture position. This allows the system, for example, to avoid having confusing posture changes with inhalation signals, and to accurately track the start of an inhalation of a new breath, independent of posture variation In some embodiments, the present invention can also be used to help provide a breath training program which can track the filtered breath signal to provide respiratory measures including time between breaths, inhalation time, inhalation depth, breath retention time after inhalation, exhalation time (both relative and absolute), breath uniformity (if staggers occur), respiration rate, diaphragmatic or reverse breathing, whether or not inhalation to a maximum depth was performed within a specified interval of time, and tracking posture. A further object of the breath training program is to provide an analytical view and game mode view of the filtered breath signal. In the analytical view, symbols are used on a graph to both identify the respiratory measures, as well as their evaluation status in comparison to the respiratory phases of a chosen breath pattern. In a game mode, inhalation, retention, and exhalation zones are displayed for a chosen or customized breath pattern, and the user controls a breath level game element by means of the filtered breath signal, with the goal of successfully guiding said element through said zones by utilizing proper breathing technique. A further object of the breath training program is to provide both a passive tracking and active training mode, allowing the user to either use the system in the background to monitor their breathing, or to consciously and proactively use the system to train with various breath exercises help induce certain physiological effects and purposely improve their breath control.

In such breath training program embodiments, the invention can optionally provide a breath training program which contains a library of breath patterns (also referred to as exercises) to choose from for training. Such patterns can include Pranayama patterns such as Sama Vritti, Kapalabhati, Bhastrika, Anulom Vilom, and other patterns including but not limited to Buteyko, Tai Chi, 4-7-8, and Lamaze. Each such pattern has associated with it a set of breath pattern parameters for comparing the filtered breath signal against. Additionally, the library may contain a set of breath sequences, which can define different breath patterns for each breath in a sequence of breaths. Furthermore, the breath training program can provide means to edit such patterns and sequences, allowing a user to customize their breath training.

In some embodiments, the present invention can also provide a method for distinguishing a diaphragmatic breath from a reverse breath, by analyzing the filtered breath signal, while utilizing a breath training device worn near the waist area.

More specifically, in some embodiments, the invention may be a device, system, or method for tracking respiration and posture from a location on a human user. This device can comprise a housing comprising a computer processor, an electronic angle sensor, a retracting belt, a retracting mechanism, a housing fastener, and an electronic breathing sensor configured to produce an electronic breathing sensor signal reporting on at least one of force and movement of the retracting belt.

The retracting belt can comprise a first belt end that is connected to the retracting mechanism, and a second belt end configured with a belt fastener that is configured to reversibly attach (e.g. attach and detach) to the housing fastener.

The housing and the retracting belt are often configured so that when the retracting belt is worn around the user's trunk and the belt fastener is attached to the housing fastener, the retracting belt experiences force, movement, or a combination of force and movement in response to user respiration. As a result, the breathing sensor produces a breathing sensor signal reporting on this respiration. Here, the electronic angle sensor is configured so that when the retracting belt is worn around the user's trunk, and the belt fastener is attached to the housing fastener, the angle sensor produces an angle sensor signal reporting on an angle of the user's posture. The device's processor(s) is also configured to process the breathing sensor signal and the angle sensor signal, and to produce one or more different types of output. For example, the output can be angle sensor data reporting on the user's posture, and breathing sensor data reporting on the user's respiration. This output can then be sent to external processors for additional processing as desired. In some embodiments, the device processors may also do additional onboard processing, and for example, also report posture corrected user respiration data.

These and other objects, advantages, features and characteristics of the present invention, as well as the methods of operation and functions of the related elements of structure and the combination of parts, will become more apparent upon consideration of the following description with reference to the accompanying drawings. All dimensions shown in the figures are provided as examples, and it is understood that many other dimensions are possible.

BRIEF DESCRIPTION OF THE DRAWINGS

FIG. 8 is a schematic view of a belt slider of the first embodiment of a breath training device of the present invention.

FIG. 11 is a schematic view of a spring return of the first embodiment of a breath training device of the present invention.

FIG. 12 is a schematic view of a spring return and displacement sensor of the first embodiment of a breath training device of the present invention.

FIG. 13 is a side schematic view of a displacement sensor and belt slider of the first embodiment of a breath training device of the present invention.

FIG. 14 is a longitudinal schematic view of a spring return and displacement sensor of the first embodiment of a breath training device of the present invention.

FIG. 41 is a schematic view of an oval shaped sensor case design.

FIG. 98B is a flowchart showing exemplary steps involved in implementing an InterruptBreath process of the present invention.

FIG. 98C is a flowchart showing exemplary steps involved in implementing a ResetTime process of the present invention.

FIG. 98D is a flowchart showing exemplary steps involved in implementing a Display live stats for passive mode process of the present invention.

FIG. 98E is a flowchart showing exemplary steps involved in implementing an alertUserForCorrectiveActions process of the present invention.

FIG. 98F is a flowchart showing exemplary steps involved in implementing a countDeepSlowBreaths process of the present invention.

FIG. 98G is a flowchart showing exemplary steps involved in implementing a countSteps process of the present invention.

FIG. 98H is a flowchart showing exemplary steps involved in implementing a find HRV maximizing breath pattern process of the present invention.

FIG. 99 is an exemplary screenshot of the filtered breath signal on a timeline graph.

FIG. 100 is an exemplary screenshot of a back and forth swing of the filtered breath signal due to body movements.

FIG. 101 is an exemplary screenshot showing signal C falling below a fully exhaled threshold line.

FIG. 102 is an exemplary screenshot of calibrating the BTD position on a user's body.

FIG. 103 is an exemplary screenshot showing the filtered breath signal graphed on the timeline during the BTD position calibration process.

Figure 104:
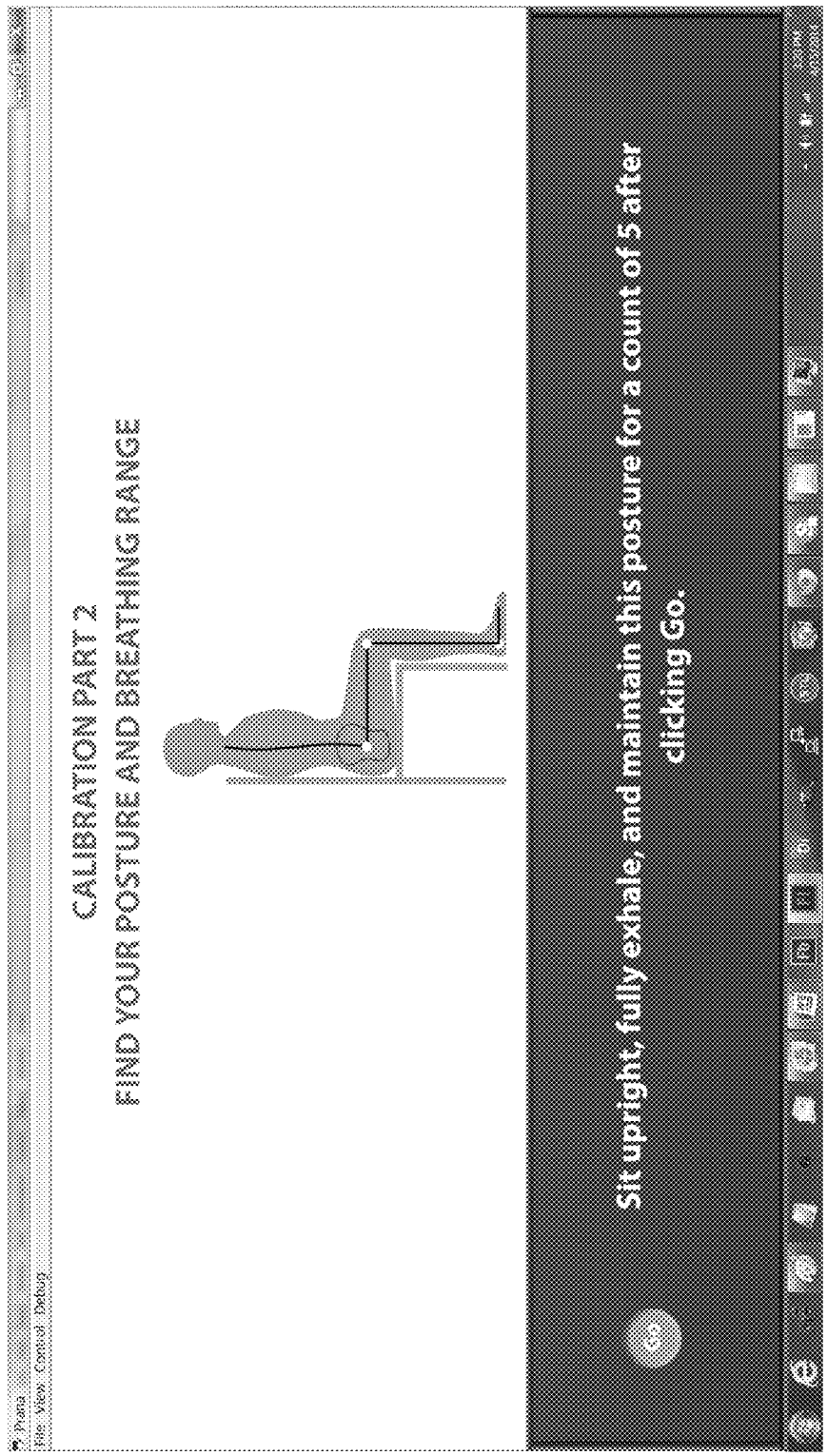

FIG. 104 is an exemplary screenshot of a process that learns a user's posture and diaphragm range of motion, instructing the user to sit upright and exhale.

Figure 105:
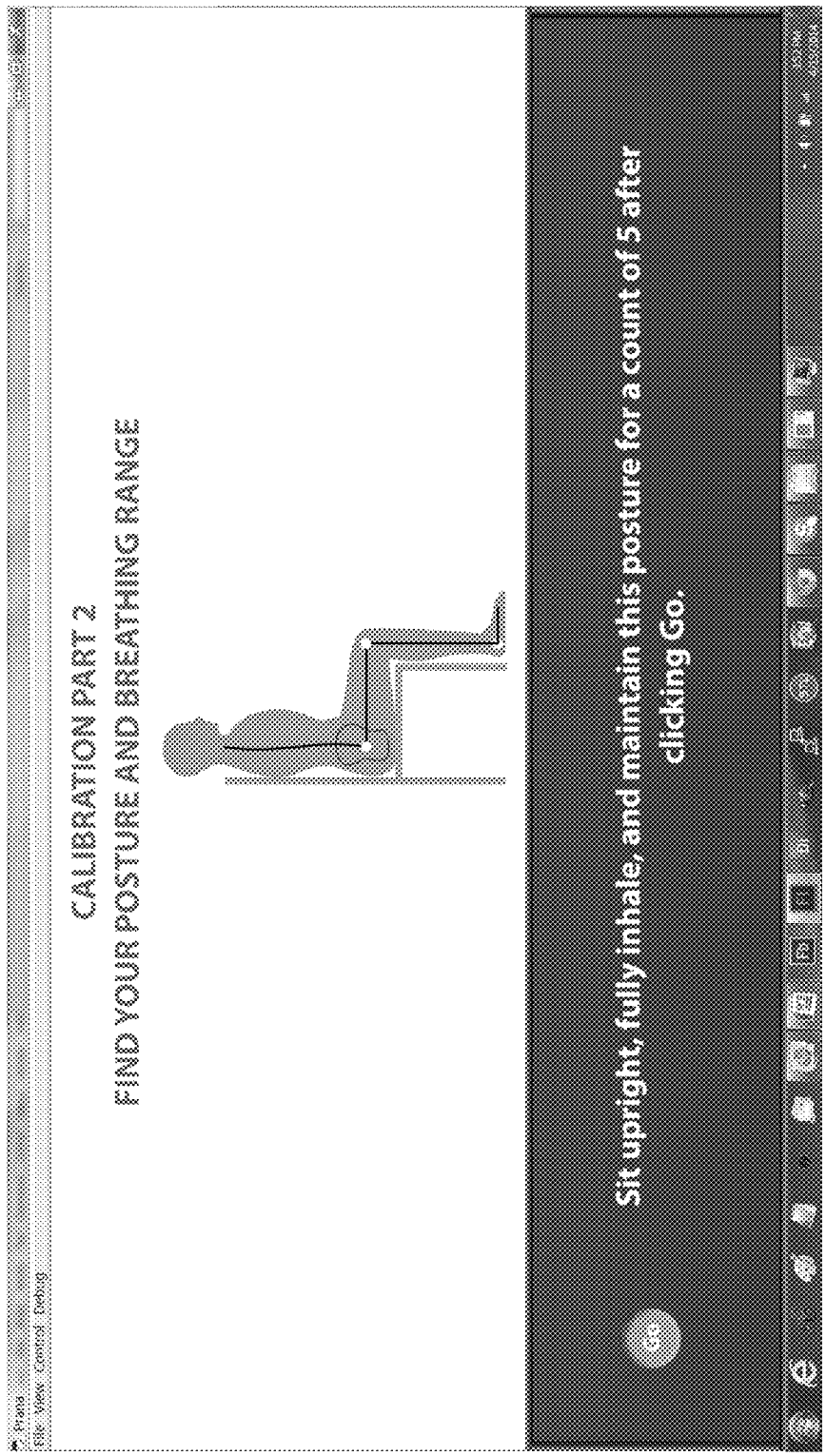

FIG. 105 is an exemplary screenshot of a process that learns a user's posture and diaphragm range of motion, instructing the user to sit upright and inhale.

Figure 106:
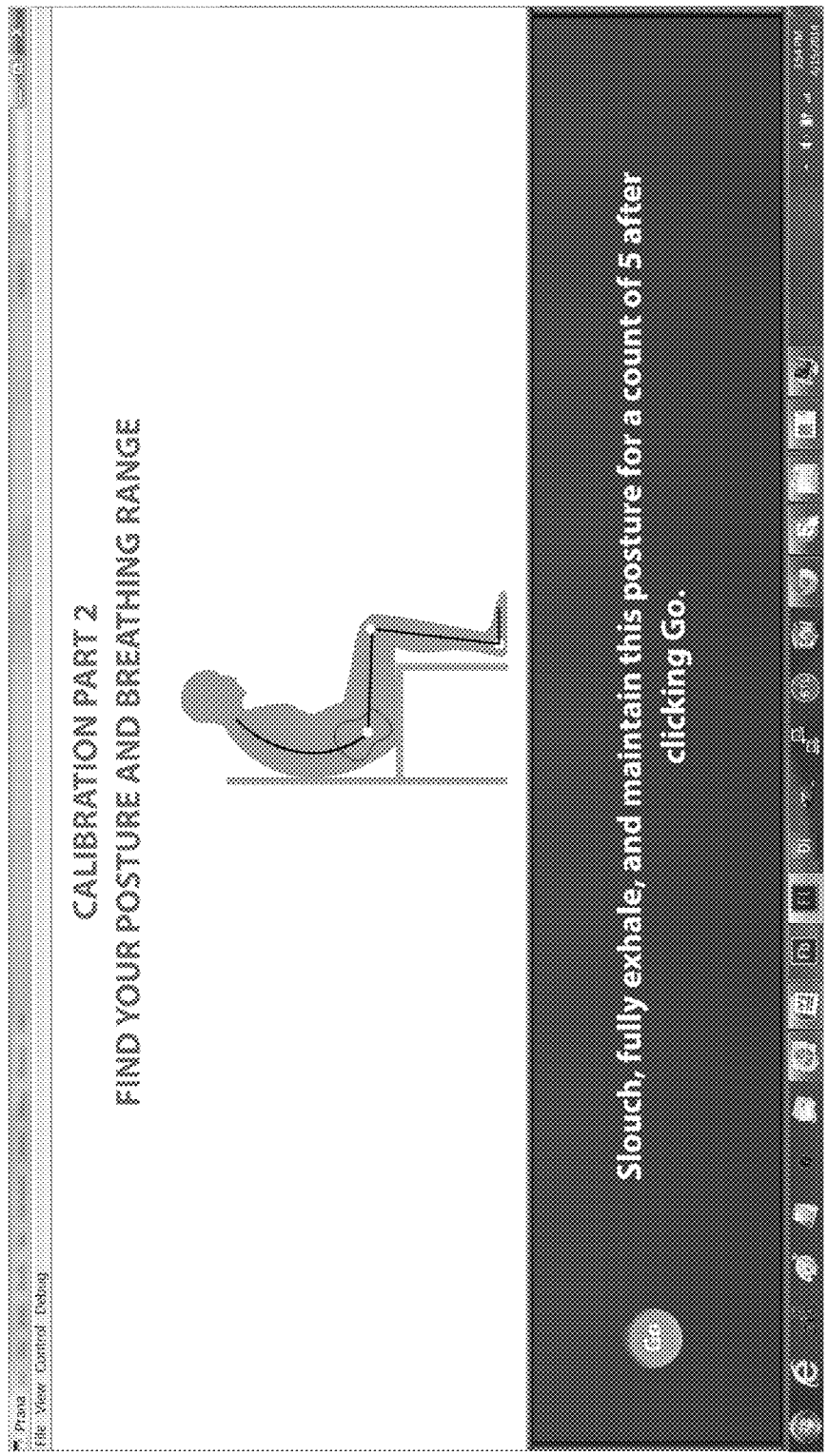

FIG. 106 is an exemplary screenshot of a process that learns a user's posture and diaphragm range of motion, instructing the user to slouch and exhale.

Figure 107:
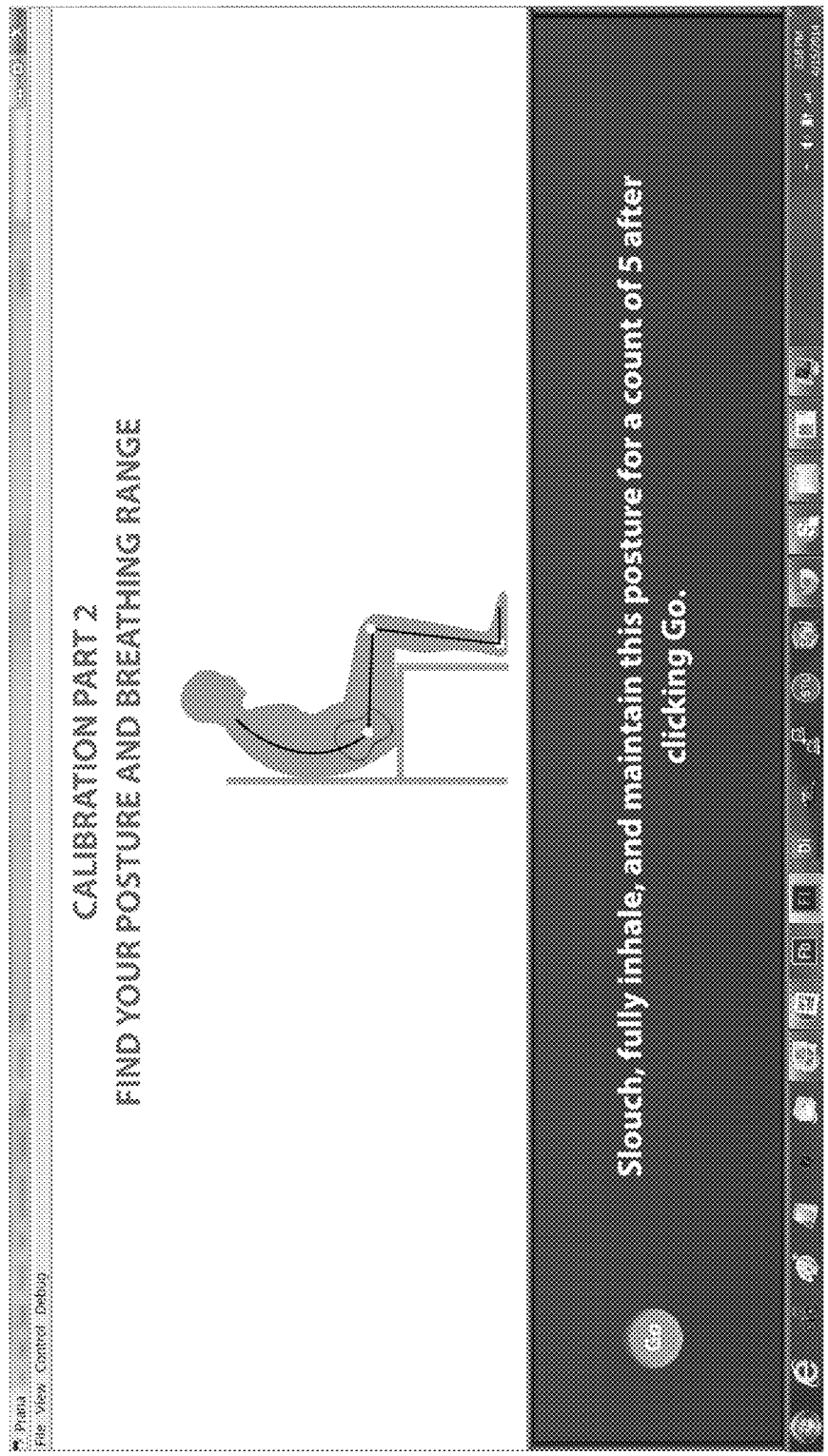

FIG. 107 is an exemplary screenshot of a process that learns a user's posture and diaphragm range of motion, instructing the user to slouch and inhale.

Figure 108:
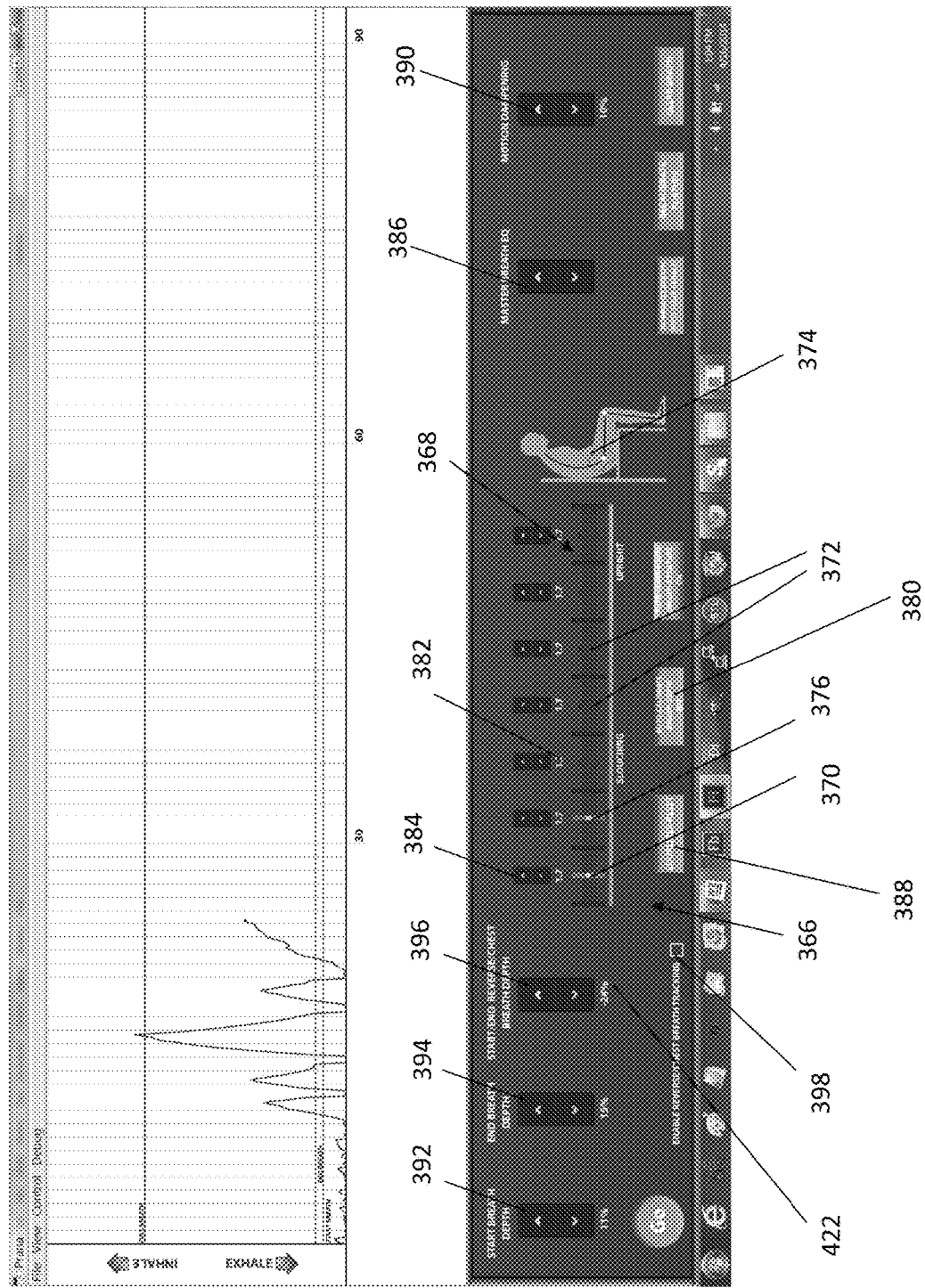

FIG. 108 is an exemplary screenshot of a calibration screen.

FIG. 108A is an exemplary screenshot of a calibration screen for a BTD=type 4.

FIG. 109 is an exemplary screenshot showing how the breath indicator position can be scaled such that approximately two posture zones of displacement represent a full diaphragmatic breath.

Figure 110:
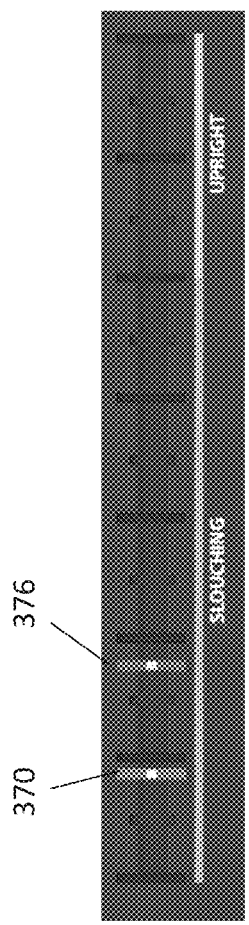

FIG. 110 is an exemplary screenshot of a modified breath indicator with a symbol indicating a diaphragmatic breath is in progress.

Figure 111:
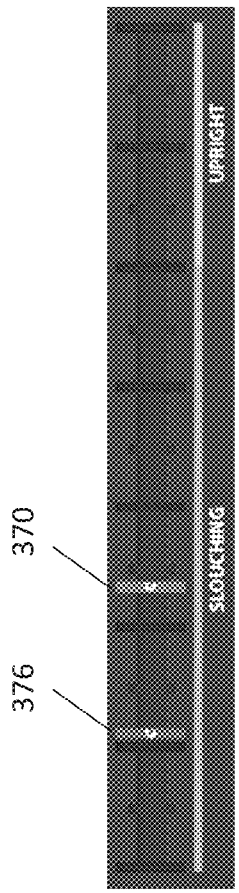

FIG. 111 is an exemplary screenshot of a modified breath indicator with a symbol indicating a reverse breath is in progress.

Figure 112:
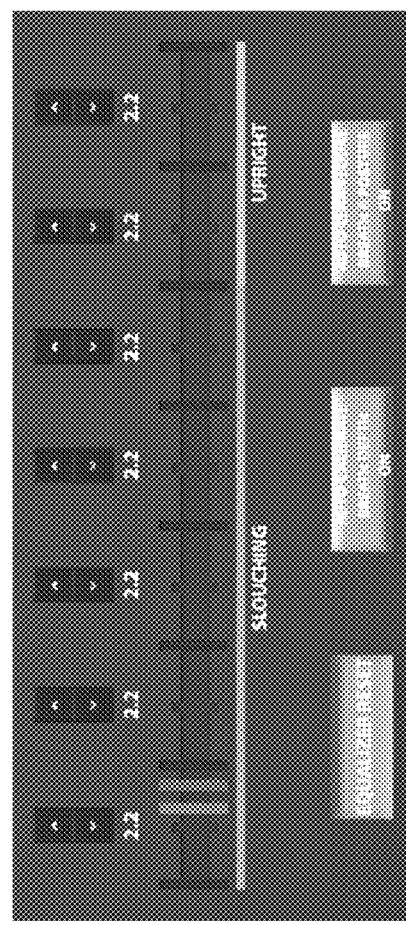

FIG. 112 is an exemplary screenshot of a posture indicator in the first posture zone.

Figure 113:
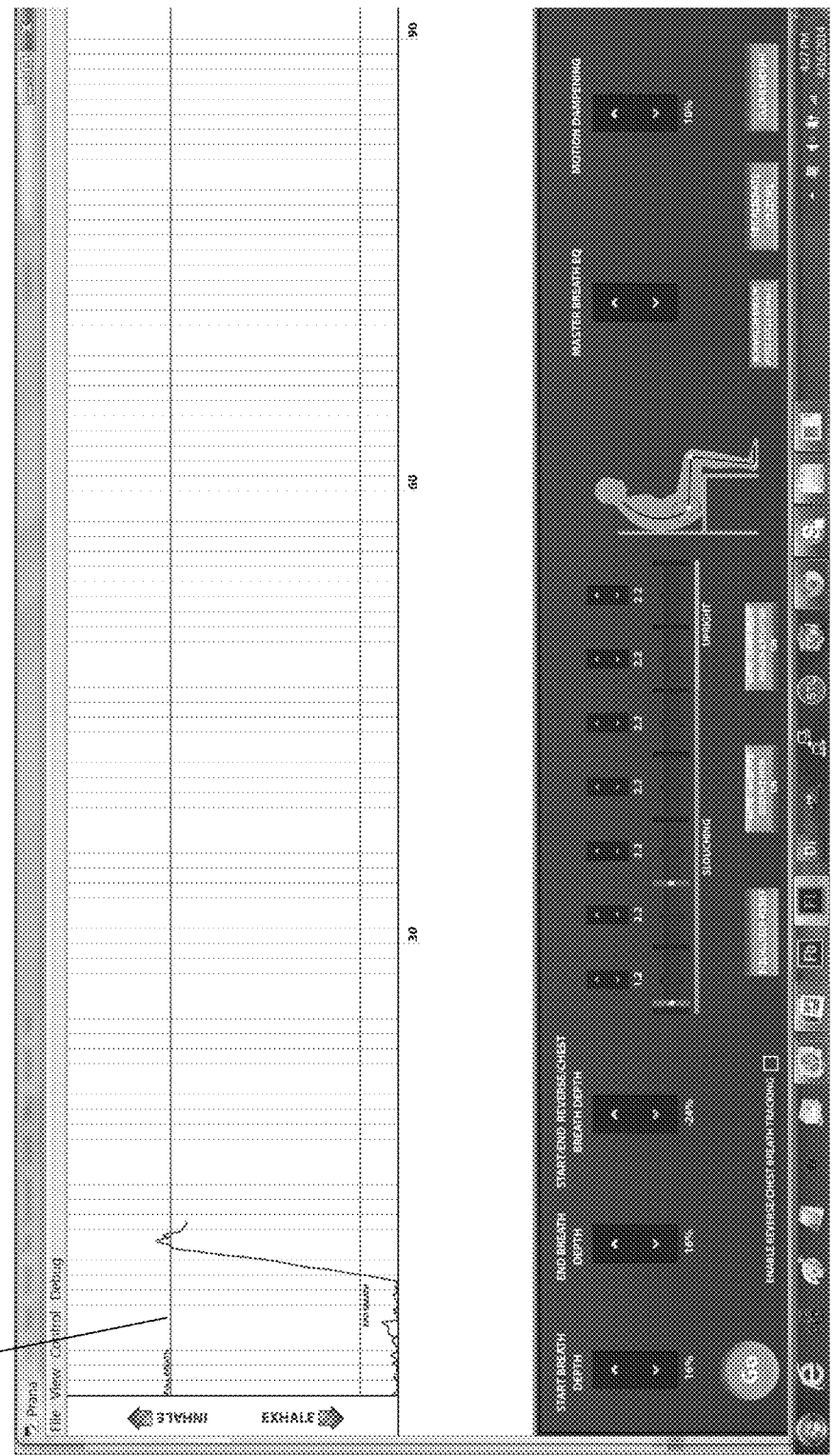

FIG. 113 is an exemplary screenshot showing the current posture zone coefficient incrementally reduced until the filtered breath signal falls below the full breath line.

Figure 114:
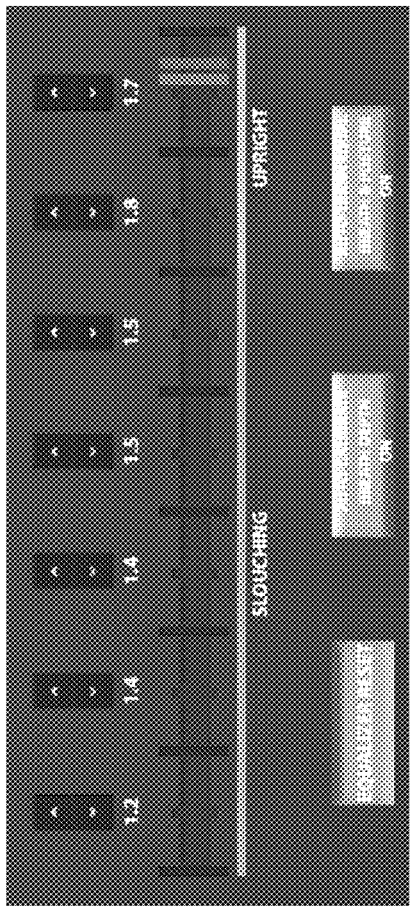

FIG. 114 is an exemplary screenshot showing all posture zone coefficients having been learned.

Figure 115:
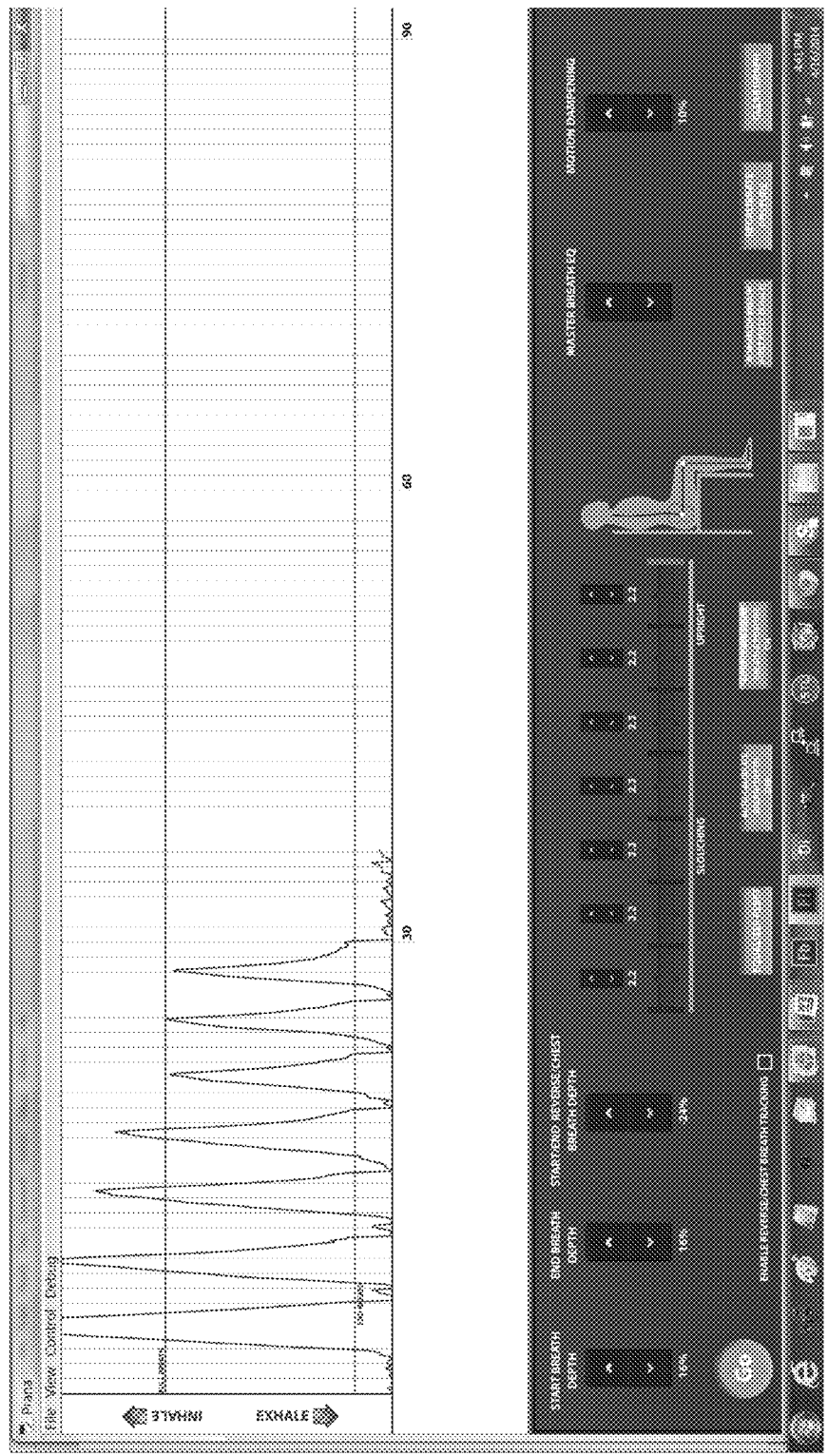

FIG. 115 is an exemplary screenshot of 7 full breaths taken, one in each posture zone from left to right, prior to learning the posture zone coefficients, and the resulting not uniformity in the filtered breath signal height.

Figure 116:
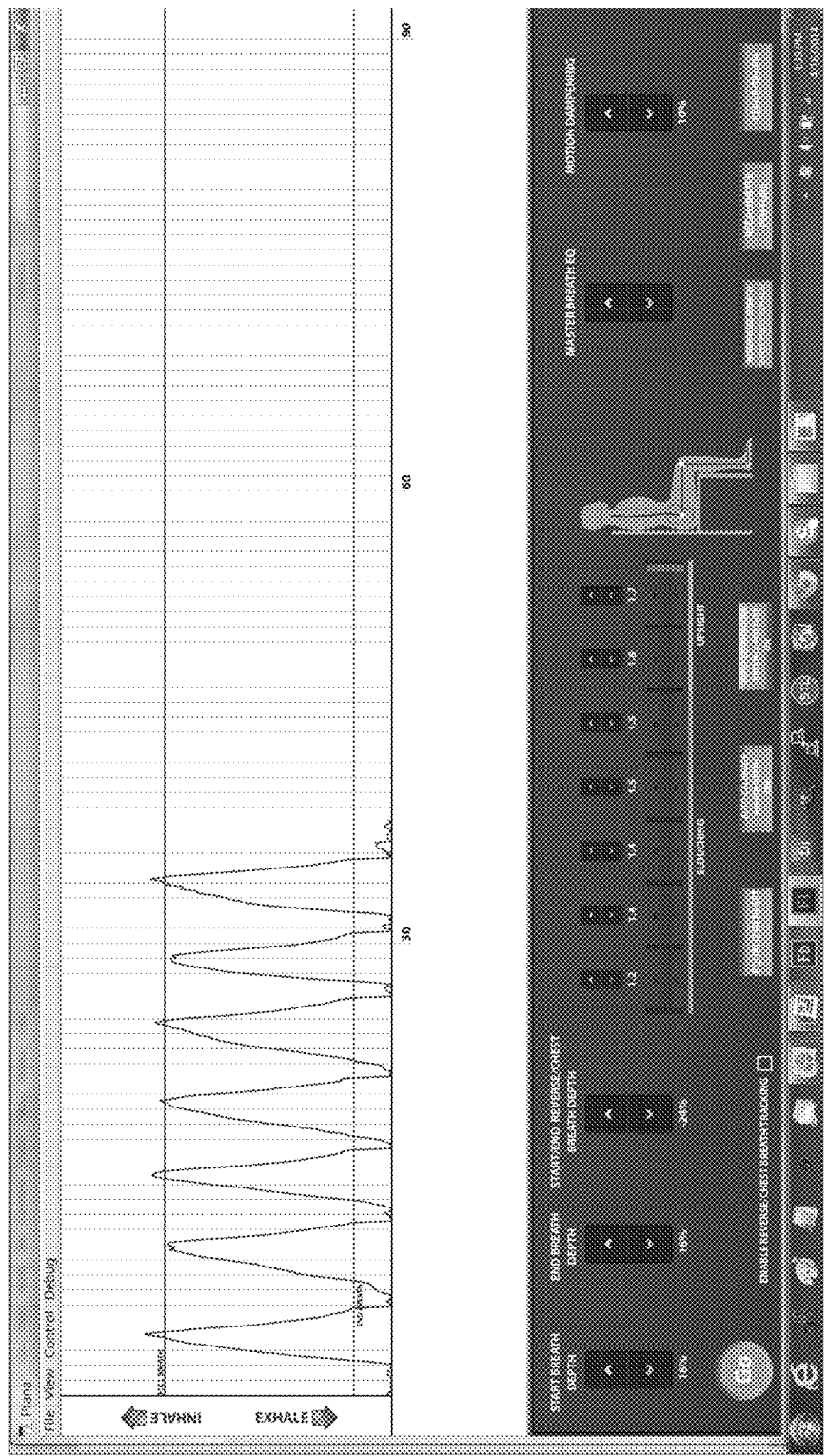

FIG. 116 is an exemplary screenshot of 7 full breaths taken, one in each posture zone from left to right, after learning the posture zone coefficients, and the resulting uniformity in the filtered breath signal height.

Figure 117:
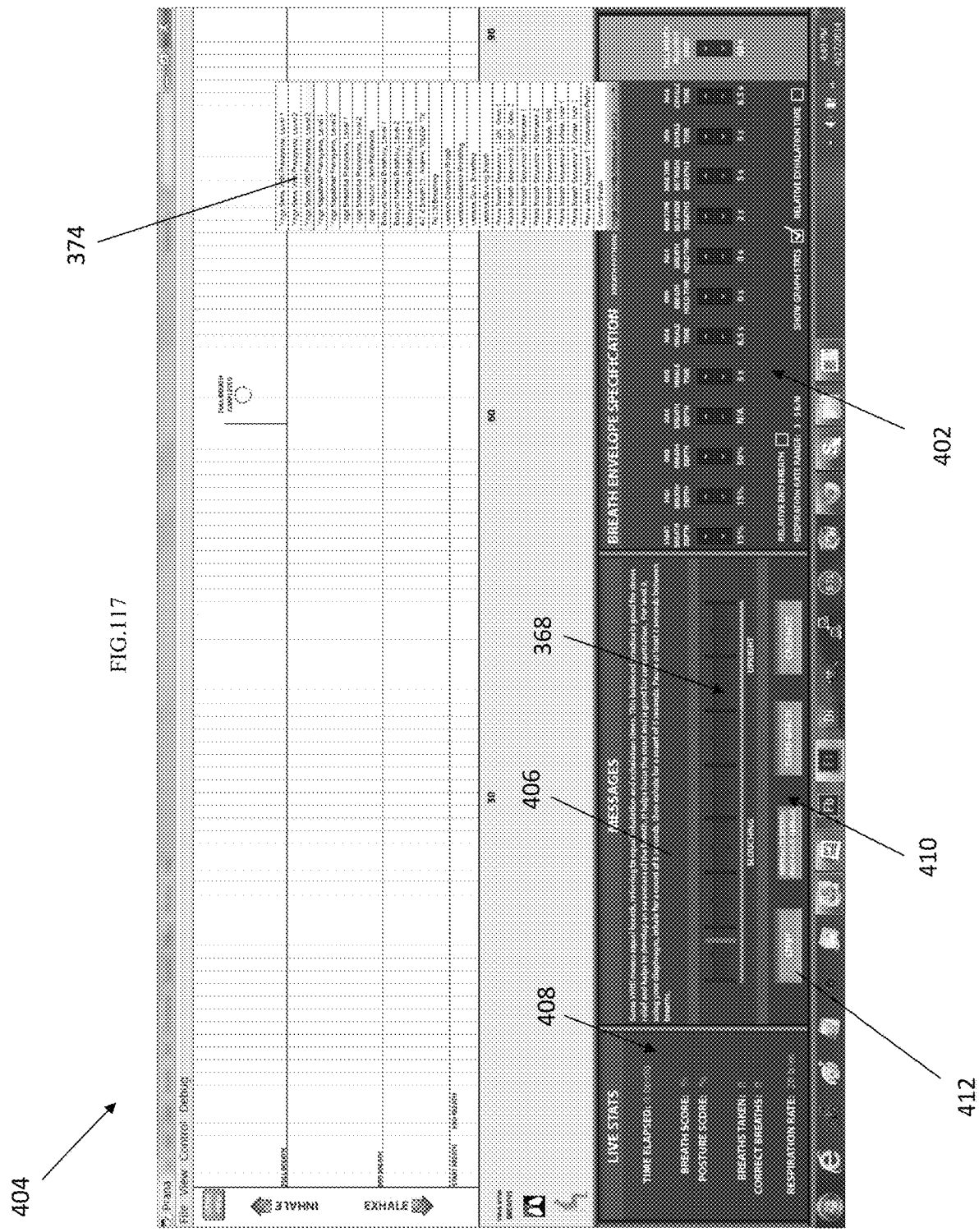

FIG. 117 is an exemplary screenshot showing a popup library of selectable breath patterns.

Figure 117A:
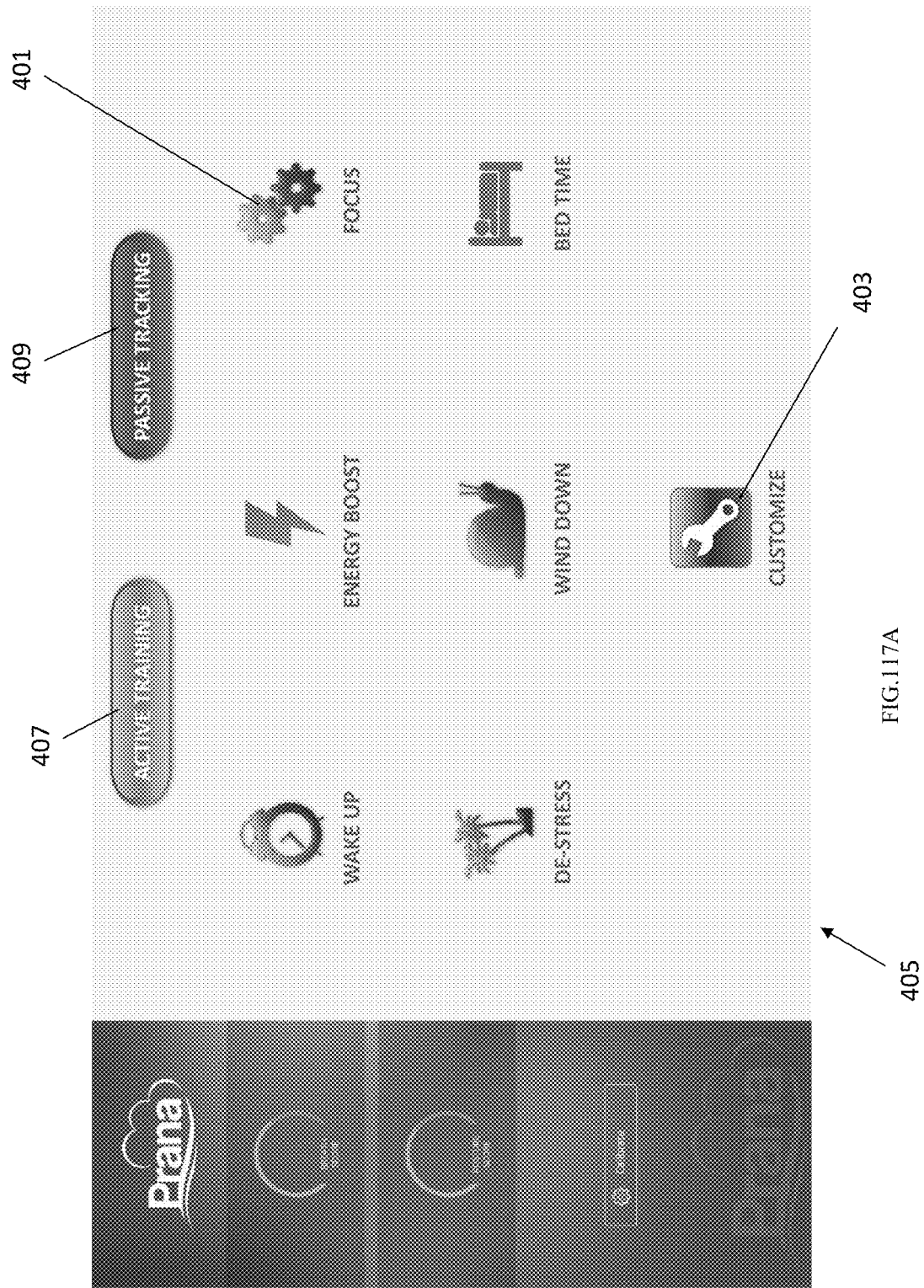

FIG. 117A is an exemplary screenshot showing an active training selection screen.

Figure 117B:
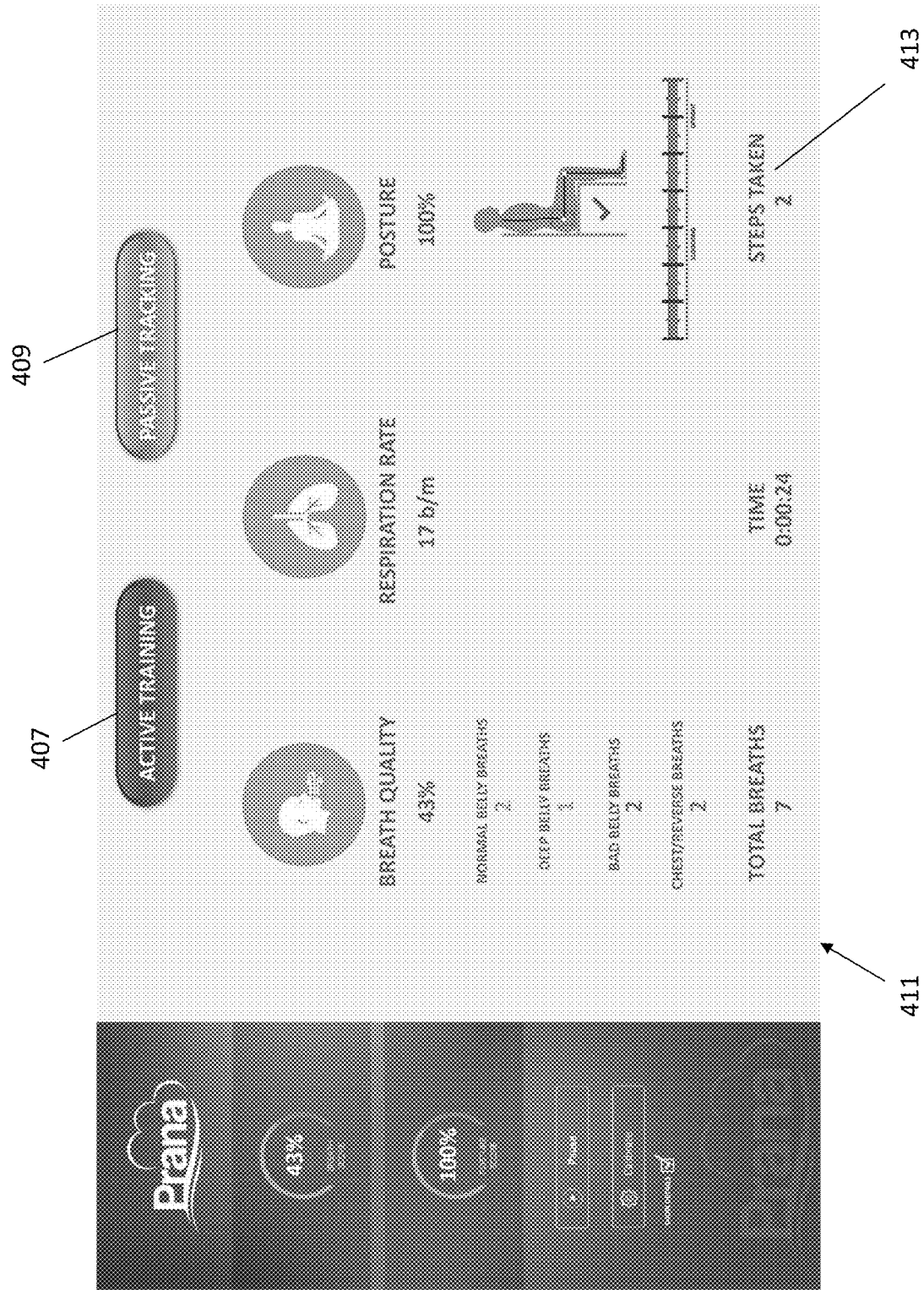

FIG. 117B is an exemplary screenshot showing a passive tracking dashboard.

Figure 118:
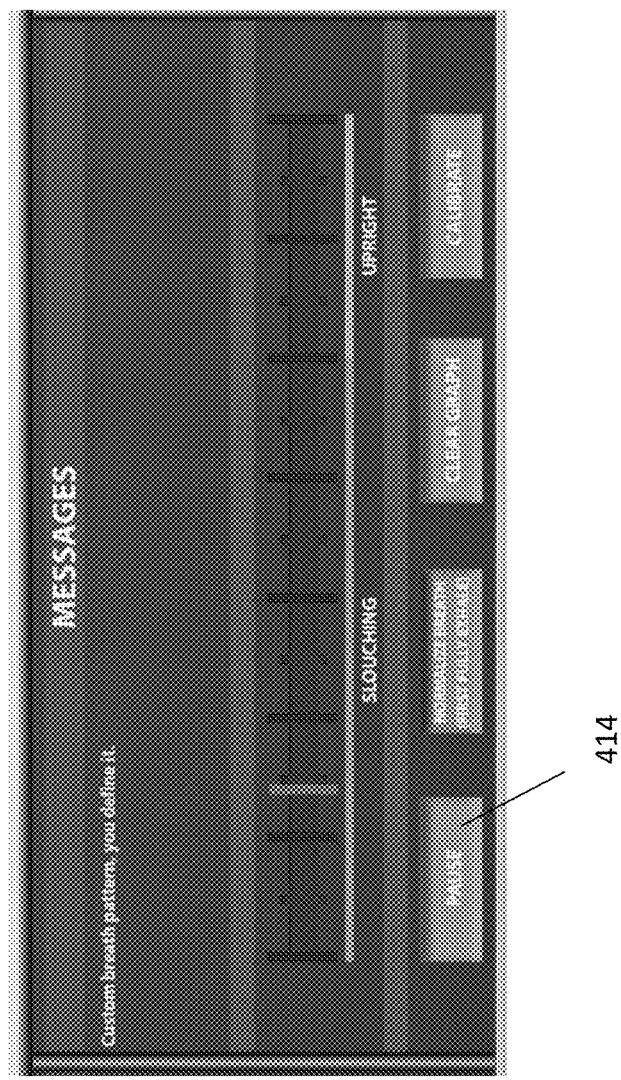

FIG. 118 is an exemplary screenshot showing a pause button.

Figure 119:
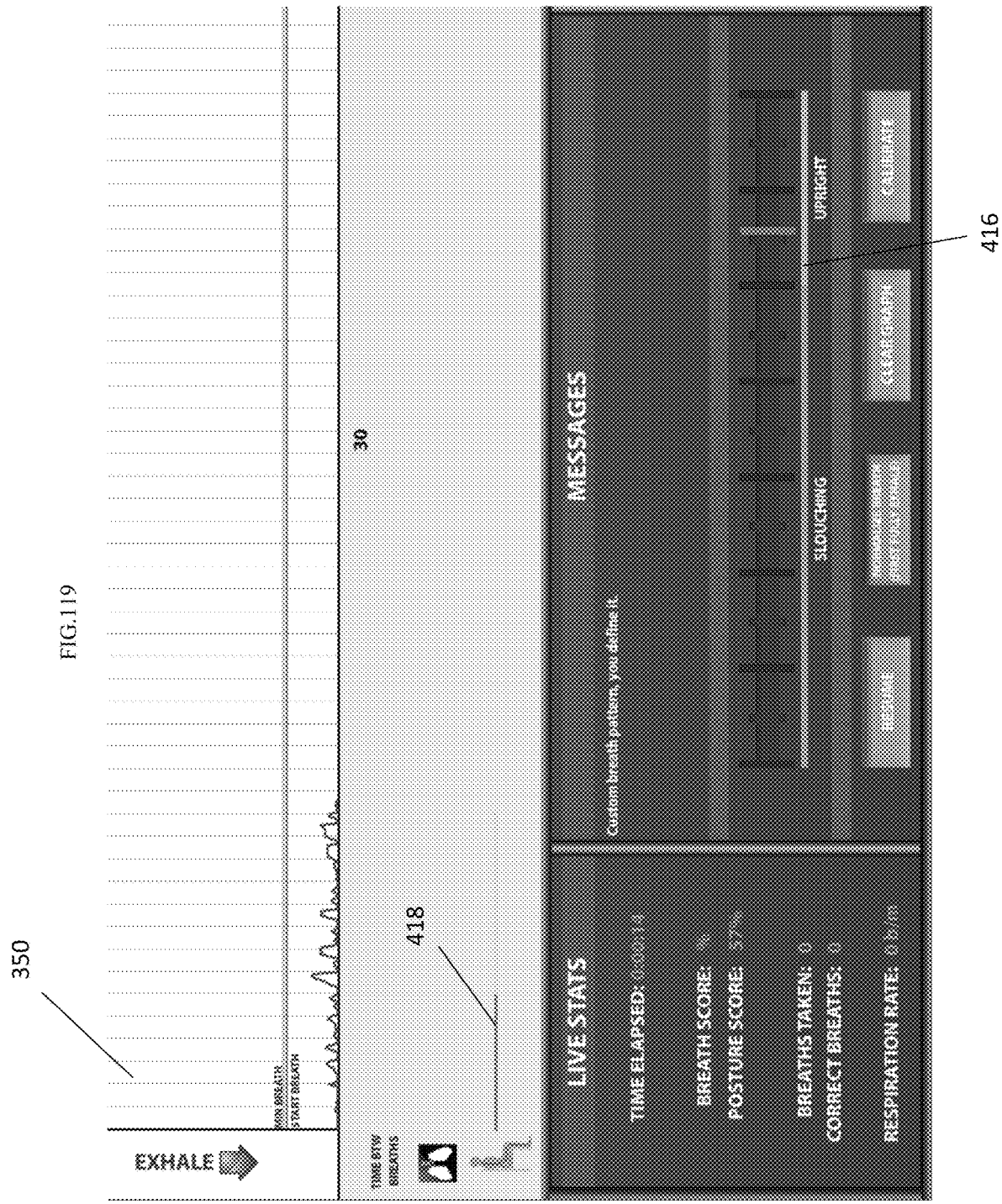

FIG. 119 is an exemplary screenshot showing a posture indicator on a breath/posture zone chart above an upright threshold.

FIG. 120 is an exemplary screenshot of a reverse breath indicator.

FIG. 121 is an exemplary screenshot when the filtered breath signal passes above the start breath threshold line.

Figure 122:
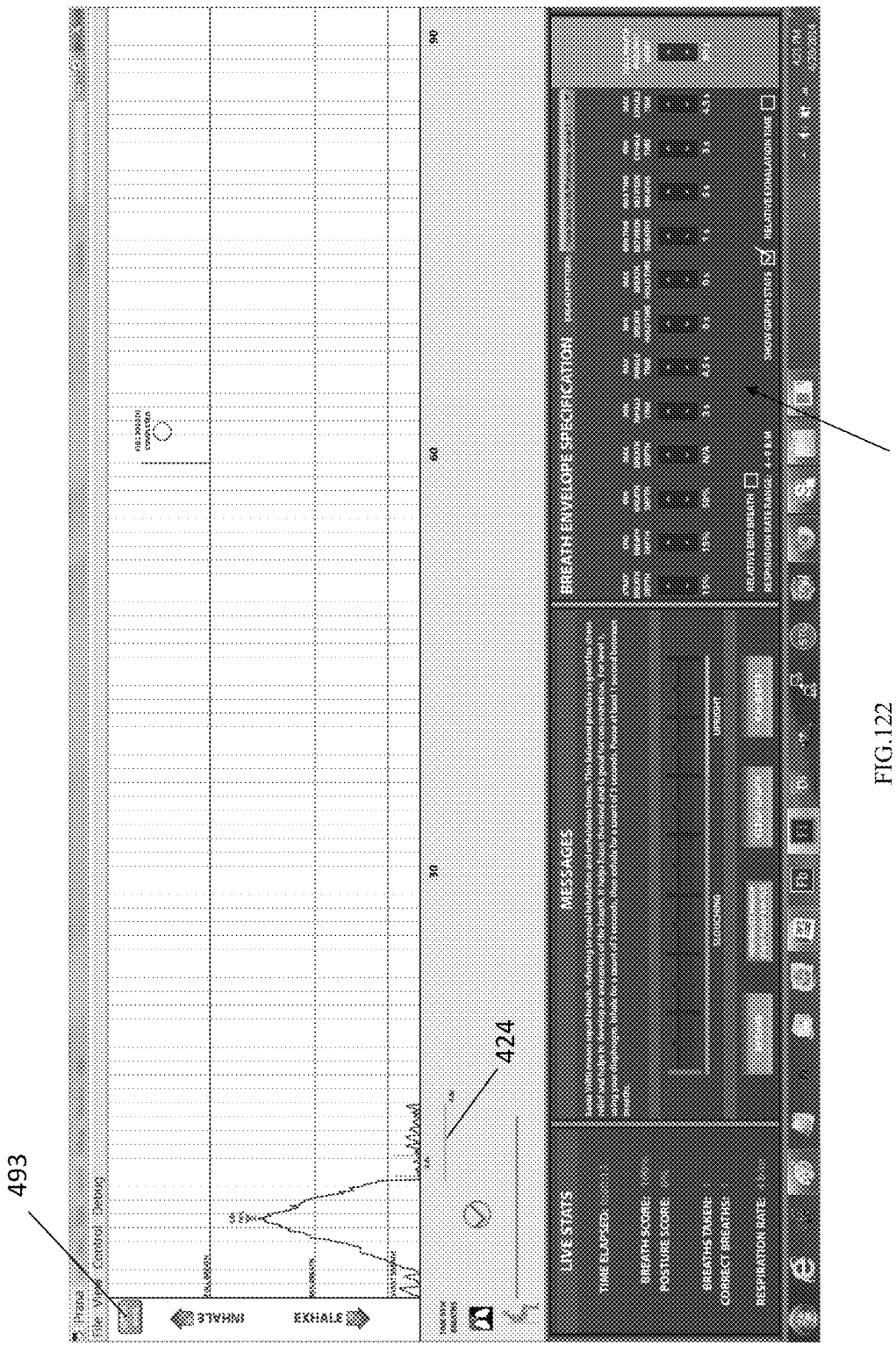

FIG. 122 is an exemplary screenshot where 4.8 seconds has passed since the projected or expected end of the last breath.

Figure 123:
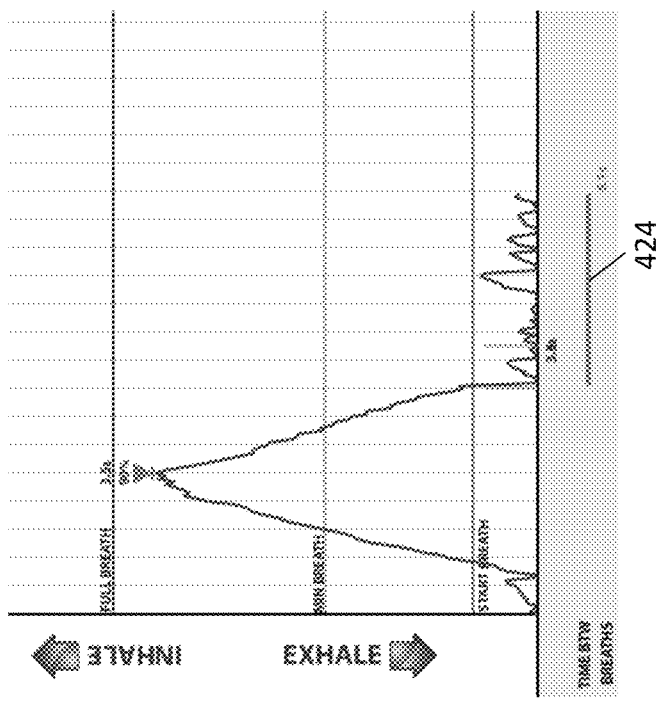

FIG. 123 is an exemplary screenshot showing an inhale status indicator in an overall positive evaluation state.

Figure 124:
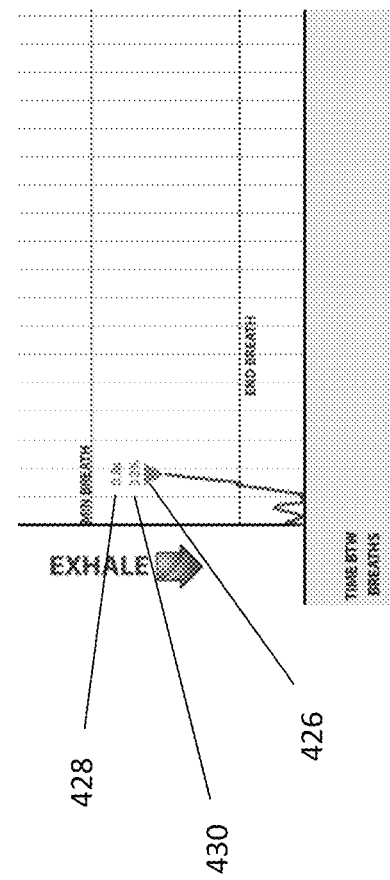

FIG. 124 is an exemplary screenshot of an inhale status indicator position near the apex of the filtered breath signal on the timeline.

Figure 125:
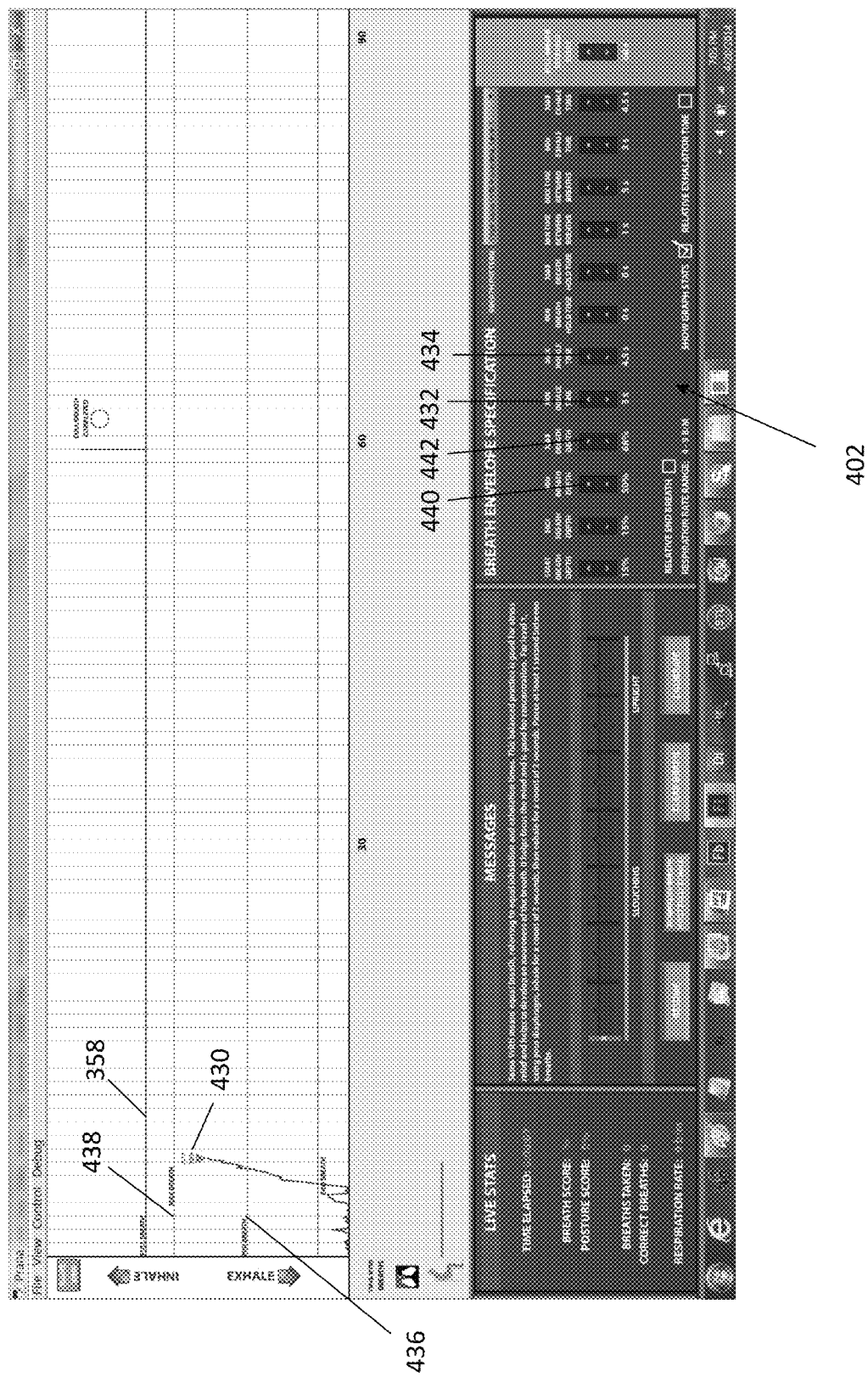

FIG. 125 is an exemplary screenshot of an inhale time in a negative evaluation state.

Figure 126:
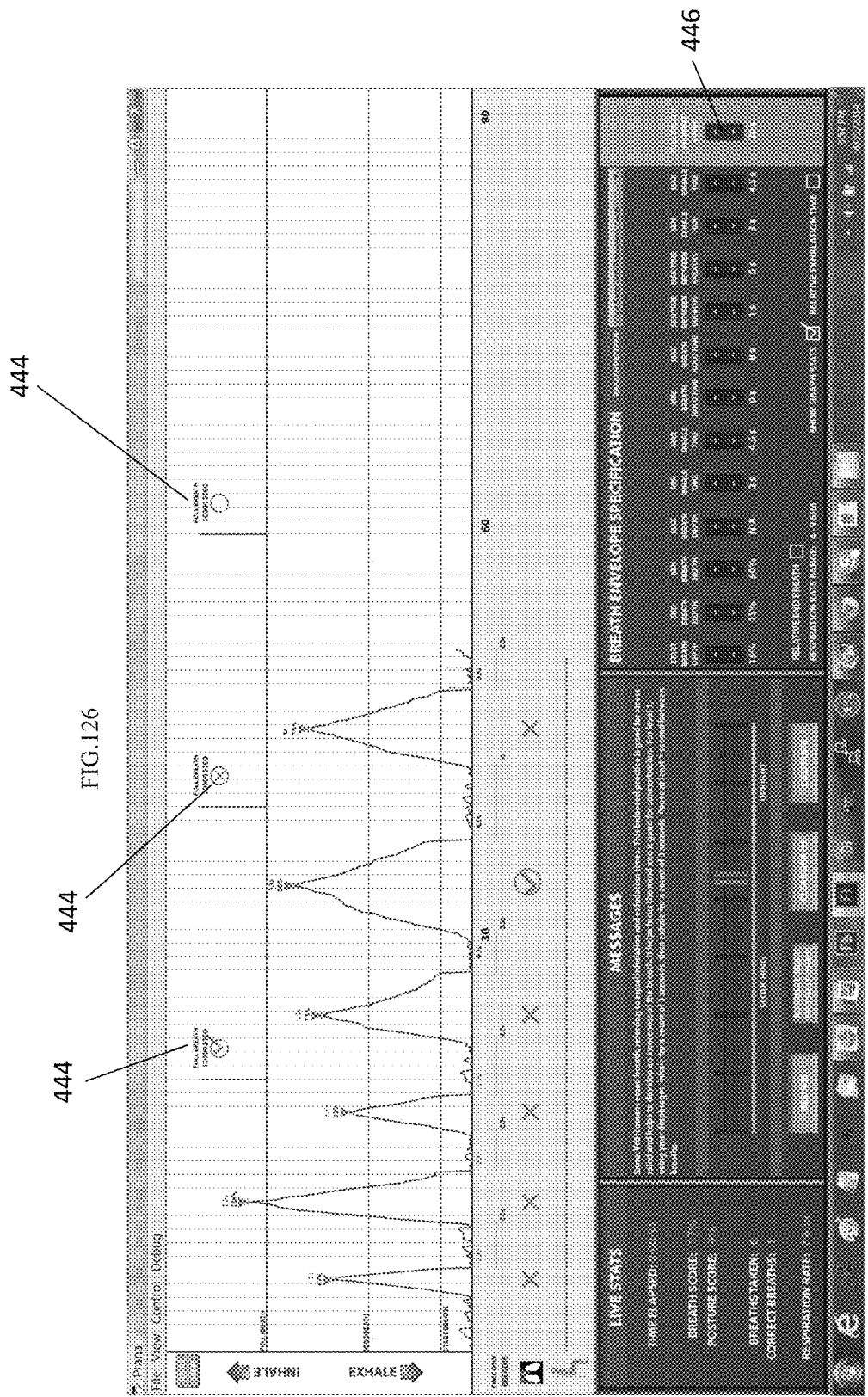

FIG. 126 is an exemplary screenshot of several full breath indicators set against the timeline.

FIG. 127 is an exemplary screenshot of a peakOfBreath icon near the detected peak in the filtered breath signal.

Figure 128:
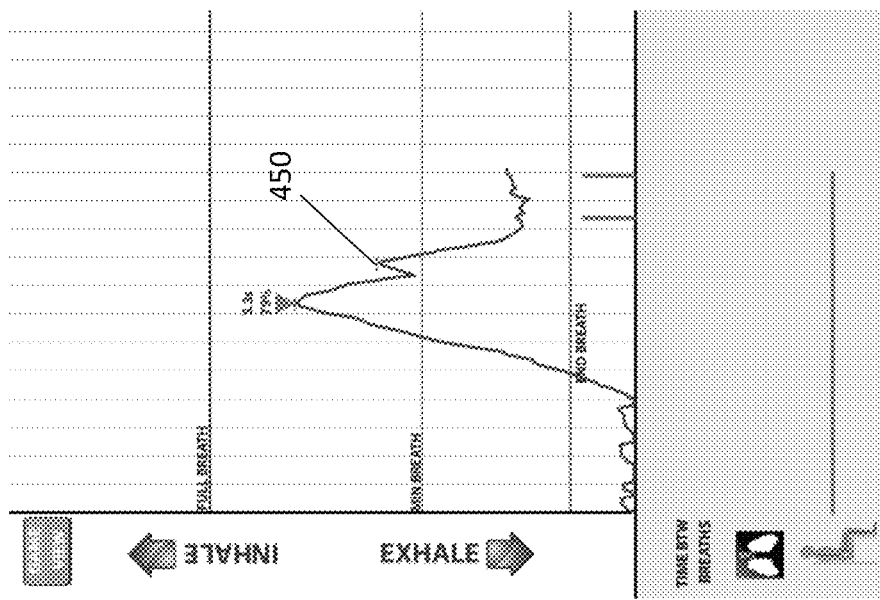

FIG. 128 is an exemplary screenshot of a peak labeled with a stagger indicator.

Figure 129:
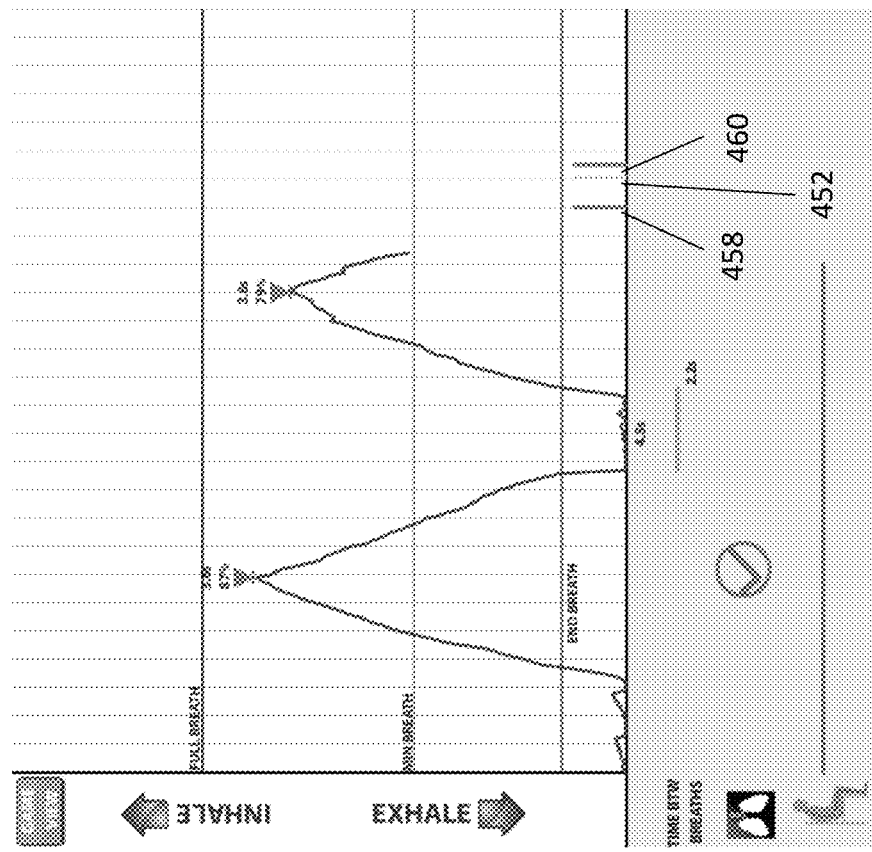

FIG. 129 is an exemplary screenshot of an endBreathTarget1 and an endBreathTarget2 on the timeline.

Figures 130, 131:
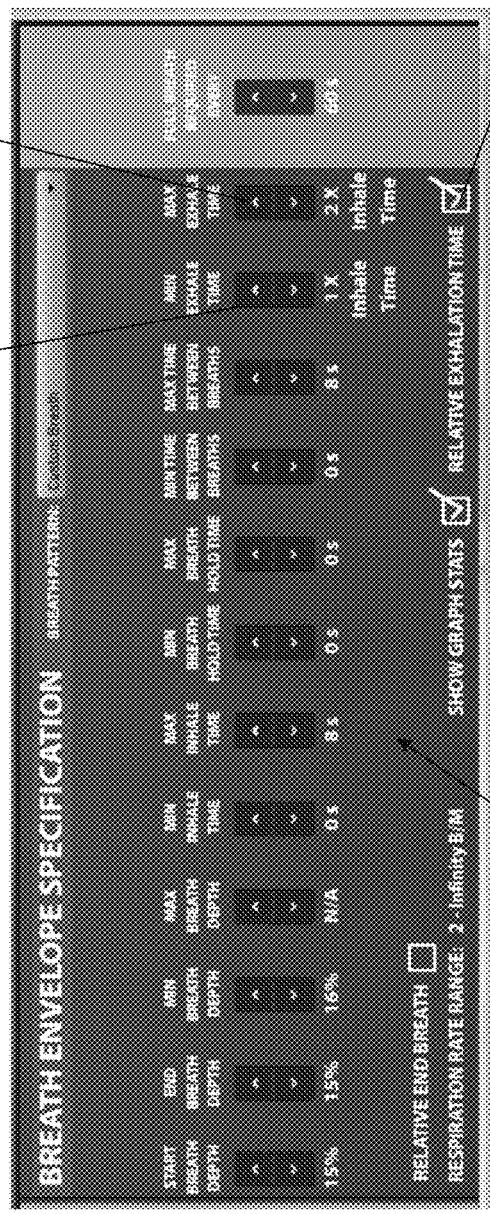

FIG. 130 is an exemplary screenshot of a breath parameters control panel with Relative Exhalation Time mode enabled.

FIG. 131 is an exemplary screenshot of a breath parameters control panel with Relative Exhalation Time mode disabled.

Figure 132:
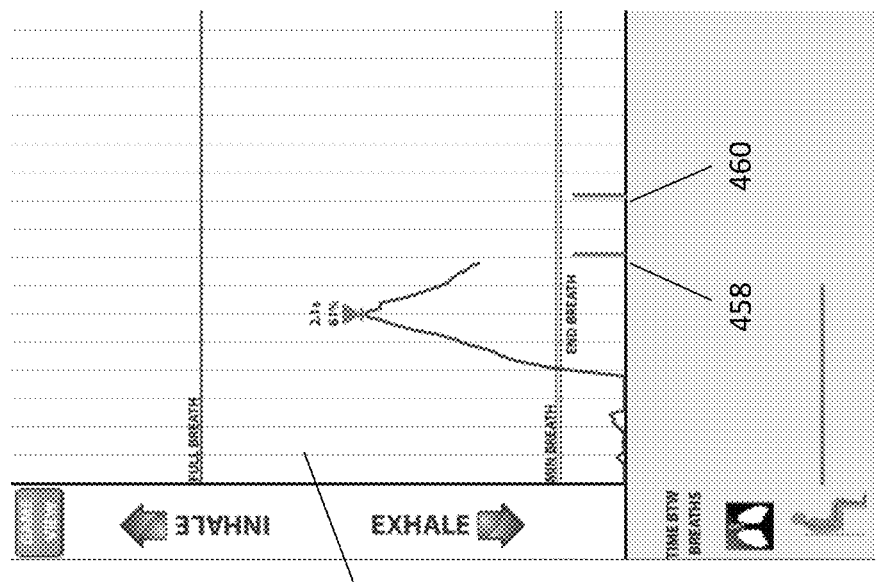

FIG. 132 is an exemplary screenshot showing end breath targets defining an acceptable range for exhalation.

Figure 133:
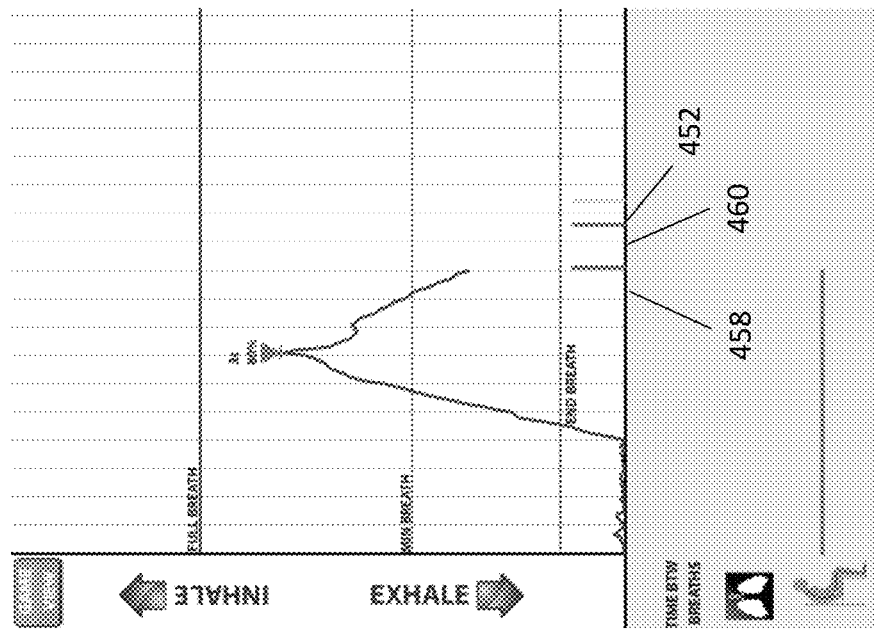

FIG. 133 is an exemplary screenshot showing end breath targets defining an acceptable range for exhalation.

Figure 134:
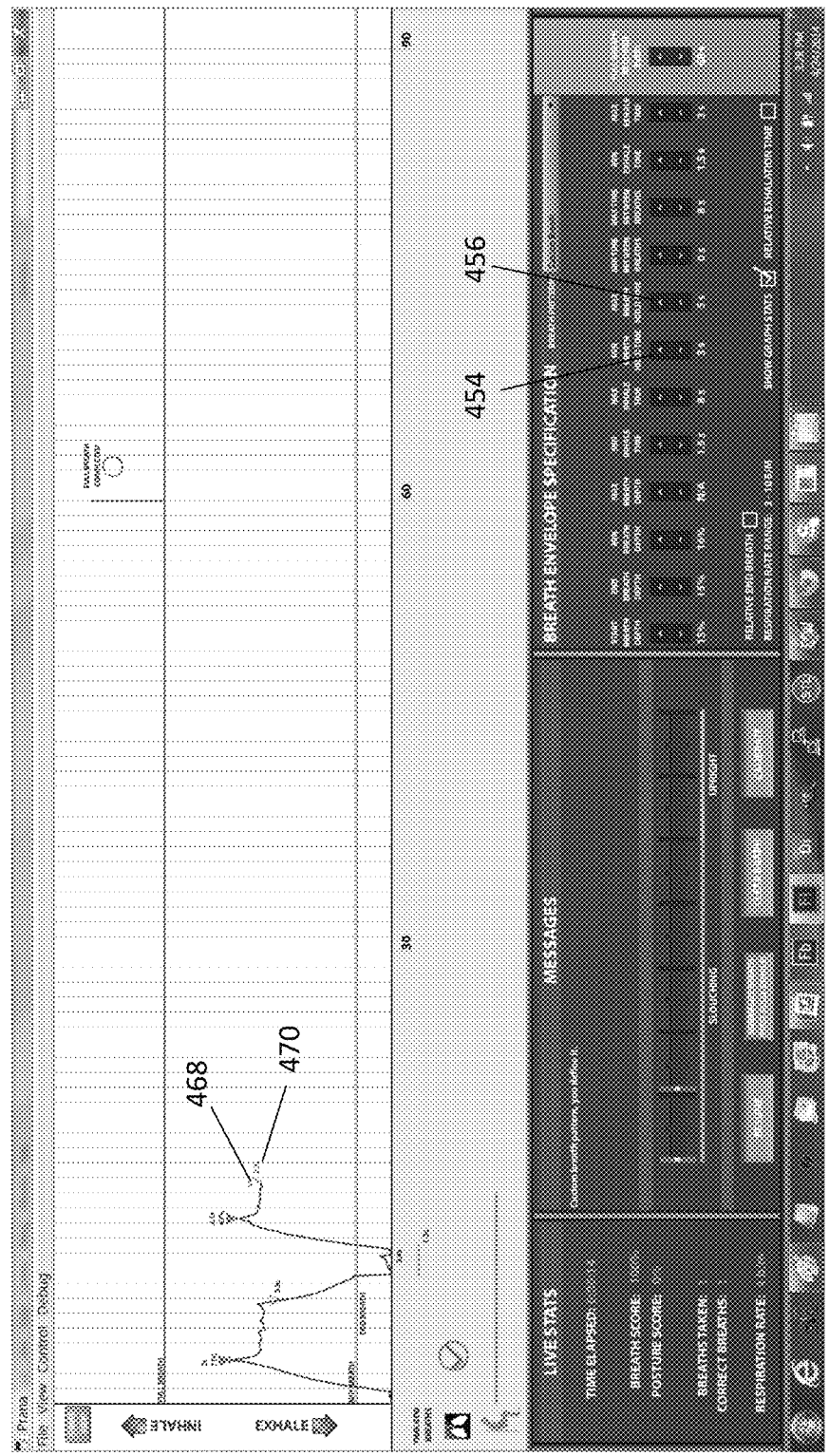

FIG. 134 is an exemplary screenshot of a breath hold indicator on the filtered breath signal, and a breath parameters control panel with Min Breath Hold Time buttons and Max Breath Hold Time buttons.

Figure 135:
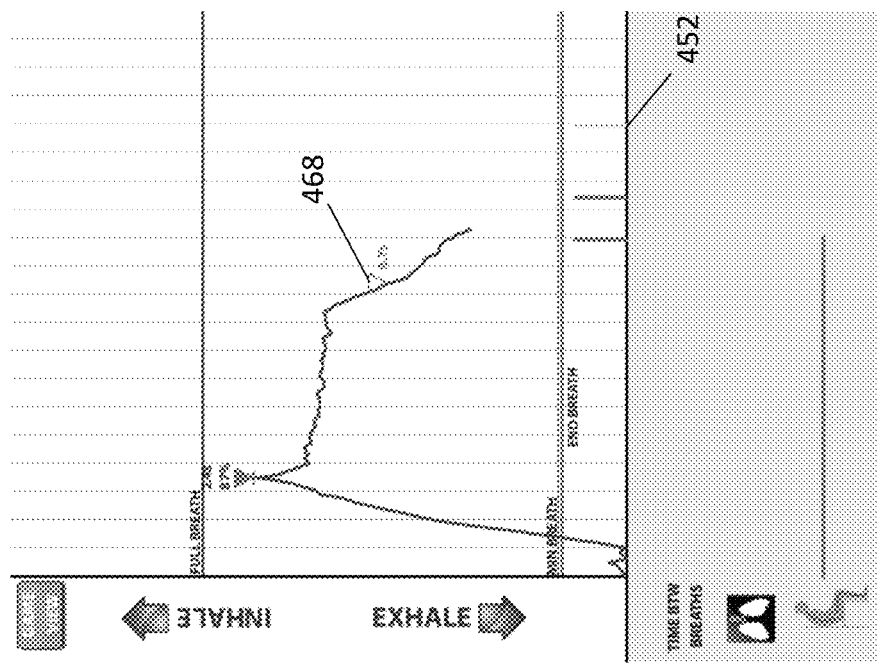

FIG. 135 is an exemplary screenshot where the filtered breath signal has fallen below ¾ the height of the filtered breath signal when the breath holding began on the timeline, ending the breath holding phase.

Figure 136:
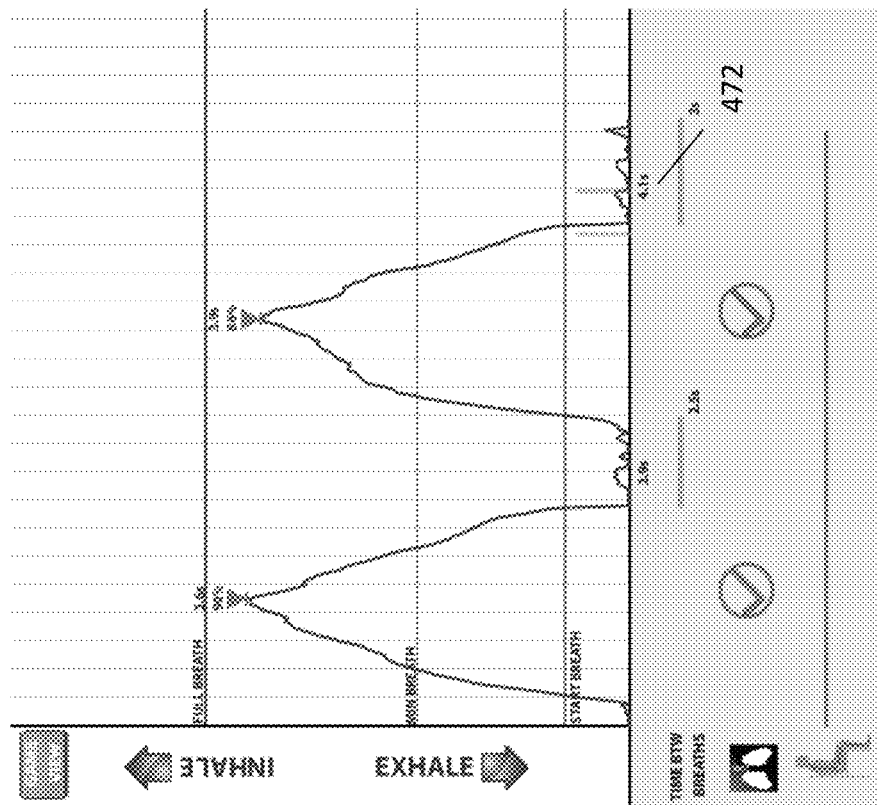

FIG. 136 is an exemplary screenshot showing the filtered breath signal between endBreathTarget1 and endBreathTarget2 when the filtered breath signal reaches the end breath threshold line.

Figure 137:
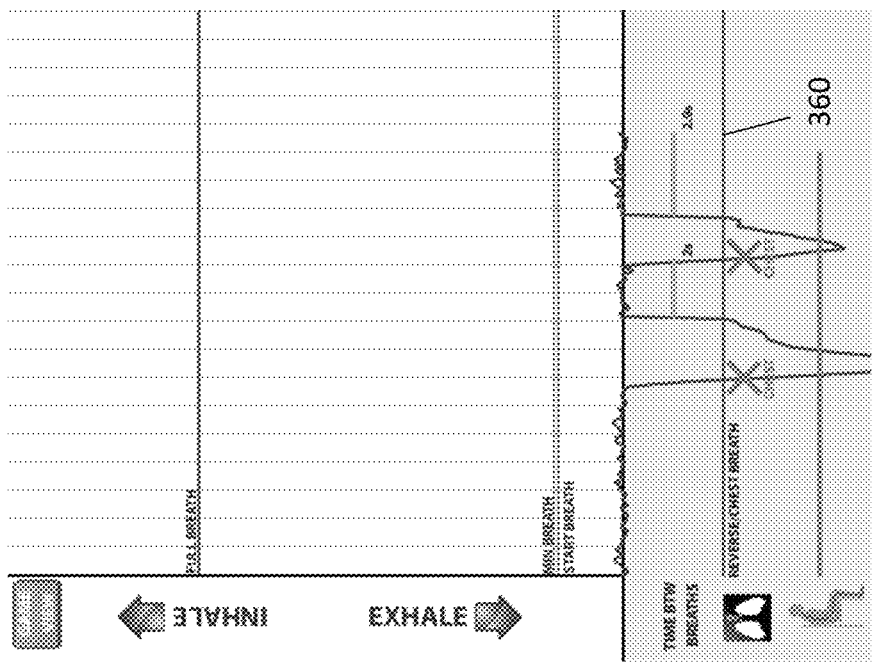

FIG. 137 is an exemplary screenshot showing the filtered breath signal having risen above the end of reverse breath threshold line.

Figure 138:
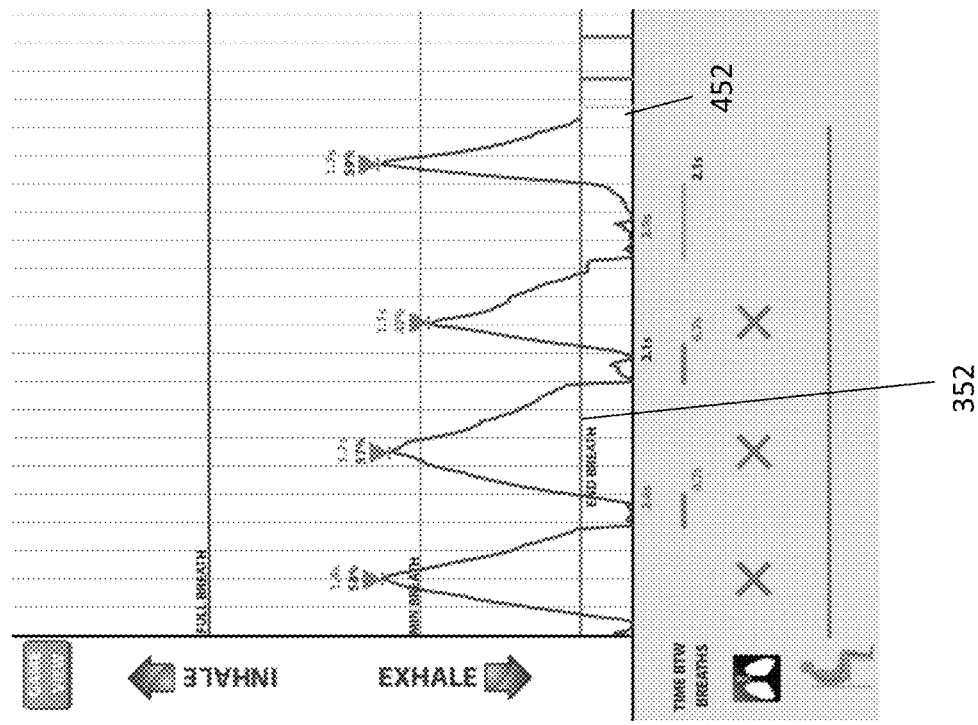

FIG. 138 is an exemplary screenshot showing a gateTarget prior to endBreathTarget1.

Figure 139:
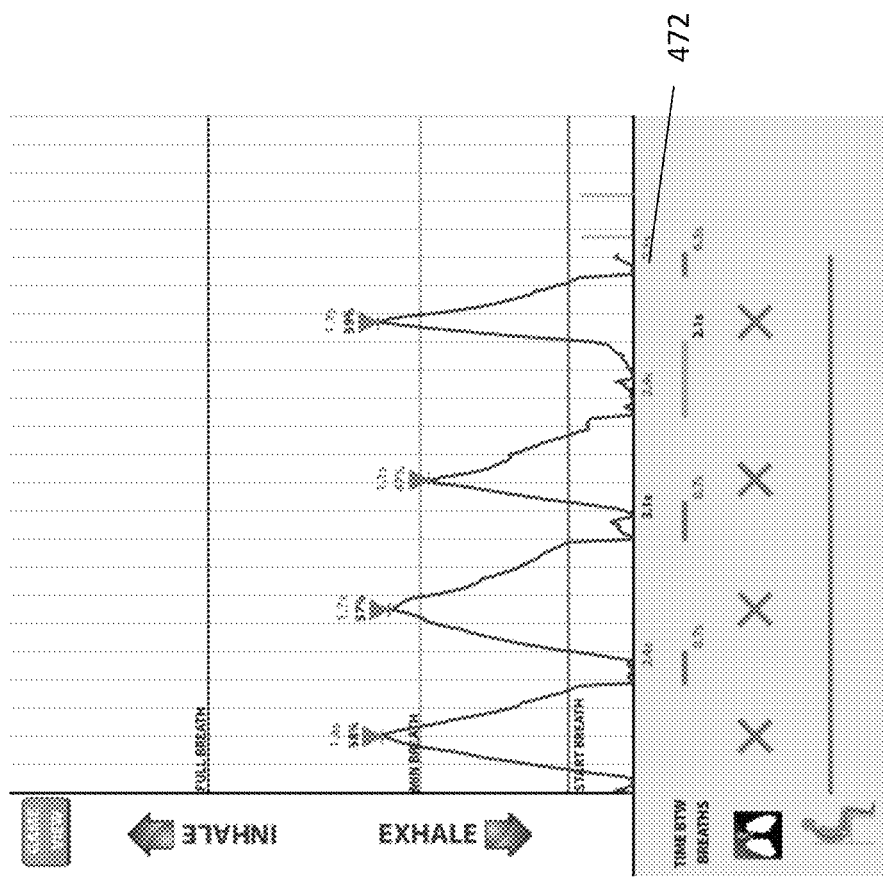

FIG. 139 is an exemplary screenshot after the filtered breath signal crosses the end of breath threshold, with gateTarget 452 then being hidden.

Figure 140:
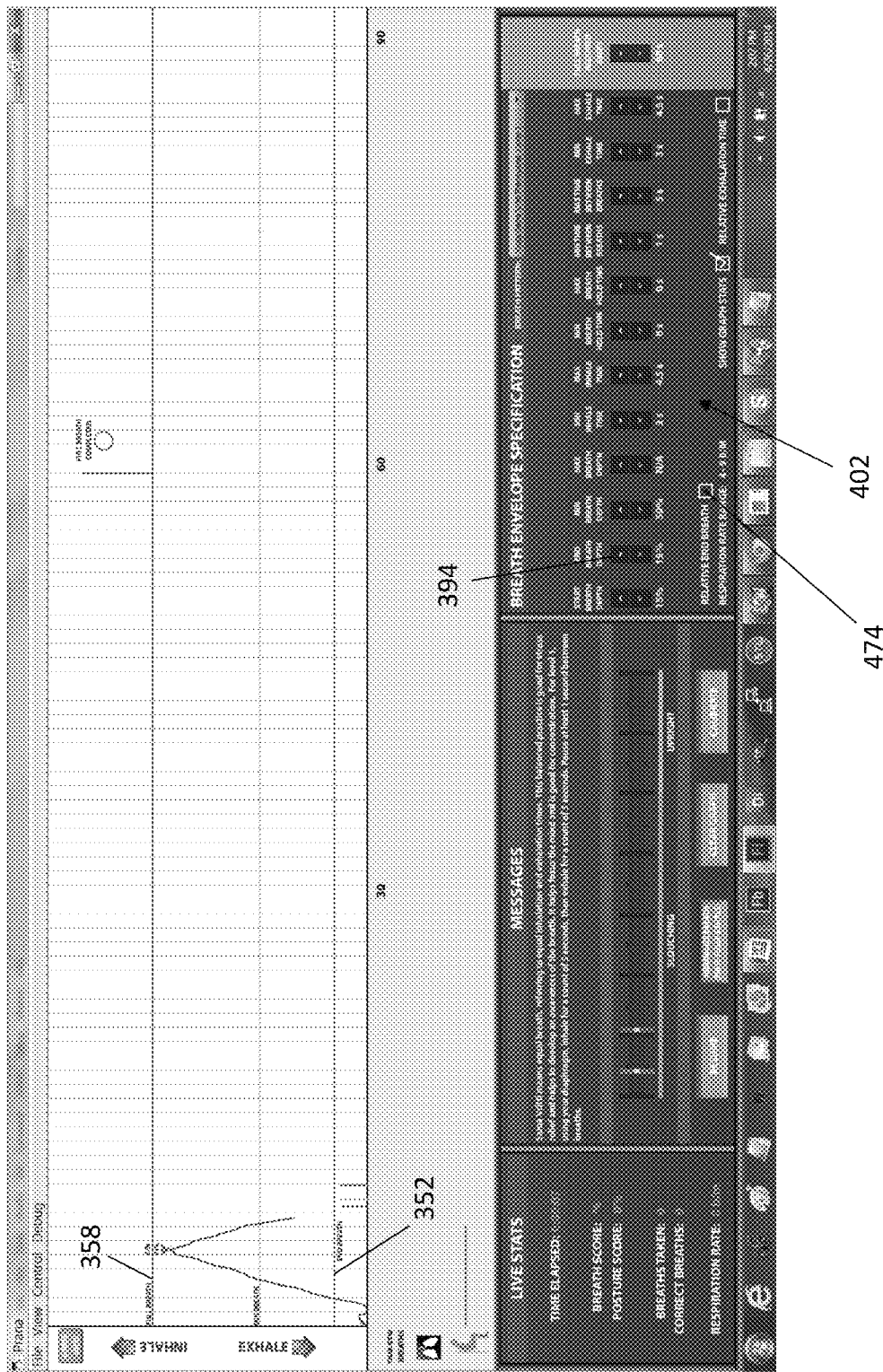

FIG. 140 is an exemplary screenshot showing a relative end breath checkbox in breath parameters control panel.

Figure 141:
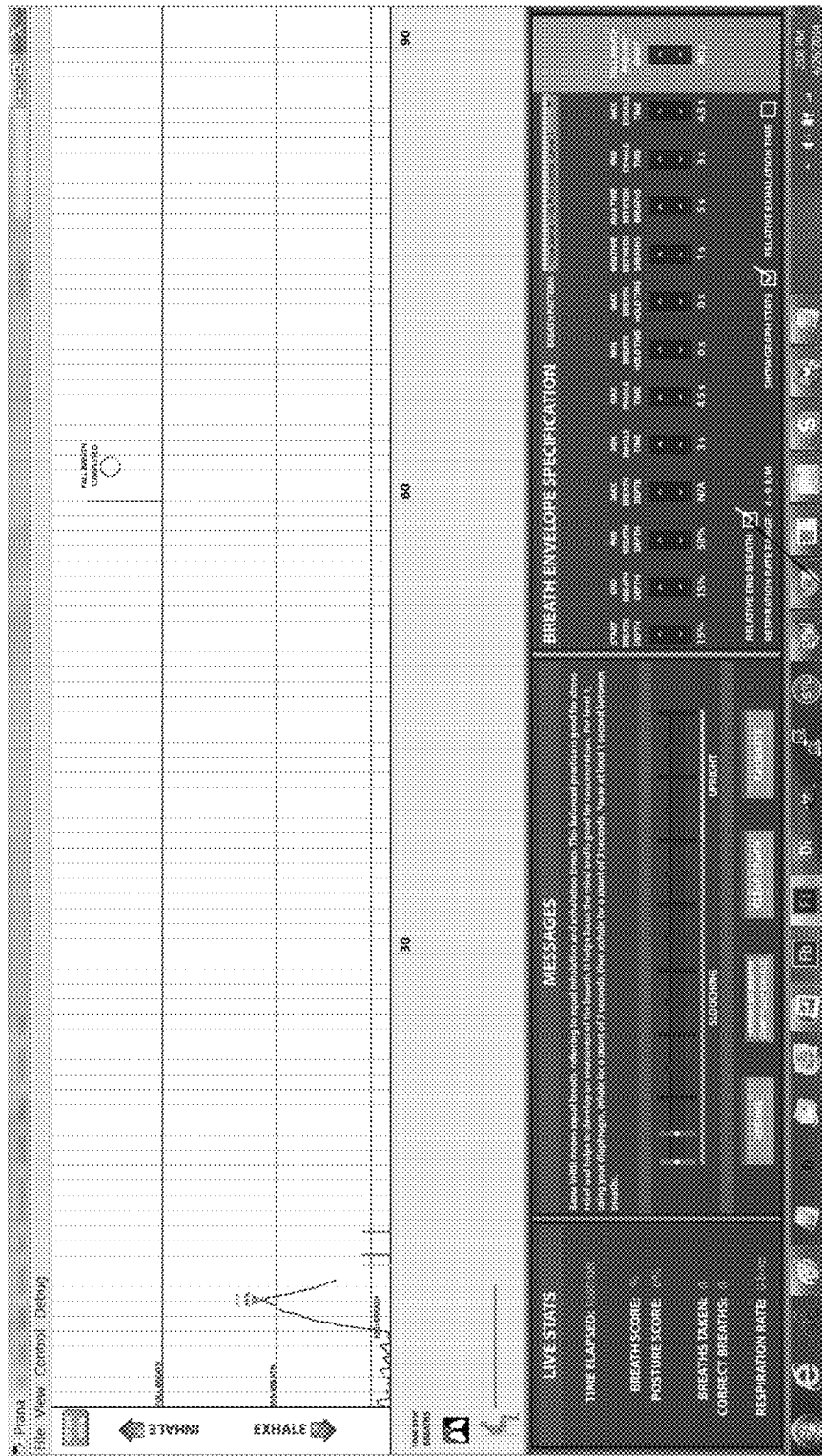

FIG. 141 is an exemplary screenshot where a relative end breath checkbox is selected causing the height of end breath threshold line to be dynamically set relative to the peak of the inhalation.

Figure 142:
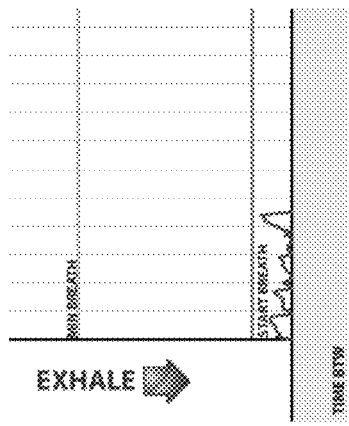

FIG. 142 is an exemplary screenshot before the start of a diaphragmatic breath with the filtered breath signal below start breath threshold line, and the end breath threshold line hidden.

Figure 143:
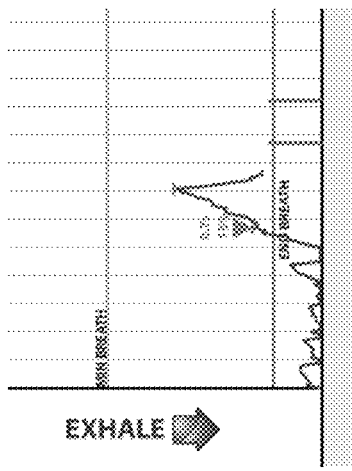

FIG. 143 is an exemplary screenshot after a diaphragmatic breath has started, with start breath threshold line hidden and end breath threshold line made visible.

Figure 144:
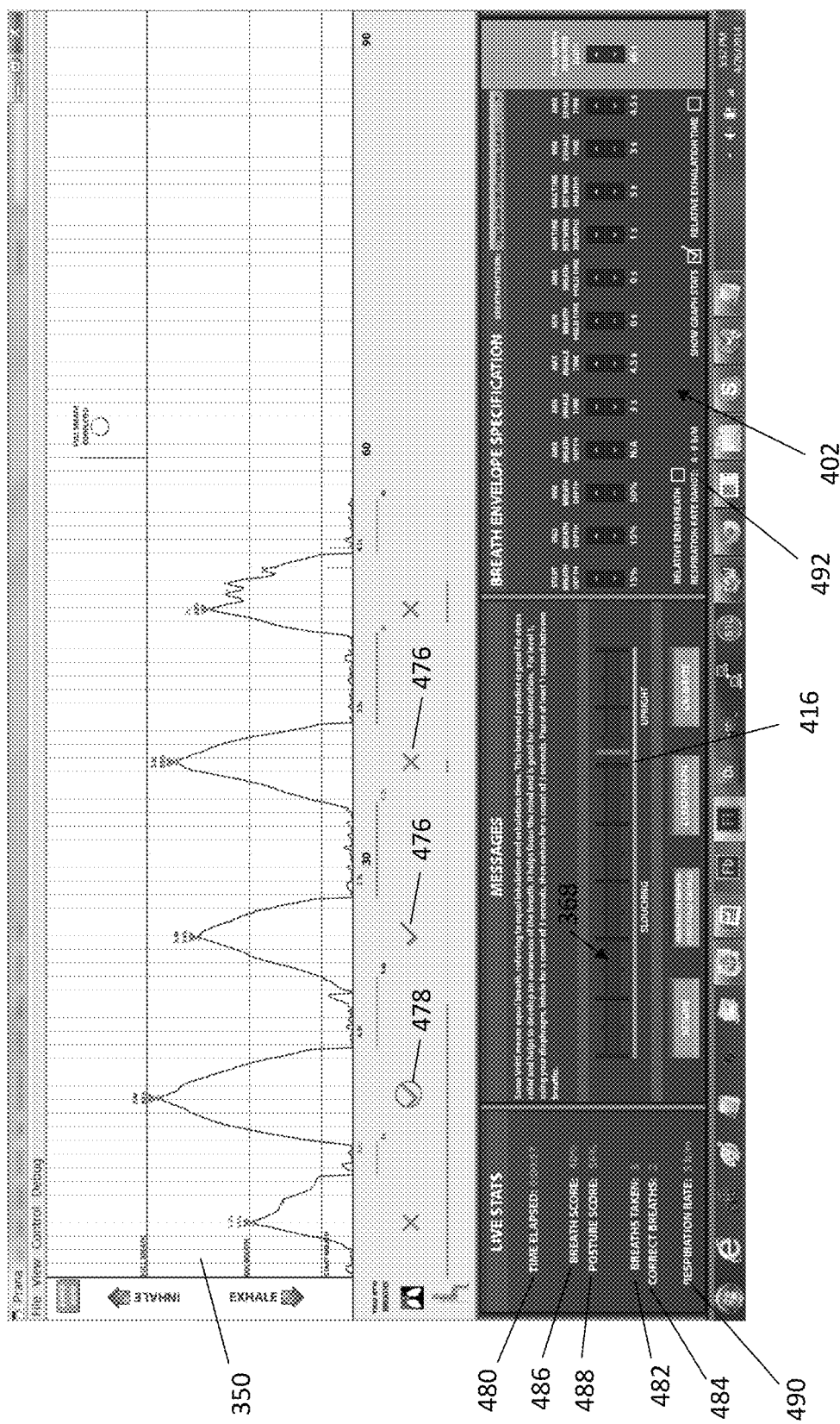

FIG. 144 is an exemplary screenshot of several breath evaluation indicators.

Figure 145:
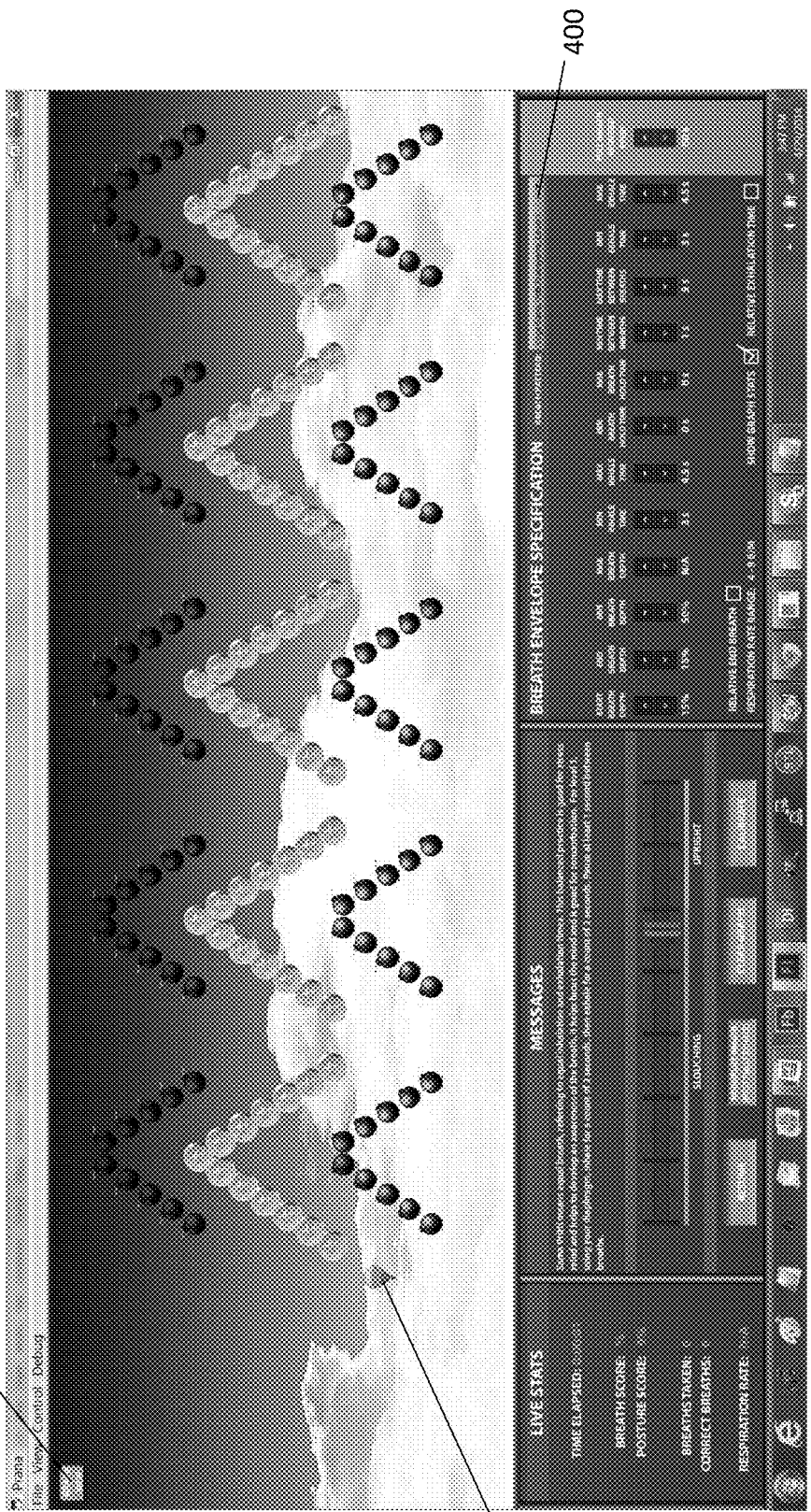

FIG. 145 is an exemplary screenshot of the start of a game session with the Sama Vritti Pranayama, Level 1 breath pattern selected.

Figure 145A:
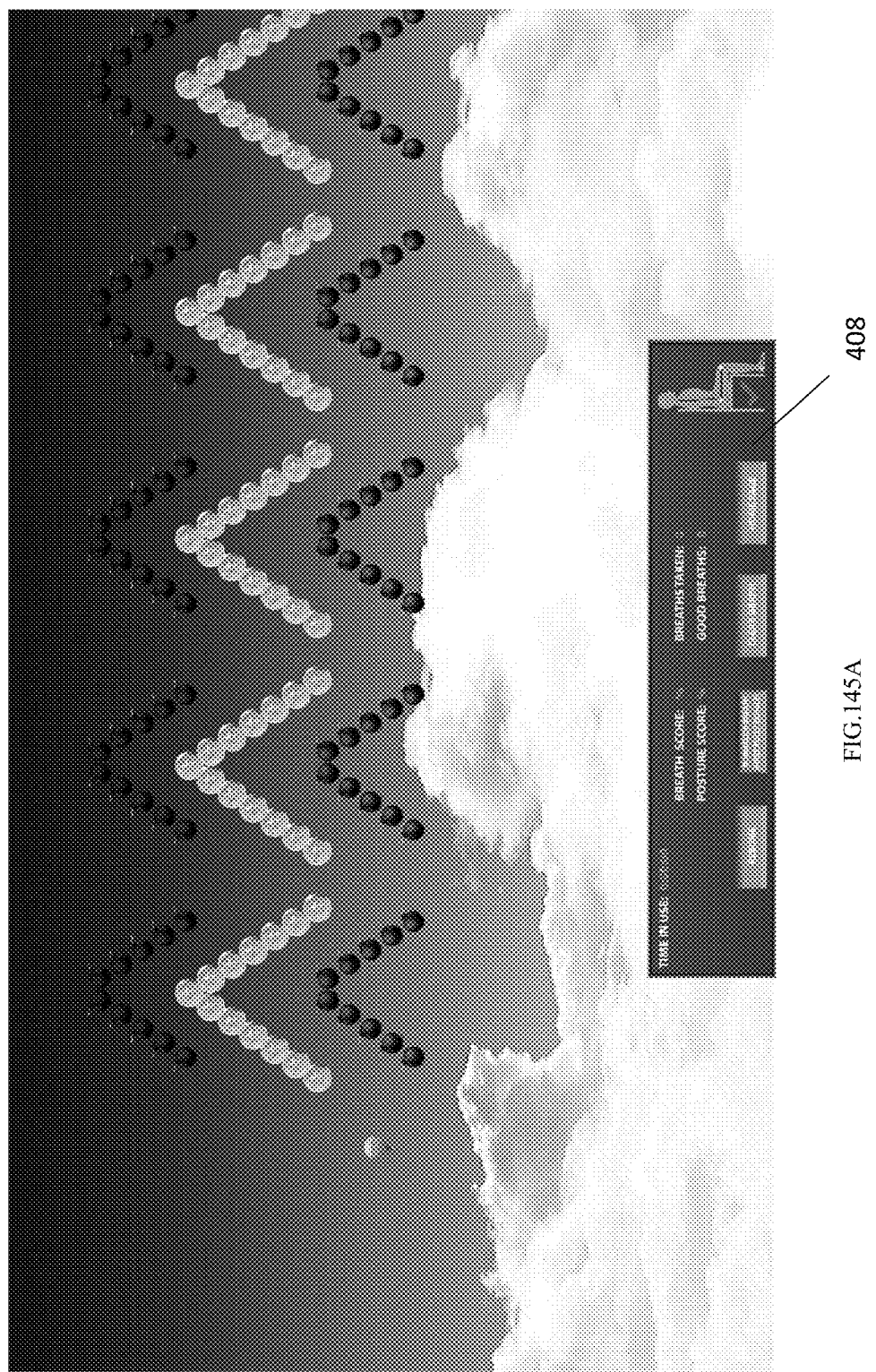

FIG. 145A is an exemplary screenshot of a simplified view of the game mode.

Figure 146:
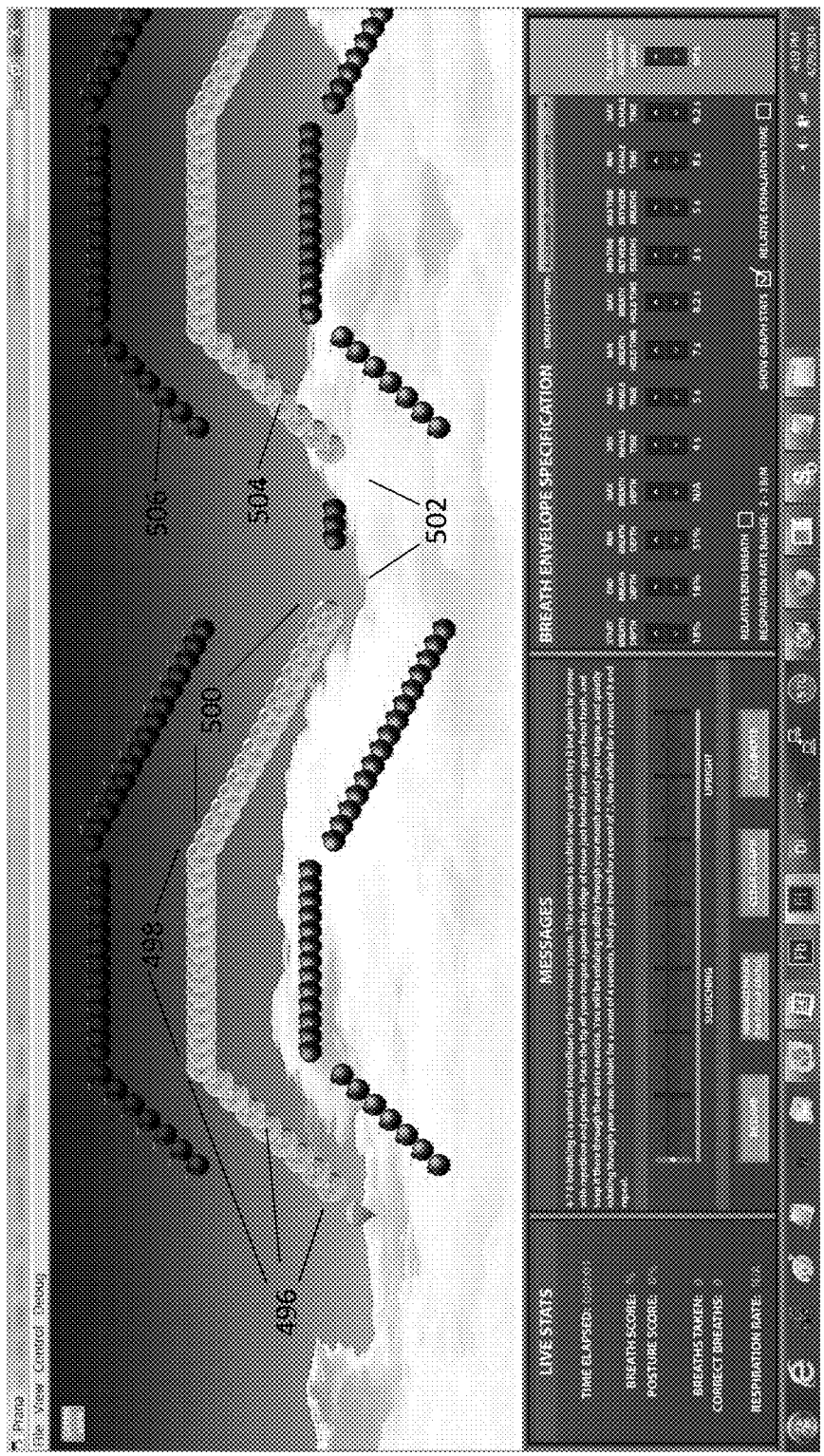

FIG. 146 is an exemplary screenshot of the start of a game session showing inhalation, retention, and exhalation zones, with a 4-7-8 breath pattern selected.

Figure 147:
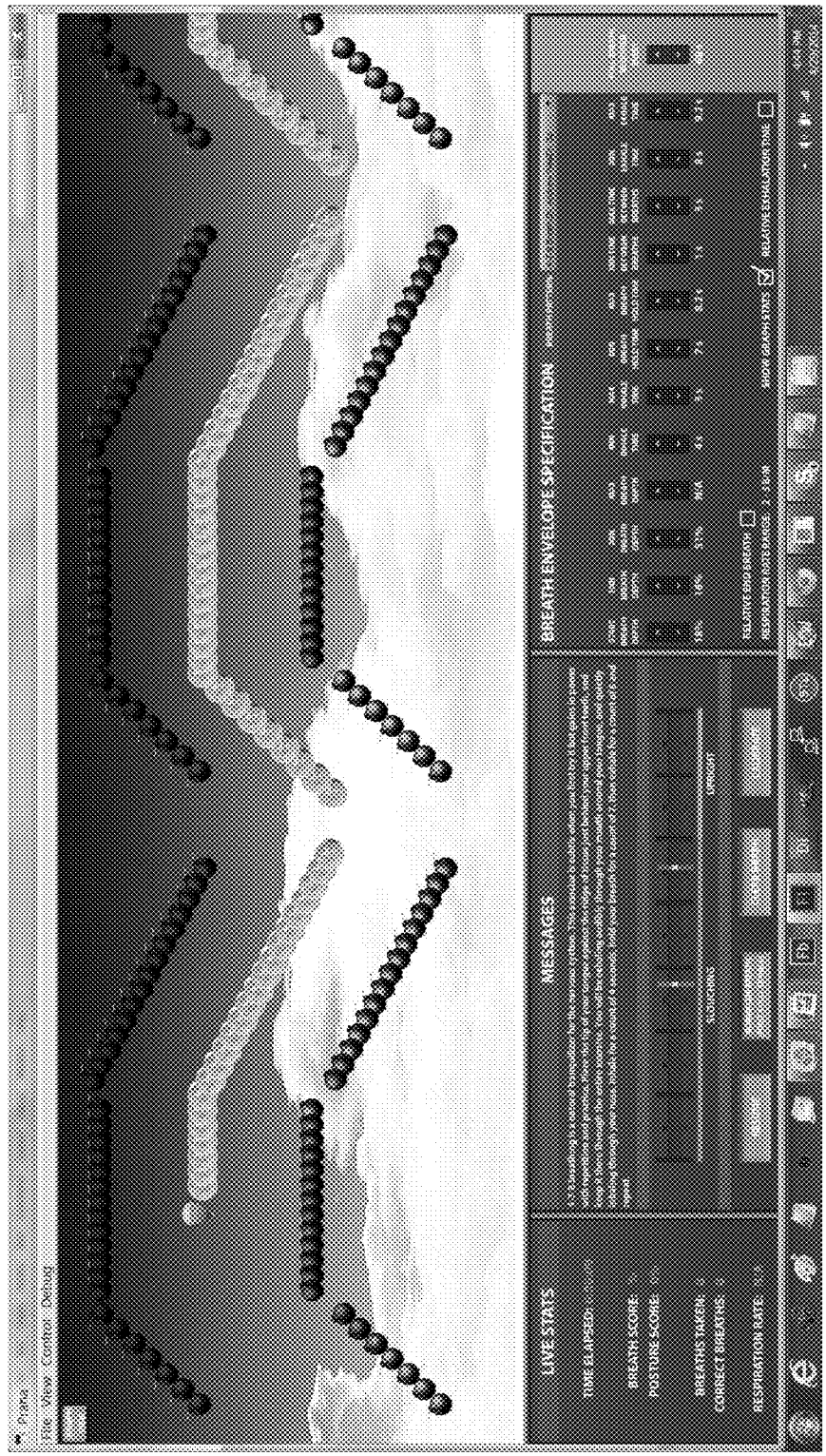

FIG. 147 is an exemplary screenshot of a game session in progress, approximately half-way through the retention after inhalation phase of the first breath for a 4-7-8 breath pattern.

Figure 148:
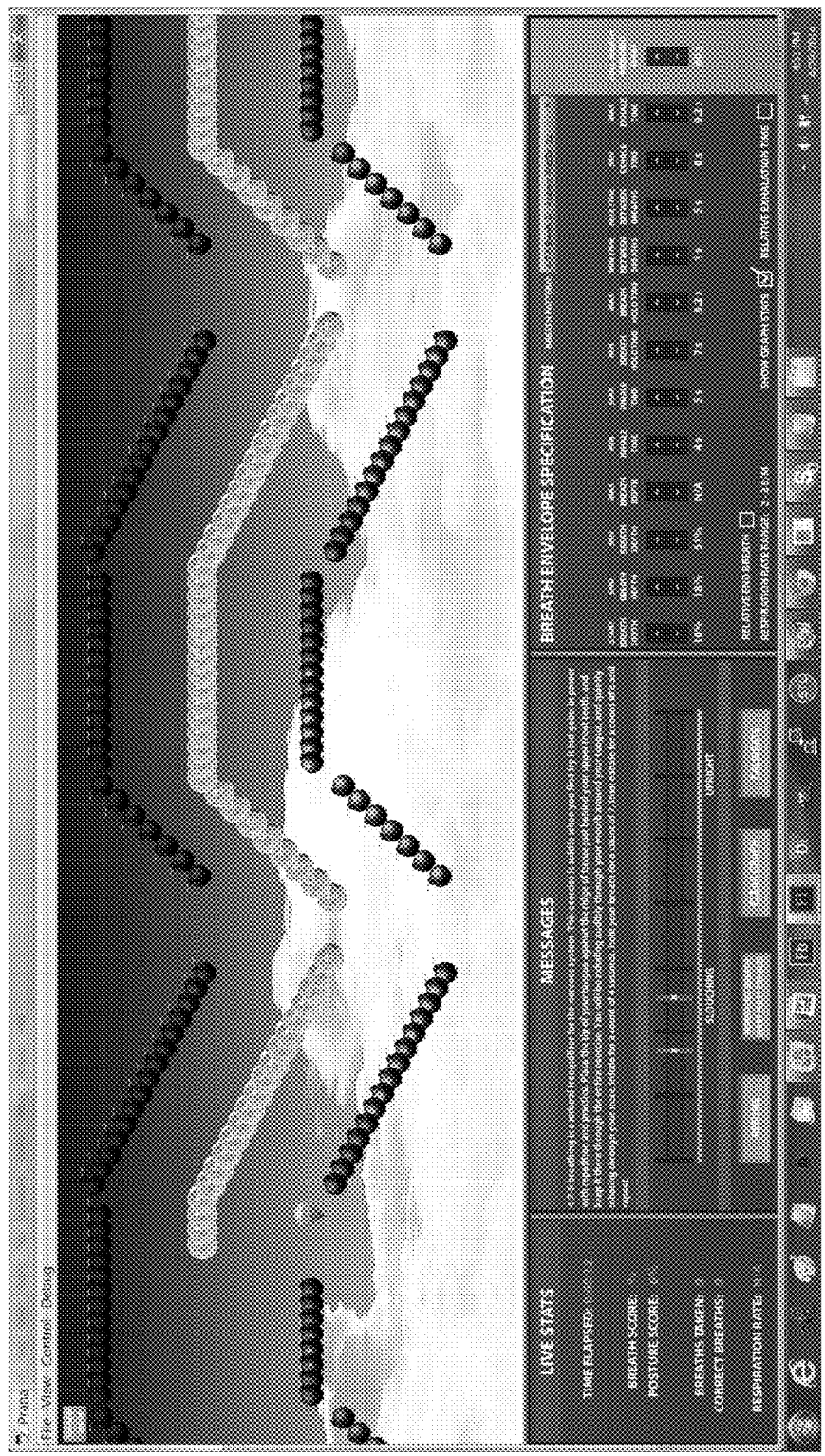

FIG. 148 is an exemplary screenshot of a game session in progress with a breath level game element having collided with several obstacle objects in a 4-7-8 breath pattern.

Figure 149:
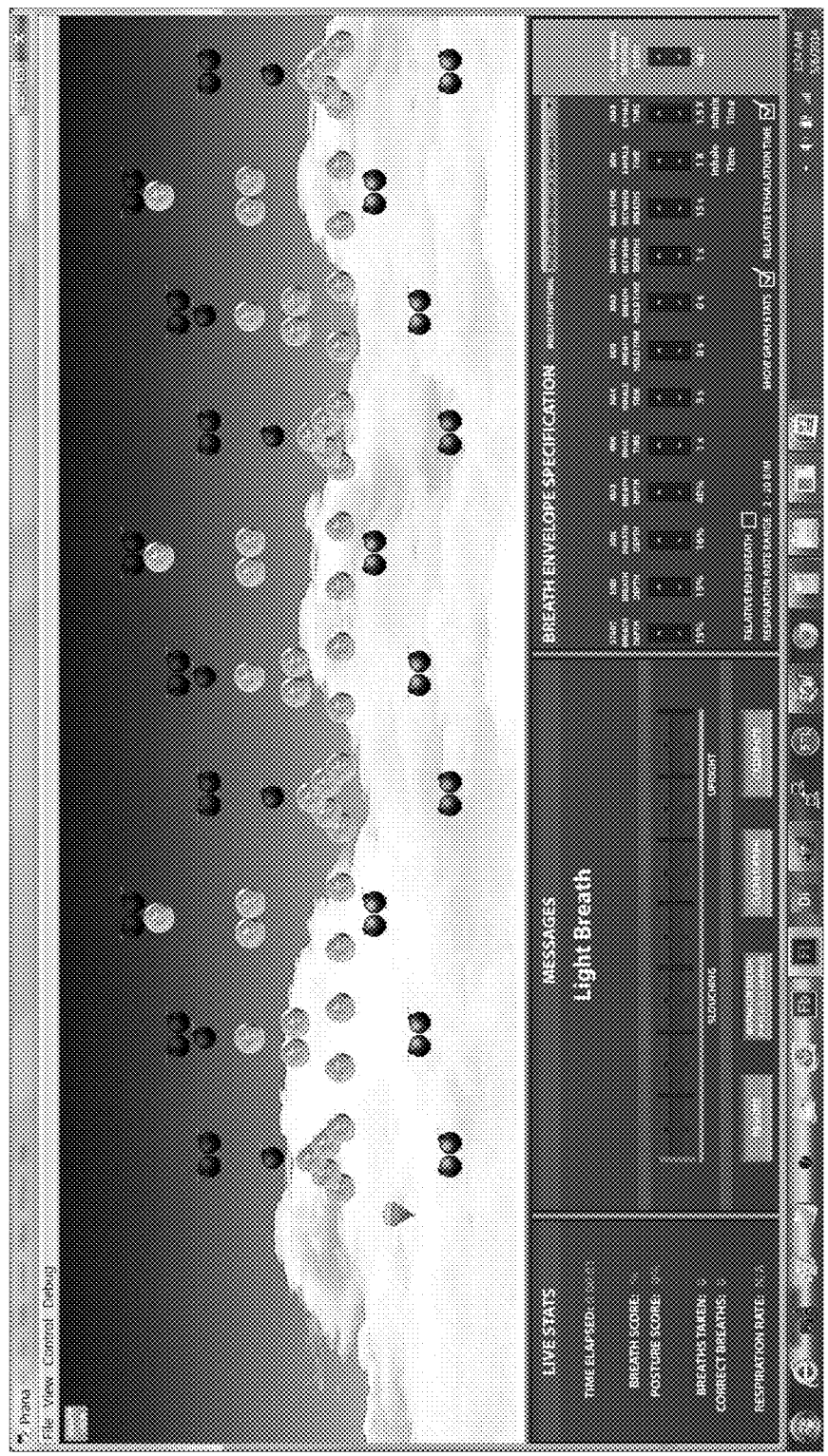

FIG. 149 is an exemplary screenshot of a breath sequence, where breathPos has passed the first current messageTriggerPoint, triggering a message in the message box.

Figure 150:
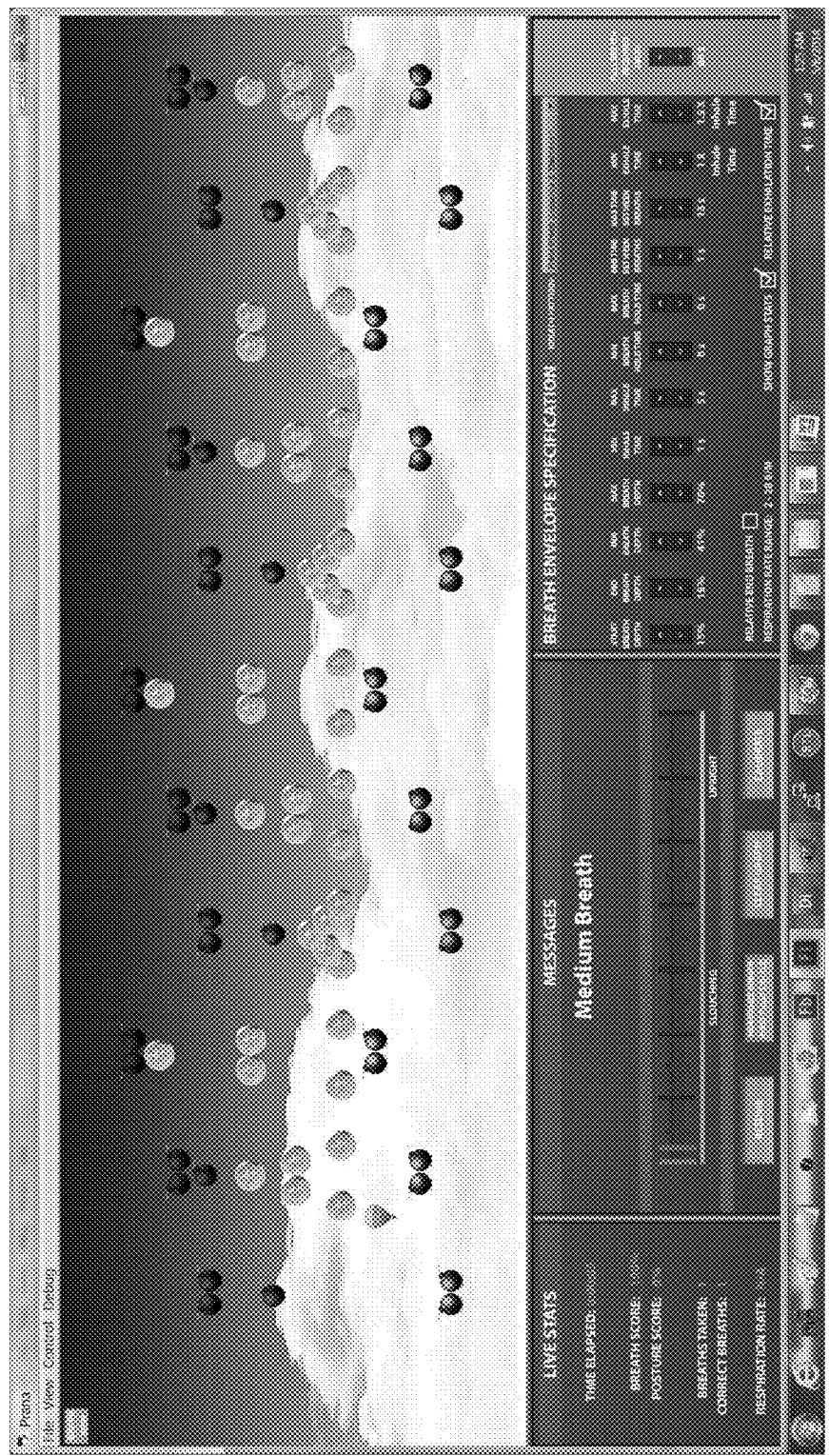

FIG. 150 is an exemplary screenshot of a breath sequence, where breathPos has passed the second messageTriggerPoint, triggering a second message in the message box.

Figure 151:
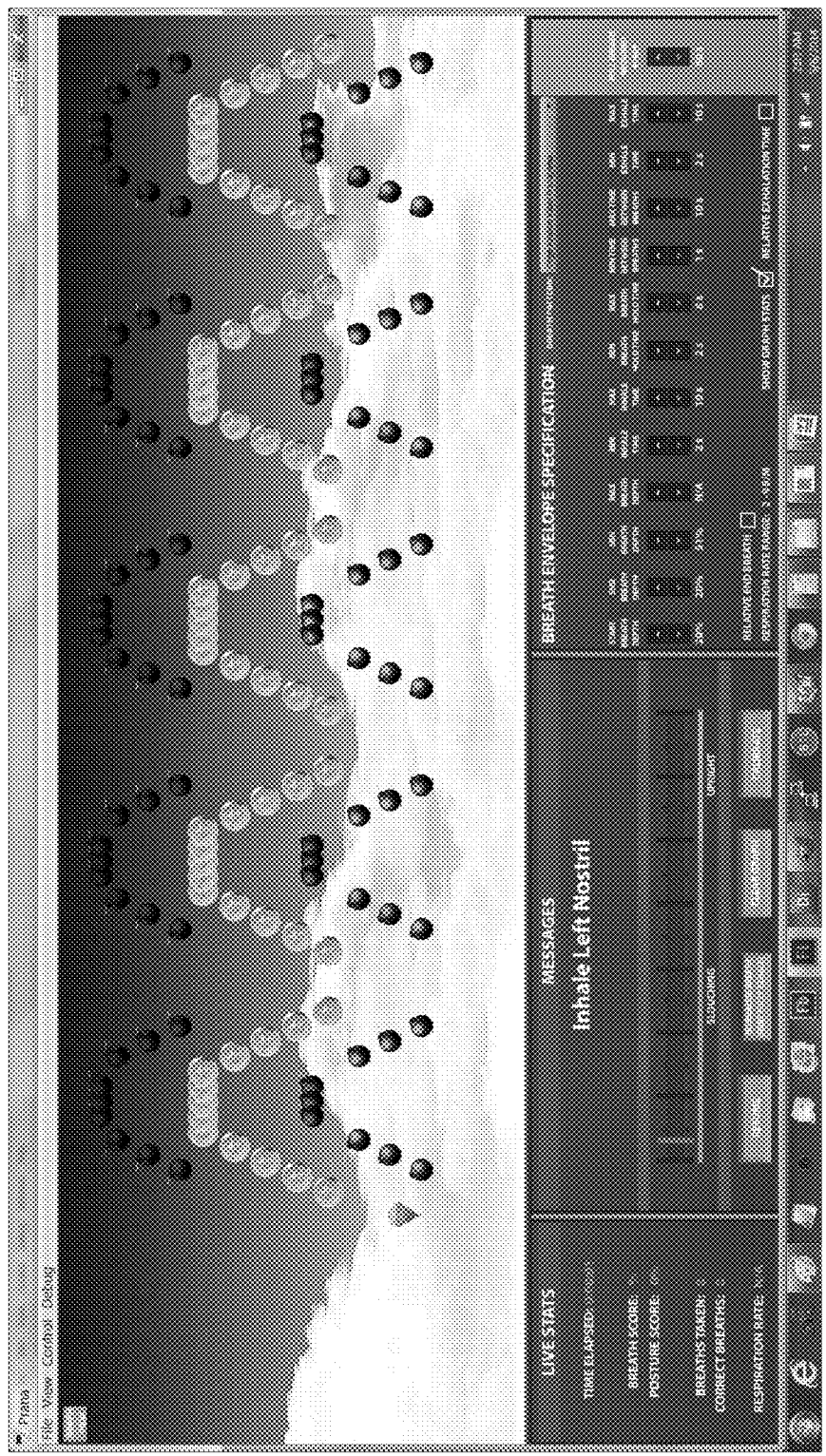

FIG. 151 is an exemplary screenshot of a game session with a breath sequence selected called "Yoga: Anulom Vilom Pranayama", and with a first message shown relating to the phase of the current breath.

Figure 152:
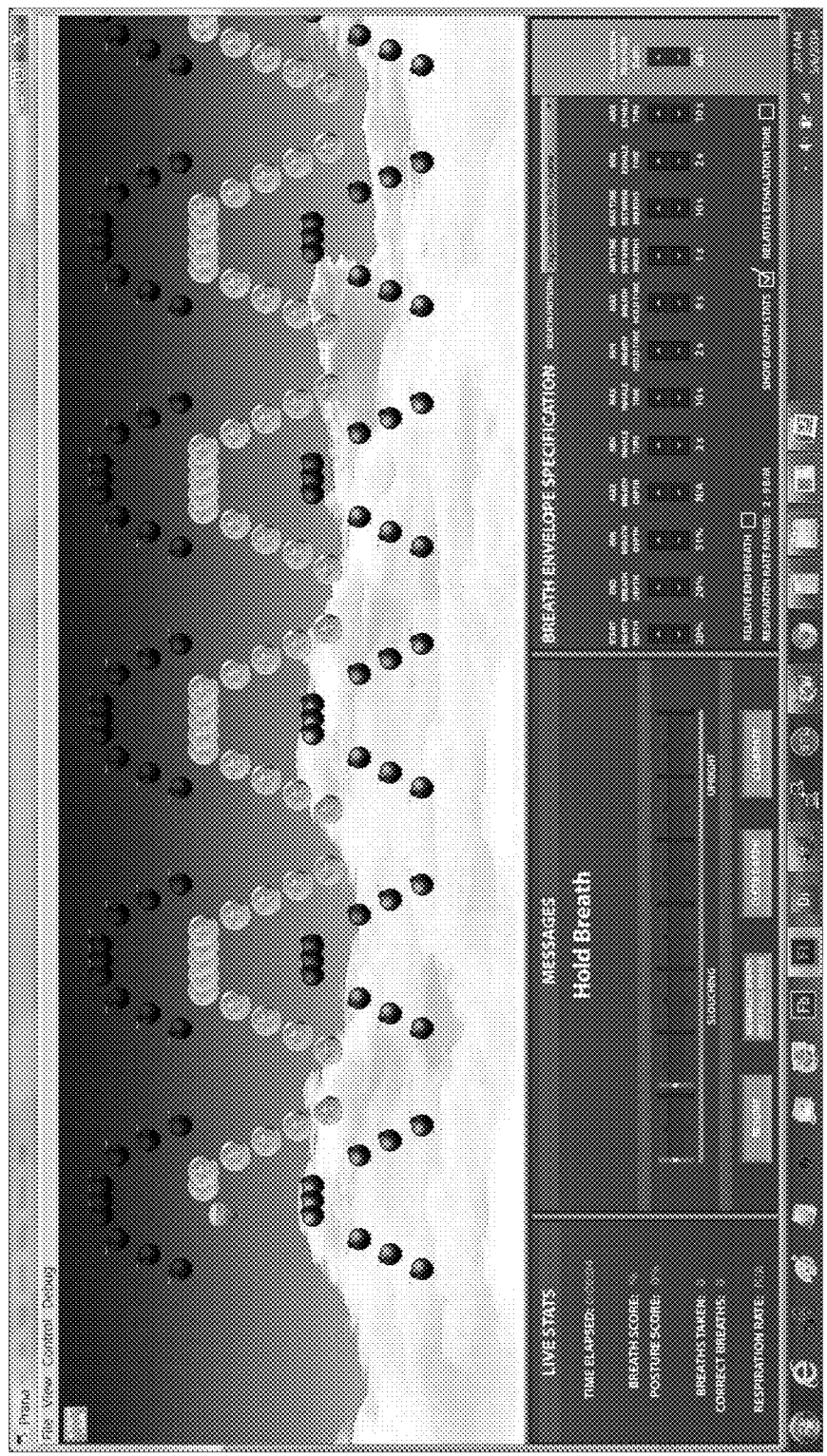

FIG. 152 is an exemplary screenshot of a game session with a breath sequence selected called "Yoga: Anulom Vilom Pranayama", and with a second message shown relating to the phase of the current breath.

Figure 153:
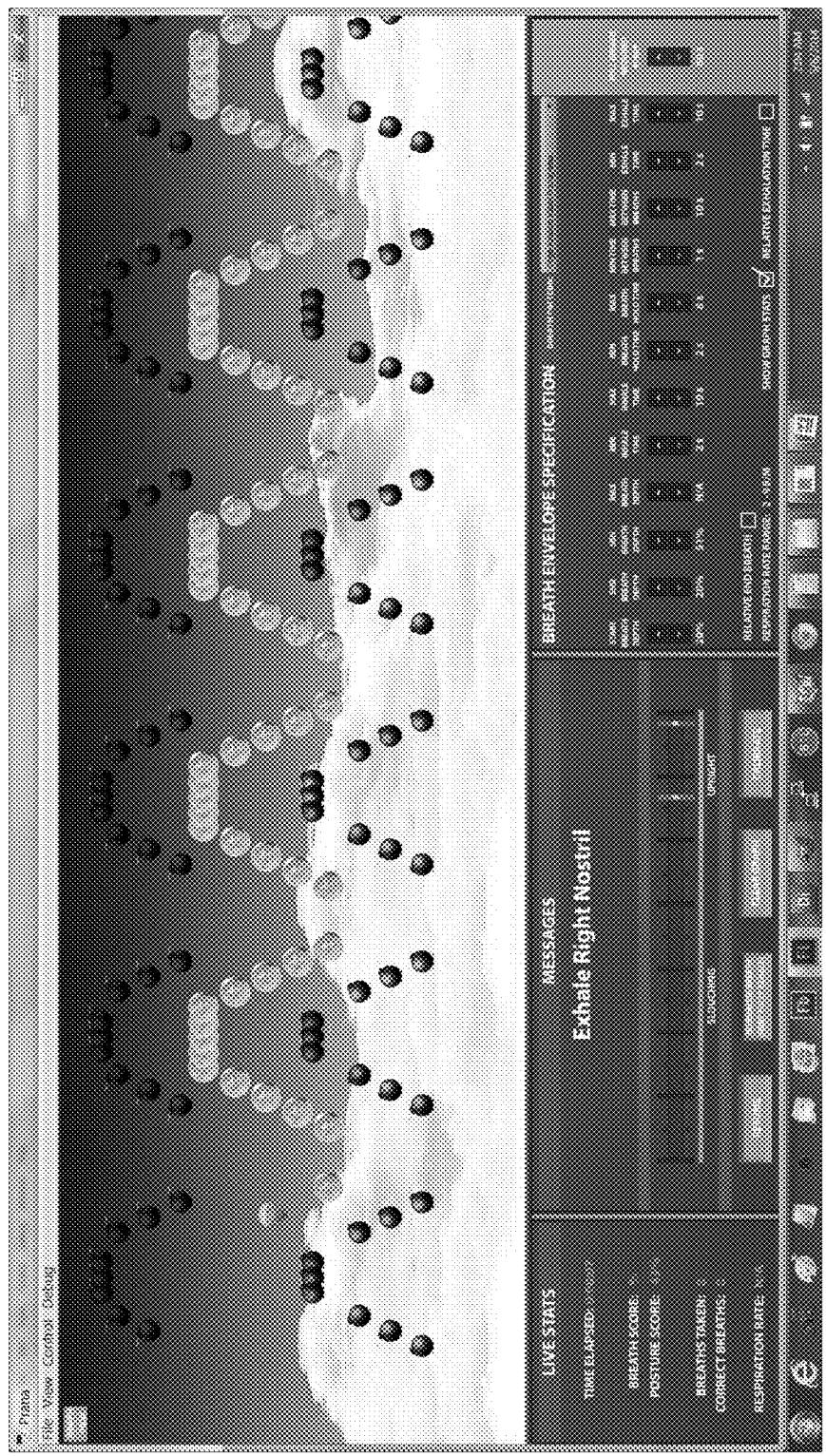

FIG. 153 is an exemplary screenshot of a game session with a breath sequence selected called "Yoga: Anulom Vilom Pranayama", and with a third message shown relating to the phase of the current breath.

Figure 154:
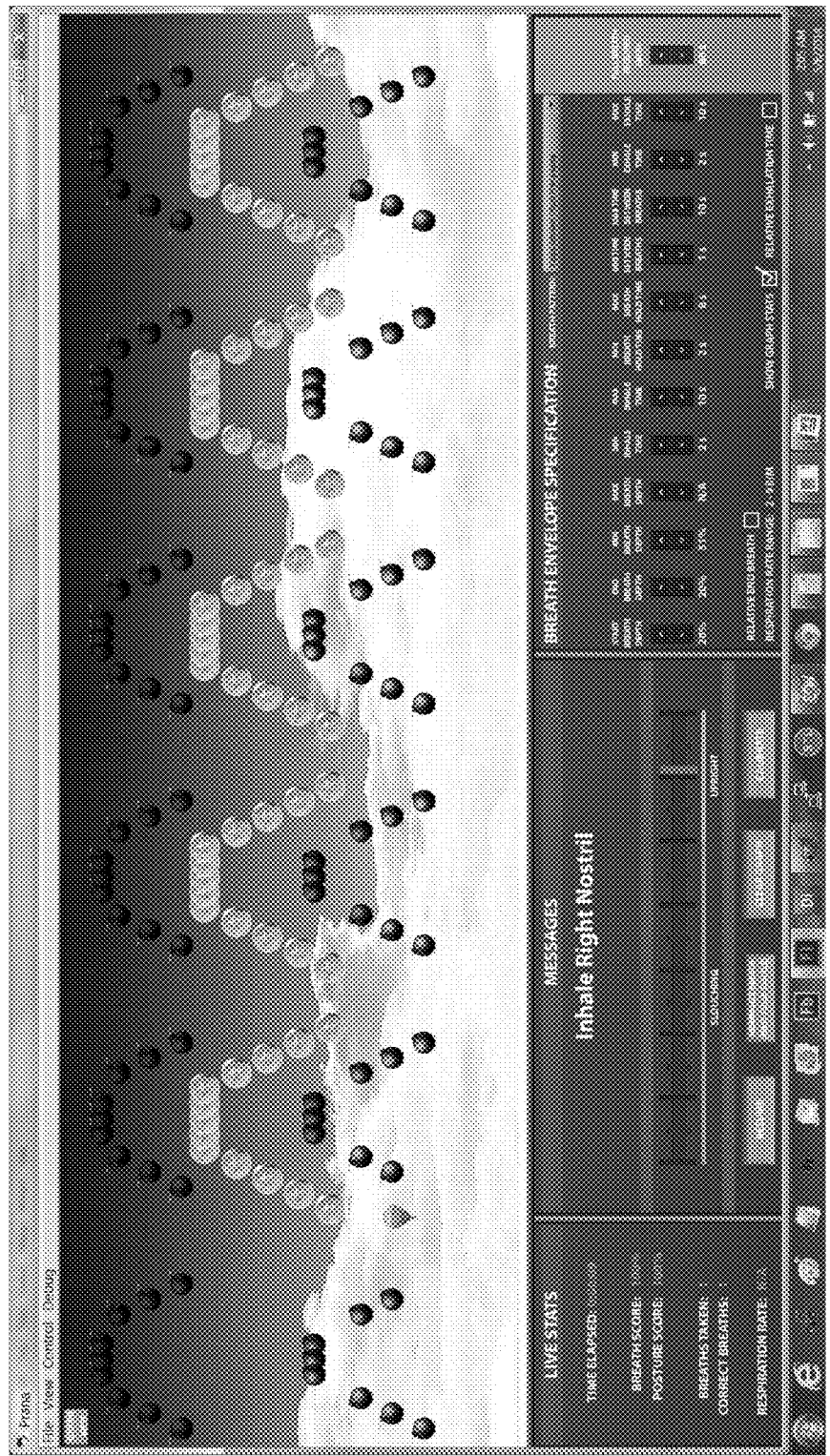

FIG. 154 is an exemplary screenshot of a game session with a breath sequence selected called "Yoga: Anulom Vilom Pranayama", and with a fourth message shown relating to the phase of the current breath.

Figure 155:
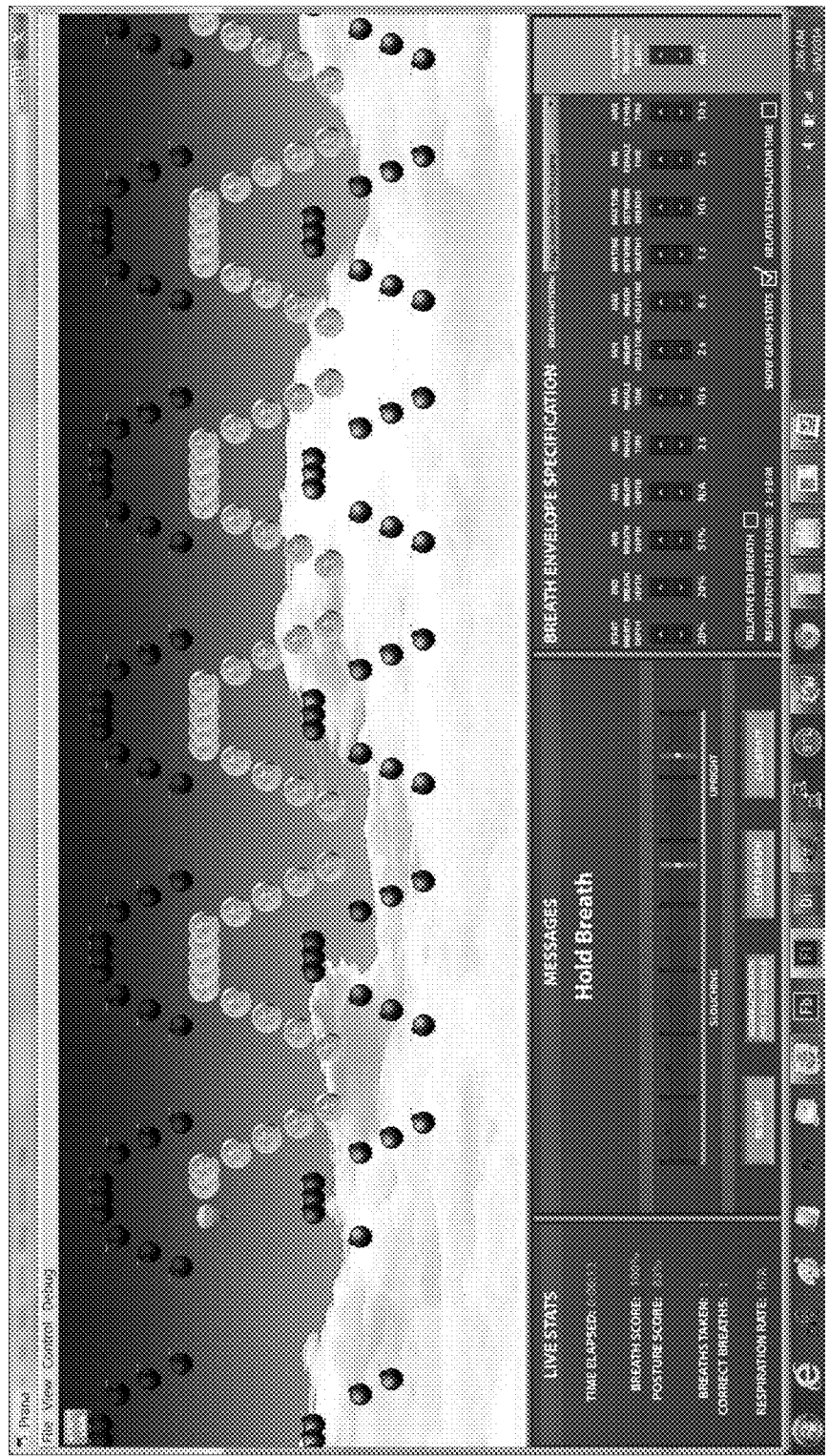

FIG. 155 is an exemplary screenshot of a game session with a breath sequence selected called "Yoga: Anulom Vilom Pranayama", and with a fifth message shown relating to the phase of the current breath.

Figure 156:
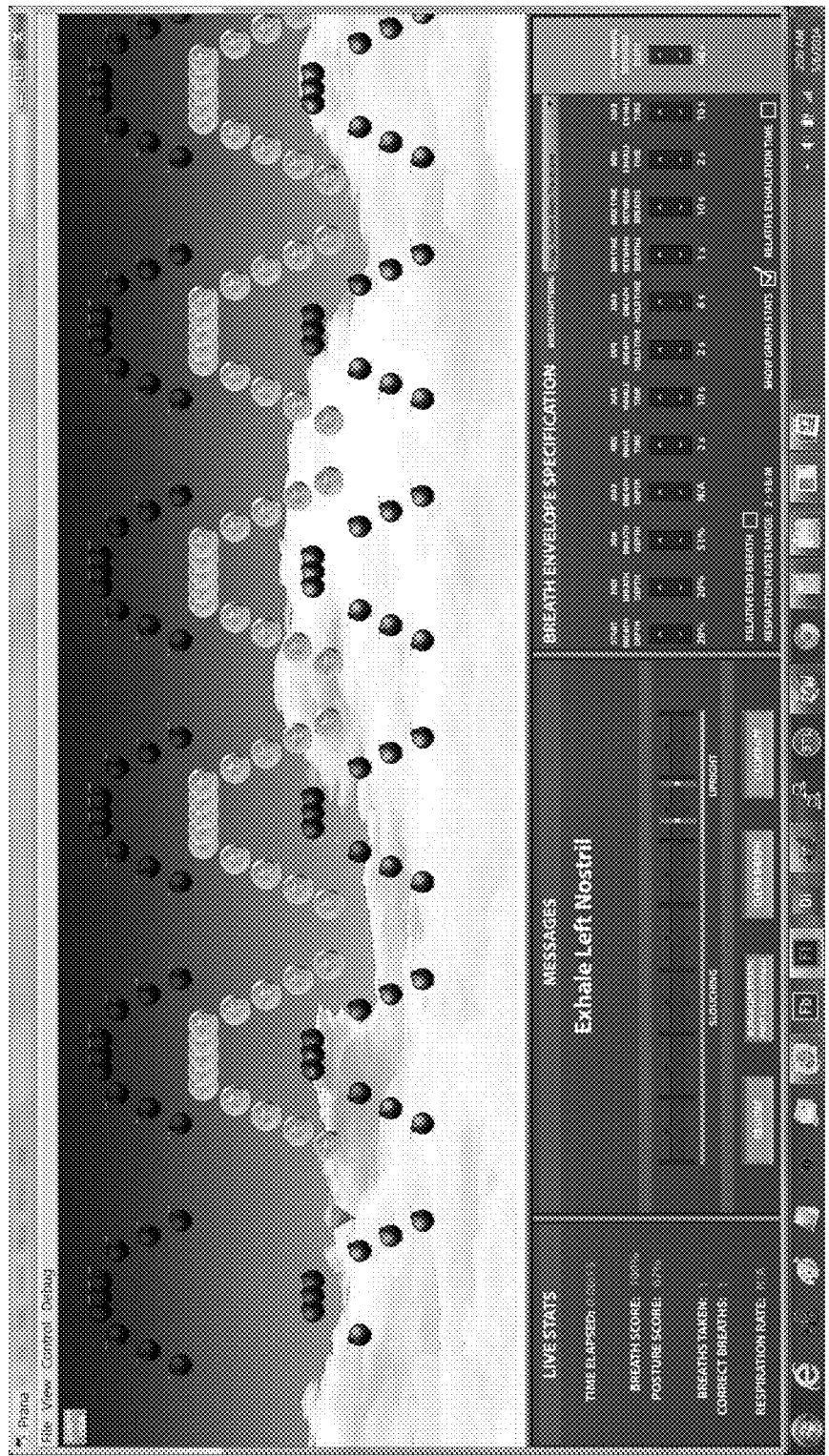

FIG. 156 is an exemplary screenshot of a game session with a breath sequence selected called "Yoga: Anulom Vilom Pranayama", and with a sixth message shown relating to the phase of the current breath.

Figure 157:
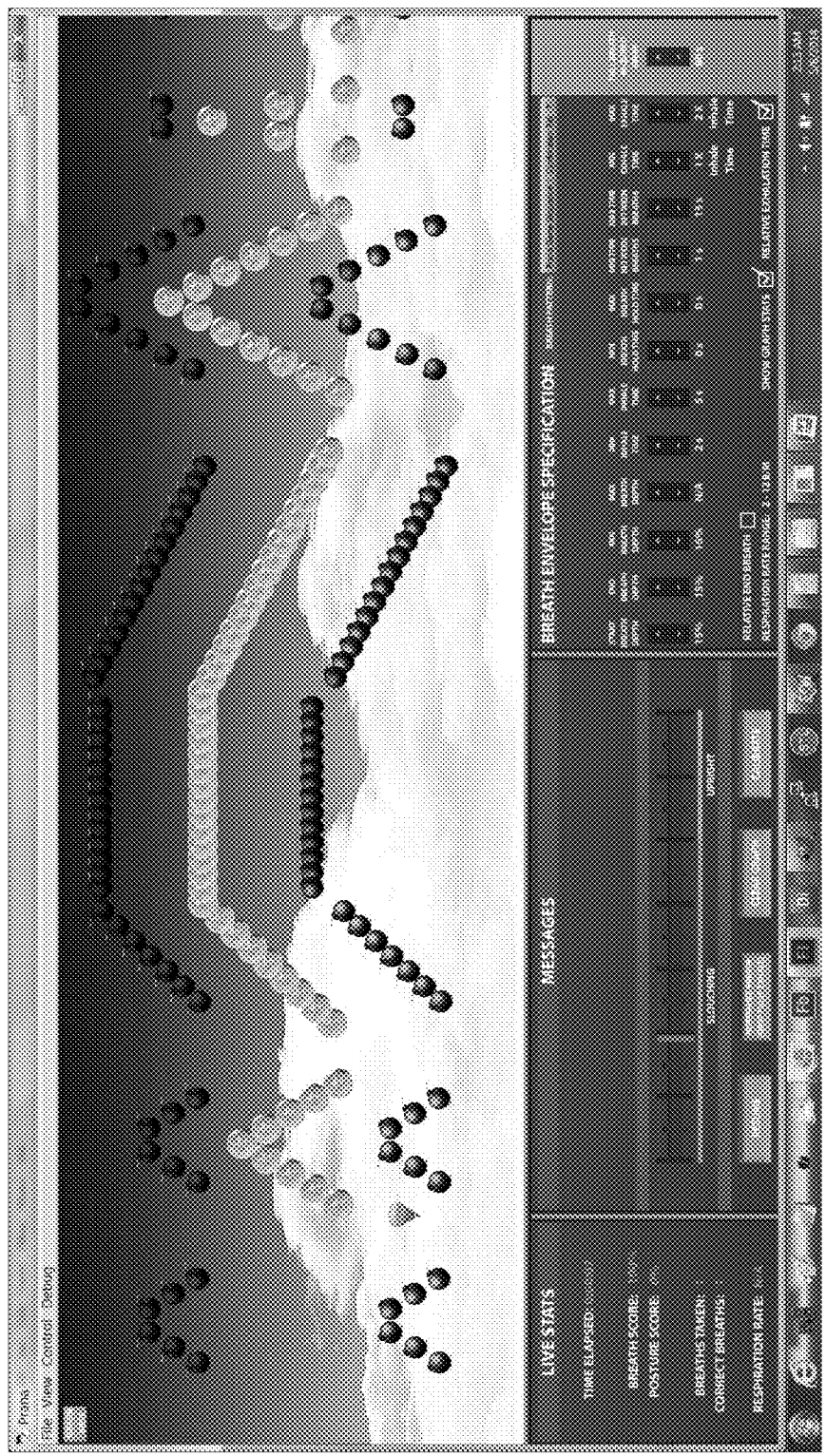

FIG. 157 is an exemplary screenshot of a breath sequence which utilizes a combination of breath patterns from a Library such as Sama Vritti Pranayama, 4-7-8, Lamaze, and Tai Chi.

Figure 158:

FIG. 158 is an exemplary screenshot of an alternate embodiment of a game session at the start of a breath pattern, where the target objects are organized into columns to make collecting the target objects easier.

Figure 159:
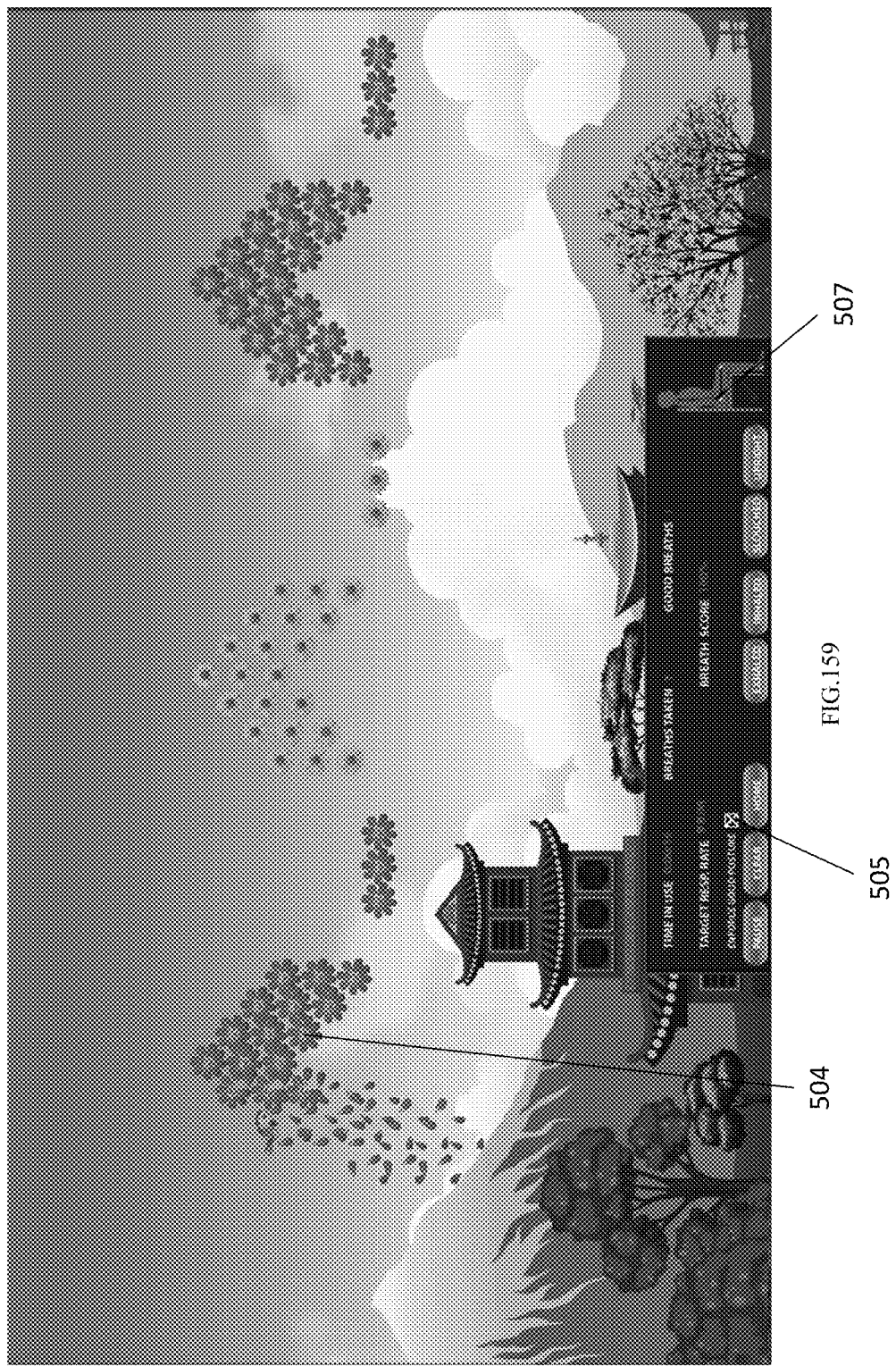

FIG. 159 is an exemplary screenshot of an alternate embodiment of a game session where scrolling has commenced and several columns of target objects have been collected.

Figure 160:
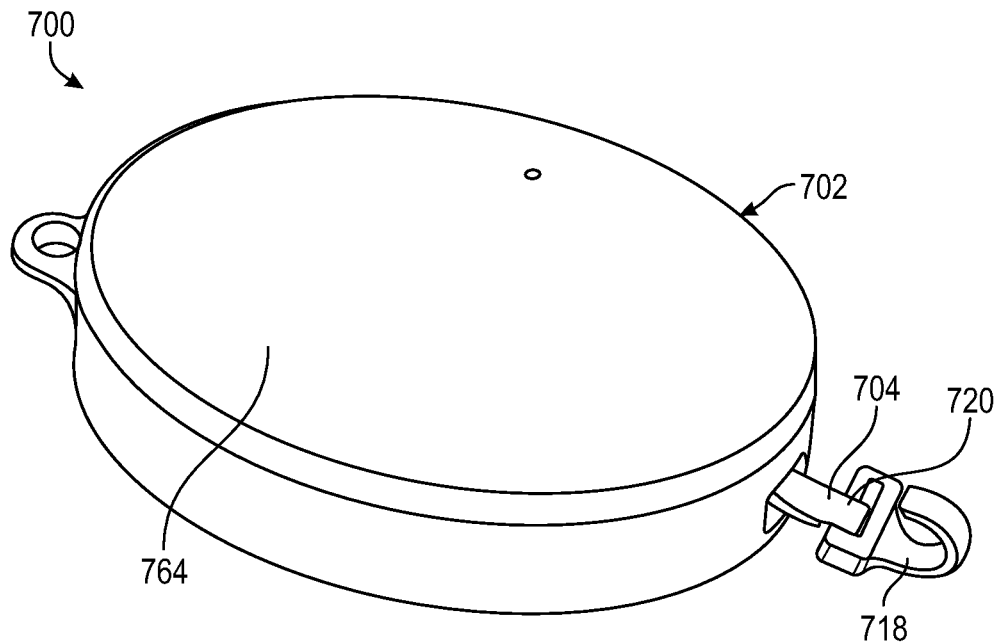

FIG. 160 shows an external view of the device housing, retracting belt, and with a first belt end connected to the retracting mechanism inside the device, and a second belt end that is presently detached from the housing fastener at the opposite end of the housing.

Figure 161:
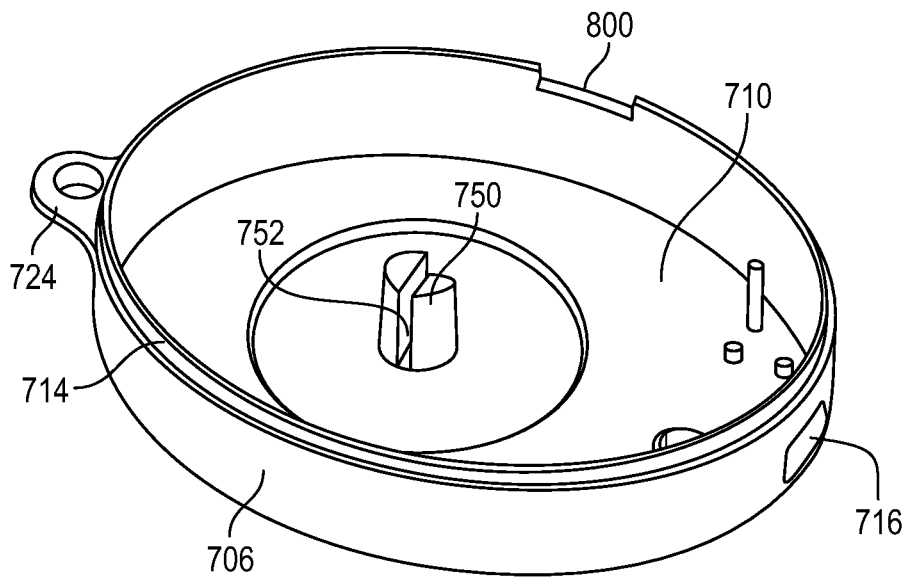

FIG. 161 shows an internal view of a bottom half of the device housing, showing a spindle (arbor) upon which the spring tensioned spool (not shown) can rotate.

Figure 162:
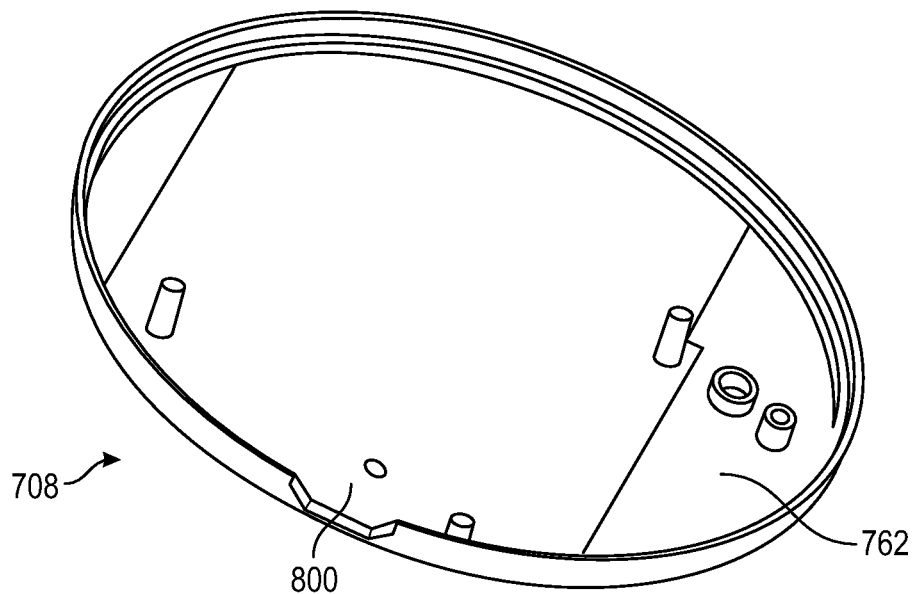

FIG. 162 shows an internal view of the top half of the device housing.

Figure 163:
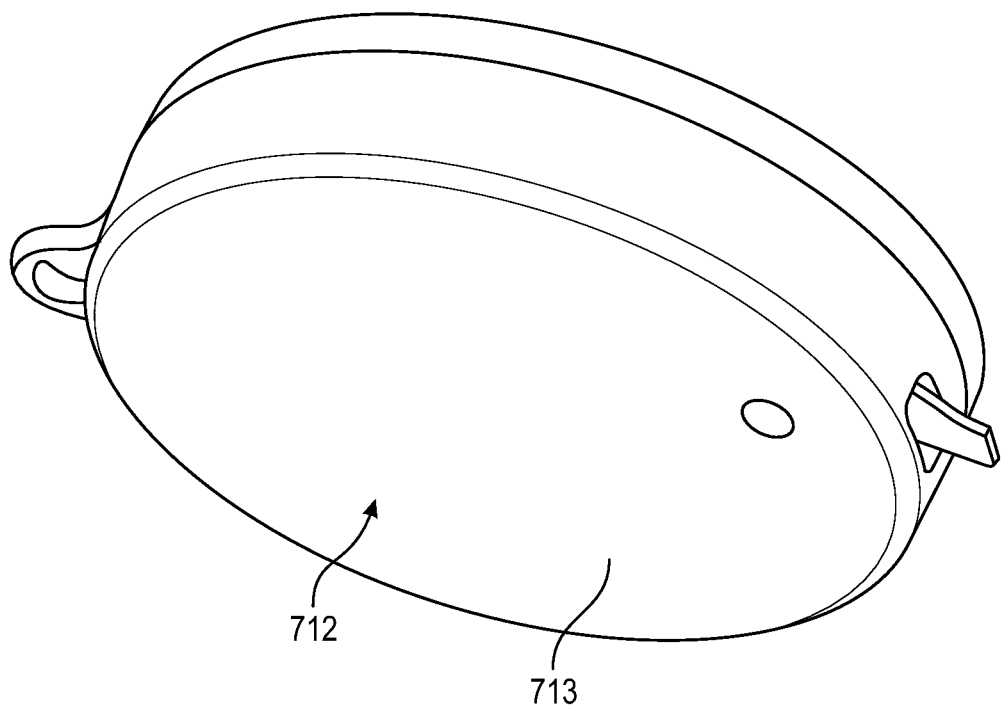

FIG. 163 shows an external view of the device housing previously shown in FIG. 160, here from a different angle. Note that the end of the belt protruding from the housing lacks a fastener.

FIG. 164 shows a photograph of a prototype of the device previously shown in FIG. 160, here with the retractable belt fully retracted onto retracting mechanism (a spring tensioned spool), not shown.

FIG. 165 shows a photograph of a prototype of the device previously shown in FIG. 160, here with the retractable belt partially extended (due to hand pressure) from the housing.

FIG. 166A shows a photograph of the device worn around the front of a user, around waist position.

FIG. 166B shows a photograph of the device worn around the back of a user.

Figure 167A:
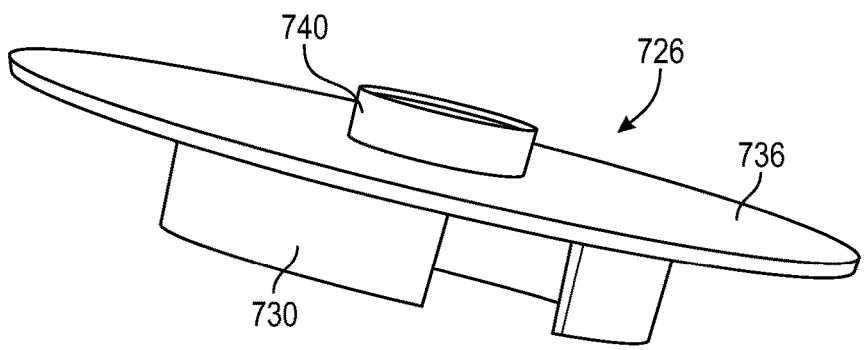

FIG. 167A shows a detail of a top view of the device's spool (reel) retraction mechanism.

Figure 167B:
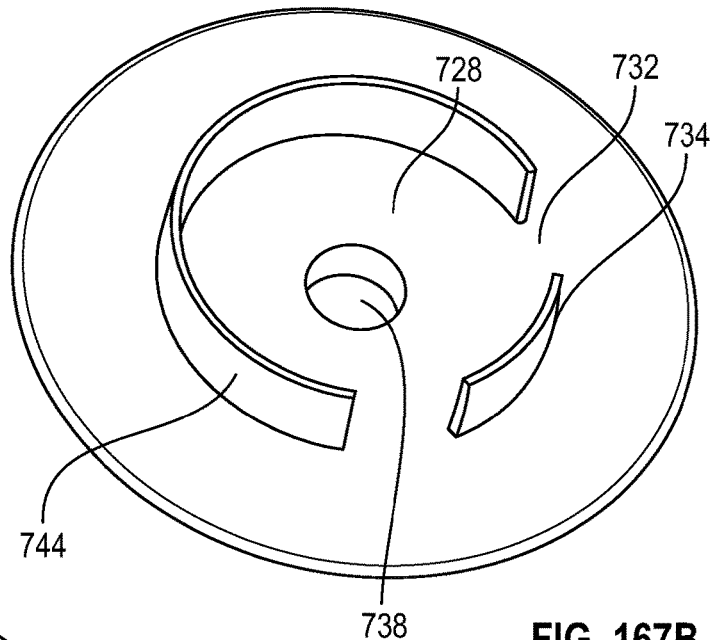

FIG. 167B shows a detail of a bottom view of the device's spool (reel) retraction mechanism.

Figure 167C:
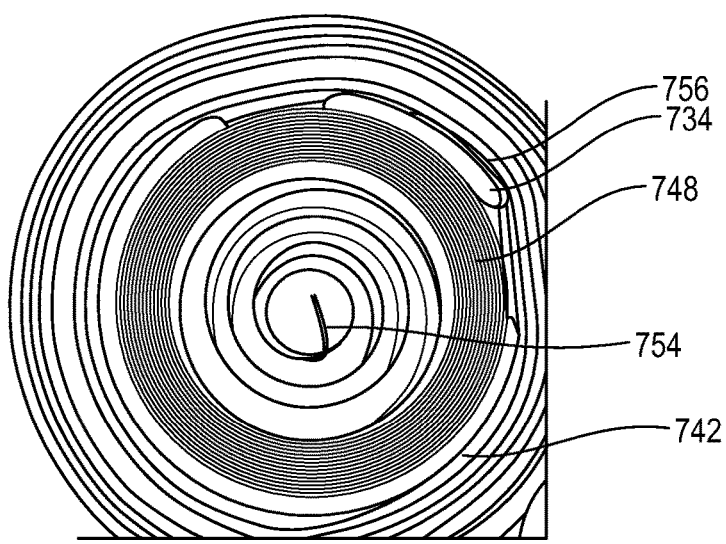
Figure 168:
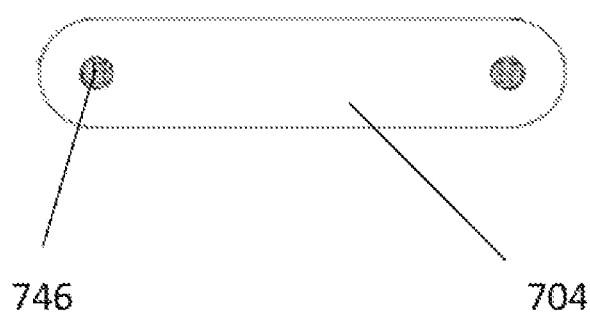

FIG. 167C shows a photograph of the spring that provides spring tensioning for the spool, and the retraction belt wound onto the spool FIG. 168 shows a cross-section of the retraction belt.

Figure 169:
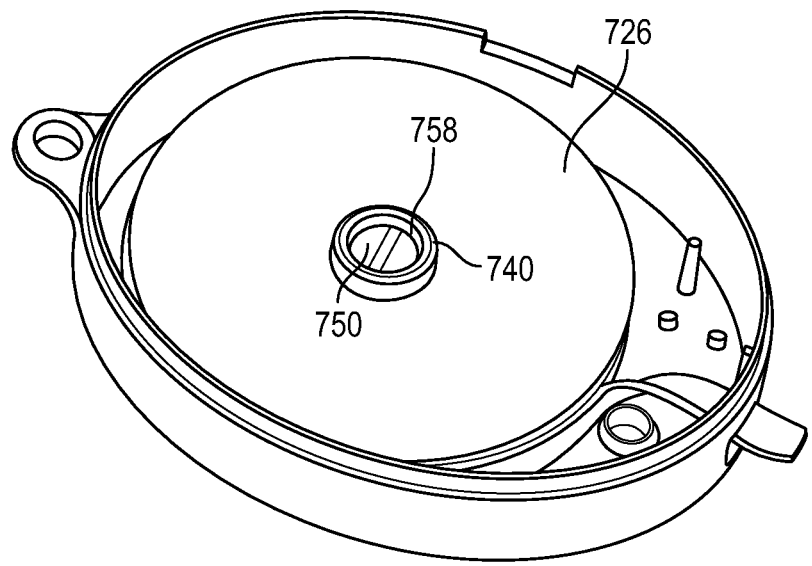

FIG. 169 shows a detail of the inner portion of the housing, with the spool retraction mechanism positioned over the spindle (arbor), and the retractable belt wound around the spool.

Figure 170:
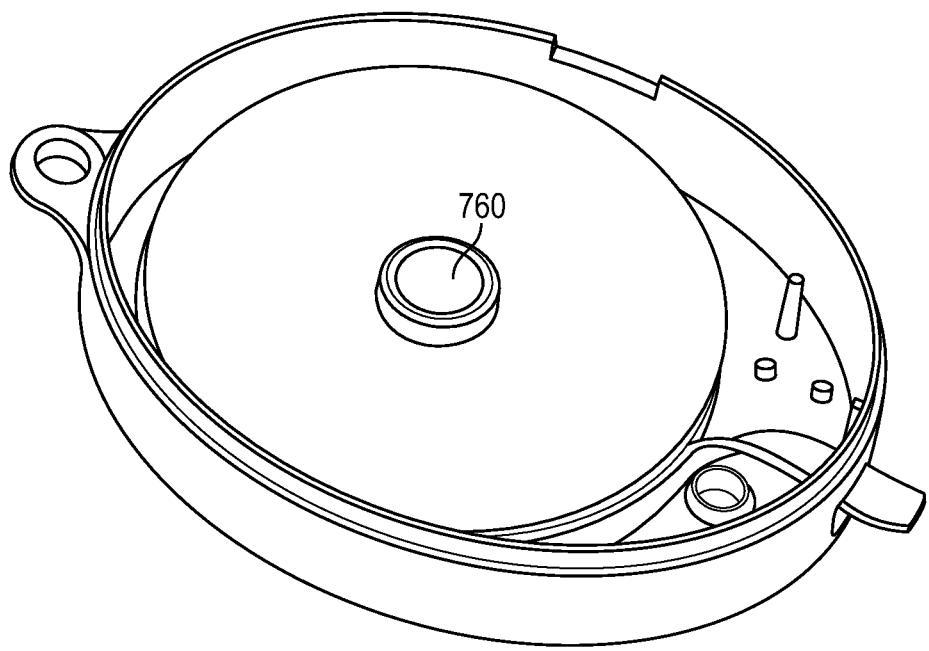

FIG. 170 shows another detail of the inner portion of the housing, with the spool retraction mechanism positioned over the spindle, and the retractable belt wound around the spool, and a magnet centrally positioned on top of the reel.

Figure 171:
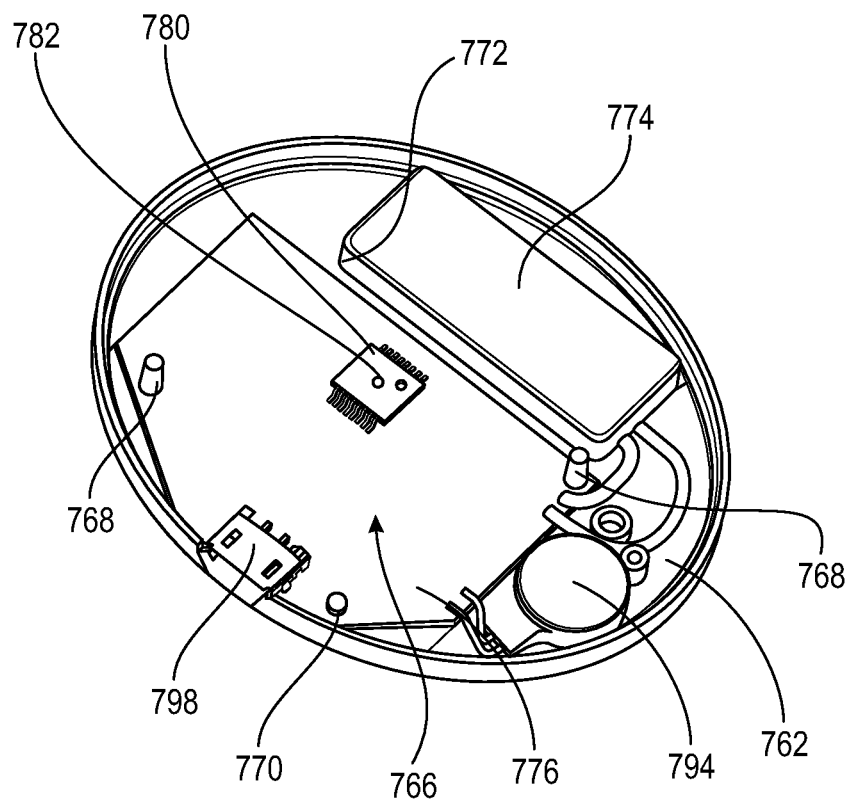

FIG. 171 shows more details of the top inner portion of the device previously shown in FIG. 162, here with additional electronics such as a printed circuit board, battery, rotary sensor (e.g. rotary encoder), notifier (an output device such as a speaker, or LED or LCD display) and other components.

Figure 172:
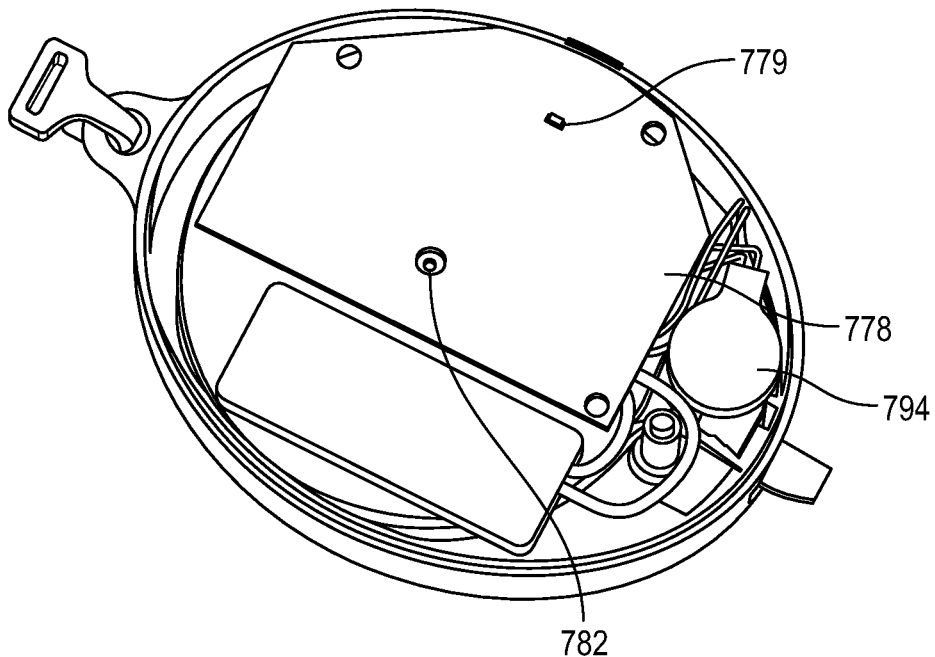

FIG. 172 shows how the electronic components previously shown in FIG. 171 are positioned on top of the components previously shown in FIG. 170 when the device is assembled.

Figure 173:
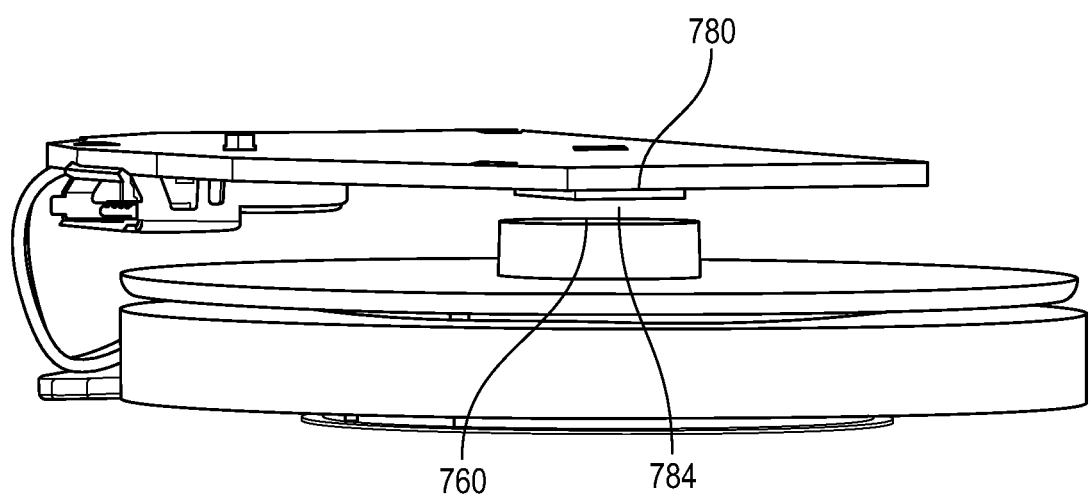

FIG. 173 shows a detail of how a magnetic rotary encoder or other sensor can fit over the spindle of the spool with a magnet on the top of the spool, detect motion (e.g. rotation of the spool), and hence displacement of the belt.

Figure 174:
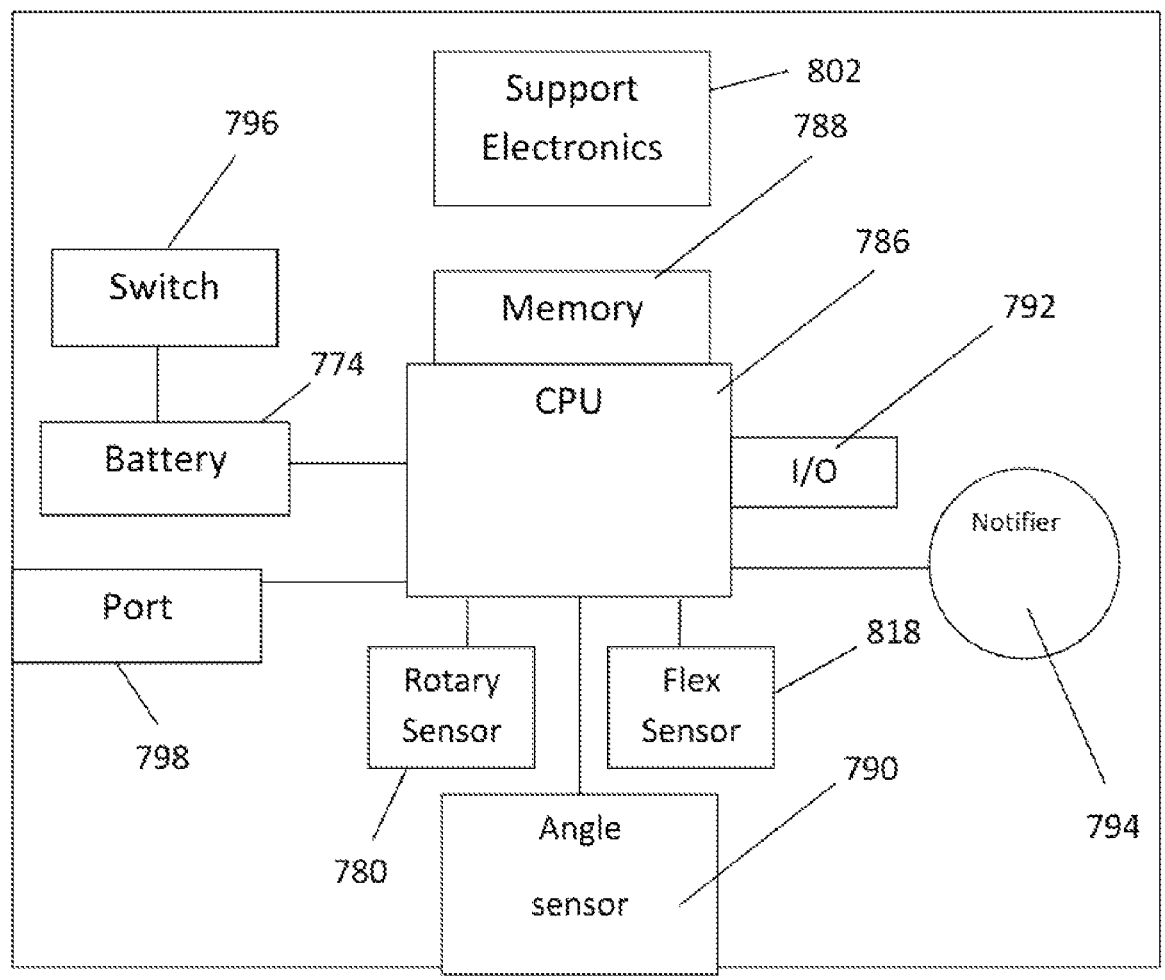

FIG. 174 shows a circuit block diagram of one embodiment of the invention.

Figure 175:
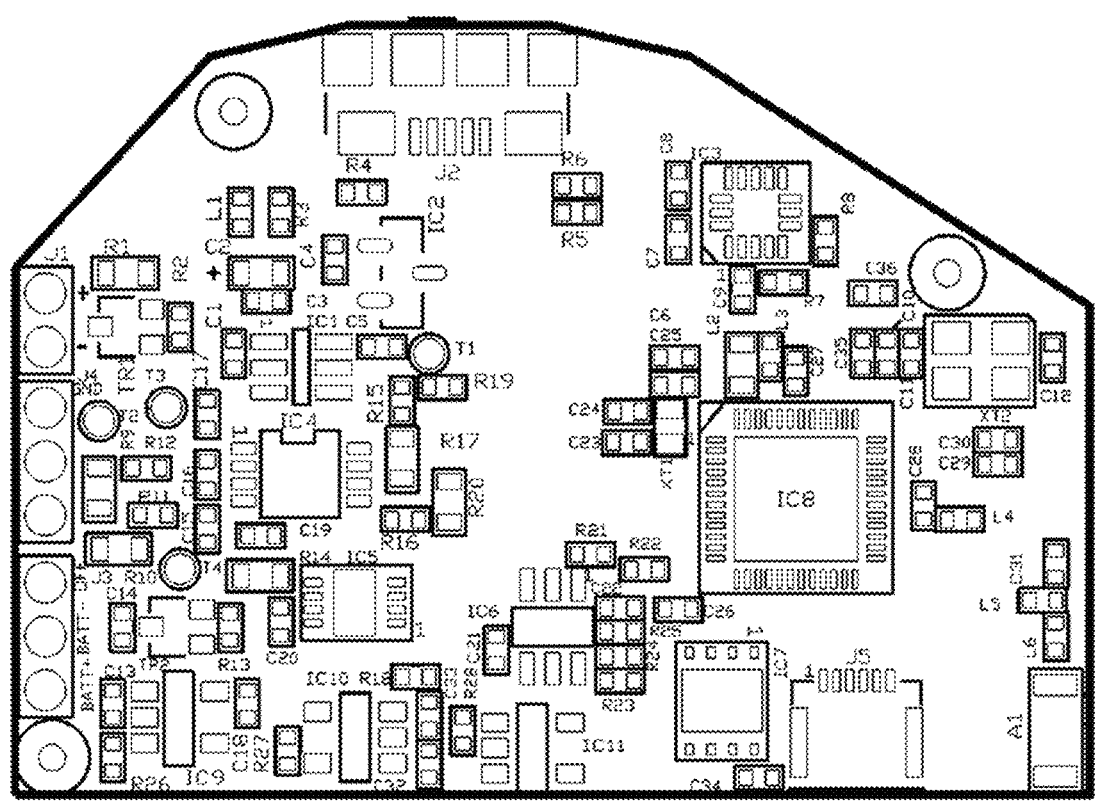

FIG. 175 shows a printed circuit layout diagram for one embodiment of the invention.

FIG. 176 shows some of the electronic parts that may be used in some embodiments of the invention.

Figure 177:
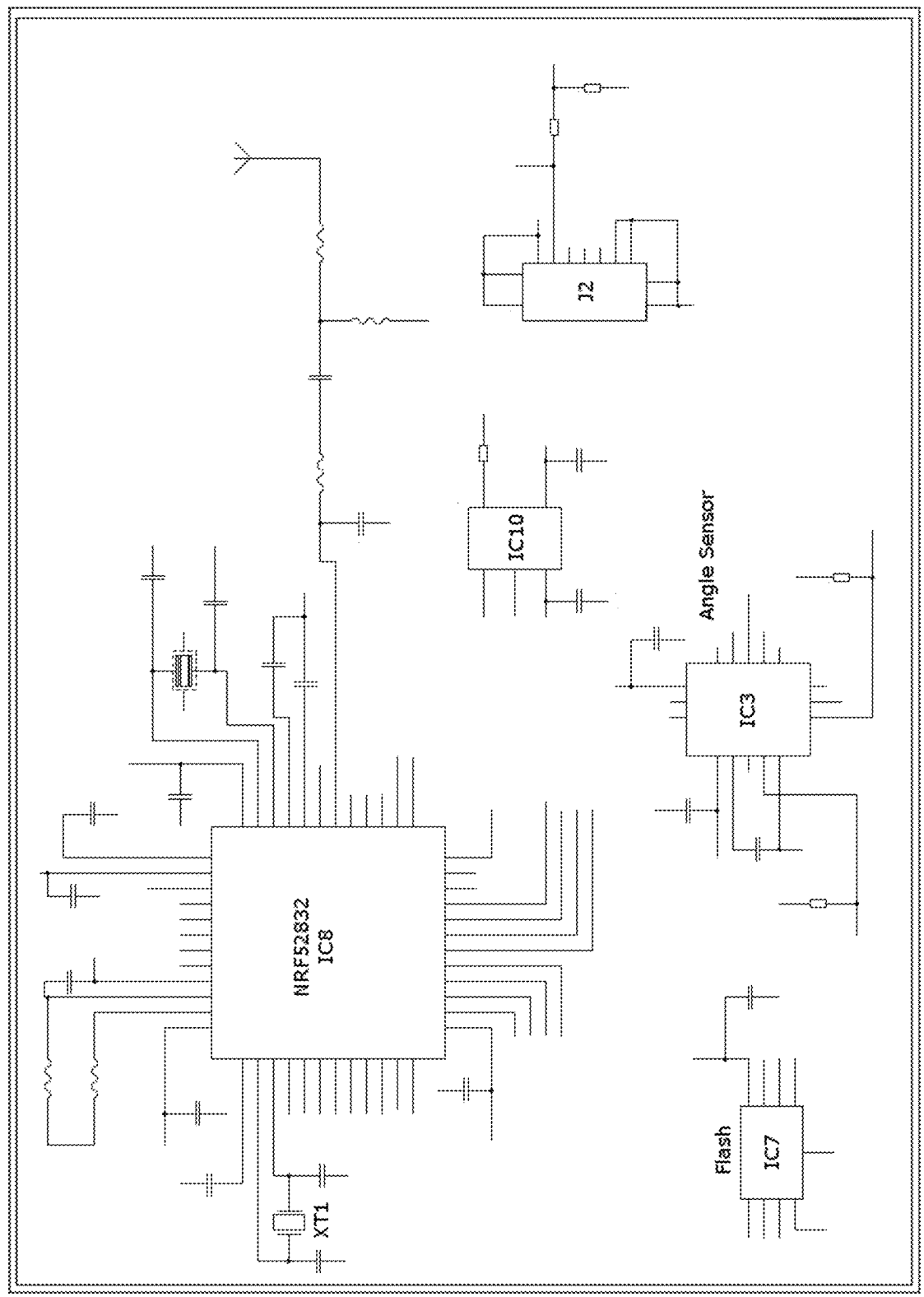

FIG. 177 shows a more detailed circuit diagram for one embodiment of the invention.

Figure 178:
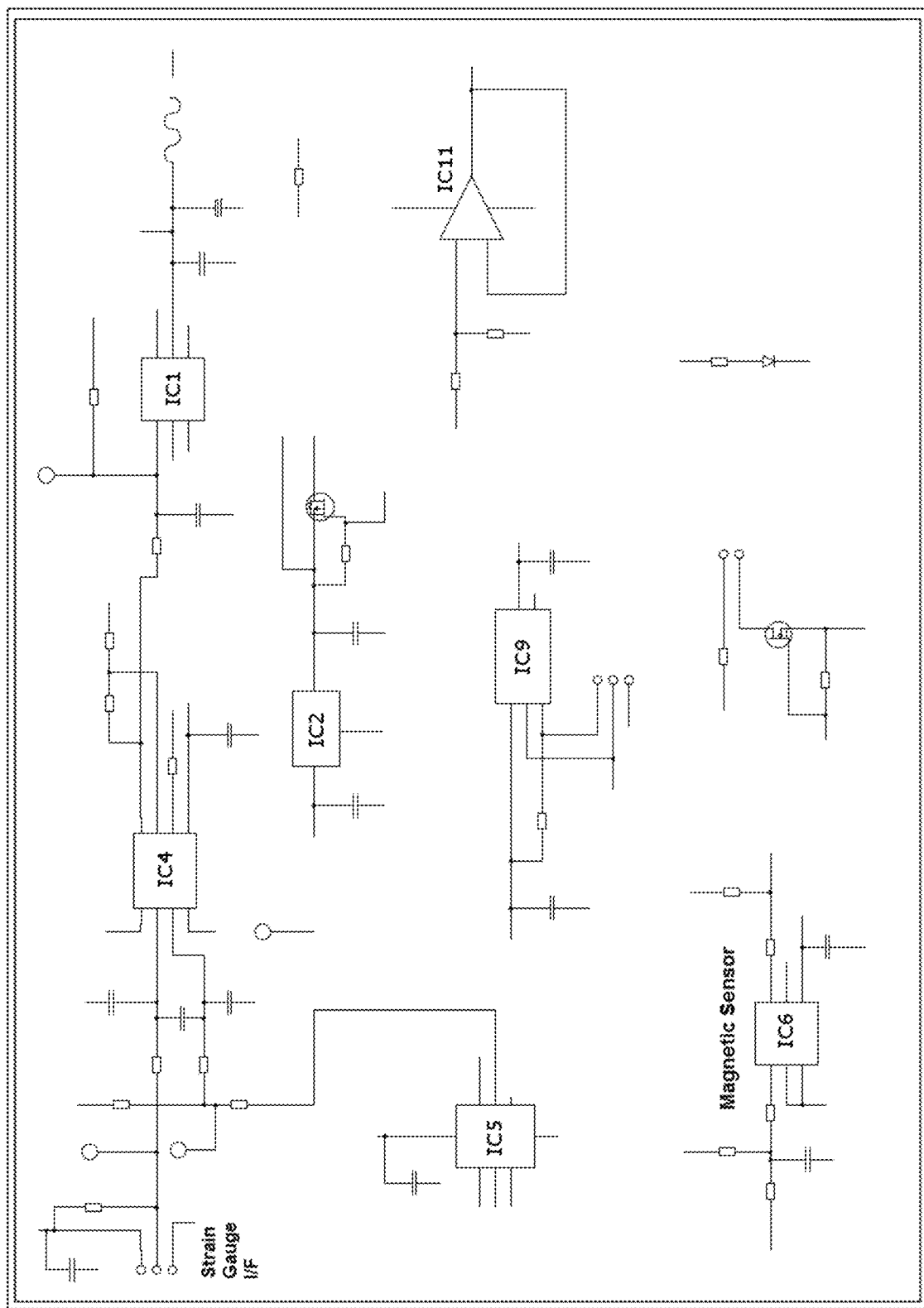

FIG. 178 shows additional details of the circuit diagram for one embodiment of the invention.

Figure 179:
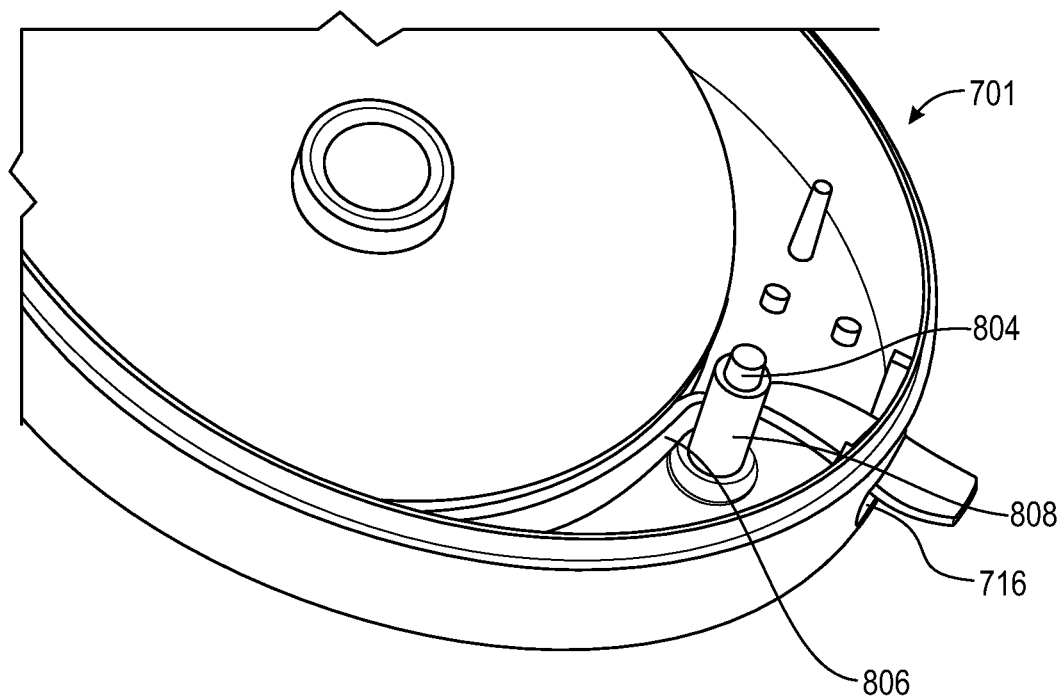

FIG. 179 shows a closer view of how the belt can wind around a belt guide shaft as the belt unwinds from the spool and untwists, and extends out of the housing opening to the outside.

Figure 180:
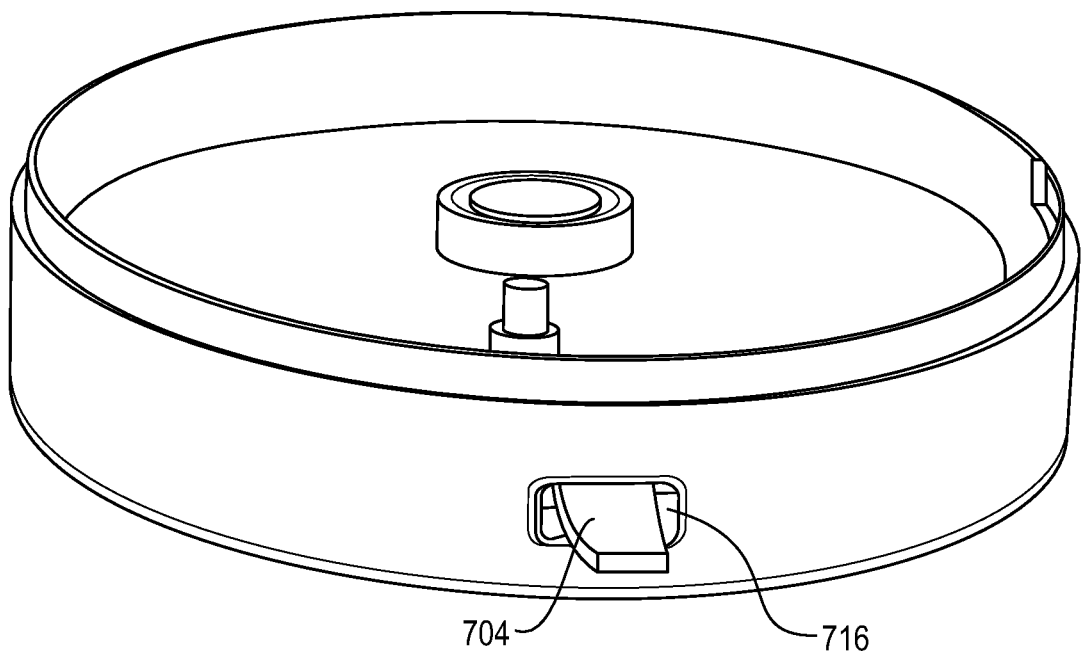

FIG. 180 shows the device of FIG. 179, here shown from a different angle.

Figure 181A:
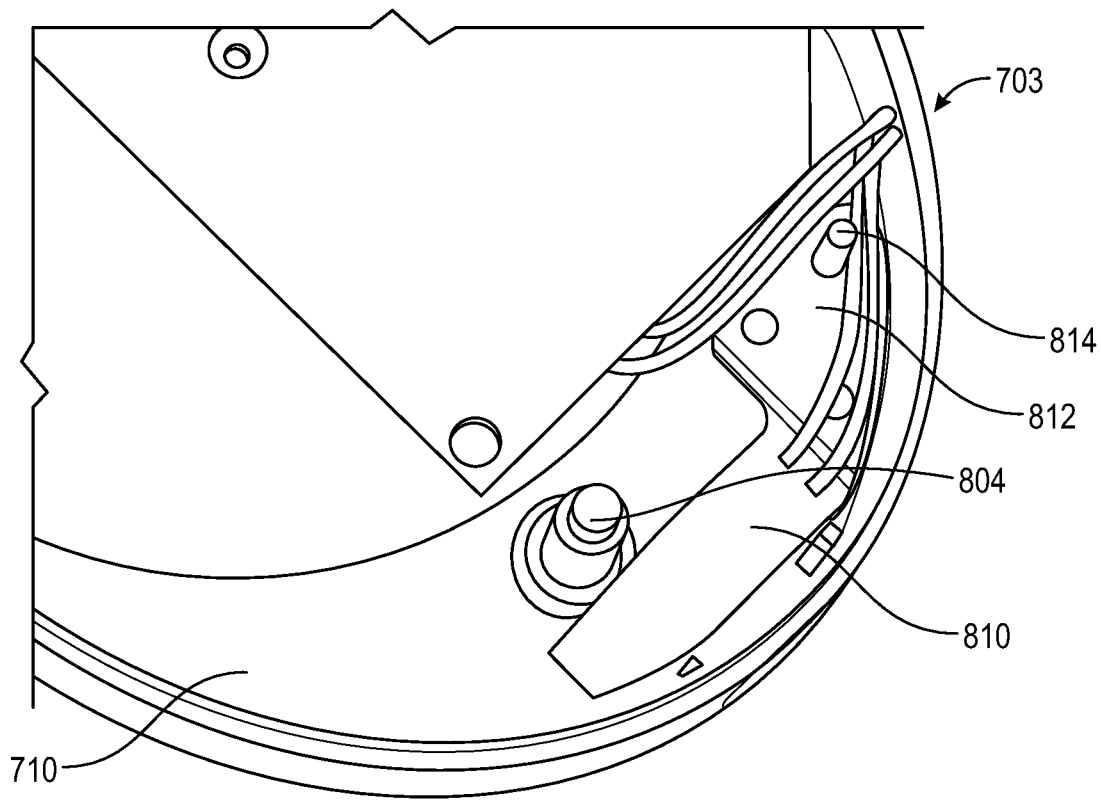

FIG. 181A shows an additional detail of how an optional device flexing element and flex sensor can be positioned.

Figure 181B:
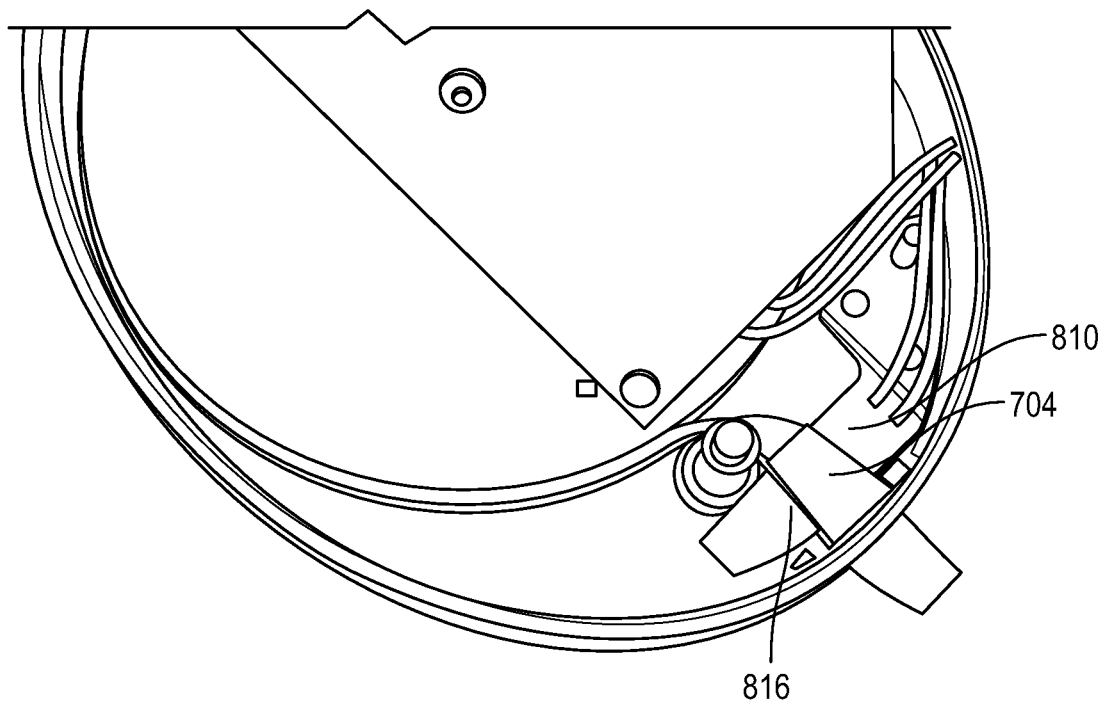

FIG. 181B shows the device of FIG. 181A, here showing the belt extending over the flexing element and flex sensor.

Figure 182:
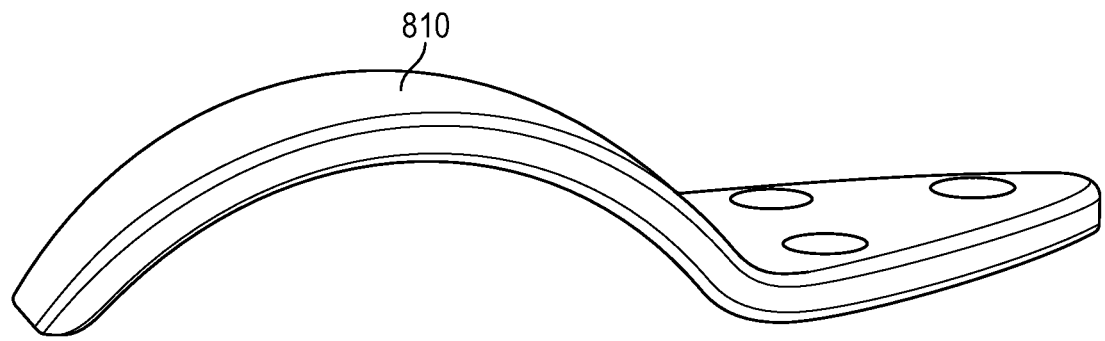

FIG. 182 shows a more detailed view of the flexing element that can be used in an optional flex sensor.

Figure 183:
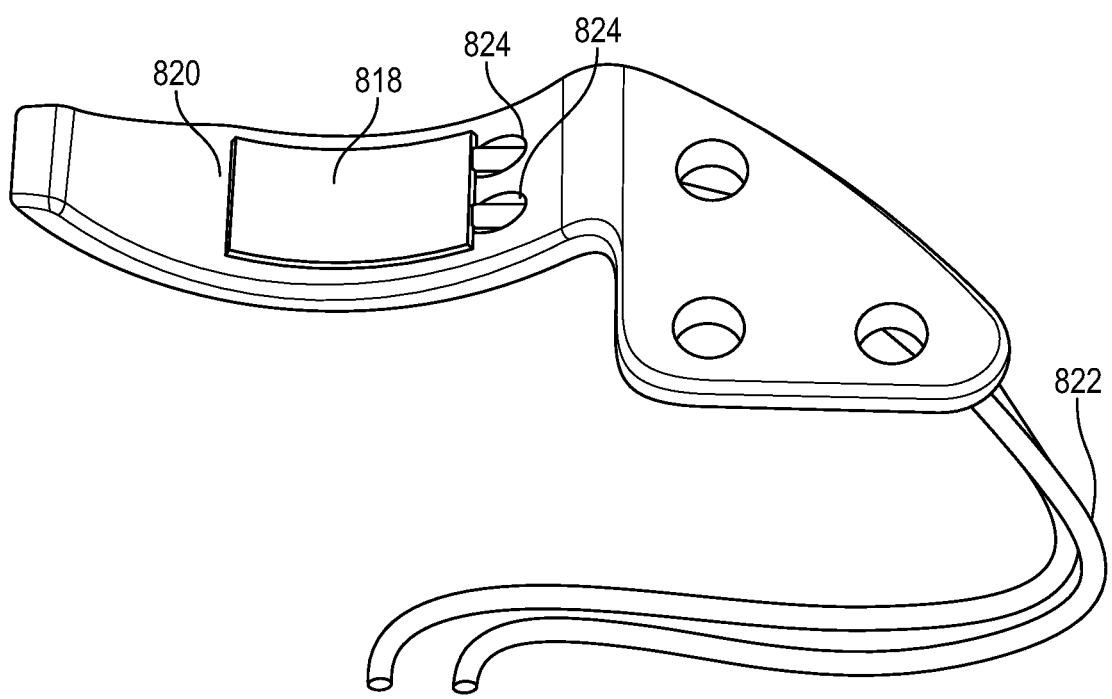

FIG. 183 shows how an electronic flex sensor device can be mounted on the flexing element.

FIG. 184 shows how alternatively, the flex sensor can be integrated into a sensor clip.

Figure 185A:
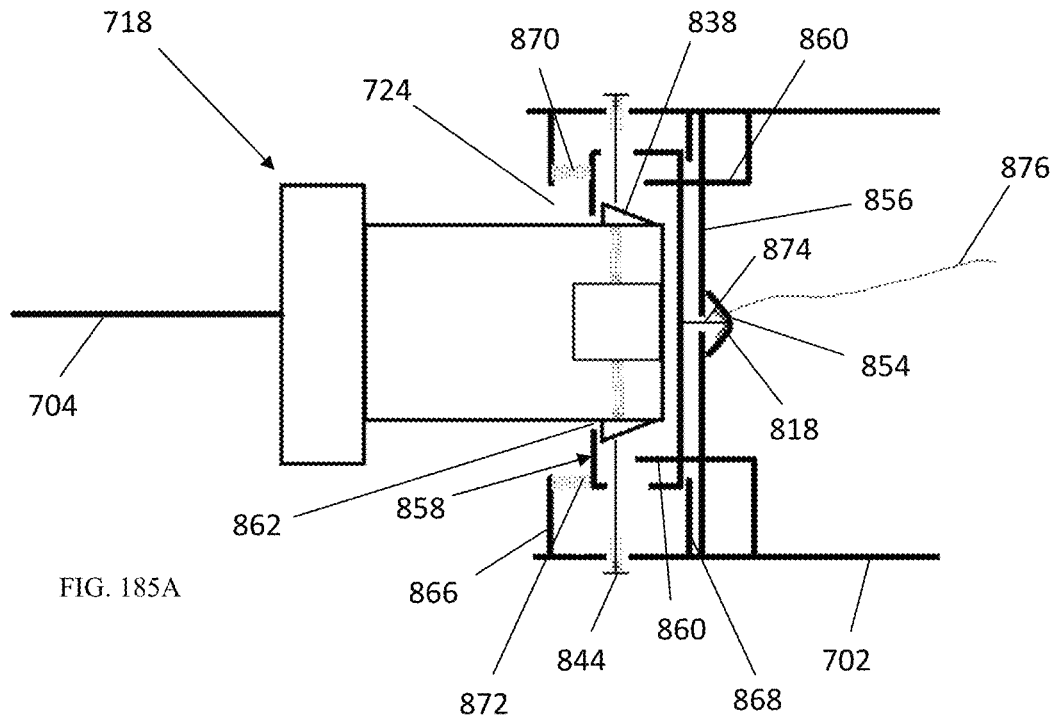

FIG. 185A shows a detail of how the flex sensor can operate in an alternative embodiment where the belt clip couples a force or displacement of the retraction belt onto the flex sensor.

Figure 185B:
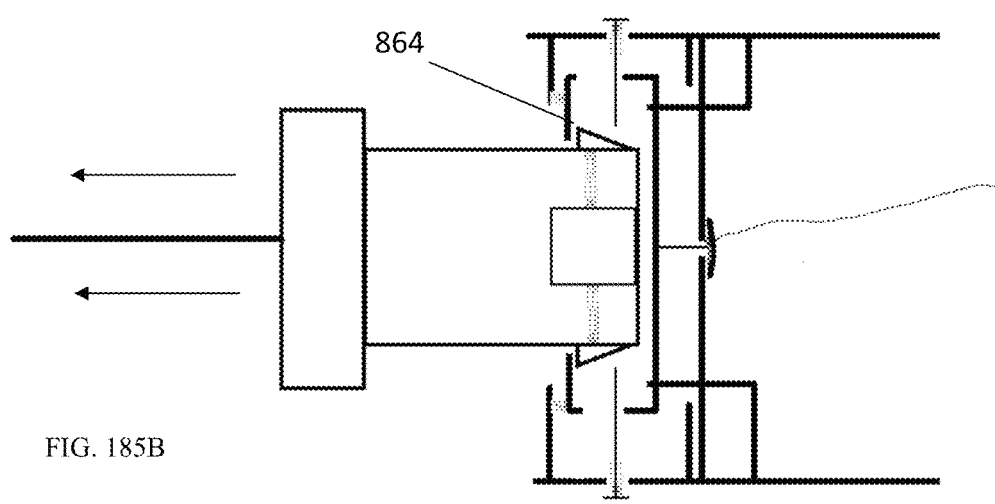

FIG. 185B shows a further detail of how the flex sensor can operate in an alternative embodiment where the belt clip couples a force or displacement of the retraction belt onto the flex sensor.

Figure 186:
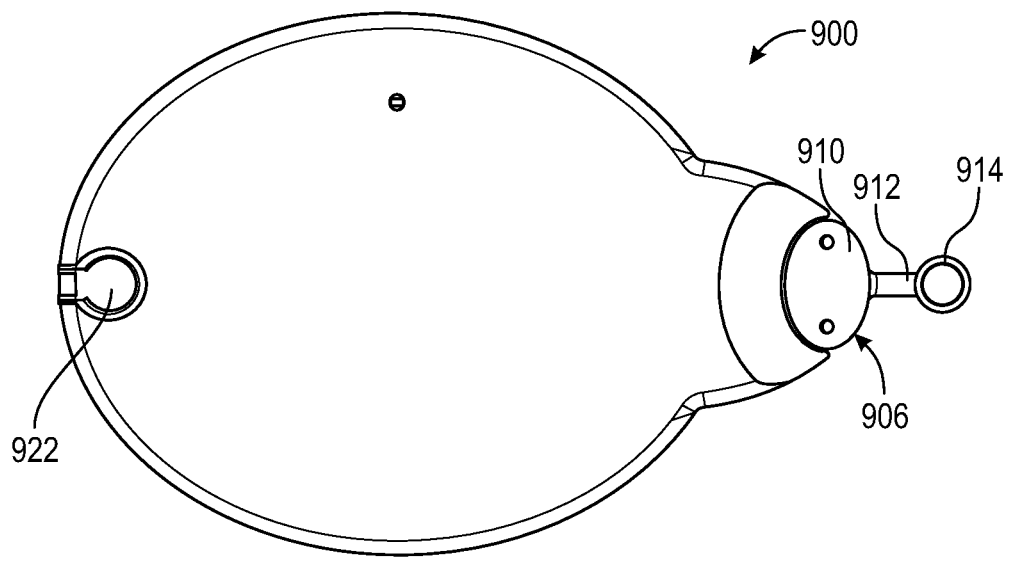

FIG. 186 shows a top-down view of a third version of the ninth embodiment of the breath training device.

Figure 187:
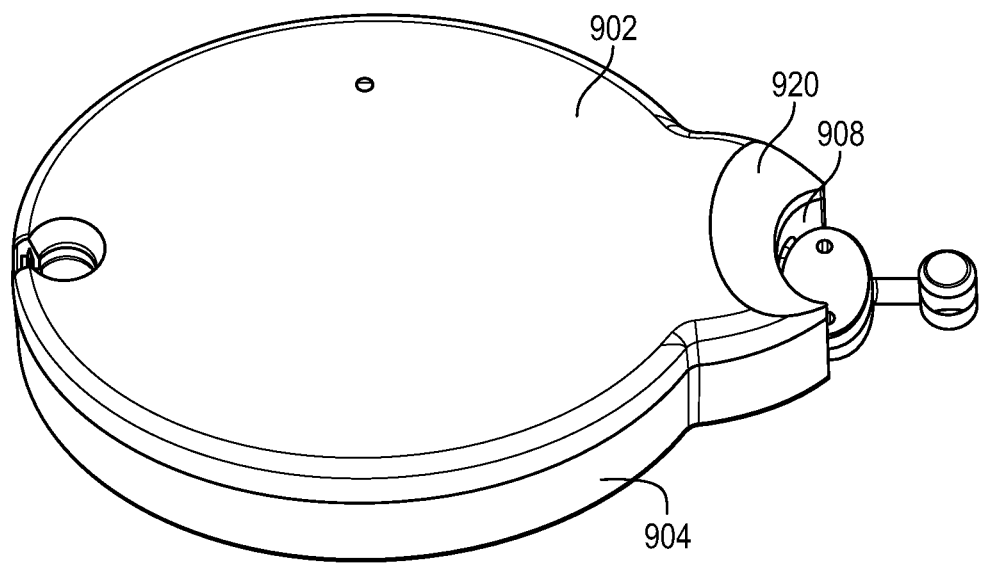

FIG. 187 shows a perspective view of a third version of the ninth embodiment of the breath training device.

Figure 188:
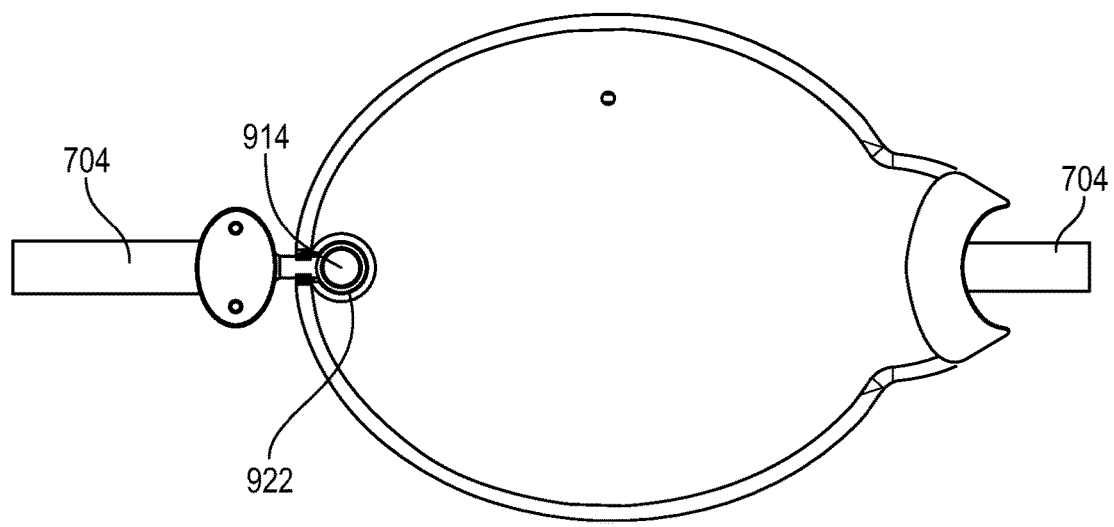

FIG. 188 shows the retractable belt deployed and plugged into the opposite side of the device housing.

Figure 189:
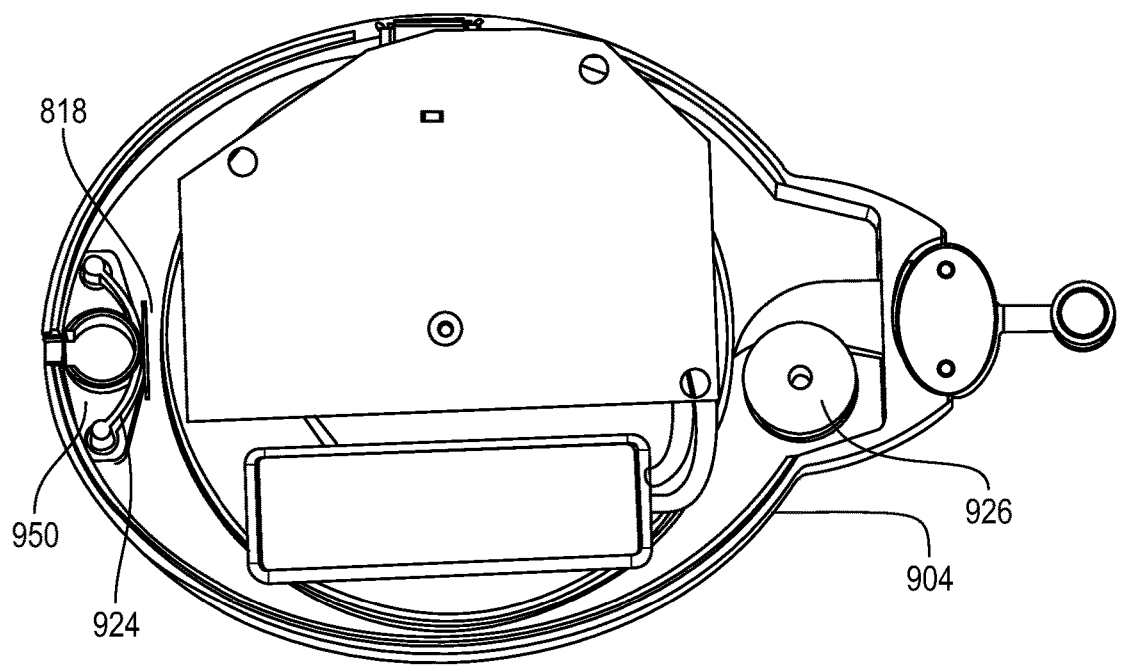

FIG. 189 shows the inside components of the device housing.

Figure 190:
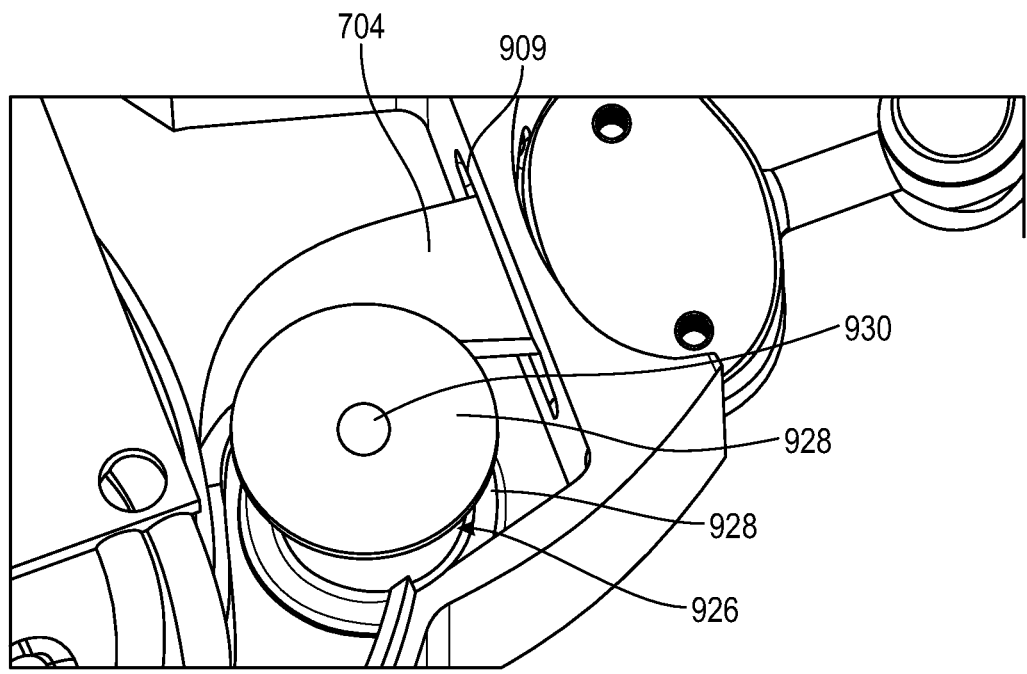

FIG. 190 shows an enlarged view of a roller, retractable belt, and belt exit slot.

Figure 191:
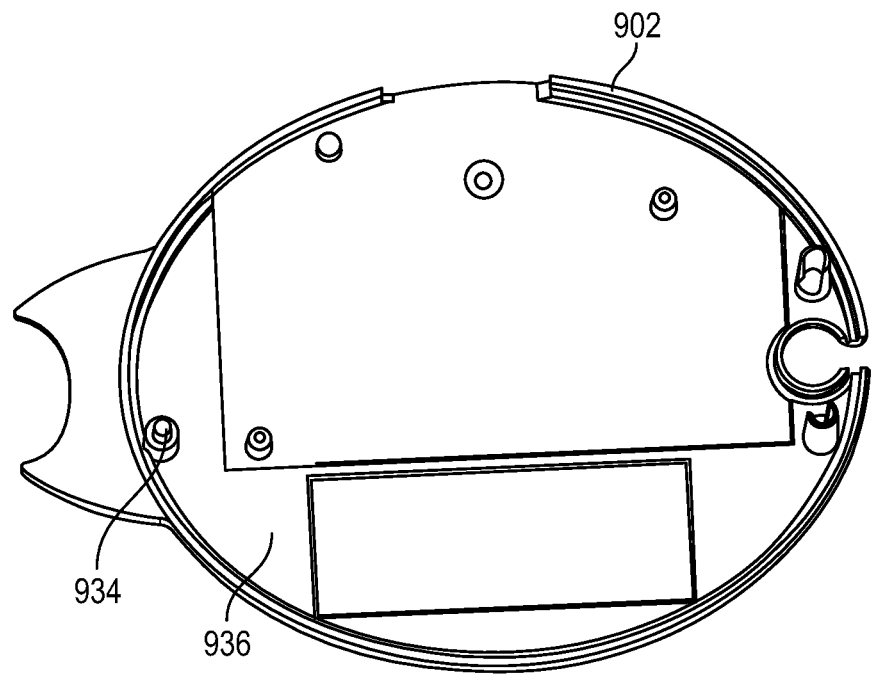

FIG. 191 shows the inner surface of a lid.

Figure 192A:
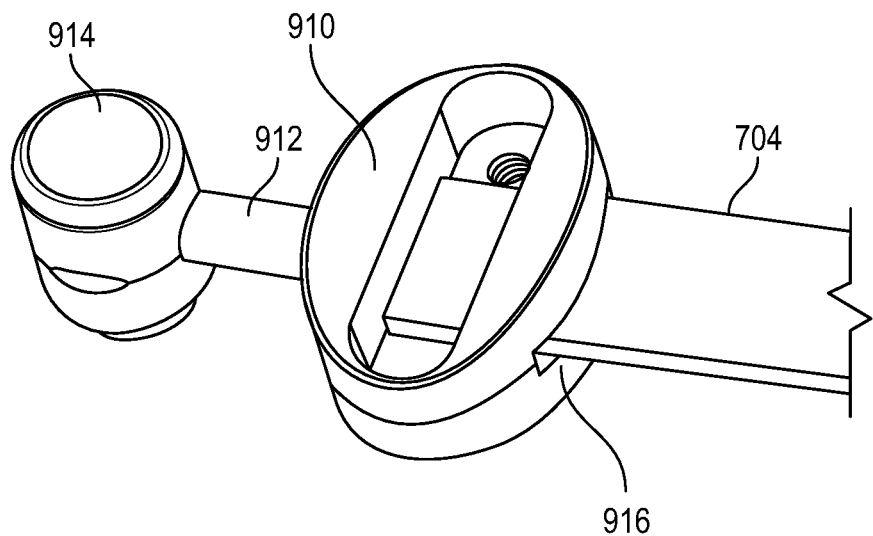

FIG. 192A shows the retractable belt inserted into a clip, prior to being clamped down.

Figure 192B:
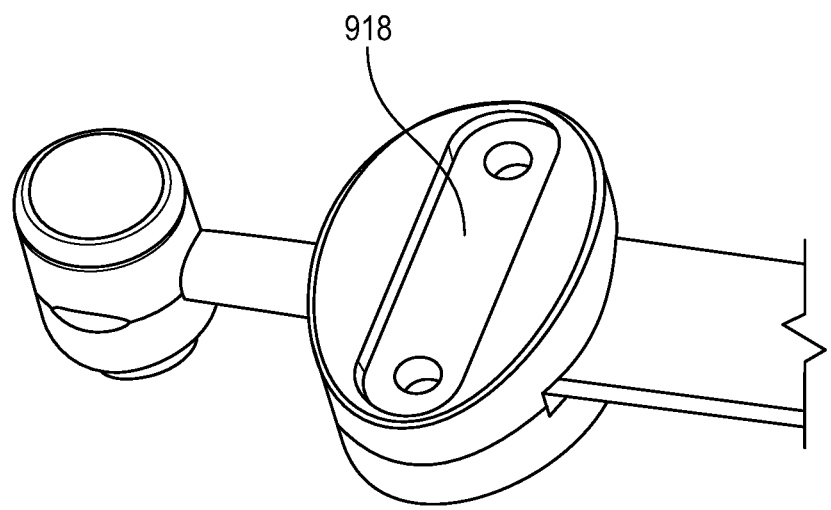

FIG. 192B shows the retractable belt inserted into a clip, clamped down with a clip plate.

Figure 193A:
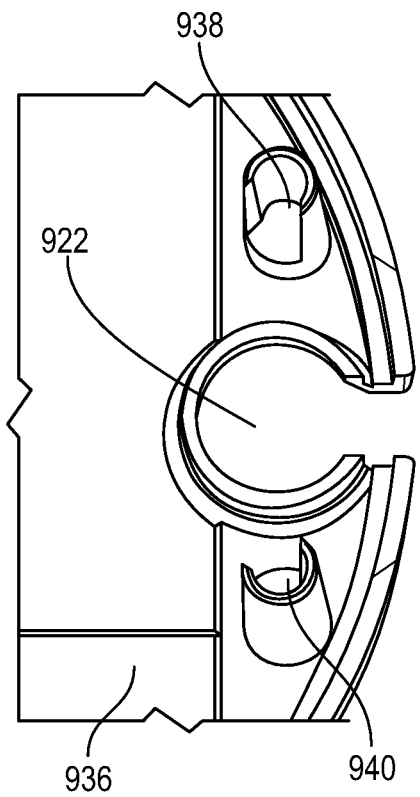

FIG. 193A shows the clip channel and flexing element holders on the inner surface of the lid.

Figure 193B:
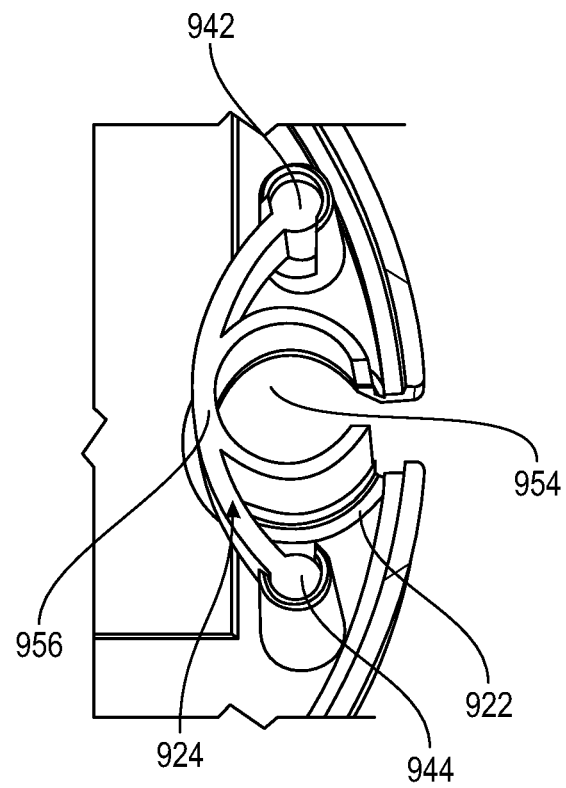
Figure 193C:
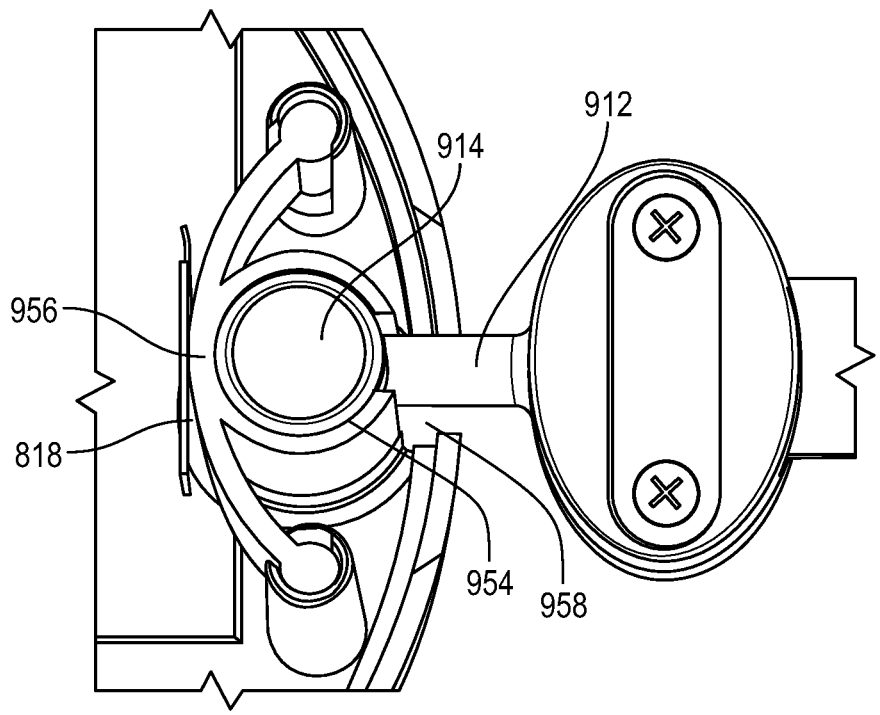

FIG. 193B shows the flexing element installed over the clip channel FIG. 193C shows the clip head fully plugged into the extended clip channel in the flexing element.

Figure 194:
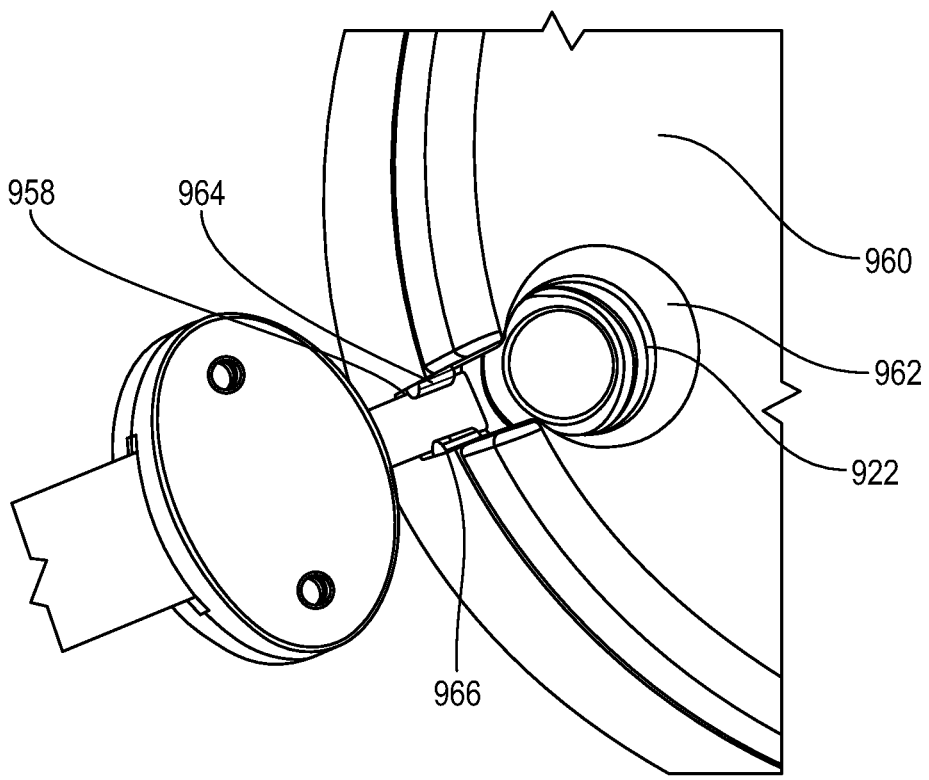
Figure 195:
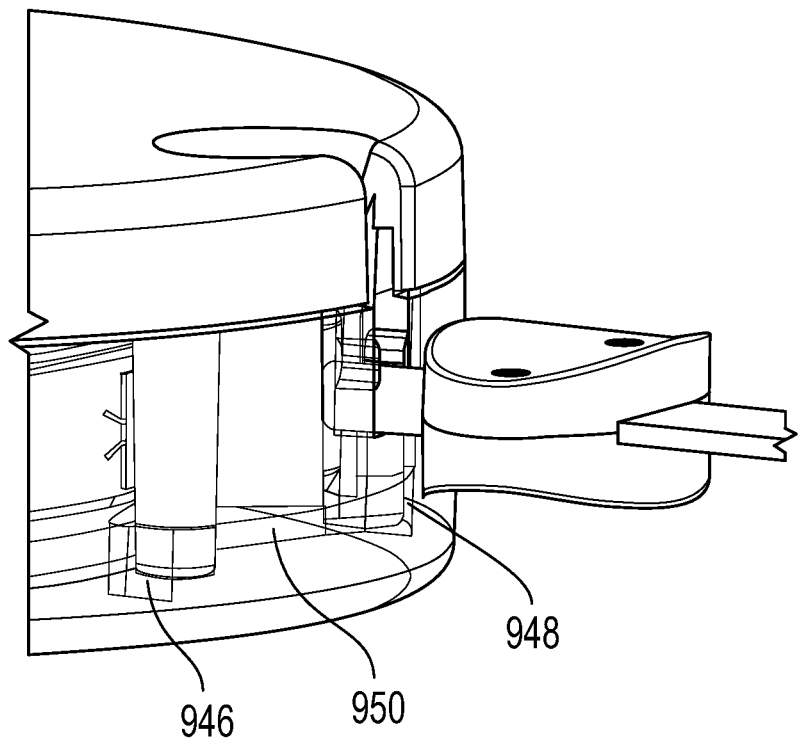
Figure 196:
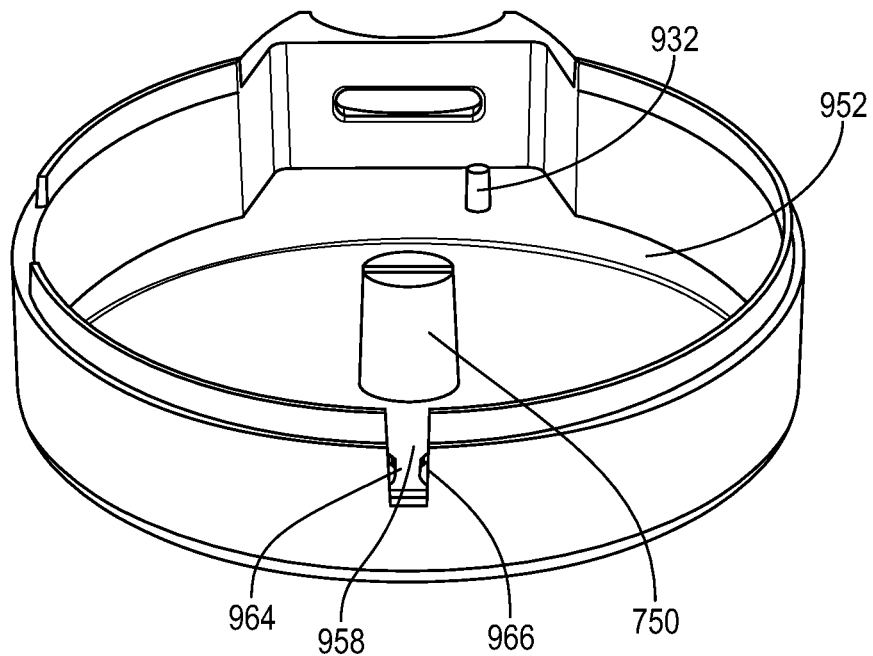

FIG. 194 shows the outer surface of the lid with the clip head plugged into the clip channel FIG. 195 shows a partially transparent view of the clip head plugged into the clip channel FIG. 196 shows an elevated view of the isolated device housing.

Figure 197A:
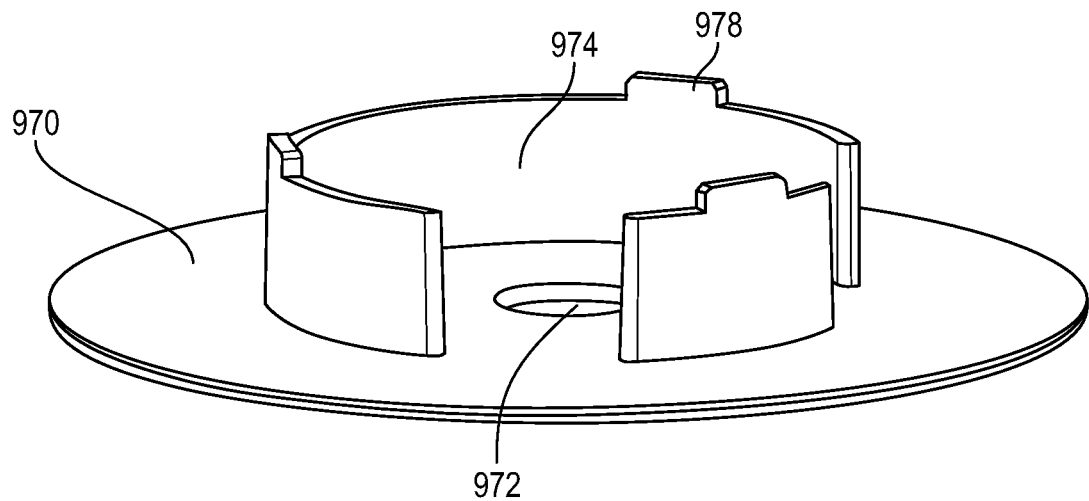

FIG. 197A shows the bottom plate with attached spring compartment of the reel.

Figure 197B:
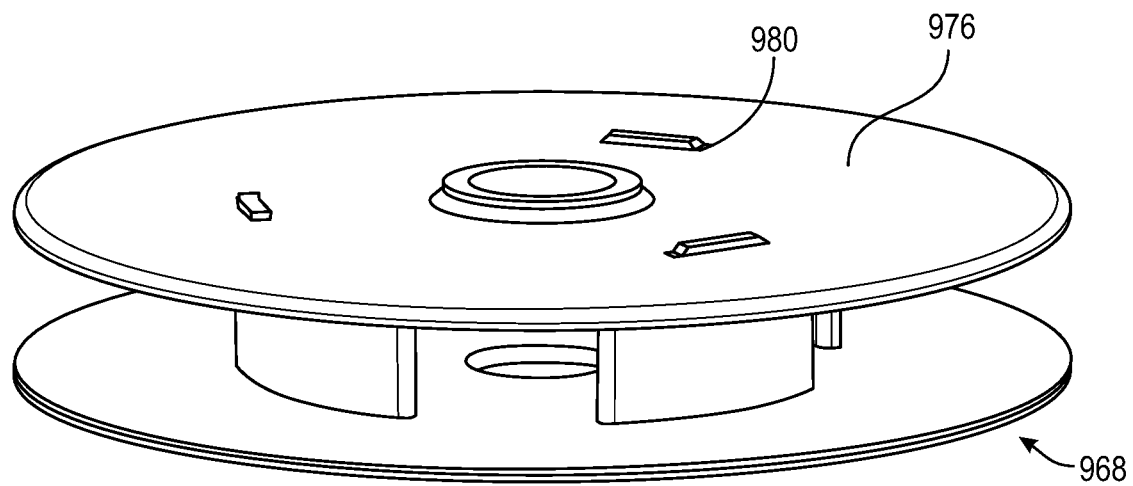

FIG. 197B shows the assembled reel with the top plate attached to the bottom plate.

Figure 198A:
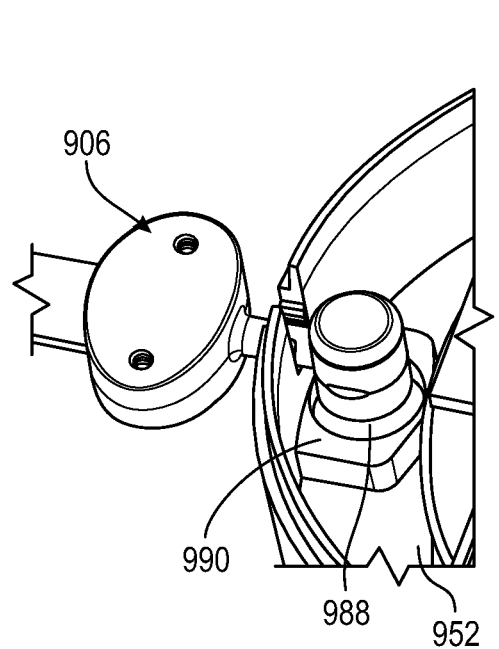

FIG. 198A shows a clip channel pedestal in the device housing.

Figure 198B:
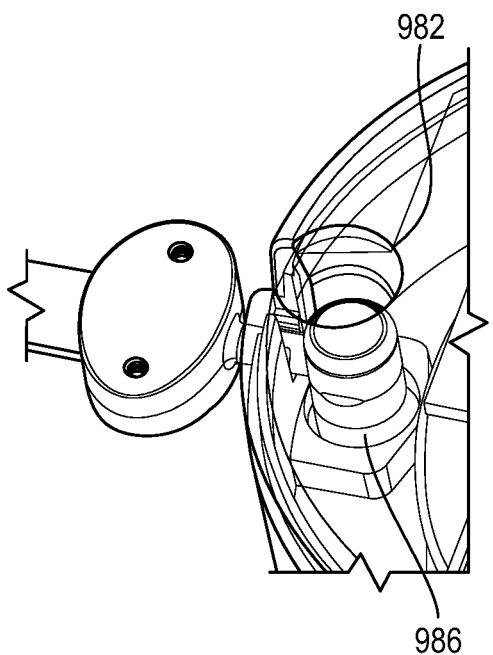
Figure 198C:
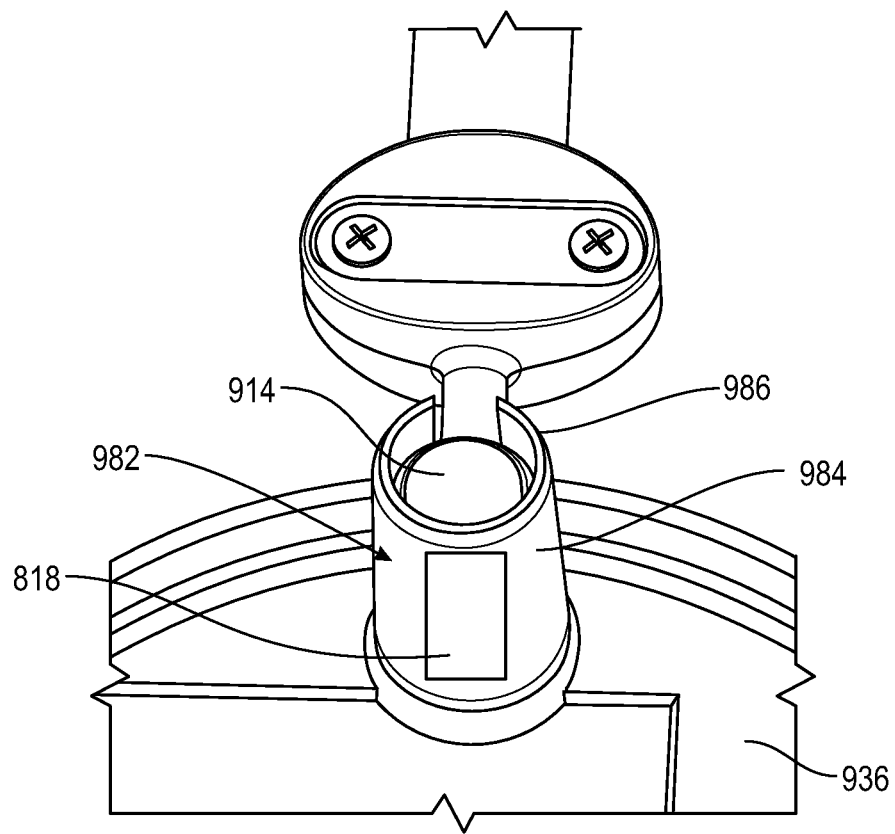

FIG. 198B shows a partially transparent view of the clip head plugged into an alternate embodiment of the clip channel FIG. 198C shows the clip channel attached to and extending from the inner surface of the lid.

Figure 199:
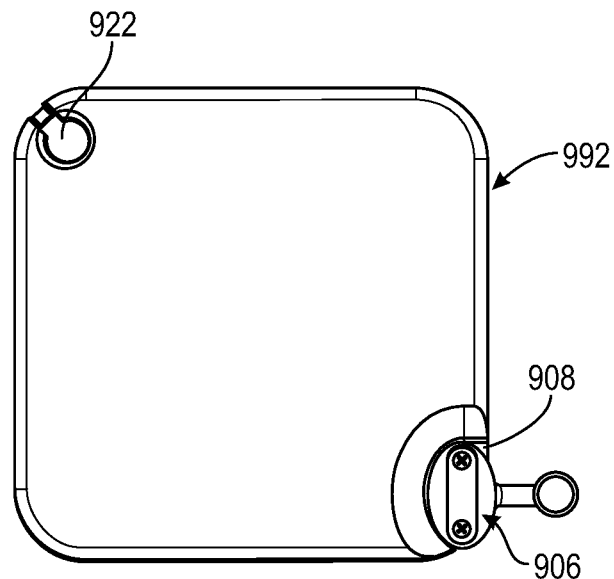

FIG. 199 shows an alternate embodiment of the third version of the ninth embodiment of the breath training device, showing a square device housing and lid, prior to the retractable belt being deployed.

Figure 200:
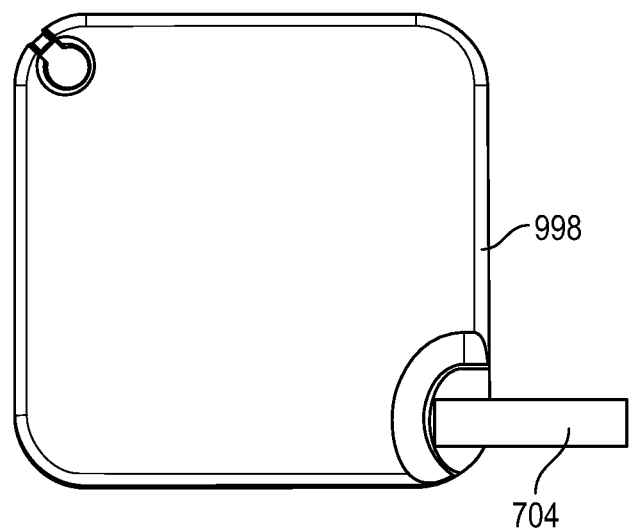

FIG. 200 shows the retractable belt has been withdrawn from the device housing, but not yet plugged in.

Figure 201:
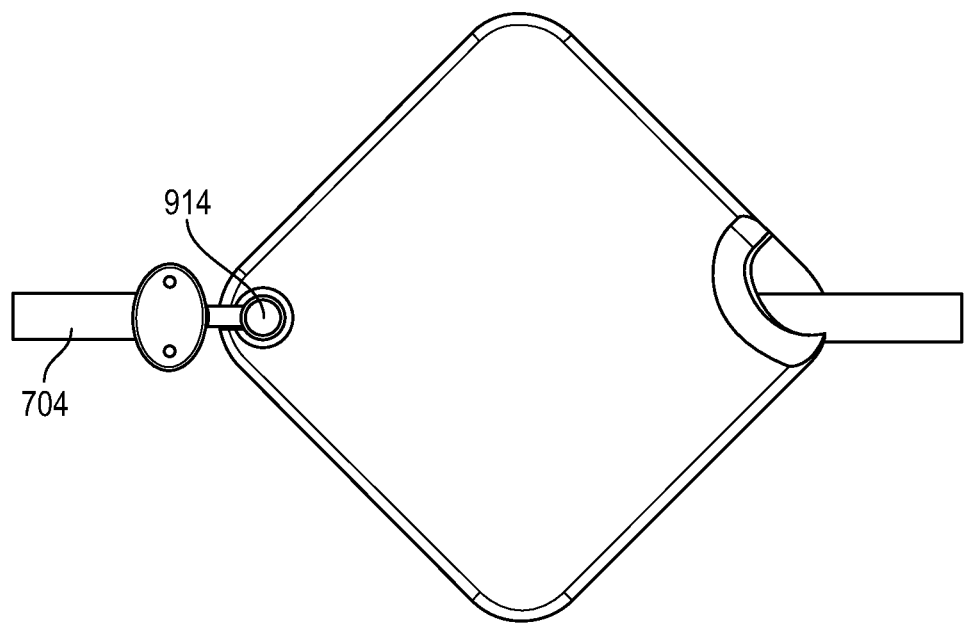

FIG. 201 shows the device housing and lid have been rotated 45 degrees after the retractable belt has been deployed, and the clip plugged into the clip channel to fasten the belt to the device housing.

Figure 202:
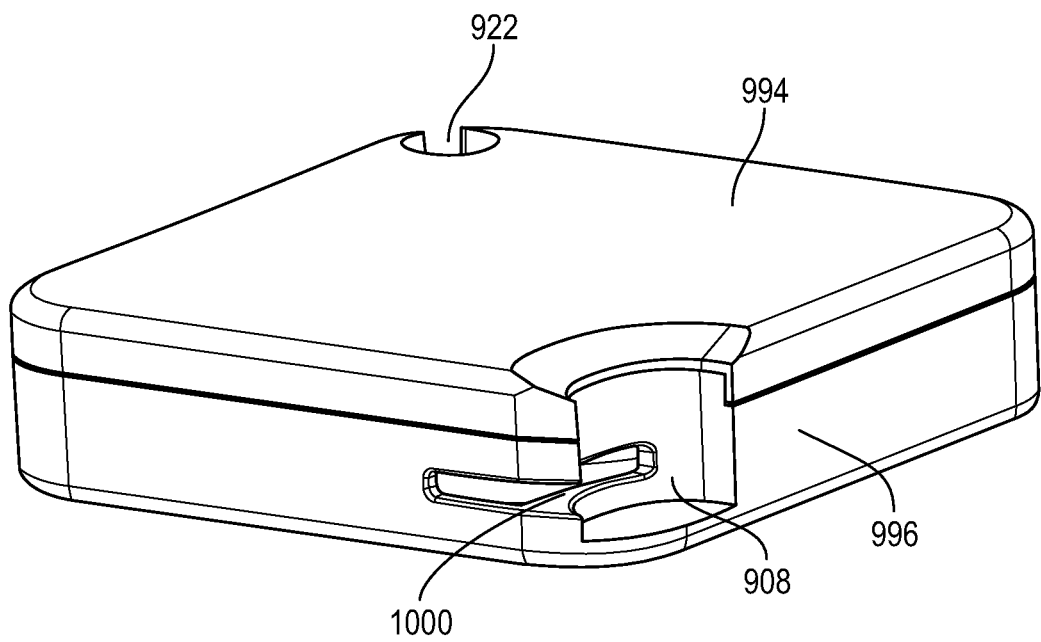

FIG. 202 shows a perspective view of the square device housing and lid, both with rounded corners.

Figure 203:
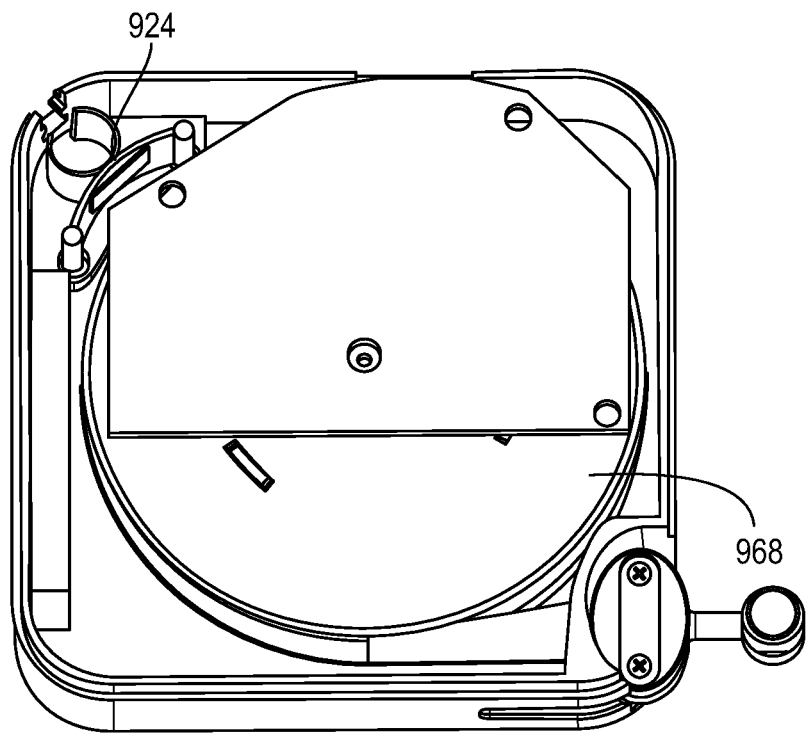

FIG. 203 shows the components inside the device housing, with the lid removed, prior to the retractable belt being deployed.

Figure 204:
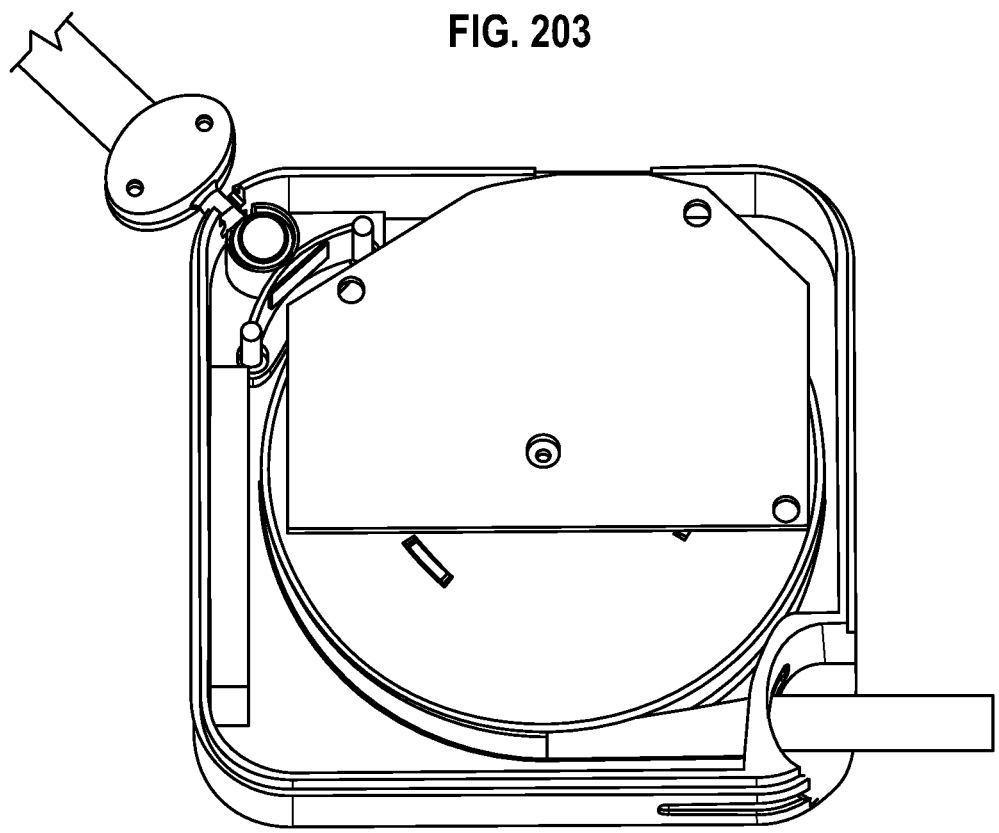

FIG. 204 shows the components inside the device housing, with the lid removed, after the retractable belt has been deployed and plugged in, but omitting the step of rotating the device housing and lid by 45 degrees.

Figure 205:
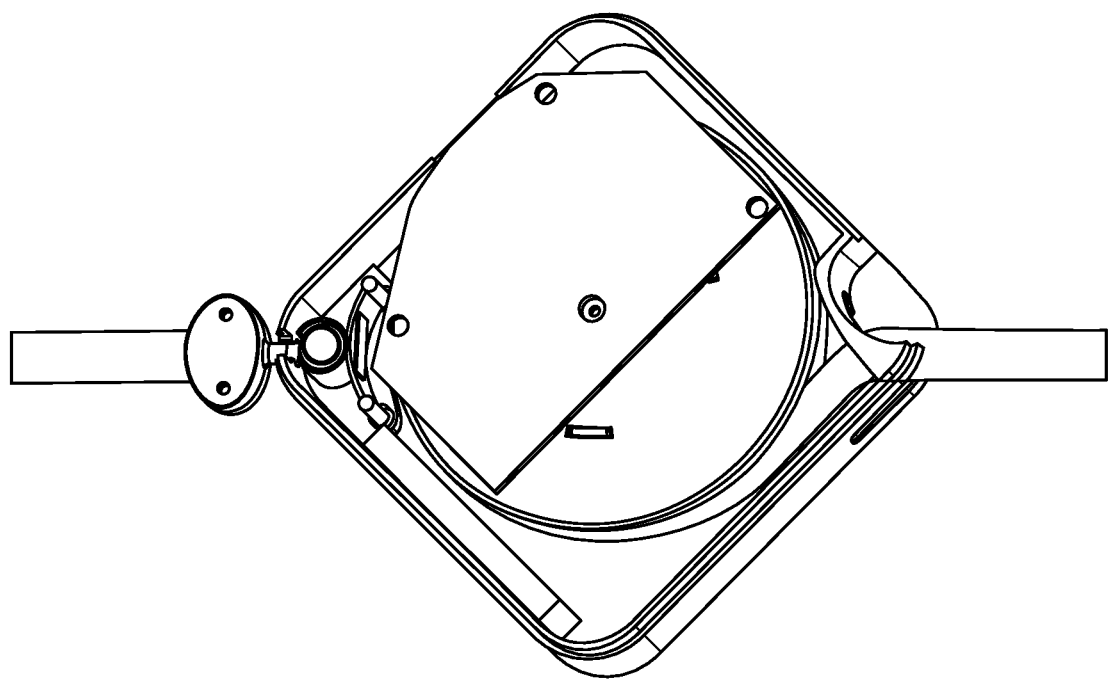

FIG. 205 shows the device housing with lid removed, having been rotated 45 degrees after the retractable belt has been deployed, and the clip plugged into the clip channel to fasten the belt to the device housing.

DETAILED DESCRIPTION OF THE INVENTION

Terminology

In the present disclosure, the terms "case" and "housing" will often be used interchangeably. The invention's device, system, and method will sometimes be referred to in the alternative by one or more of its specific uses, such as a "breath training device", "device for tracking respiration and posture", and other specific application names. Because, in some applications, the invention can be used for breath training, the invention is often referred to in the alternative as a "breath training device", but this term is not intended to be limiting. In fact, the present devices and methods can be used for a wide variety of different educational, entertainment, physiological, sports, and medical applications.

Similarly a breathing signal from a breathing sensor, as adjusted by data from other sensors such as posture sensors, is often referred to in the alternative as a "filtered breath signal".

As previously discussed, in some embodiments, the invention may be a device, system or method for tracking respiration and posture from a location on a human user.

This invention can comprise measuring user respiration by using a device comprising a housing, a computer processor, an electronic angle sensor, a belt (such as a retracting belt), one or more types of retracting mechanism, one or more types of fasteners (such as a housing mounted fastener), and an electronic breathing sensor to produce an electronic breathing sensor signal reporting on at least one of force and movement on the retracting belt.

Various types of belt or retracting belt mechanisms are possible. In some embodiments, this retracting belt can comprise a first belt end that is connected to a retracting mechanism, and a second belt end configured with a belt fastener that is configured to reversibly attach to a housing mounted fastener. This housing mounted fastener (housing fastener) can be built into the housing itself, or alternatively can be connected to the housing by a section of belt or belt-like material.

In some embodiments, the housing and the retracting belt are configured so that when the retracting belt is worn around the user's trunk, the user is "buckled in", (e.g. the belt fastener is attached to said housing fastener), the retracting belt experiences any of force and movement in response to user respiration. That is as the user inhales, the trunk expands, and there is force exerted on the belt in the direction of causing the belt to expand. As the user exhales, the trunk contracts, and any retracting force on the belt caused by the device will cause the belt to experience a force in the opposite direction, and/or will cause the belt to retract.

The breathing sensor (often called a displacement sensor, because it can measure any of a force or movement of displacement on the belt), produces a breathing sensor signal reporting on this respiration. According to the invention, an electronic angle sensor can be used to report on an angle of said user's posture with respect to a direction of gravity. This electronic angle sensor is typically configured so that when the retracting belt is worn around said user's trunk, and the belt is "buckled in" (e.g. the belt fastener is attached to the housing fastener), the angle sensor produces an angle sensor signal reporting on an angle of the user's posture (here often just the term "posture" is used). The invention can use its processor(s) to process these breathing sensor signal(s) and angle sensor signals, and produce various types of outputs. For example, in some embodiments, the invention may use the processor to produce one or more outputs reporting information such as the angle sensor data reporting on the user's posture, and breathing sensor data reporting on the user's respiration. The invention can also do more processing, either using housing mounted processors, or remote processors, and do additional processing such as reporting on posture adjusted user respiration data.

More sophisticated data processing schemes are also contemplated, and these are discussed later in this disclosure.

First Embodiment

Figure 1:
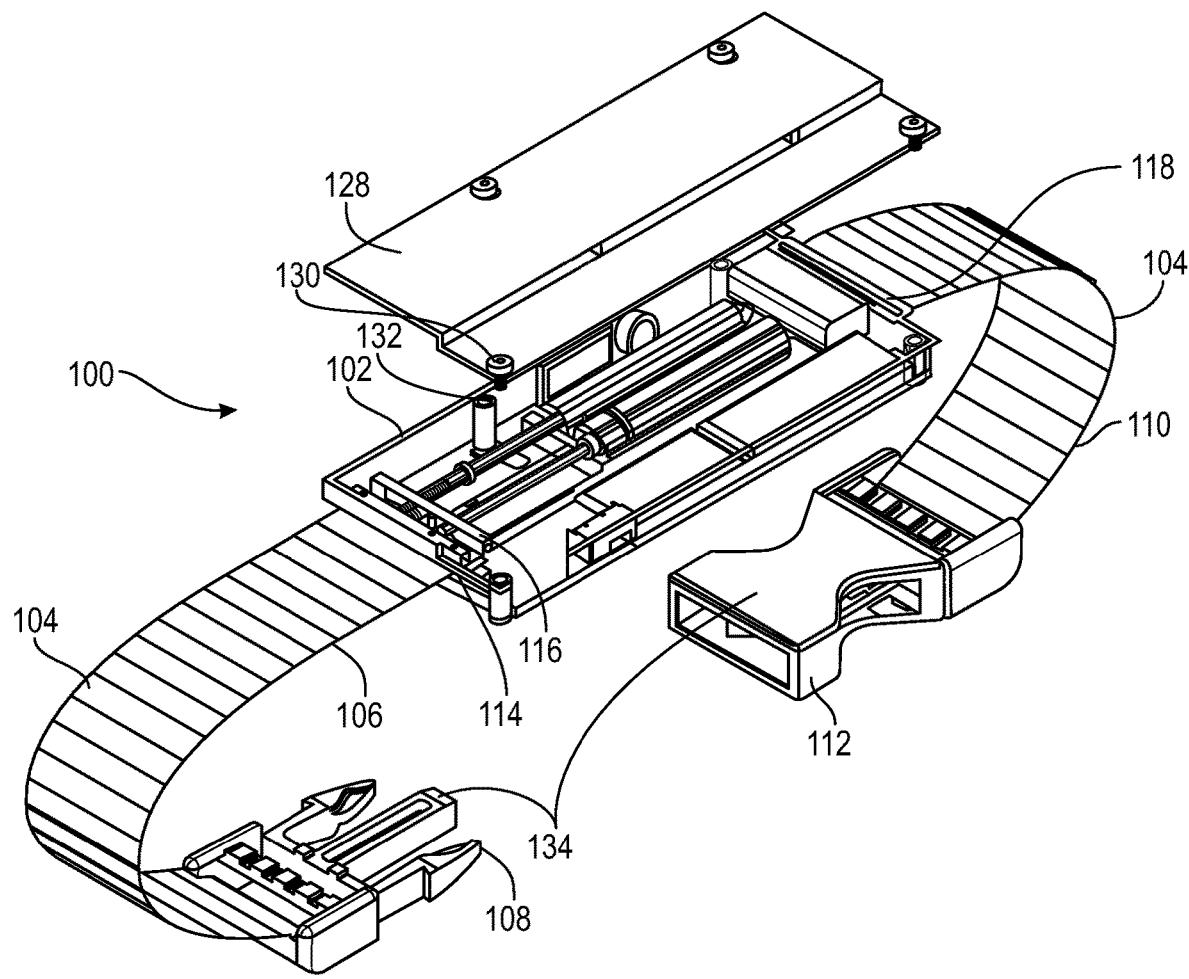
FIG. 1 is a perspective view of a first embodiment of a breath training device of the present invention.

Referring to FIG. 1, a breath training device 100 is shown according to a first embodiment of the present invention. Breath training device 100 is comprised of a case 102, a retractable respiration belt 104 that in some embodiments may be comprised of two halves including a prong belt 106 extending from its attachment point inside case 102 to a prong 108 on one end, and a fastener belt 110 (or other type of fastener) that may in some embodiments extend from an attachment point on the opposite side of case 102 to a fastener 112 on one end of the belt. In some embodiments, a prong belt travels through a slot 114 in case 102, and is attached to a belt slider 116 inside case 102. Fastener belt 110 is fixedly attached on the opposite side of case 102 to a belt loop 118. Alternately, the positions of prong 108 and fastener 112 can be swapped without altering the function of securing the belt on a user's body.

Various mechanisms can be used to make belt (104) a retractable belt that is configured with mechanisms that produce force configured to enable the belt to retract at least partially into case (102). These will be discussed in more detail shortly.

Figure 2:
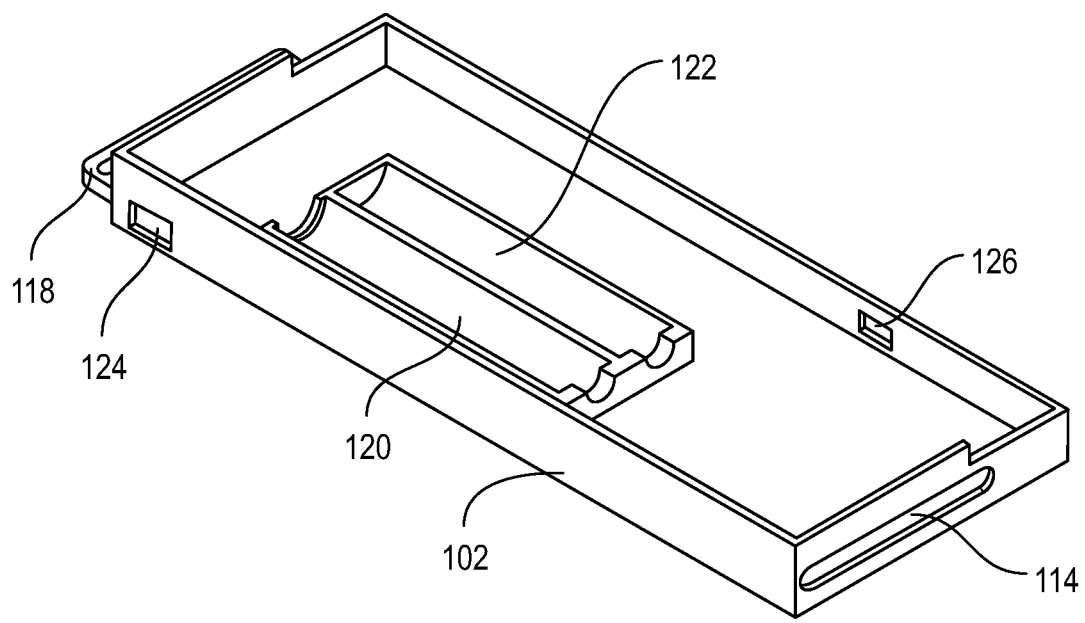
FIG. 2 is a perspective view of a case of the first embodiment of a breath training device of the present invention.
Figure 3:
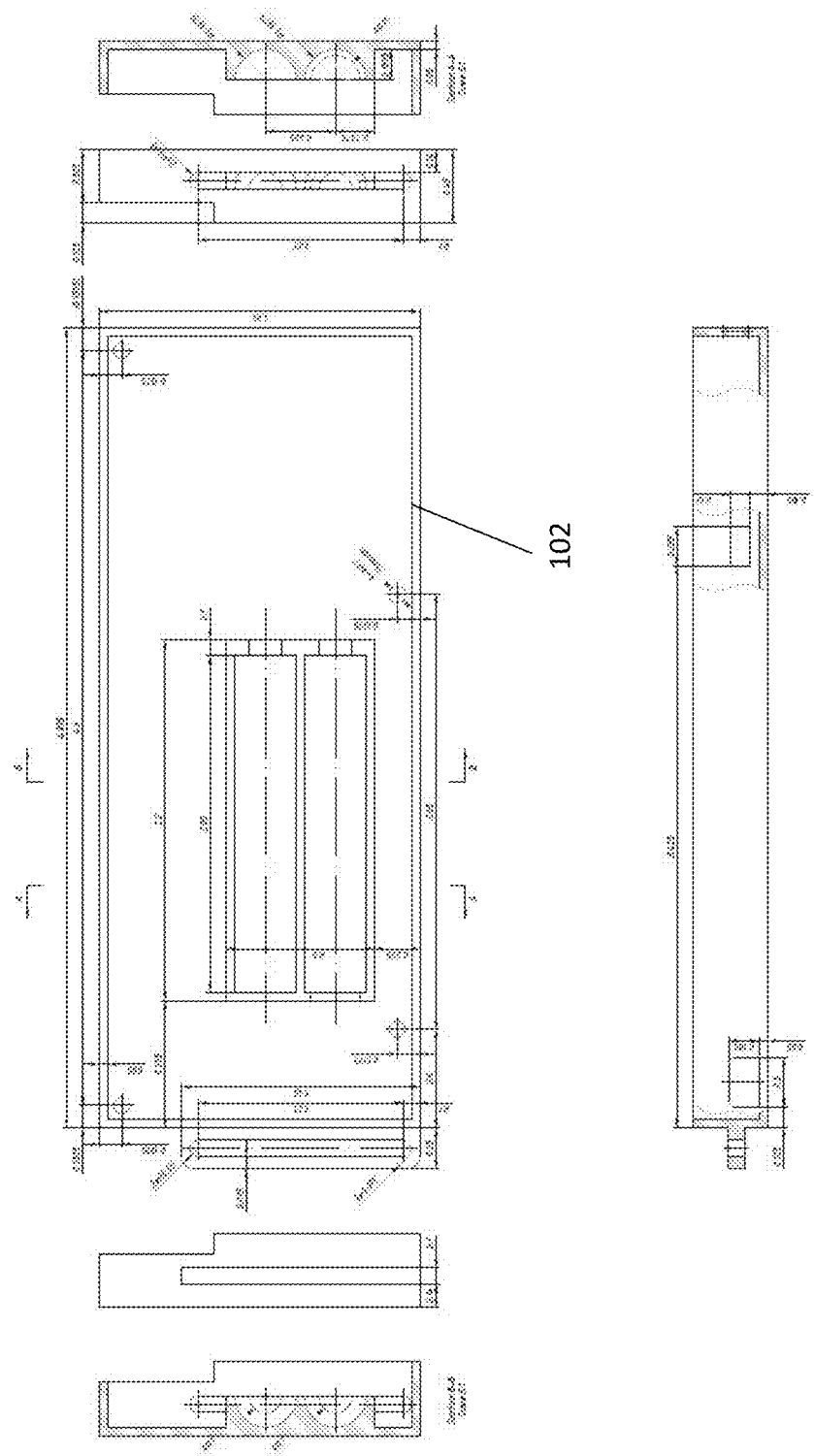
FIG. 3 is a schematic view of a case of the first embodiment of a breath training device of the present invention.

Case 102 is shown in rendered and schematic views in FIGS. 2-3. Referring to FIG. 2, case 102 can additionally have a displacement sensor (or breathing sensor) holder 120, a spring return holder 122, a port opening 124, and a switch opening 126. Case 102 can be made from plastic. As one alternative, its outer surface can be formed from a softer elastomeric material for better comfort against the body.

Respiration belt (e.g. retractable belt) 104 can be made from a variety of webbing materials, for example, including Nylon, polypropylene, polyester, seatbelt, tubular webbing, or other materials such as leather. Furthermore, respiration belt 104 can be made from an elastic material, but is preferably a non-elastic strapping material, since the expansion of a user's trunk during breathing should preferably drive the motion of belt slider 116 for measuring inhalation depth, and not drive the expansion of the belt material itself. Respiration belt 104 can be made in a range of widths, for example, between one and two inches, but smaller widths can also work.

Figure 4:
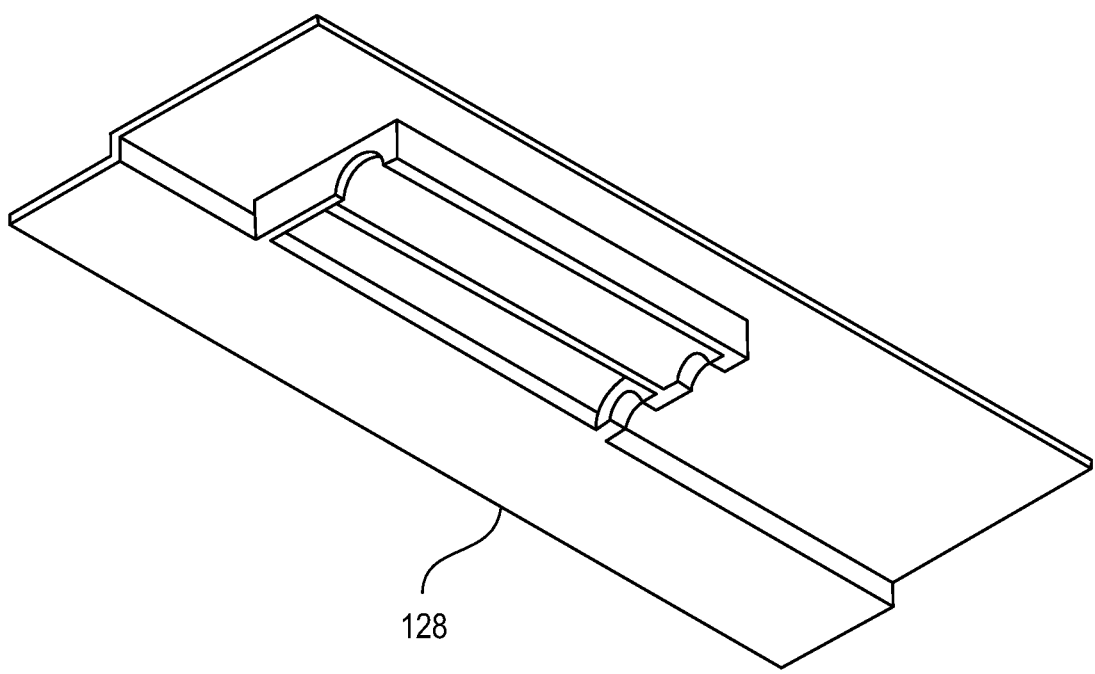
FIG. 4 is a perspective view of a lid of the first embodiment of a breath training device of the present invention.
Figure 5:
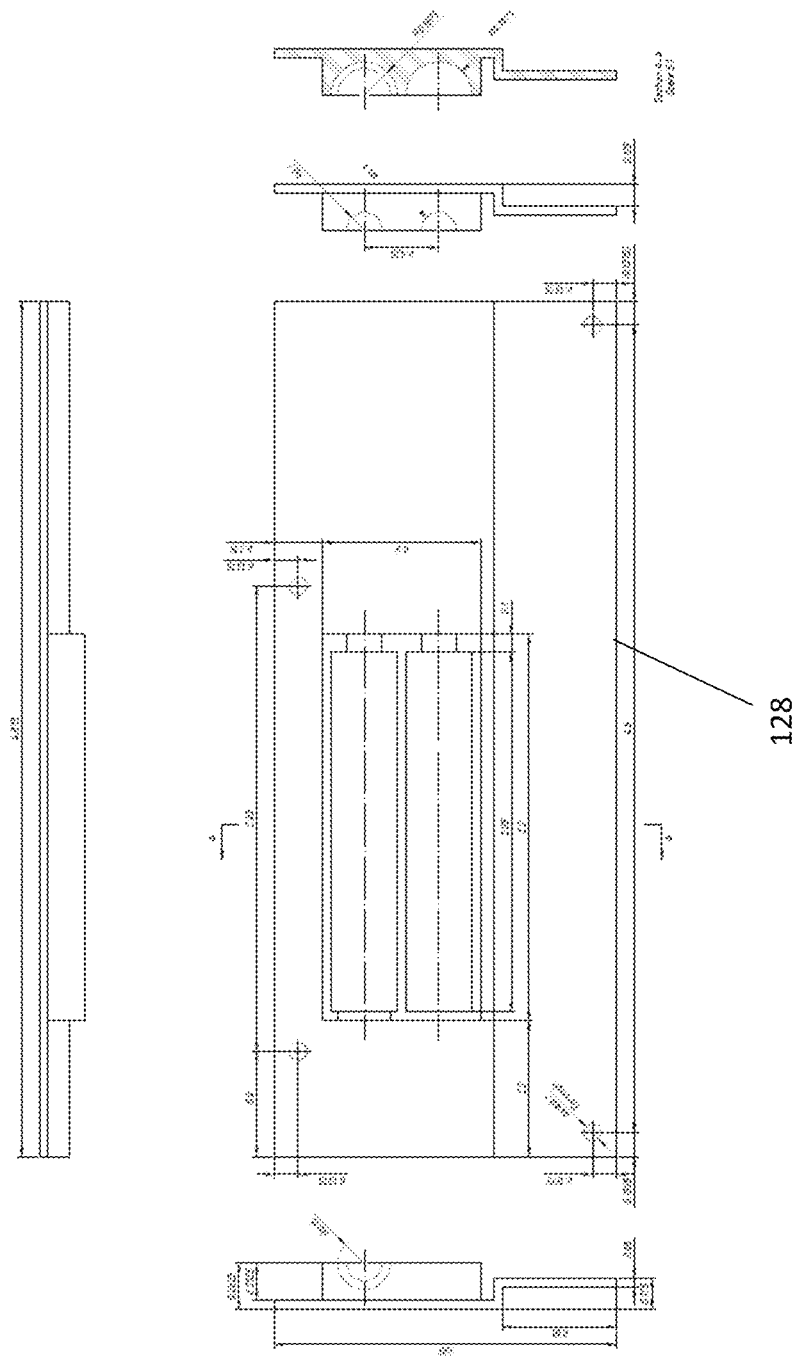
FIG. 5 is a schematic view of a lid of the first embodiment of a breath training device of the present invention.

Referring to FIG. 1, case 102 can further include a removable lid 128, with screws 130 securing said lid to sleeves 132 inside case 102. Lid 128 is further shown in rendered and schematic views in FIGS. 4-5. Alternately, case 102 can be sealed as a single piece without a removable lid.

Breath training device 100 can be worn around various portions of the user's trunk. For example, it may be worn around a user's waist or chest for tracking breathing, but preferably around the waist for detecting diaphragmatic breath, with case 102 positioned near the central lower back with lid 128 facing outwards, and belt fastener prong 108 and housing fastener 112 can be locked together around a user's navel area.

When prong 108 and fastener 112 are locked together, they form a buckle 134. Put alternatively, here the belt fastener 108 is attached to a housing fastener 112. Buckle 134 can be implemented, for example, as a dual side release buckle as shown in FIG. 1 (well known in the art), which allows prong belt 106 and fastener belt 110 to be equally lengthened or shortened to accommodate varying waist size, while keeping buckle 134 centered near the navel, and case 102 centered near the lower back of a user, with grip teeth 136 on prong 108 and fastener 112 for frictionally holding the adjusted length segments of prong belt 106 and fastener belt 110 from inadvertently changing under tension. Alternately, a central release dual buckle could be used, or many other possible well-known alternatives for securing two belt ends together, while allowing both ends to be equally adjusted in length so that case 102 can remain centered at the lower back after such length adjustments, and buckle 134 centered around the navel. For example, as an alternative, prong belt 106 and fastener belt 110 could each have a loop and separate hook fastener segment on their surface, where the hook surfaces on each belt could respectively pass through prong 108 and fastener 112, and then fold over to be pressed against its corresponding loop surface segment, at a varying distance, to symmetrically tighten and secure respiration belt 104 (not shown).

As previously discussed, because in some embodiments, the invention operates by sensing the displacement of the retractable belt during respiration, at least some embodiments of the breathing sensor will be termed the "displacement sensor". Note, however, that there can be more than one type of breathing sensor, and in some cases, useful breathing information can also be obtained from additional types of sensors as well, which will be discussed shortly.

Figure 6A:
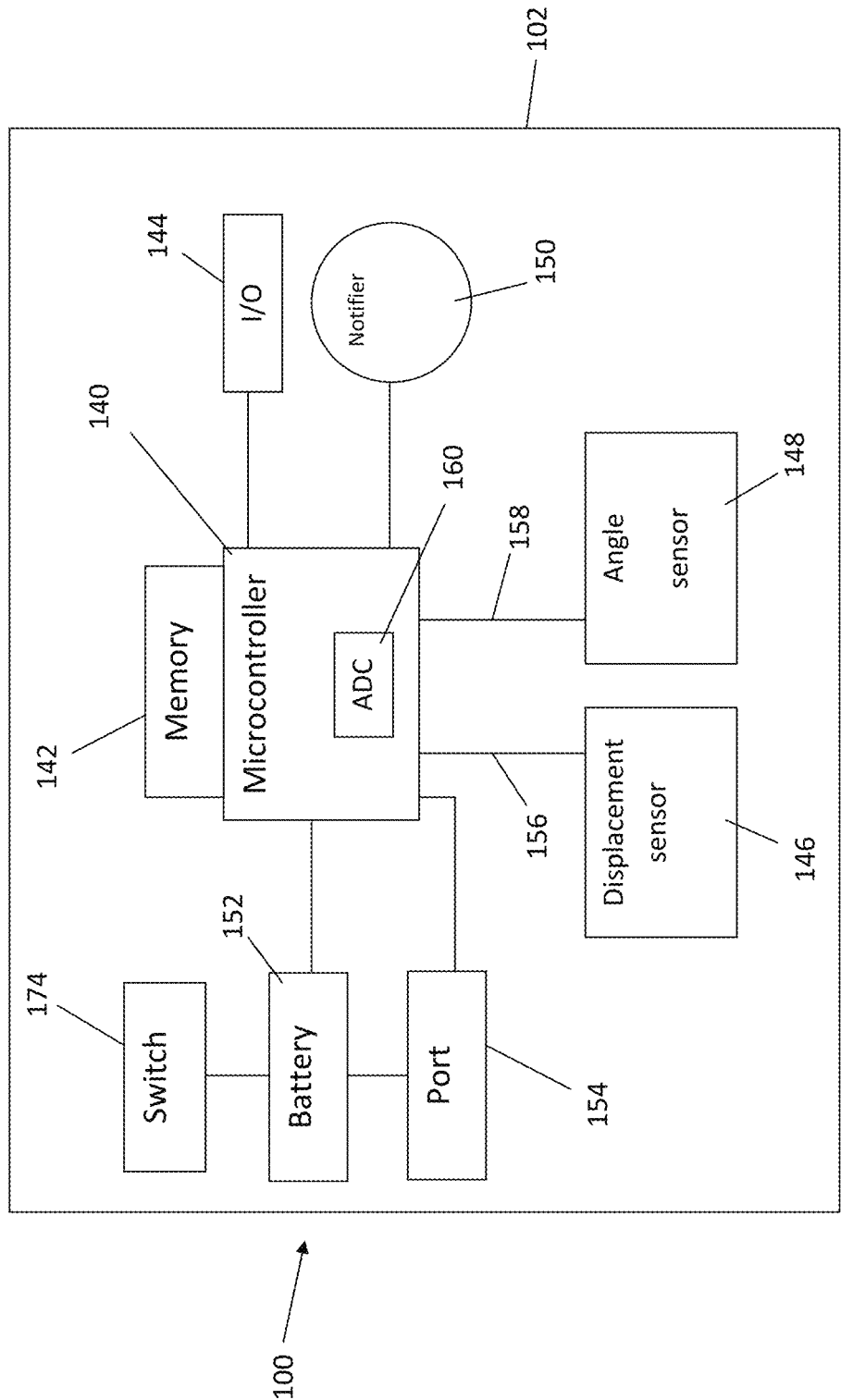
FIG. 6A is a block diagram of the electronic components of the first embodiment of the present invention.
Figure 6B:
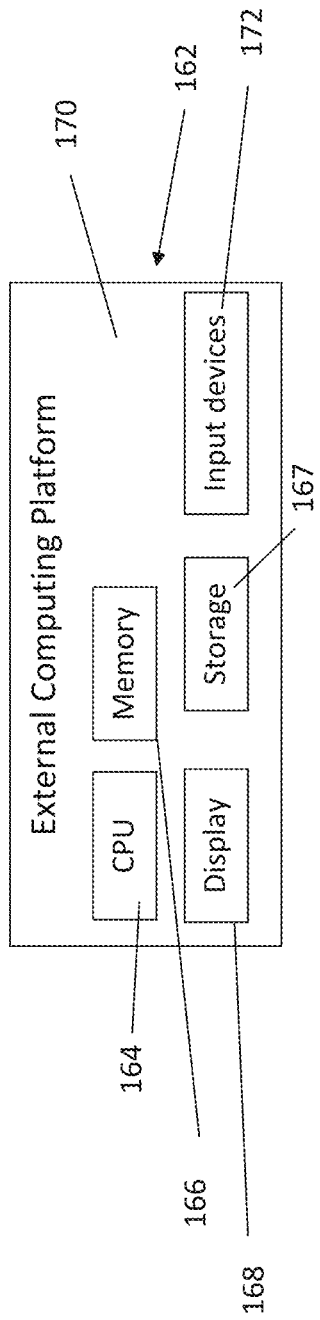
FIG. 6B is a block diagram of the electronic components of the first embodiment of the present invention

In FIGS. 6A and 6B, block diagrams of the electronic components comprising breath training device 100 are shown. Case 102 contains a microcontroller (e.g. processor) 140, a memory 142 for storing firmware and data, an I/O 144, a breathing sensor (e.g. displacement sensor) 146, an angle sensor 148, an optional notifier or output device 150 (e.g. such as an audio or visual output device) to alert the user of various states relating to breath evaluation, a battery 152, and a port 154 for battery charging and optionally for uploading new firmware and retrieving data stored in memory 142. Displacement sensor 146 and angle sensor 148 can be connected to microcontroller 140 by wires 156 and 158 for sending microcontroller 140 sensor output signals. A separate ADC (analog to digital converter) may be included (not shown), although many microcontrollers have an ADC 160 built in, as shown in FIG. 6. As one example, microcontroller 140 can be based on the Arduino platform, such as the Arduino Mini or Arduino Fio implementations, although many other microcontroller hardware platforms and brands are possible. It should be noted that the present invention is not limited to using a microcontroller. For example, a microprocessor or CPU could be utilized, with needed components such as memory, ADC, and I/O provided separately in case 102. Microcontroller 140 can simplify the hardware design by integrating many common processing-related functions in one system.

Memory 142, for example, can be a non-volatile memory, such as flash memory. Notifier 150 can be a buzzer or vibrational element which can vibrate case 102, or alternately, an audio component such as a small speaker to alert the user through audio cues in relation to certain breath states. I/O 144 is configured to allow transferring sensor output signals and other data to an external computing platform 162 with a CPU 164, memory 166, storage 167, display 168, platform I/O 170, and input devices 172 such as a keyboard, mouse, touchpad, touch screen, or one or more buttons. External computing platform 162 can, for example, be a laptop, desktop, tablet, smartphone, PDA, or watch computer, wherein data can be visualized and further evaluated using a breath training program later described in the operational section. Storage 167 can be a hard drive or flash memory for example for saving the filtered breath signal, breath scores, and other breath and posture statistics over time. I/O 144 also can be configured for receiving data from the external computing platform. I/O 144 can be wired or wireless based. For example, Bluetooth can be used to wirelessly transmit sensor output signals, as well as other wireless protocols. New firmware could also be uploaded into memory 142 using wireless transmission. If I/O is wired, a USB connection and cable, for example, could be used through port 154 to transmit data. In the first embodiment of the present invention, I/O 144 is preferably wireless based for convenience to the user to avoid cables while wearing breath training device 100. I/O 144 could be provided as a separate component from microcontroller 140 (as shown), or could be integrated on the microcontroller.

Thus in some embodiments, the invention (device) can further comprise a wireless transceiver. Here the device and processor can be further configured to use the processor and the wireless transceiver to transmit at least some of the various signals or data to an external computing platform, such as a smartphone, tablet computer, desktop computer, laptop computer, cloud server, IoT (Internet of Things) device, or other type external computing platform.

As shown in FIG. 6A, a switch 174 can further be included for switching on/off battery 152 power to all electronic components. Switch 174 could be a slider switch, push-button, rocker, or other type switch. Alternately, switch 174 could be excluded, and microcontroller 140 could be placed into a low power mode via a command through I/O 144, and similarly, woken up by a command sent through I/O 144, or when serial data arrives from I/O 144.

Displacement sensor (e.g. breathing sensor) 146 can be implemented in many different ways to measure the linear displacement of belt slider 116, and hence the change in a user's trunk girth or circumference. For example, displacement sensor 146 can be made using a linear potentiometer or slide potentiometer, a draw wire sensor or string potentiometer, a linear variable differential transformer (LVDT), a magneto-inductive displacement sensor, capacitive sensor to measure position and distance, eddy current sensor, laser distance sensor, confocal sensor, infrared sensor, sonar sensor, rotary displacement sensor such as a rotary potentiometer, flex sensor, a stretch sensor whose resistance changes when the material is stretched such as those available from Images Scientific Instruments Company, or other possible sensors which can measure displacement. Additionally, an electret foil or piezoelectric element could be used, or any element based on capacitive or inductive changes with body displacement. Additionally, textile sensors could be used which are integrated directly into a fabric or garment, using one or more of the above properties for sensing.

More generally, the breathing sensor (displacement sensor) can be coupled to at least one of the retracting mechanism and the belt. The breathing sensor can further comprise any of a linear potentiometer, a slide potentiometer, a draw wire sensor, a string potentiometer, a linear variable differential transformer, a magneto-inductive displacement sensor, a capacitive sensor, an eddy current sensor, a laser distance sensor, a confocal sensor, an infrared sensor, a sonar sensor, a rotary displacement sensor, a rotary displacement sensor comprising a magnetic rotary encoder, a rotary potentiometer, a flex sensor, a variable resistance stretch sensor, an electret foil sensor, an electric foil sensor, a piezoelectric element sensor, a magnetic rotary encoder, a strain gauge, and a textile stretch sensor.

Figure 7:
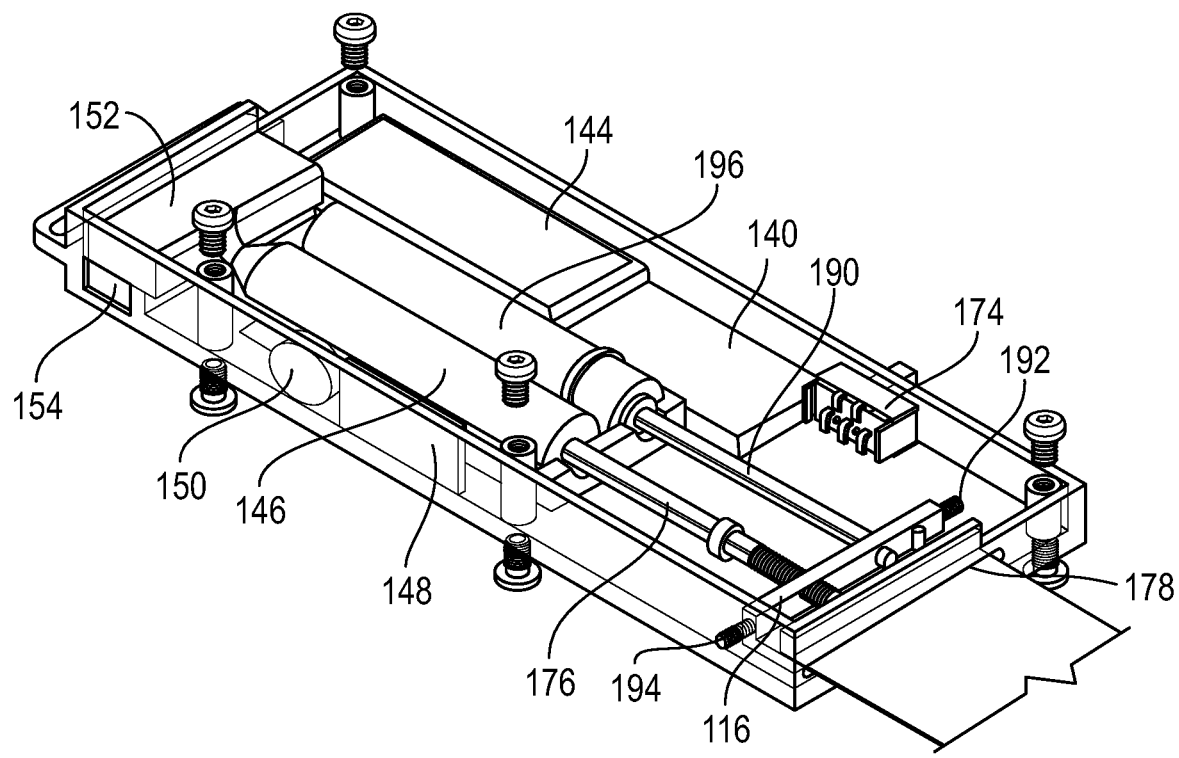
FIG. 7 is a perspective view of an open case of the first embodiment of a breath training device of the present invention.

As shown in FIG. 7, a moveable displacement sensor connector 176 connects displacement sensor 146 with belt slider 116. As will be discussed, additional mechanisms, such as one or more springs, spring loaded spools, and the like may also be used as needed to provide a retracting force on respiration belt 104 causing the belt to experience some force to at least partially retract the belt into the housing, thus creating a retracting mechanism that makes belt 116 a retractable belt. Displacement sensor connector 176 could be a rod, wire, string, belt, flexing element, or magnetic, capacitive, inductive, or other means to couple the motion of belt slider 116 with displacement sensor 146 so that said motion can be measured. See provisional application 62/519,160 the entire contents of which are incorporated herein by reference, for further discussion of the flexing element embodiment.

For example, as shown in FIG. 7, displacement sensor 146 can be made using a linear potentiometer such as the Miniature Linear Potentiometer, part LP804-01 manufactured by Omega Engineering, with displacement sensor connector 176 made as a rod, having a certain restricted range of mechanical travel, such as between one and two inches, causing a measurable and consistent change in output resistance of the linear potentiometer when said connector travels back and forth.

Angle sensor 148 can be an accelerometer for example, for measuring inclination changes or acceleration, having one or more axes along which said inclination changes or acceleration can be measured, although a variety of other sensor types with suitable sensitivity can be used. For example, one or more magnetometers or gyroscopes can be used. Magnetometers can measure angular position with respect to a magnetic field, while gyroscopes measure angular acceleration, from which angular position or inclination can be derived by integration for example.

In general, the angle sensor 148 can be any of an accelerometer, a magnetometer, and a gyroscope. Typically the angle sensor is configured to determine an orientation of the housing (case) with respect to any of a direction of gravity, a magnetic field, and/or a prior orientation of said housing. Accelerometers, for example, often operate with respect to a direction of gravity.

The additional mechanical components inside case 102 are now described. As shown in FIG. 7, a prong belt end 178 is attached to belt slider 116. Belt slider 116 can be made as a U-shaped block as shown schematically in greater detail in FIG. 8. All dimensions shown are provided as examples. Prong belt end 178 can be sandwiched between an upper jaw 180, and a lower jaw 182, with a plurality of jaw screws 184 securing both jaws together to hold prong belt end 178. Lower jaw 182 has openings 186 and 188 for holding a spring return rod 190, and displacement sensor connector 176. Stopper screws 192 and 194 can be used to fixedly secure spring return rod 190 and displacement sensor connector 176 in openings 186 and 188.

Figure 9:
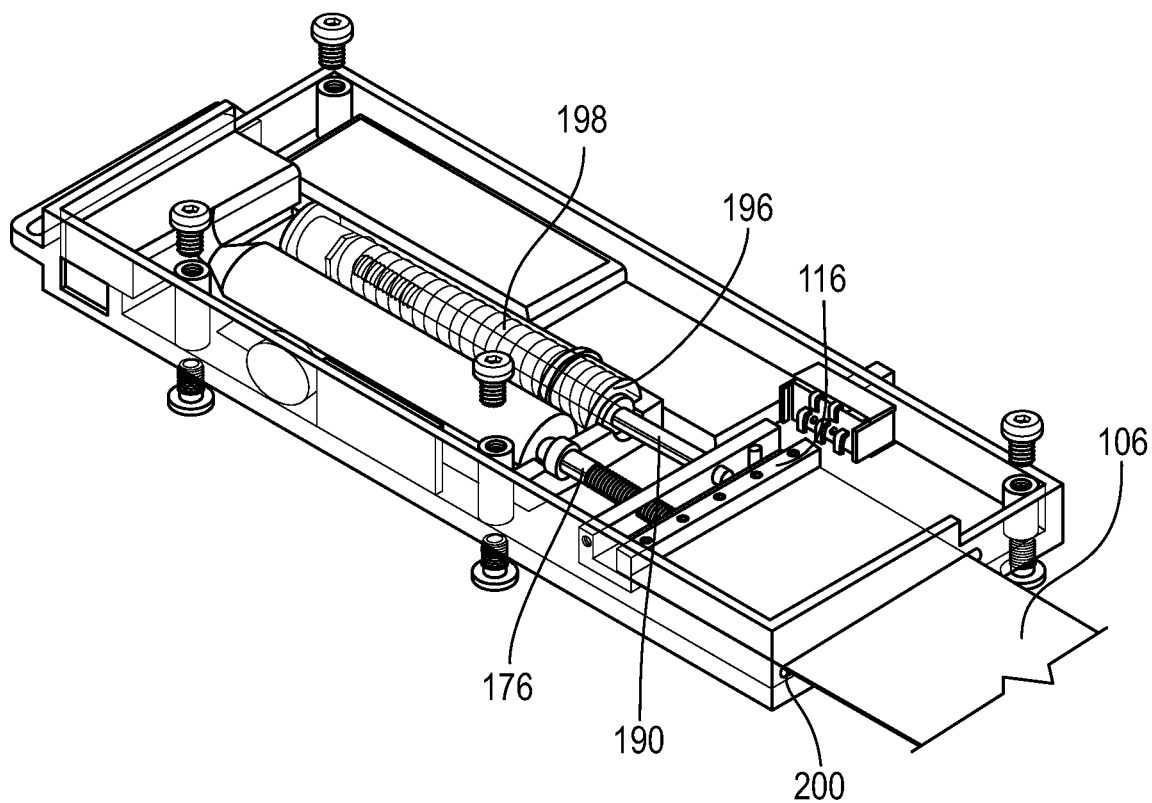
FIG. 9 is a perspective view of an open case of the first embodiment of a breath training device of the present invention with the respiration belt positioned prior to inhalation.
Figure 10:
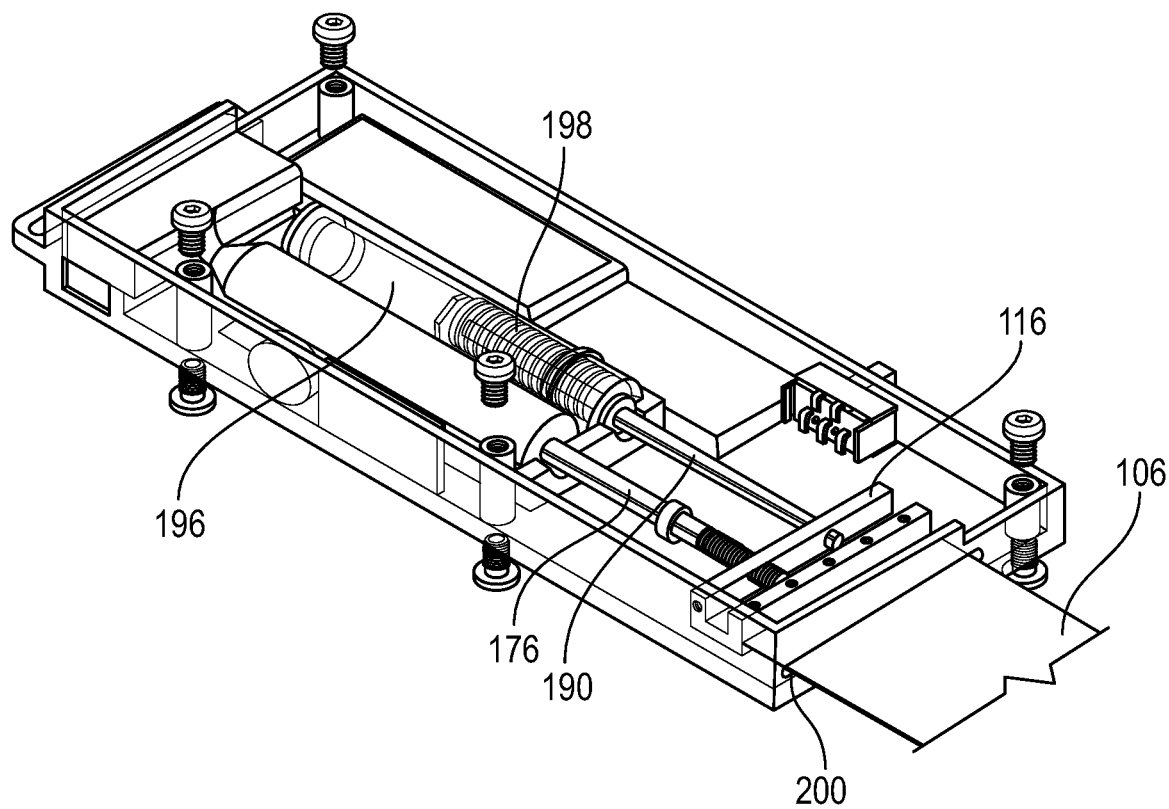
FIG. 10 is a perspective view of an open case of the first embodiment of a breath training device of the present invention with the respiration belt positioned after inhalation.
Figure 15:
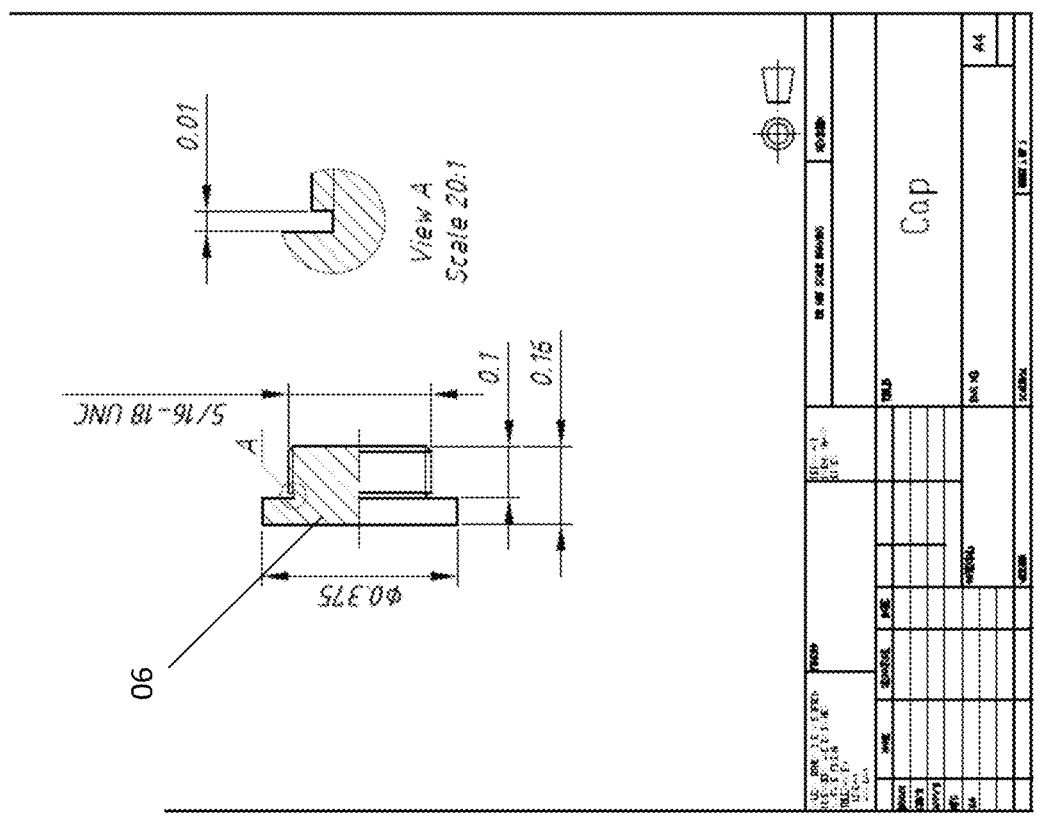
FIG. 15 is a schematic view of a cap of the first embodiment of a breath training device of the present invention.
Figure 16:
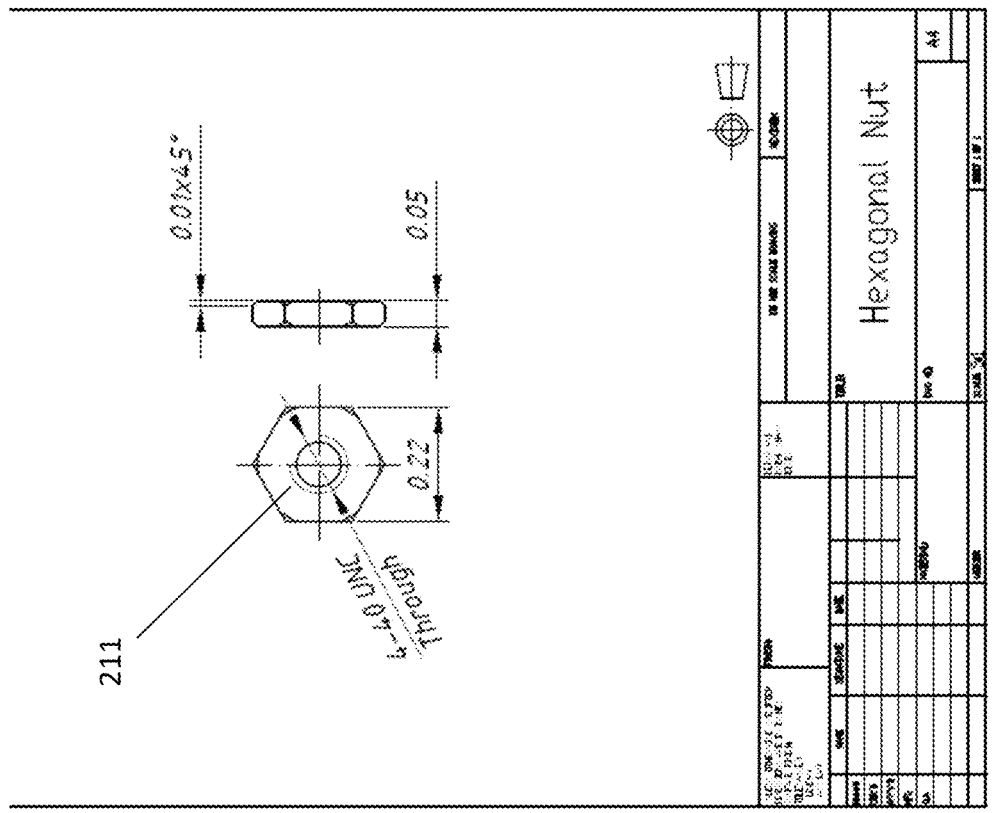
FIG. 16 is a schematic view of a hexagonal nut of the first embodiment of a breath training device of the present invention.
Figure 17:
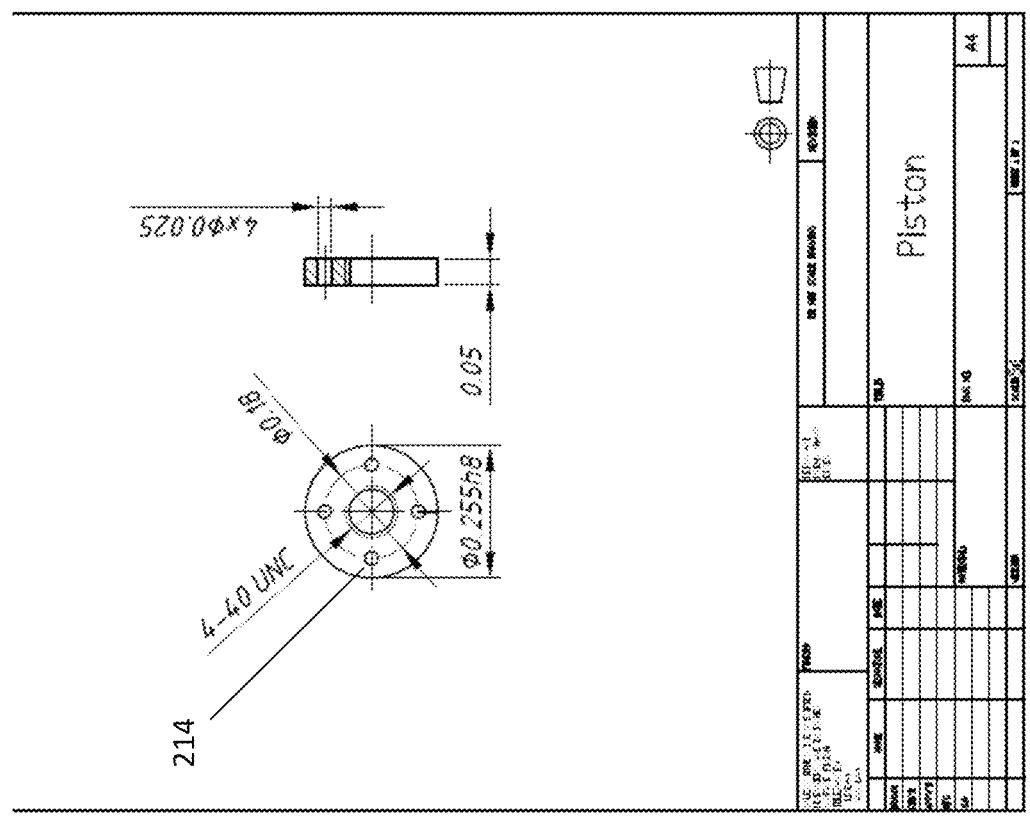
FIG. 17 is a schematic view of a piston of the first embodiment of a breath training device of the present invention.
Figure 18:
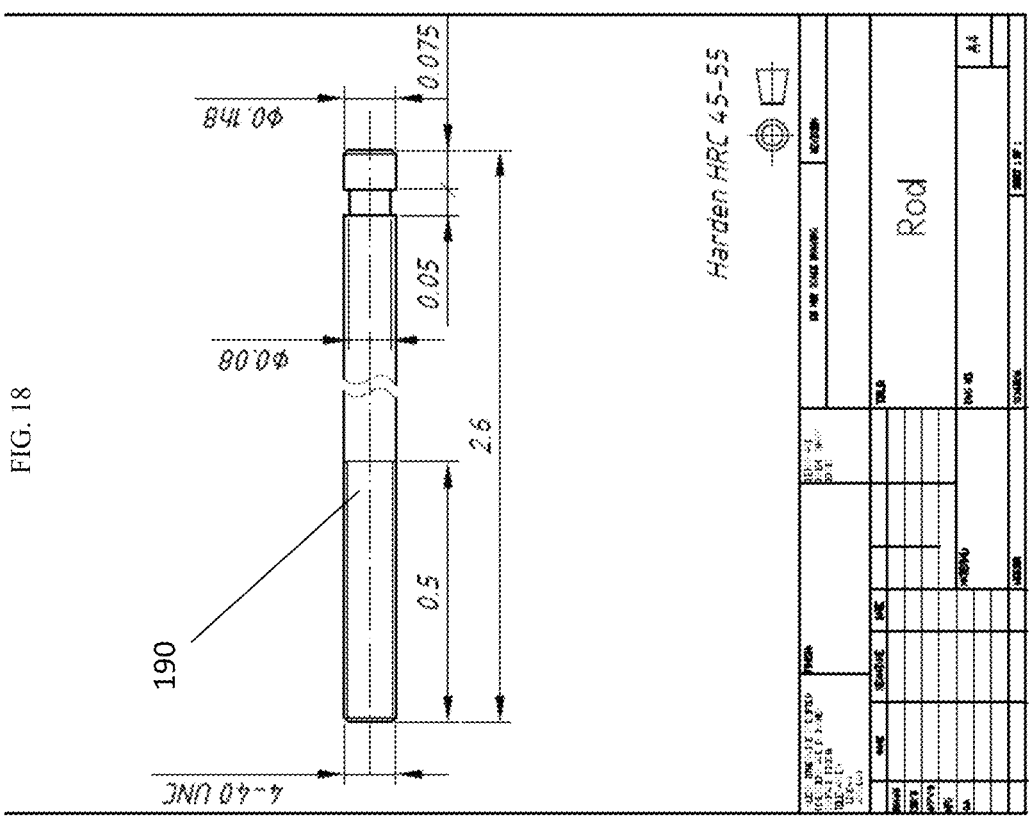
FIG. 18 is a schematic view of a rod of the first embodiment of a breath training device of the present invention.
Figure 19:
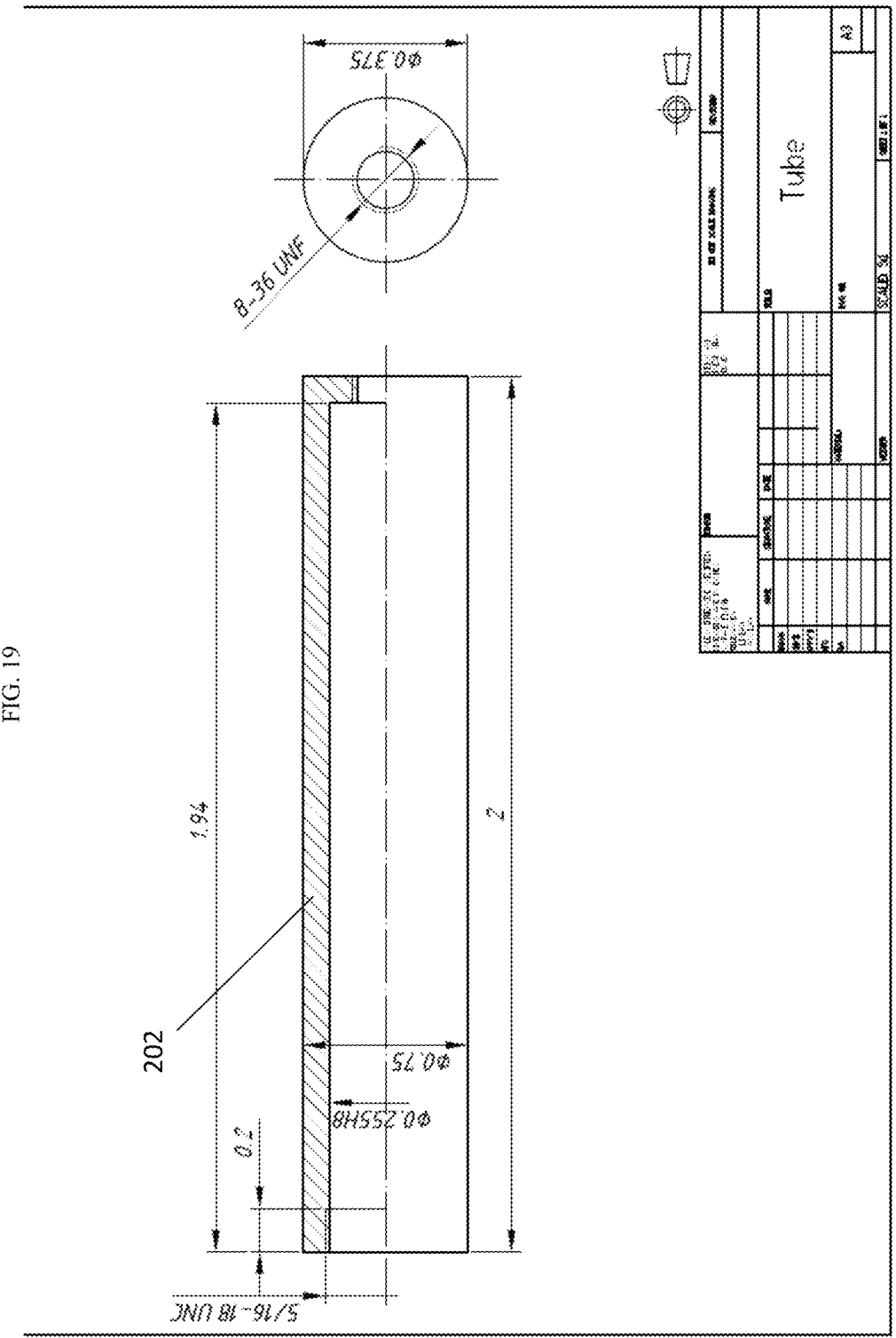
FIG. 19 is a schematic view of a tube of the first embodiment of a breath training device of the present invention.
Figure 20:
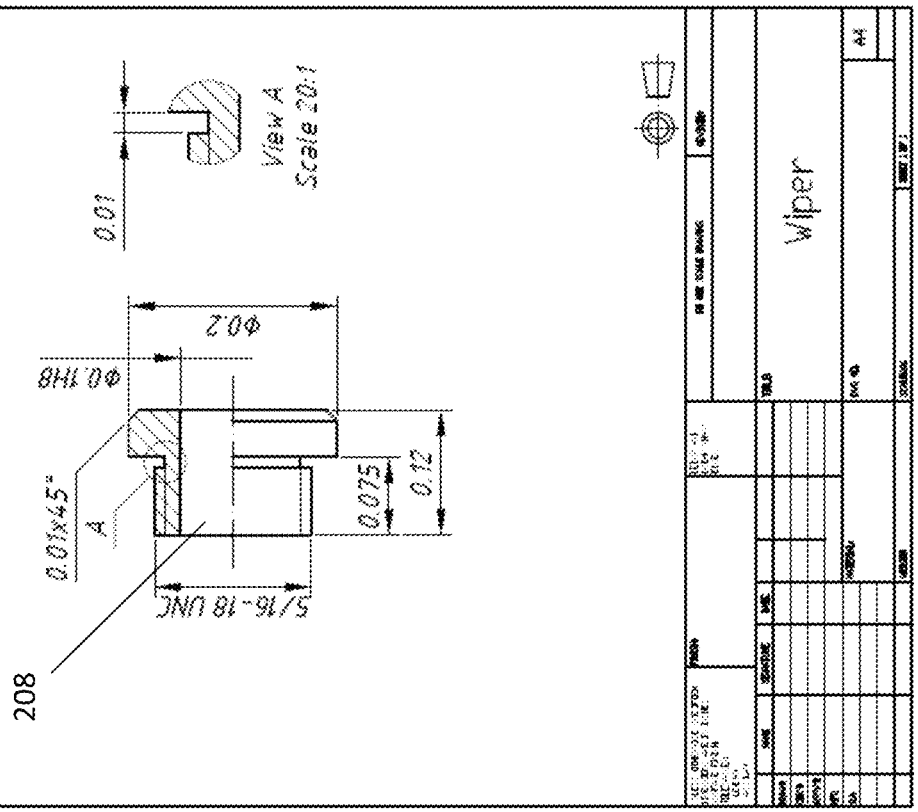
FIG. 20 is a schematic view of a wiper of the first embodiment of a breath training device of the present invention.
Figure 21:
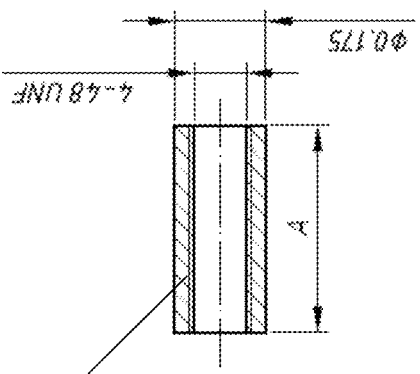
FIG. 21 is a schematic view of a sleeve of the first embodiment of a breath training device of the present invention.

Case 102 can contain a spring return 196 connected to spring return rod 190, to tension prong belt 106, causing it to return to its starting position after an exhalation is completed. As shown in FIG. 9, prong belt 106 and belt slider 116 are in a starting position, prior to a diaphragmatic inhalation, and a spring 198 inside spring return 196 is in a relaxed state. As shown in FIG. 10, an inhalation has occurred, causing an increase in trunk circumference, which pulls belt slider 116 together with spring return rod 190 and displacement sensor connector 176 towards slot 200 of case 102, causing spring 198 to be placed under tension. Then when a user is exhaling with decreasing trunk circumference, spring 198 under compression pulls spring return rod 190 back towards its starting position, together with belt slider 116, prong belt 106, and displacement sensor connector 176 as shown in FIG. 9.

In general, as will be discussed, this retracting mechanism can comprise a tension mechanism for placing the belt under tension during all phases of user respiration, so that the belt extends further out of the housing during user inhalation, and the belt retracts further into the housing during user exhalation.

Referring now to FIG. 11, a detailed description of one possible embodiment of spring return 196 is provided. Spring return 196 can comprise a tube 202, containing a central threaded channel 204, closed on one end with a cap 206, and a wiper 208 on its other end for guiding and supporting spring return rod 190 as it travels back and forth. Spring 198 resides in threaded channel 204, which also contains a hexagonal nut 211, a spring washer 212, and a piston 214 attached to spring return rod 190. The longitudinal position of hexagonal nut 211 can be adjusted to change the preload force on spring 198 and starting position of spring return rod 190. Spring return rod 190 runs through the longitudinal axis of spring 198, and piston 214 provides a support against one end of spring 198. When spring return rod 190 is pulled out of tube 202, this causes piston 214 to compress spring 198 longitudinally against narrowed end 210 of tube 202. Releasing spring return rod 190 then causes spring 198 to decompress and push piston 214 back towards the starting position of spring return rod 190, pulling prong belt 106 back with it. FIG. 12 shows a possible travel range of spring return rod 190, displacement sensor connector 176, and belt slider 116. FIG. 13 shows a side view of displacement sensor 146 with belt slider 116 attached, and FIG. 14 depicts a longitudinal view of a possible orientation of displacement sensor 146 with respect to spring return 196. FIGS. 15-21 respectively show cross sections of the components of spring return 196, including cap 206, hexagonal nut 211, piston 214, spring return rod 190, tube 202, wiper 208, and sleeves 132.

Figure 22:
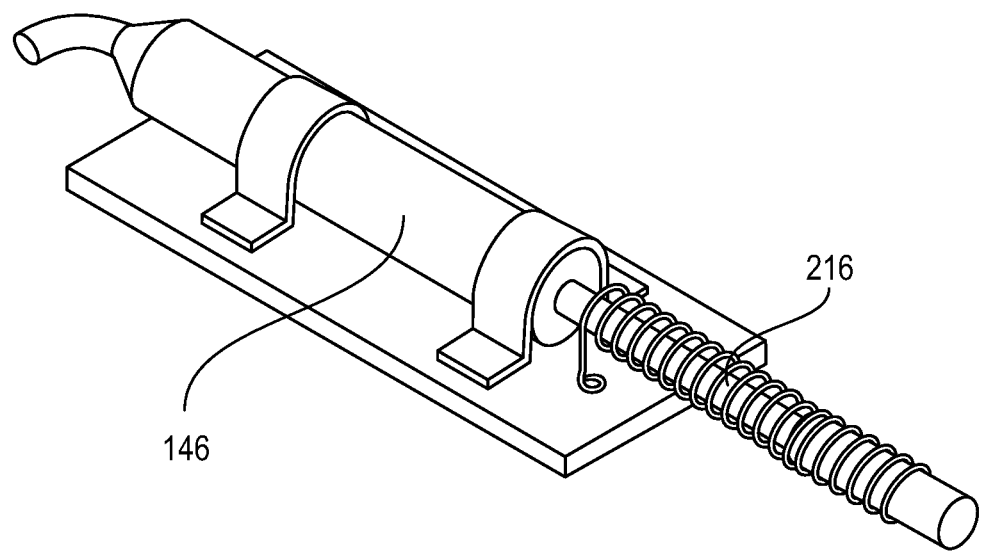
FIG. 22 is a perspective view of an alternate spring return of the first embodiment of a breath training device of the present invention.

As shown in FIG. 22, it is also possible to integrate a coaxial spring return 216 as part of displacement sensor 146, for example, by positioning a spring coaxially with displacement sensor connector 146. Alternately, spring return 196 can be made using a gas spring, which can offer the advantage of a more uniform restoration force across the various positions of spring return rod 190, compared to a compression or extension spring for example (not shown).

Figure 22A:
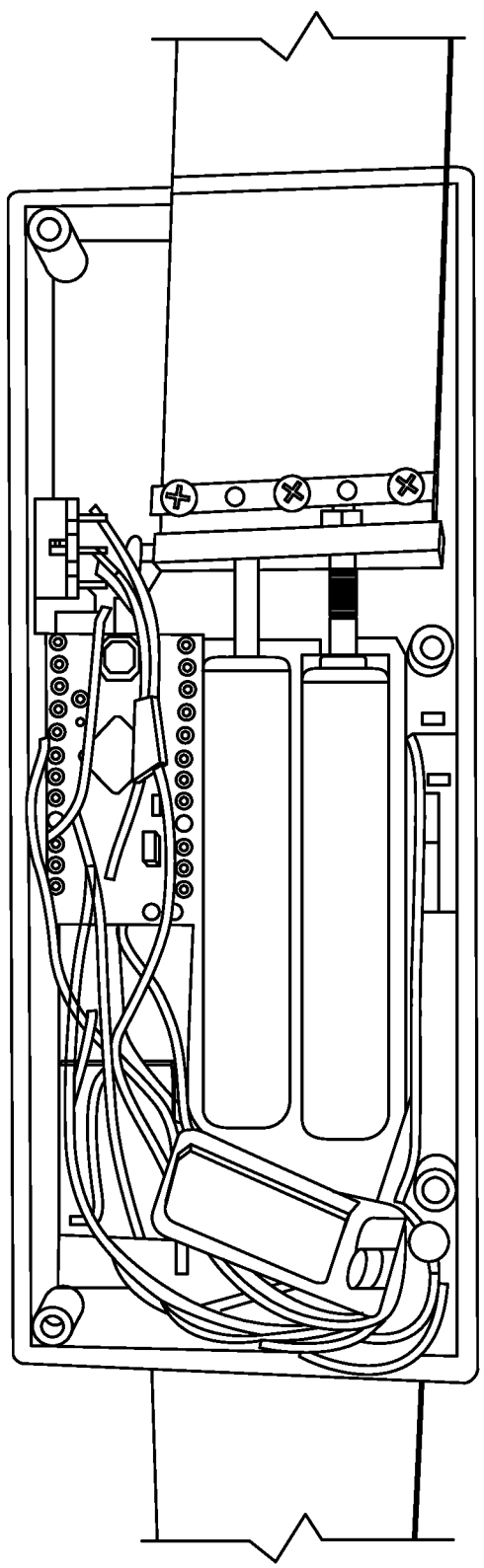
FIG. 22A is a built example of one possible implementation of the first embodiment of a breath training device of the present invention with the case opened.
Figure 22B:
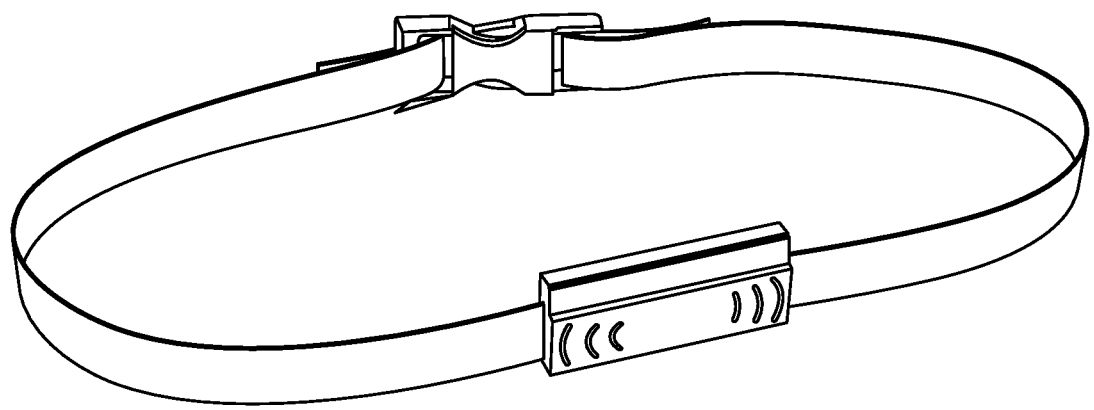
FIG. 22B is a perspective view of a built example of one possible implementation of the first embodiment of a breath training device of the present invention.

FIGS. 22A-22B show a built example of one possible implementation of breath training device 100.

Second Embodiment

Figure 23:
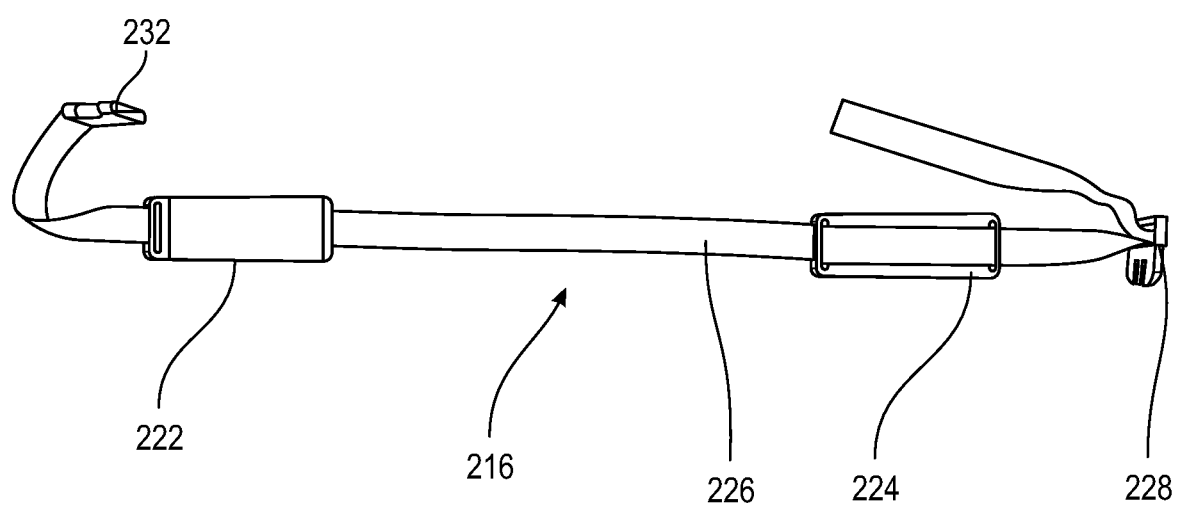
FIG. 23 is a perspective view of a second embodiment of a breath training device of the present invention.
Figure 24:
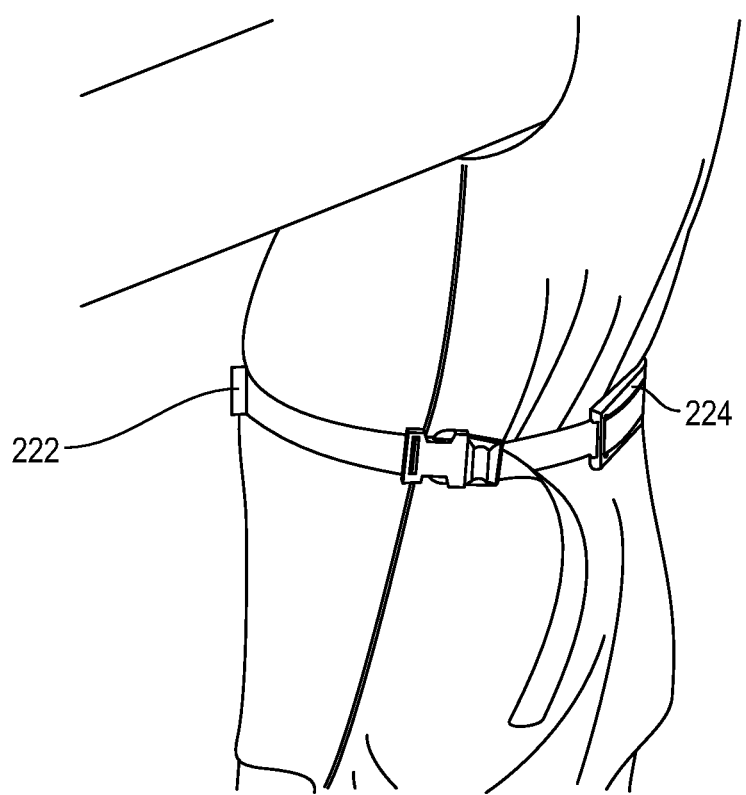
FIG. 24 is a side perspective view of a second embodiment of a breath training device of the present invention being worn by a user.
Figure 25:
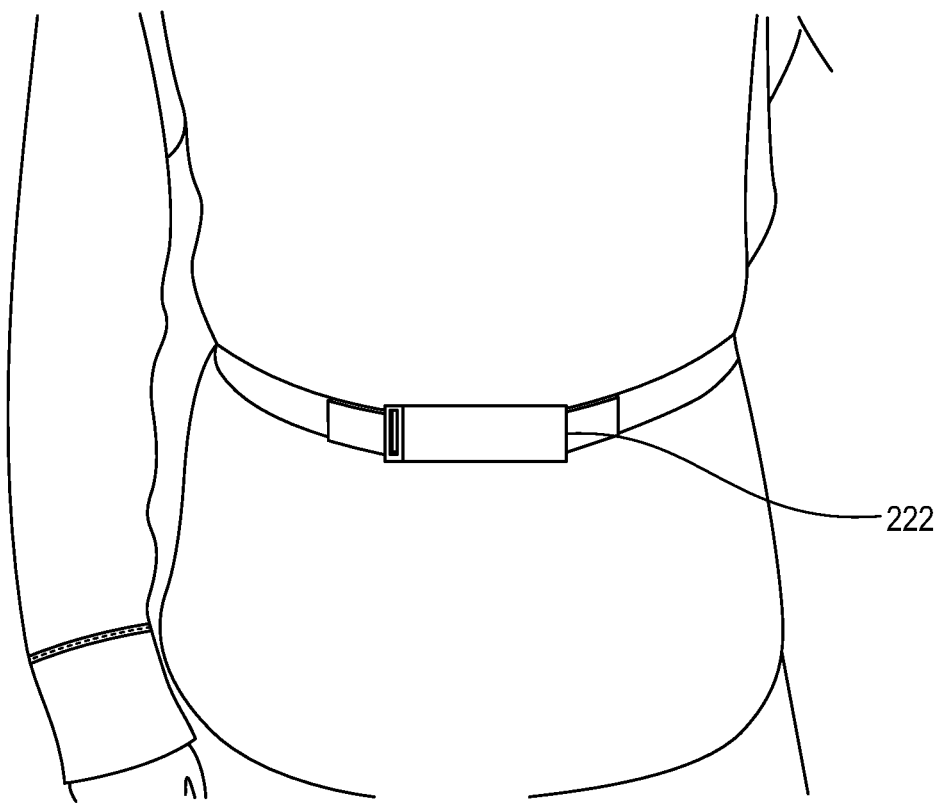
FIG. 25 is a front perspective view of a second embodiment of a breath training device of the present invention being worn by a user.
Figure 26:
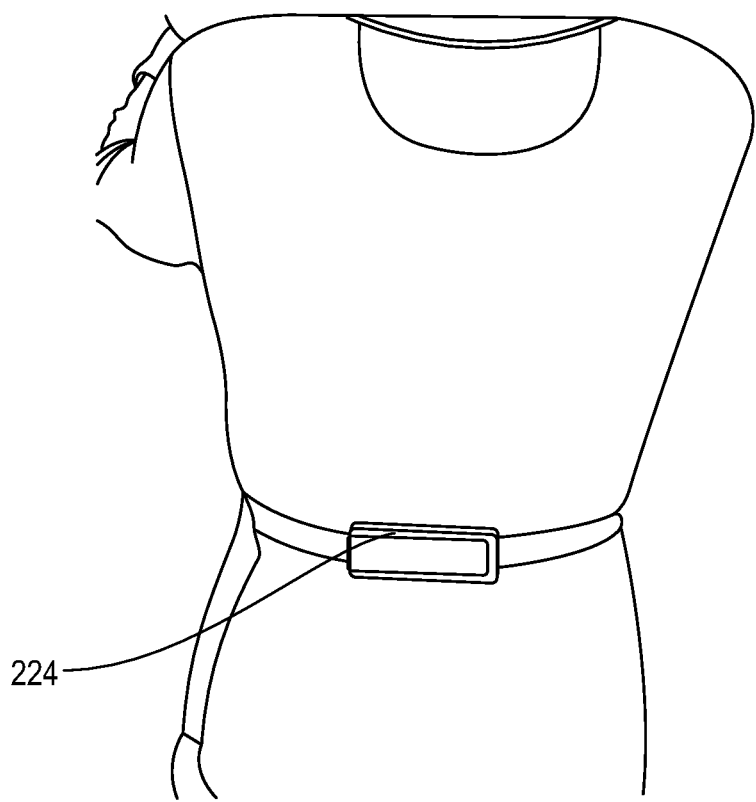
FIG. 26 is a back perspective view of a second embodiment of a breath training device of the present invention being worn by a user.

Referring to FIG. 23, a second embodiment of a breath training device 220 is shown, having a front sensor housing 222, and a back sensor housing 224. The main difference between breath training device 220, and breath training device 100 of the first embodiment is that in breath training device 220, sensors are situated on two areas of the belt such that when the belt is worn around the waist or chest, these sensors are then positioned on both the back and abdomen (or chest) areas for separately tracking those areas as shown in FIGS. 24-26. While the first embodiment of breath training device 100 offers the advantage of being more compact—having just a single case 102 and microcontroller 140 from which both breath and posture changes are tracked—an advantage of two separate sensor housings in breath training device 220 is that a greater variety of sensor types can be used, including a combination of simpler sensors, for example, having just one accelerometer in front sensor housing 222, and one accelerometer in back sensor housing 224. Also tracking from the two areas can help improve the accuracy of reverse breath tracking as later described in the operational section. Combinations of the sensor types previously discussed can be utilized in these two areas for measuring angle or acceleration, and displacement, with examples of such combinations given below.

In FIG. 23, breath training device 220 of the second embodiment comprises a respiration belt 226, the front sensor housing 222, the back sensor housing 224, a prong 228 on one end of a respiration belt 226 along with a length adjuster 230 for adjusting the circumference of respiration belt 226, and a fastener 232 on the other end of respiration belt 226 for snapping prong 228 into to join the ends of respiration belt 226 together. Front or back sensor housing 222 and 224 can be slidably attached on respiration belt 226 as shown for back sensor housing 224 in FIG. 27, depending on which sensors are being used. In the combination of sensors used and shown in FIG. 23, front sensor housing 222 is the same as case 102 of the first embodiment as shown in FIG. 1, with similar internal components as previously described therein including displacement sensor 146 and angle sensor 148, with respiration belt 226 similarly attached.

Figure 28:
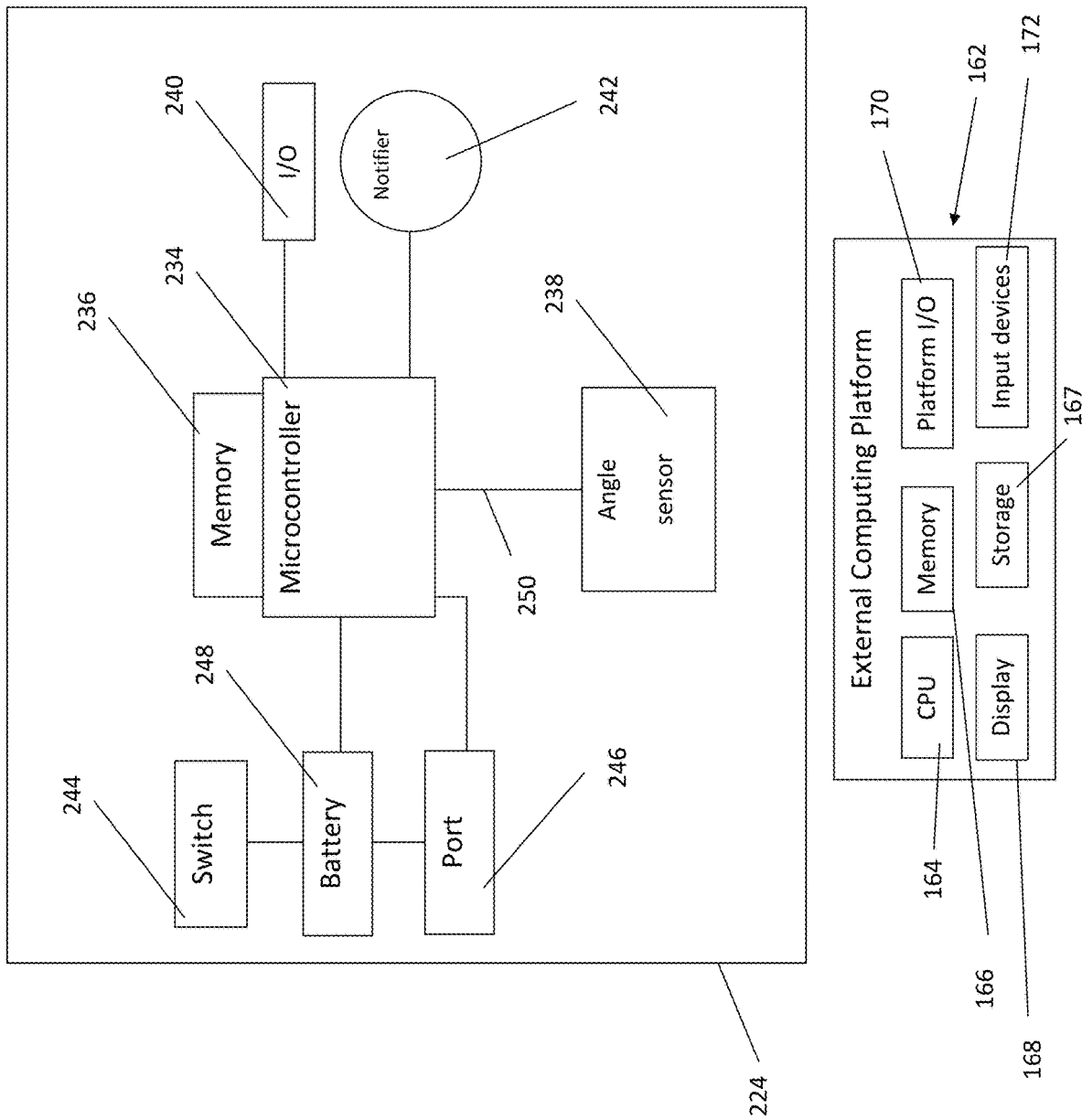
FIG. 28 is a block diagram of the electronic components of the back sensor housing of a second embodiment of the present invention.
Figure 29:
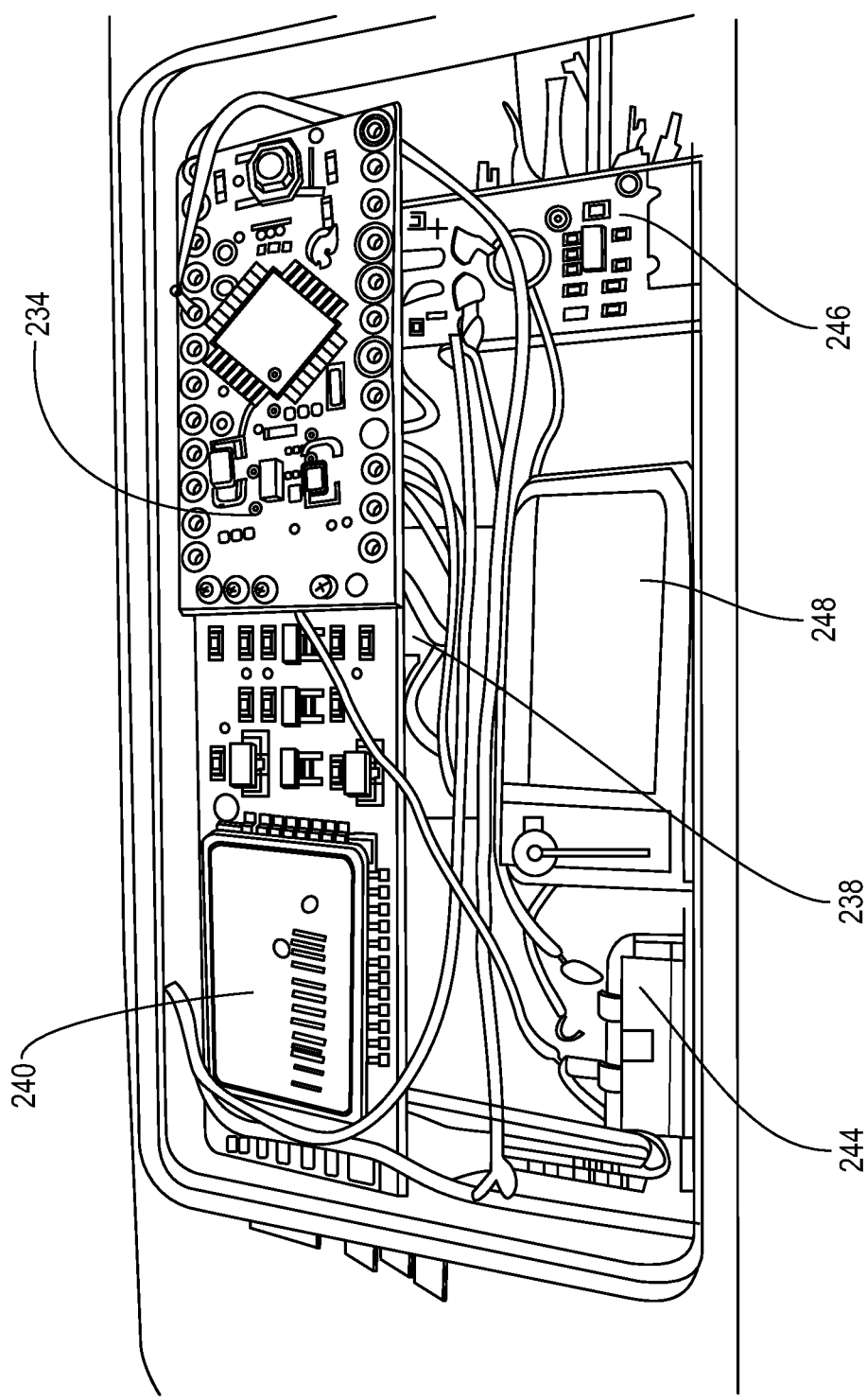
FIG. 29 is a perspective view of an opened back sensor housing showing a built example of one possible implementation of the second embodiment of the present invention.

A block diagram is shown in FIG. 28 for the electronic components contained in back sensor housing 224, which is very similar to the block diagram in FIG. 6 of the first embodiment, except there is no displacement sensor. Back sensor housing 224 comprises a microcontroller 234, memory 236, angle sensor 238, I/O 240 which is preferably wireless, optional notifier 242, optional switch 244, port 246, and battery 248. Again a CPU or microprocessor can be used instead of a microcontroller as previously discussed in the first embodiment. Angle sensor 238 can be connected to microcontroller 234 by a wire 250 for sending microcontroller 234 sensor output signals. FIG. 29 shows a built example of one such possible implementation, where I/O 240 is a Bluetooth Mate Silver modem, microcontroller 234 is an Arduino Pro Mini, battery 248 is a Polymer Lithium Ion Battery, angle sensor 238 is a BMA180 triple axis accelerometer with breakout board, port 246 is a LiPo Charger Basic—Micro-USB, and switch 244 is a slide switch.

Figure 27:
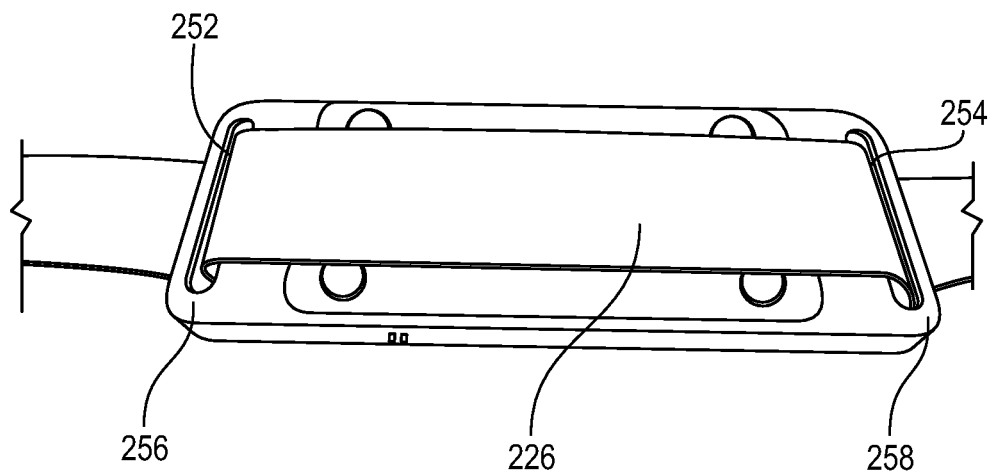
FIG. 27 is a perspective view of a back sensor housing of a second embodiment of a breath training device of the present invention.

A user wears breath training device 220 by wrapping respiration belt 226 around his/her waist with front sensor housing 222 placed over the navel area as shown in FIGS. 24-25, and fastener 232 and prong 228 then joined either on the right or left side hip area as shown in FIG. 24, depending on user preference, and respiration belt 226 tightened using length adjuster 230 so that back sensor housing 224 is moderately compressed against the user's body to help prevent it from wobbling during user body motion. A user then can adjust the position of back sensor housing 224 by sliding it along respiration belt 226 such that back sensor housing 224 is centered against the lower back as shown in FIG. 26, around the same vertical level as front sensor housing 222. Referring to FIG. 27, back sensor housing 224 can have slots 252 and 254 at its ends 256 and 258 through which respiration belt 226 passes from the back to front side of back sensor housing 224 for sliding, such that respiration belt 226 runs along the outside surface of back sensor housing 224. This arrangement aids in compressing back sensor housing 224 against the user's body when respiration belt 226 is tightened, to improve case stability for measuring angle and motion. As a variation of this second embodiment, it is also possible to interchange the positions of front sensor housing 222 and back sensor housing 224, so that there is just an angle sensor in the front, and both the angle and displacement sensor in the back, achieving similar results. In this variation, the position of front sensor housing 222 can then be adjusted by sliding it along respiration belt 226 after tightening, while the position of back sensor housing 224 is relatively fixed on respiration belt 226.

A possible disadvantage of the second embodiment of breath training device 220 as shown in FIG. 23, is that two sets of microcontrollers, memory, ports, batteries, and I/O are needed, one in front sensor housing 222, and one in back sensor housing 224, for independently communicating with and sending sensor output signals to external computing platform 162. Two sets are required since wireless I/O is preferably being utilized as shown, with no wires connecting front sensor housing 222 to back sensor housing 224.

Third Embodiment

Figure 30:
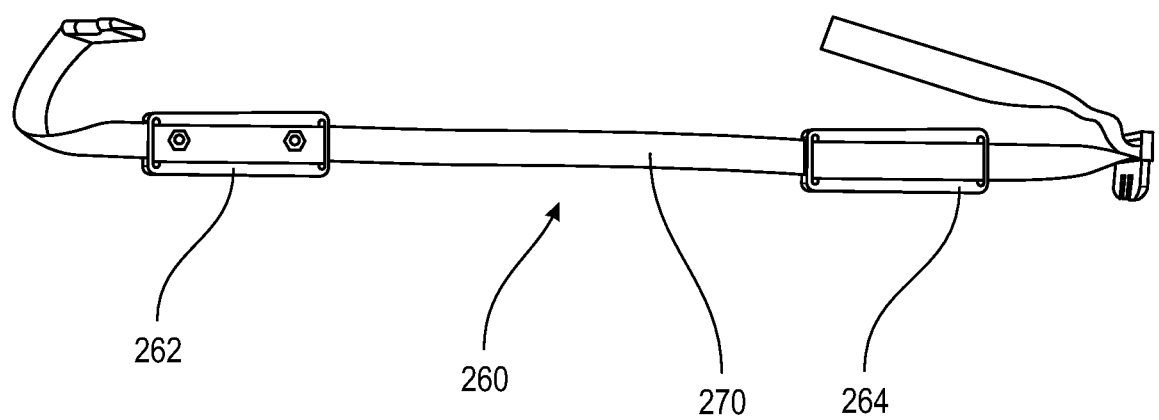
FIG. 30 is a perspective view of a third embodiment of a breath training device of the present invention.
Figure 31:
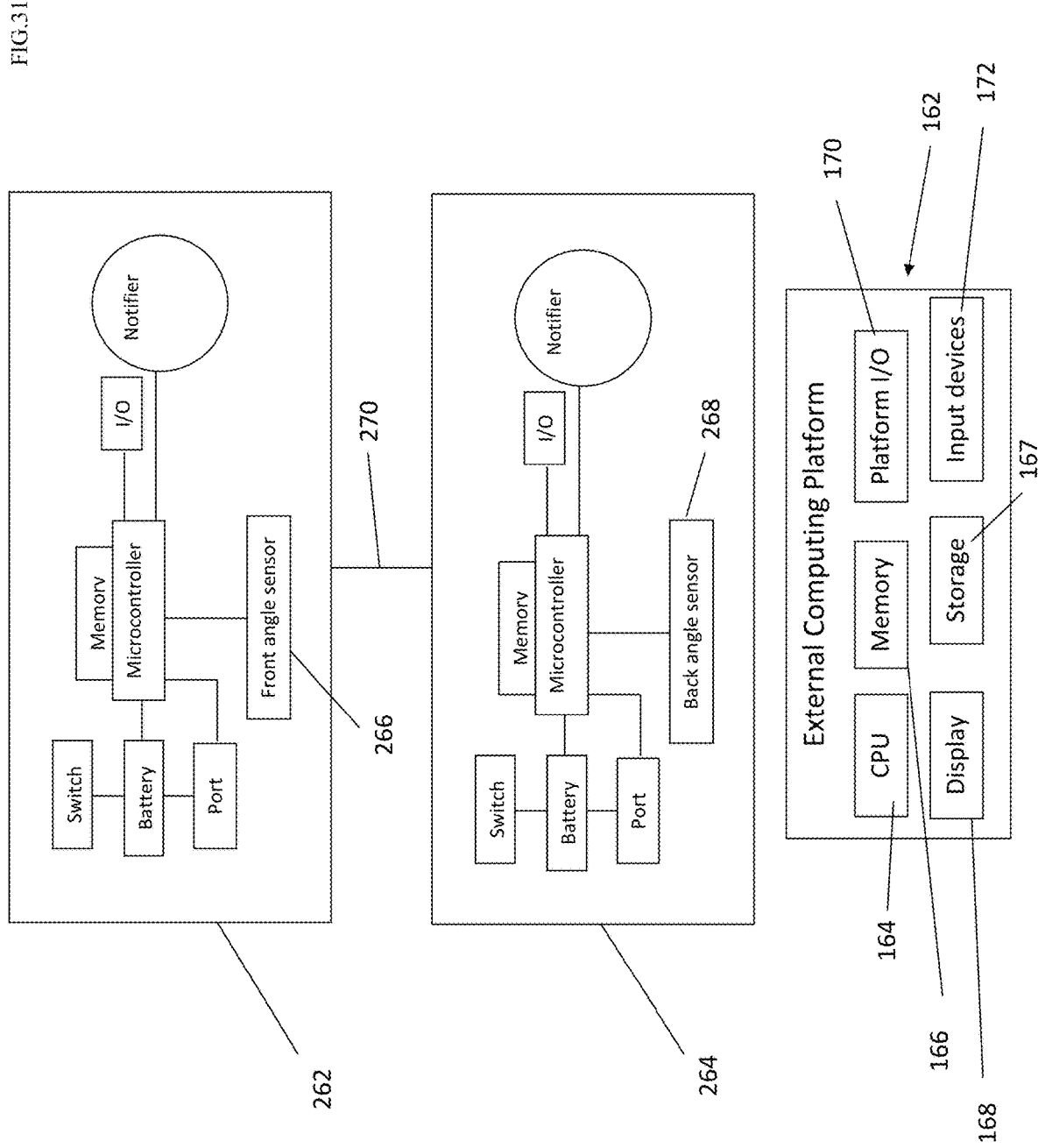
FIG. 31 is a block diagram of the electronic components of the third embodiment of the present invention.

In a third embodiment as shown in FIG. 30, a breath training device 260 is similar to breath training device 220 of the second embodiment, except that a front sensor housing 262 and a back sensor housing 264 are both the same as back sensor housing 224 described above in the second embodiment of breath training device 220, resulting in a front angle sensor 266 worn on the abdomen or chest, and a back angle sensor 268 worn on the back as shown in the block diagram in FIG. 31, with no displacement sensors utilized, and with sensor output signals wirelessly and separately transmitted by the I/O in front sensor housing 262, and the I/O in back sensor housing 264 to external computing platform 162. In this embodiment, the positions of both front and back sensor housing 262 and 264 can be slidably (e.g. so as to be movable by sliding) adjusted on the respiration belt after wearing and tightening the belt as previously described in the second embodiment. Front angle sensor 266 and back angle sensor 268 can be accelerometers as previously discussed or alternately other angle or acceleration sensing means. In the first and second embodiments, a non-elastic respiration belt can be used, since the belt circumference increases by means of moving belt slider 116. A respiration belt 270 in this third embodiment—since no belt slider is used—is preferably elastic such as woven elastic, allowing the belt to stretch during abdominal breathing when the belly expands outwards, and to return back to its taut circumference around the waist after each exhalation. A similar prong and fastener as described in the second embodiment can be used for securing respiration belt 270 while being worn.

Fourth Embodiment

Figure 32:
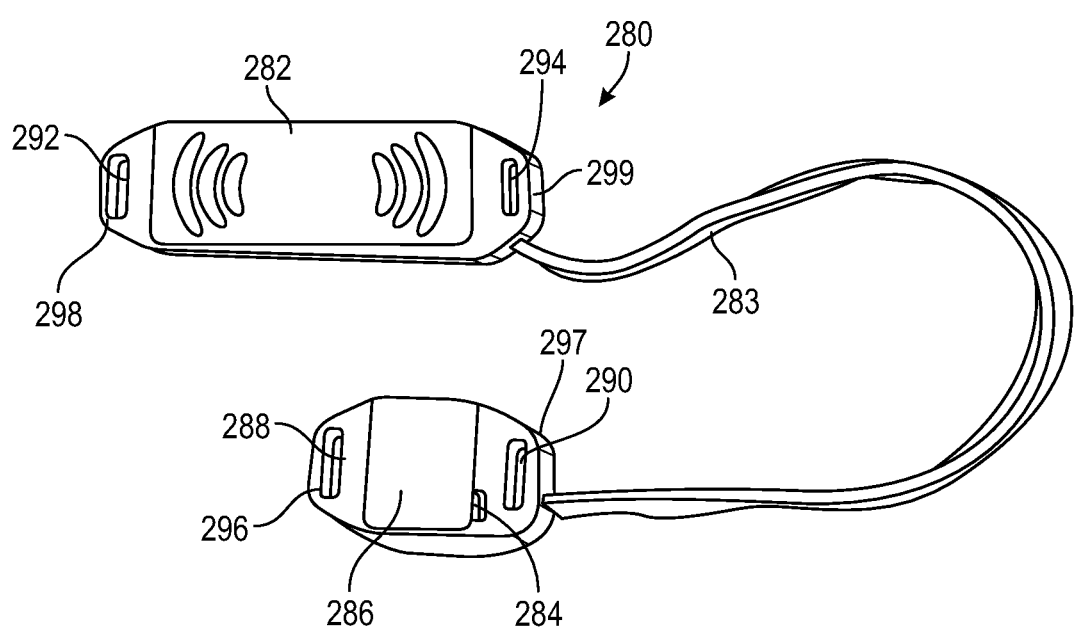
FIG. 32 is a perspective view of a fourth embodiment of a breath training device of the present invention.
Figure 33:
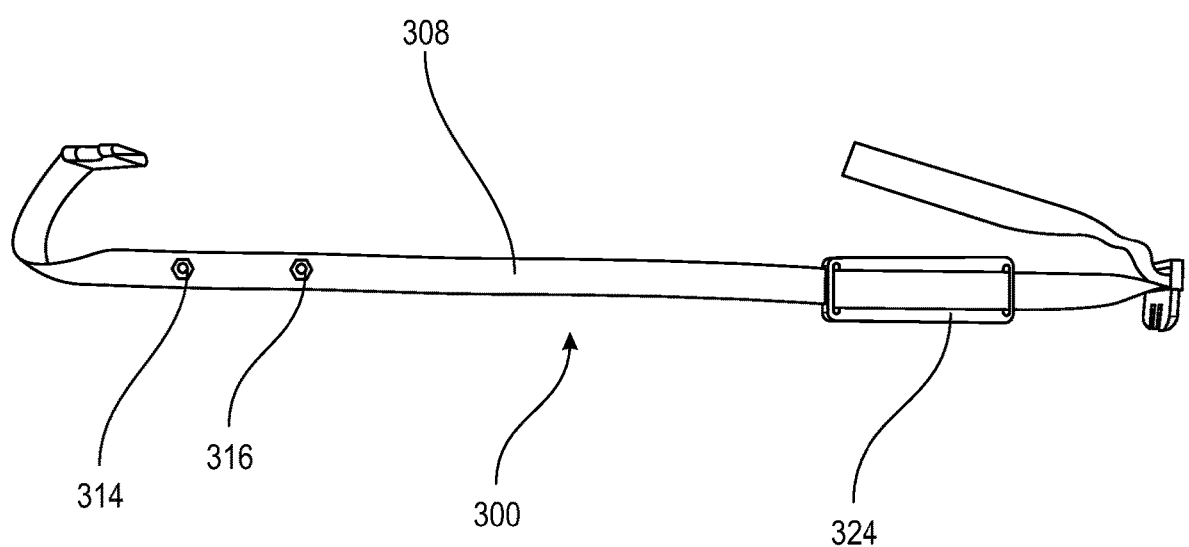
FIG. 33 is a perspective view of a fifth embodiment of a breath training device of the present invention.

In a fourth embodiment of a breath training device 280 as shown in FIG. 32, a back sensor housing 282 is shown which is again similar to back sensor housing 224 and its components as described above in the second embodiment, except that a wire 283 connects the microcontroller of back sensor housing 282 to a front sensor 284, located in front sensor housing 286. In this embodiment, front sensor housing 286 need only contain front sensor 284, connected to wire 283 for sending front sensor output signals to the microcontroller in back sensor housing 282. This arrangement avoids needing two sets of processors, batteries, and I/O, but with the disadvantage that wire 283 is required. As shown, the front sensor housing 286 can be smaller since it requires fewer components. Front sensor 284 can be based on an angle sensor, displacement sensor, or other sensing means as previously discussed. Both front and back sensor housing 286 and 282 have loops 288, 290, and 292, 294 on their ends for passing a respiration belt therethrough, similar to the arrangement of the respiration belt in the third embodiment described above. Front and back sensor housing 286 and 282 can have tapered ends 296, 297, and 298, 299 as shown.

Fifth Embodiment

Figure 34:
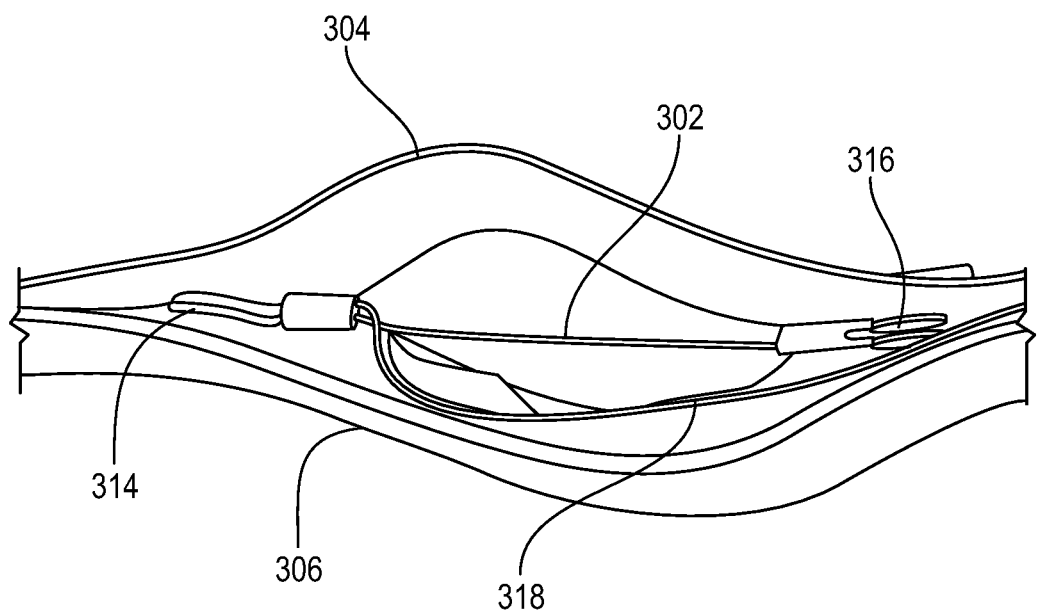
FIG. 34 is a perspective view of a displacement sensor situated between two elastic straps of a fifth embodiment of a breath training device of the present invention.
Figure 35:
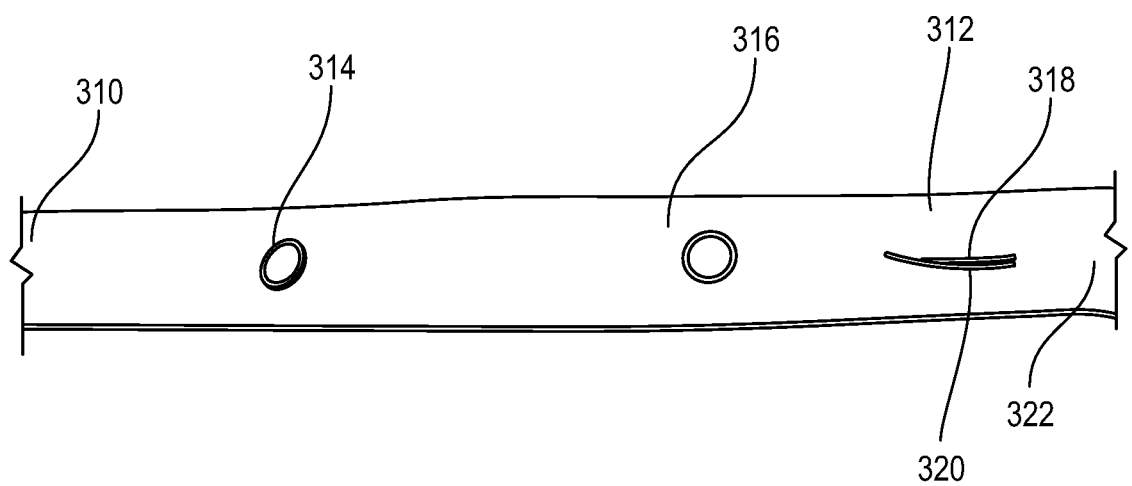
FIG. 35 is a perspective view of the snap fasteners of a fifth embodiment of a breath training device of the present invention.

A fifth embodiment of a breath training device 300 is shown in FIGS. 33-39, wherein a displacement sensor 302 can be situated between two elastic straps 304 and 306 as shown in FIG. 34, with a respiration belt 308 stitched in between on both belt ends 310 and 312, such that elastic straps 304 and 306 can be moved apart as shown in FIG. 34, and can stretch along their lengths during inhalation when a user's trunk circumference increases, placing tension on belt ends 310 and 312. As shown in FIGS. 34-35, snap fasteners 314 and 316 can be placed perpendicularly through both elastic straps 304 and 306, both equidistant from the ends of said elastic straps. As shown in FIG. 34, displacement sensor 302 can be attached to snap fasteners 314 and 316 in the area between elastic straps 304 and 306, and run therebetween, such that when elastic straps 304 and 306 expand during inhalation, snap fasteners 314 and 316 move apart, causing displacement sensor 302 to elongate, and to contract during exhalation when tension is removed on elastic straps 304 and 306. Displacement sensor 302 can, for example, be based on the flexible stretch sensor which changes in resistance when stretched, offered by Images Scientific Instruments Company. Elastic straps 304 and 306 can be relatively short compared to the length of respiration belt 308 so as to preferably localize the belt expansion just to that area where displacement sensor 302 is located. In comparison, if the entire respiration belt 308 was elastic for example, then displacement sensor 302 would elongate or stretch to a proportionately much smaller degree since the entire respiration belt would be expanding along its length. Respiration belt 308 is worn and secured around the waist or chest similar to the respiration belt of the second embodiment, with a similar prong and fastener device.

Figure 36:
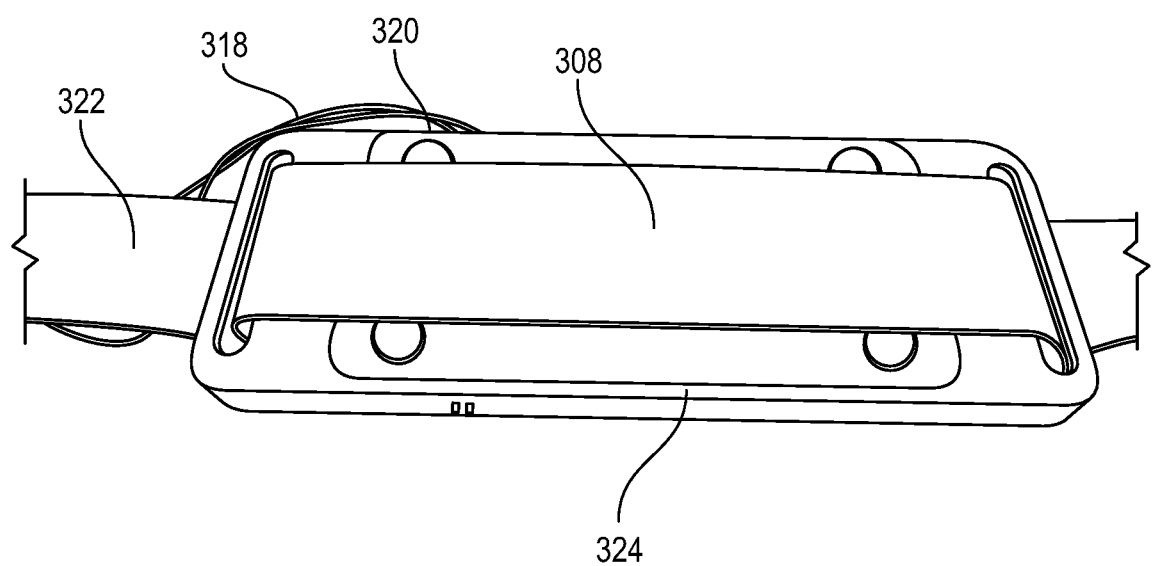
FIG. 36 is a perspective view of the back sensor housing of a fifth embodiment of a breath training device of the present invention.
Figure 37:
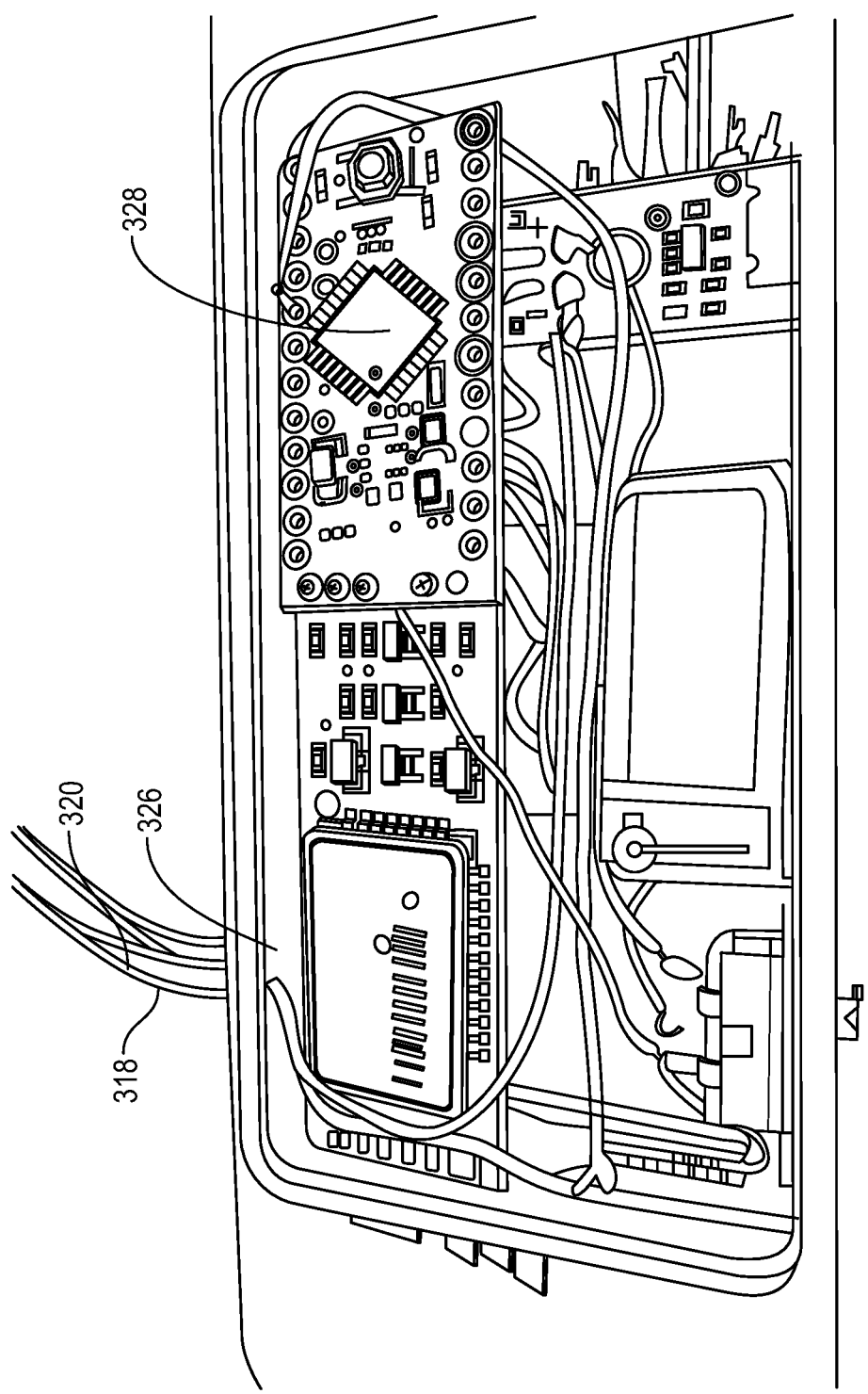
FIG. 37 is a perspective view of an opened back sensor housing showing a built example of one possible implementation of the fifth embodiment of the present invention.
Figure 38:
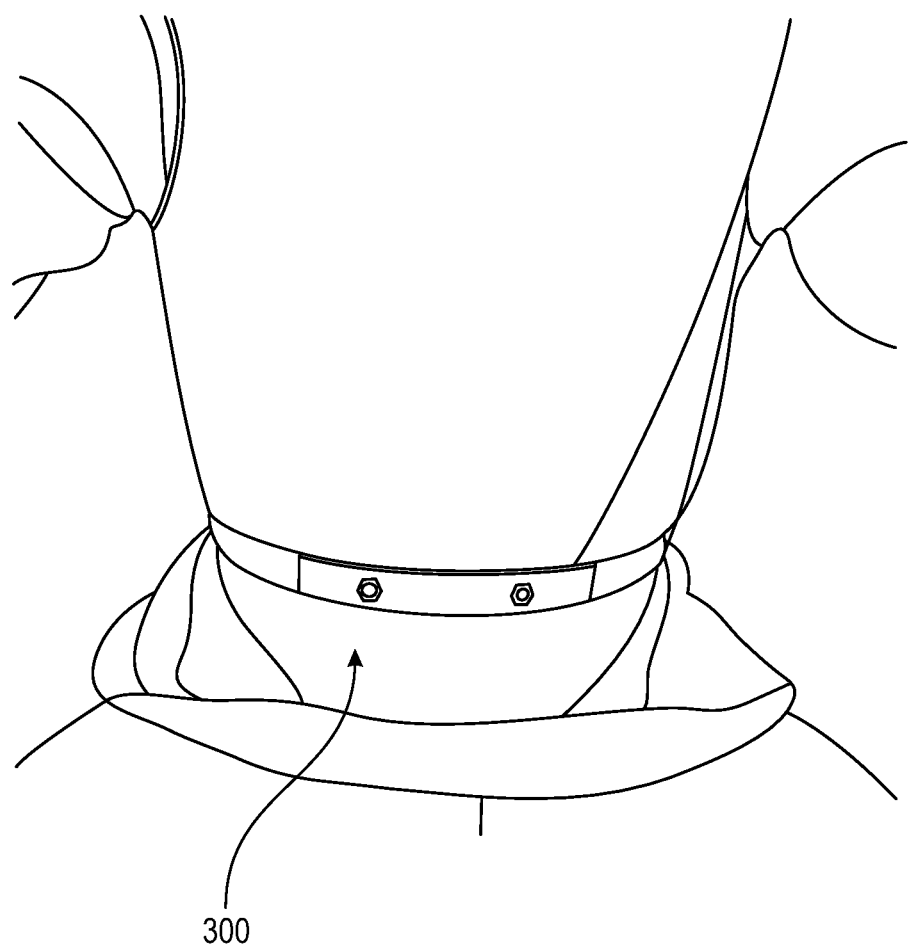
FIG. 38 is a front perspective view of a fifth embodiment of a breath training device of the present invention being worn by a user.
Figure 39:
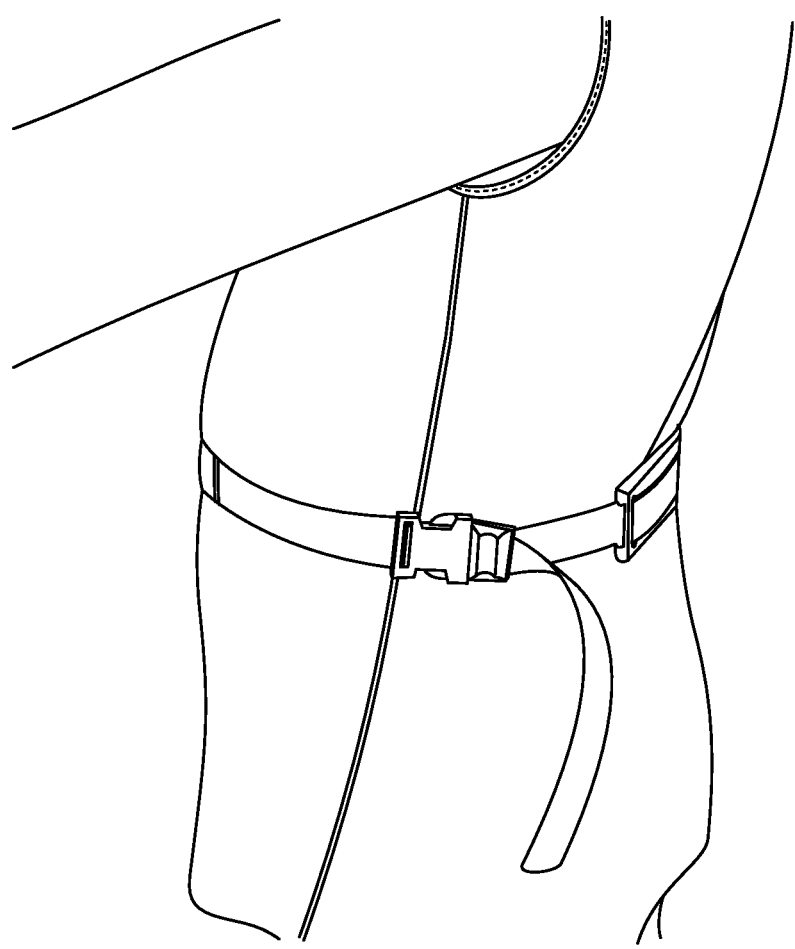
FIG. 39 is a side perspective view of a fifth embodiment of a breath training device of the present invention being worn by a user.

As shown in FIGS. 34-36, wires 318 and 320 attach to displacement sensor 302 on both its ends, and run through a channel 322 on respiration belt 302 towards a back sensor housing 324, so as to hide wires 318 and 320 and prevent them from interfering during use of breath training device 300 Channel 322 can be formed, for example, by stitching a segment of fabric on respiration belt 302. Wires 318 and 320 emerge from channel 322 near back sensor housing 324 and enter back sensor housing 324 through an opening 326, where they can attach to ground and a microcontroller 328. Back sensor housing 324 can be the same as back sensor housing 224 of the second embodiment, along with all components described therein, with the exception of the attachments of wires 318 and 320.

One advantage of this fifth embodiment of breath training device 300 is that only one microcontroller, battery, and I/O are needed, since wires 318 and 320 are used to connect displacement sensor 302 with back sensor housing 324, which also contains the microcontroller. Another advantage is the relatively simple arrangement of displacement sensor 302. The disadvantages are that wires 318 and 320 can be difficult to incorporate into the belt so as to allow length adjustments of the belt, and the wires can be unsightly and damaged by use. Furthermore, elastic straps 304 and 306 and displacement sensor 302 arranged as shown are not very precise, with the elastic straps possibly wearing out, not returning to the same positions after stretching, and displacement sensor 302 possible exhibiting a slow decay property in returning back to its baseline un-stretched resistance value if it is based on a stretch sensor.

Sixth Embodiment

Figure 40:
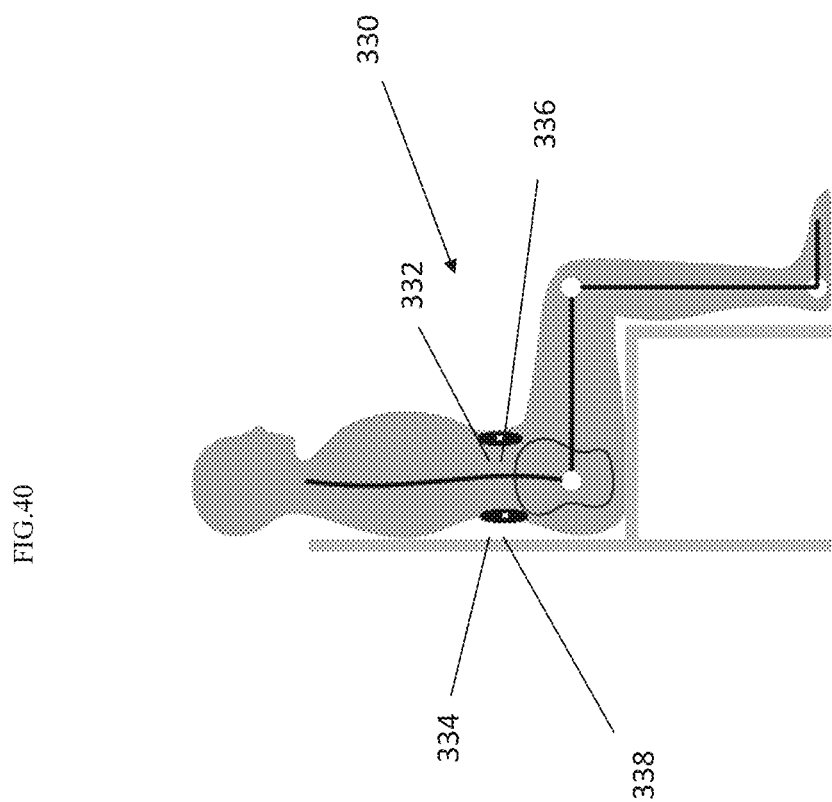
FIG. 40 is a schematic view of a sixth embodiment of a breath training device of the present invention being worn by a user.

A sixth embodiment of a breath training device 330 is shown in FIG. 40, which needs no respiration belt. Breath training device is comprised of a front sensor case 332, and a separate back sensor case 334 which can each be worn on a user's body—one over the abdomen or chest, and the other at the lower central back—by attaching to an article of clothing, or by directly taping the cases to the skin. Front sensor case 332 and back sensor case 334 can have attachment means 336 and 338 such as one or more pins, clips, magnetic buttons, fasteners, buttons, or other well-known ways of attaching a wearable object to a textile. Alternately, said cases can be taped to the skin at the target locations, using a medical tape such as 3M Micropore tape. Front sensor case 332 and back sensor case 334 can contain the same components as back case 224 of the second embodiment already fully described above and as shown in the block diagram in FIG. 28, including an angle sensor such as an accelerometer for tracking angle changes or acceleration. Alternately, the angle sensor in front sensor case 332 can be replaced with a displacement sensor, such as a stretch sensor discussed previously, wherein the stretch sensor can be directly attached to the skin by taping with a medical tape for example, for measuring expansion of abdominal skin during inhalation, rather than girth changes of the overall waist with a belt (not shown).

Although the sensor cases, such as those shown in FIG. 23 have been rectangular in shape, these particular examples are not intended to be limiting. Indeed the sensor cases can be formed in many different shapes. For example, a round or oval shape can be used as in FIG. 41. Such alternative case designs, while potentially increasing size can also help add stability by reducing wobbling against the body due to the more symmetric configuration. The front and back cases need not be identical in shape. For example, the round design could be used on a front sensor case, and a rectangular design for a back sensor case, allowing a larger logo visible on the front.

Seventh Embodiment

Figure 41A:
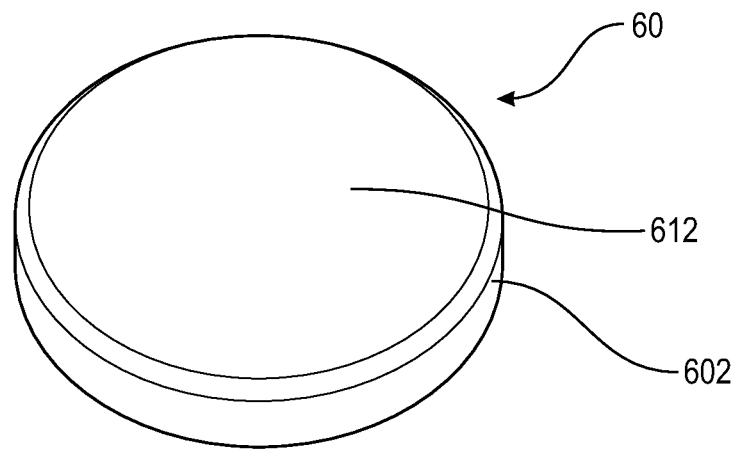
FIG. 41A is a perspective view of the top side of a sensor case of the seventh embodiment of a breath training device of the present invention.

A seventh preferred embodiment of a breath training device 600 of the present invention is shown in FIG. 41A. It differs most notably from the previous embodiments in that it consists of a single self-contained sensor case 602, from which both posture and breath monitoring are performed.

Figure 41B:
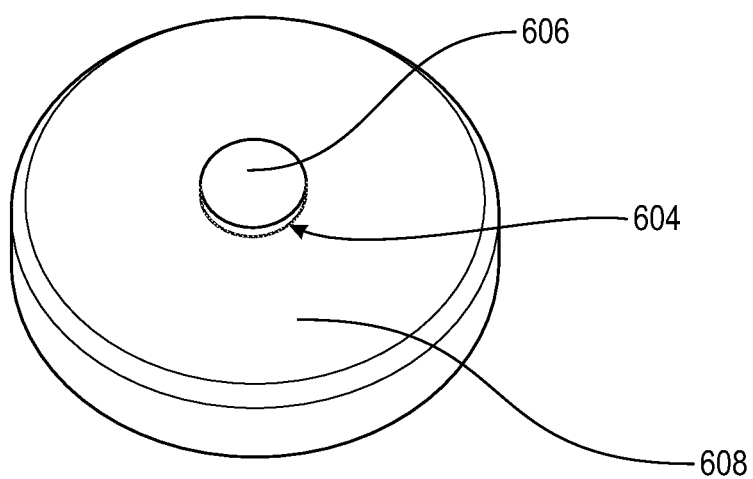
FIG. 41B is a perspective view of the back side of a sensor case of the seventh embodiment of a breath training device of the present invention.
Figure 41C:
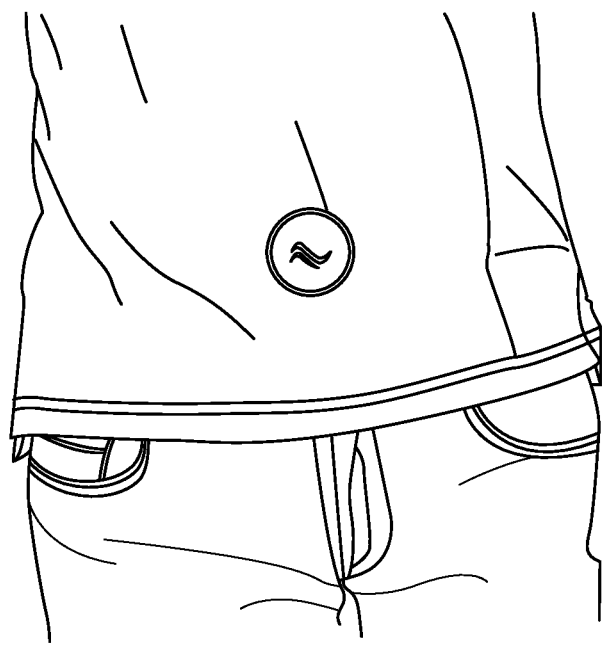
FIG. 41C is a perspective view of the seventh embodiment of a breath training device of the present invention being worn on the outside of a garment.
Figure 41D:
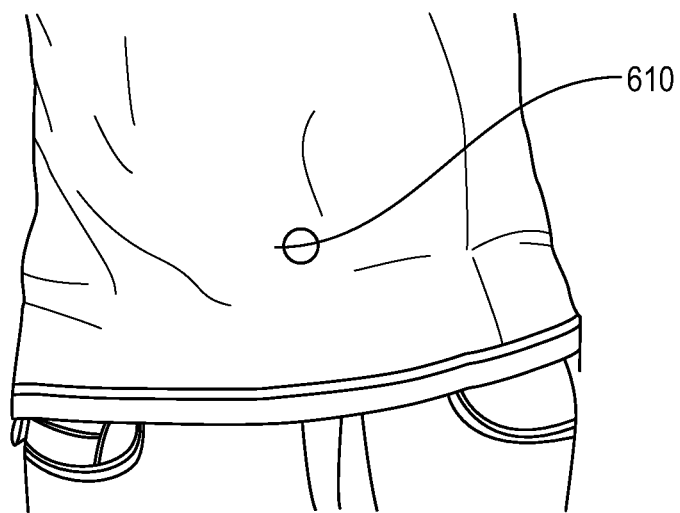
FIG. 41D is a perspective view of the seventh embodiment of a breath training device of the present invention being worn on the inside of a garment with a clasp on the outside of the garment.

Sensor case 602 can be worn near the chest, abdomen, or upper pubic area below the navel, though preferably below the chest to track diaphragmatic breathing. Sensor case 602 can have attachment means 604 such as one or more pins, clips, magnetic buttons and clasps, fasteners, buttons, detachable or permanent belt, or many other well-known ways of attaching a wearable object to a textile. For example, a magnet 606 can be situated on a back side 608 of sensor case 602 as shown in FIG. 41B, and a separate metal clasp 610 can be used to secure sensor case 602 to an article of clothing, with the clothing sandwiched between magnet 606 and the magnetically attracted clasp 610. Sensor case 602 can be worn on the inside or outside surface of a shirt or other garment as shown in FIGS. 41C-41D, with clasp 610 on the opposite side. Depending on the tightness and fit of a shirt, it may be preferable to fasten breath training device 600 in the upper pubic or front waistband area where the device could be held more tightly against the body. For example, sensor case 602 can be secured onto a waist belt using a clip, or placed underneath a waist belt between the belt and pants, or attached to the inside or outside surface of a user's underwear near the elastic waistband, or onto the inside or outside surface of a user's pants or skirt for example. Attachment device 604 could be detachable allowing breath training device 600 to be repurposed and fastened on other parts of a user's body, for example, to be attached to a wristband and worn as a watch as a traditional fitness tracker in measuring steps and calories burned. Alternately, sensor case 602 can be taped to the skin using a medical tape such as 3M Micropore tape.

As shown in FIG. 41A, sensor case 602 can have a round compact shape, but many other designs are also possible within the scope of the present invention. A removable lid 612 can be used to provide access to the battery and electronics, or alternately, sensor case 602 can be fully sealed and not intended to be opened by a user.

Figure 41E:
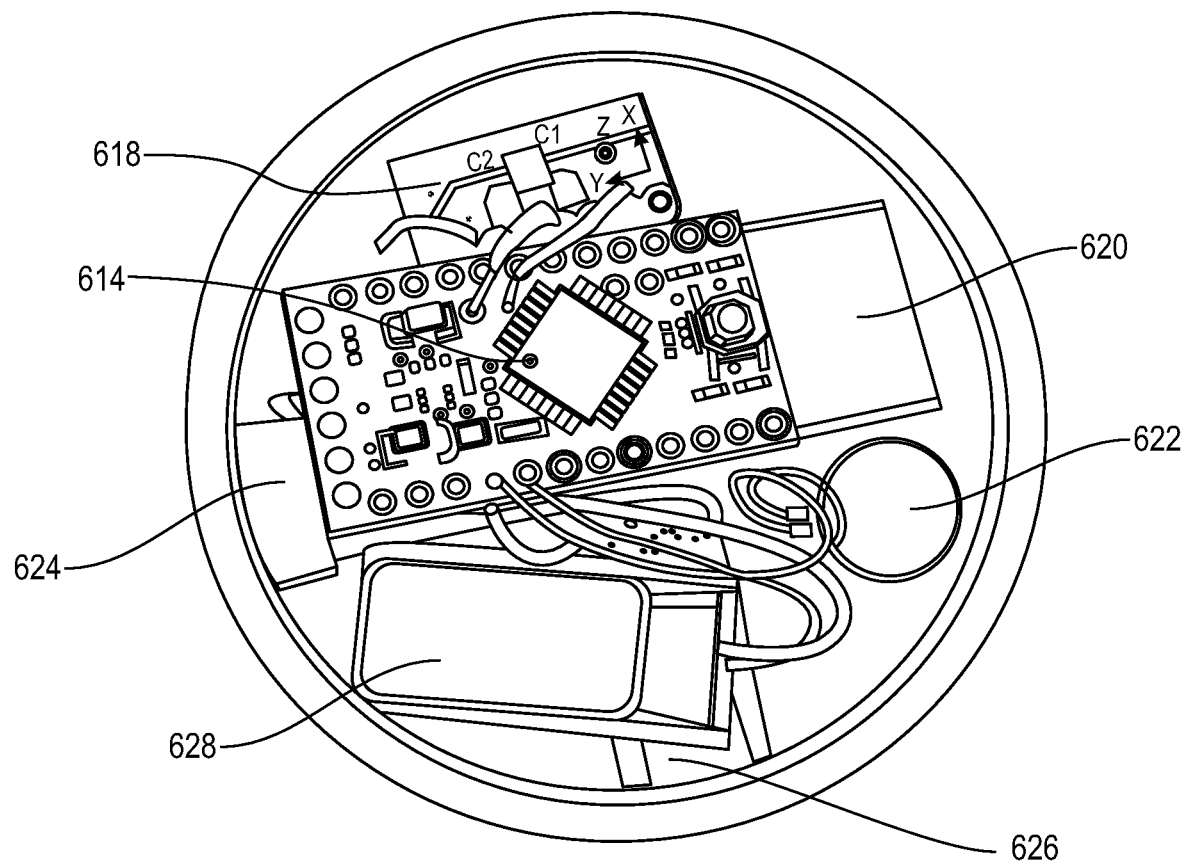
FIG. 41E shows a built example of the electronic components of the seventh embodiment of a breath training device of the present invention.
Figure 41F:
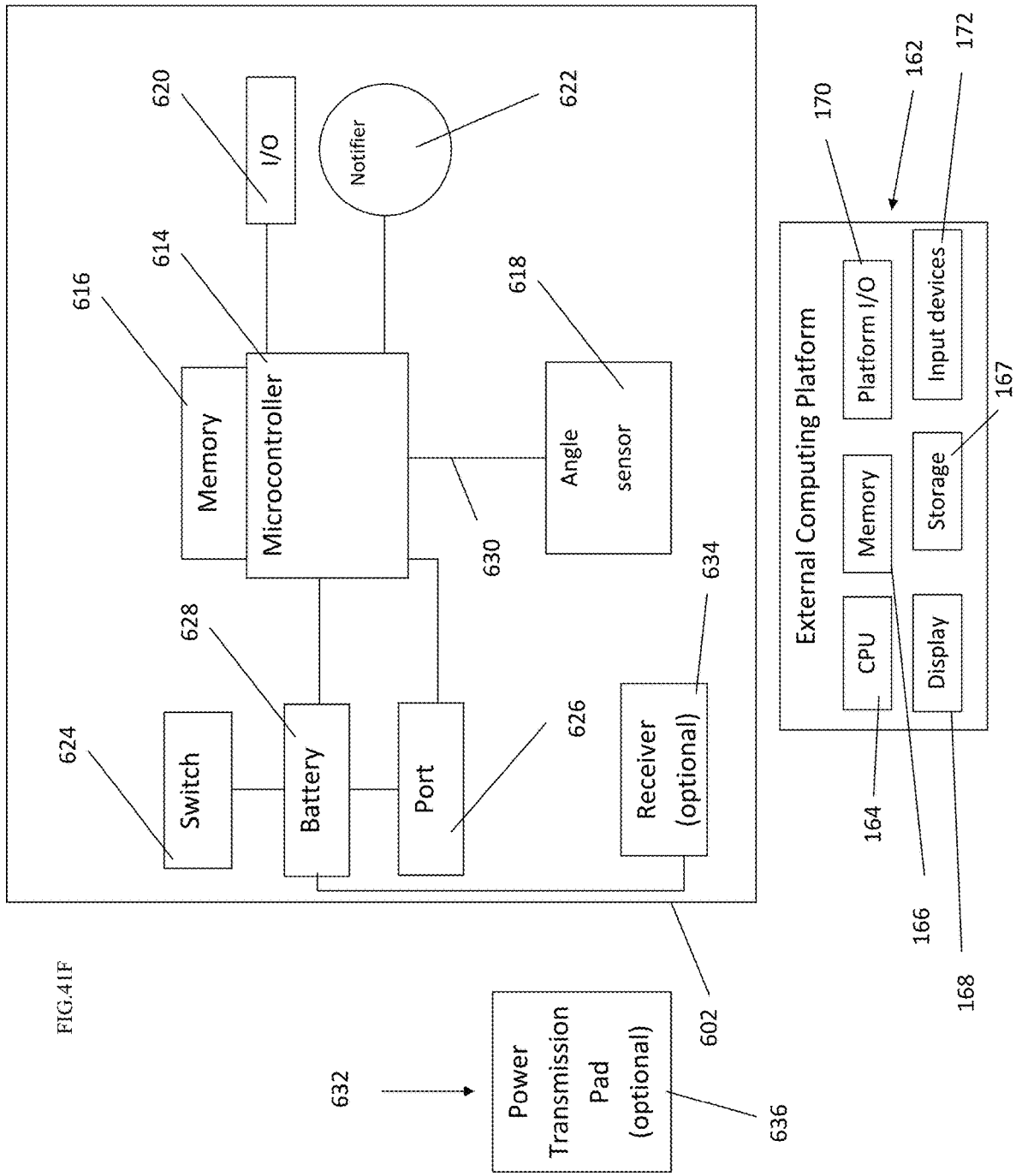
FIG. 41F is a block diagram of the electronic components of the seventh embodiment of a breath training device of the present invention.

The components of sensor case 602 are similar to the components of front sensor case 332 of the sixth embodiment and back case 224 of the second embodiment, as shown in the block diagram in FIG. 41F. Sensor case 602 can comprise a microcontroller 614, memory 616 for storing firmware and data, angle sensor 618, I/O 620 which is preferably wireless, optional notifier 622, optional switch 624, port 626, and a battery 628. Again a CPU or microprocessor can be used instead of a microcontroller as previously discussed in the first embodiment. Angle sensor 618 can be connected to microcontroller 614 by a wire 630 for sending microcontroller 614 sensor output signals. FIG. 41E shows a built example of just one such possible implementation, where I/O 620 is a Bluetooth Mate Silver modem, microcontroller 614 is an Arduino Pro Mini, battery 628 is a Polymer Lithium Ion Battery, angle sensor 618 is a BMA180 triple axis accelerometer with breakout board, port 626 is a LiPo Charger Basic—Micro-USB, and switch 624 is a slide switch, though again many other component brands and configurations are possible within the scope of the present invention. Alternately, switch 624 could be excluded, and microcontroller 614 could be placed into a low power mode via a command through I/O 620, and similarly, woken up by a command sent through I/O 620, or when serial data arrives from I/O 620. Alternately, port 626 could also be excluded and a wireless battery charging system 632 could be included with breath training device 600, for example, such as one specified by the Qi interface standard, which charges via resonant inductive electrical coupling. Wireless battery charging system 632 could consist of a receiver 634 inside sensor case 602, and an external power transmission pad 636 for coupling.

Angle sensor 618 can be an accelerometer for example, for measuring inclination changes or acceleration, having one or more axes along which said inclination changes or acceleration can be measured, although a variety of other sensor types with suitable sensitivity can be used. For example, one or more magnetometers or gyroscopes can be used. Magnetometers can measure angular position with respect to a magnetic field, while gyroscopes measure angular acceleration, from which angular position or inclination can be derived by integration for example. Alternately, angle sensor 618 can comprise a combination of sensors, for example, a 3-axis accelerometer combined with a 3-axis gyroscope as well known in the art.

Eighth Embodiment

Figure 41G:
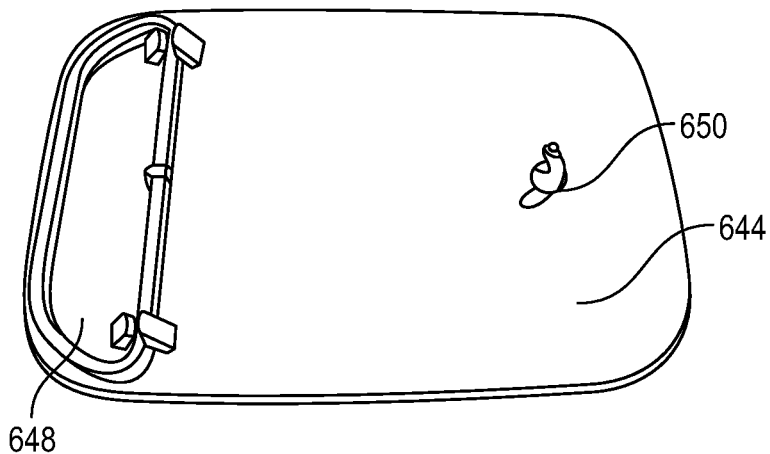
FIG. 41G is a perspective view of a buckle of the eighth embodiment of the present invention.
Figure 41H:
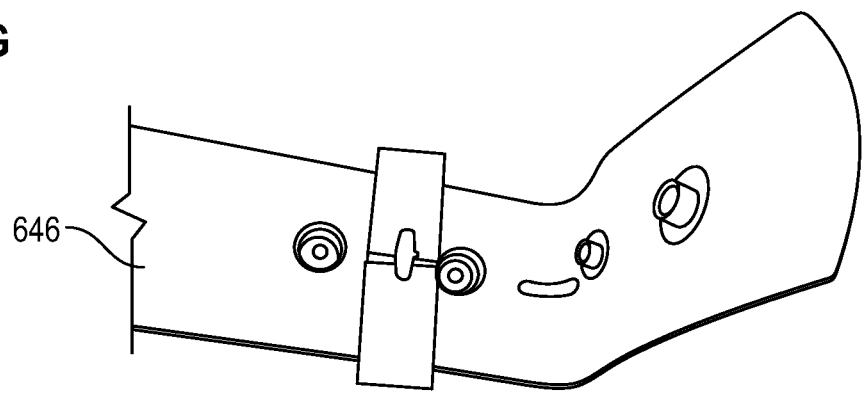
FIG. 41H is a perspective view of a snap on belt of the eighth embodiment of the present invention.
Figure 41I:
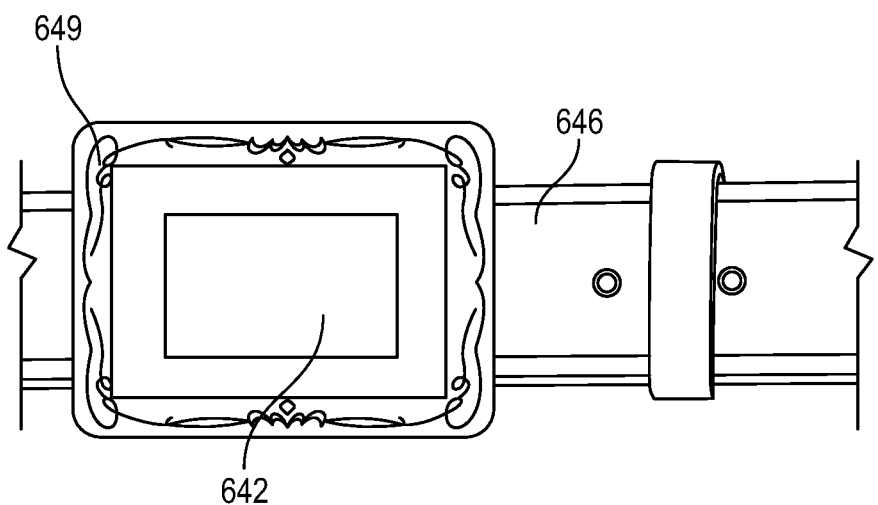
FIG. 41I is a perspective view of a breath training device of the eighth embodiment of the present invention attached to a buckle.

An eighth embodiment of a breath training device 640 is shown in FIG. 41I. Its components can be very similar to that already described for the seventh embodiment, except that a sensor case 642 is integrated into the design of a belt buckle 644 which can be fastened to a belt 646 for supporting trousers or other articles of clothing. Belt 646 can be based on the standard snap on belt design as shown in FIG. 41H, which allows for easily interchanging a buckle and attaching belt buckle 644, allowing the user to select from a wide range of existing belts. As shown in FIG. 41G, belt buckle 644 can be based on the standard hook and loop design with the snap portion of belt 646 looping through a buckle loop 648, and with a hook 650 attaching to a hole in the belt, as is well known. Sensor case 642 can be attached to the front facing side 649 of belt buckle 644 as shown in FIG. 41I, where belt buckle 644 has been fastened to belt 646. An advantage of this arrangement is that the user is free to select whichever style of Snap-On belt they prefer. Another advantage is that belt training device 640 is reliably and securely attached to the belt, and naturally centered on the belt.

Figure 41J:
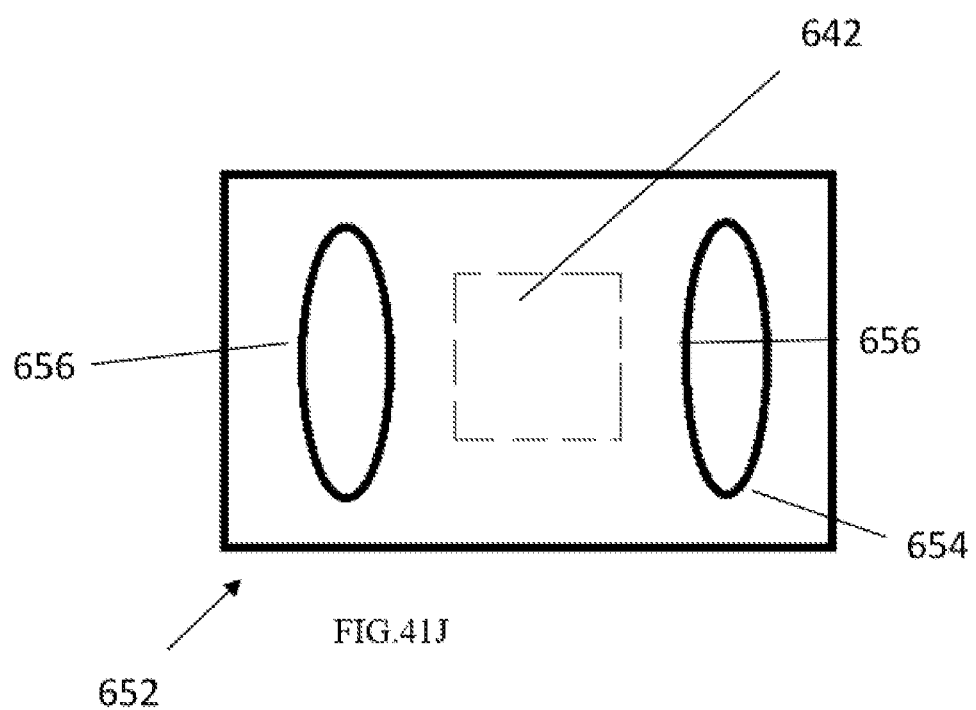
FIG. 41J is a perspective view of an alternate buckle of the eighth embodiment of the present invention.

An alternate buckle 652 is shown in FIG. 41J, which has a plate 654 with two loops 656 on its back surface. Sensor case 642 can be mounted on a front side of plate 654. Buckle 652 can be slid onto any regular belt, with the belt passing through loops 656. The advantage of this arrangement is that a snap-on belt is not necessary. After sliding on buckle 652, and fastening the belt around the waist, the user can shift and rotate the belt's existing built-in buckle several inches away from the body center, allowing room for buckle 652 to be slid to the center of the belt. Sensor case 642 could alternately be attached to many other buckle types and variations within the scope of the present invention, such as a military buckle or a tang or pin buckle.

Many other combinations of above sensors, front and back sensor housings, and ways of fastening and adjusting a sensor case or respiration belt around the waist or chest are possible, both in wired and wireless variations, and with both single and multiple microcontrollers, all within the scope of the present invention.

Classification of Breath Training Devices

For the purpose of discussing the flow of processing operations and device usage, the previously described embodiments of the breath training device (BTD) are categorized into four types, as some processing steps and algorithms may vary depending on the type being used (and these variations will be described herein): Type 1 comprises two separate angle (or acceleration) sensors, one on the abdomen or chest, and one on the user's back. Examples of type 1 are breath training device 260 in the third embodiment, breath training device 280 in the fourth embodiment, and breath training device 330 in the sixth embodiment. Type 2 comprises one angle (or acceleration) sensor, and one displacement sensor, such as breath training device 100 in the first embodiment, and breath training device 300 in the fifth embodiment. Type 3 comprises three sensors including two separate angle (or acceleration) sensors, one on the abdomen or chest, and one on the back, and one displacement sensor. An example of type 3 is breath training device 220 of the second embodiment. Type 4 comprises one angle sensor in one sensor case, such as breath training devices 600 and 640 in the seventh and eighth embodiments.

Description of Anatomy and Usage

We now explain the anatomic principles behind how the sensors of the different BTD types measure breath and posture, and how measured posture can help gauge the depth of an inhalation.

Type 1 BTD

Figure 42:
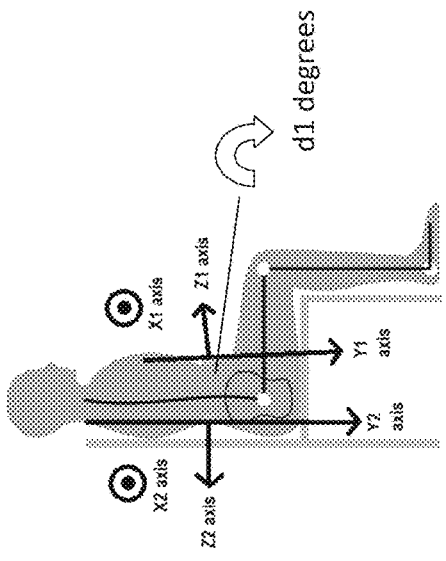
FIG. 42 is a schematic view of type 1 BTD being worn around a user's waist, in an upright posture prior to inhalation.
Figure 43:
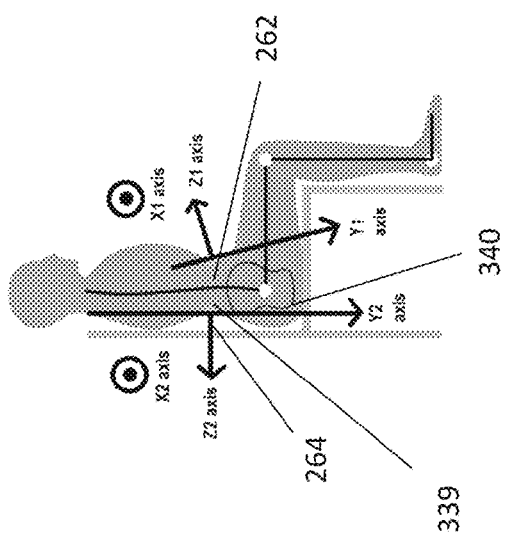
FIG. 43 is a schematic view of type 1 BTD being worn around a user's waist, in an upright posture after inhalation.
Figure 44:
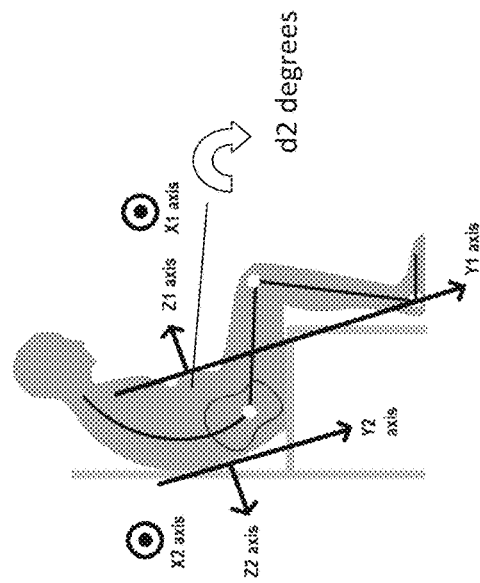
FIG. 44 is a schematic view of type 1 BTD being worn around a user's waist, in a slouched posture prior to inhalation.
Figure 45:
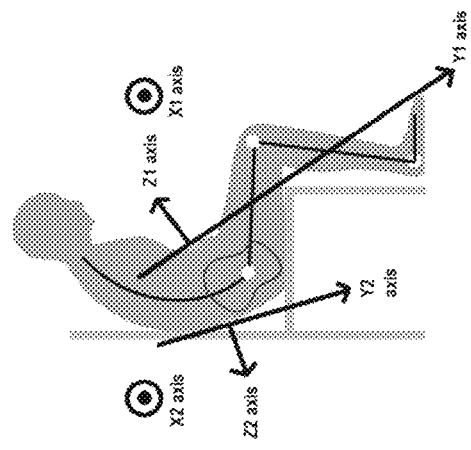
FIG. 45 is a schematic view of type 1 BTD being worn around a user's waist, in a slouched posture after inhalation.

FIGS. 42-45 provide an example of a type 1 BTD being worn around a user's waist, which uses angle sensors on the user's back and abdomen, such as front angle sensor 266 and back angle sensor 268 inside front sensor housing 262 and back sensor housing 264 of the third embodiment, shown in these figures (or alternately the sixth embodiment which uses no respiration belt). Front and back angle sensors 266 and 268 can be mounted and oriented inside front sensor housing 262 and back sensor housing 264, for example, to measure angles (or directions) of three perpendicular axes each, the X1, Y1, Z1 and X2, Y2, Z2 axes respectively as shown (with the X axes being into the page). Back angle sensor 268 can measure a posture angle using the Z2 axis or vector, which is roughly perpendicular to a user's lumbar spine 339. Posture angle can be the tilt of the Z2 axis with respect to the horizontal. When a user is sitting upright in a good posture state, Z2 is approximately level as shown in FIG. 42. When a user slumps into a poor posture, this causes his/her pelvis 340 to rotate backwards or posteriorly, causing a convex or kyphotic curvature in the lumbar spine and the Z2 axis to tilt downwards, as shown in FIG. 44. During the calibration process later described, this range of change of posture and the Z2 axis direction is determined.

Referring to FIG. 42, front angle sensor 266 can measure a belly angle to infer the extent of diaphragm contraction—and thus the extent of an inhalation—by measuring the Z1 axis direction, which is roughly normal to the skin of the anterior abdominal wall around the navel area. The belly angle can be the tilt of the Z1 axis with respect to the horizontal, similar to posture angle. When the user inhales diaphragmatically, this causes his/her diaphragm to contract and move downwards, causing the user's rib cage to move upwards and outwards. This simultaneous upwards and outwards movement causes the Z1 axis to tilt, as shown after an inhalation in FIG. 43. When the user exhales, the diaphragm relaxes, with the Z1 axis returning to its previous level (assuming no changes in posture occurred).

Now we explain how the measured posture angle in a type 1 BTD can affect the assessment of the depth of a measured inhalation or exhalation. In FIG. 42, the user is sitting upright in a fully exhaled state. In FIG. 43, the user has inhaled diaphragmatically to his/her full capacity, while maintaining the same upright posture, causing the Z1 axis to undergo an orientation change, where the Z1 and Y1 axes have rotated by a certain angle d1. Now for comparison, in FIG. 44, the user is in an alternate slumped posture in an exhaled state. In FIG. 45, the user has again inhaled diaphragmatically to his/her full capacity, while maintaining this same alternate posture, causing Z1 axis to undergo an orientation change, where the Z1 and Y1 axes have rotated by a certain angle d2. The angles d1 and d2 may be quite different. As previously mentioned, posture can have a significant effect on the extent of diaphragmatic excursion during breathing due to a variety of complex anatomical factors, such as the distribution of weight of visceral organs on the diaphragm. The processes and algorithms described below therefore take into account posture angle to help standardize changes in belly angle, utilizing posture zone coefficients as described, for determining the assessed depth of an inhalation across the user's posture range.

Thus in some embodiments, the invention can be further configured to standardize different user inhalation depths across different user postures, or to reduce the impact of varying user posture on user respiration measurements.

The above examples of changes in the Z1 direction during inhalation assumed the user is relatively stationary while seated, without significantly altering his/her posture. In practice, of course, the user may change their posture or exhibit various body movements while breathing, such as rocking back and forth, which are non-breath related. For example, between FIG. 42 and FIG. 44, the user has significantly changed his/her seated posture while in an exhaled state, causing the Z1 axis direction to significantly change due to non-breath related movement, which can create ambiguity in a system attempting to track breath state directly from the Z1 direction. To overcome this problem, the present invention provides a mapping process for learning the correspondence of how posture and belly angles (Z2 and Z1 axes tilts) change across their ranges during body movement, while not breathing, to establish a baseline from which to extract a net angle. Since front angle sensor 266 and back angle sensor 268 are placed on different parts of the body, generally, they may not experience body movement or posture changes in precisely the same way, with the difference in the sensor signal outputs generally not being linear. The advantage of placing front angle sensor 266 near the user's navel, and back angle sensor 268 near the central lower back, is that these body areas tend to experience body motions due to posture changes, such as rocking back and forth, in roughly a similar way which can be canceled out (still not precisely linear), with inhalation generally providing a further additive effect to the angle change of the Z1 axis relative to Z2. The processes and algorithms described below describe a signal processing method which includes subtracting a version of the posture angle from the belly angle to establish such a learned baseline in an exhaled state across a posture angle range, and then to measure a net angle (or filtered breath signal) which can be primarily attributed to inhalation level relative to the learned exhaled baseline level to disambiguate from body movement and cancel out such body movement noise.

Type 2 BTD

Figure 46:
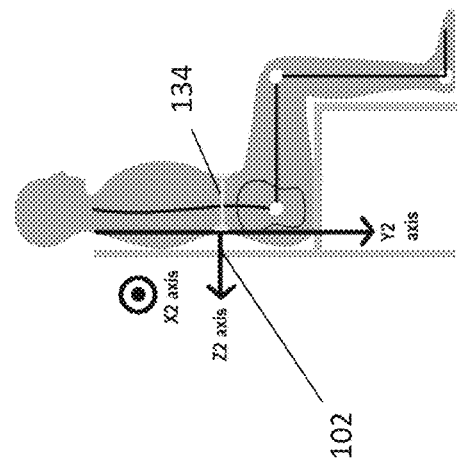
FIG. 46 is a schematic view of type 2 BTD being worn around a user's waist, in an upright posture prior to inhalation.

FIGS. 46-49 provide an example of a type 2 BTD being worn around a user's waist, such as the breath training device 100 of the first embodiment, shown in these figures. Posture angle here is measured in the same way as already discussed for a type 1 BTD above. Breath, on the other hand, is measured by a displacement sensor which tracks changes in the user's trunk circumference or girth during inhalation and exhalation. For example, breath training device 100 of the first embodiment utilizes a single case 102 placed on the lower back as shown in FIG. 46, with a buckle 134 near the navel for securing the belt. Case 102 contains both angle sensor 148 and displacement sensor 146, though the displacement sensor can be located in a separate area from the angle sensor, such as in the fifth embodiment above, and still be a type 2 BTD.

The user's posture (often measured by the angle sensor data) can have a significant impact on the user's respiration data, and thus various methods of producing posture adjusted user respiration data are often desirable.

In some embodiments, the device's processor (and/or an external computing program processor receiving data from the device) can be further configured to correct for effects of different relative user posture positions. Various schemes are possible here.

For example, in some embodiments, while the user is in a defined respiratory state (e.g. the user may be instructed to inhale all the way or exhale all the way), the system can sample and store the breathing sensor data across a plurality of different relative user posture positions (as defined by said angle sensor data). This can be used to create a set of first calibration data.

Here the instructions might be: "inhale all the way, and then gradually change your posture from a fully reclined to a fully upright position, and then exhale all the way, and then gradually change your posture from a fully upright to a fully reclined position". The system can be storing data all during this procedure.

The system's processors (or other processors) can then produce posture adjusted user respiration data by using this first calibration data, the breathing sensor data, and the angle sensor data to correct the breathing sensor data for variations in the user's posture. Here, as previously discussed above, the defined respiratory state can be any of a defined exhalation state and a defined inhalation state.

Figure 47:
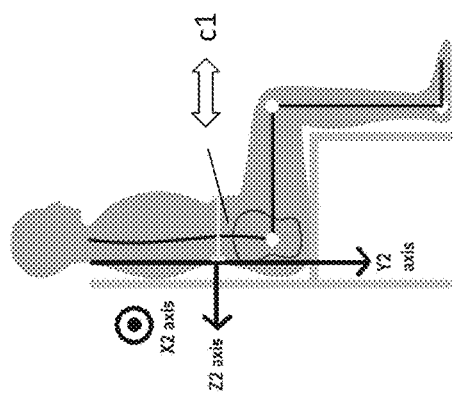
FIG. 47 is a schematic view of type 2 BTD being worn around a user's waist, in an upright posture after inhalation.
Figure 48:
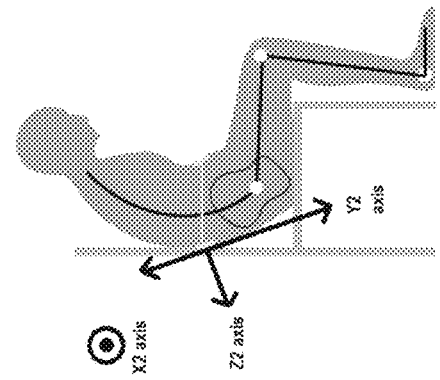
FIG. 48 is a schematic view of type 2 BTD being worn around a user's waist, in a slouched posture prior to inhalation.
Figure 49:
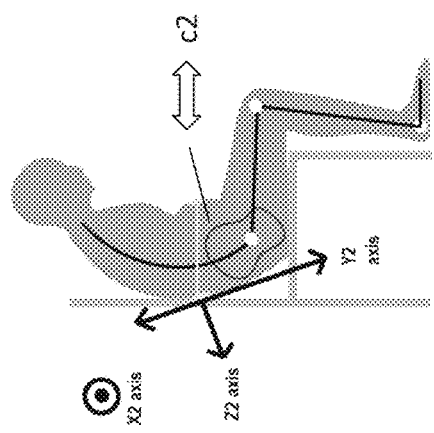
FIG. 49 is a schematic view of type 2 BTD being worn around a user's waist, in a slouched posture after inhalation.

Referring back to FIG. 46, the user is sitting upright while in a fully exhaled state. In FIG. 47, the user has fully inhaled diaphragmatically, while maintaining the same posture, causing an increase c1 in his/her waist circumference as measured by displacement sensor 146. Now in FIG. 48, the user is in an alternate slumped posture while fully exhaled. Now the user has inhaled to his/her full capacity as in FIG. 49, while maintaining this alternate slumped posture, causing an increase c2 in his/her waist circumference as measured by displacement sensor 146. Again, c1 and c2 may be different, just like d1 and d2 were different in a type 1 BTD discussed above, due to variations in diaphragmatic excursion at different posture levels. The processes and algorithms described below therefore also take into account posture angle to help standardize variations in the output of a displacement sensor signal, utilizing posture zone coefficients as described, for assessing the depth of an inhalation, across the user's posture range.

For a type 2 BTD, a signal processing method is also provided below to help cancel out body movement noise during breathing. For example, between FIGS. 46 and 48, the user has changed their posture, while in an exhaled state. This alone can result in a fluctuation in trunk circumference and thus a change in the output of the displacement sensor which should not be attributed to breathing. A process described below, for example, can learn a user's baseline trunk circumference (in an exhaled state) across a range of posture angles, and a filtered breath signal can be computed relative to this to provide a net inhalation level.

Type 3 BTD

Figure 50:
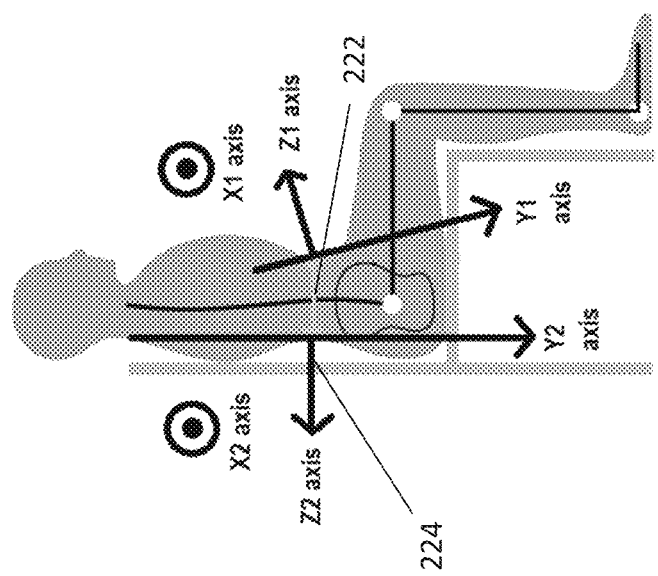
FIG. 50 is a schematic view of a type 3 BTD worn around a user's waist.

A type 3 BTD is simply a combination of type 1 and type 2, in that both a displacement sensor, and two angle sensors are used (one angle sensor on the abdomen and one angle sensor on the back) for a total of three sensors. For example, FIG. 50 shows breath training device 220 of the second embodiment being worn (a type 3 BTD), which has a displacement and angle sensor in its front sensor housing 222, and an angle sensor in its back sensor housing 224. Alternately, the positions of the front and back sensor housings can be interchanged, again, since trunk circumference can be measured from any point around the waist. The advantage of a type 3 BTD is that both methods of measuring breath—as explained for type 1 BTD and type 2 BTD above—are simultaneously used (while also measuring posture angle as previously explained therein), which can help in certain cases for more accurate breath tracking as explained later.

Type 4 BTD

A type 4 BTD measures both respiration and posture from one location on the body near the abdomen, or upper pubic area below the navel, such as with sensor case 602 of the seventh embodiment in FIG. 41A. In this approach, front sensor housing 262 shown in FIGS. 42-45 is replaced with sensor case 602 containing angle sensor 618, and no sensor is utilized on the user's back. Referring to FIGS. 42 and 44 showing upright and slumped poses, it should be noted that posture can be reasonably approximated utilizing the direction of just the Z1 axis from the user's anterior, provided that that user is retaining their breath. As previously discussed for a type 1 BTD, when the direction of the Z1 axis changes, this can be due to several confounding factors including posture change, body movement, or breathing. In that version, the Z2 axis is utilized as a reference to help disambiguate the cause and determine the component of breathing contributing to the Z1 direction change. In a type 4 BTD, since the Z2 axis is not available, other techniques must be used. An alternate signal processing method is described below for type 4 BTD's which includes basic inference reasoning and assumptions to help separate and isolate a relative diaphragm position and relative posture position from a single angle sensor output for deriving a filtered breath signal, allowing to select a likely cause for the Z1 direction change given the sensor signal data evidence, and to still be able to gauge the depth of an inhalation given the determined posture.

Description of Operation, Software, Algorithms

First Embodiment of Breath Training Process

Figure 51:
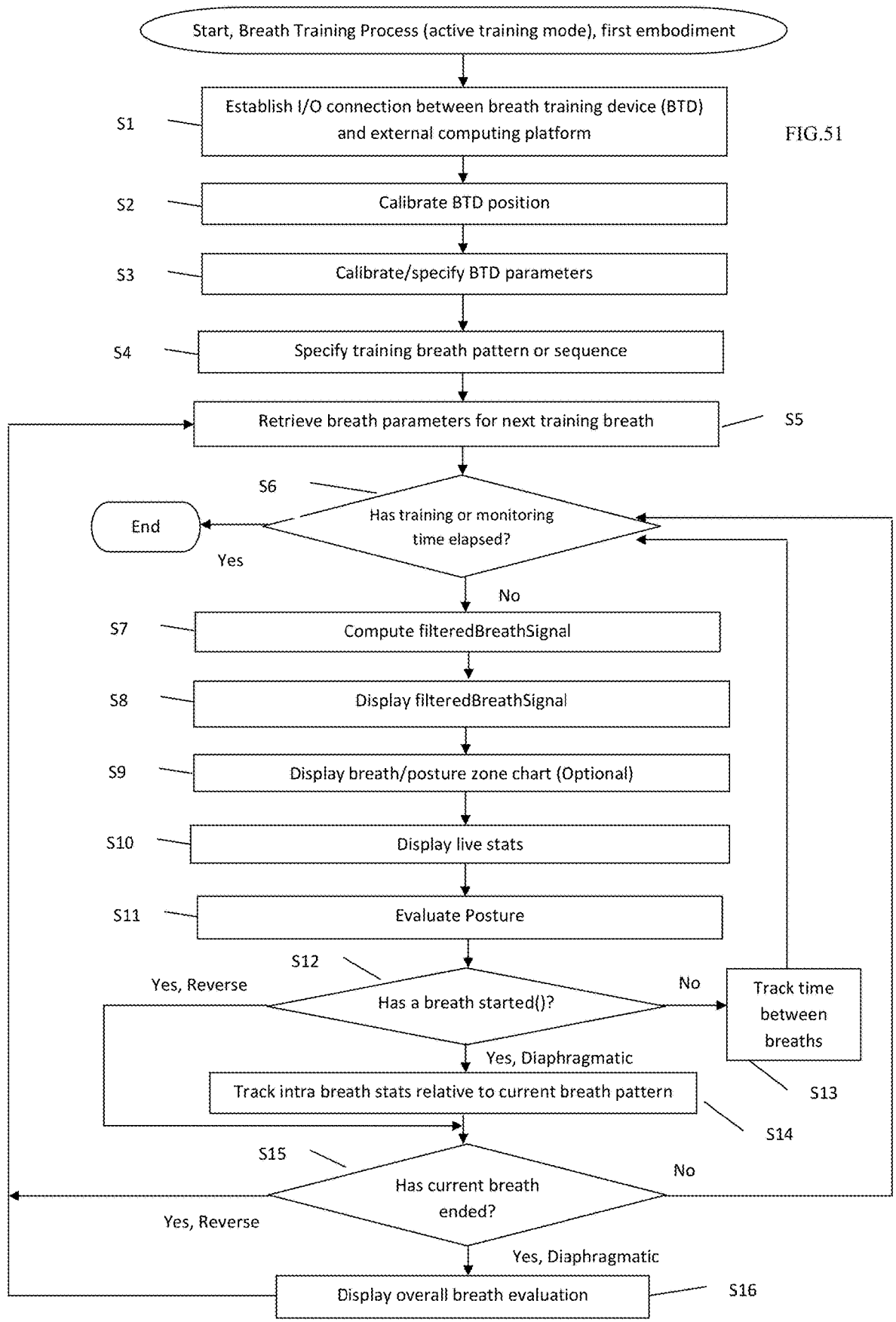
FIG. 51 is a flowchart showing exemplary steps involved in implementing a first embodiment of a breath training process of the present invention.

A first embodiment of a breath training process of the present invention shown in a flowchart in FIG. 51 is stored as a breath training program in memory 166 of external computing platform 162, and executed by CPU 164. This process can receive, process, display, and evaluate sensor output signals sent from one of the breath training devices described in the previous embodiments while being worn by a user. This process can start, for example, when a user presses a button or a software button on a touch screen as part of input devices 172 of external computing platform 162. This process is considered to be an active training mode in the present invention.

Referring to FIG. 51, the overall flow of the breath training process of the first embodiment is now described, and the details of many modules will be discussed hereinafter. In step S1, an I/O connection is established between platform I/O 170 of external computing platform 162 and the I/O of the BTD being used (such as I/O 144 of BTD 100), again, preferably wireless-based such as Bluetooth. If the embodiment of the BTD being used has more than one I/O and microcontroller, such as BTD 220 of the second embodiment, then a separate I/O connection is established between each of the plurality of I/O's of the BTD and platform I/O 170 of the external computing platform 162 for receiving multiple streams of sensor output signals and other data. The user can, for example, click a software button on display 168 of external computing platform 162 to commence the I/O connection. Prior to this, the user first turns on the BTD if it has switch 174, or alternately, step S1 can change the BTD from a low power mode to normal power mode if the given BTD does not utilize switch 174 as previously discussed. If the connection fails for any reason, such as battery 152 not being charged, an error message can be displayed on the user interface of the breath training program on display 168. If the connection is successful, process flow proceeds to the next step.

In step S2, the user now is asked to calibrate the position of the BTD on his/her body to ensure optimal positioning for breath and posture tracking. In step S3, the user performs an in-depth calibration in order for the breath training program to learn the range of motion of the user's body, and to fine-tune the parameters of the BTD. Then in step S4, the user selects the specific breath pattern he/she wishes to train with, and in step S5, the parameters associated with the selected pattern are retrieved and set by the breath training program. Then, the breath and posture evaluation process starts with step S6. The user may end the process at any time, for example, by pressing a button on external computing platform 162, or by setting a timer for the current evaluation session, with the session ending when the time limit is reached.

Put alternatively, and as previously discussed, the device can be used to calibrate for effects of different relative user posture positions while said user is in a defined respiratory state, sampling and storing the breathing sensor data across a plurality of different relative user posture positions as defined by the angle sensor data, thereby creating first calibration data. The device can also produce posture adjusted user respiration data by using this first calibration data, said breathing sensor data, and the angle sensor data to correct the breathing sensor data for variations in the user posture. Again this defined respiratory state is any of a defined exhalation state and a defined inhalation state.

Thus, for example, in step S7, a filtered breath signal is computed based on the sensor output signals received from the BTD through I/O 170 of external computing platform. In step S8, the filtered breath signal is graphed in real time, providing visual feedback for the complete breath. In step S9, a breath/posture zone chart is displayed, which tracks in real time which zone the user's posture is in, displaying a posture indicator (from slouched to upright), as well as a breath indicator shown relative to the posture indicator. In step S10, live stats are displayed, showing time elapsed, user's breath and posture scores, respiration rate, and other real-time data. In step S11, the user's posture is evaluated and real-time visual feedback provided on a posture graph, showing if the user is upright or slouched.

Processing step S12 looks for the start of a breath, whether it is a reverse or diaphragmatic breath. If no start of breath is detected, the breath training program tracks the time between breaths in step S13 and loops back to step S6 to repeat. In step S12, if a reverse breath has started, the breath training program jumps ahead to step S15 to monitor for the end of the reverse breath, looping back to step S6 if the reverse breath has not ended, and looping back to step S5 to retrieve the next breath parameters if the reverse breath has completed. In step S12, if a diaphragmatic breath has started, the breath training program performs the processes in step 14, wherein it tracks the diaphragmatic breath relative to the parameters of the current breath pattern. Then in step 15, if the diaphragmatic breath has not completed, the breath training program loops back to step S6. If the diaphragmatic breath has completed, the breath training program loops back to step S5 to retrieve the next breath parameters. It should be noted that the order of steps S8 to S11 are not critical and can be performed in varying orders.

Now the details of the specific processes in steps S1 to S16 in FIG. 51 will be described, as well as the sub-processes of those processes where relevant to the present invention. We first will describe the signal processing of step S7, for computing the filtered breath signal, as this is utilized by many processes that follow and is an important part of the present invention.

Figure 60:
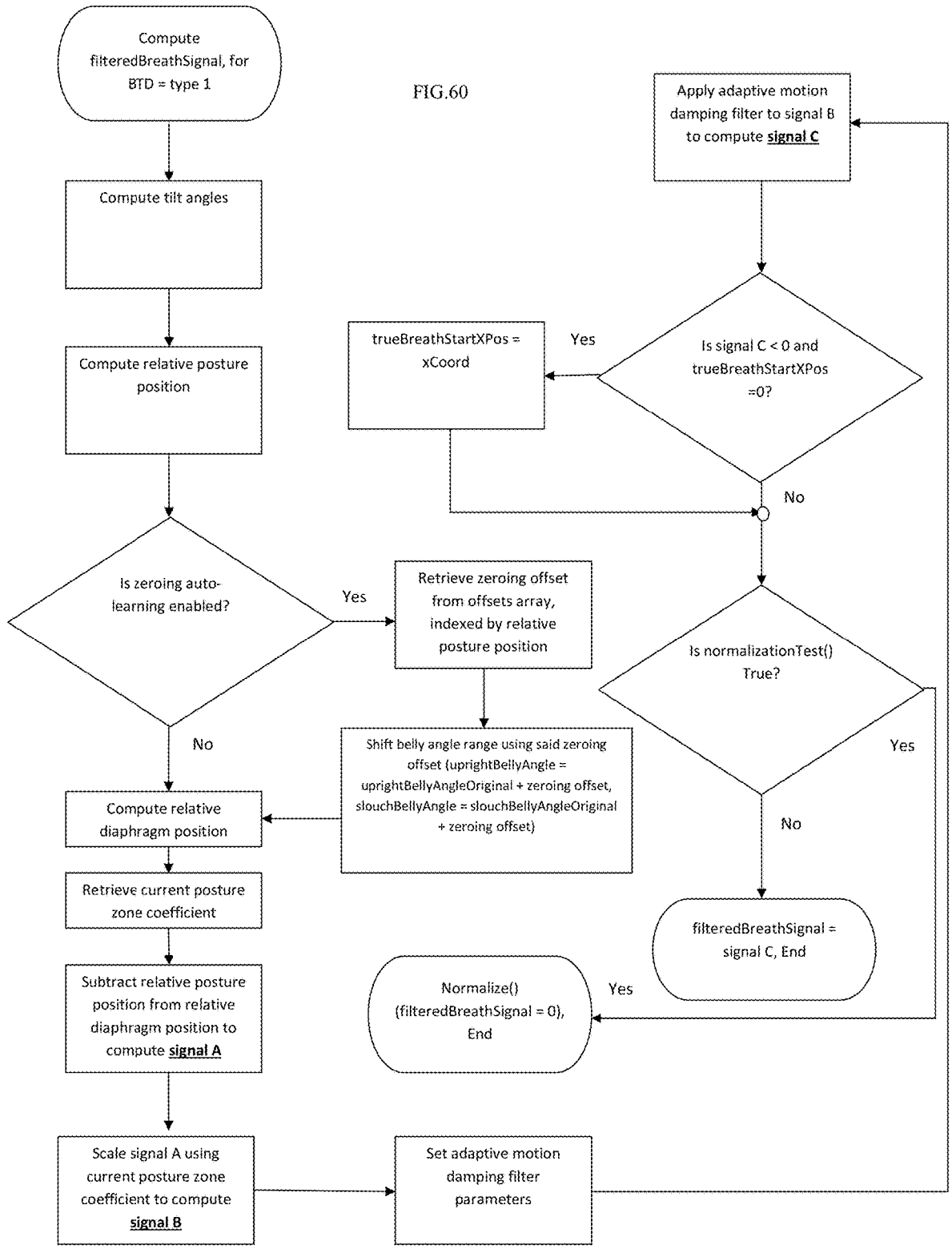
FIG. 60 is a flowchart showing exemplary steps involved in implementing a Compute filteredBreathSignal, for BTD=type 1 process of the present invention.

The filtered breath signal is a posture and body-motion-noise adjusted signal, indicating a real-time diaphragmatic inhalation depth. Its computation steps depend on the BTD type. FIG. 60 shows a flowchart detailing the process of computing the filtered breath signal for a type 1 BTD, which uses angle sensors on the user's back and abdomen, such as front angle sensor 266 and back angle sensor 268 of the third embodiment, shown being worn in FIG. 42.

Figure 62:
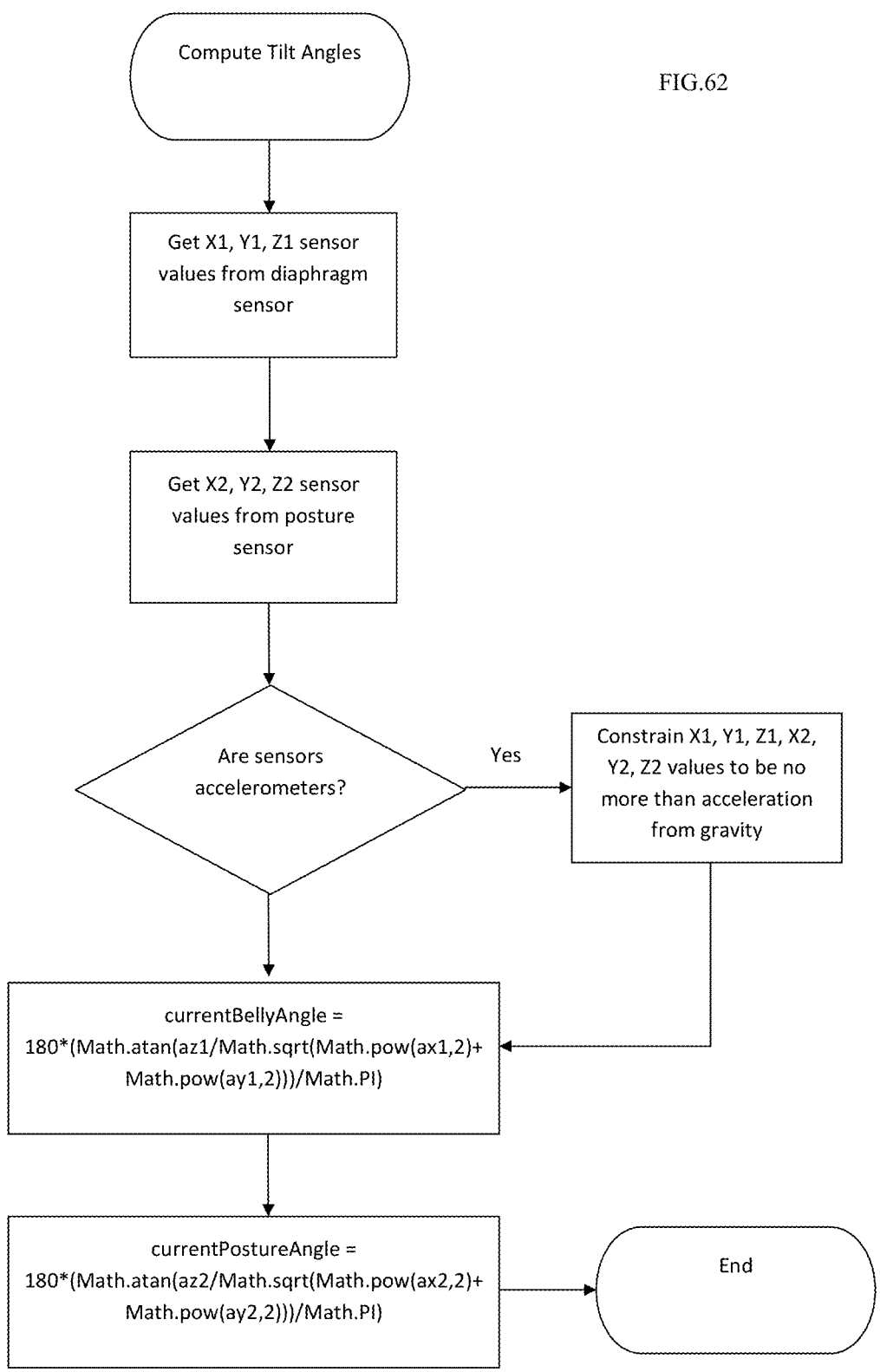
FIG. 62 is a flowchart showing exemplary steps involved in implementing a Compute Tilt Angles process of the present invention.
Figure 64:
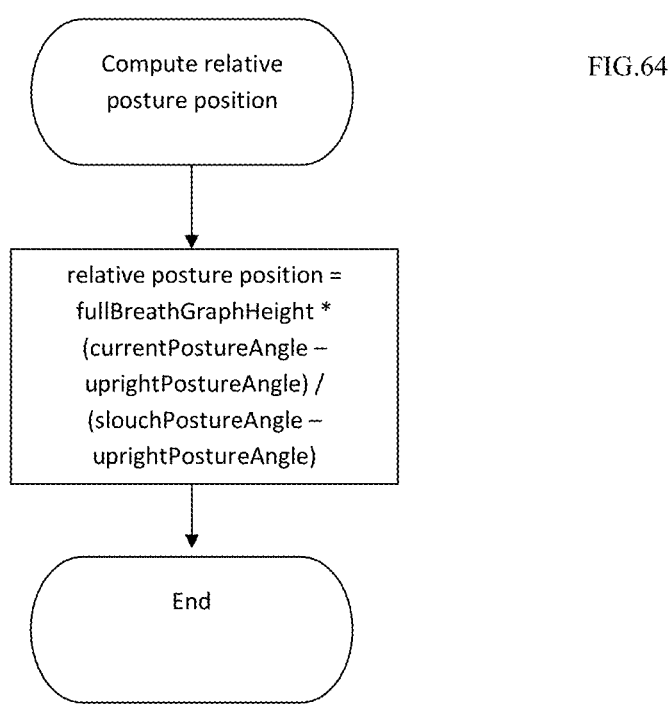
FIG. 64 is a flowchart showing exemplary steps involved in implementing a Compute relative posture position process of the present invention.

The first step is the sub-process of computing the tilt angles as shown in the flowchart in FIG. 62 as one example of determining the inclination of the sensors. In this sub-process, the X, Y, and Z axes sensor output signals for both the posture and diaphragm sensors are first retrieved (such as front angle sensor 266 and back angle sensor 268 respectively). If said sensors are accelerometers, then these sensor output signals can be constrained to be no more than +−1 g (constraining the magnitudes of the vectors X1, Y1, Z1, and X2, Y2, Z2), to primarily consider the effects of gravity for measuring the angles. This can be done for example by setting the accelerometer to a 1 g scale mode, so that 1 g of acceleration along any axis produces the maximum output level for that axis. Next step is computing currentBellyAngle and currentPostureAngle based on the well-known trigonometric formula for such 3 axes computation as shown in FIG. 62, where the tilt of the Z axes is found relative to the orientation of the corresponding X-Y plane (currentBellyAngle is the belly angle or tilt of the Z1 axis previously discussed, and currentPostureAngle is the posture angle or tilt of the Z2 axis previously discussed as shown in FIGS. 42-45). Returning to FIG. 60, the next step is computing the relative posture position, as detailed in the sub-process in the flowchart shown in FIG. 64. The formula (currentPostureAngle−uprightPostureAngle)/(slouchPostureAngle−uprightPostureAngle) gives a ratio value of approximately 0 to 1 representing the current posture angle of the user within the posture angle range, with this value approaching 1 as the user's posture approaches a slouched position, and 0 as the user's posture approaches an upright position, where uprightPostureAngle and slouchPostureAngle are sampled during a calibration process as later described. This ratio is then scaled by multiplying by the constant full-BreathGraphHeight, and the resulting value is assigned to relative posture position. Returning to FIG. 60, the next step is checking if a zeroing auto-learning flag is set. If yes, then a zeroing offset from an offsets array is retrieved, indexed by relative posture position (zeroing offsets are continuously learned and stored as later described during normalization), and the belly angle range can then be shifted by uprightBellyAngle=uprightBellyAngleOriginal+zeroing offset, slouchBellyAngle=slouchBellyAngleOriginal+zeroing offset, which has the effect of dynamically adjusting the relative diaphragm position computation so that this value is near equal to relative posture position at a given posture, when the user is in a fully exhaled state, as a baseline.

Figure 65:
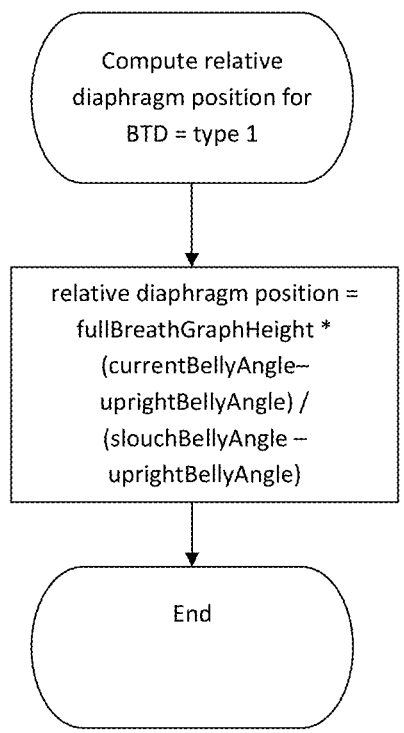
FIG. 65 is a flowchart showing exemplary steps involved in implementing a Compute relative diaphragm position for BTD=type 1 process of the present invention.

The next step is computing the relative diaphragm position, as detailed in the sub-process in the flowchart in FIG. 65. The formula (currentBellyAngle−uprightBellyAngle)/(slouchBellyAngle−uprightBellyAngle) also gives a ratio value of approximately 0 to 1 representing the current belly angle of the user within the belly angle range while fully exhaled, with this value approaching 1 as the user's posture approaches a slouched position while fully exhaled, and 0 as the user's posture approaches an upright position while fully exhaled, allowing this value to be compared to relative posture position. uprightBellyAngle and slouchBellyAngle are sampled during a calibration process as later described. Further, this value may be less than 0 if the user inhales in the upright posture state, since the belly angle may then exceed the uprightBellyAngle. This ratio is then scaled by multiplying by the constant fullBreathGraphHeight, and the resulting value is assigned to relative diaphragm position.

Whereas the posture angle varies primarily due to actual changes in posture, the belly angle varies due to both posture changes and diaphragmatic excursion during inhalation and exhalation. For example, when a user changes his/her seated posture from slouched to upright without breathing, this has the effect of moving the belly outwards and tilting the belly angle, similar to how the belly angle tilts when independently diaphragmatically inhaling, though the angle change is generally less during inhalation than the change from slouched to upright movement. Thus the two effects are generally additive to the belly angle. The present invention provides a process for separating the two for isolating the inhalation depth. The reason that relative diaphragm position is computed relative to where the current belly angle falls within a slouched to upright posture range (slouchBellyAngle to uprightBellyAngle) is to place it on the same scale as relative posture position to aid in cancelling out such non-breath related posture changes or body movements, which involves subtracting relative posture position from relative diaphragm position later described, with the difference generally revealing the net level of actual inhalation. For example, if the user fully exhales in a fully slouched posture, then both relative posture position and relative diaphragm position should be close to 1. Now if the user maintains his/her exhaled state and changes posture to a fully upright position, then both relative posture position and relative diaphragm position should approach close to 0 (with the near 0 difference between them correctly indicating that the user has not inhaled diaphragmatically). But all the points in between are not precisely linearly mapped as previously mentioned, and this is why the zeroing offset can be used to first dynamically correct the relative diaphragm position for the given posture angle level before subtracting relative posture position from it, so that this difference is near 0 across the entire range from slouched to upright posture, while the user maintains a fully exhaled state. Then when the user inhales (even while simultaneously changing posture), the net resulting belly angle change can be determined as described below to indicate the actual inhalation level.

Figure 67:
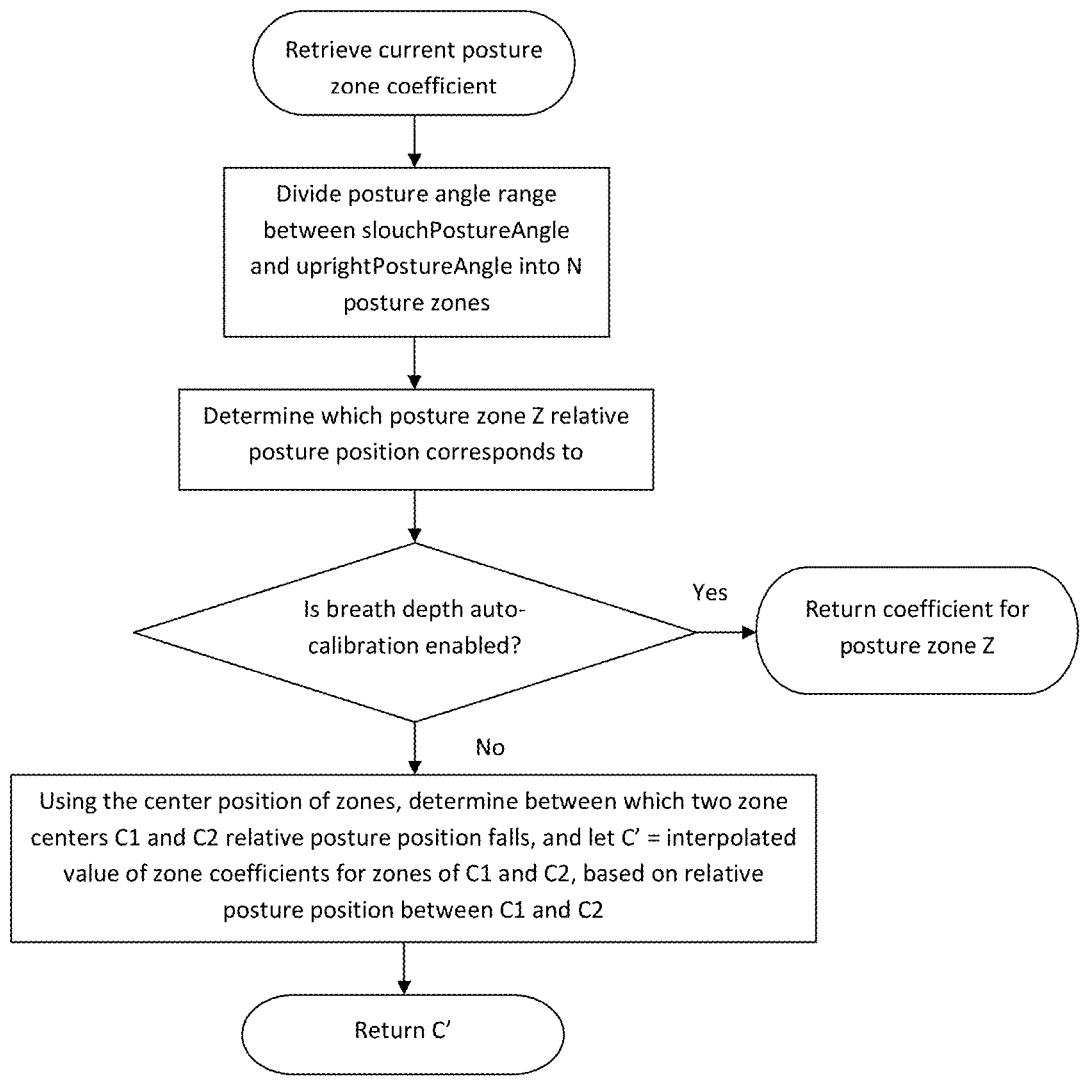
FIG. 67 is a flowchart showing exemplary steps involved in implementing a Retrieve current posture zone coefficient process of the present invention.

Returning to FIG. 60, the next step is retrieving the current posture zone coefficient, as detailed in the sub-process in the flowchart in FIG. 67. First, the posture angle range between slouchPostureAngle and uprightPostureAngle is divided into N posture zones. Next, it is determined which zone relative posture position corresponds to. Next, if the breath depth auto-calibration flag is set for learning a zone coefficient, then return the stored posture zone coefficient for the determined zone. If it is not set, then using the center position of zones, determine between which two zone centers C1 and C2 relative posture position corresponds to, and let C'=interpolated value of posture zone coefficients for zones of C1 and C2, based on relative posture position between C1 and C2, and return C' as the current posture zone coefficient.

Returning to FIG. 60, the next step is to subtract relative posture position from relative diaphragm position to compute a signal A. Then, signal A is scaled by multiplying using the current posture zone coefficient to compute signal B, for standardizing the depth of inhalations across different postures as previously explained.

Figure 68:
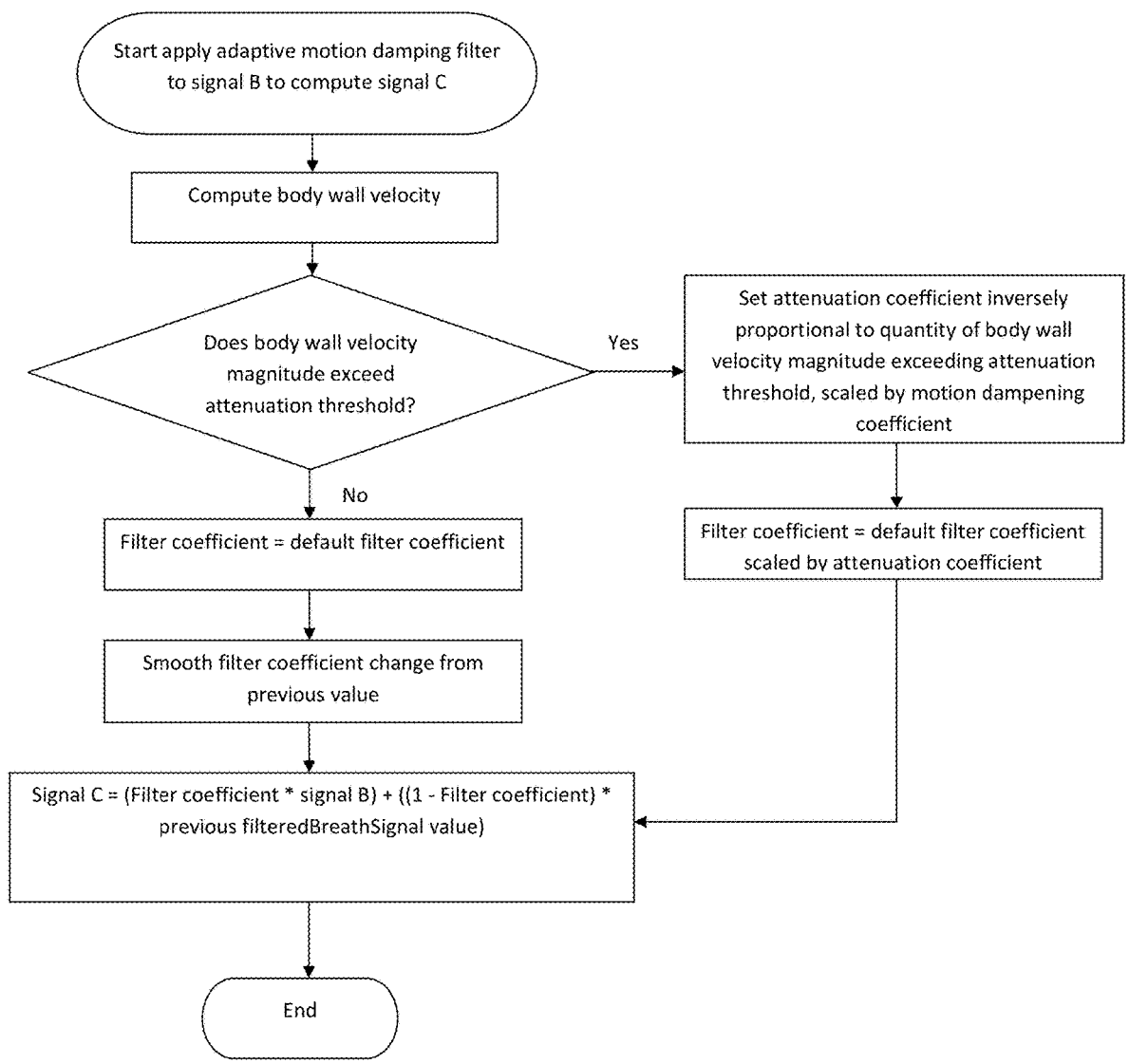
FIG. 68 is a flowchart showing exemplary steps involved in implementing (e.g. applying) an adaptive motion damping filter to signal B to compute signal C process of the present invention.

The next step is to apply an adaptive motion damping filter to signal B to compute a signal C, as detailed in the sub-process in the flowchart in FIG. 68, for further mitigating the effects of body motion noise. First, the body wall velocity is computed. For type 1-3 BTD's, the rate of change of relative posture position at the current time is used for the body wall velocity. For a type 4 BTD, the rate of change of relative diaphragm position at the current time is used for the body wall velocity. Then if the magnitude of the body wall velocity exceeds an attenuation threshold, then set an attenuation coefficient inversely proportional to the quantity of the body wall velocity magnitude exceeding the attenuation threshold, scaled by a motion dampening coefficient. For example, this formula can achieve this:

ac=attenuationThreshold/((motionDampening*
(Math.abs(bodyWallVelocity)−attenuation-
Threshold))+attenuationThreshold);

Then set a filter coefficient (damper[count]) equal to a default filter coefficient scaled by this attenuation coefficient. For example: damper[count]=filterValue*ac; //filterValue is the default filter coefficient If the magnitude of body wall velocity does not exceed an attenuation threshold, then set a filter coefficient equal to the default filter coefficient, and smooth any filter coefficient change from its previous value, using this code, for example:

damper[count]=filterValue;

damper[count]=damper[count]*(0.5)+damper[count−
1]*(1.0−0.5); // Smooth filter coefficient change
from previous value This smoothing is helpful, for example, when a user is rapidly altering their posture and then suddenly stops, making the transition from using the scaled filter coefficient to the default filter more gradual, to avoid a spike in the filtered breath signal.

Signal C can then be computed as follows for example:

Signal C=Math.round(damper[count]*signalB+(1.0−
damper[count])*filteredBreathSignal[count−1]);

Generally, the larger the body wall velocity (meaning the faster the current posture angle or current belly angle is changing at the present time depending on the type of BTD used), the smaller the filter coefficient (damper[count]) will be, resulting in a greater damping effect on the change of Signal C from its previous value. Furthermore, a motion-Dampening coefficient set during calibration can be used to further scale the damping effect.

Returning to FIG. 60, the next step is to check if signal C<0 and trueBreathStartXPos=0. If yes, then set trueBreathStartXPos=xCoord, which tracks where in time (as an X coordinate on the timeline) an inhalation begins, as later described.

The final steps of computing the filtered breath signal (for a type 1 BTD) are to do a normalization test on Signal C. If true, then a Normalize( ) function is called, which results in the filtered breath signal being set to 0. If false, the filtered breath signal is set to Signal C as above.

Before the normalization test and normalization processes are described, a timeline graph 350 on display 168 of external computing platform, as part of the breath training program, is first introduced, which provides a visualization of the filtered breath signal according to the first embodiment of the breath training process.

Figure 99:
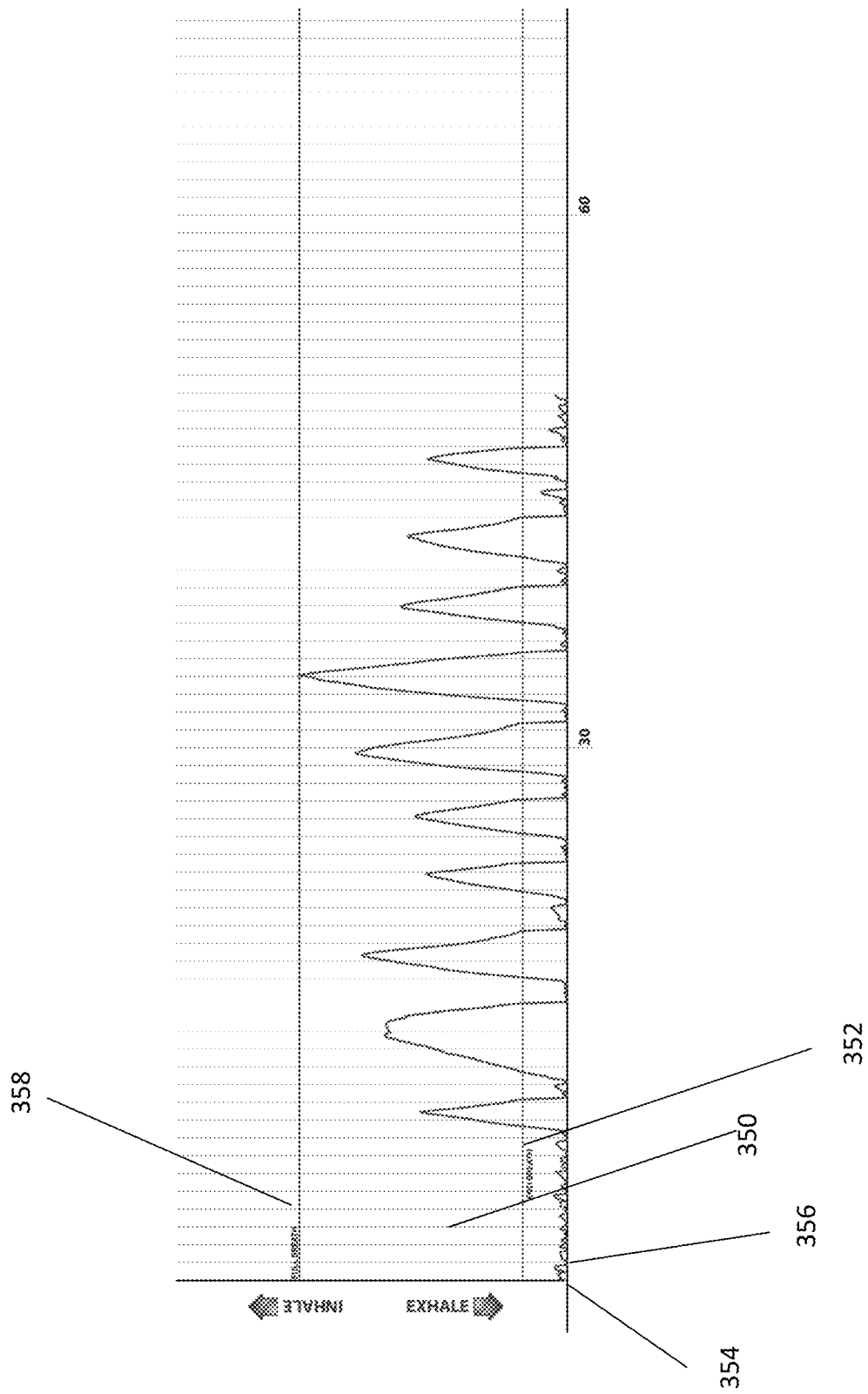

In FIG. 99, the filtered breath signal is displayed on the Y axis of timeline graph 350, and the X axis represents time in seconds, with each vertical interval line shown being one second for example. A horizontal end breath threshold line 352 is shown, which represents the cut off point for triggering when a diaphragmatic breath has ended, that is, when the filtered breath signal falls below this line. It should be noted that for the purpose of these descriptions and code examples, the convention is that the origin 354 is located as shown in FIG. 99, and the negative Y axis points upwards, and positive X axis points right, so that the filtered breath signal is negative when above the origin line, referred to as fully exhaled line 356 (where the filtered breath signal=0), and the filtered breath signal is positive when below fully exhaled line 356. When a user diaphragmatically inhales and their belly moves outwards, this causes filtered breath signal to decrease and the graph to rise on timeline 350. As they exhale and their belly moves inwards, filtered breath signal increases and the graph falls. It should be noted that signal C is essentially the same as the filtered breath signal on the timeline graph, except that it is prior to the normalization test, which could result in the filtered breath signal being set to 0. A full breath threshold line 358 represents a maximum diaphragmatic inhale, later described.

The normalization test is now described which applies to type 1-3 BTD's, as detailed in the sub-processes in the flowcharts in FIGS. 69-72, wherein four variations of such a test are disclosed. FIGS. 72A-72B details a normalization test for a type 4 BTD, later described.

Figure 69:
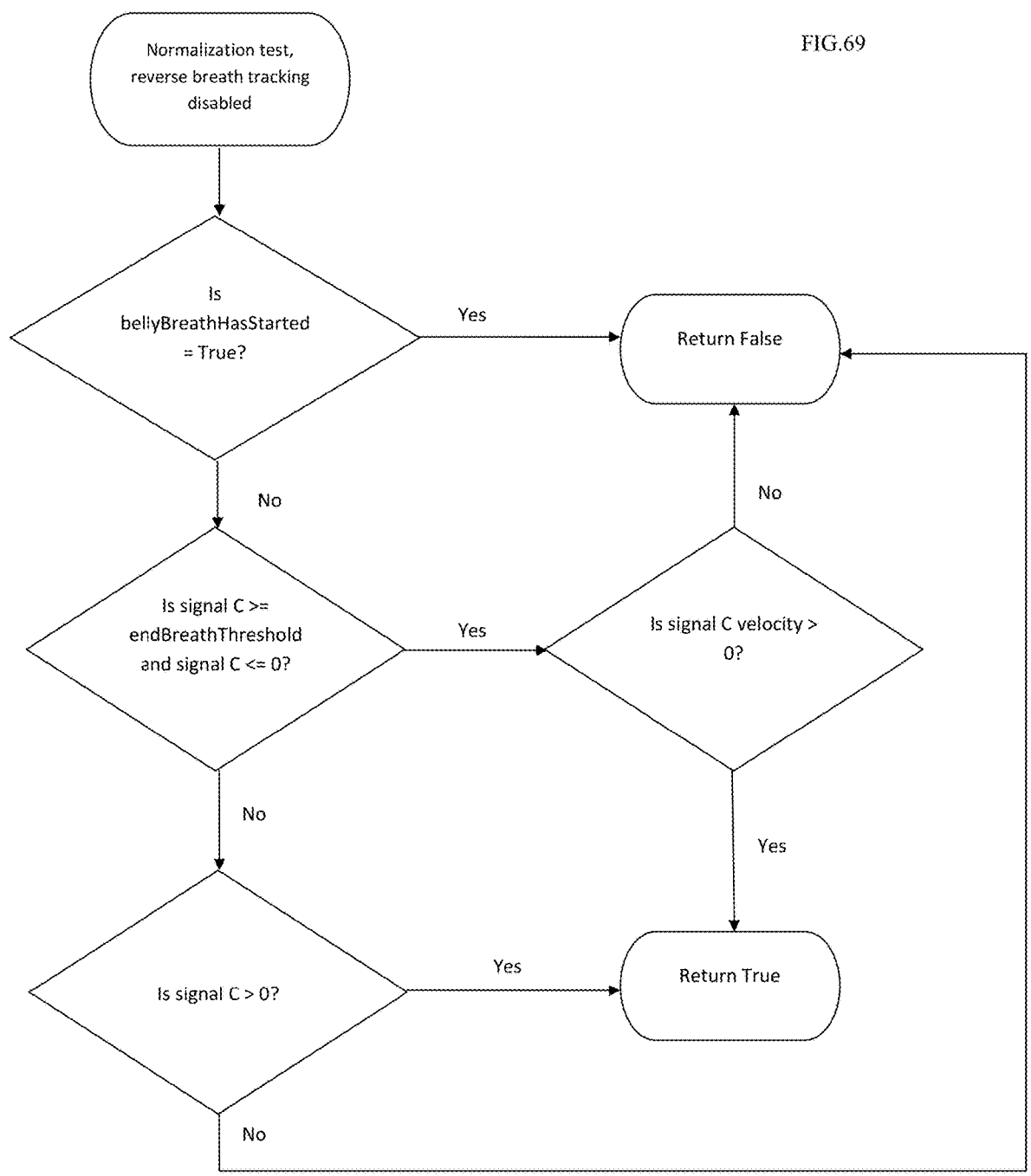
FIG. 69 is a flowchart showing exemplary steps involved in implementing a Normalization test, reverse breath tracking disabled process of the present invention.
Figure 100:
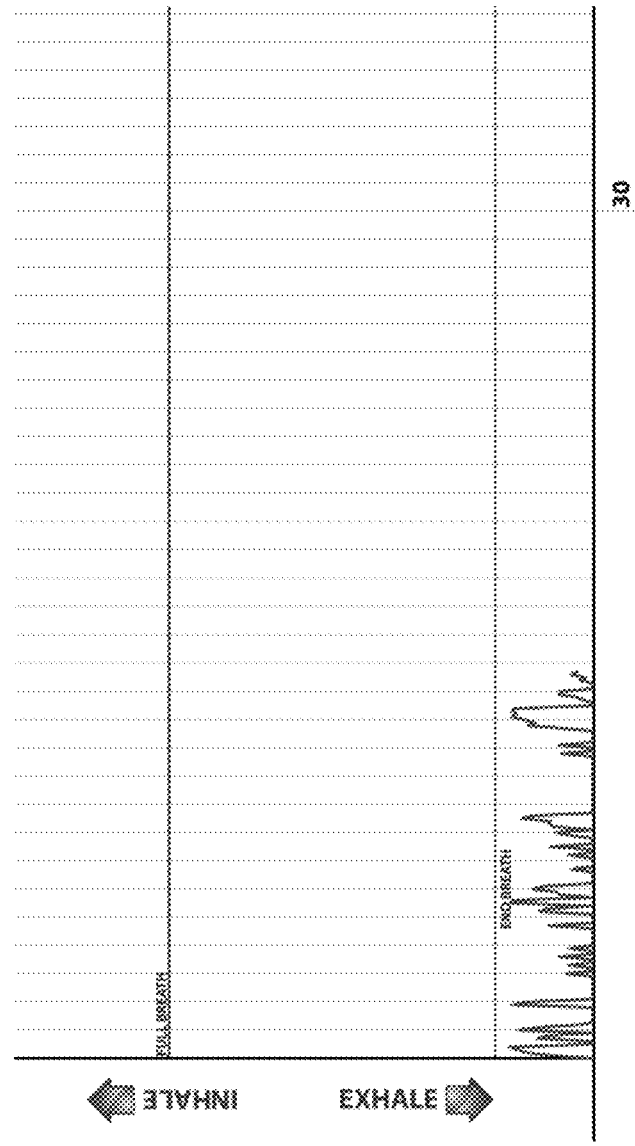

FIG. 69 details the process steps of a normalization test with reverse breath tracking disabled. First, if a bellyBreathHasStarted flag is set to True, this process returns False, since a diaphragmatic breath is underway and already being tracked (where Normalization may occur as part of that process later described). If bellyBreathHasStarted is set to False, then if signal C>=endBreathThreshold and signal C<=0, then if signal C velocity>0, then return True, otherwise if signal C velocity is <=0, then return False. If signal C>0, then return False. Signal C velocity is defined as the rate of change of signal C at the current time. Referring back to FIG. 99, a visual interpretation of these steps on timeline graph 350 is explained. When signal C is between fully exhaled line 356 and end of breath threshold 352, and signal C falls at any point (increases), then signal C (or the filtered breath signal) is set to 0 on timeline 350 (or normalized in this context). End of breath threshold 352 can also be thought of as a noise threshold line. When signal C (or a user's inhalation depth level) is below this line and above 0, then only a rising signal C on the timeline (signal C value decreasing) will avoid normalization (or setting back to 0). In other words, if a user's belly is consistently moving outwards in the zone between fully exhaled line 356 and the end of breath threshold 352 (appearing consistently to be a diaphragmatic inhalation signal), then this signal direction is allowed to continue, otherwise if there is any stagger in inhalation or momentary dip or reversal in signal C while in this zone, the signal is normalized or reset back to a baseline, as it is deemed to be noise, and not a true inhalation. This process offers several advantages for breath tracking. One challenge as previously discussed is that it is not practical to rely on a user's absolute body position parameters to determine an inhalation depth, especially when the user is changing his/her body position. For example, a user could have a current posture angle of 10 degrees, and a current belly angle of 6 degrees, while in a fully exhaled state, with the filtered breath signal being near 0. Several minutes later, due to a variety of factors, at a 10 degree current posture angle, a belly angle of 8 degrees may now actually correspond to the fully exhaled state. Such factors can include a shift in the respiration belt position or sensor case, movement or bunching of clothes under the belt, eating or drinking which can temporarily expand the belly, other changes in body position such as reseating, as well as sensor drift. Without a process to dynamically compensate for this, the fully exhaled level would often drift, such that when a user fully exhales, the filtered breath signal would not return to the 0 level, and thus the end point of a breath or exhalation could not be accurately determined. The process described above can provide such a dynamic normalization test, for determining a new fully exhaled level at a given posture. When the breath training program normalizes as described below (when the normalization test is true), it learns a new correspondence between relative posture position and relative diaphragm position by learning a new zeroing offset at a given posture level, which corresponds to a new 0 level or fully exhaled state of the user, causing filtered breath signal to be computed as near 0 at this given posture and diaphragm position, in an exhaled state. This functions to continuously standardize the exhalation level. Also as mentioned above, if signal C is >0, this also triggers normalization. For example, when a user's exhalation reaches end of breath threshold line 352 and filtered breath signal is set to 0 (so that the graph jumps down to 0), the user's belly may continue moving inwardly (as the breath has not truly ended yet), and thus signal C may continue to increase, dropping below the 0 level, in which case, the process can be seen as overcorrecting signal C. The process above will continuously normalize in this case until the signal's tendency to increase has ended while it resides near 0 (and the fully exhaled level is now accurately judged), meaning the user's belly has stopped moving inwards. This process can be seen as continuously funneling signal C to the correct 0 level or fully exhaled level at any given posture. This process also helps filter out body movement noise from being considered as an inhalation signal. Body movements are often characterized by a back and forth swing of the filtered breath signal as shown in the example in FIG. 100, which shows the remaining non-inhalation component which has not been filtered out by the signal processing method described above for computing the filtered breath signal, including subtracting relative posture position from relative diaphragm position, scaling this difference with the posture zone coefficient, and applying the adaptive motion damping filter. If this swing is happening under the end of breath threshold 352, then signal C at some point is falling, which triggers normalization back to 0. This helps to prevent a false upward inhalation trend from forming. Again, without such a normalization testing process and normalization, the back and forth body movements as shown in FIG. 100 could cause a cumulative error effect, where the filtered breath signal could tend to move upwards, causing a user's fully exhaled state, for example, to be incorrectly deemed to be near the center of the graph along the Y axis between fully exhaled line 356 and full breath line 358.

Figure 70:
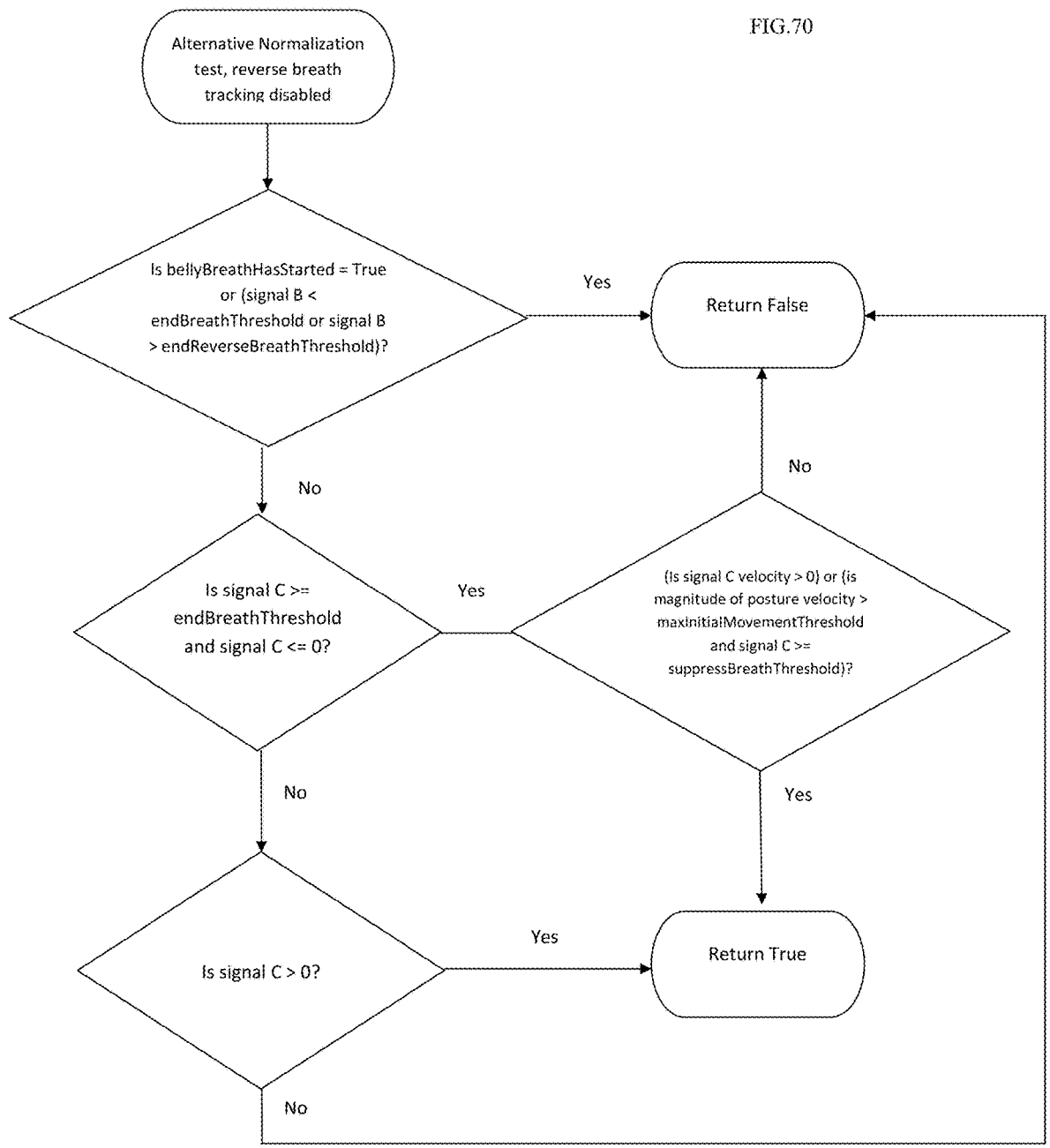
FIG. 70 is a flowchart showing exemplary steps involved in implementing an Alternative Normalization test, reverse breath tracking disabled process of the present invention.

FIG. 70 shows the process for an alternate normalization test when reverse breath tracking is disabled. The only difference compared to the process in FIG. 69 is the step: "Is signal C velocity>0", is replaced with "(Is signal C velocity>0) or (is magnitude of posture velocity>maxInitialMovementThreshold and signal C>=suppressBreathThreshold)", which allows body movement or when relative posture position rate of change goes beyond a maxInitialMovementThreshold to also trigger normalization when signal C is below a suppressBreathThreshold line. The idea here is to make admission of an inhalation signal even more rigorous, by dismissing such a trend (even if it is consistently going up on timeline 350) when it is accompanied by a significant degree of body movement near the start of such a signal, to further reduce the chance of a false positive inhalation signal (with the tradeoff that some valid inhalation signals may be ignored on occasion, when they occur with intense body movements for example).

Figure 71:
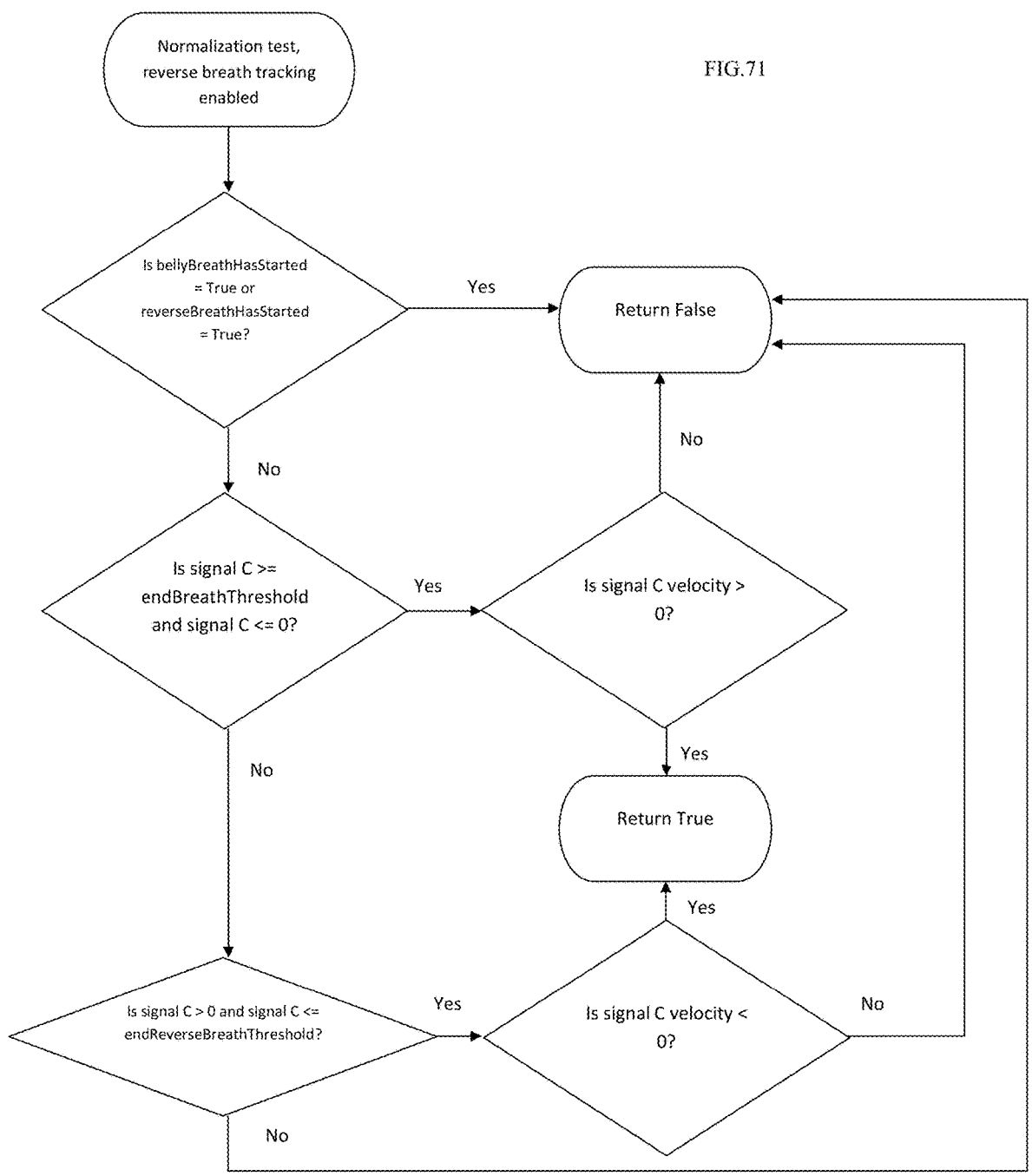
FIG. 71 is a flowchart showing exemplary steps involved in implementing a Normalization test, reverse breath tracking enabled process of the present invention.
Figure 101:
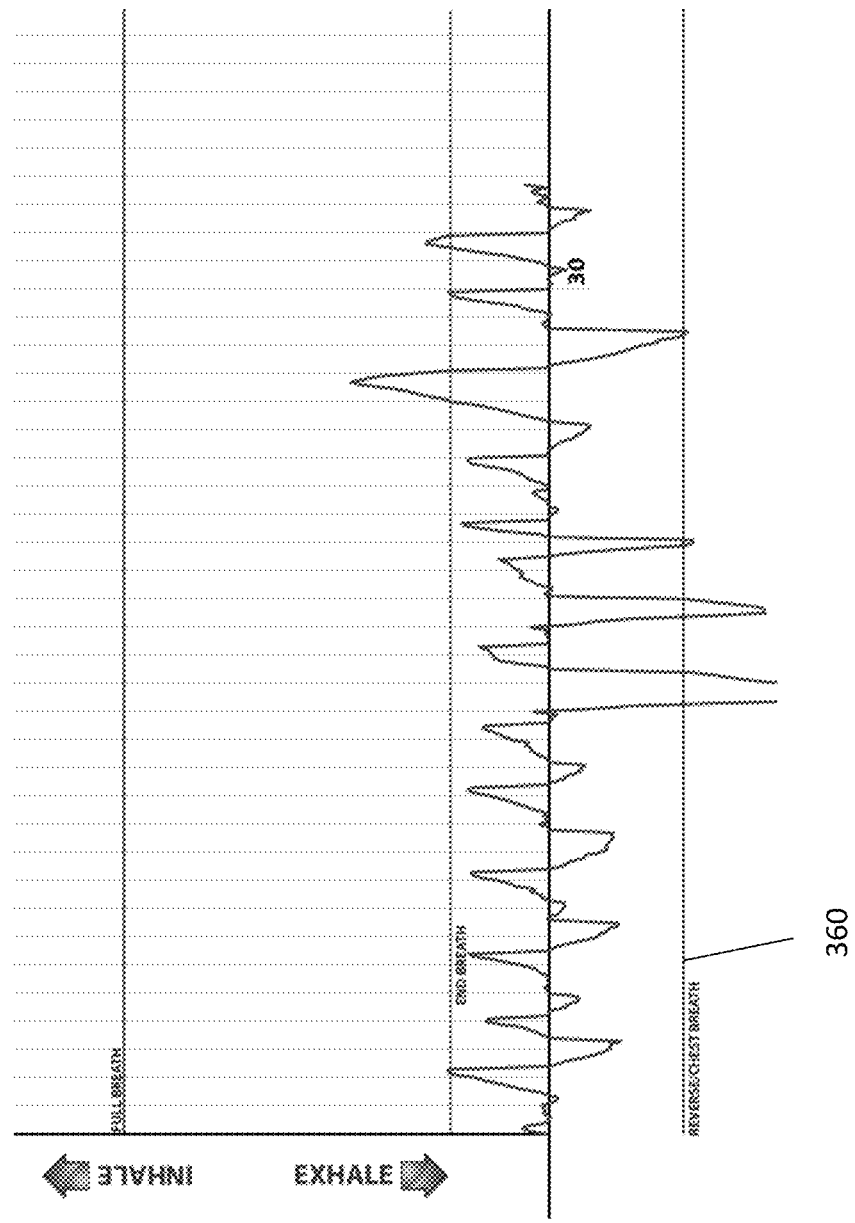

FIG. 71 shows the process for a normalization test with reverse breath tracking enabled. A reverse breath, also known as a paradoxical breath, happens when a user's belly moves inwards during an inhalation, which often occurs when a user is chest breathing. This process allows signal C to fall below the fully exhaled line 356, as shown in FIG. 101, without immediately triggering normalization back to 0, to also allow breath tracking below fully exhaled line 356. First, if a bellyBreathHasStarted flag is set to True or a reverseBreathHasStarted flag is set to True, then this process returns False, since a diaphragmatic breath or reverse breath is underway and already being tracked (where Normalization may occur as part of that process later described). If bellyBreathHasStarted and reverseBreathHasStarted are both set to False, then if signal C>=endBreathThreshold and signal C<=0, then if signal C velocity>0, then return True (just like the normalization test in FIG. 69 for a diaphragmatic inhalation), otherwise if signal C velocity is <=0, then return False. If signal C>0 and signal C<=endReverseBreathThreshold (for reverse breath testing), then if signal C velocity<0, then return True, otherwise if signal C velocity>0, return False (to allow tracking the downward trend of a reverse breath within the zone below fully exhaled line 356 and above an end of reverse breath threshold line 360, as shown in FIG. 101). This process provides similar advantages to the normalization test process described in FIG. 69, with similar dynamic standardization of an exhalation level, but extending to both diaphragmatic and reverse breathing.

Figure 72:
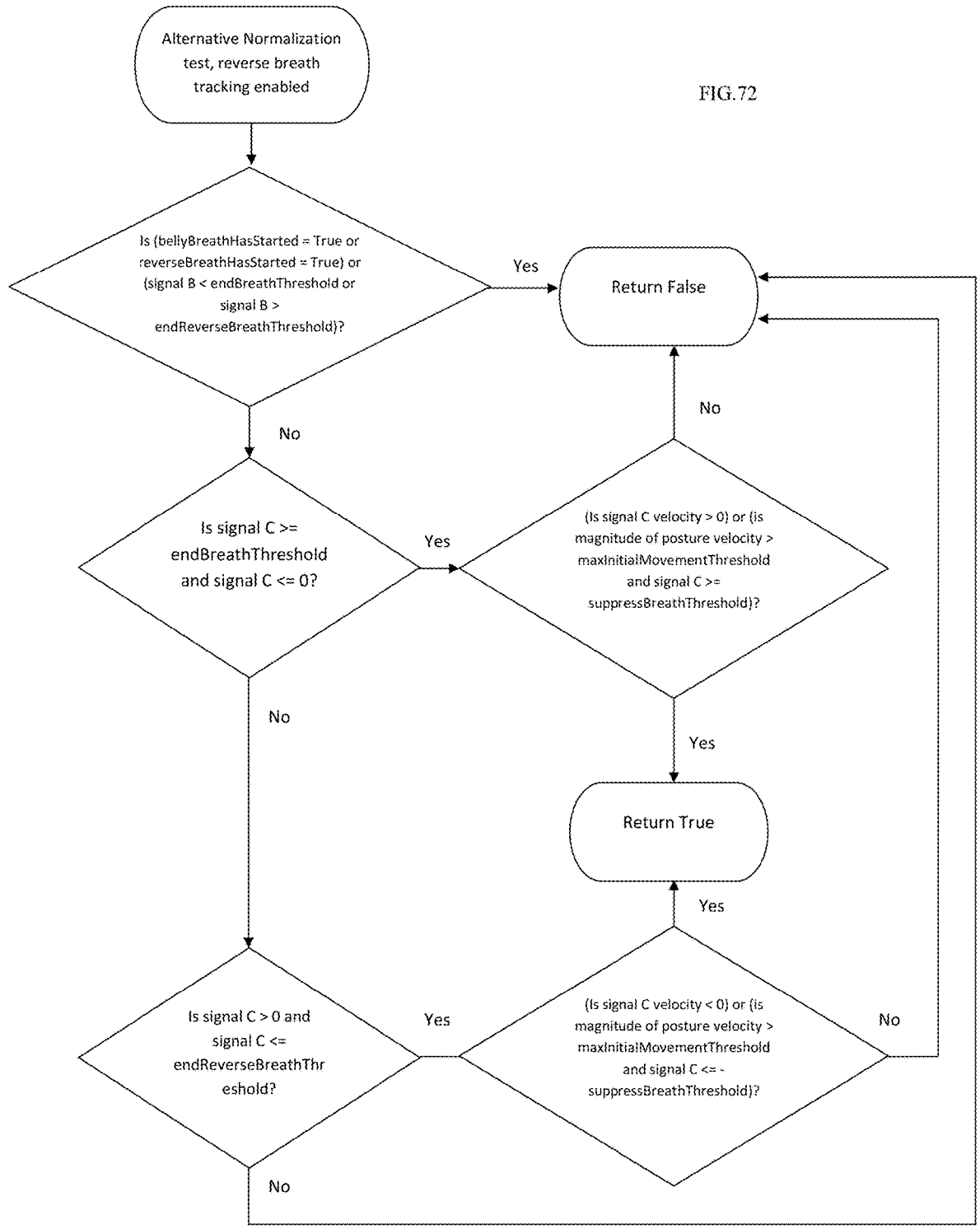
FIG. 72 is a flowchart showing exemplary steps involved in implementing an Alternative Normalization test, reverse breath tracking enabled process of the present invention.
Figure 72A:
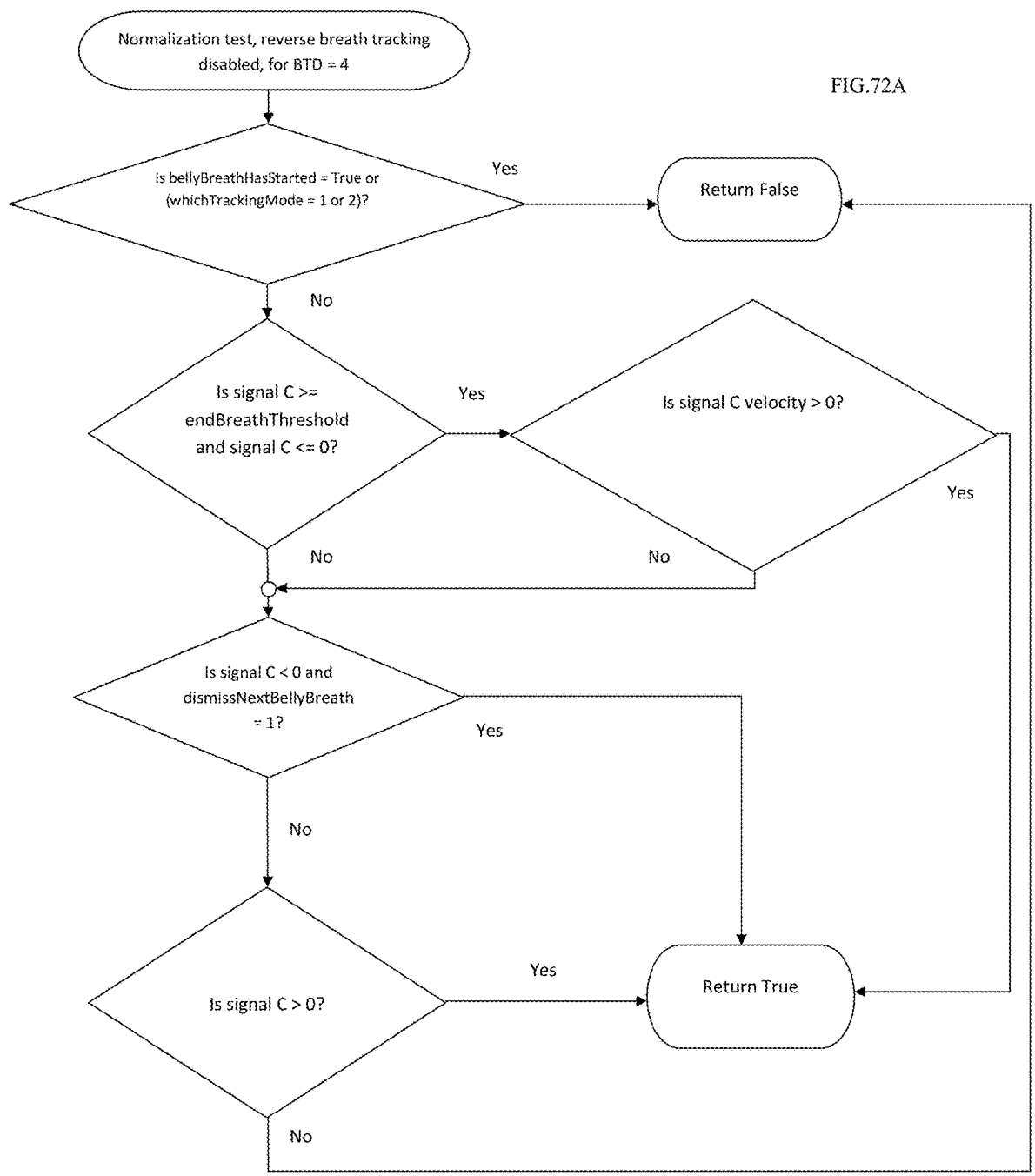
FIG. 72A is a flowchart showing exemplary steps involved in implementing a Normalization test, reverse breath tracking disabled process of the present invention for a BTD=type 4.
Figure 72B:
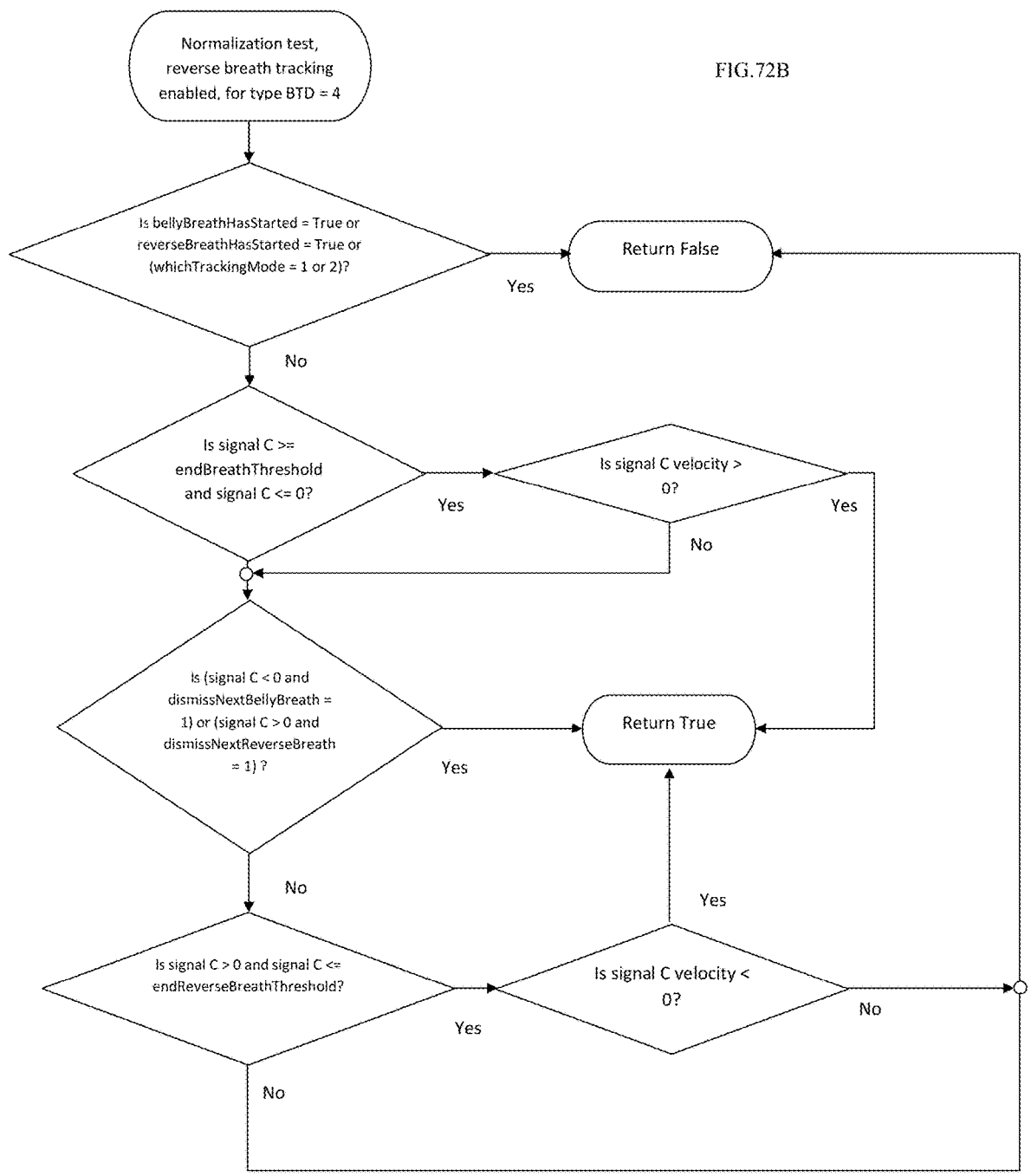
FIG. 72B is a flowchart showing exemplary steps involved in implementing a Normalization test, reverse breath tracking enabled process of the present invention for a BTD=type 4.

FIG. 72 shows the process for an alternate normalization test when reverse breath tracking is enabled, with the only differences compared to the process in FIG. 71 are the steps: "Is signal C velocity>0?" and "Is signal C velocity<0?" are replaced with "(Is signal C velocity>0) or (is magnitude of posture velocity>maxInitialMovementThreshold and signal C>=suppressBreathThreshold)?" and "(Is signal C velocity<0) or (is magnitude of posture velocity>maxInitialMovementThreshold and signal C<=−suppressBreathThreshold)?" respectively, to similarly allow body movement or when the relative posture position rate of change goes beyond a maxInitialMovementThreshold to also trigger normalization when signal C is within a zone bounded by the +−suppressBreathThreshold line, with similar advantages as previously described for the process in FIG. 70, but extended to reverse breath tracking.

Figure 73:
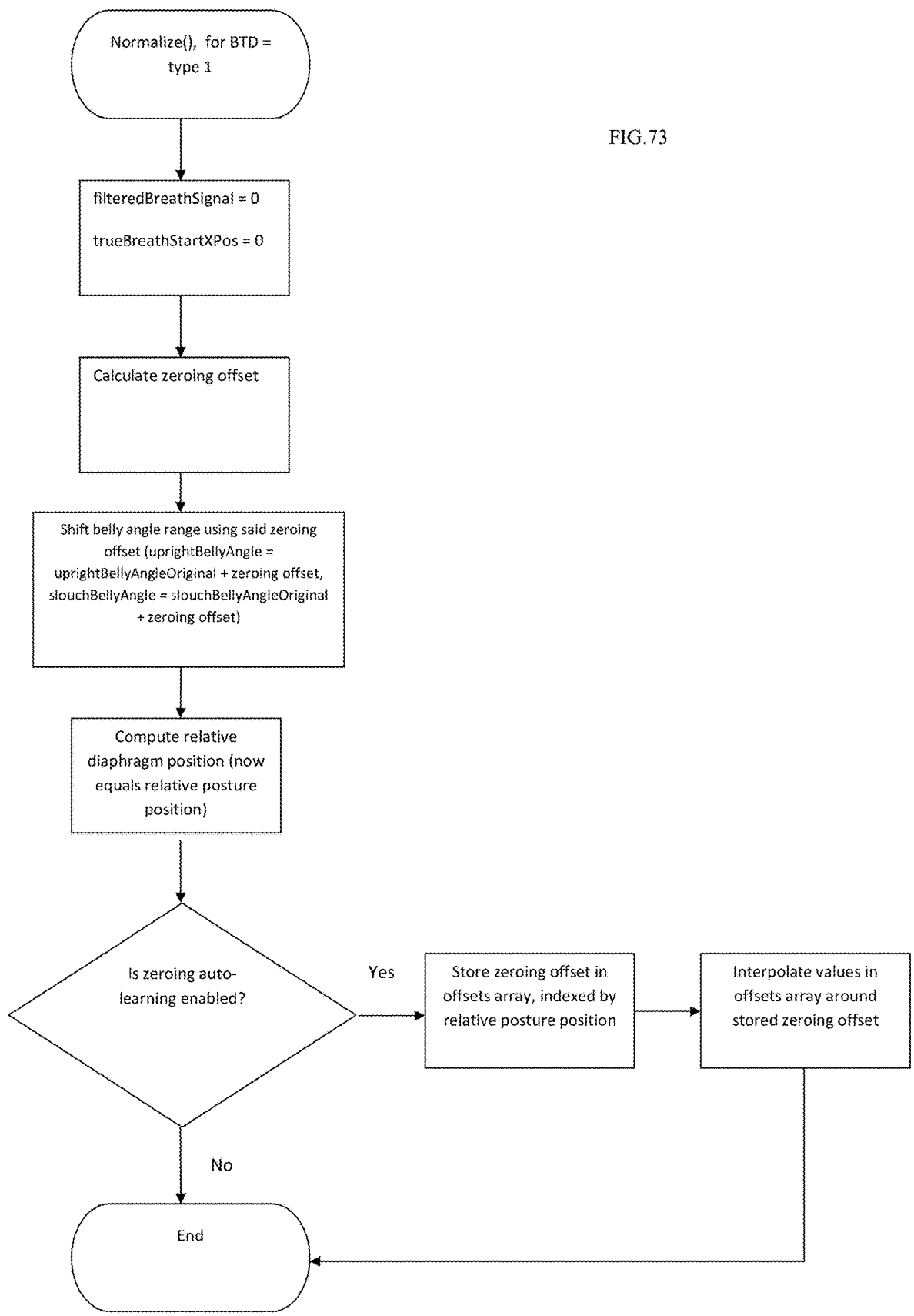
FIG. 73 is a flowchart showing exemplary steps involved in implementing (e.g. normalizing) a Normalize( ), for BTD=type 1 process of the present invention.
Figure 75:
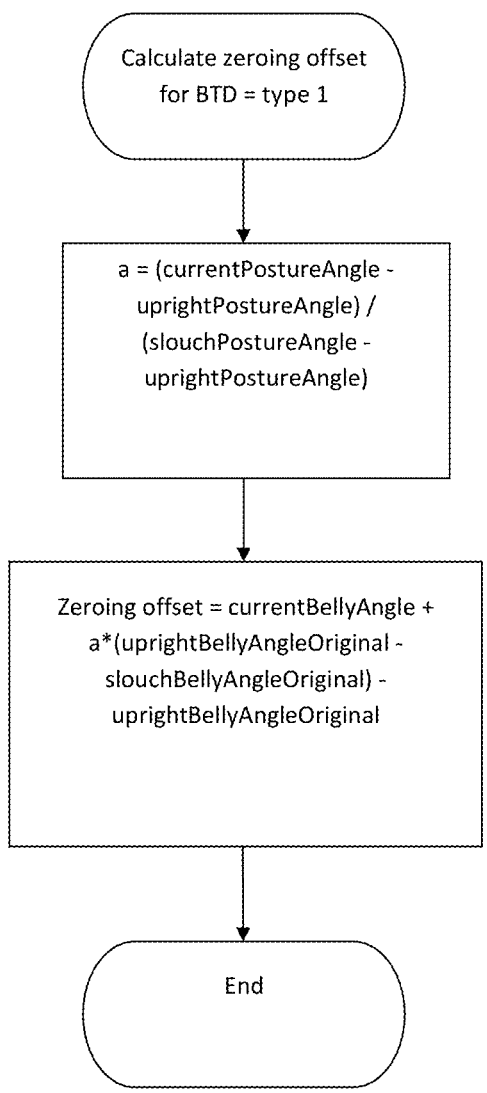
FIG. 75 is a flowchart showing exemplary steps involved in implementing a Calculate zeroing offset for BTD=type 1 process of the present invention.

The normalize process is now described for a BTD type 1, as detailed in the flowchart in FIG. 73, which executes in response to the Normalization test returning True as previously discussed. The underlying assumption by the previously explained Normalization test is that the user is in an exhaled state (or very close thereto) when the test returns True. Therefore the first step is setting the filtered breath signal to 0, so that it returns to the fully exhaled level 356 on timeline 350. Also, trueBreathStartXPos is set to 0. Next is to calculate the zeroing offset as detailed in the sub-process flowchart in FIG. 75, for a type 1 BTD. Referring to FIG. 75, the first step is setting a=(currentPostureAngle−uprightPostureAngle)/(slouchPostureAngle−uprightPostureAngle), and then setting zeroing offset=currentBellyAngle+a*(uprightBellyAngleOriginal−slouchBellyAngleOriginal)−uprightBellyAngleOriginal. Returning to FIG. 73, the next step is to shift the belly angle range using this zeroing offset with (uprightBellyAngle=uprightBellyAngleOriginal+zeroing offset, slouchBellyAngle=slouchBellyAngleOriginal+zeroing offset). This has the effect of making the next relative diaphragm position computation (FIG. 65) in the next step of this process equal to the relative posture position (which has the effect of making the filtered breath signal=0 during that computation as previously explained). The next step is checking if the zeroing auto-learning flag is enabled. If yes, then store this zeroing offset in the offsets array, indexed by relative posture position. The idea as previously explained in the filtered breath signal computation process, is that if the user returns back to this posture level, this last zeroing offset can be retrieved for this posture level to help zero the filtered breath signal when the user is actually fully exhaled (so that an inhalation depth can then be accurately gauged relative to this fully exhaled dynamic baseline). In this manner, Normalize( ) continuously learns new updated zeroing offsets for any given posture such that when the filtered breath signal is very close to fully exhaled line 356, the chances are very high that the user is in fact very close to a fully exhaled state. The last step of this process is to interpolate values in the offsets array around the new stored zeroing offset, within a range of +−interpolationRange for example, so as to make a smooth transition from previous zeroing offsets in the vicinity of the current relative posture position to this new offset.

Figure 61:
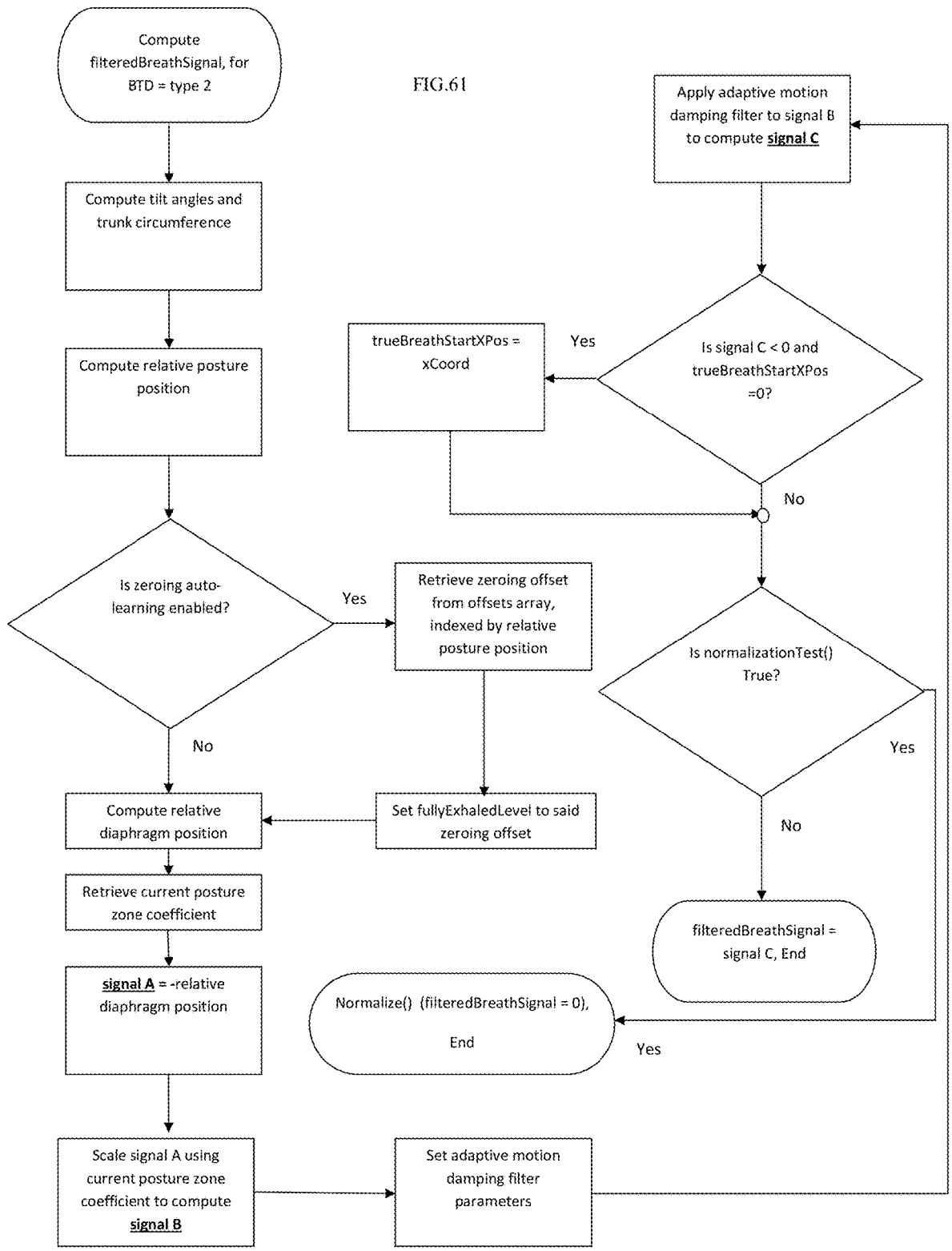
FIG. 61 is a flowchart showing exemplary steps involved in implementing a Compute filteredBreathSignal, for BTD=type 2 process of the present invention.
Figure 63:
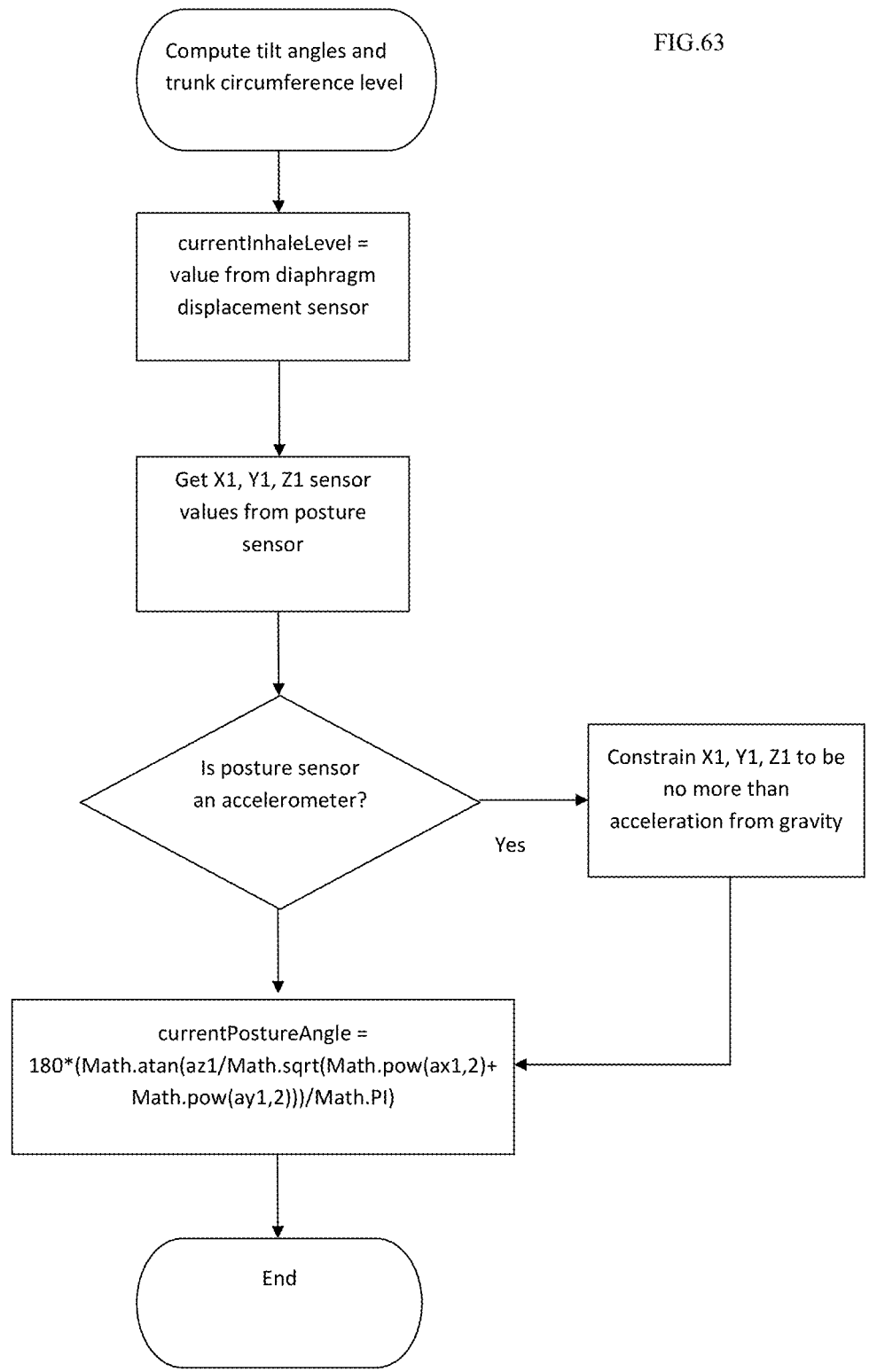
FIG. 63 is a flowchart showing exemplary steps involved in implementing a Compute tilt angles and trunk circumference level process of the present invention.
Figure 66:
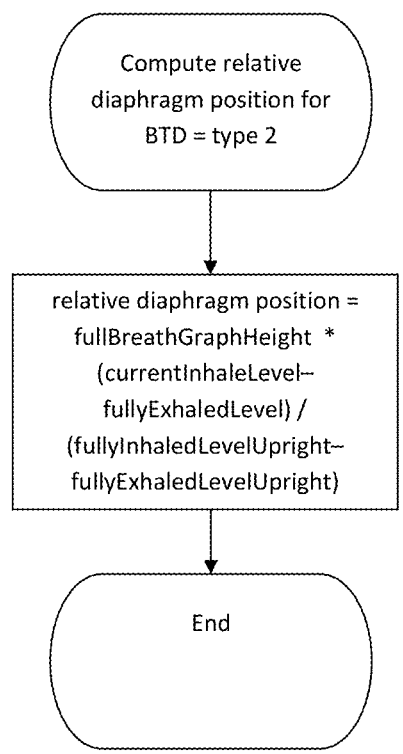
FIG. 66 is a flowchart showing exemplary steps involved in implementing a Compute relative diaphragm position for BTD=type 2 process of the present invention.

FIG. 61 shows a flowchart detailing the process of computing the filtered breath signal for a type 2 BTD, which uses the combination of an angle sensor on the user's back and a displacement sensor for tracking changes in waist circumference, such as angle sensor 148 and displacement sensor 146 of the first embodiment, shown in FIG. 7. This process is similar to the steps for computing the filtered breath signal for a type 1 BTD already described in FIG. 60 and above, with the differences explained below. The first step is the sub-process of computing the tilt angles and trunk circumference as shown in the flowchart in FIG. 63. Referring to FIG. 63, the first step there is setting a currentInhaleLevel=value from diaphragm displacement sensor. This value represents the degree to which the displacement sensor has sensed a displacement within its displacement range, such as due to an increase or decrease in trunk circumference as previously discussed. The rest of this sub-process for computing the currentPostureAngle is the same as in the flowchart in FIG. 62. Returning to FIG. 61, the next step is computing relative posture position which is the same sub-process as in FIG. 64. The next step is checking if a zeroing auto-learning flag is set. If yes, then a zeroing offset from an offsets array is retrieved, indexed by relative posture position, then a fullyExhaledLevel is set equal to this zeroing offset. The next step is computing the relative diaphragm position, which differs from the approach for a type 1 BTD. FIG. 66 shows the flowchart for this sub-process for a type 2 BTD. Instead of using a belly angle range and the current angle within that range, a trunk circumference range or displacement range is used, and the current displacement in that range, using this relationship: (currentInhaleLevel−fullyExhaledLevel)/(fullyInhaledLevelUpright−fullyExhaledLevelUpright), which also produces a value from about 0 to 1, with 0 representing the user being fully exhaled, and 1 fully inhaled. This value is the multiplied by fullBreathGraphHeight (for graph scaling on timeline 350) and relative diaphragm position is set to this value. Returning to FIG. 61, the next step is retrieving the current posture zone coefficient, which is the same process as detailed in the sub process in the flowchart in FIG. 67. The next step is setting signal A=−relative diaphragm position. This differs from the similar step in FIG. 60 for a type 1 BTD, where the relative posture position was subtracted from the relative diaphragm position, which was possible since both of those values are based on angle sensors, with the values generally changing in tandem as a user changes posture, making it possible to cancel out body movement or posture changes with this subtraction. In a type 2 BTD, these values can have a more independent relationship since relative diaphragm position is based on a displacement sensor and relative posture position based on an angle sensor, and thus the latter is not subtracted from the former. Instead, the zeroing offset previously explained directly does the job of keeping the filtered breath signal (inhalation depth) accurate with respect to the fully exhaled line 356.

The remaining steps in FIG. 61, including computing signal B, applying the motion damping filter, and the normalization tests are the same as in FIGS. 69-72, already described. The last difference is in the normalization process for a type 2 BTD, as shown in the flowchart in FIG. 74. Overall this process is quite similar to the normalization process for a type 1 BTD in FIG. 73 already described, except that there is no need to compute a zeroing offset or shift a belly angle range. Instead, the fullyExhaledLevel is set equal to currentInhaleLevel and this value is also stored as the zeroing offset in the same manner as described for FIG. 73, and with the relative diaphragm position set to 0. The general idea is that when normalizing for a type 2 BTD, the filtered breath signal is zeroed by simply setting the fullyExhaledLevel equal to the currentInhaleLevel at the given posture (or for all postures if the zeroing auto-learning flag is set to False). As one clarifying example, if a user changes his/her posture back and forth while maintaining a fully exhaled state, the currentInhaleLevel may also still fluctuate to a certain degree, due to the nature of the displacement sensor. This normalization process together with the computation of the filtered breath signal for a type 2 BTD can learn these fluctuations at the different postures, so as to cancel them out and help maintain the filtered breath signal close to the 0 level when the user hasn't actually inhaled.

Figure 61A:
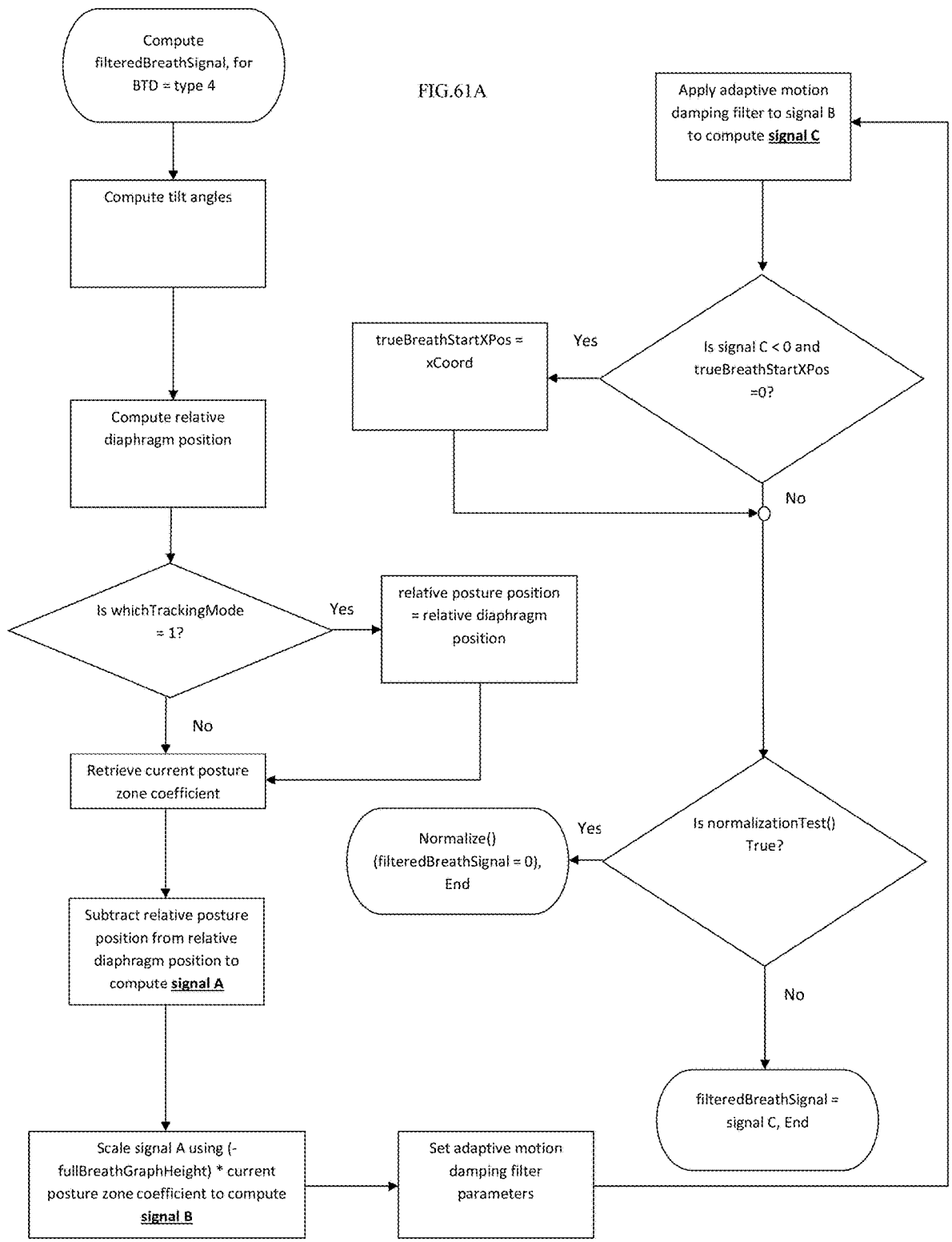
FIG. 61A is a flowchart showing exemplary steps involved in implementing a Compute filteredBreathSignal, for BTD=type 4 process of the present invention.

FIG. 61A shows a flowchart detailing the process of computing the filtered breath signal for a type 4 BTD, which uses one angle sensor near the user's abdomen or upper pubic area, such as angle sensor 618 of the seventh embodiment, shown in FIG. 7. This process differs from the processes in FIGS. 60-61 in that both a relative diaphragm position and a relative posture position must be derived from an angle sensor located in just one area of the body. The main idea is that the relative posture position is set based on the measured currentBellyAngle only when the Normalize( ) function is called (with several exceptions as will be described), and with relative diaphragm position being set the rest of the time based on the measured currentBellyAngle. Normalize( ) can be called at the start of the breath training process to set relative posture position to an initial value.

Figure 63A:
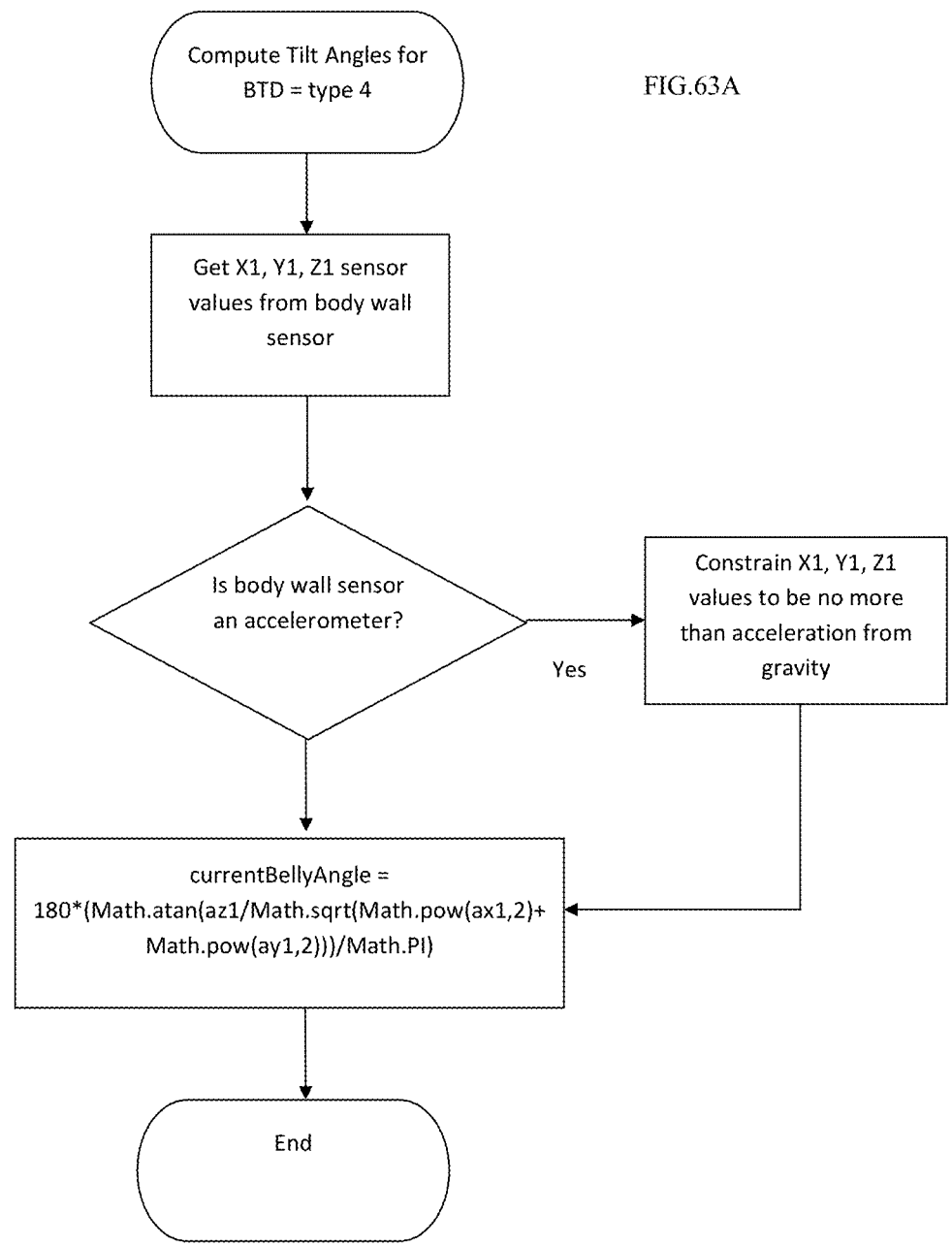
FIG. 63A is a flowchart showing exemplary steps involved in implementing a Compute Tilt Angles for BTD=type 4 process of the present invention.

The first step is the sub-process of computing the tilt angles as shown in the flowchart in FIG. 63A as one example of determining the inclination of the sensors. This process is similar to the steps already described in FIG. 62, except that it applies to just the one angle sensor for computing currentBellyAngle (utilizing X, Y, Z axes).

Figure 66A:
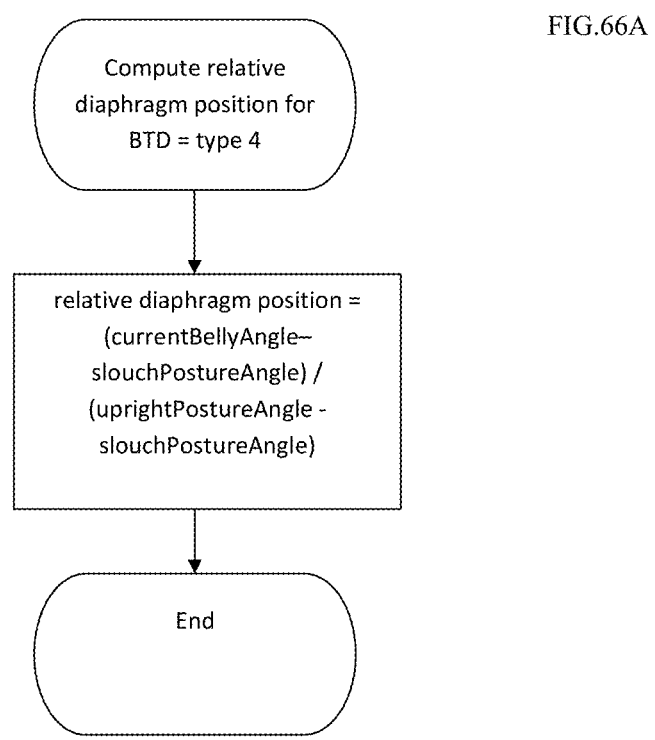
FIG. 66A is a flowchart showing exemplary steps involved in implementing a Compute relative diaphragm position for BTD=type 4 process of the present invention.

Returning to FIG. 61A, the next step is computing the relative diaphragm position, as detailed in the sub-process in the flowchart in FIG. 66A. The formula relative diaphragm position=(currentBellyAngle−slouchPostureAngle)/(uprightPostureAngle−slouchPostureAngle) gives a ratio value of approximately 0 to 1 representing the current belly angle of the user within the resulting belly angle range between upright and slouched postures as measured in the range measuring process in FIG. 56A. This value approaches 1 as the user's posture approaches an upright position while fully exhaled, and 0 as the user's posture approaches a slouched position while full exhaled. Further, this value may be greater than 1 if the user inhales in the upright posture state, since the belly angle may then exceed the uprightPostureAngle.

In the next step in FIG. 61A, flag whichTrackingMode is checked if it is set to 1. When set to 1, this corresponds to a posture tracking mode 351 being enabled in a calibration screen 357 for type 4 BTD's, as shown in FIG. 108A. If set to 1, then relative posture position is set equal to relative diaphragm position, resulting in the filtered breath signal being computed as 0. In this mode, currentBellyAngle is interpreted to track only the user's posture, resulting in both the breath and posture indicators on the breath/posture zone chart 368 to fall in the same location corresponding to the posture level, as detailed in the flowchart in FIG. 77. This mode is convenient in aiding to learn posture zone coefficients as later described for a type 4 BTD. The next step is retrieving the current posture zone coefficient, as detailed and previously described in the sub-process in the flowchart in FIG. 67.

Returning to FIG. 61A, the next step is to subtract relative posture position from relative diaphragm position to compute a signal A. Then, signal A is scaled by multiplying by ((−fullBreathGraphHeight)*current posture zone coefficient) to compute signal B, for standardizing the depth of inhalations across different postures as previously explained. The reason fullBreathGraphHeight is set to minus is due to the convention here that the filtered breath signal is negative above the X axis on timeline graph 350 as shown in FIG. 99. The opposite convention could be used with fullBreathGraphHeight positive within the scope of the present invention.

The remaining steps in FIG. 61A are the same as those already described in FIG. 60, with setting and applying the adaptive motion damping filter to compute Signal C, setting trueBreathStartXPos, and conducting a normalization test, with the exceptions of utilizing a different normalization test and Normalize( ) function for type 4 BTD's.

FIG. 72A details the process steps of a normalization test for a BTD=type 4 with reverse breath tracking disabled. First, if a bellyBreathHasStarted flag is set to True, this process returns False, since a diaphragmatic breath is underway and already being tracked (where Normalization may occur as part of that process later described). The process also returns False if whichTrackingMode=1 or 2, which corresponds to either a posture tracking mode 351 or breath tracking mode 353 enabled in calibration screen 357 as shown in FIG. 108A. When breath tracking mode 353 is selected, only the relative diaphragm position is updated (since normalization does not occur) and relative posture position is held constant (last value which relative posture position was set to). If bellyBreathHasStarted is set to False and whichTrackingMode is not 1 or 2, then if signal C>=endBreathThreshold and signal C<=0, and signal C velocity>0, then return True, otherwise if signal C velocity is <=0, then return False, for similar reasons already explained in FIG. 69. Next, if signal C<0 and dismissNextBellyBreath=1, then return True. The idea here is to prevent a diaphragmatic breath from starting while the dismissNextBellyBreath flag is set to 1. Next, if signal C>0, then return False (since reverse breath is not tracked here).

FIG. 72B shows the process for a normalization test with reverse breath tracking enabled for a BTD=type 4. A reverse breath, also known as a paradoxical breath, happens when a user's belly moves inwards during an inhalation, which often occurs when a user is chest breathing. This process allows signal C to fall below the fully exhaled line 356, as shown in FIG. 101, without immediately triggering normalization back to 0, to allow breath tracking below fully exhaled line 356. First, if a bellyBreathHasStarted flag is set to True, or a reverseBreathHasStarted flag is set to True, or whichTrackingMode=1 or 2 (for same reasons explained in FIG. 72A), then this process returns False, since a diaphragmatic breath or reverse breath is underway and already being tracked (where Normalization may occur as part of that process later described), or posture tracking mode 351 or breath tracking mode 353 has been selected. If not, then if signal C>=endBreathThreshold and signal C<=0, and if signal C velocity>0, then return True (just like the normalization test in FIG. 69 for a diaphragmatic inhalation). Otherwise, check if (signal C<0 and dismissNextBellyBreath=1) or (signal C>0 and dismissNextReverseBreath=1). If True, then return True. The idea here is to prevent either a diaphragmatic or reverse breath from starting if either corresponding flag is set to 1. Otherwise, if signal C>0 and signal C<=endReverseBreathThreshold (for reverse breath testing), and if signal C velocity<0, then return True, otherwise return False (to allow tracking the downward trend of a reverse breath within the zone below fully exhaled line 356 and above end of reverse breath threshold line 360, as shown in FIG. 101).

Figure 74:
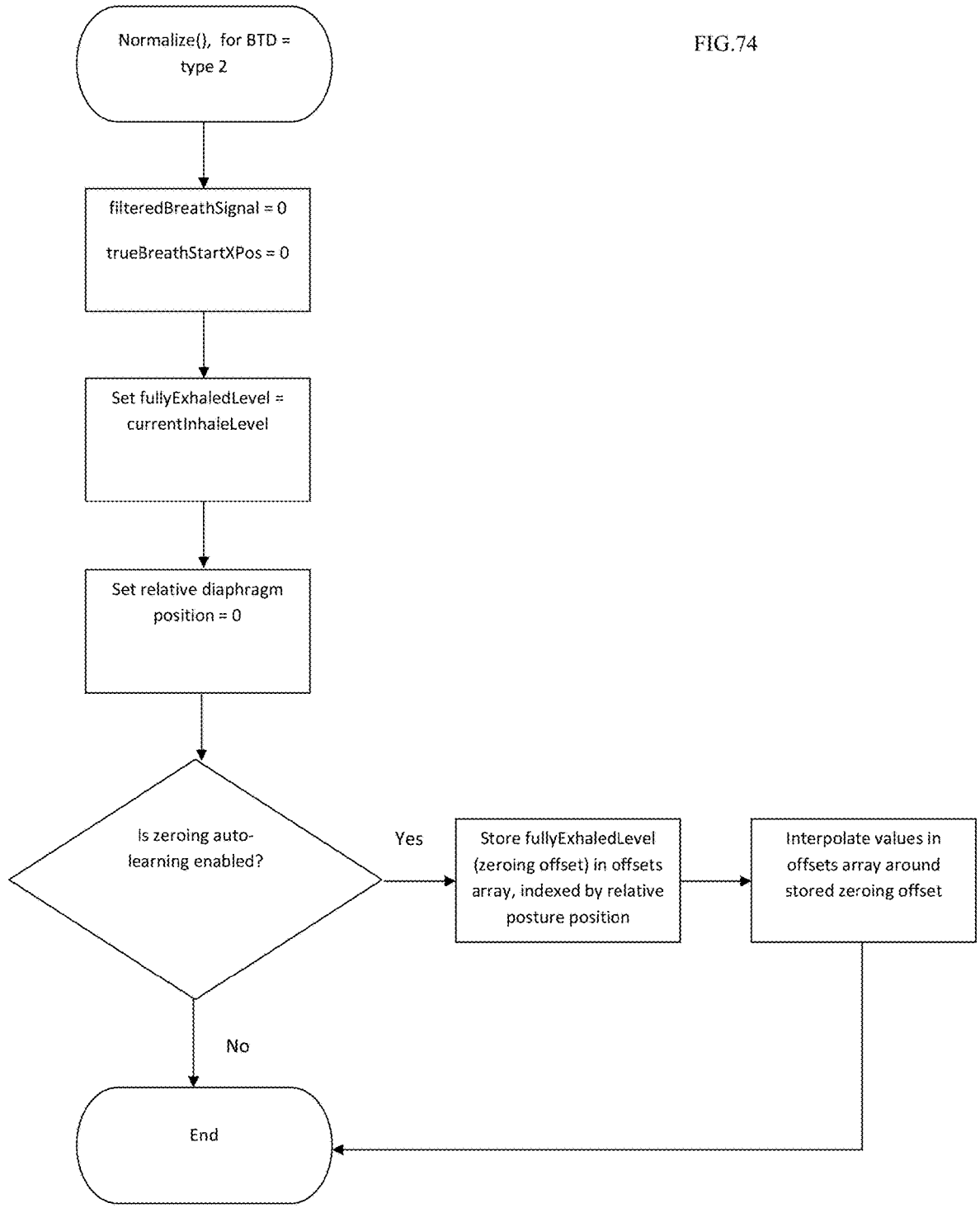
FIG. 74 is a flowchart showing exemplary steps involved in implementing a Normalize( ), for BTD=type 2 process of the present invention.
Figure 74A:
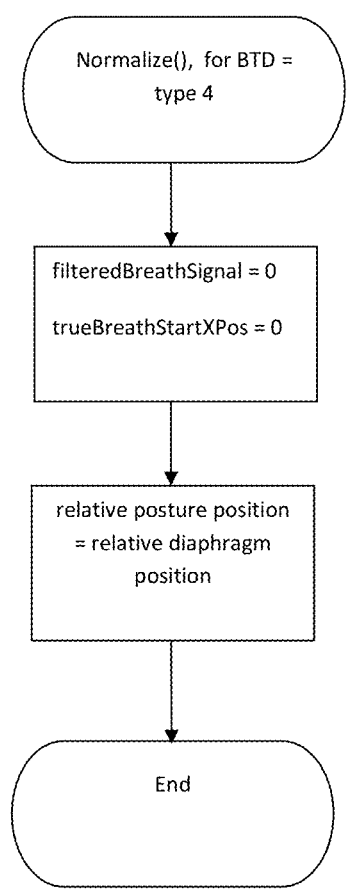
FIG. 74A is a flowchart showing exemplary steps involved in implementing a Normalize( ), for BTD=type 4 process of the present invention.

FIG. 74A details the normalization process for a type 4 BTD, which is generally simpler than those explained for type 1-2 BTD's previously in FIGS. 73-74, because no zeroing offsets need to be set. In the first step, both filteredBreathSignal and trueBreathStartXPos are set to 0. Next, relative posture position is set equal to relative diaphragm position. In a type 4 BTD, relative posture position is updated whenever normalization occurs.

Figure 53:
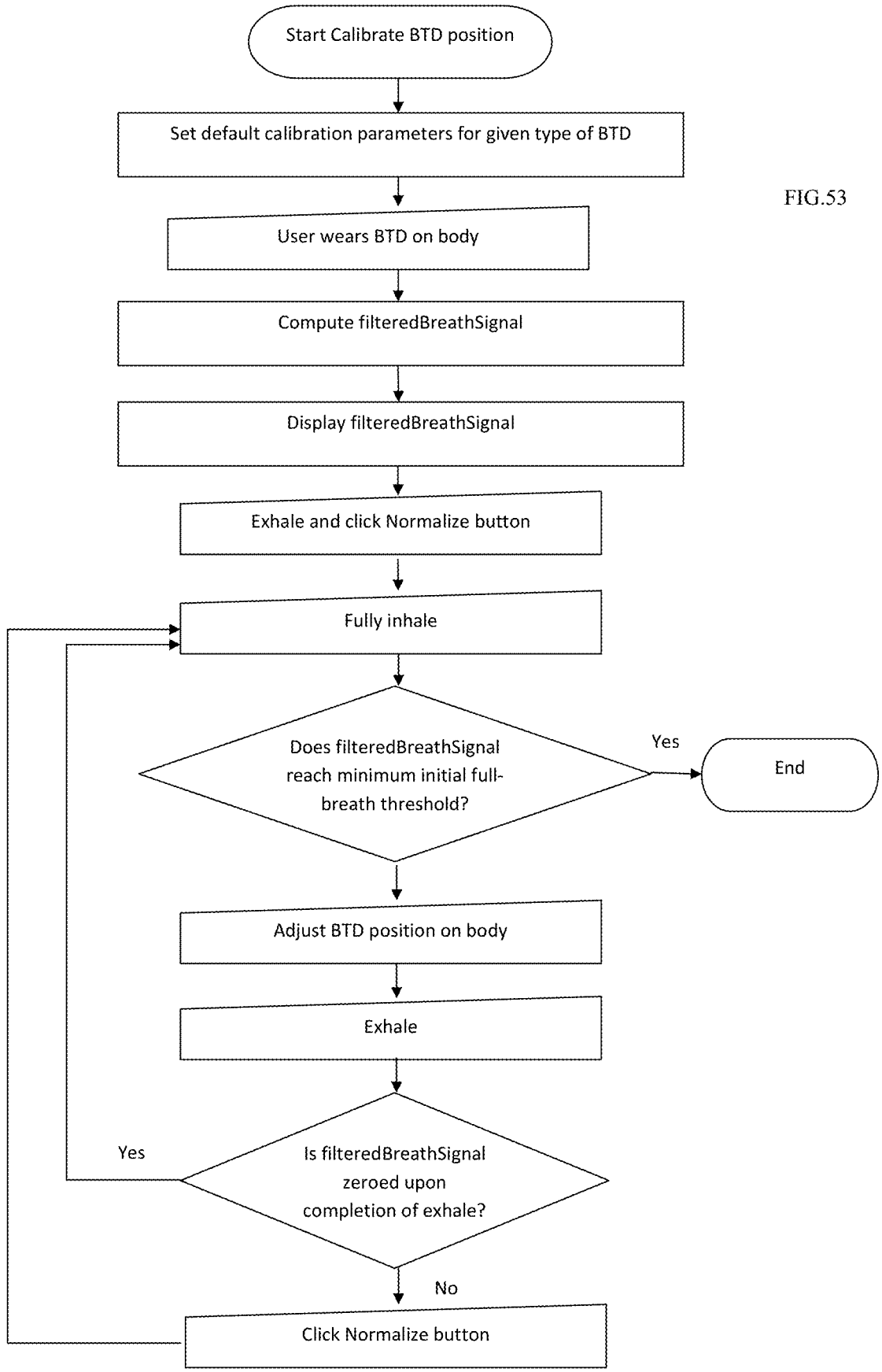
FIG. 53 is a flowchart showing exemplary steps involved in implementing a calibrate BTD position process of the present invention.

Returning to FIG. 51, we now discuss step S2 for calibrating the BTD position on a user's body, as detailed in the sub-process in the flowchart in FIG. 53. The goal here is to find the sweet spot or optimal location of the BTD on a user's trunk, so that diaphragmatic breaths and posture can be optimally tracked. The first step in this sub-process is to set default calibration parameters for the given type of BTD being used, which includes setting uprightBellyAngle, slouchBellyAngle, uprightBellyAngleOriginal, slouchBellyAngleOriginal for a type 1 BTD, and fullyExhaledLevel, fullyInhaledLevelUpright, fullyExhaledLevelUpright for a type 2 BTD, and slouchPostureAngle, uprightPostureAngle for both as well as for type 4 BTD's. These values are set to average values across most users for this initial calibration step, and refined later.

Figure 76:
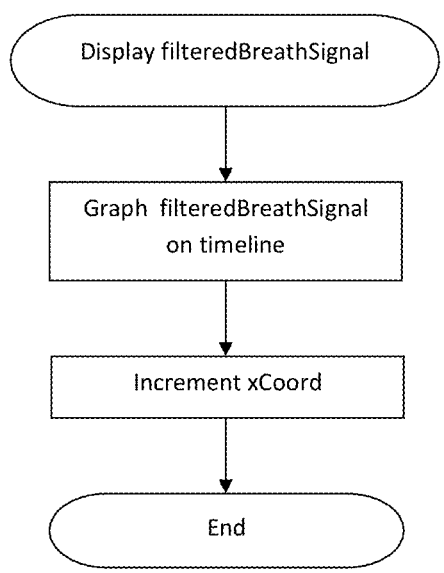
FIG. 76 is a flowchart showing exemplary steps involved in implementing a Display filteredBreathSignal process of the present invention.
Figure 103:
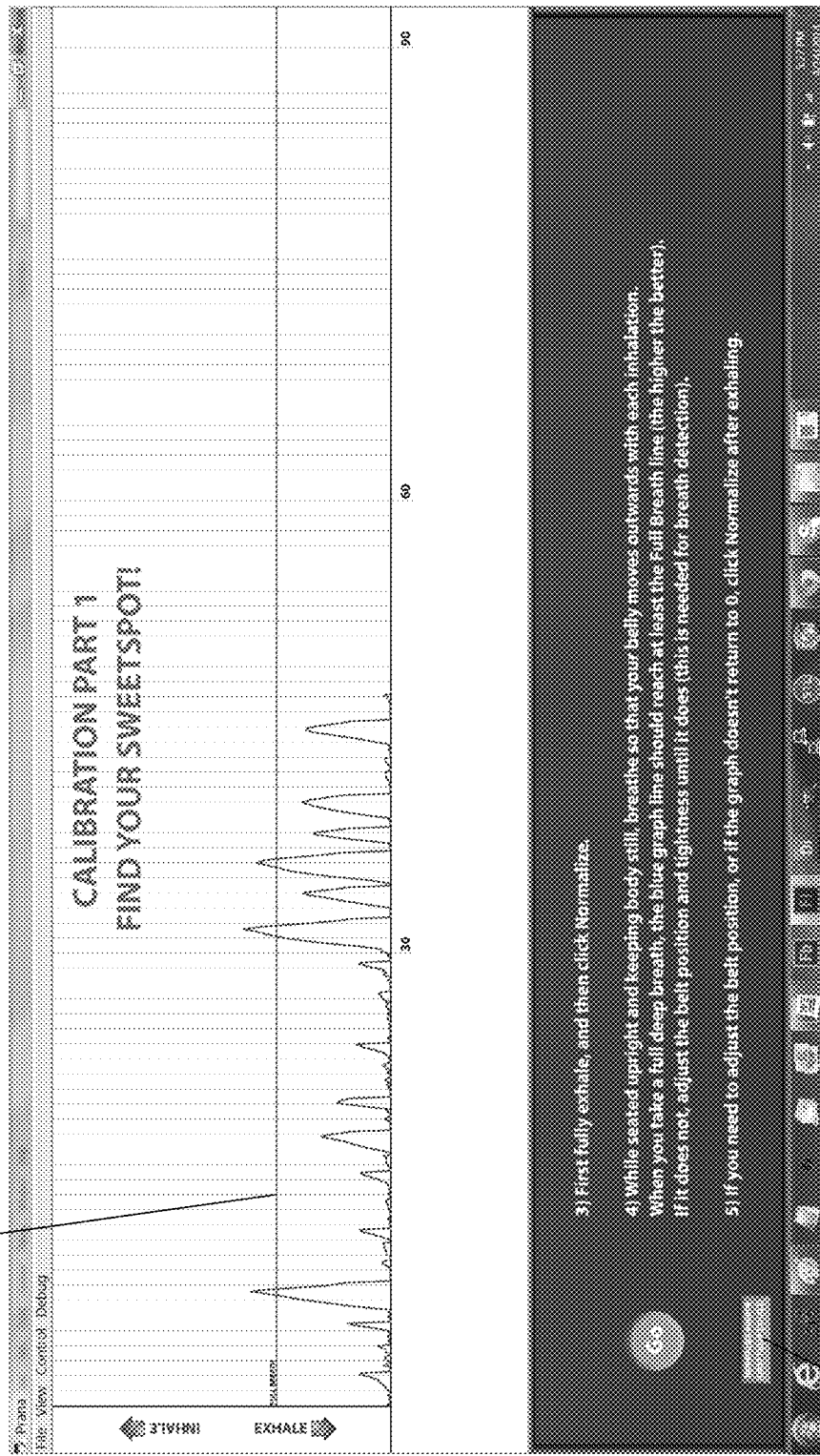

In the next step, the user is instructed to wear the BTD on his/her body, as shown in FIG. 102 on display 168, as a user interface example as part of the breath training program. The user is instructed to sit upright and orient the BTD so that the front sensor housing is placed over the belly area, and the back sensor housing is against the central lower back, and then the respiration belt is secured and tightened (unless an embodiment is being used, such as embodiments 6 or 7, without a respiration belt). If a BTD which only has one sensor housing (such as embodiment one) is used, then it is placed against the central lower back and the belt secured. If a BTD type 4 is used, then the single sensor case is fastened near the abdomen or waistband as previously described. Next, the filtered breath signal is computed as previously explained, using the default average ranges, and then displayed using the sub-process shown in the flowchart in FIG. 76. Referring to FIG. 76, the first step is graphing the filteredBreathSignal on timeline 350, where the signal has been appropriately scaled for the screen resolution and ranges between fully exhaled line 356, and full breath line 358. Next step is to increment the xCoord which is the x coordinate of the filtered breath signal when graphed on timeline 350. How much xCoord is incremented by can depend on how often the filtered breath signal is computed each second (based on how often an updated sensor output signal is received). For example, if filtered breath signal is computed 10 times per second, and if one vertical interval on timeline 350 represents one second and is 20 pixels wide, then xCoord can be incremented by 2 every 1/10 of a second, assuming the filtered breath signal is graphed as often as it is computed. FIG. 103 shows the filtered breath signal graphed on timeline 350 during this calibration process. Returning to FIG. 53, in the next step, the user is instructed to fully exhale and click a Normalize button 362 as shown in FIG. 103. Clicking this button forces the system's normalize process to execute (bypassing the normalization tests), with the appropriate version of the normalize function being called depending on the type of BTD being worn. This manually forces the filtered breath signal to the fully exhaled line or 0 line (as shown on the right end of the graph in FIG. 103), by either appropriately shifting the belly angle range (type 1 BTD), or by setting fullyExhaledLevel=currentInhaleLevel (type 2 BTD), or setting relative posture position equal to relative diaphragm position for a type 4 BTD as previously explained. At this stage, the zeroing auto-learning flag is set to False so that the zeroing offsets are not utilized for computing the filtered breath signal (as they haven't been learned yet and this refinement is not yet needed for finding the sweet spot). Returning to FIG. 53, in the next step, the user is instructed to fully inhale using their diaphragm so that their belly moves outwards. Then the user is asked to manually check and see if the filtered breath signal graph has at least reached the height of the preliminary full breath line 358. The goal here is that the user has positioned the BTD well enough on his/her body so that at least this level of signal strength is initially reached with a full inhale. If the full breath line 358 is not reached, the user is instructed to reposition the BTD and try again until this minimum threshold is reached (exhaling, clicking Normalize button 362 again if needed to zero the signal, and then inhaling again).

Figure 54:
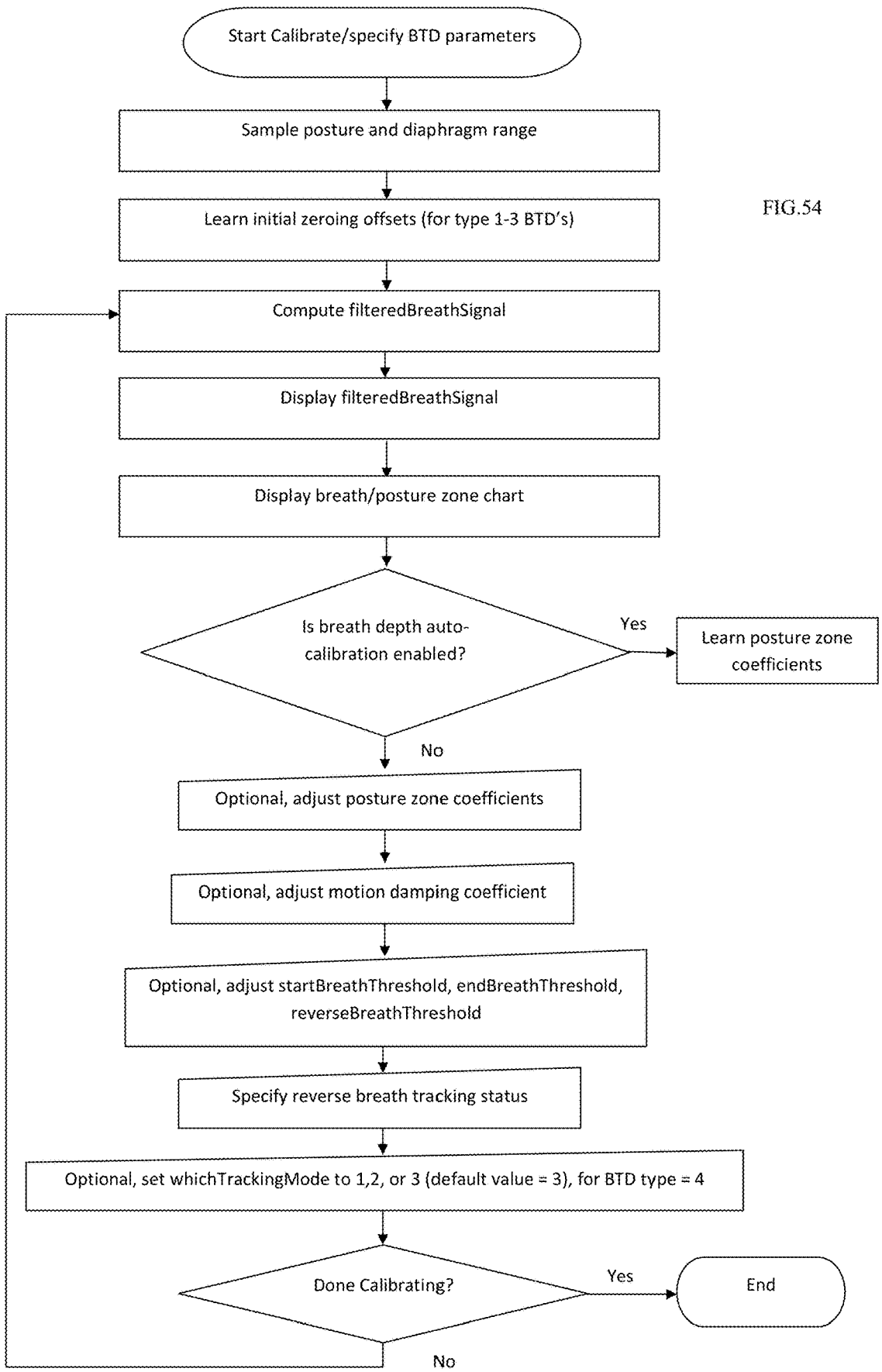
FIG. 54 is a flowchart showing exemplary steps involved in implementing a calibrate/specify BTD parameters process of the present invention.
Figure 55:
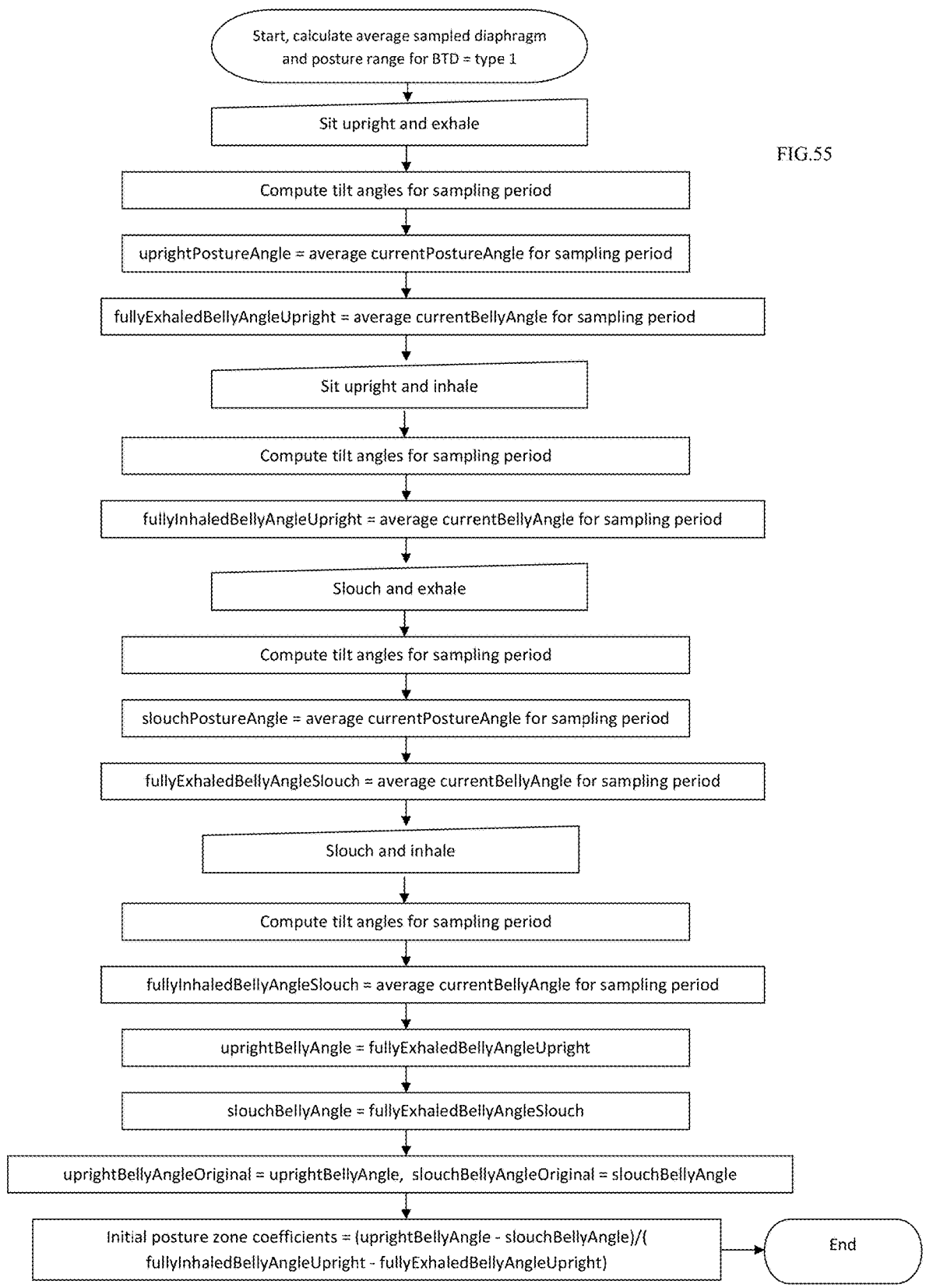
FIG. 55 is a flowchart showing exemplary steps involved in implementing (e.g. calculating) average sampled diaphragm and posture range for BTD=type 1 process of the present invention.

Returning to FIG. 51, we now discuss step S3 for calibrating and specifying BTD parameters, as detailed in the sub-process in the flowchart in FIG. 54. The first step of this sub-process is to sample and learn the user's posture and diaphragm range of motion, as detailed in the sub-process flowchart in FIG. 55 for a type 1 BTD. These ranges are important to establish for computing the relative posture and diaphragm positions as in FIGS. 64-66. Referring to FIG. 55, the user is asked to sit upright and fully exhale in the first step, as shown in the UI example in FIG. 104 on display 168. Next, Compute Tilt Angles (previously described in FIG. 62) is called for a sampling period of time, and uprightPostureAngle is set to the average currentPostureAngle for this sampling period, and fullyExhaledBellyAngleUpright set to the average currentBellyAngle for this sampling period.

Next, the user is asked to sit upright and fully inhale, as shown in FIG. 105, and then Compute Tilt Angles is called again for a sampling period of time, and fullyInhaledBellyAngleUpright is set to the average currentBellyAngle for this sampling period. Next, the user is asked to slouch and exhale as shown in FIG. 106, and then Compute Tilt Angles is called again for a sampling period of time, and slouchPostureAngle is set to the average currentPostureAngle for this sampling period, and fullyExhaledBellyAngleSlouch is set to the average currentBellyAngle for this sampling period. Finally, the user is asked to slouch and inhale as shown in FIG. 107, and then Compute Tilt Angles is called again for a sampling period of time, and fullyInhaledBellyAngleSlouch is set to the average currentBellyAngle for this sampling period. Next, uprightBellyAngle is set to fullyExhaledBellyAngleUpright, slouchBellyAngle set to fullyExhaledBellyAngle Slouch, uprightBellyAngleOriginal set to uprightBellyAngle, and slouchBellyAngleOriginal set to slouchBellyAngle, for computing relative diaphragm position, and in shifting the belly angle range as explained in FIG. 60. Final step is setting all the posture zone coefficients to the initial value of (uprightBellyAngle−slouchBellyAngle)/(fullyInhaledBellyAngleUpright−fullyExhaledBellyAngleUpright). This ratio is used as the preliminary value to scale signal A to compute signal B in FIG. 60, such that when a user takes a full deep diaphragmatic breath, signal B (prior to motion damping) will approximately reach full breath line 358 on timeline 350, as shown in FIG. 108. For example, this ratio may be 4.0, which means that the change in a user's belly angle between an upright and slouched posture is 4 times greater than the change in belly angle which occurs from an inhaled to an exhaled state, while fully upright. Therefore in this example, multiplying signal A by 4.0 when a user has fully inhaled (given how relative posture position and relative diaphragm position are calculated), should approximately cause the filtered breath signal to reach fullBreathGraphHeight.

Figure 56:
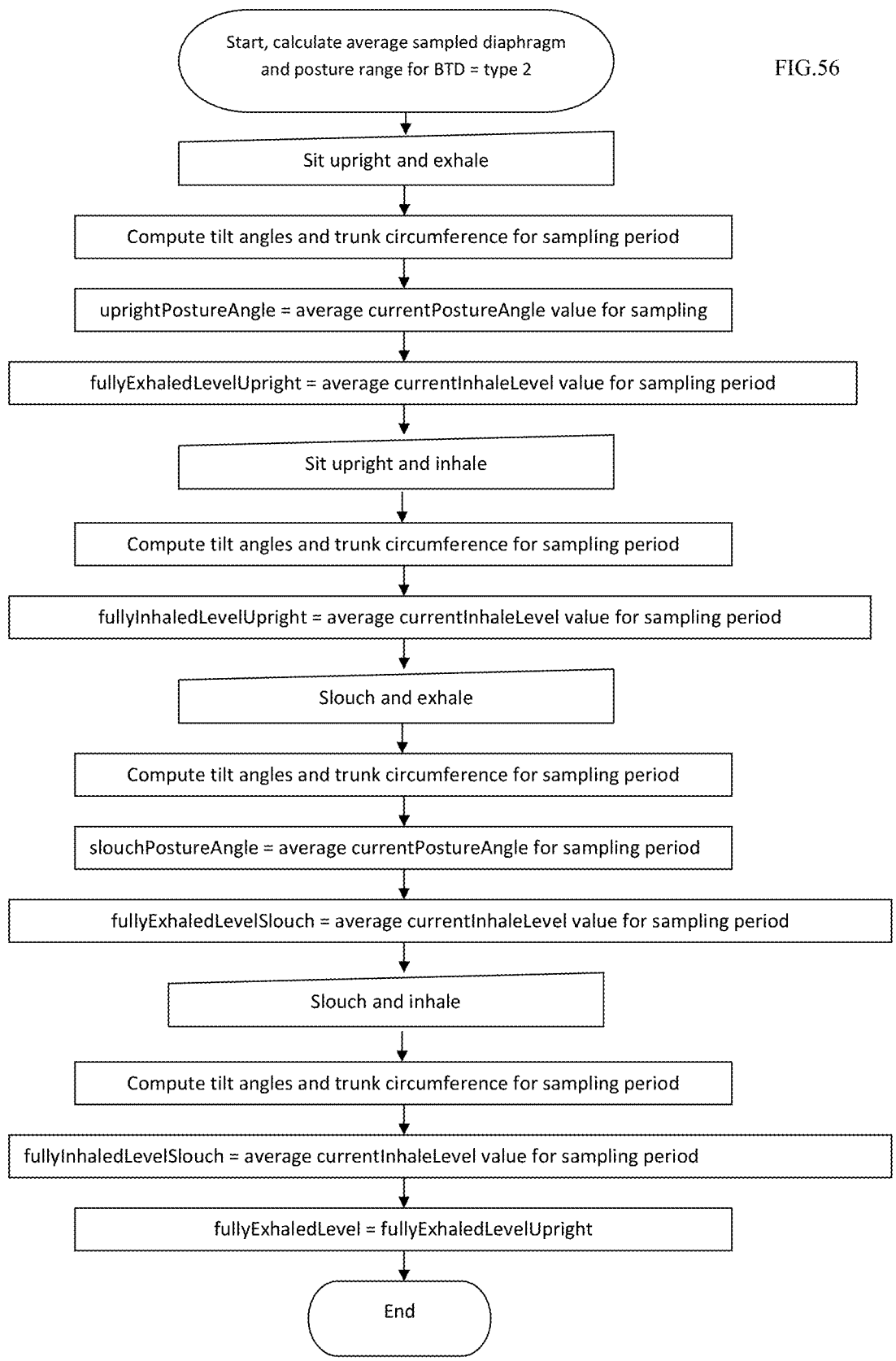
FIG. 56 is a flowchart showing exemplary steps involved in implementing (e.g. calculating) average sampled diaphragm and posture range for BTD=type 2 process of the present invention.

The flowchart in FIG. 56 details the sub-process to sample and learn the user's posture and diaphragm range of motion for a type 2 BTD. Referring to FIG. 56, the user is asked to sit upright and fully exhale in the first step, as shown in the UI example in FIG. 104 on display 168. Next, Compute tilt angles and trunk circumference (previously described in FIG. 63) is called for a sampling period of time, and uprightPostureAngle is set to the average currentPostureAngle for this sampling period, and fullyExhaledLevelUpright is set to the average currentInhaleLevel value for this sampling period. Next, the user is asked to sit upright and fully inhale, as shown in FIG. 105, and then Compute tilt angles and trunk circumference is called again for a sampling period of time, and fullyInhaledLevelUpright is set to the average currentInhaleLevel value for this sampling period. Next, the user is asked to slouch and exhale as shown in FIG. 106, and then Compute tilt angles and trunk circumference is called again for a sampling period of time, and slouchPostureAngle is set to the average currentPostureAngle for this sampling period, and fullyExhaledLevelSlouch is set to the average currentInhaleLevel value for this sampling period. Finally, the user is asked to slouch and inhale as shown in FIG. 107, and then Compute tilt angles and trunk circumference is called again for a sampling period of time, and fullyInhaledLevelSlouch is set to the average currentInhaleLevel value for this sampling period. Finally, fullyExhaledLevel is set to fullyExhaledLevelUpright as the initial exhaled reference level for the computation of the relative diaphragm position for a type 2 BTD.

Figure 56A:
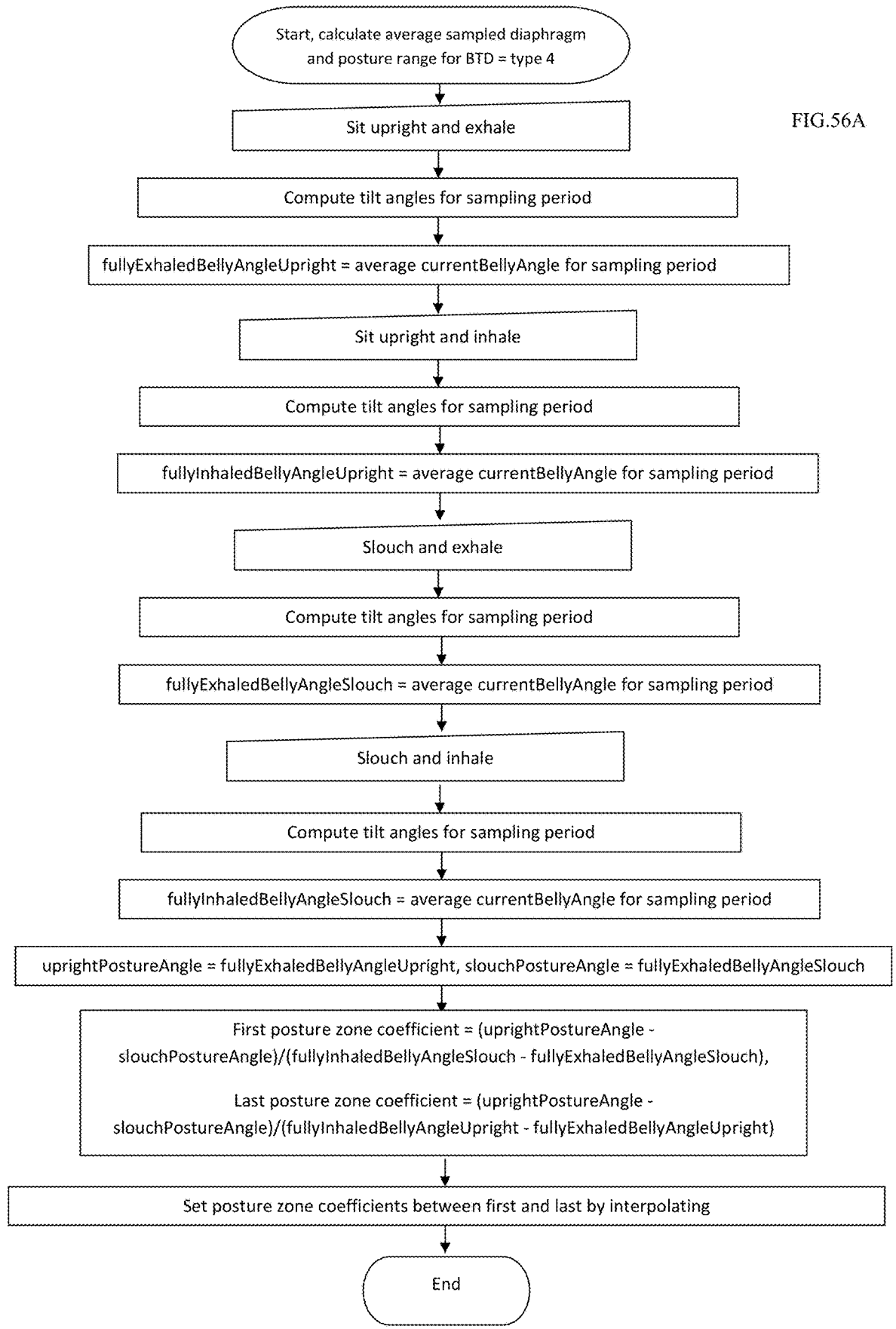
FIG. 56A is a flowchart showing exemplary steps involved in implementing (e.g. calculating) average sampled diaphragm and posture range for BTD=type 4 process of the present invention.

The flowchart in FIG. 56A details the sub-process to sample and learn the user's posture and diaphragm range of motion for a type 4 BTD. In the first step, the user is asked to sit upright and fully exhale. Next, Compute Tilt Angles (previously described in FIG. 63A for a type 4 BTD) is called for a sampling period of time, and fullyExhaledBellyAngleUpright is set to the average currentBellyAngle for this sampling period. Next, the user is asked to sit upright and fully inhale, and then Compute Tilt Angles is called again for a sampling period of time, and fullyInhaledBellyAngleUpright is set to the average currentBellyAngle for this sampling period. Next, the user is asked to slouch and exhale, and then Compute Tilt Angles is called again for a sampling period of time, and fullyExhaledBellyAngleSlouch is set to the average currentBellyAngle for this sampling period. Finally, the user is asked to slouch and inhale, and then Compute Tilt Angles is called again for a sampling period of time, and fullyInhaledBellyAngle Slouch is set to the average currentBellyAngle for this sampling period. Next, uprightPostureAngle is set to fullyExhaledBellyAngleUpright and slouchPostureAngle is set to fullyExhaledBellyAngleSlouch for computing relative diaphragm position. Next step is setting the first and last posture zone coefficients. The first posture zone coefficient is set to (uprightPostureAngle−slouchPostureAngle)/(fullyInhaledBellyAngle Slouch−fullyExhaledBellyAngleSlouch) and the last posture zone coefficient is set to (uprightPostureAngle−slouchPostureAngle)/(fullyInhaledBellyAngleUpright−fullyExhaledBellyAngleUpright) as previously explained for FIG. 55 (but here, both the first and last coefficients are set). Final step is setting the rest of the posture zone coefficients between the first and last by interpolating.

Figure 57:
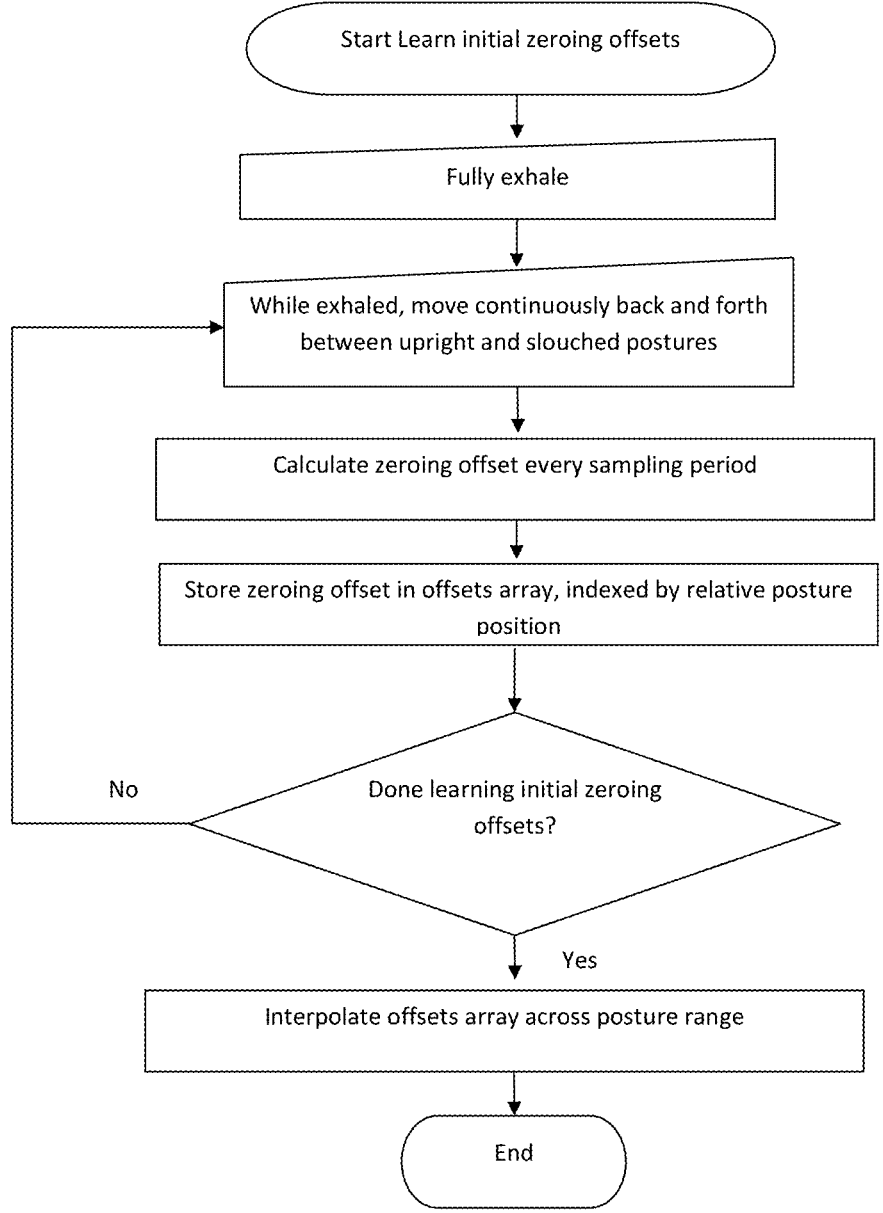
FIG. 57 is a flowchart showing exemplary steps involved in implementing (e.g. learning or storing) the initial zeroing offsets process of the present invention.

Returning to FIG. 54, if a type 1-3 BTD is being used, the next step is to learn the initial zeroing offsets, as detailed in the sub-process in the flowchart in FIG. 57. Referring to FIG. 57, the user is first asked to fully exhale. Next, the user is asked to move continuously back and forth between a slouched and upright posture, while maintaining an exhaled state. Next, at every sampling period of time (such as every 100 milliseconds), a zeroing offset is calculated at the given posture. If a type 1 BTD is being used, then the process in FIG. 75 can be used to calculate this zeroing offset, previously explained. If a type 2, then the zeroing offset is simply the currentInhaleLevel from the displacement sensor. Next, this zeroing offset is stored in the offsets array, indexed by relative posture position. Next, the user may choose to continue this initial learning process as long as they prefer for as many zeroing samples as they wish across their posture range (again for zeroing the filtered breath signal when the user is fully exhaled). When they end it, the offsets array is interpolated across the entire posture range, as previously explained, for a gradation of offsets in the array.

Figure 77:
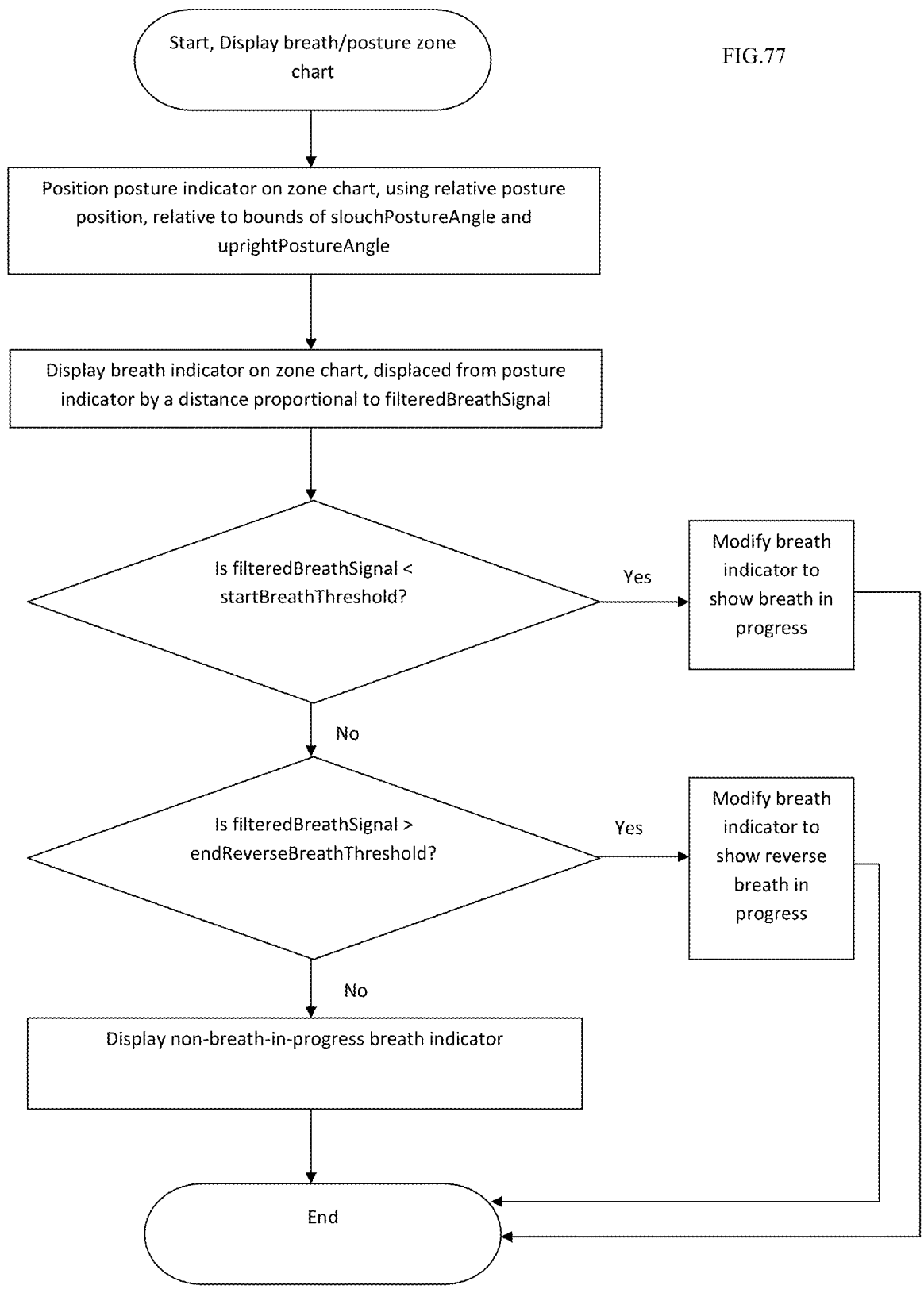
FIG. 77 is a flowchart showing exemplary steps involved in implementing a Display breath/posture zone chart process of the present invention.

Returning to FIG. 54, in the next step, the filtered breath signal is computed using the sampled range values just described, and then displayed on timeline 350 in a calibration screen 364 with a calibration control panel 366 as shown in FIG. 108. Next, a breath/posture zone chart 368 is updated and displayed, as detailed in FIG. 77 for this sub-process. Referring to FIG. 77, the first step is to position a posture indicator 370 on breath/posture zone chart 368, using relative posture position, relative to bounds of slouchPostureAngle and uprightPostureAngle. If the posture calibration was accurately performed, then posture indicator 370 should move to the right towards the upright zones as the user sits upright, and towards the left when the user slouches to reflect the user's real-time posture for type 1-3

BTD's, as shown in FIG. 108 (for type 4 BTD, posture indicator 370 is updated only upon normalizing, or continuously when whichTrackingMode=1).

Breath/posture zone chart 368 can be divided into a number of posture zones 372, with 7 shown as an example in FIG. 108, though more or fewer can be used. A posture status graphic 374 can additionally be provided, showing an anatomical representation of the user's current or last updated posture. Next, a breath indicator 376 is displayed on breath/posture zone chart 368, displaced from posture indicator 370 by a distance proportional to the filtered breath signal, as an alternate way to view the filtered breath signal if timeline 350 is not being viewed. For example, breath indicator 376 position can be scaled such that approximately two posture zones of displacement represent a full diaphragmatic breath, as shown in FIG. 109. For a type 1 BTD, for example, if a user rocks back and forth altering his/her posture while maintaining an exhaled state, breath indicator 376 and posture indicator 370 should move back and forth across breath/posture zone chart 368 more or less in unison, indicating that the relative posture position and relative diaphragm position are approximately equal after zeroing offsets are applied. The divergence of breath indicator 376 from posture indicator 370 is due to the angle difference of the belly beyond the expected belly angle change due to just posture changes, that is, the angle difference due to a diaphragmatic breath (for type 1 BTD's). Returning to FIG. 77, in the next step, if the filtered breath signal is less than startBreathThreshold (that is, on timeline 350, it is above a start breath threshold line 378), then modify breath indicator 376 to show a symbol of a diaphragmatic breath in progress, as shown in FIG. 110 with the "B" symbol indicating a belly breath. If the filtered breath signal is greater than end of reverse breath threshold 360, then modify breath indicator 376 to show a symbol of a reverse breath in process, as shown in FIG. 111 with the "C" symbol indicating a chest breath (or reverse breath), where the filtered breath signal would be below fully exhaled line 356 on timeline 350. If neither a belly nor reverse breath are in progress, then breath indicator 376 is displayed in its default state. With a type 2 BTD, breath/posture zone chart 368 works similarly, except that the divergence of breath indicator 376 from posture indicator 370 is not due to a residual belly angle change, but due to a difference in the user's waist circumference beyond the fullyExhaledLevel at a given posture. With a type 4 BTD, the divergence of breath indicator 376 from posture indicator 370 is directly due to a change in currentBellyAngle, as it is assumed that changes in currentBellyAngle are due to diaphragmatic breathing, unless other features in the filtered breath signal are observed as discussed for process checkIfBreathInterrupted( ) in FIG. 98A, which then causes the Normalize( ) process to execute resulting in posture indicator 370 position being updated (in general, posture indicator 370 position is updated whenever the Normalize( ) process is called, such as when the filtered breath signal crosses end of breath threshold 352 or end of reverse breath threshold line 360 after a diaphragmatic or reverse breath has started).

Figure 58:
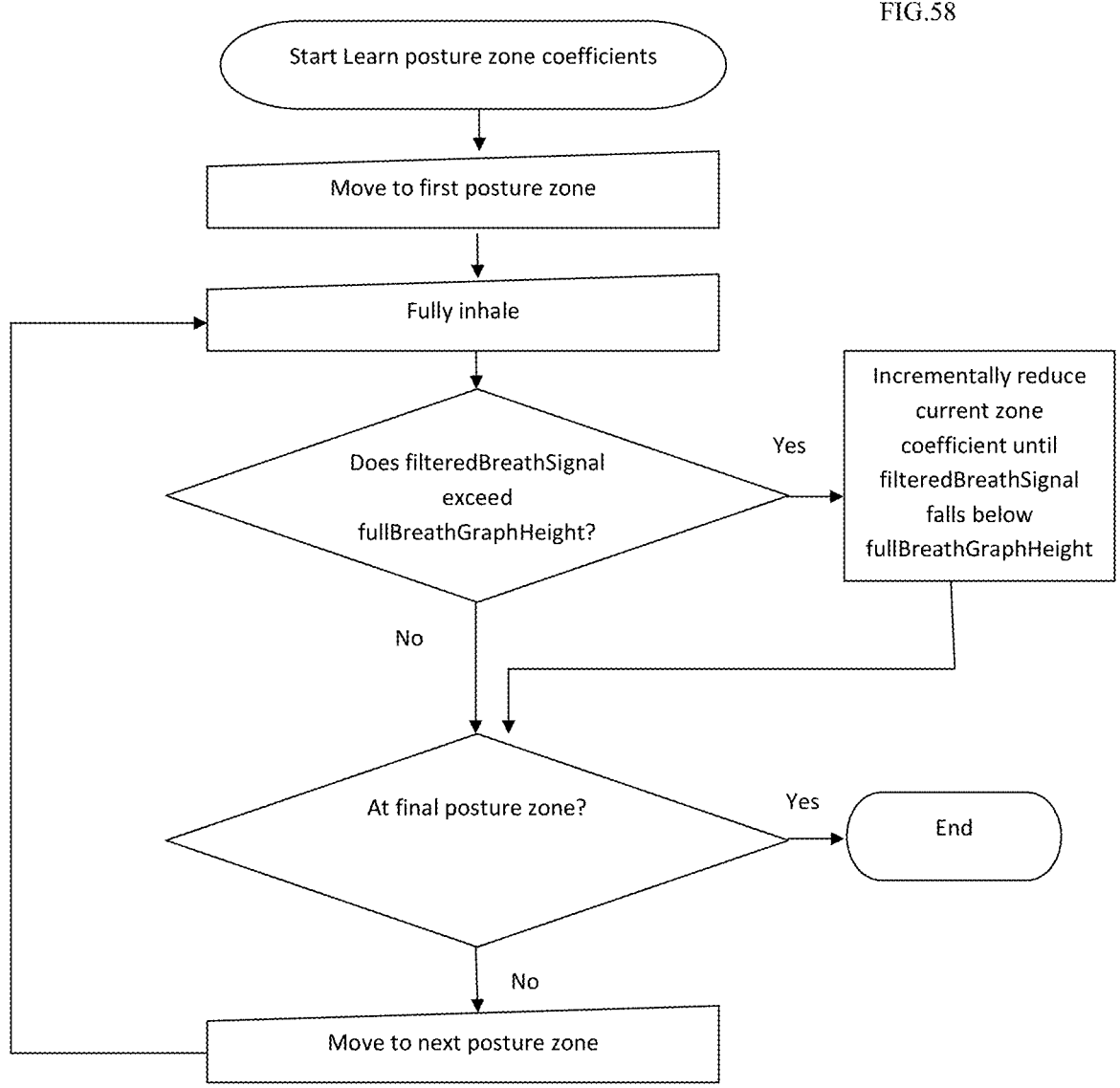
FIG. 58 is a flowchart showing exemplary steps involved in implementing a learn posture zone coefficients process of the present invention.

Returning to FIG. 54, the next step is checking if a breath depth auto-calibration flag is enabled. This can be set by the user by clicking an Auto-Calibrate breath depth button 380 on calibration control panel 366 as shown in FIG. 108. If on, then posture zone coefficients 382 above posture zones 372, are learned in the sub-process in the flowchart in FIG. 58. At this stage, all posture zone coefficients 382 are set to preliminary values for a type 1 or type 4 BTD as previously discussed, or can be set to 1.0 for a type 2 BTD. Referring to FIG. 58, in the first step, the user changes his/her posture so posture indicator 370 falls in the first posture zone, as shown in FIG. 112. The user then fully inhales. If the filtered breath signal exceeds full breath line 358, then the current posture zone coefficient is incrementally reduced until the filtered breath signal falls below full breath line 358, as shown in FIG. 113, where the current posture zone coefficient has been reduced to 1.2 from its initial value of 2.2. This means that when a user's posture is in this posture zone, for example, then signal A will be scaled by 1.2, so that a full diaphragmatic breath causes filtered breath signal to approximately reach full breath line 358. Next, the same steps are repeated for each subsequent posture zone, until all posture zone coefficients 382 are learned or refined, as shown in FIG. 114 as an example. FIG. 115 shows what happens with the filtered breath signal on timeline 350 prior to posture zone coefficients 382 being learned when a user fully diaphragmatically inhales. As shown, 7 full breaths have been taken, one in each posture zone from left to right. Due to the effects of posture on breath (breathing) as previously discussed, this results in the filtered breath signal not uniformly reaching full breath line 358 across these zones. But after posture zone coefficients have been learned or refined as shown in FIG. 116 according to the present invention, then full breaths taken across these zones much more uniformly reach full breath line 358, allowing inhalation depths to be more accurately compared between breaths, independent of the effects of posture. For a BTD type=4, posture tracking mode 351 as shown in FIG. 108A can be selected to aid in moving between posture zones, since a change in the belly angle only changes the position of posture indicator 370 as previously discussed in this mode. Then when in the desired zone, breath tracking mode 353 can be selected, which has the effect of freezing the position of posture indicator 370, so that when a breath takes place, the corresponding posture zone coefficient can be more conveniently learned and set.

Returning to FIG. 54, the next optional step in calibration is allowing the user to manually adjust posture zone coefficients 382, by using zone arrows 384, as shown in FIG. 108, where each coefficient can be increased or decreased by an incremental amount. Alternately, master breath EQ buttons 386 can be used to increase or decrease all posture zone coefficients 382 in tandem. Also, the user may reset all posture zone coefficients to a default value such as 1.0 by clicking an Equalizer Reset button 388 on calibration control panel 366. In the next step, the user can optionally adjust the motionDampening coefficient previously discussed which affects the degree of applied motion damping, by clicking motion dampening buttons 390 on calibration control panel 366. Next, the user can optionally adjust start breath threshold line 378 (later described), end breath threshold line 352, end of reverse breath threshold line 360, and enable/disable reverse breath tracking by using start breath depth buttons 392, end breath depth buttons 394, start/end reverse breath depth buttons 396, and an enable reverse breath tracking checkbox 398, all on calibration control panel 366 as shown in FIG. 108.

Next (for BTD type=4), the user can optionally set whichTrackingMode to 1, 2, or 3 (default value=3). Modes 1 and 2 were previously discussed. Default mode 3 corresponds to tracking both posture and breath as shown by a track both 355 selector in FIG. 108A. In this mode, the breath training program attempts to separate and isolate the relative posture position and relative diaphragm position components or signals from a single angle sensor. Generally as part of this strategy, a change in currentBellyAngle as computed in FIG. 63A is assumed to be due to diaphragmatic breathing thus changing relative diaphragm position, unless the filtered breath signal exceeds certain bounds, or remains unresolved beyond a specified duration of time (meaning either a diaphragmatic or reverse breath in progress has not ended as expected by crossing either the end breath threshold line 352 or reverse breath threshold line 360). When these exceptions occur, the breath training program can infer and interpret the change in currentBellyAngle occurred as a result of a posture change, which triggers the Normalize( ) process to execute in FIG. 74A, which updates the relative posture position to be equal to the current relative diaphragm position (derived from currentBellyAngle). Furthermore, the elapsed time can be backed up to the starting point of the event in question, retroactively dismissing this stretch of data so as to not unfairly affect the calculation of the respiration rate (for example, if the event took 7 seconds and was judged to be a posture-related change, not resetting the time to the start of the event would result in a 7 second absence of any breath data, which could unfairly underestimate the respiration rate). These details are discussed in greater detail for FIGS. 98A-98C.

The user may continue the calibration process as long as they wish for refining the settings and parameters of the BTD device as shown at the end of FIG. 54.

Figure 59:
FIG. 59 is a flowchart showing exemplary steps involved in implementing a Breath Pattern or Sequence Specification process of the present invention.

Returning to FIG. 51, we now discuss the next step S4 for specifying a training breath pattern or sequence, as detailed in the sub-process in the flowchart in FIG. 59. First, the user can decide if they wish to use an existing breath pattern or sequence from a library 400 of existing patterns, as shown in FIG. 117. Library 400 can be implemented as a popup menu for example as part of a breath parameters control panel 402. Alternately, breath patterns or exercises can be organized by breath exercise icons 401 as shown in an active training selection screen 405 in FIG. 117A for simplified selection, where one click of an icon selects and activates that particular breath exercise, preferably defaulting to the game view mode as detailed later for FIG. 52, with breath parameters control panel 402 optionally hidden to provide a simplified and streamlined view as shown in FIG. 145A. As two examples, the breath exercises could be organized and named by which time of the day they are most applicable to (as roughly shown in FIG. 117A), or by the intended effect and benefit, rather than by the technical name of the exercise, to make selection of an appropriate exercise more intuitive and convenient for the user. For example, a set of exercises organized by the stage of a workday they best apply to could be named: "Wakeup", "Energy Boost", "Focus", "De-Stress", "Wind Down", and "Bed Time" as shown in FIG. 117A. These could each be associated with a particular breath pattern (exercise) in library 400. For example, "De-Stress" could select and activate the "4-7-8" breath pattern. "Energy Boost" could select and activate "Bhastrika Pranayama". In this manner, breath exercise icons 401 can be thought of as capsules, where one click selects and activates everything the user needs to immediately start training with that exercise, for that particular benefit. A "Customize" icon 403 on active training selection screen 405 could alternately open the analytical view of the active training mode as described below, with breath parameters control panel 402 visible for selecting a breath pattern and modifying its parameters if desired, and then training in either the analytical or game mode view.

Breath parameters control panel 402 is part of a breath evaluation screen 404, which can also include breath/posture zone chart 368, a message box 406, timeline 350, a live stats box 408, and mode controls 410. In FIG. 117 for example, the user is shown selecting an existing breath pattern called Yoga: Sama Vritti Pranayama, Level 3. The breath training program as in step S5 then retrieves the parameters associated with the selected pattern, and sets them in breath parameters control panel 402, as shown in FIG. 117. The breath parameters retrieved can include:

Start Breath Depth (startBreathThreshold)
End Breath Depth (endBreathThreshold)
Min Breath Depth (minBreathDepth)
Max Breath Depth (maxBreathDepth)
Min Inhale Time (minInhalationTime)
Max Inhale Time (maxInhalationTime)
Min Breath Hold Time (minBreathHoldTime)
Max Breath Hold Time (maxBreathHoldTime)
Min Time Btw Breaths (minTimeBetweenBreaths)
Max Time Btw Breaths (maxTimeBetweenBreaths)
Min Exhale Time (minExhalationTime)
Max Exhale Time (maxExhalationTime)
Min Exhale Relative Time (minExhalationRelativeTime)
Max Exhale Relative Time (maxExhalationRelativeTime)
Full Breath Interval (fullBreathTime)
Relative End Breath Mode (relativeEndBreathVal)
Relative Exhalation Time Mode (relativeExhalationTime)
breathPatternMessages H (which can appear in message box 406, indexed by breathStage)

The user can then optionally adjust any of the parameters for the selected breath pattern by using the controls in the breath parameters control panel 402 to increase or decrease any of the parameter values (these parameters are described in detail hereinafter). If the user selected a breath sequence, then there is a distinct set of breath parameters for each breath in the sequence. The user can similarly edit any of these by first selecting the particular breath in the cycle (such as the third of 5 breaths), and then adjusting the breath parameters for that breath (not shown). The user, for example, can simply use arrow buttons to designate the current breath in the sequence to edit. If the user is not using an existing library pattern, they can select the "Custom Breath" option as visible near the bottom of library 400 in FIG. 117, and specify from scratch all the breath parameters in breath parameters control panel 402, including a sequence of breaths similar as above.

Figure 79:
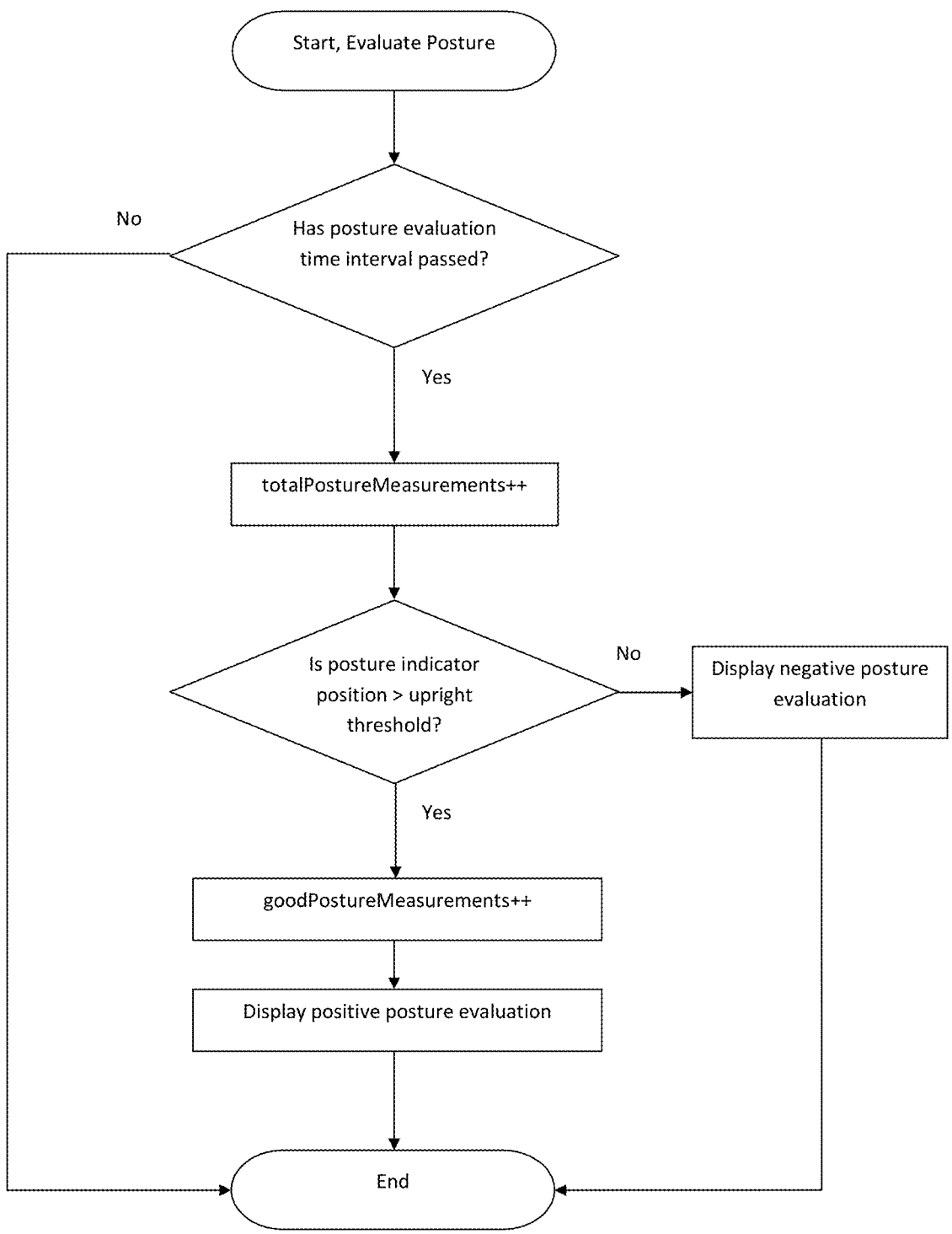
FIG. 79 is a flowchart showing exemplary steps involved in implementing a Start, Evaluate Posture process of the present invention.

Returning to FIG. 51, once the breath training pattern has been specified as above, the user can press a start button 412 in mode controls 410 as shown in FIG. 117 to move on to step S6 and begin the breath and posture evaluation processes. In step S6, if the training or monitoring time has not elapsed, or if a pause button 414 has not been pressed in mode controls 410 (start button 412 can change into pause button 414 when clicked as shown in FIG. 118), the evaluation process continues on to step S7. In step S7, the filtered breath signal is computed as previously explained for the given type of BTD. In step 8, the filtered breath signal is displayed and graphed on timeline 350 as discussed for FIG. 76. In step S9, breath/posture zone chart 368 can be displayed as previously discussed for the flowchart in FIG. 77. Jumping ahead to step S11 for discussion, the user's posture is evaluated as in the sub-process in the flowchart in FIG. 79, for example. Referring to FIG. 79, the first step is checking if a posture evaluation time interval has passed (such as one second for example). If no, the process is ended. If yes, totalPostureMeasurements is incremented, and then if posture indicator 370 on breath/posture zone chart 368 is above an upright threshold 416 as shown in FIG. 119, then goodPostureMeasurements is incremented, and a positive posture evaluation for the current time interval is displayed on a posture evaluation chart 418 as shown in FIG. 119, which can be viewable relative to timeline 350 so it is clear to the user when this particular posture evaluation took place. If posture indicator 370 on breath/posture zone chart 368 is below upright threshold 416, then a negative posture evaluation for the current time interval is displayed. For example, posture evaluation chart 368 can be a line as shown in FIG. 119, with a red color indicating a negative posture evaluation, and a green color indicating a positive posture evaluation. Upright threshold 416 can be placed at varying points on breath/posture zone chart 368 as a good posture cutoff. As shown, it is located at the start of the second to last zone of posture zones 372, so that the upper two posture zones reflect good posture, and the lower 5 reflect bad posture (if 7 posture zones 372 are utilized).

Figure 80:
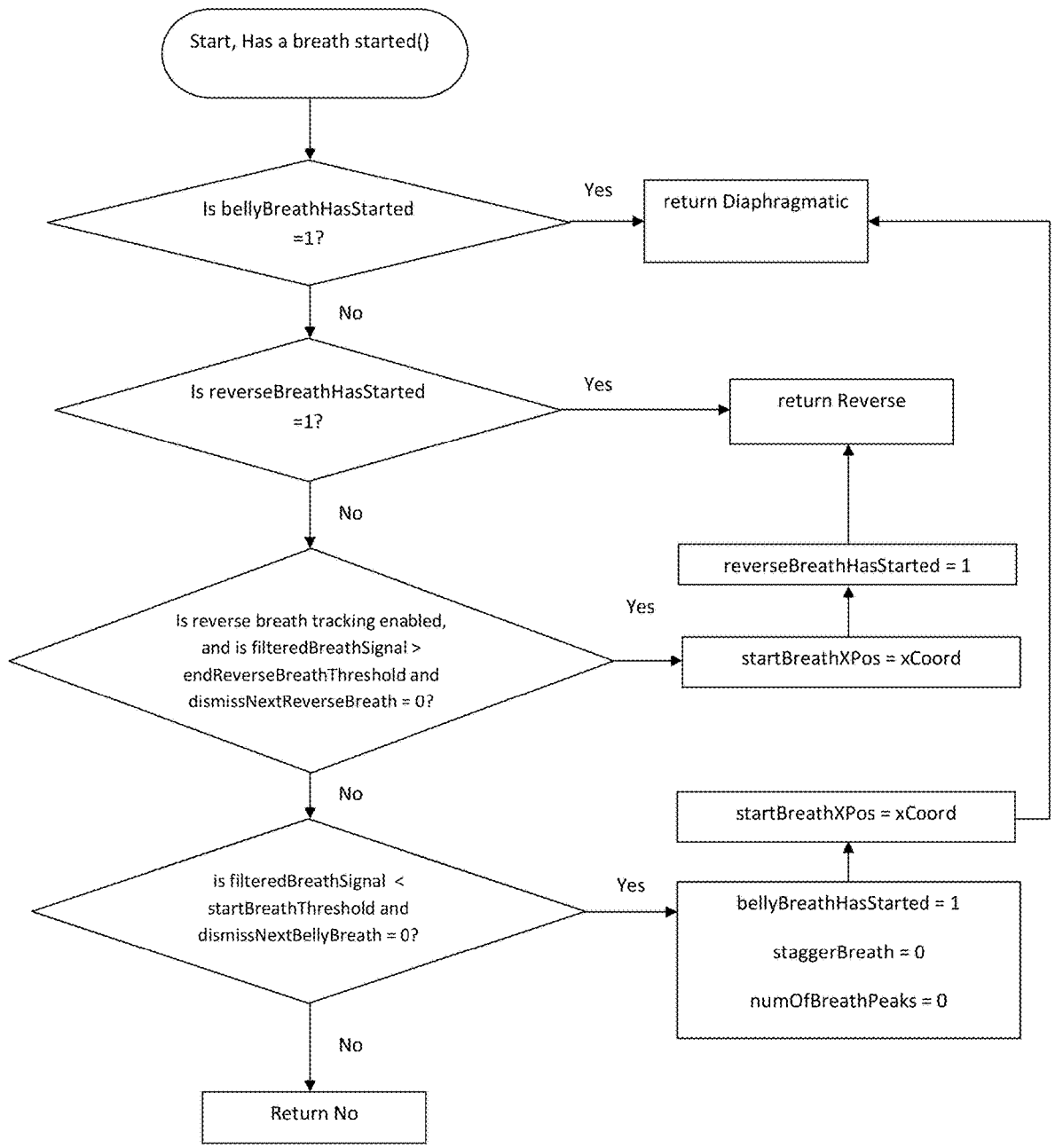
FIG. 80 is a flowchart showing exemplary steps involved in implementing a "Has a breath started( )" process of the present invention.

Returning to FIG. 51, in the next step S12, a test is conducted if a breath has started or already ongoing, as detailed in the flowchart in the sub-process in FIG. 80. Referring to FIG. 80, if bellyBreathHasStarted flag is set to 1, then this process returns a value representing a diaphragmatic breath is in progress. If reverseBreathHasStarted flag is set to 1, then this process returns a value representing a reverse breath is in progress. If neither of these flags are set, then in the next step, if reverse breath tracking is enabled, and if the filtered breath signal is greater than endReverseBreathThreshold and dismissNextReverseBreath=0, then startBreathXPos is set to xCoord (to record where the reverse breath began on the timeline), set reverseBreathHasStarted flag=1, and then this process returns a value representing a reverse breath is in progress. As shown in the example in FIG. 120, the filtered breath signal has passed below the end of reverse breath threshold line 360 which triggers the start of a reverse breath. The reason for checking if a dismissNextReverseBreath is set—to exclude allowing the start of a reverse breath—is because after the completion of diaphragmatic breath (as later discussed), the filtered breath signal may continue to move downwards on the graph, due to a certain momentum in the inward movement of the belly (when reverse breath tracking is enabled), which could result in a false reverse breath start signal if this flag is not checked (and it is set after each diaphragmatic breath as later discussed). As shown in FIG. 108 on calibration screen 364, the user can control the vertical level of the end of reverse breath threshold line 360 by using the start/end reverse breath depth buttons 396. An end of reverse breath threshold percentage 422 is shown as a negative value, which can be expressed relative to full breath line 358 but in the opposite direction. For example, if the user has only a slight inward belly movement during the start of a reverse breath, they can set this to a low percentage to catch that occurrence. For simplicity, end of reverse breath threshold line 360 can function as both the start and end threshold for a reverse breath, though a separate start reverse breath threshold line could be provided, analogous to start breath threshold line 378.

Returning to FIG. 80, in the next step, if the filtered breath signal is less than the startBreathThreshold (above this line on the graph) and dismissNextBellyBreath=0, then set bellyBreathHasStarted=1, set staggerBreath=0 (later described), set numOfBreathPeaks=0 (later described), and set startBreathXPos=xCoord (to record where the diaphragmatic breath began on the timeline 350), and then this process returns a value representing a diaphragmatic breath is in progress. As shown in the example in FIG. 121, when the filtered breath signal passes above the start breath threshold line 378, this triggers a diaphragmatic breath. The reason for checking if a dismissNextBellyBreath is set—to exclude allowing the start of a diaphragmatic breath—is because after the completion of reverse breath (as later discussed), the filtered breath signal may continue to move upwards on the graph, due to a certain momentum in the outward movement of the belly (when reverse breath tracking is enabled), which could result in a false diaphragmatic breath start signal if this flag is not checked (and it is set after each reverse breath as later discussed).

Figure 81:
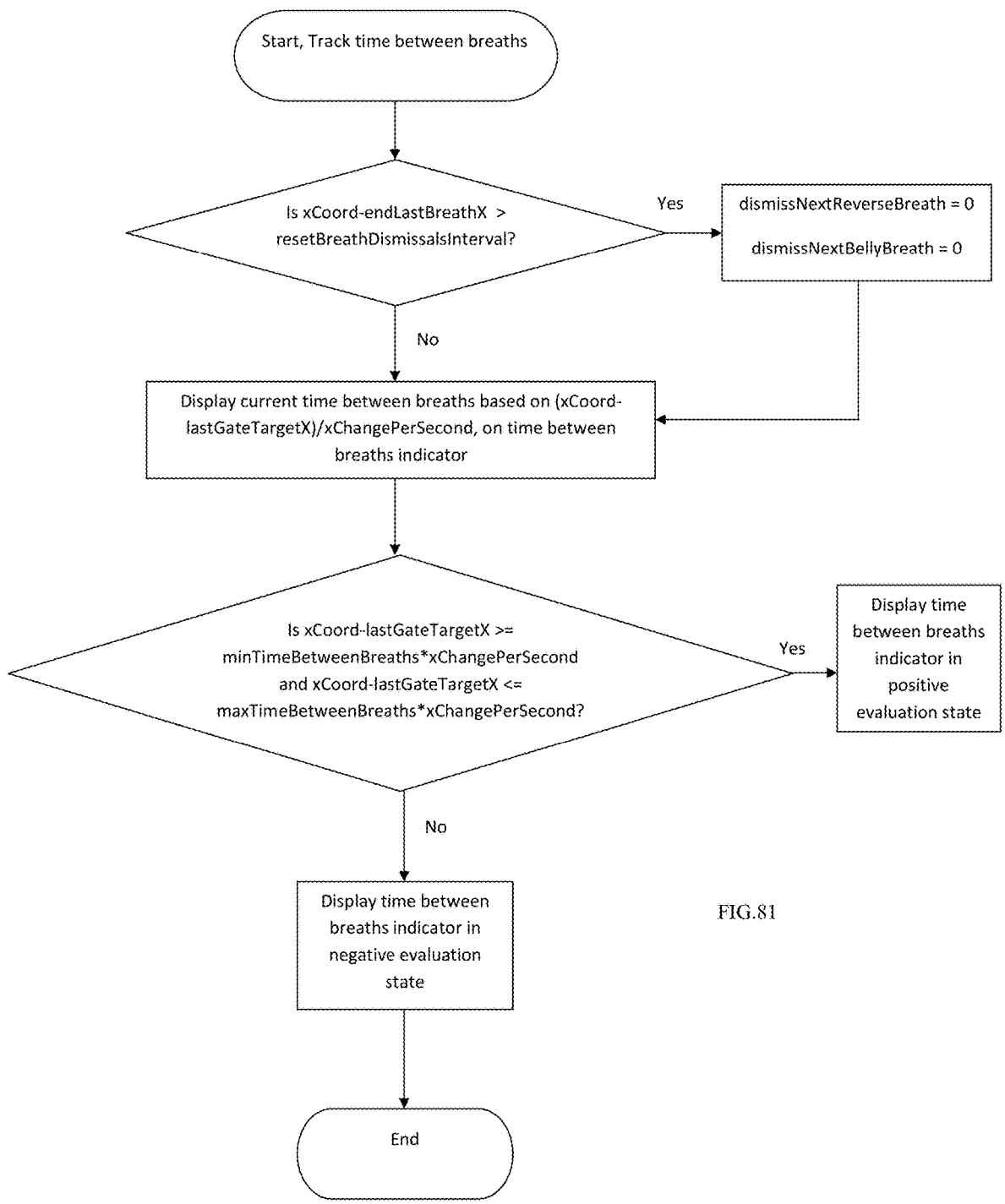
FIG. 81 is a flowchart showing exemplary steps involved in implementing a Track time between breaths process of the present invention.

Returning to FIG. 51, in the next step S13, if a breath has not started (either diaphragmatic or reverse), then a sub-process to track the time between breaths is executed, as in the flowchart in FIG. 81. Referring to FIG. 81, first step is to check if xCoord-endLastBreathX is greater than resetBreathDismissalsInterval. If yes, then set dismissNextReverseBreath=0 and dismissNextBellyBreath=0. The idea is that if more than a resetBreathDismissalsInterval of time has passed (indirectly measured by a change in xCoord) since the end of the last breath, then dismiss checking for a false breath start signal due to the possible momentum of the user's belly moving inwards or outwards after a breath, since enough time has passed where this natural momentum should no longer be a cause of such a false breath start. Next, display a time between breaths indicator 424 based for example on (xCoord-lastGateTargetX)/xChangePerSecond. lastGateTargetX is where the previous breath was projected to have ended as later described, and xChangePerSecond is how much the X Coordinate changes per second on the graph of the filtered breath signal on timeline 350, so that the final units are in time for this indicator. Next, if xCoord-lastGateTargetX is greater or equal to minTimeBetweenBreaths*xChangePerSecond and xCoord-lastGateTargetX is less than or equal to maxTimeBetweenBreaths*xChangePerSecond, then display time between breaths indicator 424 in a positive evaluation state (since this time is within the acceptable defined window of time), as shown in the example in FIG. 122, where 4.8 seconds has passed since the projected or expected end of the last breath, and as shown in breath parameters control panel 402, minTimeBetweenBreaths is set to 1, and maxTimeBetweenBreaths is set to 5, therefore time between breaths indicator 424 is displayed in a positive evaluation state. If xCoord-lastGateTargetX is outside these bounds, then display time between breaths indicator 424 in a negative evaluation state, as shown in FIG. 123, where 6.1 seconds has passed. For example, an elongating line as shown can be used for time between breaths indicator 424 against timeline 350 (along with a decimal time shown adjacent to the leading edge of the line), and this line can be green for example to indicate a positive evaluation state, and red for a negative evaluation state as shown in the examples. After completion of this process, the breath training program loops back to step S6 in FIG. 51.

Figure 82:
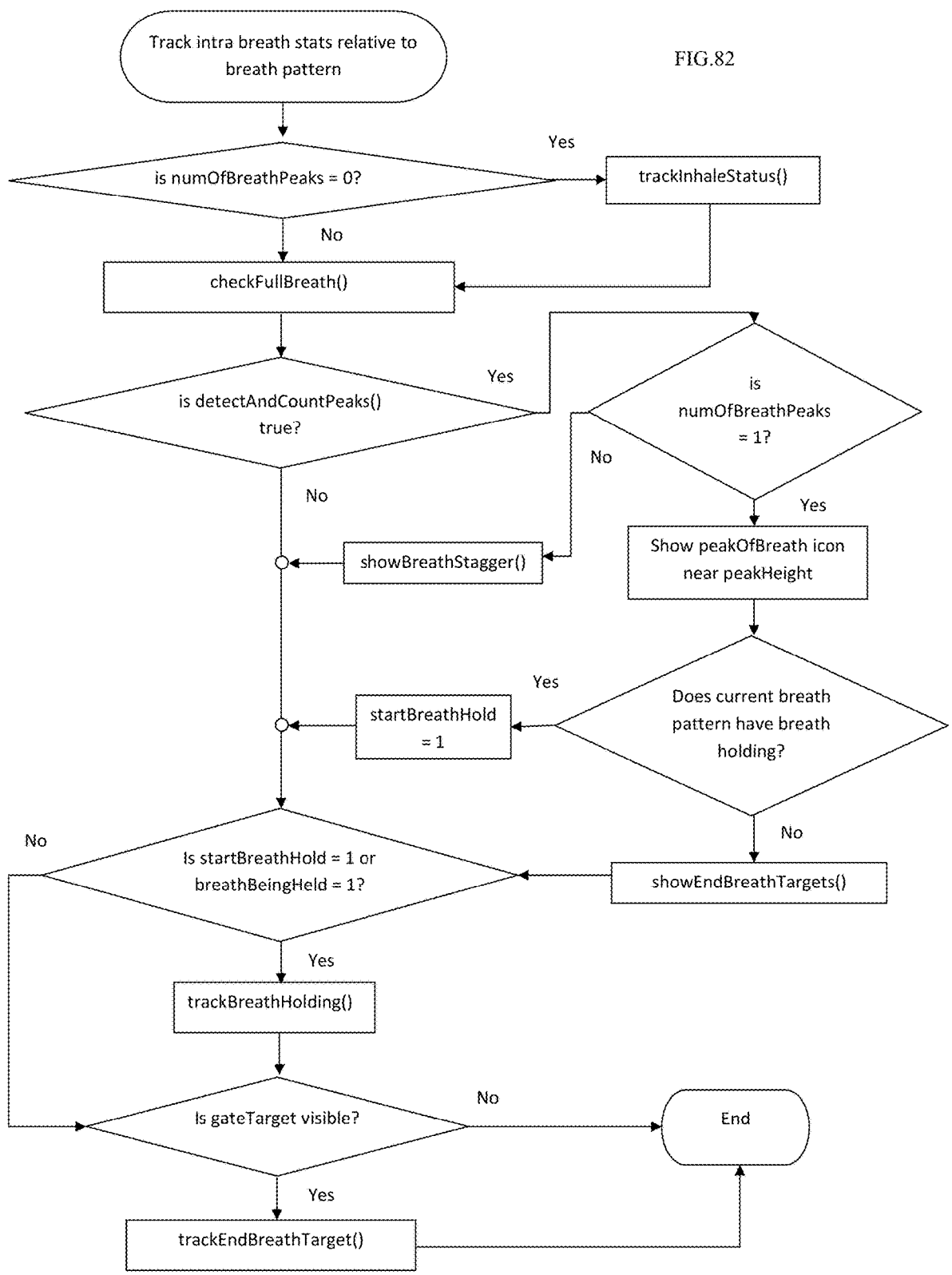
FIG. 82 is a flowchart showing exemplary steps involved in implementing a Track intra-breath stats (statistics) relative to the breath pattern process of the present invention.
Figure 83:
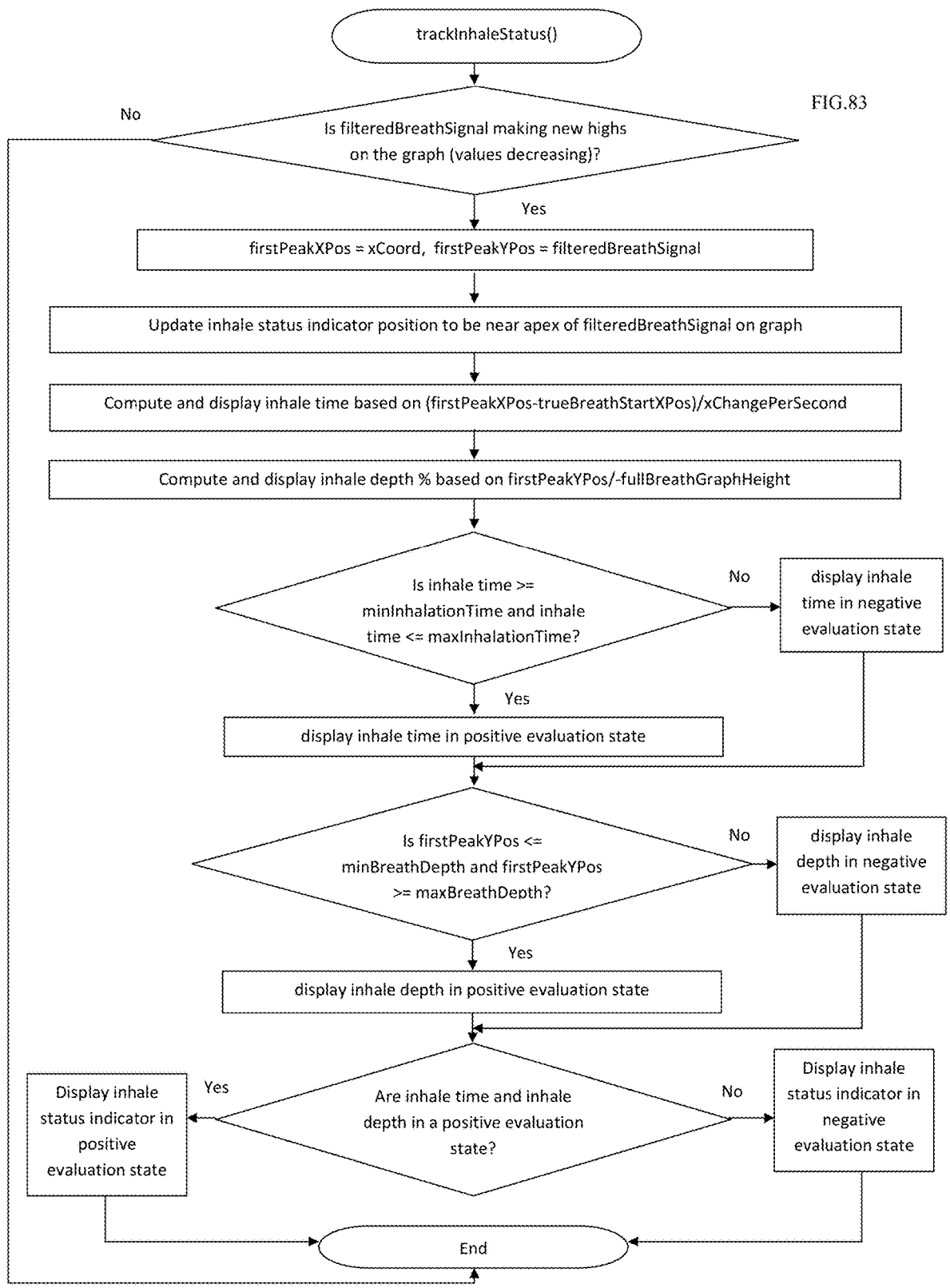
FIG. 83 is a flowchart showing exemplary steps involved in implementing a trackInhaleStatus( ) process of the present invention.

Returning to FIG. 51, step S14 executes if a diaphragmatic breath has started. Step S14 is an important sub process of the present invention to track intra-breath stats (statistics) relative to the current breath pattern as detailed in the flowchart in FIG. 82. Referring to FIG. 82, the first step is to check if numOfBreathPeaks is equal to 0 (an inhalation peak has not yet been detected). If yes, then execute the sub-process trackInhaleStatus( ) as shown in the flowchart in FIG. 83, for tracking the inhalation phase of a breath. Referring to FIG. 83, the first step is to check if the filtered breath signal is making new highs on timeline 350 (values decreasing). If no, then end this process. If yes, that means the user is actively inhaling Next, set firstPeakXPos=xCoord and firstPeakYPos=filtered breath signal to record the real-time highest point coordinates of an inhalation relative to timeline 350. Next, update an inhale status indicator 426 position to be near the apex of the filtered breath signal on timeline 350, as shown in the example in FIG. 124. Next, compute and display a current inhale time 428 based on (firstPeakXPos−trueBreathStartXPos)/xChangePerSecond. Next, compute and display an inhale depth % 430 based on firstPeakYPos/−fullBreathGraphHeight. Next, if inhale time 428 is greater or equal to minInhalationTime and inhale time 428 is less than or equal to maxInhalationTime, then display inhale time 428 in positive evaluation state. If not, display inhale time 428 in negative evaluation state. In FIG. 124, for example, inhale time 428 of 0.8 seconds is displayed in a negative evaluation state by means of showing the time in a red color. It is displayed negative here because in FIG. 125 for example, minInhalationTime is set to 3 seconds, and maxInhalationTime to 4.5 seconds, and 0.8 seconds is not in this range of time for an acceptable inhalation. minInhalationTime and maxInhalationTime can be set with Min Inhale Time buttons 432, and Max Inhale Time Buttons 434 in breath parameters control panel 402 as shown in FIG. 125. Next, is firstPeakYPos less than or equal to minBreathDepth and is firstPeakYPos greater or equal to maxBreathDepth (again, firstPeakYPos is smaller the higher it goes in the example coordinate system in the breath training program). If yes, then display inhale depth % 430 in a positive evaluation state. If not, then display inhale depth % 430 in a negative evaluation state. Again, colors can be used, such as green and red for positive and negative evaluation states respectively. Referring to the example in FIG. 125, a minimum inhalation depth line 436 and a maximum inhalation depth line 438 are shown on timeline 350, defining a visible zone of acceptable inhalation depth. The positions of these lines can be controlled by Min Breath Depth buttons 440 and Max Breath Depth buttons 442 in breath parameters control panel 402, which function to set minBreathDepth and maxBreathDepth respectively. As shown in the example, minBreathDepth and maxBreathDepth are set to 50% and 86% respectively, and the inhale depth % 430 is at 70% on the graph, which is within this acceptable depth window, therefore inhale depth % 430 is displayed in a positive evaluation state (green color for example). These percentages are relative to full breath line 358, representing 100% inhalation depth. In the example in FIG. 122, a maximum inhalation depth line 438 is not specified, with N/A shown near the Max Breath Depth buttons 442. In this case, the inhale depth % 430 is displayed in a positive evaluation state as long as it is greater than the minBreathDepth. Returning to FIG. 123, if both the inhale time 428 and inhale depth % 430 are in a positive evaluation state, then inhale status indicator 426 is shown in an overall positive evaluation state, where inhale status indicator 426 is shown in a green color to indicate this positive status. If not, then inhale status indicator 426 is shown in a negative evaluation state, such as in FIG. 124, where inhale status indicator 426 can be shown in a red color to indicate this negative status. In this way, an acceptable inhalation occurs when both the inhale time and inhale depth are within the parameter-defined ranges.

Figure 84:
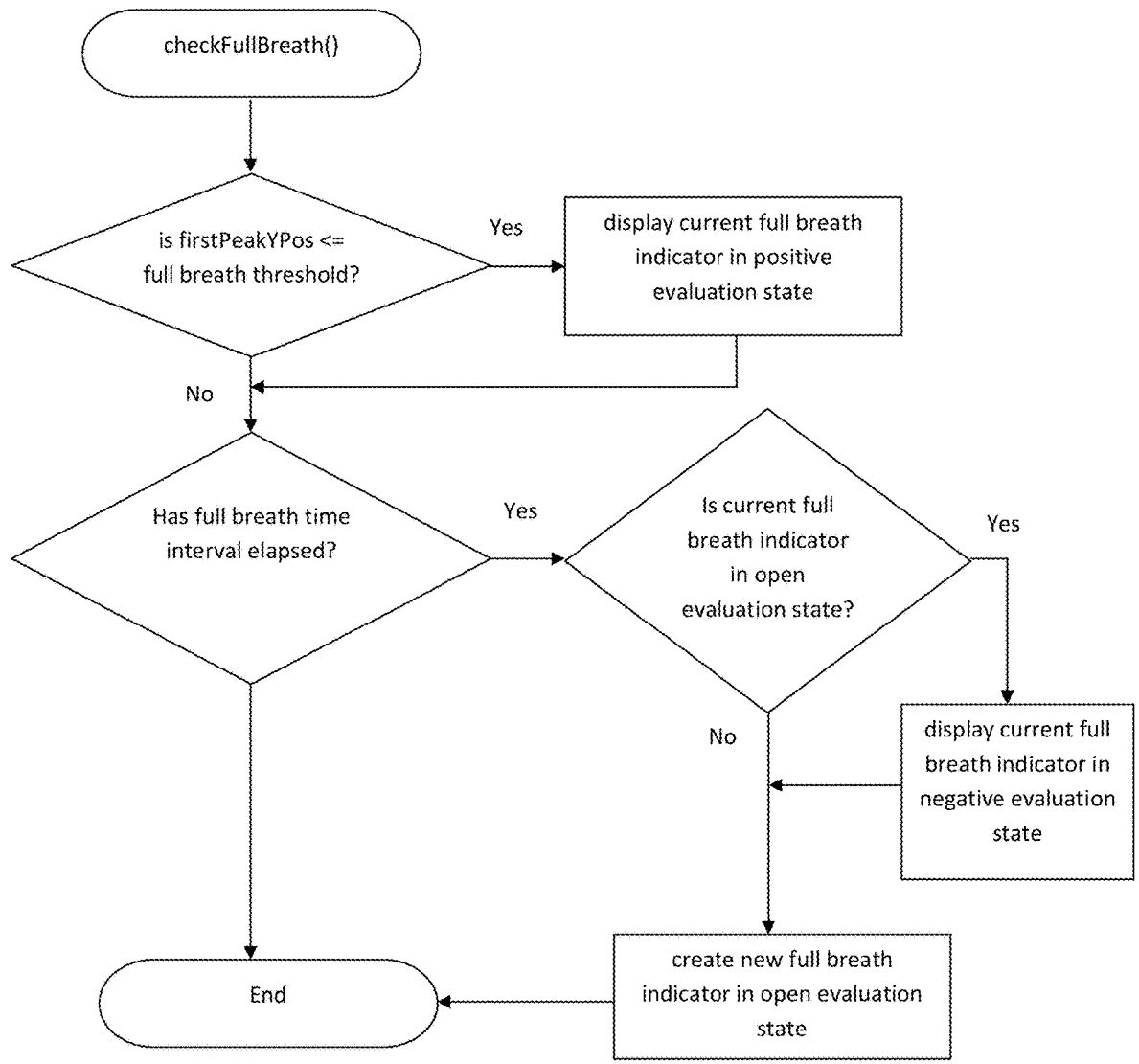
FIG. 84 is a flowchart showing exemplary steps involved in implementing a checkFullBreath( ) process of the present invention.

Returning to FIG. 82, a sub process to check if a full breath has occurred within a specified interval of time is run as detailed in the flowchart in FIG. 84. This process is designed to help train a user to take at least one full deep diaphragmatic inhalation within a specified interval of time. Referring to FIG. 84, the first step is to check if firstPeakYPos is less than or equal to full breath threshold line 358. If yes, then display a full breath indicator 444 in positive evaluation state as shown in FIG. 126. Full breath indicator 444 shows if a full breath has occurred at some point within the last interval of time specified by fullBreathTime, which can be set by full breath time interval buttons 446 as shown in breath parameters control panel 402. In the example shown, fullBreathTime is set to 20 seconds, and one breath at approximately 11 seconds on timeline 350 rose above full breath threshold line 358, causing the current full breath indicator 444 to be shown in a positive evaluation state. Returning to FIG. 84, the next step is to check if fullBreathTime has elapsed? If yes, then check if current full breath indicator 444 is in an open evaluation state. If yes, then display current full breath indicator in a negative evaluation state, as shown in the example in FIG. 126, where no full breath occurred between 20 and 40 seconds, with the full breath indicator 444 at 40 seconds shown in a negative evaluation state. Next (if fullBreathTime has elapsed), then create a new open full breath indicator 444 on timeline 350 for the next interval of time, as shown at 60 seconds in this example. This process can easily be extended to track and require any number of full breaths within a specified interval of time. For example, a counter can be incremented each time firstPeakYPos goes above the full breath threshold line 358 (once at most for each breath), and then compared to a threshold minimum number of full breaths when the full breath time interval is reached to determine how to set the current full breath indicator 444.

Figure 85:
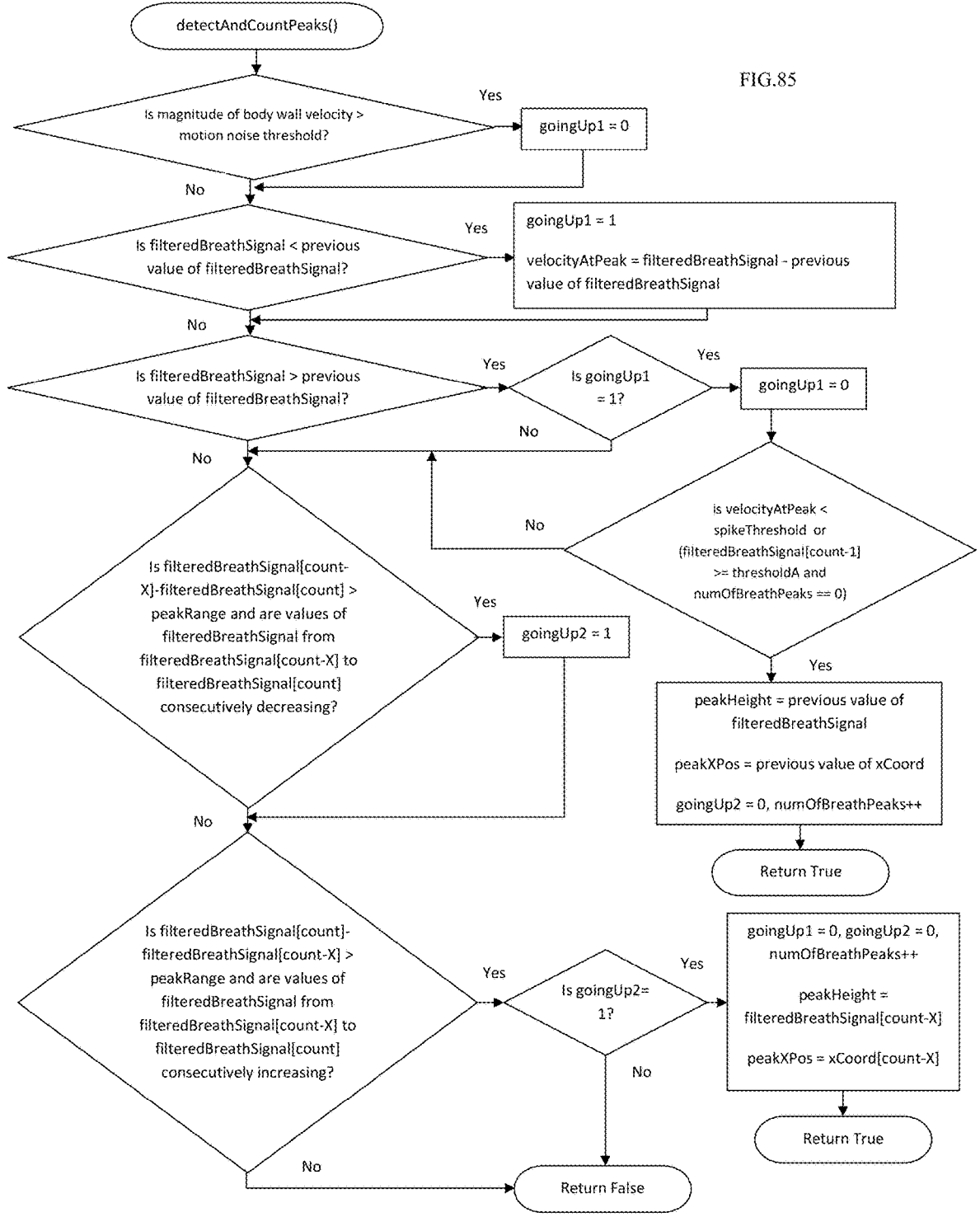
FIG. 85 is a flowchart showing exemplary steps involved in implementing a detectAndCountPeaks( ) process of the present invention.

Returning to FIG. 82, the next step is to check if a peak has occurred in the filtered breath signal as in the detectAndCountPeaks( ) sub process, shown in the flowchart in FIG. 85. This is an important sub process of the present invention for finding and distinguishing between a legitimate end of an inhalation phase of a breath or a breath stagger, versus body motion noise or other signal noise which may cause misleading peaks in the filtered breath signal. This process consists of two or more distinct multi-stage peak detectors, looking for different sets of features in the filtered breath signal for qualifying as a peak. Referring to FIG. 85, in the first peak detector, the first step is to check if the magnitude of body wall velocity is greater than a motion noise threshold? If true, then set goingUp1=0. For type 1-3 BTD's, the rate of change of relative posture position at the current time is used for the body wall velocity. For a type 4 BTD, the rate of change of relative diaphragm position at the current time is used for the body wall velocity. The idea here is to reset the first peak detector if there is more than a specified threshold of body movement since this could confound this first detector. Next, check if filtered breath signal is less than the previous value of the filtered breath signal (previous value of the filtered breath signal can be implemented for example as filteredBreathSignal[count−1] if an array of filtered breath signal values are stored, and count is the latest entry. This implementation is used going forward for the examples). If true, then set goingUp1=1 and velocityAtPeak=(filteredBreathSignal[count]−filteredBreathSignal[count−1]). Next, check if filteredBreathSignal[count]>filteredBreathSignal[count−1]. If yes, then check if goingUp1=1? If yes, then first set goingUp1=0, and then check if velocityAtPeak is less than a spikeThreshold, or (filteredBreathSignal[count−1] is greater or equal to thresholdA and numOfBreathPeaks=0). If true, then set peakHeight=filteredBreathSignal[count−1], peakXPos=previous value of xCoord to save the coordinates of the peak, goingUp2=0, and increment numOfBreathPeaks, then return True, since a peak has been detected by the first peak detector. The idea with the first peak detector is to detect the filtered breath signal first moving up, and then at some subsequent point, moving down (without the user's body movement exceeding a specified threshold level in the intervening time which resets this detector), and if this occurs, to then further test if there was a spike in the filtered breath signal (meaning that a rapid inhalation occurred), or if the peak of the filtered breath signal occurred below a thresholdA (which can generally be set not far above fully exhaled line 356). If either is true, then this qualifies as a peak by the first peak detector. The condition or feature of the filtered breath signal moving up, and then subsequently moving down is very lenient, and could trigger many false peak signals, thus the subsequent additional conditions to qualify as a peak under this test are that a rapid inhalation occurred (spike in the signal), or that the user took a shallow subtle inhalation with the peak below thresholdA. If the first peak detector does not detect a peak, then process flow moves on to the next step in FIG. 85, which is the start of the second peak detector. The first step of the second peak detector is to check if filteredBreathSignal[count−X]−filteredBreathSignal[count] is greater than a peakRange, and are values of filteredBreathSignal from filteredBreathSignal[count−X] to filteredBreathSignal[count] consecutively decreasing (filtered breath signal is moving upwards)? If yes, then set goingUp2=1. Next, check if filteredBreathSignal[count]−filteredBreathSignal[count−X]>peakRange and are values of filteredBreathSignal from filteredBreathSignal[count−X] to filteredBreathSignal[count] consecutively increasing (filtered breath signal is moving downwards)? If yes, then check if goingUp2=1? If true, then a peak has been detected by the second peak detector. Next, set goingUp1=0 (to reset the first independent peak detector), goingUp2=0, increment numOfBreathPeaks, peakHeight=filteredBreathSignal[count−X], and peakXPos=xCoord[count−X] to save the coordinates of the peak, and return True (peak detected). Otherwise, return False (no peak detected). The idea with the second peak detector is to look for a pattern of the filtered breath signal consistently moving upwards across a minimum number of steps (without any breaks in the upward movement), and then at some subsequent point, consistent moving downwards across a number of minimum steps (without any breaks in the downward movement). Additionally, in both cases, the distance between filteredBreathSignal[count−X]−filteredBreathSignal[count] (for upward movement) and filteredBreathSignal[count]−filteredBreathSignal[count−X] (for downward movement) must exceed a peakRange value, which helps to filter out false peaks caused by body movement noise which could cause such consistent upward or downward movement, but typically occurring across a smaller distance (as the motion damping filter previously discussed would typically dampen out the larger swings due to body motion).

Figure 86:
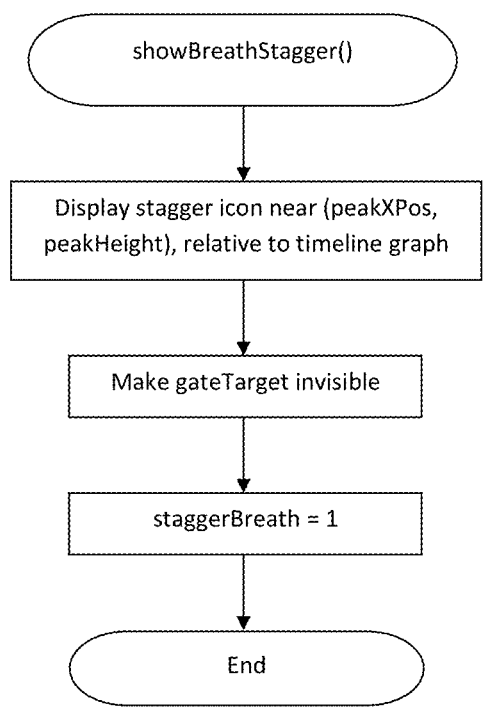
FIG. 86 is a flowchart showing exemplary steps involved in implementing a showBreathStagger( ) process of the present invention.
Figure 87:
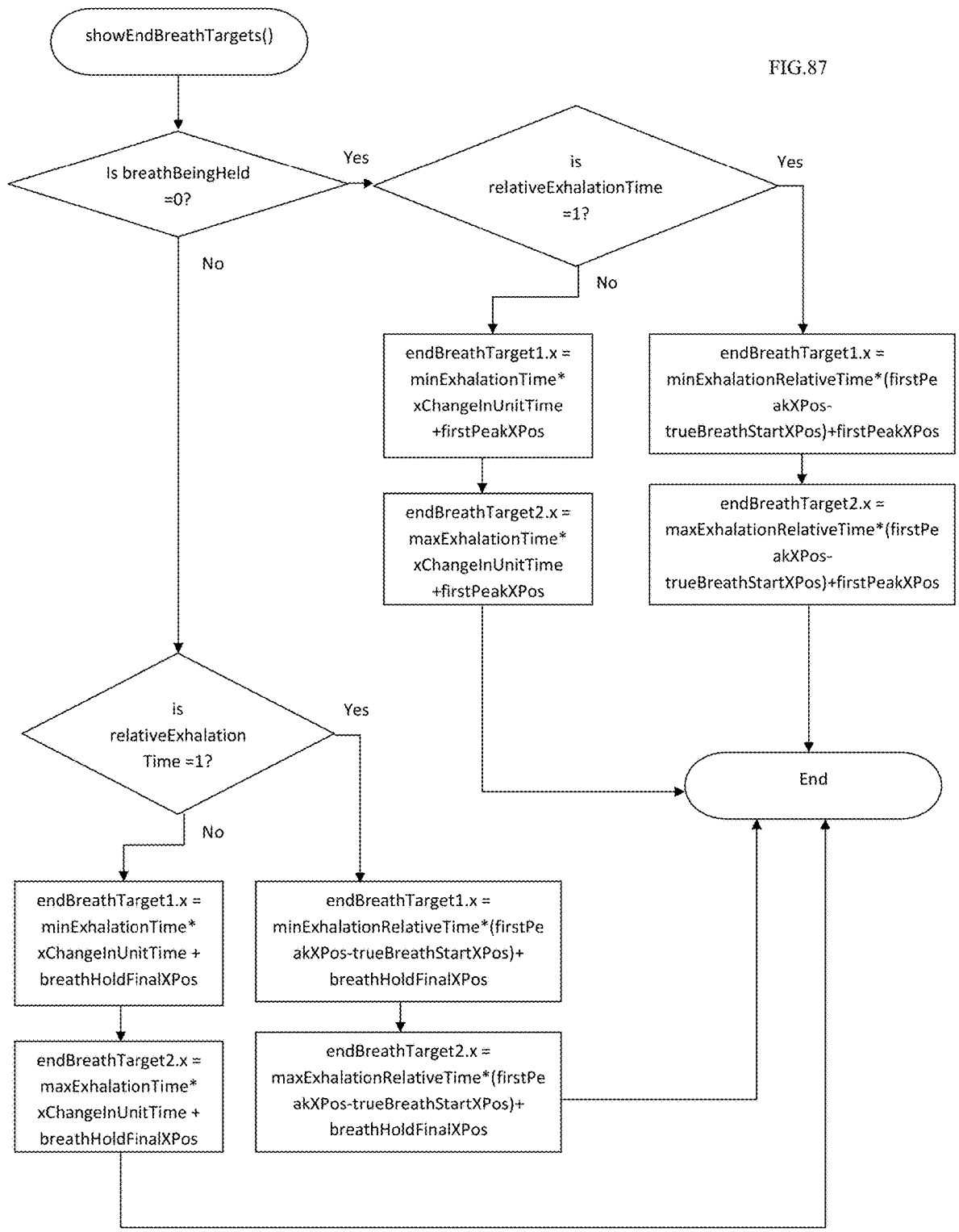
FIG. 87 is a flowchart showing exemplary steps involved in implementing a showEndBreathTargets( ) process of the present invention.

Returning to FIG. 82, the next step in tracking intra breath stats is that if detectAndCountPeaks( ) returns True, then check if numOfBreathPeaks=1? If true, this means that the peak just detected was the very first peak in the current breath, which qualifies as the end point of the inhalation phase according to the present invention, therefore show a peakOfBreath icon 448 near peakHeight to represent this end of inhalation on timeline 350 (peakHeight was determined in the detectAndCountPeaks( ) sub process). peakOfBreath icon 448 is shown in the example in FIG. 127 near the detected peak in the filtered breath signal next to inhale status indicator 426, where the user just completed his/her inhalation, and is now exhaling, with the filtered breath signal subsequently moving downwards. peakOfBreath icon 448 can be shown in a green color, similar to inhale status indicator 426, if the inhalation was within the acceptable defined parameter ranges, or red if it was not. If numOfBreathPeaks is greater than 1, then the peak is interpreted as a breath stagger and the sub process showBreathStagger( ) is executed as shown in the flowchart in FIG. 86, where the peak is labeled with a stagger indicator 450 as shown in the example in FIG. 128, and then a gateTarget 452 is made invisible (discussed hereinafter), and then staggerBreath is set to 1. According to the present invention, there should only be one continuous inhalation phase in a single breath of good quality. If the user is exhaling but then inhales again prior to completion of the exhale, this peak is considered a staggered breath. Stagger indicator 450 can be shown in a red color to indicate it will negatively impact the evaluation of the given breath. Returning to FIG. 82, if numOfBreathPeaks was set to 1, and after the step of showing the peakOfBreath icon, then the process checks if the current breath pattern has breath holding or retention associated with it after the inhalation phase, that is, if minBreathHoldTime is greater than 0. If false, then the sub process showEndBreathTargets( ) is executed as shown in the flowchart in FIG. 87. If true, then startBreathHold is set to 1. As shown in FIG. 134 in breath parameters control panel 402, Min Breath Hold Time buttons 454 and Max Breath Hold Time buttons 456 can function to set minBreathHoldTime and maxBreathHoldTime respectively, and in this example, are shown as 3 seconds and 5 seconds respectively. Referring now to FIG. 87, the sub process showEndBreathTargets( ) is responsible for displaying an endBreathTarget1 458 and an endBreathTarget2 460 on timeline 350 as shown in FIG. 129, which visually indicates to the user the acceptable range of time within which their exhalation should be completed, so as to help the user guide his/her exhalation to end up within this range. The minExhalationTime and maxExhalationTime (or minExhalationRelativeTime and maxExhalationRelativeTime) are retrieved for the selected breath pattern as previously discussed, or can be adjusted or set in the breath parameters control panel 402 as shown in FIG. 130 using the min exhale time buttons 462 and max exhale time buttons 464. Furthermore, breath parameters control panel 402 has a relative exhalation time button 466 to turn on or off a relativeExhalationTime mode. When turned on (or set to 1), as shown in FIG. 130, minExhalationRelativeTime and maxExhalationRelativeTime are defined relative to the user's actual inhalation time. In this example, minExhalationRelativeTime is set to 1.0×Inhale Time, and maxExhalationRelativeTime is set to 2.0×Inhale Time. If the user's inhalation time was, for example, 2 seconds, then an acceptable range of exhalation time in this example would be between 1.0×2 seconds to 2.0×2 seconds=between 2 second to 4 seconds (after the inhalation peak), as shown in the example in FIG. 132, where the user inhaled for 2.1 seconds, with the inhalation ending at approximately 6 seconds on timeline 350, and then endBreathTarget1 458 displayed around the 8 second mark, and endBreathTarget2 460 at about the 10 second mark, with this window defining the acceptable range for the exhalation. Alternately if relativeExhalationTime is turned off as shown in FIG. 131, then minExhalationTime and maxExhalationTime are defined in absolute seconds, independent of the inhalation time. In this example, they are set to 3.0 seconds and 4.5 seconds respectively. As shown in FIG. 133, an inhalation for the current breath has completed at approximately 7 seconds on timeline 350, with endBreathTarget1 458 then displayed at about 10 seconds, and endBreathTarget2 460 at about 11.5 seconds. These targets can only be displayed after an inhalation has completed since their position depends on the end point of the inhalation. Furthermore, if the current breath pattern requires breath holding after an inhalation, then endBreathTarget1 458 and endBreathTarget2 460 are displayed only after the completion of the breath holding phase (from sub process trackEndBreathTarget( )), since the exhalation would begin after this phase in this case. Referring now to the flowchart in FIG. 87, the first step is to check if breathBeingHeld=0 (meaning that there is no breath holding after inhalation for the current breath pattern). If yes, then check if relativeExhalationTime=1? If yes, then set the X coordinate of endBreathTarget1 458 on timeline 460 based on minExhalationRelativeTime*(firstPeakXPos−trueBreathStartXPos)+firstPeakXPos, and set the X coordinate of endBreathTarget2 460 based on maxExhalationRelativeTime*(firstPeakXPos−trueBreathStartXPos)+firstPeakXPos with firstPeakXPos and trueBreathStartXPos previously defined. If relativeExhalationTime=0, then set the X coordinate of endBreathTarget1 458 on timeline 350 based on minExhalationTime*xChangeInUnitTime+firstPeakXPos, and set the X coordinate of endBreathTarget2 460 based on maxExhalationTime*xChangeInUnitTime+firstPeakXPos, with xChangeInUnitTime being set to how much the xCoord of the filtered breath signal is incremented each second. If breathBeingHeld is not equal to 0 (current breath pattern has breath holding after inhalation), then check if relativeExhalationTime=1? If yes, then set the X coordinate of endBreathTarget1 458 on timeline 350 based on minExhalationRelativeTime*(firstPeakXPos−trueBreathStartXPos)+breathHoldFinalXPos, and set the X coordinate of endBreathTarget2 460 based on maxExhalationRelativeTime*(firstPeakXPos-trueBreathStartXPos)+breathHoldFinalXPos with breathHoldFinalXPos described later. If relativeExhalationTime=0, then set the X coordinate of endBreathTarget1 458 on timeline 350 based on minExhalationTime*xChangeInUnitTime+breathHoldFinalXPos, and set the X coordinate of endBreathTarget2 460 based on maxExhalationTime*xChangeInUnitTime+breathHoldFinalXPos.

Figure 88:
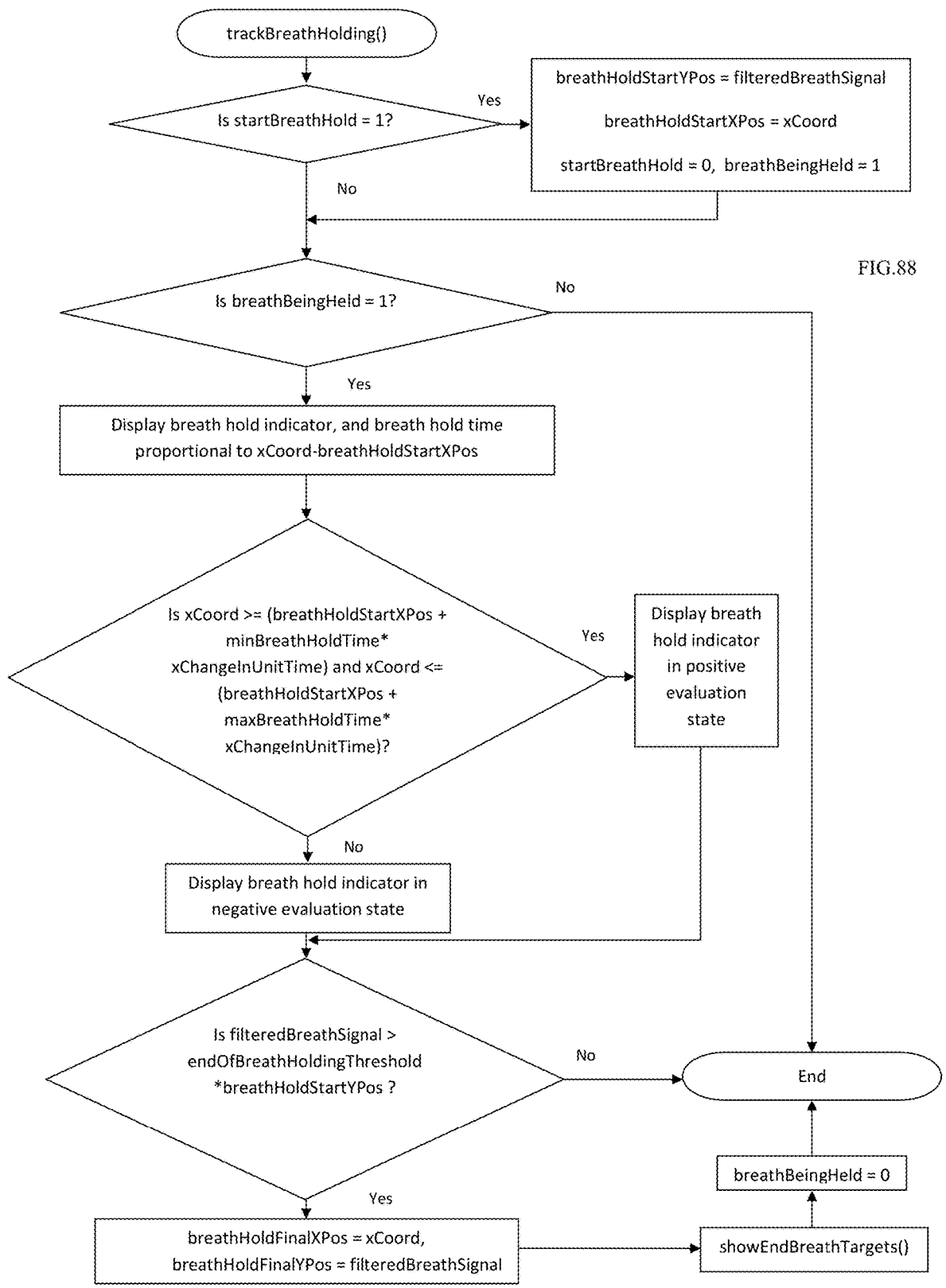
FIG. 88 is a flowchart showing exemplary steps involved in implementing a trackBreathHolding( ) process of the present invention.

Returning to FIG. 82, the next step in tracking intra breath stats is to check if startBreathHold=1 or breathBeingHeld=1? (meaning breath holding has just started after inhalation, or is already ongoing). If yes, then execute the sub process trackBreathHolding( ) as detailed in the flowchart in FIG. 88. Referring to FIG. 88, the first step is to check if startBreathHold=1? If yes, then record the coordinates of the start of the breath holding with breathHoldStartYPos=filtered breath signal, breathHoldStartXPos=xCoord, and set startBreathHold=0, breathBeingHeld=1. Next, check if breathBeingHeld=1? If no, then end the process. If yes, then display a breath hold indicator 468 on timeline 350 near the real time graphed filtered breath signal as shown in FIG. 134 (this indicator can move along with the graph), and a breath hold time 470 proportional to xCoord-breathHoldStartXPos. Next, check if xCoord>=(breathHoldStartXPos+minBreathHoldTime*xChangeInUnitTime) and xCoord<=(breathHoldStartXPos+maxBreathHoldTime*xChangeInUnitTime)? If yes, then display breath hold indicator 468 in a positive evaluation state (such as in a green color) since the breath holding time is within the acceptable defined range, and if no, then display breath hold indicator 468 in a negative evaluation state (such as in a red color), as shown in the example in FIG. 134, where the breath hold time 470 is 2.3 seconds which is not within the range of 3 seconds and 5 seconds as shown in the breath parameters control panel 402, where minBreathHoldTime and maxBreathHoldTime can be set with Min Breath Hold Time buttons 454, and Max Breath Hold Time Buttons 456. Next, check if the filtered breath signal>endOfBreathHoldingThreshold*breathHoldStartYPos? If yes, then the breath holding phase is complete and the exhalation phase has begun, and set breathHoldFinalXPos=xCoord, breathHoldFinalYPos=filtered breath signal to record the coordinates of the end of the breath holding, and then execute showEndBreathTargets( ) as previously discussed to show the exhalation targets in relation to the end of the breath holding coordinates in this case, then set breathBeingHeld=0. If no, then end the process. For example, endOfBreathHoldingThreshold can be set to 0.75, in which case, when the filtered breath signal has fallen below ¾ the height of the filtered breath signal when the breath holding began on timeline 350, then the breath holding phase is ended, as shown in the example in FIG. 135, where breath holding indicator 468 is no longer moving on timeline 350 with the filtered breath signal.

Figure 89:
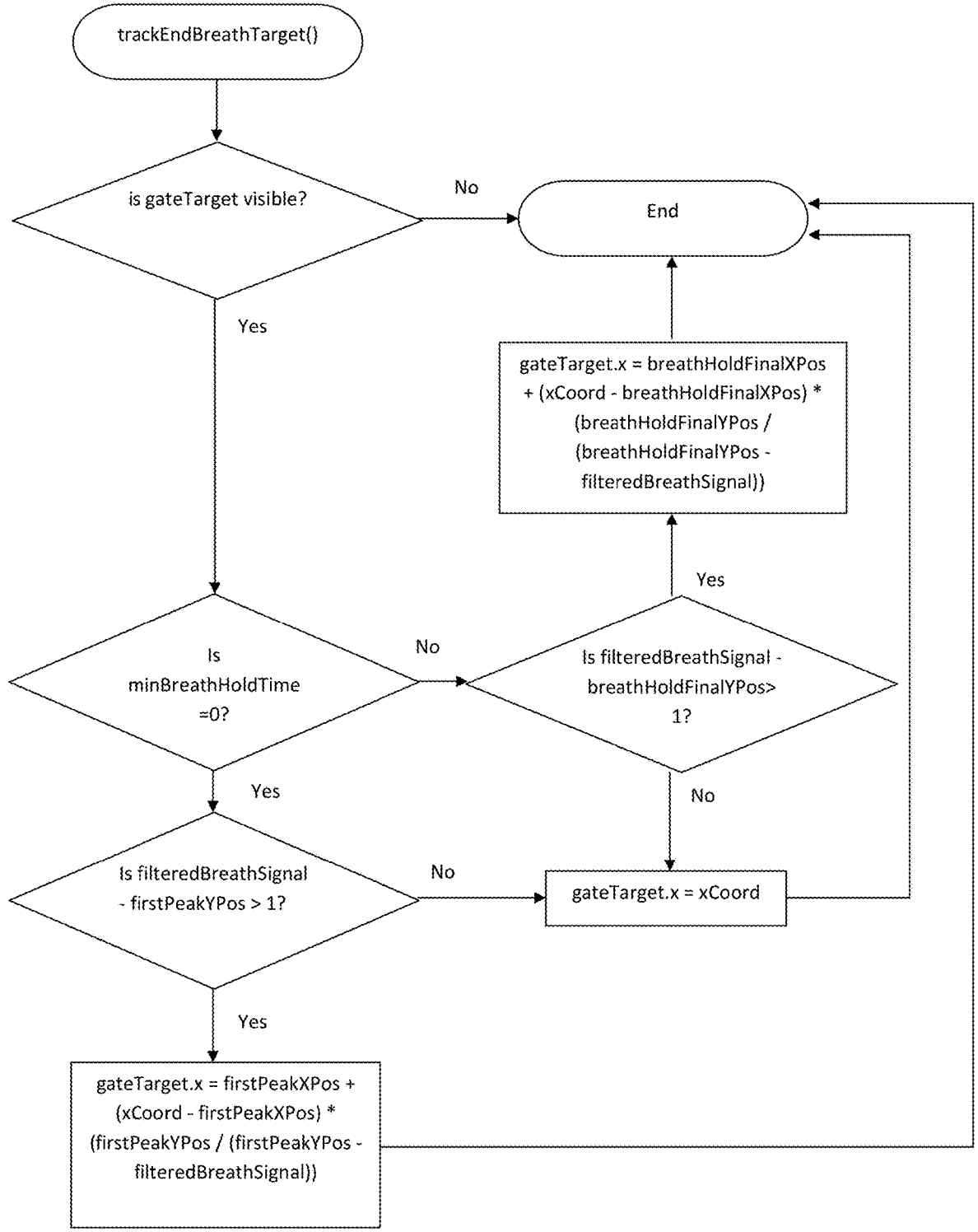
FIG. 89 is a flowchart showing exemplary steps involved in implementing a trackEndBreathTarget( ) process of the present invention.

Returning to FIG. 82, the next step in tracking intra breath stats is to check if a gateTarget 452 is visible, as shown in FIG. 129. If no, then end the process in FIG. 82. If yes, then execute sub process trackEndBreathTarget( ) as shown in the flowchart in FIG. 89, and then end the process in FIG. 82. Referring to FIG. 89, the trackEndBreathTarget( ) process is responsible for positioning gateTarget 452 on timeline 350, which is the real time projected or estimated point where the user's exhalation will end, given the average rate or slope of the current ongoing exhalation. This moving visual indicator is helpful in guiding a user to pace their exhalation so that it ends within the acceptable range given by parameters minExhalationTime and maxExhalationTime, or minExhalationRelativeTime and maxExhalationRelativeTime. As shown in the example in FIG. 129 and FIG. 136, the goal is to uniformly exhale at such a pace so that gateTarget 452 lies between endBreathTarget1 458 and endBreathTarget2 460 when the filtered breath signal reaches end breath threshold line 352. If the user is exhaling too slowly, then gateTarget 452 will lay beyond endBreathTarget2 460, as shown in FIG. 133 and FIG. 135. If exhaling too quickly, then it will be prior to endBreathTarget1 458 as shown in FIG. 138. Referring to FIG. 89, the first step is to check if gateTarget 452 is currently visible. If no, then end the process. If yes, then check if minBreathHoldTime=0? If no (meaning the current breath pattern has breath holding after inhalation), then check if filtered breath signal−breathHoldFinalYPos>1? (meaning that the filtered breath signal is below the final breath holding level). If yes, then position gateTarget 452 relative to the end of breath holding X coordinate using gateTarget.x=breathHoldFinalXPos+(xCoord−breathHoldFinalXPos)*(breathHoldFinalYPos/(breathHoldFinalYPos−filteredBreathSignal)). This extrapolates where the filtered breath signal's X coordinate will be when it's Y coordinate reaches fully exhaled line 356, assuming that the average slope or trend of the exhalation continues to the end of the exhalation, and sets the X coordinate of gateTarget 452 to this value. If minBreathHoldTime=0 is True, then check if filtered breath signal−firstPeakYPos>1? If yes, then position gateTarget 452 relative to the end of the inhalation X coordinate using gateTarget.x=firstPeakXPos+(xCoord−firstPeakXPos)*(firstPeakYPos/(firstPeakYPos−filteredBreathSignal)). If in either case, the filtered breath signal−breathHoldFinalYPos>1 is not True or, filtered breath signal−firstPeakYPos>1 is not True, then set gateTarget.x=xCoord (in this case, the user is not actively exhaling since the filtered breath signal is not below the start of the exhalation level, and thus such an extrapolation of the exhalation trend is not possible).

Figure 90:
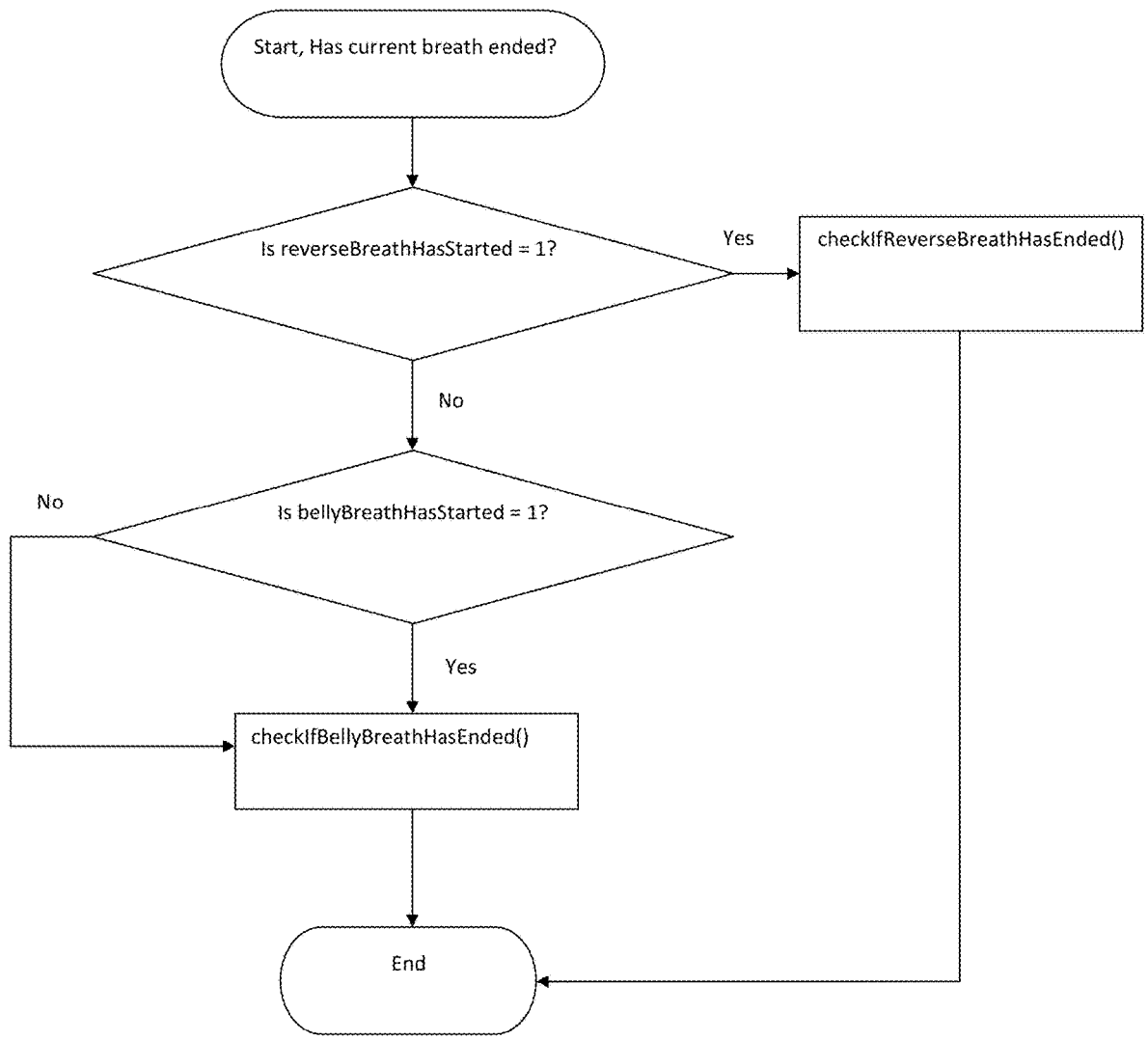
FIG. 90 is a flowchart showing exemplary steps involved in implementing a Has current breath ended process of the present invention.

Returning to FIG. 51, the next step S15 is to check if the current breath has ended, as detailed in the sub process in the flowchart in FIG. 90. Referring to FIG. 90, the first step is to check if reverseBreathHasStarted=1? If yes, then execute process checkIfReverseBreathHasEnded( ) If no, then check if bellyBreathHasStarted=1? If yes, then execute process checkIfBellyBreathHasEnded( )

Figure 92:
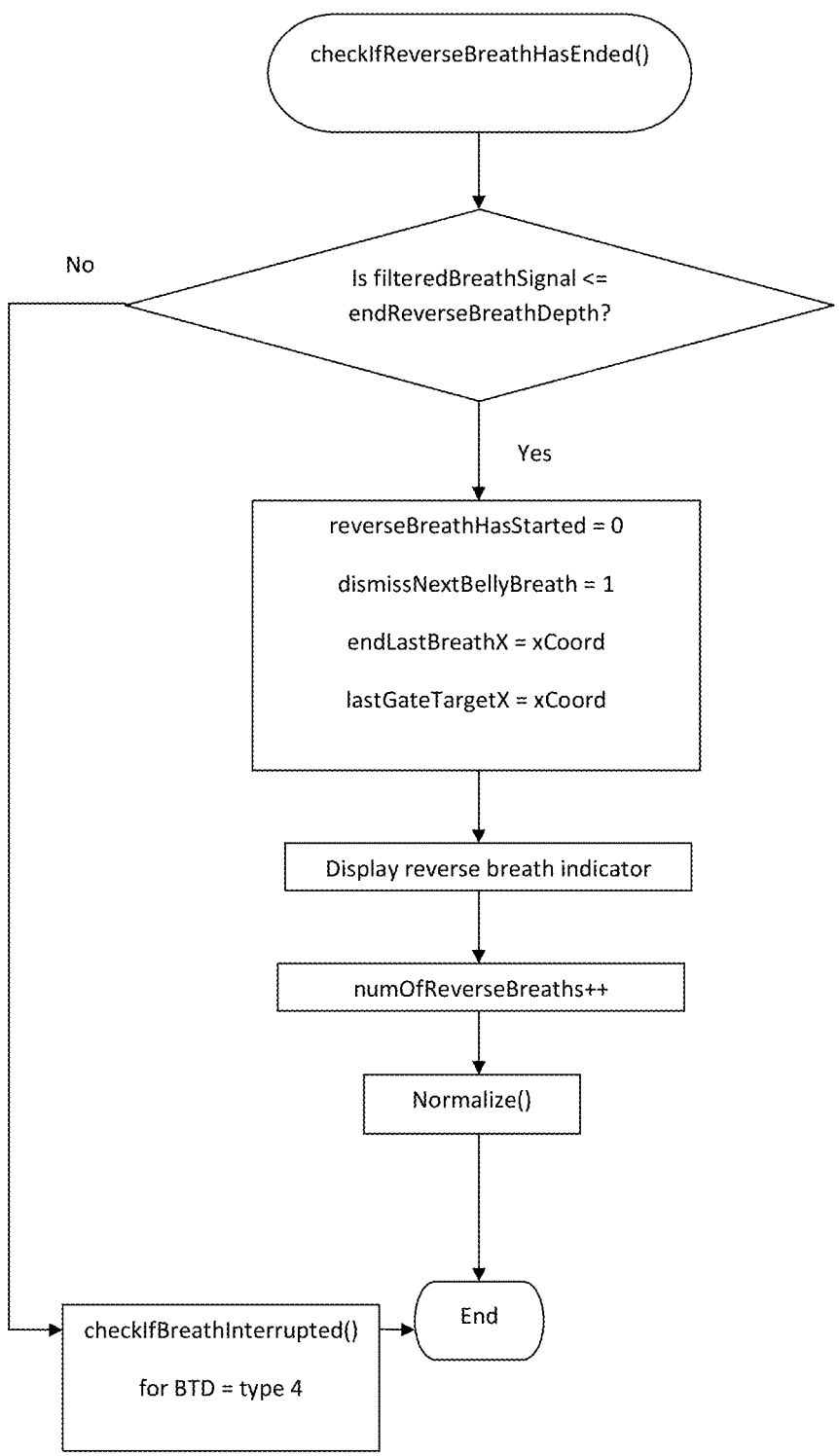
FIG. 92 is a flowchart showing exemplary steps involved in implementing a checkIfReverseBreathHasEnded( ) process of the present invention.

Referring to the flowchart in the FIG. 92, the process for checkIfReverseBreathHasEnded( ) is detailed. The first step is to check if the filtered breath signal<=endReverseBreathDepth (meaning the filtered breath signal has risen above the end of reverse breath threshold line 360 as shown in FIG. 137). If no, then execute process checkIfBreathInterrupted( ) if a type 4 BTD is being used as explained below, then end the process. If yes, then the reverse breath is considered to have completed. Next, set reverseBreathHasStarted=0, dismissNextBellyBreath=1, endLastBreathX=xCoord, lastGateTargetX=xCoord. Next, display a reverse breath indicator 420 against timeline 350 as shown in FIG. 120. Next, increment numOfReverseBreaths and execute the Normalize( ) process for the given type of BTD, and then end the process. Optionally, for BTD's type=1-3, a condition can be added for normalizing such as if signalB>=endBreathThreshold and signalB<=endReverseBreathThreshold? If no, then end the process instead of normalizing. If yes, then execute Normalize( ) The reason for this optional condition is to avoid learning a zeroing offset if signalB is outside the bounds of endBreathThreshold and endReverseBreathThreshold, which could subsequently cause an inaccurate assessment of a user's inhalation level at that same posture.

Figure 91:
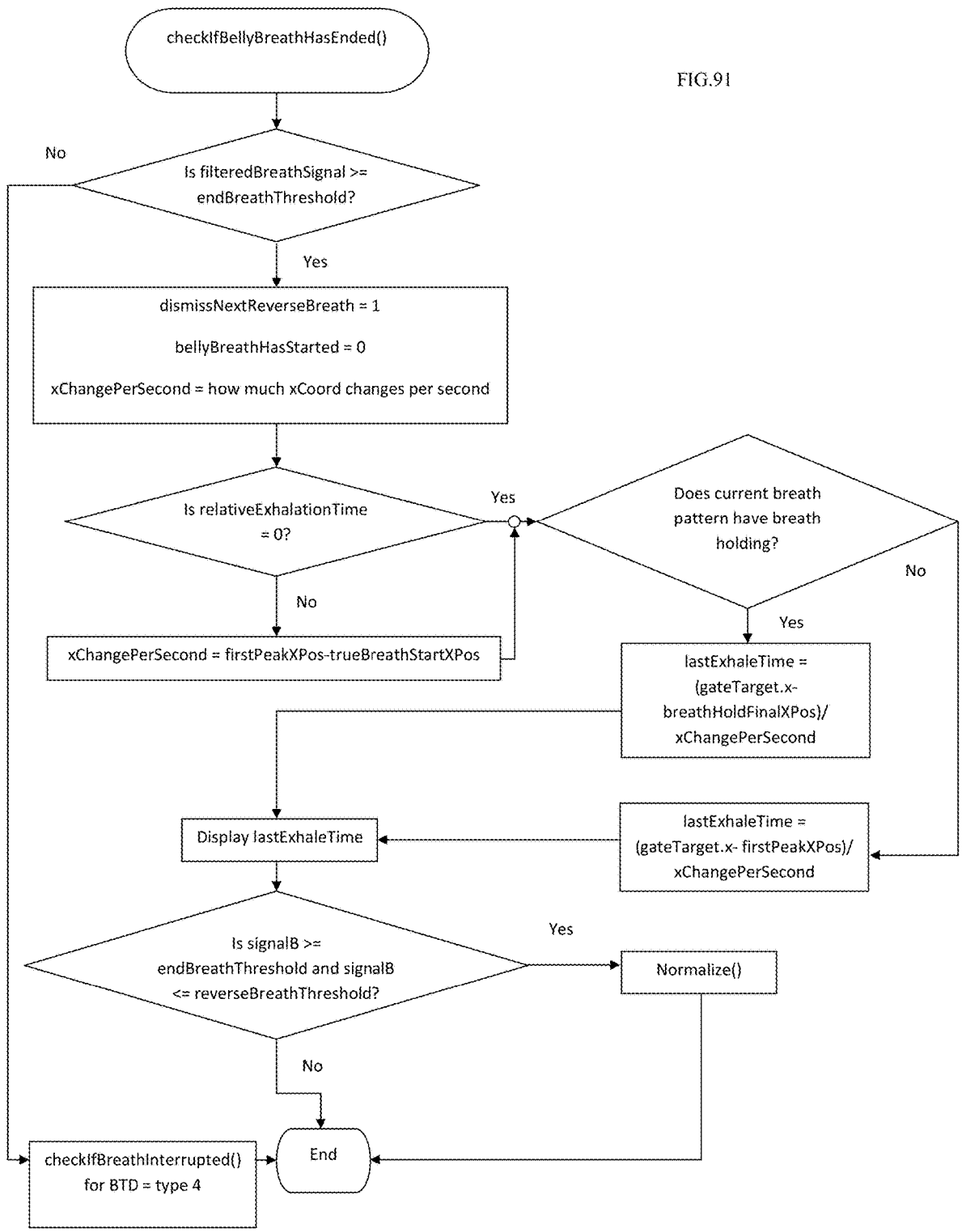
FIG. 91 is a flowchart showing exemplary steps involved in implementing a checkIfBellyBreathHasEnded( ) process of the present invention.

Referring to the flowchart in the FIG. 91, the process for checkIfBellyBreathHasEnded( ) is detailed. The first step is to check if filtered breath signal>=endBreathThreshold? If false, then execute process checkIfBreathInterrupted( ) if a type 4 BTD is being used as explained below, then end the process. If true, then the diaphragmatic breath is considered to have completed, as shown in the example in FIG. 138, where the filtered breath signal is on the verge of crossing end breath threshold line 352. Next, set dismissNextReverseBreath=1, bellyBreathHasStarted=0, xChangePerSecond=how much xCoord changes per second. Next, check if relativeExhalationTime=0? If no, set xChangePerSecond=firstPeakXPos-trueBreathStartXPos. Next, check if the current breath pattern has breath holding? If true, then set lastExhaleTime=(gateTarget.x−breathHoldFinalXPos)/xChangePerSecond. If false, then set lastExhaleTime=(gateTarget.x−firstPeakXPos)/xChangePerSecond. Next, display an exhale time indicator 472 on timeline 350 based on lastExhaleTime, as shown in the example in FIG. 136, which shows how long the user's exhalation was. It should be noted that this exhalation time is the projected time to reach the position of gateTarget 452, not the time when the filtered breath signal crossed end breath threshold line 352. The reason for this is that while end breath threshold line 352 can be positioned at any percentage level, this doesn't mean the exhalation actually ends at this level. It is simply the chosen cutoff level to trigger the end of the breath (and this level is chosen to balance the need to detect an exhalation versus avoiding body motion noise in the system for example). The process assumes the exhalation will continue at the same trend to the fully exhaled line 356. Exhale time indicator 472 can be shown at the last position of gateTarget 452 immediately after the filtered breath signal crosses end of breath threshold 352, with gateTarget 452 then being hidden (FIGS. 138-139). If the exhalation time was within the acceptable range given by parameters minExhalationTime and maxExhalationTime, or minExhalationRelativeTime and maxExhalationRelativeTime, then exhale time indicator 472 is shown in a positive evaluation state (such as a green color) and if not, then it is shown in a negative evaluation state (such as a red color). Next, check if signalB>=endBreathThreshold and signalB<=reverseBreathThreshold? If no, then end the process. If yes, then execute the Normalize( ) process for the given type of BTD. The reason to avoid normalizing if signalB is outside the bounds of endBreathThreshold and endReverseBreathThreshold is to avoid learning a zeroing offset which is beyond these bounds (for BTD types=1-3), which could subsequently cause an inaccurate assessment of a user's inhalation level at that same posture. After completion of a diaphragmatic breath, time between breaths indicator 424 (as discussed in the flowchart in FIG. 81), begins to count the elapsed time from the last gateTarget 452 position on timeline 350, until the start of the next breath. It should be noted that this time, in one scenario, may be negative for a short duration. Referring to FIG. 138, if the filtered breath signal crosses end breath threshold line 352 before the position of gateTarget 452 as shown in this example, then this time between the crossing point and the position of gateTarget 452 is displayed as negative and counting up to 0 on time between breaths indicator 424, since technically this breath hasn't completed yet; It has just fallen below the end of breath threshold line 352, below which the breath level is not being tracked (again because it is assumed this level also represents a noise threshold). The process assumes the filtered breath signal will continue with the same average downward slope until it reaches fully exhaled line 356 and the last horizontal position of gateTarget 452, at which point, time between breaths indicator 424 starts counting time from 0 upwards. This approach also prevents time from being lost on timeline 350, as it accounts for these pockets of time between breaths.

Figure 98:
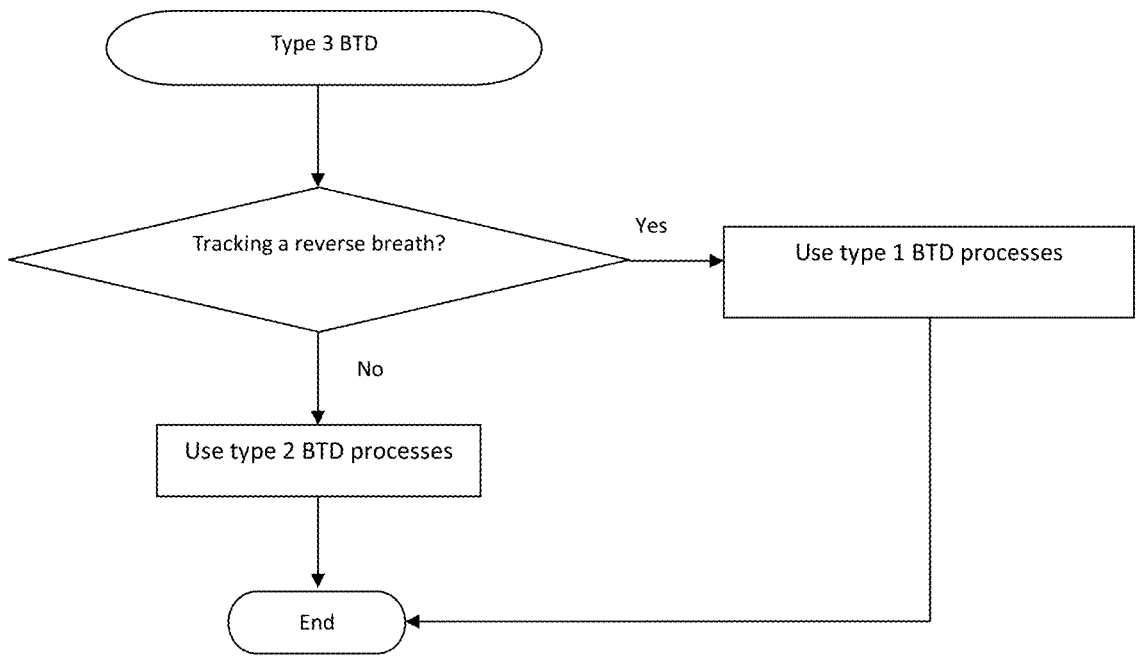
FIG. 98 is a flowchart showing exemplary steps involved in implementing a Type 3 BTD process of the present invention.
Figure 98A:
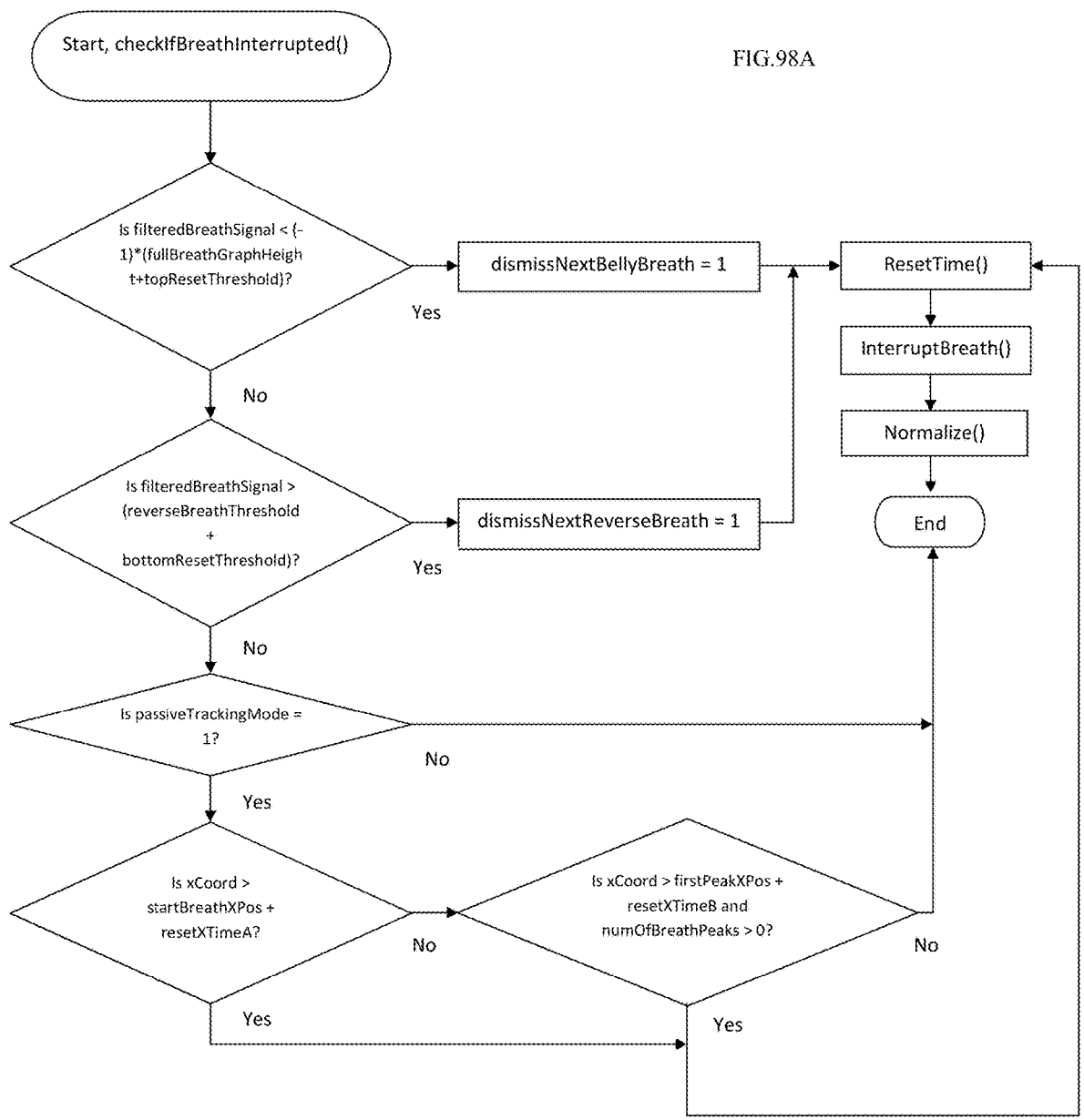
FIG. 98A is a flowchart showing exemplary steps involved in implementing a checkIfBreathInterrupted process of the present invention.

Referring to the flowchart in FIG. 98A, the process for checkIfBreathInterrupted( ) is detailed. As previously discussed, when whichTrackingMode is set to 3 for a BTD type=4, then when certain features in the filtered breath signal are observed, these can be inferred as posture related events rather than due to diaphragmatic breathing, as one strategy for disambiguating the confounded posture and diaphragm signals from one angle sensor. One such feature is if the filtered breath signal exceeds specified bounds above the full breath line 358 (fullBreathGraphHeight value) or below reverse breath threshold line 360 (reverseBreathThreshold value). The idea here is that if the BTD has been properly calibrated, and posture zone coefficients have been appropriately set so that a full deep diaphragmatic breath (without any accompanying posture change) does not significantly exceed the full breath line 358 for any given posture as shown in FIG. 116, then if the filtered breath signal is observed to rise significantly above this point, that can cancel an in-progress diaphragmatic breath, and be inferred as a posture change rather than a breath event. This stems from the observation that the angle range given between uprightPostureAngle and slouchPostureAngle as measured during the calibration process is generally significantly larger than the angle range between an exhaled and inhaled state (at any posture). In the first step in FIG. 98A, check if filteredBreathSignal<(−1)*(fullBreathGraphHeight+topResetThreshold)—where topResetThreshold can be a certain percentage of fullBreathGraphHeight, such as 33%—then set dismissNextBellyBreath=1, execute ResetTime( ), interruptBreath( ), Normalize( ), and then end the process. The reason to set dismissNextBellyBreath=1 here and prevent the immediate next diaphragmatic breath from starting is to address the scenario, for example, where the user is changing their posture from slouched towards upright, causing this breath interruption due to the filtered breath signal exceeding topResetThreshold, but then the user continues to change posture further towards upright, which could be incorrectly interpreted as a start of a new belly breath after the normalization process was called. If filteredBreathSignal is not <(−1)*(fullBreathGraphHeight+topResetThreshold), then similarly check if filteredBreathSignal>(reverseBreathThreshold+bottomResetThreshold). If yes, then this filtered breath feature can be inferred as due to the user significantly altering their posture towards a more slouched position rather than a reverse breath, and dismissNextReverseBreath is set to 1 (for similar reasons as explained above, but to prevent the continued change in posture towards slouched from being interpreted as the start of a new reverse breath), and then execute ResetTime( ) interruptBreath( ) Normalize( ) and then end the process. This top and bottom boundary check also can provide a method for the user to purposefully normalize the filtered breath signal if they notice it is improperly tracking, by intentionally rocking back and forth from slouched to upright or vice versa to cause the filtered breath signal to exceed topResetThreshold or bottomResetThreshold, preferably while in an exhaled state, providing a convenient way to reset or normalize breath tracking without needing to press any buttons on a user interface.

Figure 98B:
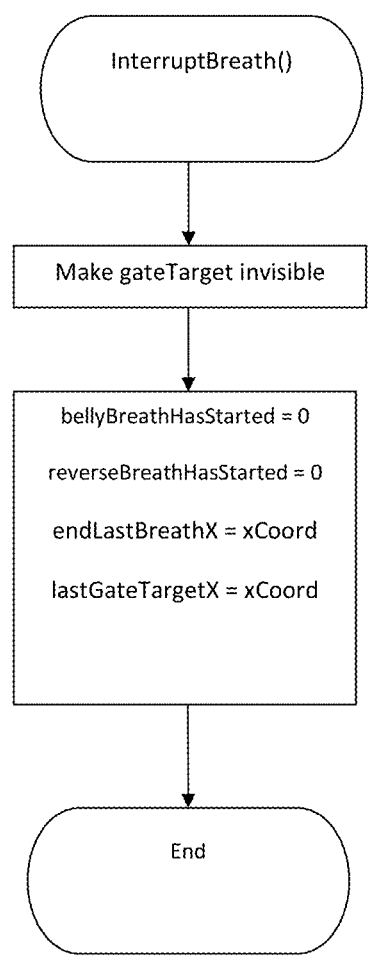
Figure 98C:
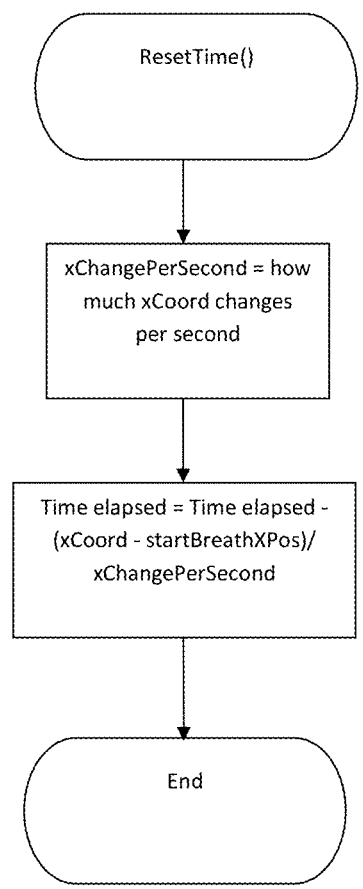

Referring to the flowchart in FIG. 98C, the process for ResetTime( ) is detailed. Generally, this process can be called whenever features are observed in the filtered breath signal after a breath has started, which suggest that these features are due to posture or body movements rather than an actual diaphragmatic breath. The effect is to reset backwards the elapsed time to the moment when the event in question started, essentially discounting the observed data in that interval so as to not distort the calculation of the respiration rate and other considered metrics. In the first step, xChangePerSecond is set to how much xCoord changes per second. Next, Time elapsed is set to Time elapsed−(xCoord−startBreathXPos)/xChangePerSecond, which sets time backwards to when startBreathXPos was set for the start of the breath. Alternately, instead of converting from the change in x coordinates to time, the time corresponding to when startBreathXPos was set could be stored and then elapsed time could be directly reset to this value. Then end this process.

Referring to the flowchart in FIG. 98B, the process for InterruptBreath( ) is detailed. When in the analytical view of the breath training program, then in the first step, gateTarget 452 can be made invisible or hidden. Next, set bellyBreathHasStarted=0, reverseBreathHasStarted=0, endLastBreathX=xCoord, lastGateTargetX=xCoord which cancels any ongoing breath, and the end the process.

Returning to FIG. 98A, the next steps for interrupting a tracked breath in progress apply if the user is in the passive tracking mode (but could optionally be enabled for active training mode if desired). First check if passiveTrackingMode=1? If false, then end the process. If true, then check if xCoord>startBreathXPos+resetXTimeA? If true, then execute ResetTime( ), interruptBreath( ), Normalize( ), and then end the process. The idea here is that since in passive tracking mode the user is not observing the progress of each breath (and thus not potentially manually correcting the filtered breath signal if it is improperly tracking, such as by clicking Normalize button 362 in the active training mode), an additional condition can be added to automatically interrupt and normalize an ongoing breath to improve chances of proper breath tracking. In this case, if a specified interval of time has elapsed since the start of the last breath (as represented here by resetXTimeA in terms of x coordinates), then interrupt and cancel the breath. This attempts to address a scenario such as the user altering their posture by a limited degree from slouched towards upright (not triggering the bounds interruption as explained above), and then maintaining this new posture. As previously explained, a change in currentBellyAngle in a type 4 BTD as computed in FIG. 63A is usually assumed and attributed to be due to diaphragmatic breathing Thus such a moderate change in posture could falsely trigger the start of a diaphragmatic breath as detailed in FIG. 80. And if the user maintains the new posture, this could be further improperly interpreted as the user holding their breath after the start of the breath. Therefore by observing when an interval of time specified by resetXTimeA (in terms of x coordinates here) has elapsed without a breath concluding, the breath can be canceled. This value could correspond to 7 seconds or more for example. The idea is that it is more likely that the user altered their posture rather than having started a breath, and then held their breath for over 7 seconds (or other time) in the passive tracking mode (in the active training mode, this feature for interruption is not enabled by default, since for many breath exercises, the user does in fact hold their breath for extended periods of time). Also, when this period of time given by resetXTimeA transpires without a breath concluding, it can be interpreted in a different way: the user may have taken a chest breath or reverse breath, which was not detected. Then when exhaling, this caused a pulse of expansion near the abdomen, causing the filtered breath signal to rise above start breath threshold line 378, but with no corresponding conclusion to the breath since the exhalation was mistaken as an inhalation phase for starting a new breath, and now with the filtered breath signal possibly lingering indefinitely above start breath threshold line 378. Thus monitoring for when a specified interval of time has elapsed since the start of the last breath (as given by resetXTimeA), provides a method to help screen for possible undetected reverse or chest breaths. In this case, while the reverse or chest breath is not classified as such since it was not explicitly detected, at least it is not classified as a good diaphragmatic breath, and is excluded by resetting the time, interrupting the breath, and normalizing. Next in FIG. 98A, if xCoord>startBreathXPos+resetXTimeA is not true, then check if xCoord>firstPeakXPos+resetXTimeB and numOfBreathPeaks>0? This offers a more narrow condition to interrupt a breath, when detecting the feature in the filtered breath signal of a specified interval of time given by resetXTimeB (in x coordinates) elapsing after a detected first peak in the inhalation phase (generally applying to diaphragmatic breaths). For example, resetXTimeB could be set to a smaller value than resetXTimeA, such as 4 seconds, allowing a breath to be more rapidly canceled once a first peak is detected.

Referring to FIG. 140, a relative end breath checkbox 474 in breath parameters control panel 402 is shown. When not enabled as shown, end breath depth buttons 394 function to set the height of end breath threshold line 352 as an absolute percentage of full breath line 358, set at 15% in the given example.

When relative end breath checkbox 474 is selected as shown in FIG. 141, then the height of end breath threshold line 352 is dynamically set relative to the peak of the inhalation, or firstPeakYPos, where the percentage selected with end breath depth buttons 394 is the percentage height of the inhalation peak where end breath threshold line 352 is positioned. In the example in FIG. 141, end breath threshold line 352 is set lower than in FIG. 140 since the 15% end breath depth setting is relative to the peak shown at approximately 7 seconds, as opposed to 15% of full breath line 358 in FIG. 140. If the user is training with a breath pattern requiring very shallow breaths for example, such as when maxBreathDepth is set at a low value such as 25% of full breath threshold line 358, then it may be preferable to enable relative end breath checkbox 474 and to set end breath threshold line 352 relative to the inhalation peak so as to more reliably detect the end of breaths. This way, the user can experiment and find an optimal end breath threshold level, relative or absolute, for any given breath pattern.

It should be noted that start breath threshold line 378 and end breath threshold line 352 can be independently set, although in most cases, it may be desirable to set end breath threshold line 352 above start breath threshold line 378, so as to maximize the accuracy of detecting the start and end of breaths. For example, if a user is breathing very shallow, it would be preferable to set start breath threshold line 378 at a fairly low percentage, such as 9%, and end breath threshold line 352 a bit higher, such as 11%, as shown in FIGS. 142 and 143. As shown in FIG. 142, before the start of a diaphragmatic breath with the filtered breath signal below start breath threshold line 378, the end breath threshold line 352 can be hidden to avoid visual confusion. Once a diaphragmatic breath has started, then start breath threshold line 378 can in turn be hidden and end breath threshold line 352 made visible, as shown in FIG. 143. After the completion of the diaphragmatic breath, start breath threshold line 378 can again be made visible and end breath threshold line 352 hidden. Also it should be noted that minimum inhalation depth line 436 can only be set above start breath threshold line 378 as shown in FIG. 137, since the threshold level to start a diaphragmatic breath must obviously be lower than a required minimum inhalation depth after a breath has started.

Figure 93:
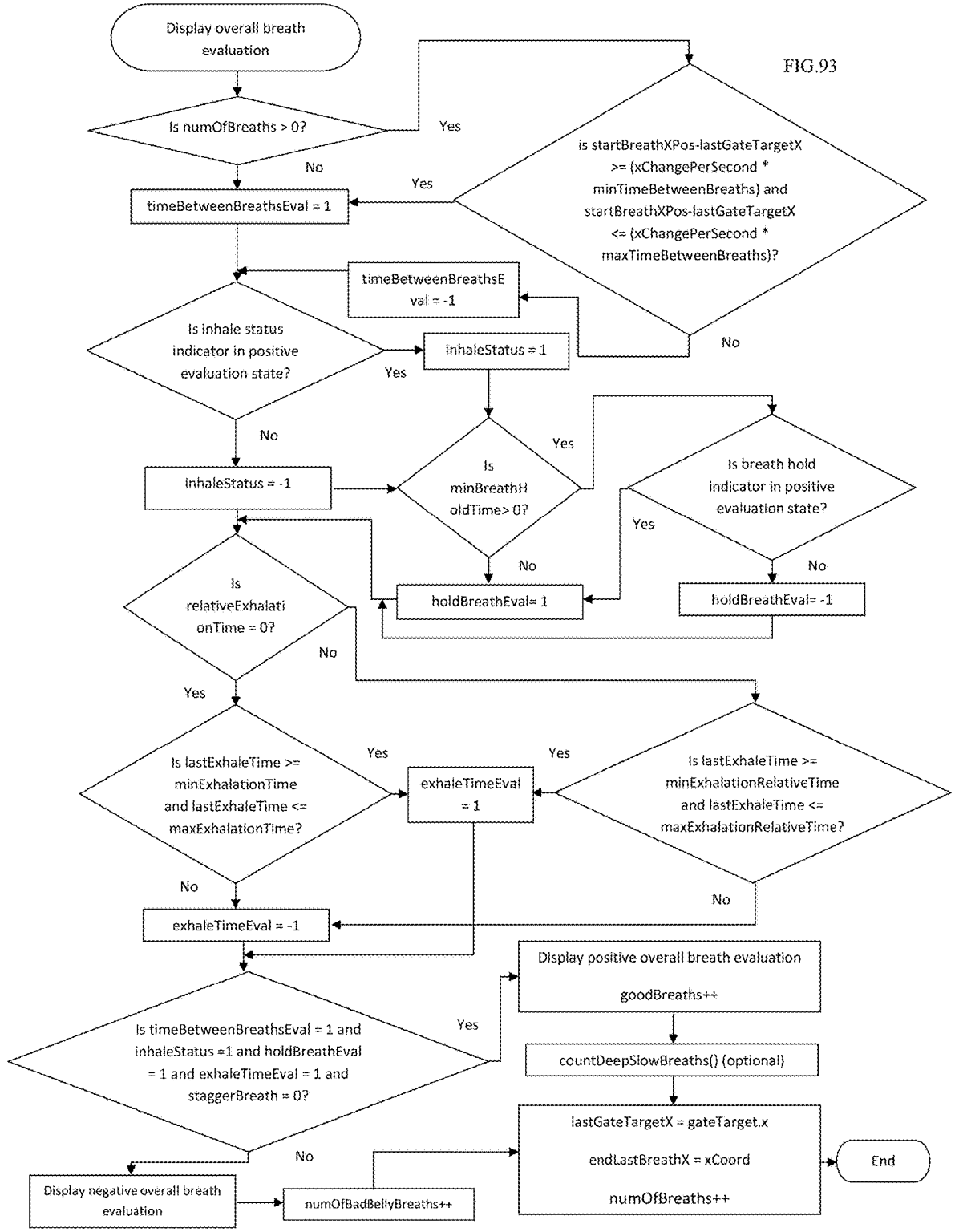
FIG. 93 is a flowchart showing exemplary steps involved in implementing a Display overall breath evaluation process of the present invention.
Figure 98D:
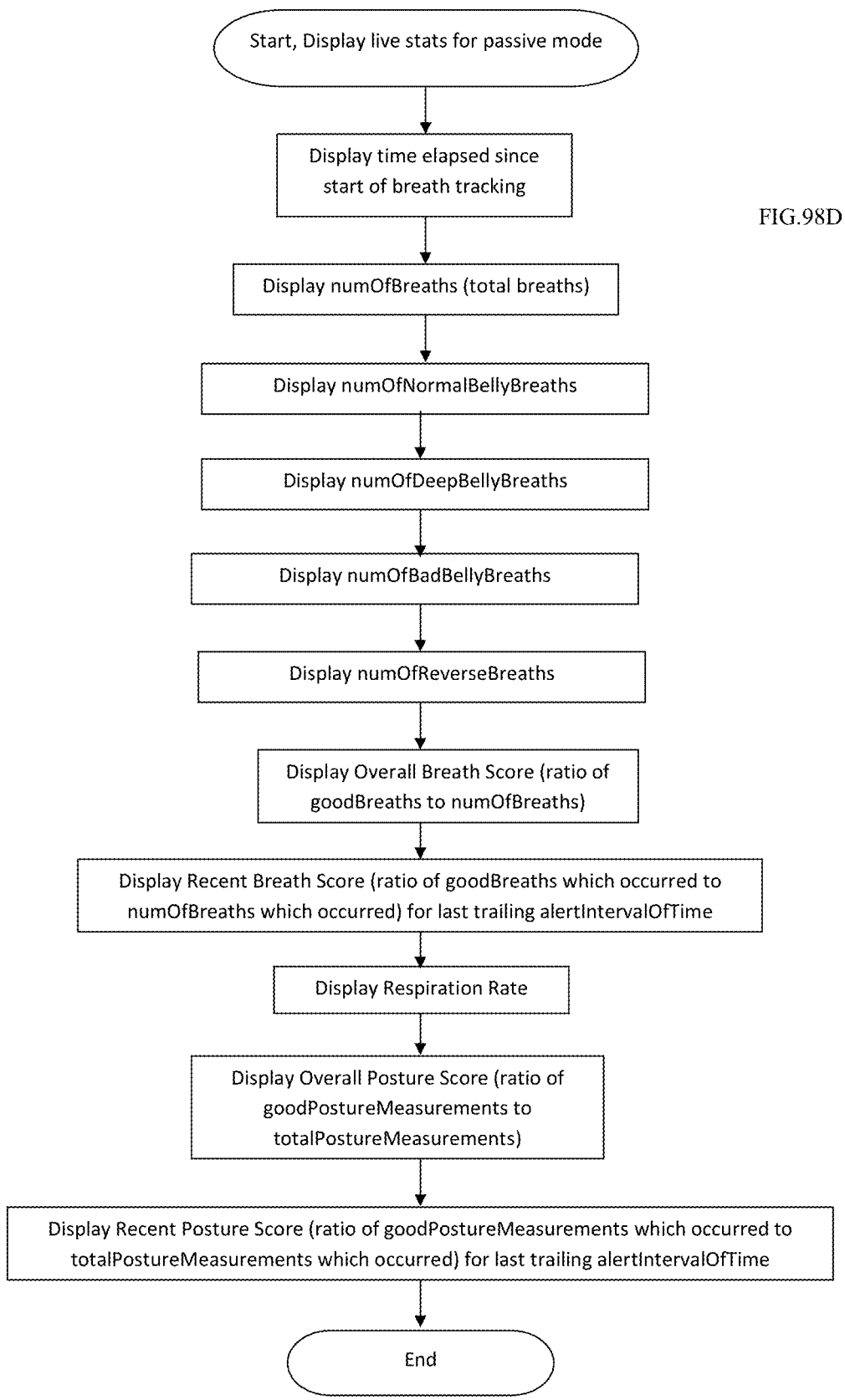
Figure 98E:
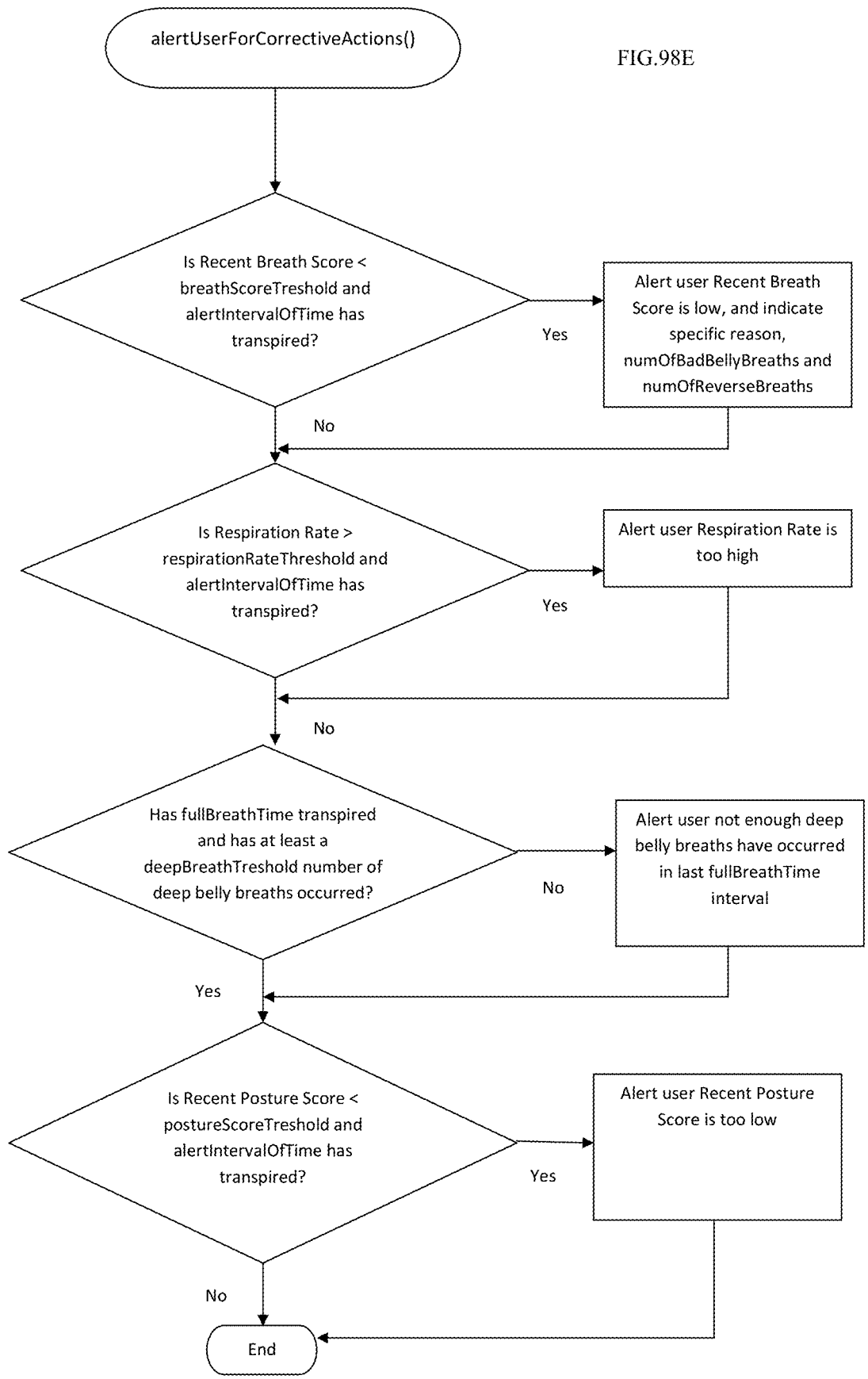
Figure 98F:
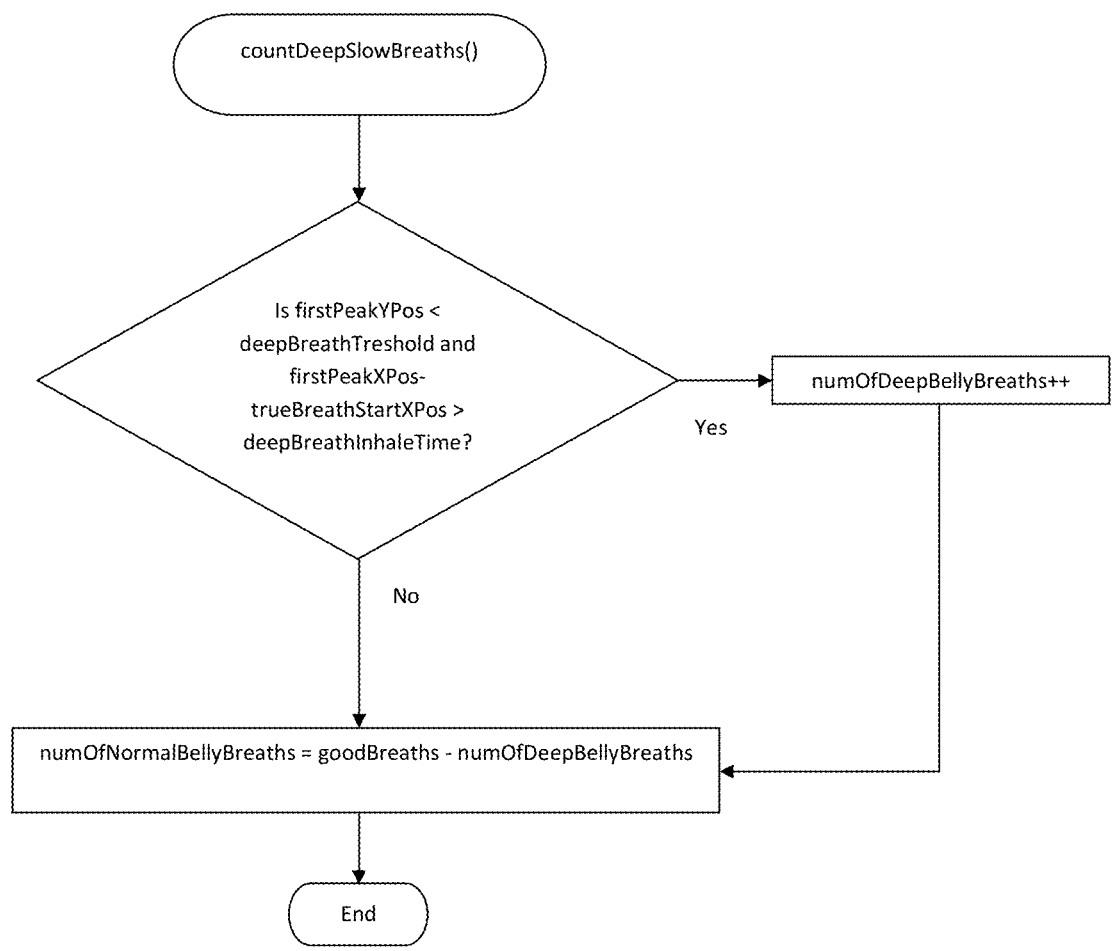

Returning to FIG. 51, after step S15, if a current breath has not completed, then process flow loops back to step S6 to continue tracking and evaluating the ongoing breath, between steps S6 and S15. If a reverse breath has completed, then loop back to step S5 to retrieve the breath parameters for the next training breath or pattern to evaluate against (these may be the same or can change if a breath sequence has been selected as previously discussed). If a diaphragmatic breath has completed, then flow moves on to step S16, where an evaluation is displayed for rating the overall breath quality, as detailed in flowchart in FIG. 93. Referring to FIG. 93, this process checks if the user's breath has complied with all the breath parameters previously discussed. First, check if numOfBreaths>0? If yes, then check if time between breaths indicator 424 is in a positive evaluation state, that is, if startBreathXPos−lastGateTargetX>= (xChangePerSecond*minTimeBetweenBreaths) and startBreathXPos−lastGateTargetX<= (xChangePerSecond*maxTimeBetweenBreaths)? If yes, then set timeBetweenBreathsEval=1, otherwise set timeBetweenBreathsEval=−1. If numOfBreaths=0 (first breath in the training session), then skip this step and set timeBetweenBreathsEval=1 since there is no previous breath to compare this time against. Next, check if inhale status indicator 426 is in positive evaluation state as previously discussed (both the inhalation depth and inhalation time fell within the defined parameter ranges). If yes, then set inhaleStatus=1, otherwise set inhaleStatus=−1. Next, check if minBreathHoldTime>0? If no, then set holdBreathEval=1 and skip this step since there was no breath holding after inhalation in this pattern. If yes, then check if breath hold indicator 468 is in positive evaluation state as previously discussed? If yes, then set holdBreathEval=1, otherwise set holdBreathEval=−1. Next, check if relativeExhalationTime=0? If yes, then check if lastExhaleTime>=minExhalationTime and lastExhaleTime<=maxExhalationTime? If yes, the set exhaleTimeEval=1, otherwise set exhaleTimeEval=−1. If relativeExhalationTime is not equal to 0, then check if lastExhaleTime>=minExhalationRelativeTime and lastExhaleTime<=maxExhalationRelativeTime? If yes, the set exhaleTimeEval=1, otherwise set exhaleTimeEval=−1. Next, for the evaluation result, check if timeBetweenBreathsEval=1 and inhaleStatus=1 and holdBreathEval=1 and exhaleTimeEval=1 and staggerBreath=0? If true, then increment goodBreaths and display a breath evaluation indicator 476 in a positive evaluation state, such as a green checkmark as shown in FIG. 144, placed approximately under the peak of the inhalation for the given breath on timeline 350 so that it is clear to the user which breath this evaluation applies to. Next, optionally, a countDeepSlowBreaths( ) process can be executed to determine if the evaluated breath qualifies as a deep and slow breath (useful in particular in the passive tracking mode when scanning for signs of stressed breathing patterns). Referring to FIG. 98F, the first step in this process is to check if firstPeakYPos<deepBreathTreshold and firstPeakXPos−trueBreathStartXPos>deepBreathInhaleTime? For example, deepBreathTreshold can be set at about the 75% level of the fullBreathGraphHeight, and deepBreathInhaleTime can be set to a value corresponding to at least 1 second, so that the user must have inhaled for at least 1 second and to a depth of at least 75% of maximum capacity (though other combination of values can be used to qualify as a deep and slow breath). If true, then increment numOfDeepBellyBreaths, and set numOfNormalBellyBreaths=goodBreaths−numOfDeepBellyBreaths (useful in passive breath tracking), and then end the process. Returning to FIG. 93, If the overall evaluation check result is false, then display a breath evaluation indicator 476 in a negative evaluation state, such as a red X mark as shown in FIG. 144, and increment numOfBadBellyBreaths. Furthermore, if the breath evaluation is positive, but at any point during the breath the user maintained a posture below upright threshold 416 on breath/posture zone chart 368, then this positive breath evaluation can be further qualified with a negative posture symbol 478 as shown in FIG. 144, where the green checkmark of breath evaluation indicator 476 has a red circle around it indicating the imperfect posture during this time. This can be helpful to the user since breath quality and posture are interrelated as previously discussed, therefore if the posture was not upright throughout the time of a breath, even though all the breath parameters were met, the user can still know that his/her posture could have been improved during this time. Next, set lastGateTargetX=gateTarget.x, endLastBreathX=xCoord, increment numOfBreaths, then end the process. Referring to FIG. 144, it can be seen that any combination of negative evaluations for any breath parameters (as long as there is at least one) can cause an overall negative breath evaluation. For example, for the first breath shown on timeline 350, the inhalation was not satisfactory, as both the inhalation time and depth did not adhere to the parameter ranges, and the exhalation time also was not satisfactory, being 4.9 seconds in this example, when 4.5 seconds was the cut off as shown in the breath parameters control panel 402. Similarly, the 5$^{th}$ breath in this example has an unsatisfactory inhalation, an unsatisfactory time between breaths (after the fourth breath), and also one or more breath staggers, causing a negative overall evaluation. It is also possible to allow for a more lenient evaluation, where for example, it is allowed to not adhere to one of the breath parameter ranges and still receive a positive overall evaluation. As previously discussed, a red color can be used on timeline 350 for the various negative sub evaluations, such as bad inhalation time, or bad breath holding time, and green for positive. This provides the convenience to the user of visually organizing the evaluations, so that in one glance, it is readily clear if the overall evaluation will be negative for a given breath if any red color is visible during that time for example, and what factors are causing the negative evaluation so that the user can know how to adjust his/her breathing to better adhere to the selected breath pattern.

Returning to FIG. 51, after the evaluation in step S16 has been completed and displayed, then the process loops back to step S5 to retrieve the breath parameters for the next training breath or pattern to evaluate against (again these may be the same or can change if a breath sequence has been selected as previously discussed).

Figure 78:
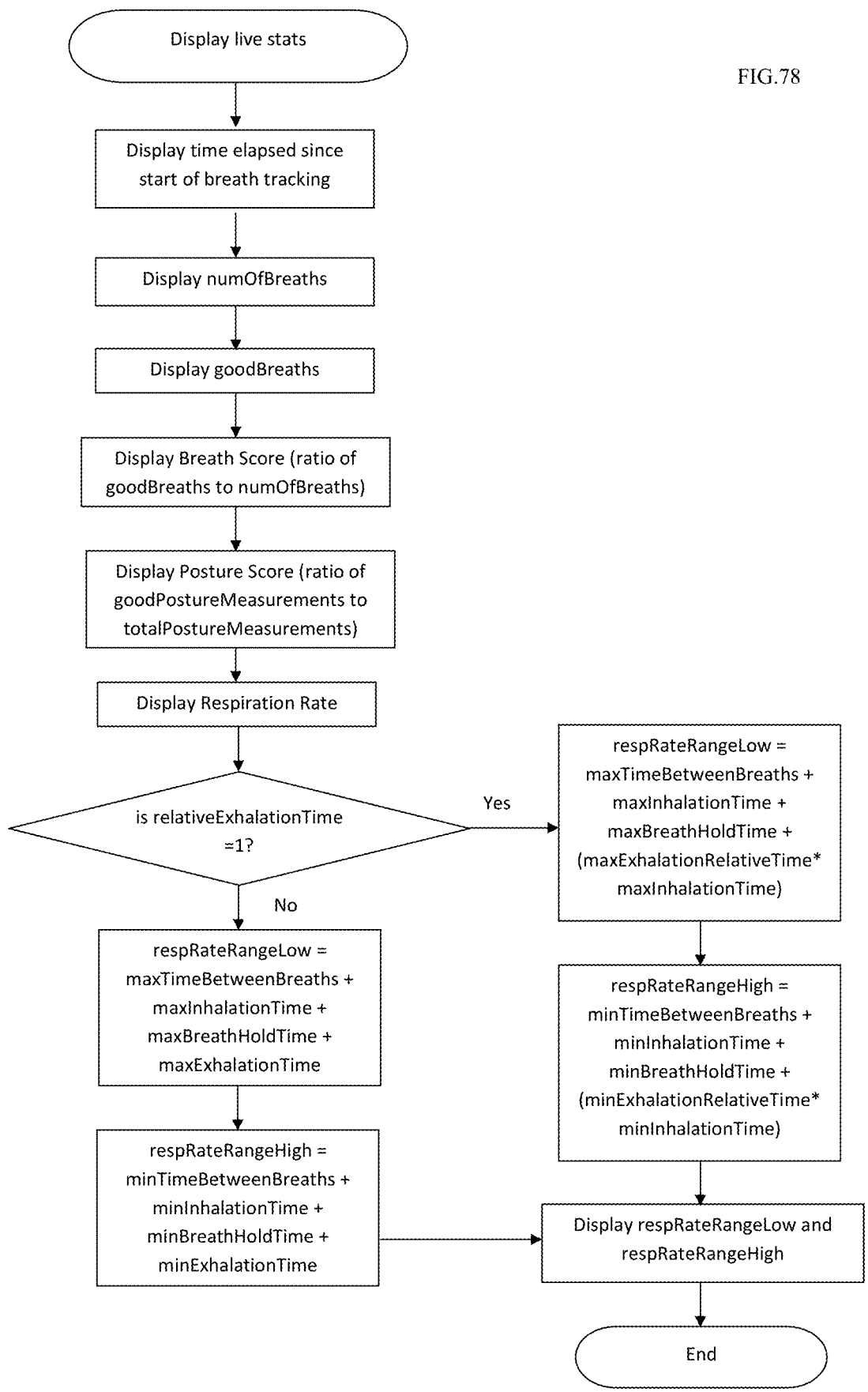
FIG. 78 is a flowchart showing exemplary steps involved in implementing a Display live stats process of the present invention.

Referring to FIG. 51, we know discuss step S10, which is the sub process to display live stats as shown in the flowchart in FIG. 78. Referring to FIG. 78, the first step is to display the time elapsed 480 since start of breath tracking as shown in FIG. 144. Next, display numOfBreaths on a Breaths Taken indicator 482. Next, display goodBreaths on a Correct Breaths indicator 484. Next, display a Breath Score 486 percentage (ratio of goodBreaths to numOfBreaths). Next, display a Posture Score 488 (ratio of goodPostureMeasurements to totalPostureMeasurements). Next, display the current respiration rate on Respiration Rate indicator 490, which is just the total number of breaths (both diaphragmatic and reverse) which have occurred within the last trailing minute of elapsed time on timeline 350 (resetTime( ) can adjust this elapsed time as previously discussed under certain conditions). Next, check if relativeExhalationTime=1? If yes, then set respRateRangeLow=maxTimeBetweenBreaths+maxInhalationTime+maxBreathHoldTime+ (maxExhalationRelativeTime*maxInhalationTime) and respRateRangeHigh=minTimeBetweenBreaths+minInhalationTime+minBreathHoldTime+ (minExhalationRelativeTime*minInhalationTime). If no, then set respRateRangeLow=maxTimeBetweenBreaths+ maxInhalationTime+maxBreathHoldTime+maxExhalationTime and respRateRangeHigh=minTimeBetweenBreaths+ minInhalationTime+minBreathHoldTime+ minExhalationTime. Next, display a Respiration Rate Range indicator 492 using respRateRangeLow and respRateRangeHigh, as shown, for example, in the breath parameters control panel 402 in the lower left, and then end the process. This range gives the theoretical acceptable respiration rate range given the current combination of breath parameters. The primary goal for the user, when training with a selected breath pattern, is to achieve as high a Breath Score 486 as possible over any given training period, and secondarily, to achieve the highest possible Posture Score 488.

Operation for a Type 3 BTD

We now briefly discuss operations for a type 3 BTD, such as in the second embodiment of the present invention shown in FIG. 23, which comprises three sensors including separate angle (or acceleration) sensors—one on the abdomen or chest, and one on the back—and one displacement sensor. A type 3 BTD combines both approaches of type 1 and type 2 BTD's, concurrently using both sets of processes discussed above to compute two independent filtered breath signals as shown in the flowcharts in FIG. 60 and FIG. 61. While there is some redundancy, an advantage of this combination is that under certain circumstances, the filtered breath signal may be more accurate for the type 1 BTD versus the type 2 BTD or vice versa. For example, in reverse breath tracking as shown in FIG. 120, a type 1 BTD may be more accurate in measuring the inward movement of the belly and resulting angle changes, and thus the type 1 processes and filtered breath signal can be selected and utilized in this circumstance as shown in the sub process in flowchart in FIG. 98, whereas for diaphragmatic breath tracking, the type 2 BTD may be more accurate, and those processes used during that time.

Second Embodiment of Breath Training Process (Game Mode)

Figure 52:
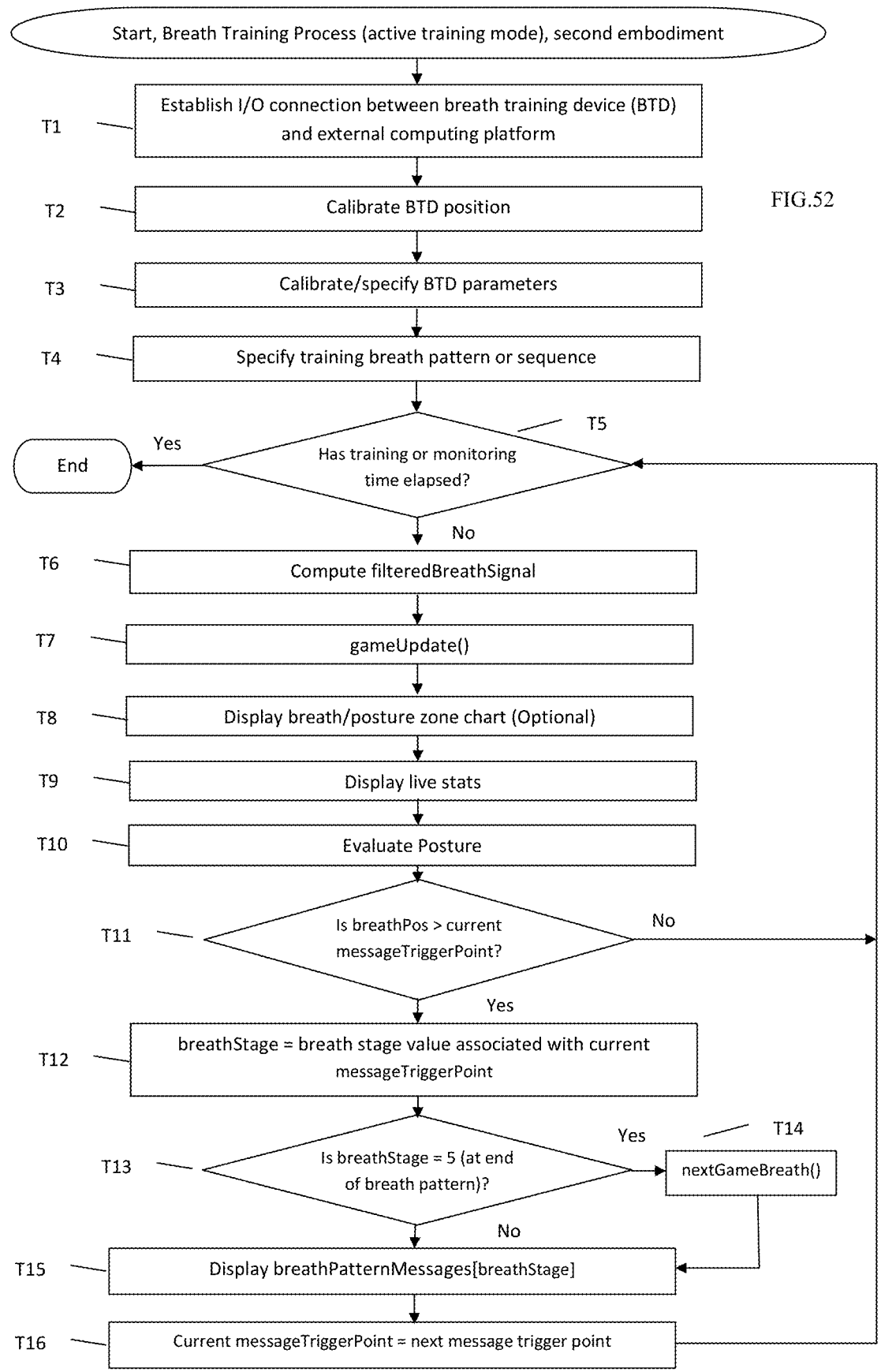
FIG. 52 is a flowchart showing exemplary steps involved in implementing a second embodiment of a breath training process of the present invention.

A second embodiment of a breath training process of the present invention shown in a flowchart in FIG. 52 is stored as a breath training program in memory 166 of external computing platform 162, and executed by CPU 164. This process can also start, for example, when a user presses a button or a software button on a touch screen as part of input devices 172 of external computing platform 162. This process shares many of the steps of the first embodiment in FIG. 51 and is also considered an active training mode, with a principal difference being that instead of graphing and displaying the filtered breath signal on timeline 350 along with the various evaluation indicators previously discussed, a game mode process is used wherein the user guides a breath level game element via the filtered breath signal through inhalation, retention, and exhalation zones derived from the specified breathing parameters, and the user's breathing and adherence to a currently selected breath pattern is evaluated based on how successful the user is in guiding said breath level game element. A view mode button 493 as shown in FIGS. 122 and 145 can toggle between the analytical and game process modes of viewing the filtered breath signal during an active training session. FIG. 145 shows an example of the start of a game session with the initial set of breath patterns created and displayed on display 168, with breath parameters control panel 402 visible. If a game session is started by clicking a breath exercise icon 401 as previously discussed for FIG. 117A, the breath parameters control panel 402 could be hidden for a simplified view of the game as shown in FIG. 145A, with just live stats box 408 visible in addition to the game elements.

Referring to FIG. 52, steps T1 to T4 are the same as steps S1 to S4 previously discussed in the first embodiment of the breath training process. Furthermore, steps T5 and T6 are the same as steps S6 and S7, and steps T8 to T10 are the same as steps S9 to S11.

Figure 94:
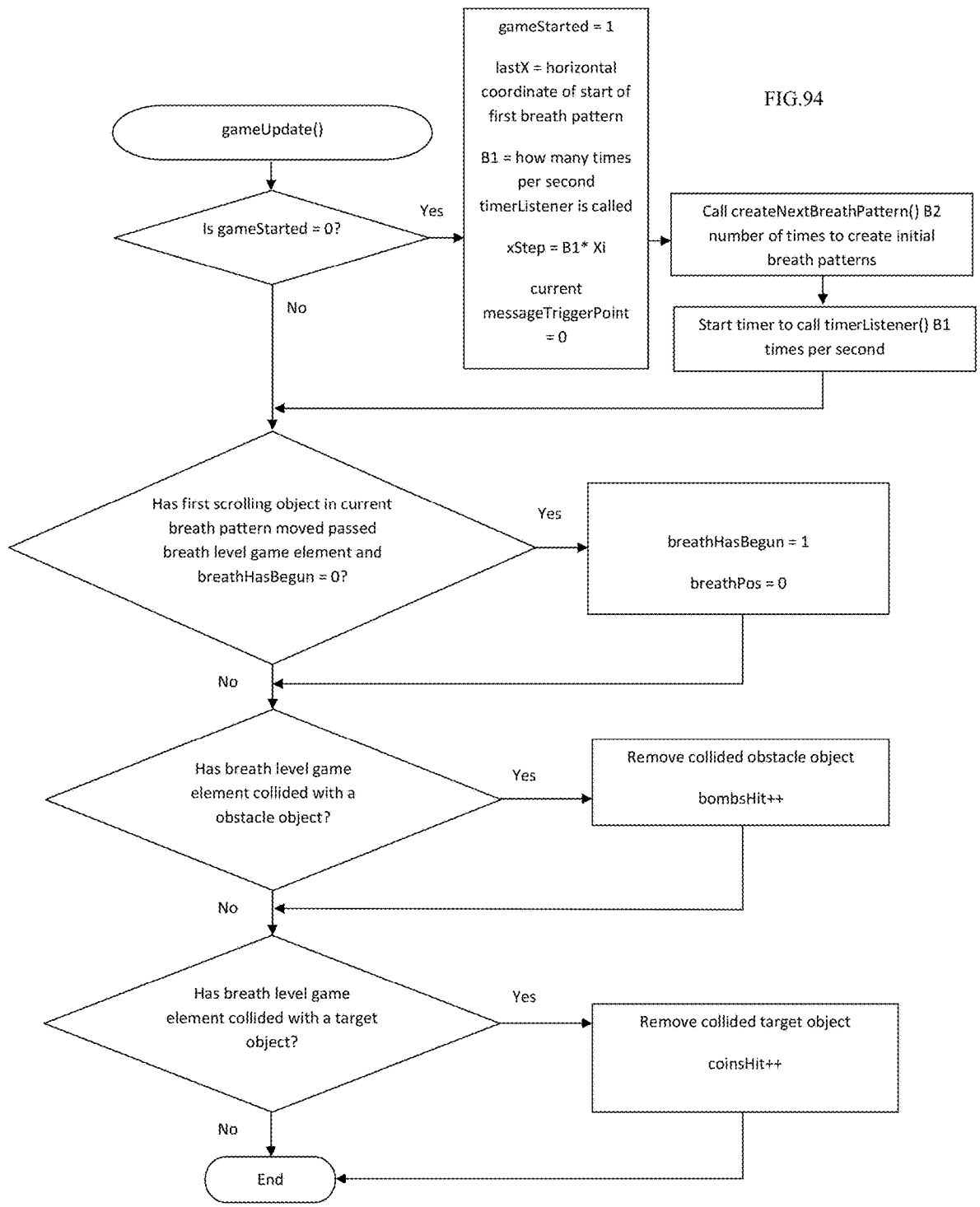
FIG. 94 is a flowchart showing exemplary steps involved in implementing a gameUpdate( ) process of the present invention.

Referring to step T7, the exemplary sub process gameUpdate( ) is detailed in the flowchart in FIG. 94. Referring to FIG. 94, the first step is to check if gameStarted=0? If true, then set gameStarted=1, set lastX=the horizontal coordinate of the start of the first breath pattern, set B1=how many times per second timerListener is called, set xStep=B1*Xi (where Xi is how many pixels along the x axis the obstacle and target objects are moved per increment as later described), set current messageTriggerPoint=0, and then call createNextBreathPattern( ) B2 number of times to create and display the initial set of breath patterns for the game. B2 may be set to 10 for example. In the example shown in FIG. 145, "Sama Vritti Pranayama Level 1" has been selected as the breath pattern from library 400, which has the same repeating pattern for each breath. A breath level game element 494 is shown in FIG. 145. In this example, the vertical position (Y axis) of breath level game element 494 is controlled by the filtered breath signal, such that breath level game element 494 rises during inhalation and falls during exhalation and stays at the same level when breath holding (similar to the previously discussed filtered breath signal when graphed on timeline 350). Breath level game element 494 can be implemented in any type of gaming theme. In the sample shown, a hot air balloon theme is used, along with clouds in the background, with the balloon rising upon inhalation, and falling when exhaling Referring to the example in FIG. 146, a modified 4-7-8 breath pattern has been selected for the game, where the user inhales for 4 seconds, holds breath for 7 seconds, then exhales for 8 seconds, and then holds breath for 3 seconds before the start of the next breath. As shown, each breath can consist of an inhalation zone 496, a retention after inhalation zone 498 (provided the breath pattern has breath holding after inhalation), an exhalation zone 500, and a retention after exhalation zone 502 (provided the breath pattern has breath holding after exhalation). Each zone can consist of target objects 504 and obstacle objects 506. In this example, both target objects 504 and obstacle objects 506 scroll to the left on display 168 at a steady pace, while the horizontal position of breath level game element 494 can remain unchanged with only its vertical position changing during breathing. The goal of the game is for the user to guide breath level game element 494 successfully through the zones by avoiding obstacle objects 506—staying within their bounds—while optionally collecting target objects 504 as they both scroll by. Any type of gaming theme can be used for target objects 504 and obstacle objects 506. In the example shown, gold coins are used for target objects 504, and bombs for obstacle objects 506. Animations can be provided when coins are collected and removed (when breath level game element 494 touches them), and of the bombs exploding if they are touched by breath level game element 494. In FIG. 147, an example shows the user has progressed through approximately the first half of the first 4-7-8 breath (with 9 seconds having elapsed as shown by time elapsed 480), having collected all target objects in inhalation zone 496, and about half in retention after inhalation zone 498. In the example in FIG. 148, the user has exhaled too soon, causing breath level game element 494 to fall and touch several obstacle objects 506 on the lower boundary of retention after inhalation zone 498, causing said obstacle objects to disappear. How the zones bounded by obstacle objects 506 are derived and drawn from the given breath parameters will now be discussed in the exemplary createNextBreathPattern( ) sub process.

Figure 96:
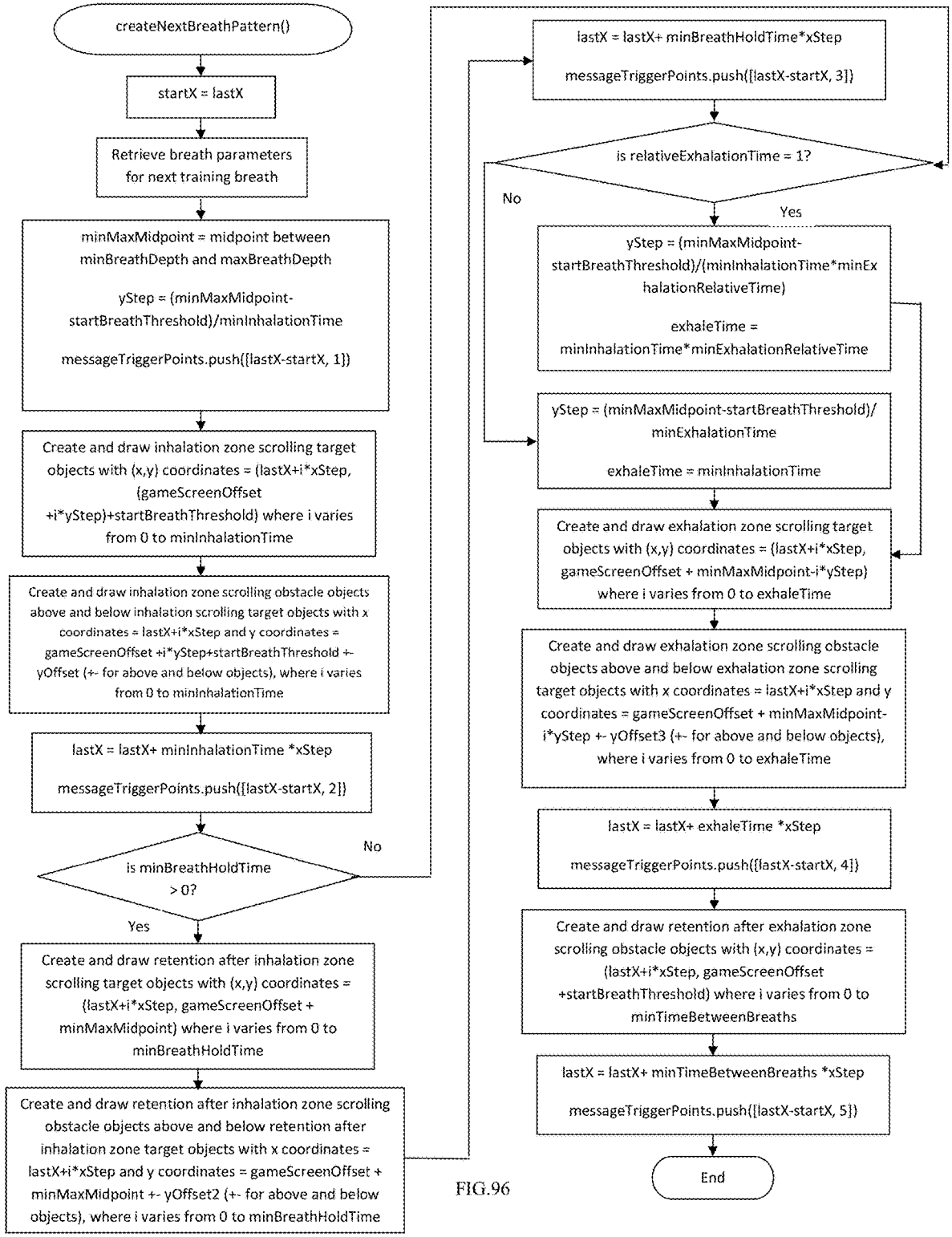
FIG. 96 is a flowchart showing exemplary steps involved in implementing a createNextBreathPattern( ) process of the present invention.

The sub process for createNextBreathPattern( ) is shown in the flowchart in FIG. 96 for drawing target objects 504 and obstacle objects 506 for the next breath pattern. If a breath sequence is not being used, then this sub process draws the same breath pattern each time it is called, offset on display 168 from the previously drawn pattern by a distance corresponding to the timing given by the breath parameters, and by the scroll rate of target objects 504 and obstacle objects 506 as will be discussed. If a breath sequence has been selected, then the breath pattern can vary from breath to breath as previously discussed, and this sub process will draw the next breath pattern in the cycle whenever it is called, and also position it relative to the previous pattern by the proper offset. This sub process may draw breath patterns off screen, such that they will eventually scroll into view on display 168. For example, in FIG. 145, five breath patterns are visible, but if createNextBreathPattern( ) was called 10 times initially at the start of the game session, then five more such patterns will have been drawn to the right off screen, which eventually scroll into view as time elapses during the game session. Referring to FIG. 96, the first step in createNextBreathPattern( ) is to set startX=lastX (which is the horizontal or x coordinate of the first object in the next breath pattern currently being drawn). Next, retrieve breath parameters for the next breath pattern. Next, set minMaxMidpoint=midpoint between minBreathDepth and maxBreathDepth (if maxBreathDepth is not specified, then use full breath line 358 instead), yStep=(minMaxMidpoint−startBreathThreshold)/minInhalationTime, and messageTriggerPoints.push([lastX−startX, 1]). While in the first embodiment of the breath training process, a range of acceptable graphs (generated by the user's breathing) is possible which fall within the ranges set by the breathing parameters, in the second embodiment, it is preferable to select specific coordinates to draw the boundaries and positions of the obstacle and target objects defining the breath patterns. In this example, the midpoint between minBreathDepth and maxBreathDepth has been chosen as an average final depth to which the user will inhale as the end point for defining a target object path from startBreathThreshold to this end point. For example, in FIG. 146, the Y axis position of the first target object 504 at the bottom of inhalation zone 496 corresponds to the position of startBreathThreshold, and the Y axis position of the final target object 504 at the top of the inhalation zone where it transitions to retention after inhalation zone 498 corresponds to minMaxMidpoint, with the path connecting them being a straight line for example. It should be noted that many other target object paths within the bounds of the inhalation zone (bounded by the obstacle objects 506) are possible within the scope of the present invention. In the next step in FIG. 96, this target object path can be drawn with the following exemplary steps: Create and draw inhalation zone scrolling target objects with (x,y) coordinates=(lastX+i*xStep, (gameScreenOffset+i*yStep)+startBreathThreshold) where i varies from 0 to minInhalationTime. xStep is set in the gameUpdate( ) process as previously discussed, and represents the distance in pixels the target and obstacle objects 504 and 506 scroll each second along the X axis. For example, xStep could be set to 40. The index i varies from 0 to minInhalationTime. For example, minInhalationTime is set to 4 in the example in FIG. 146, therefore if xStep is set to 40, then the final target object's X coordinate would be 4*40=160+lastX in this example. The index i can vary in smaller increments than 1 for creating a higher density of target and obstacle objects. For example, it can increase by 0.5. By setting yStep=(minMaxMidpoint−startBreathThreshold)/minInhalationTime, this has the effect that when i reaches minInhalationTime, then i*yStep is equal to minMaxMidpoint−startBreathThreshold, and adding startBreathThreshold to this value as above then produces gameScreenOffset+minMaxMidpoint as the Y coordinate for the last target object 504 in the target object path before it transitions to retention after inhalation zone 498. In the next step in FIG. 96, the obstacle objects are drawn above and below the target object path to create the bounds of inhalation zone 496 within which the user is required to maintain breath level game element 494 in order to adhere to the current breath pattern. These obstacle object paths can be drawn with the following steps: Create and draw inhalation zone scrolling obstacle objects above and below inhalation scrolling target objects with x coordinates=lastX+i*xStep and y coordinates=gameScreenOffset+i*yStep+startBreathThreshold+−yOffset (+− for above and below objects), where i varies from 0 to minInhalationTime. It can be seen that the path of the obstacle objects is the same as the target objects defined above, but offset above and below the target object path by yOffset, which can be a wide range of values within the scope of the present invention. For example, the smaller this offset is, the narrower the zone bounds are, making it more difficult to stay within the zone, whereas a larger value makes it more lenient. This offset could be set to 160 for example. In the next step in FIG. 96, set lastX=lastX+minInhalationTime*xStep, and messageTriggerPoints.push([lastX−startX, 2]). This has the effect of setting lastX to the X coordinate value of the final target object 504 in inhalation zone 496, and then associating this value minus startX, with a second messageTriggerPoint (the first messageTriggerPoint was associated above with the relative start coordinate of the breath pattern, being 0).

In the next step, if minBreathHoldTime>0, then the current breath pattern has breath holding after inhalation, and retention after inhalation zone 498 is now drawn with the following steps (otherwise skip to drawing exhalation zone 500): Create and draw retention after inhalation zone scrolling target objects with (x,y) coordinates=(lastX+i*xStep, gameScreenOffset+minMaxMidpoint) where i varies from 0 to minBreathHoldTime. This defines the target object path for retention after inhalation zone 498, using the constant minMaxMidpoint for the Y coordinates of the target objects 504, as shown in the example in FIG. 146, although other coordinates are possible within the scope of the present invention. Similarly (as discussed for inhalation zone 496 with the yOffset), obstacle objects for retention after inhalation zone 498 can be drawn with the following steps: Create and draw retention after inhalation zone scrolling obstacle objects above and below retention after inhalation zone target objects with x coordinates=lastX+i*xStep and y coordinates=gameScreenOffset+minMaxMidpoint+−yOffset2 (+− for above and below objects), where i varies from 0 to minBreathHoldTime. Next, set lastX=lastX+minBreathHoldTime*xStep and messageTriggerPoints.push([lastX−startX, 3]). This has the effect of setting lastX to the X coordinate value of the final target object 504 in retention after inhalation zone 498, and then associating this value minus startX, with a third messageTriggerPoint. In the next section in FIG. 96, exhalation zone 500 is drawn. The next step is to check if relativeExhalationTime=1? If yes, then set yStep=(minMaxMidpoint−startBreathThreshold)/(minInhalationTime*minExhalationRelativeTime) and exhaleTime=minInhalationTime*minExhalationRelativeTime. If no, then set yStep=(minMaxMidpoint-startBreathThreshold)/minExhalationTime and exhaleTime=minInhalationTime. This sets yStep and exhaleTime accordingly based on whether or not relative exhalation time is being utilized, as previously discussed. Next, exhalation zone 500 can be drawn with the following steps: Create and draw exhalation zone scrolling target objects with (x,y) coordinates=(lastX+i*xStep, gameScreenOffset+minMaxMidpoint−i*yStep) where i varies from 0 to exhaleTime. This has the effect of defining the target object path in exhalation zone 500 from the final previous target object in the previous zone (at Y level minMaxMidpoint) decreasing down to the startBreathThreshold, as shown in the example in FIG. 146. Next, set lastX=lastX+exhaleTime*xStep and messageTriggerPoints.push([lastX−startX, 4]), which has the effect of setting lastX to the X coordinate value of the final target object 504 in exhalation zone 500, and then associating this value minus startX, with a fourth messageTriggerPoint. In the next step in FIG. 96, retention after exhalation zone 502 is drawn (provided minTimeBetweenBreaths is greater than 0). This zone can be drawn with the following steps: Create and draw retention after exhalation zone scrolling obstacle objects with (x,y) coordinates=(lastX+i*xStep, gameScreenOffset+startBreathThreshold) where i varies from 0 to minTimeBetweenBreaths (in this particular example, just the obstacle objects are drawn, although target objects could be added as previously discussed). Retention after exhalation zone 502 defines a horizontal line after exhalation zone 500 as shown in the example in FIG. 146 below which the user is required to maintain breath level game level 494 prior to the start of the next breath pattern.

Figure 95:
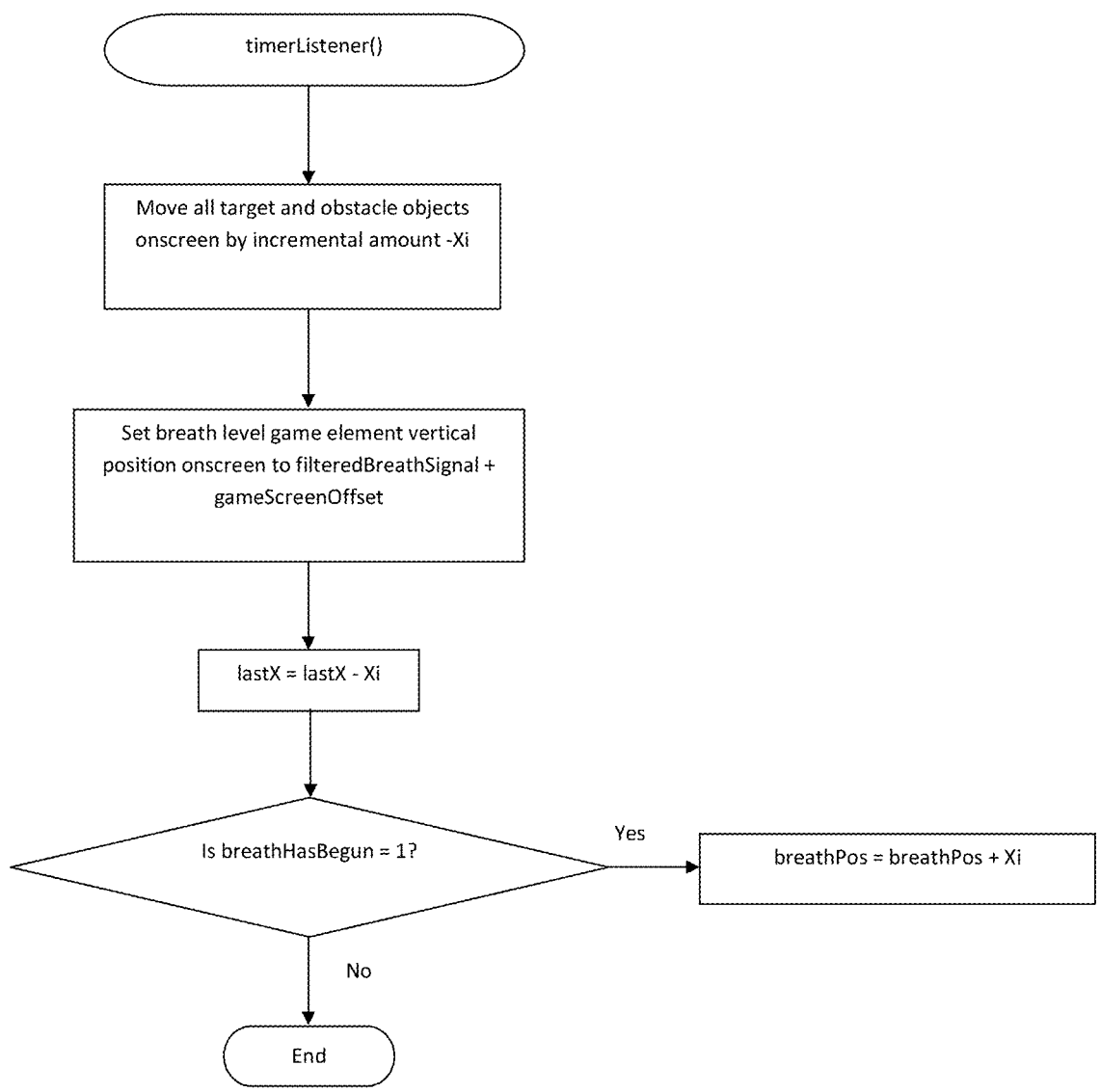
FIG. 95 is a flowchart showing exemplary steps involved in implementing a timerListener( ) process of the present invention.

Returning to the flowchart in FIG. 94, the next exemplary step is to start a timer which calls a timerListener( ) sub process B1 times per second. This process is detailed in the flowchart in FIG. 95 and is responsible for updating the positions of target and obstacle objects 504 and 506, breath level game element 494, other real time coordinates. Referring to FIG. 95, the first step is to move all target and obstacle objects onscreen by incremental amount −Xi. This can be along the X axis for example, and Xi could be set to 2 for example so that scrolling is perceived as smooth. For example, if B1 is set to 20, and Xi is set to 2, then all target and obstacle objects 504 and 506 will move 40 pixels to the left each second (and thus xStep will be set to 40 in this example). In the next step, set the Y axis of breath level game element 494 onscreen to filteredBreathSignal+gameScreenOffset, so that its position corresponds to the depth of the user's inhalation or exhalation. Next, set lastX=lastX−Xi. This is needed since the process createNextBreathPattern( ), as shown in the flowchart in FIG. 96, uses lastX as the starting reference point for drawing the next target and obstacle objects 504 and 506 relative to the previous one, and since these objects are scrolling to the left continuously, the coordinate for a next object to be drawn should be updated. Next, if breathHasBegun=1, then set breathPos=breathPos+Xi. breathPos provides a real time relative coordinate of how far into the current breath pattern the user is located.

Returning to FIG. 94, the next step is to check if the first scrolling object (whether target or obstacle) in current breath pattern has moved passed breath level game element 494, and breathHasBegun=0? If yes, then set breathHasBegun=1 and breathPos=0. Next, check if breath level game element 494 has collided with an obstacle object 506? If yes, then remove that collided obstacle object 506 off display 168, and increment bombsHit. Next, check if breath level game element 494 has collided with a target object 504? If yes, then remove that collided target object 504 off display 168, and increment coinsHit.

Figure 97:
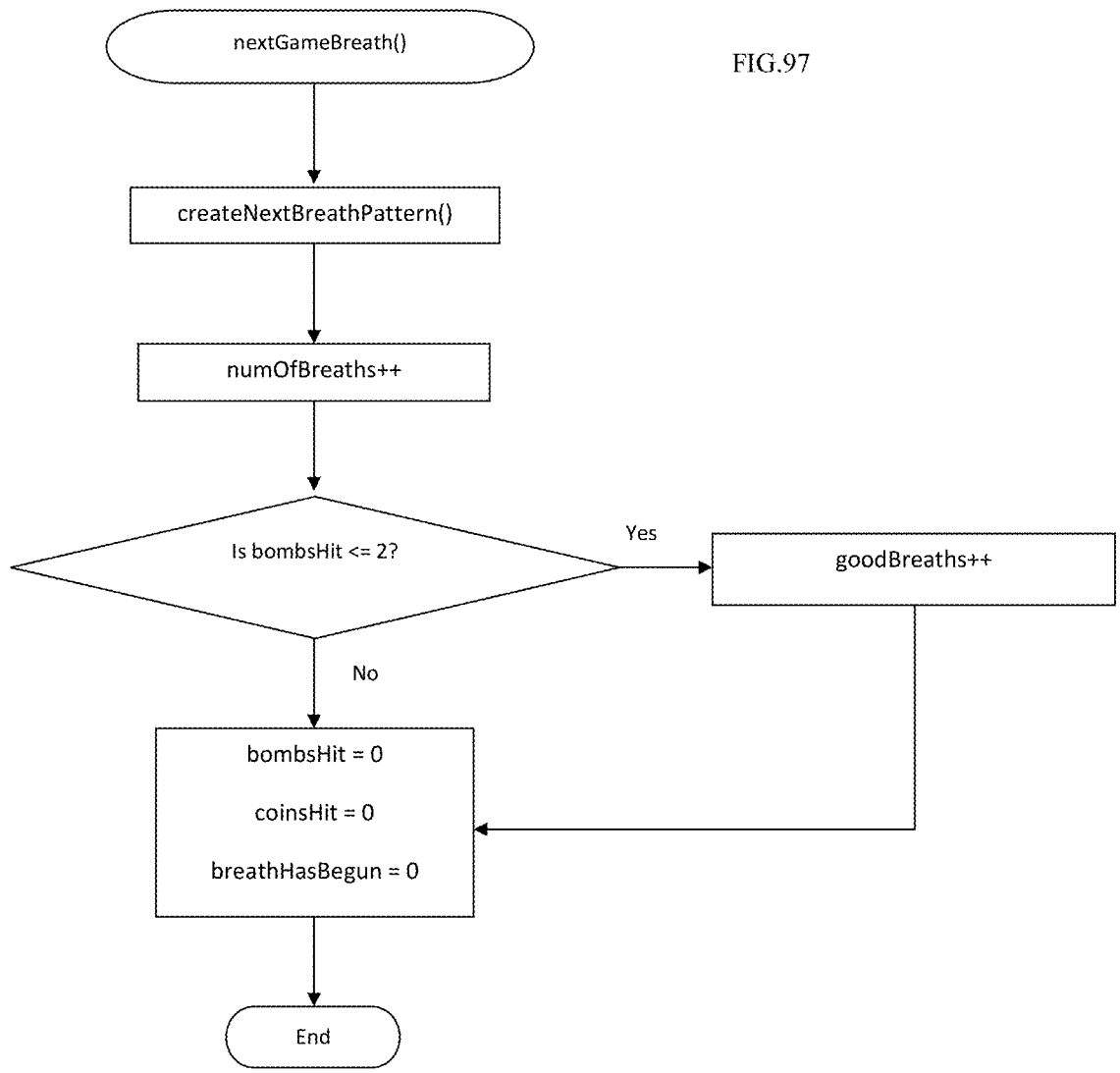
FIG. 97 is a flowchart showing exemplary steps involved in implementing a nextGameBreath( ) process of the present invention.

Returning to FIG. 52, next, steps T8 to T10 are executed, with these sub processes previously discussed. Next, in step T11, check if breathPos>current messageTriggerPoint? The array messageTriggerPoint contains a sequence of arrays, each with two elements (as an example implementation). The first element is a coordinate of a message trigger point, and the second element is the breath stage or phase associated with that message trigger point. The current messageTriggerPoint is set to the coordinate of the next message trigger point in array messageTriggerPoint. When breathPos>current messageTriggerPoint, then breath level game level 494 has passed this next message trigger point, which can trigger a message to appear in message box 406, giving the user tips for that breath or a stage within a breath. For example, in FIG. 149, the game has started and breathPos has passed the first current messageTriggerPoint, which by default is set to 0 (the relative coordinate of the start of the first breath). Returning to FIG. 52, this causes the next step T12 to execute, which is setting breathStage=breath stage value associated with current messageTriggerPoint in the 2 element arrays, which is a 1 for the start of a breath, 2 after inhalation is complete, 3 after retention after inhalation is complete (if that is part of the current breath pattern), 4 after exhalation is complete, and 5 after retention after exhalation is complete. Next, check if breathStage=5 (at end of breath pattern)? If it is not, then display breathPatternMessages[breathStage] in step T15, with breathPatternMessages set for each breath (containing a list of possible messages for this breath indexed by the breath phase or stage). Returning to FIG. 149, the first message displayed says "Light Breath", instructing the user that the first breath in the chosen breath sequence (Prana Breath Sequence 3: Staircase 1) is a light breath in terms of depth. In FIG. 150, the user has progressed to the next breath in the sequence, with breathPos surpassing the next message trigger point, triggering the message "Medium Breath" to appear in message box 406 (both of these messages were for the start of a breath). Returning to FIG. 52, in the next step T16, the current messageTriggerPoint is set to the next message trigger point in array messageTriggerPoint, and the process loops back to step T5. If breathPos is not greater than the current messageTriggerPoint, then the process also loops back to step T5 without displaying any messages. If the breathStage=5 (at end of breath pattern), then the process calls nextGameBreath( ) in step T14 before proceeding to step T15. Referring to FIG. 97 which details the sub process nextGameBreath( ) the first step is to call createNextBreathPattern( ) to create the next breath pattern since the end of the previous breath has been reached. Then numOfBreaths is incremented. Next, check if bombsHit<=2? If yes, then increment goodBreaths (which affects Breath Score 486 as previously discussed). In this example, if 2 or fewer bombs (obstacle objects 506) were hit by breath level game element 494 throughout all zones for that breath, then that is considered a satisfactory breath for the game score. Fewer or more obstacle objects 506 could be allowed to be hit to make scoring more stringent or lenient, within the scope of the present invention. Next, set bombsHit=0, coinsHit=0, breathHasBegun=0 for the next breath and then end the process.

In FIGS. 151-156, a breath sequence has been selected called "Yoga: Anulom Vilom Pranayama", providing an example of message trigger points within a breath. In this breath sequence, while the breath patterns appear the same for each breath, the user is instructed to breath with alternating nostrils, causing the messages to alternate for each breath. In FIG. 151, the user is told "Inhale Left Nostril". In FIG. 152, the user is told "Hold Breath". In FIG. 153, the user is told "Exhale Right Nostril". Then in the next breath in FIG. 154 (different messages from previous breath), the user is told "Inhale Right Nostril". In FIG. 155, the user is told "Hold Breath". And in FIG. 156, the user is told "Exhale Left Nostril".

FIG. 157 provides an example of a sequence which has a combination of many breath patterns from Library 400, such as Sama Vritti Pranayama, 4-7-8, Lamaze, and Tai Chi, displayed according to the second embodiment of the breath training process as in FIG. 52.

FIGS. 158-159 show an alternate embodiment of a game session where target objects 504 are organized into columns to make it easier for the user to collect them using breath level game element 494. Instead of a single line of target objects (i.e., one target object in each horizontal space increment) outlining the breath pattern as previously shown in FIG. 146, a column of a multiplicity of target objects can be provided outlining the breath pattern shape. If the user controls breath level game element 494 to touch any target object 494 within a column, this can cause all target objects in that column to be cleared and collected, as shown in FIG. 159 where several columns have been cleared. This makes the game more forgiving where the user does not need to be as precise with their breathing, and can more approximately follow the outline of the breathing pattern. Also in this embodiment, obstacle objects 506 can be eliminated to make the game even easier, so the user is not penalized for breathing out of the bounds of the breath pattern.

Additionally as shown in FIG. 159, an enforce good posture option 505 can be provided in the user interface. When this option is selected, the game will not start until the user is sitting upright, as confirmed by game posture indicator 507, thus tying a requirement of good posture into the breathing game. Many ways of enforcing good posture within a game are possible. In this embodiment, if the user slouches at any point during the game, the scrolling of the game can stop, thus preventing the user from further advancing in the breath pattern until they correct their posture. As shown in FIGS. 158-159, enforce good posture option 505 is selected, and game posture indicator 507 shows an upright posture, thus enabling the shown horizontal scrolling to have taken place.

It should be noted that this second embodiment of the breath training process is not limited to side scrolling, but could equivalently be implemented with vertical scrolling of target and obstacle objects, with the breath level game element, for example, moving sideways with inhalation and exhalation, within the scope of the present invention. Furthermore, this embodiment is not limited to a 2D implementation. For example, breath level game element and its passage through inhalation, retention, and exhalation zones could equivalently be implemented in 3D, where for example, breath level game element rises upwards in the 3D world when inhaling, and falls in the 3D world when exhaling, and instead of scrolling, the breath level game element could move forward in the 3D world with the passage of time, with inhalation, retention, and exhalation zones shown in perspective and moving past the user in perspective.

Passive Tracking Versus Active Training Modes

The processes as discussed in FIGS. 51-52 provide an active training mode wherein the user can select a breath exercise to train against, and then train in either an analytical or game view with a real time evaluation and score for each breath. By consciously altering and controlling breath as previously discussed, the user can induce a physiological response such as lowering heart rate, blood pressure, and activating the parasympathetic nervous system, as well as learning and becoming more efficient with a particular pattern of respiration. The user may train for any desired time span, although a physiological response and benefit, such as lowering heart rate or signs of stress, may occur within just several minutes of use. Active training mode does require the conscious attention and participation of the user.

Figure 52A:
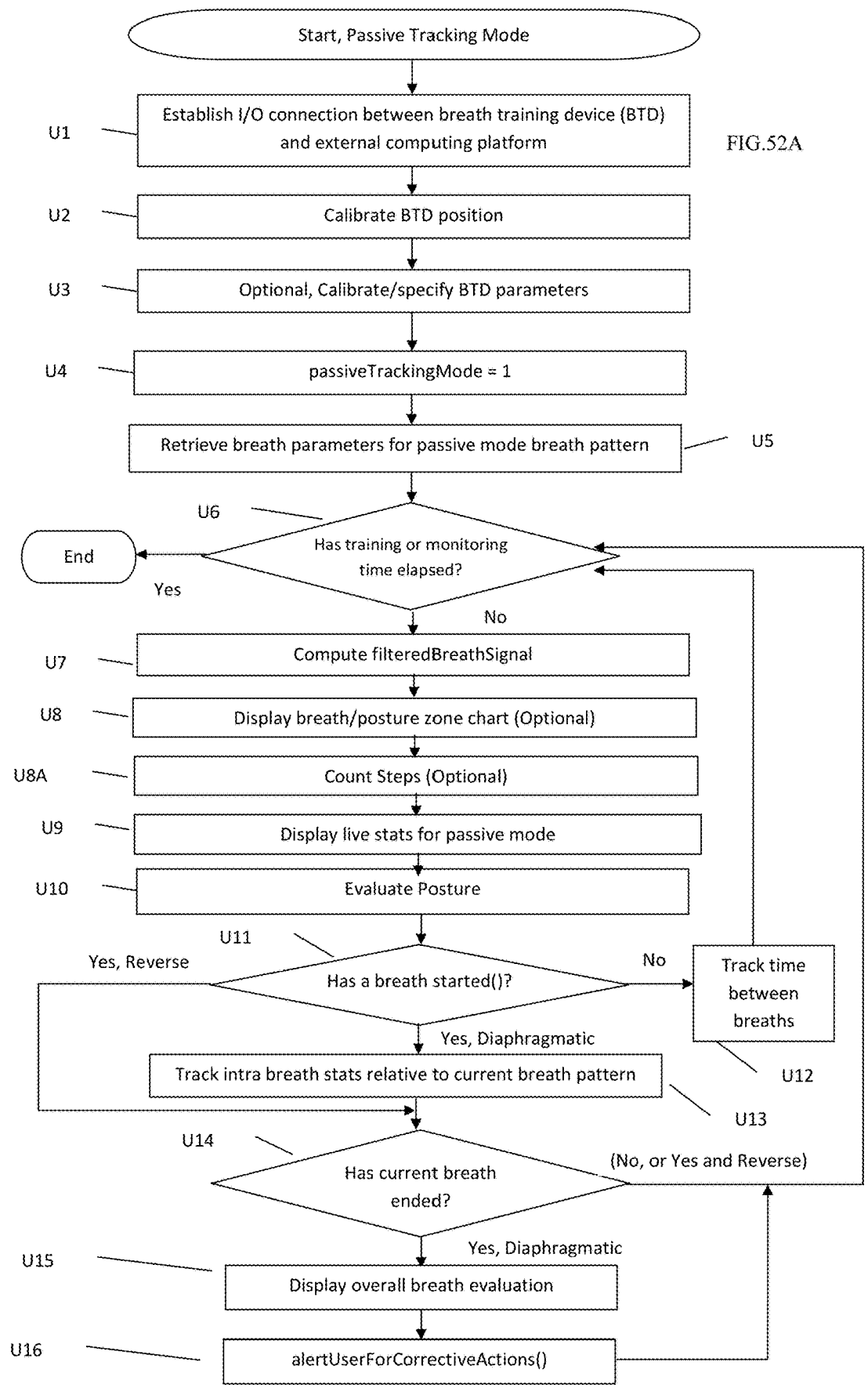
FIG. 52A is a flowchart showing exemplary steps involved in implementing a passive tracking mode process of the present invention.

The breath training device of the present invention may also be used in a passive tracking mode capacity as detailed in the process in the flowchart in FIG. 52A. In this mode, the user can wear the device while going about their normal business as the device monitors their breathing and posture. Generally, a goal of the passive tracking mode is to monitor a user's breathing and posture, and optionally warn the user when their breathing or posture takes on undesirable characteristics, so that the user can at least momentarily consciously alter their breathing or posture, or optionally switch to the active training mode for a session of focused training to help improve their breathing. Another goal is to collect breath and posture data over time while classifying the quality of each breath, so that the user can review and understand which events in their day can be related to extended periods of poor quality breathing or posture.

An active training mode selector 407 and a passive tracking mode selector 409 can be provided in the breath training program as shown in FIG. 117A for selecting either the active training mode or passive tracking mode. When active training mode selector 407 is enabled, then active training selection screen 405 can be visible for selecting a breath exercise icon as previously discussed or a customize option. When passive tracking mode selector 409 is enabled, then a passive tracking dashboard 411 can be visible, as shown in FIG. 117B.

The steps in FIG. 52A for passive tracking can be similar to a subset of steps in FIG. 51 already discussed for active training Steps U1-U3 are the same as steps S1-S3. In step U4, a passiveTrackingMode flag is set to 1, which alters some processes discussed previously, such as adding a feature in checkIfBreathInterrupted( ) which can interrupt an ongoing breath. In step U5, breath parameters for a passive mode breath pattern are retrieved. This differs from steps S4-S5 where any breath exercise can be selected for training. In passive mode, it may not be desirable to use elaborate breath training patterns since the user is not actively paying attention and modifying their breath. Instead, a default pattern is automatically selected with more lenient parameters which the user is evaluated against, and which helps to detect signs of stressed breathing. Often in stressful breathing, the user will breathe more rapidly, or breathe from the chest instead of diaphragmatically. The breaths may also become uneven or staggered, or with incomplete exhalations, or rapid inhalations, and with an absence of deep breaths. For example, a breath pattern for passive mode can have the following parameters: startBreathThreshold=14%, endBreathThreshold=50%, minBreathDepth=14%, maxBreathDepth=100%, minInhalationTime=0.4 s, maxInhalationTime=8 s, minBreathHoldTime=0, maxBreathHoldTime=1 s, minTimeBetweenBreaths=0, maxTimeBetweenBreaths=8 s, minExhalationRelativeTime=0.7, maxExhalationRelativeTime=3, relativeExhalationTime=1. A high endBreathThreshold, such as 50%, helps to increase chances that the end of a breath is reliably detected in this passive mode.

Next, steps U6 to U13 are similar to steps S6 to S13, except that the filtered breath signal need not be displayed in real time, as in step S8 (though optionally can be). In step U9, live stats are displayed for the passive mode, as detailed in the flowchart in FIG. 98D, which displays each evaluated breath classified into one of four types: normal belly breath, deep and slow belly breath, non-satisfactory belly breath, and chest/reverse breath (based on count variables computed in previously described processes), as well as breath and posture scores. FIG. 117B shows passive tracking dashboard 411 with these variables displayed. Referring to FIG. 98D, the detailed steps there are to display time elapsed since start of passive breath tracking, display numOfBreaths (total breaths), display numOfNormalBellyBreaths, (set in countDeepSlowBreaths( ) for example), display numOfDeepBellyBreaths, display numOfBadBellyBreaths, display numOfReverseBreaths, display overall Breath Score (ratio of goodBreaths to numOfBreaths), display recent Breath Score (ratio of goodBreaths which occurred to numOfBreaths which occurred) for last trailing alertIntervalOfTime, display Respiration Rate for last trailing minute of elapsed time, display overall Posture Score (ratio of goodPostureMeasurements to totalPostureMeasurements), and display recent Posture Score (ratio of goodPostureMeasurements which occurred to totalPostureMeasurements which occurred) for last trailing alertIntervalOfTime, then end the process. All this passive data can be saved by the breath training program, and reviewed by the user any time in a calendar view, as is well known in the art for presenting such data. For example, the user could select a particular day, and then see a breakdown of the data at various levels of granularity, such as by the hour, or in 5 minute intervals. Color codes can be used to indicate when the breath or posture scores are above or below the chosen warning thresholds, as well as seeing the total number of tracked breaths of each classification type for the chosen time interval.

Referring back to FIG. 52A, step U14 is the same as step S14, except that if the current breath has not ended, or if it has ended and was a reverse breath, then loop back to step U6 (new breath parameters need not be retrieved for a next breath, since in passive tracking mode, the same parameters can be used for all breaths). Step U15 can be the same as step S15 except that a good or bad breath evaluation can be displayed on passive tracking dashboard 411 instead of timeline 350, or indirectly displayed through the breath classification as discussed above. Next, step U16 calls the process alertUserForCorrectiveActions( ) to optionally warn the user when undesirable breath or posture characteristics are detected, as detailed in the flowchart in FIG. 98E. Referring to FIG. 98E, the first step is to check if Recent Breath Score<breathScoreTreshold and alertIntervalOfTime has transpired? If true, then alert the user that Recent Breath Score is low (below a settable breathScoreTreshold), and indicate a specific reason in the alert, such as a preponderance of bad belly breaths as given by numOfBadBellyBreaths, or too many reverse breaths as given by numOfReverseBreaths. Such customized alerts could be sent to the user's smartphone for example using push technology or text messaging. Next, check if Respiration Rate>respirationRateThreshold and alertIntervalOfTime has transpired? If true, then alert the user that their Respiration Rate is too high (above a settable respirationRateThreshold), which is a common sign of stressful breathing Next, check if fullBreathTime transpired and if at least a deepBreathTreshold number of deep belly breaths occurred? If false, then alert the user not enough deep belly breaths have occurred in the last fullBreathTime interval (as given by settable value deepBreathTreshold). Another possible sign of stressful breathing is that a deep breath does not at least periodically occur, and this test warns of that scenario. Next, check if Recent Posture Score<postureScoreTreshold and alertIntervalOfTime has transpired? If true, then alert the user Recent Posture Score is too low (as given by a settable postureScoreTreshold). These alerts may also be made by activating the optional notifier in the breath training device worn by the user, such as notifier 622 in the seventh embodiment (for example, causing a vibration which can be felt by the user). With the notifier, it is also possible to customize or code the alerts, for example, by buzzing with a specific pattern representing various alert states, such as 1 buzz for breath related warnings, and 2 rapid buzzes for posture related warnings.

Figure 98G:
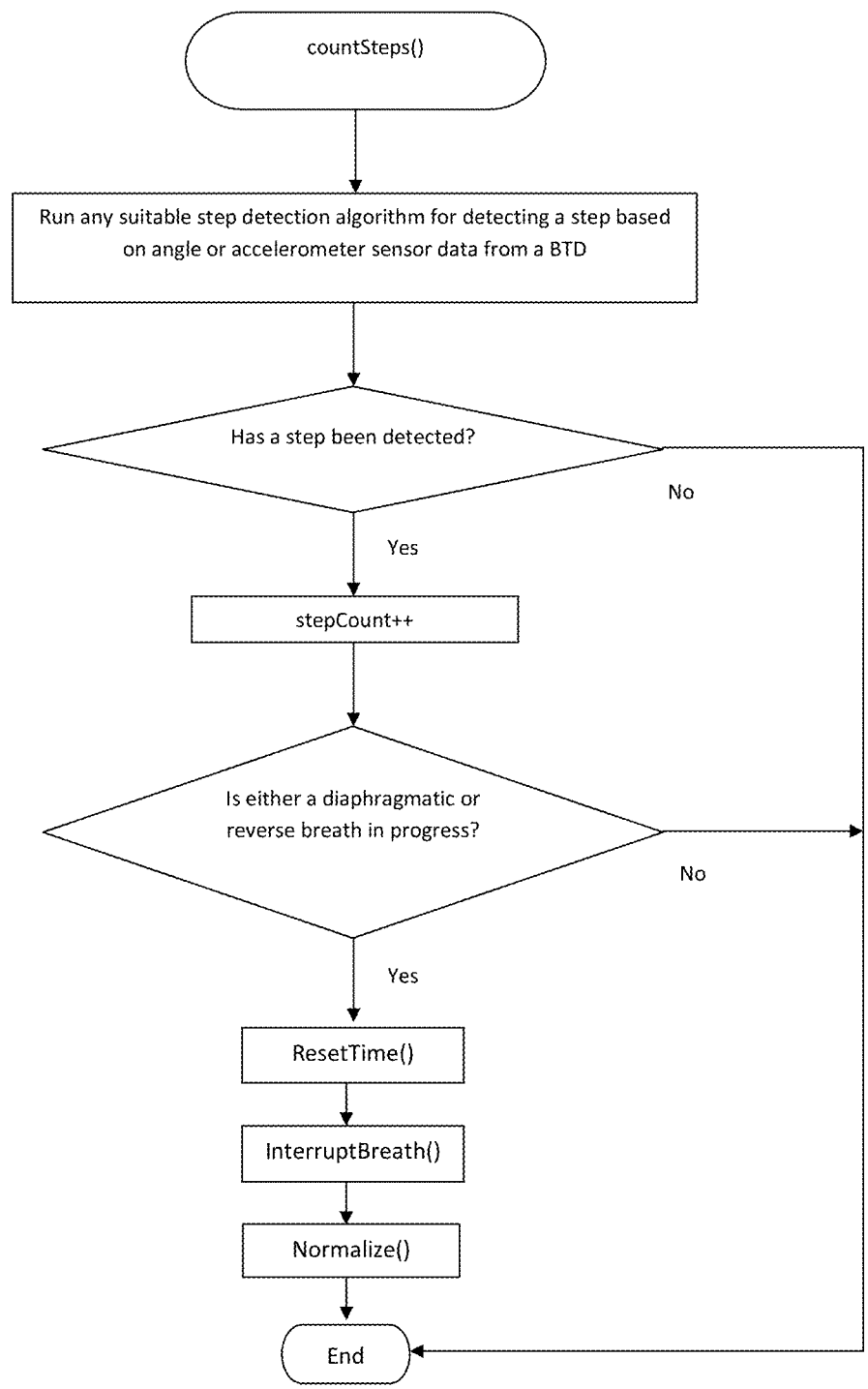

In the passive tracking mode in step U8A in FIG. 52A, if a user stands up and starts to walk, a step counting algorithm can optionally detect and count the number of steps taken, as shown in the flowchart in FIG. 98G. There are many such well-known algorithms for detecting and deriving a step count from a 3-axis accelerometer, for example, which can be used here. The current step count (stepCount) can be displayed on a steps taken indicator 413 on passive tracking dashboard 411 as shown in FIG. 117B. With a BTD type 4 in particular, since an angle sensor is employed in only one body location, each time a step is taken, this type of body motion may inadvertently trigger the start and conclusion of a diaphragmatic or reverse breath, leading to an inaccurate breath count, score, and respiration rate. To help avoid this, when a step is detected, if either a diaphragmatic or reverse breath is in progress, that breath can be interrupted by the process in FIG. 98G. The first step there is to run any suitable step detection algorithm for detecting a step based on angle or accelerometer sensor data. Next, check if a step has been detected? If false, end the process. If true, then increment stepCount, and then check if either a diaphragmatic or reverse breath is in progress? If false, end the process. If true, then execute ResetTime( ), interruptBreath ( ), and Normalize( ) to cancel any ongoing breath, and then end the process. This strategy helps to suppress and discount angle changes of the abdominal wall due to walking as possible breath related events.

Heart Rate Variability Sensor Combined with the Breath Training Device

Figure 98H:
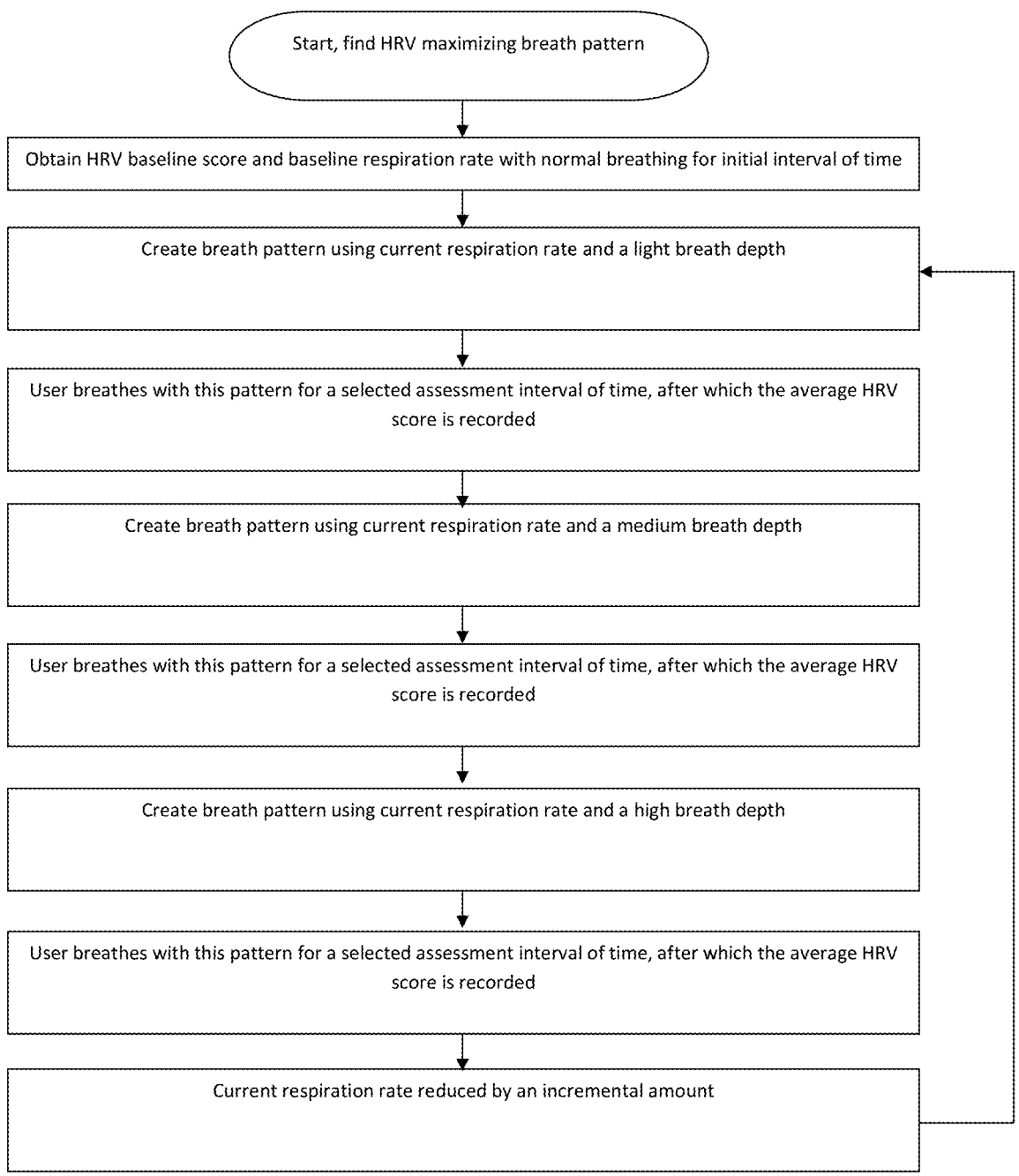

It is well known that breath patterns, abdominal breathing, and respiration rate can significantly influence heart rate variability (HRV). Two published studies in this area include "Relationship between dysfunctional breathing patterns and ability to achieve target heart rate variability with features of "coherence" during biofeedback" by Courtney R, Cohen M, van Dixhoorn J. in Altern. Ther. Health Med. 2011 May-June; 17(3):38-44, and "The Effects of Specific Respiratory Rates on Heart Rate and Heart Rate Variability" by Song, Hye-Sue, Lehrer, Paul M. in Applied Psychophysiology & Biofeedback; March 2003, Vol. 28 Issue 1, p 13. The breath training device of the present invention can be used in combination with a heart rate variability sensor in a biofeedback capacity to help a user discover a resonant breath pattern which tends to maximize at rest HRV. Existing heart rate variability sensors, such as those produced by HeartMath LLC, could be integrated with the breath training device of the present invention so that, for example, an HRV live score indicator could be provided on live stats box 408, visible during an active training session in either the analytical or game view modes. Alternately, a separate HRV sensor could be used concurrently with the breath training device. Since respiration rate and inhalation depth have been found to have a significant effect on HRV, the following method is proposed as detailed in the flowchart in FIG. 98H to help a user discover an HRV maximizing breath pattern. In the first step in FIG. 98H, the user first breathes normally for an initial interval of time (1 minute for example) to obtain a baseline at rest HRV score and a baseline respiration rate (Current respiration rate for the next step) without any active breath training enabled. Next, the breath training program, preferably in the previously described game mode, can start a breath training and HRV evaluation session with a created and displayed breath pattern corresponding to the current respiration rate, and targeting a light breath depth. For example, if a user's at rest baseline respiration rate was measured at 14 breaths/min, this step could start with a breath pattern corresponding to 14 breaths/minute and targeting a light breath depth, where minBreathDepth and maxBreathDepth could be set to 10% and 25% for example (and minInhalationTime, maxInhalationTime, minExhalationTime, maxExhalationTime set consistent with the targeted respiration rate). In the next step, the user breathes with this pattern for a selected assessment interval of time (2 minutes for example), after which the average HRV score is recorded. In the next step, the breath pattern is altered to again increase the breath depth. For example, minBreathDepth and maxBreathDepth could be set to 25% and 50%. In the next step, the user breathes with this pattern for a selected assessment interval of time (2 minutes for example), after which the average HRV score is again recorded for this time. In the next final step in the current cycle, again the breath pattern is altered to increase the breath depth. For example, minBreathDepth and maxBreathDepth could be set to 50% and 75%. In the next step, the user breathes with this pattern for a selected assessment interval of time (2 minutes for example), after which the average HRV score is again recorded. Then this process could decrease the current respiration rate by a specified interval, such as 2 breaths/min, and then loop back to step 2, where the varying breath depths are again tested at this new slower respiration rate (the user could pause at this point for several minutes to allow their HRV to return closer to their baseline before beginning the new patterns). The user can continue this process in this manner to the lowest possible respiration rate they can comfortably train with. For example, this process could start with 12 breaths/min, training with 3 varying inhalation depths, then reduce to 10 breaths/min again with 3 varying inhalation depths, all the way down to 4 or even 2 breaths/min. At the end of the session, the breath training program could select and point out which pattern produced the best HRV score relative to the baseline HRV score, allowing the user to train (as in FIGS. 51-52 for example) with this pattern for HRV-specific benefits. Alternately, a third or fourth breath parameter could similarly be introduced into the above cycles as part of the HRV assessment. For example, minBreathHoldTime, maxBreathHoldTime, or minTimeBetweenBreaths, maxTimeBetweenBreaths could be varied while the other parameters held constant, to determine the HRV effect of breath retention (after inhalation and after each breath) on HRV.

Independent of HRV, the process just described could be used in conjunction with the Buteyko breath pattern. The goal of the Buteyko breathing method generally is to breathe as lightly as possible and at a slow respiration rate to decrease the volume of air breathed each minute, for efficient respiration. The process described, varying the parameters of minBreathDepth, maxBreathDepth and minInhalationTime, maxInhalationTime, and minExhalationTime, maxExhalationTime, and minTimeBetweenBreaths, maxTimeBetweenBreaths, and preferably in the game mode, could help a user discover the slowest respiration rate and lightest breath depth pattern they can sustain. Instead of decreasing respiration rate each cycle as described above, the user could jump or start with an ambitiously slow rate and light depth, and see if they can sustain it, and adjust the breath parameters accordingly. In the game mode, when a specified quantity of obstacle objects are hit by the breath level game element as previously discussed, that lowers the breath score. This feedback allows the user to discover their current level in terms of Buteyko breathing, with a pattern they can sustain. The user can then train and progressively decrease the respiration rate and/or the breath depth over time.

Other Types of Sensors

It should be noted that other sensors such as a microphone placed near a user's mouth, or spirometer, can be used for computing the filtered breath signal and to drive the active and passive breath training processes in FIGS. 51-52A. For example, a type 2 BTD definition can be extended such that the displacement sensor can be replaced with a microphone, spirometer, pulse oximeter, or many other existing sensors, and the range of values of that sensor (due to inhalation and exhalation) can be used to determine the currentInhaleLevel as previously discussed, and used as part of computing the filtered breath signal. In this manner, the effects of posture and body movement noise can still be taken into account and corrected for in combination with these types of sensors. It is also possible to optionally omit the posture correcting steps in combination with these sensor types or previously discussed sensors in the breath training processes in FIGS. 51-52.

A typical consumer smartphone available today such as an iPhone or Android phone, could serve as a type 4 BTD as described above, provided that such a smartphone have an angle sensing means (most smartphones today ship with accelerometers). In this case, the smartphone could be placed and worn over the belly or upper pubic area as previously described. Many such smartphones also have Bluetooth available which would allow transmitting data to an external computing platform where in an active training mode, the filtered breath signal could be more conveniently visualized in real time.

While the examples of the breath training processes shown above compute and correct the filtered breath signal based on a variety of seated postures, these processes and calibration steps can be extended to similarly function while a user is standing and wearing a breath training device, to measure the range of posture and diaphragm motions in a variety of standing poses, with similar posture zone coefficients and zeroing offsets learned across a range standing postures to help correct the filtered breath signal as previously discussed.

The breath training program and processes as discussed above can alternately be stored in the memory of the breath training devices (BTD's) disclosed above, and executed by the microcontrollers or CPU's of these devices instead of running on an external computing platform. The advantage of this arrangement is that the breath training device can then be entirely self-contained, including all needed software to evaluate respiration. In this case, it may be desirable to add a display on the given breath training device to visualize the filtered breath signal and data as previously discussed. For example, if a smartphone is used as a type 4 BTD, then the breath training program could fully execute on the smartphone, and the filtered breath signal could be displayed on its display (with a possible disadvantage in that the user may need to look downwards at the phone near their belly area to participate in an active training mode).

Ninth Embodiment

In some embodiments, the device retraction mechanism can be a spring tensioned spool. In these embodiments, the belt can wind around this spring tensioned spool, and the motion or force on the spool or belt can be measured. Here the breathing sensor can be any of a rotary encoder, a magnetic rotary encoder, and a strain gauge. Other rotary encoders, such as optical rotary encoders, may also be used.

Further, in some embodiments, such a spring tensioned spool and the rotary encoder can further be used to measure a displacement of the belt (e.g. how far the belt has extended or retracted from the housing). This displacement can be used for other applications such as computing any of a dimension or change in dimension of a user body part or muscle.

For example, a ninth embodiment of a breath training device 700 of the present invention is shown in FIG. 160. In addition to tracking breathing and posture, breath training device 700 is able to measure and track the circumference of a person's waist as part of a weight loss and health application, as well as to measure and track the size of major muscle groups on the body, such as by measuring the circumference of arms and legs, for a body building application.

It has been discussed for quite a few years in medical literature that how fat is distributed in the body can provide important insights beyond simply the overall weight of a person or even their body mass index (BMI). In particular, visceral fat or concentrations of fat in the abdominal area can be especially harmful to health over the long term. It is also well known that building muscle over time can help decrease fat concentrations. It is thus a further object of the present invention to allow tracking waist circumference, preferably around the navel, as well as to track major muscle sizes, as an aid to assist in decreasing belly fat, as well as to help increase overall strength and fitness.

As shown in FIG. 160, breath training device 700 consists of a device housing 702, containing a retractable belt 704. As shown in FIGS. 161-162, device housing 702 can consist of a bottom housing 706, and a lid 708. Bottom housing has an internal surface 710, and an outer surface 712 as shown in FIG. 163. Bottom housing 706 can have a recessed lip 714 around its top edge as shown in FIG. 161, over which lid 708 can be placed and glued when device housing 702 is assembled. Many other means of securing lid 708 over bottom housing 706 can be utilized as well known in the art, such as by snap fitting, or by adding support columns in bottom housing 706 into which lid 708 can be screwed into place. Bottom housing 706 can have a belt opening 716 through which retractable belt 704 moves in and out of breath training device 700. A clip 718 (an example of a belt fastener) is attached to a distal end 720 of retractable belt 704 as shown in FIG. 160. Device housing 702 can be made of plastic such as by injection molding, aluminum, steel, or other materials known in the art.

As shown in FIGS. 164-166, a user wears breath training device 700 by pulling clip 718 to withdraw retractable belt 704, and wrapping the belt around his/her waistline or chest to form a belt loop 722. The user then secures retractable belt 704 by fastening clip 718 onto a clip receptacle 724 (an example of a housing fastener) located on an opposite side of bottom housing 706 relative to the position of belt opening 716, as shown in FIG. 161. Device housing 702 can be worn at multiple positions along the trunk, but preferably near the lower back area as shown in FIG. 166B for measuring breathing and posture as previously discussed for a type 2 BTD. Device housing 702 is worn with outer surface 712 of bottom housing 706 against the body. Outer surface 712 can have a cushionable layer 713 on it, formed from Neoprene or foam for example, or by silicone overmolding for creating a more comfortable soft surface against the body. Alternately for just measuring breathing, device housing 702 can be worn near the navel or on the chest as shown in FIG. 166A. An important advantage of breath training device 700 over previous embodiments is that it does not need to be attached to clothing or clipped onto a waistband to be supported on the body. The retractable belt can be worn directly against the skin, or can be worn over clothing, without relying on a particular configuration of clothing, and can be easily worn at multiple locations. Also breath training device 700 is much more compact than previously described belt designs, since retractable belt 704 can be entirely contained inside device housing 702 when not in use, and does not need belt length adjusters, as the retractable design allows the belt length to automatically adjust to a variety of body sizes and shapes, while maintaining adequate tightness around the body.

As shown in FIGS. 167A-C, bottom housing 706 contains a reel 726 onto which retractable belt 704 is wound and unwound. Reel 726 consists of a power spring compartment 728 contained inside a spool 730, a spring engagement opening 732 in a spool wall 734, a plate 736, a rotation axis opening 738, and a flange 740. Retractable belt 704 is wound around spool 730, with the width of said belt preferably smaller than the height of spool wall 734. A proximal end 742 of retractable belt 704 can be secured to an external side 744 of spool wall 734 as an anchor point for winding, by means of gluing, bonding, crimping, or other well-known means in the art. When retractable belt 704 is fully wound onto spool 730, the outer diameter of the stacked wound belt is preferably smaller than the width of plate 736, as shown in FIG. 167C, to help support the stability of retractable belt 704 on spool 730.

Retractable belt 704 can be made from a variety of materials and configurations including but not limited to PVC plastic, TPE, TPU, fiberglass, silicone, and many other different plastic and rubber materials, or other materials such as leather, nylon, or from various fabrics as well known in the art. It is preferable that the material be flexible and suitable for retraction, and durable for long cycle life. It is also preferable that the material be nontoxic for contact against skin, and comfortable for extended wearing. In a preferred embodiment, retractable belt 704 can be relatively flat in configuration, as shown sectionally in FIG. 168, allowing a suitable length to be wound onto spool 730 for accommodating most waist sizes, while minimizing the overall width of reel 726 and consequently overall size of device housing 702, since a flat belt winds more compactly. A flat belt configuration also aids in comfort since a greater surface area can be in contact with the skin, preventing a cutting sensation or leaving marks on the skin. For accurately measuring waist circumference, it is preferable that retractable belt 704 resist longitudinally stretching when a moderate force is applied. In order to help minimize such stretching, one or more strengthening strands 746 can be included along the inside length. Strands 746 can be made from nylon for example, or from copper wire or other wire material to resist longitudinal stretching. As one example, retractable belt 704 can be made from PVC with nylon strands inside, approximately 50 inches in length for accommodating most waist sizes, and approximately 5 mm wide by 0.6 mm thick, which helps keep device housing 702 relatively flat. Alternately, retractable belt 704 can be implemented as a string to help further decrease size and thickness of device housing 702. Such a string can be made from materials previously discussed, or many other materials including metals. The disadvantage of a string is that it may not be as comfortable against skin as a flat belt configuration.

As shown in FIG. 167C, power spring compartment 728 contains a power spring 748. Power spring 748 can be a flat spiral spring as well known in the art, typically made of stainless steel, carbon, or other materials, similar to springs found inside retractable tape measures or badge holders. Power spring 748 provides the torque for rewinding retractable belt 704 onto reel 726. Power spring 748 can be preloaded by several turns of reel 726, increasing the base level of torque when retractable belt 704 is initially withdrawn by the user from device housing 702.

Bottom housing 706 contains an arbor 750 with a spring slot 752 as shown in FIG. 161. As shown in FIG. 169, reel 726 can be positioned inside bottom housing 706 with power spring compartment 728 facing downwards. Internal surface 710 can have a layer of Teflon tape covering it for example, to help decrease frictional forces of the rotation of reel 726 against internal surface 710. Rotation axis opening 738 on reel 726 fits over arbor 750, such that reel 726 can engage and rotate around arbor 750. As shown in FIG. 167C, power spring 748 has a catch 754 on its centrally located end which is placed into spring slot 752, and a hook 756 near its peripheral end for attaching over spool wall 734, accessible by spring engagement opening 732, allowing power spring 748 to be wound and unwound around arbor 750 as reel 726 rotates when retractable belt 704 is pulled out or drawn into breath training device 700.

Referring to FIGS. 169-170, flange 740 is situated around rotation axis opening 738 on reel 726, such that flange 740 extends above arbor 750 when reel 726 is positioned on arbor 750, creating a magnet recess 758. A magnet 760 can be glued into magnet recess 758 against the inside surface of flange 740, but not in contact with arbor 750, such that magnet 760 can rotate together with reel 726. Magnet 760 can be a disc shaped magnet for example, preferably diametrically magnetized with north and south poles on the same surface, and can be made from Neodymium, ceramic, or other materials as well known in the art.

Lid 708 has an inner surface 762 and outer surface 764. As shown in FIG. 171, inner surface 762 can have a printed circuit board 766 attached to it by bonding for example. Lid 708 can have a plurality of registration posts 768 which fit through mounting holes 770 in printed circuit board 766 to help secure and orient printed circuit board 766. Registration posts 768 can also function as a stop to prevent reel 726 from moving upwards as it rotates, preventing reel 726 from colliding with printed circuit board 766. A battery recess 772 on lid 708 can contain a battery 774 for powering printed circuit board 766. Battery 774 can be secured to lid 708 by bonding for example. Battery 774 can be a rechargeable Polymer Lithium Ion Battery for example.

A first surface 776 of printed circuit board 766 faces reel 726 when lid 708 is secured over bottom housing 706, and a second surface 778 faces inner surface 762 of lid 708 as shown in FIG. 172. Printed circuit board 766 has a rotary sensor 780 mounted on first surface 776. Rotary sensor 780 can be, for example, a hall effect magnetic sensor as well known in art, which is capable of detecting a changing magnetic field, and capable of detecting an angle position through a 360 rotation of a nearby rotating magnet. Rotary sensor 780 is positioned on printed circuit board 766 such that its magnetic center 782 is positioned over the center of magnet 760 in reel 726. This arrangement is for the purpose of tracking the rotation of reel 726. When a user wears breath training device 700, inhalation and exhalation can cause the circumference of belt loop 722 to increase and decrease, which causes retractable belt 704 to unwind and wind from spool 730, causing reel 726 to rotate in one direction and then in an opposite direction which rotary sensor 780 can track. In the ninth embodiment, rotary sensor 780 can function as displacement sensor 146 previously discussed. A clearance gap 784 is provided between magnet 760 and rotary sensor 780 as shown in FIG. 173. Many commercial IC's options are available for rotary sensor 780, such as but not limited to AS5048 Magnetic Rotary Encoder from AMS, or part TLV493DA1B6HTSA2 from Infineon Technologies. Second surface 778 of printed circuit board 766 could have additional electronic components such as a status LED 779 for example.

Thus in some embodiments, the invention may be an even more capable device, system or method for tracking respiration and posture from a location on a human user. As previously discussed, this device will typically comprise a housing comprising a computer processor, an electronic angle sensor, a retracting belt, a retracting mechanism, a housing fastener, and an electronic breathing sensor configured to produce an electronic breathing sensor signal reporting on at least one of force and movement of the retracting belt.

In some embodiments, as previously discussed, the electronic angle sensor may be an accelerometer.

Also, as previously discussed, the retracting belt may comprise a first belt end that is connected to the retracting mechanism, and a second belt end configured with a belt fastener that is configured to reversibly attach to a housing fastener.

Further, as previously discussed, the housing and the retracting belt can be configured so that when the retracting belt is worn around the user's trunk, and the belt fastener is attached to the housing fastener, the retracting belt experiences any of force or movement in response to user respiration, and the breathing sensor produces a breathing sensor signal reporting on this respiration.

Further, as previously discussed, the retracting mechanism can comprise a tension mechanism for placing the belt under tension during all phases of user respiration, so that the belt extends further out of the housing during user inhalation, and the belt retracts=(into the housing during user exhalation.

However in this ninth embodiment, the retraction mechanism can be a spring tensioned spool, where the belt winds around this spring tensioned spool, and the breathing sensor can be at least one of a strain gauge, a rotary encoder, and a magnetic rotary encoder (optical rotary encoders may also be used).

As before, the electronic angle sensor may be configured so that when the retracting belt is worn around the user's trunk, and the belt fastener is attached to the housing fastener, the angle sensor produces an angle sensor signal reporting on an angle of the user's posture.

As previously discussed, in some embodiments, this processor can be configured to process the breathing sensor signal and the angle sensor signal, and to produce various types of outputs. These can include outputs reporting on the angle sensor data reporting on the user's posture, and breathing sensor data reporting on the user's respiration. The processor (or external processors) can also be configured to report on posture adjusted user respiration data. Although the device may be configured to simply store all of the signals or data on internal or removable memory, in a preferred embodiment, the device will additionally comprise a wireless transceiver (e.g. a Bluetooth, Wi-Fi, or other type wireless transceiver) and be configured to use the processor and the wireless transceiver to transmit at least some of the signals or data to an external computing platform. Often the device will also be configured so that the housing is worn on the user's back.

Components of printed circuit board 766 are shown in the block diagram in FIG. 174. The components can include a CPU 786, a memory 788 for storing firmware and data, angle sensor 790, I/O 792 which is preferably wireless, optional notifier 794 such as a vibrating motor, optional switch 796, port 798, and rotary sensor 780 previously described. As shown in FIGS. 161-162, a port opening 800 can be formed in bottom housing 706 and lid 708 to provide access to port 798 for charging battery 774. Port 798 can be a USB port. A microcontroller can be used instead of a CPU or microprocessor as previously discussed in the first embodiment. Angle sensor 790 and rotary sensor 780 can be electrically connected to CPU 786 on printed circuit board 766 for sending CPU 786 sensor output signals. FIG. 175 shows an example of just one such possible implementation of printed circuit board 766, where CPU 786 is a Nordic semiconductor nRF52832 ARM processor, I/O 792 is provided by Bluetooth support integrated on the nRF52832 chip, angle sensor 790 is a MMA8452QR1 3 axis accelerometer provided by NXP USA Inc., and rotary sensor 780 is a TLV493DA1B6HTSA2 provided by Infineon Technologies. FIG. 176 shows the bill of materials for the example PCB in FIG. 175, and FIGS. 177 and 178 show an example schematic. Additional support electronics 802 as shown in FIG. 174 are also provided on printed circuit board 766 as well known in the art to make it functional, such as a battery charging circuit, analog to digital converter, digital pot for calibration, voltage regulator, voltage reference, and op amp, though many other component brands and configurations are possible within the scope of the present invention. Alternately, switch 796 could be excluded, and CPU 786 could be placed into a low power mode via a command through I/O 792, and similarly, woken up by a command sent through I/O 792, or when serial data arrives from I/O 792, or when rotary sensor 780 or angle sensor 790 senses corresponding rotation of reel 726 or changing angle of device housing 702. Alternately, port 798 could be excluded and a wireless battery charging system as previously described could be included with breath training device 700, such as one specified by the Qi interface standard, which charges via resonant inductive coupling.

As shown in FIG. 179, bottom housing 706 can contain a belt guide shaft 804. Belt guide shaft 804 can help guide retractable belt 704 towards belt opening 716 as it unwinds from spool 730. In the preferred embodiment, retractable belt 704 is flat in configuration as previously described. A flat surface 806 of retractable belt 704 can move in contact against a rotating roller 808 situated on belt guide shaft 804 to decrease frictional forces. As retractable belt 704 passes belt guide shaft 804 towards belt opening 716, retractable belt 704 twists 90 degrees in orientation before exiting belt opening 716, such that retractable belt 704 leaves device housing 702 in a flat orientation relative to a user's body. This twisting is necessary since retractable belt 704 is wound onto spool 730 in a vertical orientation, which is 90 degrees relative to its desired flat exit orientation. As shown in FIG. 180, belt opening 716 can be slit shaped in a horizontal orientation to help constrain retractable belt 704 in a flat orientation when outside device housing 702. There is preferably enough distance between belt guide shaft 804 and belt opening 716 to allow retractable belt 704 to twist 90 degrees. This twisting distance depends on factors such as the width and thickness of retractable belt 704, as well as the flexibility of its material.

In a second version 703 of the ninth embodiment of breath training device 700, a flexing element 810 can be added between belt guide shaft 804 and belt opening 716 as shown in FIGS. 181A-B. Flexing element 810 can rest on internal surface 710 of bottom housing 706 and secured there by a mounting element 812 and mounting posts 814, and bonded thereto. Flexing element 810 can be bow shaped as shown in FIG. 182, and made from a material such as plastic, rubber, or a thin metal such as stainless steel, which allows flexing when a downward force or pressure is applied. Flexing element 810 can be a flat metal spring for example, or an injection molded or 3D printed plastic part, or could be a compression spring, or other springy structure. As shown in FIG. 181B, retractable belt 704 passes over a contact surface 816 of flexing element 810 before exiting belt opening 716. When breath training device 700 is worn around the body and when the user breathes, the expansion of the abdomen or chest can increase tension on retractable belt 704. As retractable belt 704 exits belt opening 716, it is inclined at a downward angle relative to outer surface 712 of bottom housing 706 as visible in FIG. 166B, since outer surface 712 is worn against the body and retractable belt 704 must travel towards the plane defined by outer surface 712 as it loops around the body to form belt loop 722. Therefore when a user inhales and when tension on retractable belt 704 increases, there is a component downward vector of force applied against flexing element 810, causing it to temporarily deform, and then spring back when tension on retractable belt 704 is released after exhaling.

A flex sensor 818 can be mounted on an under surface 820 of flexing element 810 to measure such deformation as shown in FIG. 183. Flex sensor 818 can be a strain gauge, such as a semiconductor strain gauge or foil strain gauge for example, or other types of strain gauges can be utilized as well known in the art for measuring strain on a material, which generally provide a variation in resistance values based on strain. Similarly, force sensitive resistors can be used, piezo-electric sensors such as piezo film sensors, variable capacitors such as a sensor including two or more metal plates, where small variations in the distance between the plates can be measured through changing capacitance, variable inductance sensors, or other sensor types for measuring strain. Flex sensor 818 can be connected by wires 822 to CPU 786 for sensing strain on the sensor. Flexing element holes 824 can be provided to facilitate passage of wires 822 from under surface 820. A Wheatstone bridge circuit as well known in the art can be provided on printed circuit board 766 as part of support electronics 802 to help increase sensitivity of flex sensor 818. In one embodiment, flex sensor 818 is a semiconductor strain gauge with a high gauge factor for enhanced sensitivity, and with a flexible backing material or film, which is bonded with epoxy to under surface 820.

Thus in some embodiments, the breathing sensor can sensor further comprise an electronic strain gauge configured to report strain type force on said belt to said processor.

In a variation of second version 703, flex sensor 818 can instead be integrated in a sensor clip 826 as shown in FIG. 184. Flex sensor 818 can be mounted on a flex element 828, similar to the mounting on flexing element 810 on under surface 820 as already shown in FIG. 183. In this embodiment, distal end 720 of retractable belt 704 can be looped over flex element 828 forming loop 830 for the purpose of transmitting a pulling force or pressure onto flex element 828 during respiration to cause a measurable strain on flex sensor 818. Flex element 828 can be mounted on a support surface 832 of sensor clip 826 against which loop 830 can pull flex element 828. Support surface 832 can have belt loop openings 834 in order for retractable belt 704 to pass into and out of sensor clip 826 to form loop 830. Sensor clip 826 can have an outer housing 836 connected to support surface 832, with a spring loaded catch 838 positioned near a distal end 840 of outer housing 836. Sensor clip 826 can be plugged into clip receptacle 724, causing spring loaded catch 838 to move inwards into sensor clip 826 to allow entry, and then preventing removal of sensor clip 826 when it is pulled by retractable belt 704, by engaging with a catch wall 842 in clip receptacle 724. The user can remove sensor clip 826 to allow power spring 748 to wind retractable belt 704 back into device housing 702, by pressing a clip release button 844, which functions to disengage spring loaded catch 838 from catch wall 842 to allow removal. Sensor wires 846 can travel from flex sensor 818 and connect to electrical contacts 848 at distal end 840 of sensor clip 826. Electrical contacts 848 can interface with receiving electrical contacts 850 inside clip receptacle 724. Receiving electrical contacts 850 can have connected wires 852 which travel and connect to CPU 786 for sending signals from flex sensor 818.

In a further variation of second version 703, flex sensor 818 can be alternately located inside clip receptacle 724 inside device housing 702, as shown in FIGS. 185A-B, similarly mounted on an internal flexing element 854 which is mounted against a support wall 856. When clip 718 is plugged into clip receptacle 724, clip 718 can releasably engage with a sliding element 858, which can ride on rails 860. Sliding element 858 can be a rectangular hollow plastic piece for example with a clip engagement opening 862 and internal wall 864. Clip 718 can have spring loaded catch 838 as previously described, and clip release button 844 on device housing 702, with spring loaded catch 838 engaging with internal wall 864 of sliding element 858, and clip release button 844 disengaging clip 718 from sliding element 858 when pressed. The range of motion of sliding element 858 can be limited by a proximal stop 866 and a distal stop 868. Sliding element springs 870 and 872, such as compression springs, can push sliding element 858 so that it normally rests against distal stop 868 when no pulling force is applied on retractable belt 704 as shown in FIG. 185A, corresponding to a user having exhaled. A force transmission element 874 such as a rod, belt, or other connecting means can connect sliding element 858 to internal flexing element 854 so that when sliding element 858 is pulled in the proximal direction by a pulling force on retractable belt 704 and hence on clip 718 due to inhalation for example, internal flexing element 854 can flex against support wall 856 as shown in FIG. 185B. Flex sensor 818 can have wires 876 connected to CPU 786.

FIGS. 186-187 show a third version 900 of the ninth embodiment of breath training device 700, similar to the already described second version 703, with key differences described below. Third version 900 can have a lid 902 and a device housing 904. FIGS. 186-187 show retractable belt 704 prior to being deployed or withdrawn from the device, with a clip 906 (another example of a belt fastener) held in a clip holder 908 which is part of device housing 904. Clip 906 can have a clip body 910, a clip neck 912, and a clip head 914. FIGS. 192A-192B show one example of how retractable belt 704 can be attached to clip 906, where one end of retractable belt 704 is inserted through a clip slot 916 and secured in place by a clip plate 918 which can be screwed or bonded to clamp down on retractable belt 704. Referring back to FIG. 187, clip holder 908 can be recessed and can have an inverse shape of clip body 910 for mating with and holding clip 906. Clip holder 908 can have a narrow belt exit slot 909 for keeping retractable belt 704 in a flat orientation after it twists 90 degrees inside device housing 904 prior to exiting, as shown in FIG. 190. Lid 902 can have a sloped finger recess 920 to facilitate easier user access for grabbing clip 906 as shown in FIG. 187. When retractable belt 704 is pulled out and worn around a user's body, clip head 914 can plug into a clip channel 922 (another example of a housing fastener) in lid 902 as shown in FIG.

188 for reversibly attaching clip 906 (along with attached retractable belt 704) to device housing 904. Clip head 914 can be hammer head shaped, spherical, or many other possible shapes, and can be made from metal, plastic, or other materials, but preferably a durable material such as stainless steel or bronze.

FIG. 189 shows the inside of device housing 904 with lid 902 removed. A flexing element 924 can be used for mounting previously discussed flex sensor 818 thereto. A roller 926 can be used to guide retractable belt 704 for exiting device housing 904. As shown in FIG. 190, roller 920 can be cylindrically shaped with end plates 928 and an open central shaft 930. As shown in FIG. 196, device housing 904 can have a bottom spindle 932 on which roller 926 is situated. Lid 902 can have a top spindle 934 on its inner surface 936 as shown in FIG. 191 so that roller 926 is held from both ends for stable rotation around bottom spindle 932 and top spindle 934 when lid 902 is covering device housing 904.

In FIG. 193A, flexing element holders 938 and 940 are shown on opposite sides of clip channel 922 extending from inner surface 936 of lid 902. Flexing element 924 can have flexing element posts 942 and 944 which can be inserted and frictionally held in flexing element holders 938 and 940 as shown in FIG. 193B. As shown transparently in FIG. 195, when lid 902 is covering device housing 904, flexing element holders 938 and 940 can be inserted into and held in openings 946 and 948 in a flexing element pedestal 950 located on an inner side 952 of device housing 904, also visible in FIG. 189. Referring back to FIG. 193B, flexing element 924 can further consist of an extended clip channel 954, which is situated over to continue clip channel 922, and an arch 956. Flex sensor 818 can be bonded to arch 956 as shown in FIG. 193C.

When fastening retractable belt 704 around the waist or other area on the trunk, the user presses clip 906 into clip channel 922, and continues to press it until clip head 914 continues deeper into extended clip channel 954 as shown in FIG. 193C, where it can be frictionally held. A neck slot 958 in lid 902 and device housing 904 allows passage of clip neck 912 as shown in FIG. 193C and FIG. 194. Clip head 914 can be hammer shaped to prevent rotation of clip 906 when plugged into extended clip channel 954, where said channel can be cylindrically shaped. Respiration causes a force to be applied onto retractable belt 704, and consequently onto clip 906. Clip neck 912 is able to move outwards and inwards from device housing 904 through neck slot 958 during inhalation and exhalation, transmitting this force onto clip head 914 inside extended clip channel 954, causing flexing arch 956 to flex or strain, which flex sensor 818 can detect. By holding flexing element holders 938 and 940 in openings 946 and 948 as shown in FIG. 195, flexing element holders 938 and 940 are prevented from bending when a pulling force is applied on retractable belt 704, causing such a force instead to tend to flex or strain arch 956 to help maximize the strain detected by flex sensor 818.

FIG. 194 shows a top surface 960 of lid 902, with clip head 914 plugged into clip channel 922. Clip channel 922 can have a funnel shaped entrance 962, wider than the diameter of clip channel 922 and extended clip channel 954, in order to help guide the plugging in of clip 906, especially when a user is doing this behind their back. Also as shown in FIG. 194, neck slot 958 can have neck tabs 964 and 966 for locking clip neck 912 vertically in place when clip neck 912 in pushed downwards beyond neck tabs 964 and 966 where it clicks into place, which corresponds to clip head 914 fully plugged into extended clip channel 954. The user can easily withdraw clip 906 when discontinuing to use the device, by using sufficient force to lift clip 906 past neck tabs 964 and 966 and out of clip channel 922.

FIGS. 197A and 197B show an alternate embodiment of a reel 968 used for winding retractable belt 704. Reel 968 can consists of a bottom plate 970 with an arbor opening 972, an attached spring compartment 974, and a separately attachable top plate 976 which can be bonded onto spring compartment tabs 978 through plate holes 980. This arrangement of assembling reel 968 from two parts provides the advantage that retractable belt 704 and power spring 748 can be enclosed and protected on both sides by bottom plate 970 and top plate 976. Additionally, when reel 968 is placed over and rotates around arbor 750 in FIG. 196, reel 968 rotates around the bottom of arbor 750 since arbor opening 972 is at the bottom of reel 968. This can create more stability for the rotation of reel 968 compared to reel 726 which has rotation axis opening 738 near its top.

FIGS. 198A-C show an alternate embodiment of a clip channel 982, where clip channel 982 is a single continuous channel extending from inner surface 936 of lid 902, for holding clip head 914, not utilizing flexing element 924 with arch 956. Flex sensor 818 can be attached to a back side 984 of clip channel 982 as shown in FIG. 198C. When lid 902 is secured over device housing 904 as shown transparently in FIG. 198B, a distal end 986 of clip channel 982 can be held in an optional clip channel holder 988 in a clip channel pedestal 990 on inner side 952 of the device housing 904. This is for restraining clip channel 982 so that it can only flex or buckle when retractable belt 704 is pulled during respiration when clip 906 is plugged in, otherwise, the entire clip channel 982 could bend relative to inner surface 936, potentially decreasing the straining force detected by flex sensor 818.

FIG. 199 shows an alternate embodiment 992 of third version 900 of breath training device 700, utilizing similar components as just described, with key differences discussed below. Embodiment 992 can have a square lid 994 and square housing 996 with optionally rounded corners, as shown in FIG. 202. In this embodiment, clip holder 908 for holding clip 906 is positioned not centrally, but near a corner of housing 996, as shown in FIG. 199. Retractable belt 704 is withdrawn off-center relative to housing 996 as shown in FIG. 200. Retractable belt 704 is pulled out directly straight from housing 996, forming a 90 degree angle with respect to an adjoining side 998 of housing 996. Once the user has fully looped retractable belt 704 around their trunk (or other body area), the user then simply rotates housing 996 with lid 994 by 45 degrees as shown in FIG. 201, and then plugs clip head 914 into clip channel 922, where clip channel 922 is situated at the opposite diagonal corner relative to clip holder 908. FIG. 205 shows the same view with lid 994 removed. A belt exit slot 1000 as shown in FIG. 202 wraps around a corner of housing 996, allowing retractable belt 704 to follow a 45 degree exit path relative to side 998 when housing is rotated by 45 degrees, so that retractable belt 704 can exit housing 996 at the same angle as it clips to housing 996 on the other side so as to be collinear. This arrangement ensures that retractable belt 704 is centered across the device for stability while being worn on the body, even though retractable belt 704 is pulled out off-center. FIG. 204 shows that retractable belt 704 is not collinear if the 45 degree rotation step is omitted.

One important advantage provided by embodiment 992 is that retractable belt 704 follows its natural tangential path as it leaves reel 968 and exits housing 996, and when retracted back onto reel 968 as shown in FIGS. 203-204. There is no need for roller 926 to redirect the path of retractable belt 704, as was necessary in previous embodiments, where retractable belt 704 was guided to centrally exit the device housing. By not needing roller 926, the lifespan of retractable belt 704 can be increased, as well as the perceived smoothness of the deployment of retractable belt 704 due to lower frictional forces.

Clip 718 and clip receptacle 724 can be implemented in many ways known in the art and within the scope of the present invention. For example, clip 718 can be hook shaped as shown in FIG. 161, and clip receptacle 724 can be ring shaped to allow attaching the clip. Alternately, clip 718 and sensor clip 826 can utilize a spring loaded catch as previously described, with clip receptacle 724 forming an opening for receiving clip 718 inside housing 702. Alternately, clip 718 can form a springy structure as shown in FIG. 164, which is securable inside clip receptacle 724, with the user compressing clip 718 to narrow it to release it from clip receptacle 724.

Device housing 702 can be elliptically shaped as shown in FIGS. 160-166, or ladybug shaped as shown in FIG. 186. This provides for a stylish appearance, as well as providing an enclosure geometry which accommodates the distribution of functional components as described in breath training device 700. As shown in FIG. 170 and FIG. 179, more space inside device housing 702 is generally needed along the horizontal axis to accommodate belt guide shaft 804 and the twisting and release of retractable belt 704, than in the vertical axis, thus forming an ellipse. Many other shapes of device housing 702 can be used within the scope of the present invention, such as rectangular, polygonal, circular, or square as shown in FIG. 199

Operational Description

It should be noted that a first version 701 of the ninth embodiment of breath training device 700, as shown in FIG. 179, differs from second version 703 as shown in FIG. 181A, in that it does not contain flex sensor 818 or the corresponding flexing element it rests upon, and relies only on rotary sensor 780 for tracking breathing, as well as for measuring waist and muscle circumferences, and with angle sensor 790 used for tracking posture. First version 701 functions similar to a type 2 BTD (breath training device) with similar breath training processes applying as previously described for tracking both breathing and posture.

In second version 703, the motivation for adding flex sensor 818 is to be able to reliably track very light breathing, particularly unconscious breaths. During light breathing, when the tidal volume of breaths are minimal, rotary sensor 780 may not always detect such breaths. This can be due to several factors. The first is the resistance provided by power spring 748, which should be overcome to cause rotation of reel 726. A second is the changing arrangement of clothing on the body. For example, a user may inhale and cause a measurable rotation of reel 726, but then the clothing can shift prior to the time that the user exhales in such a way as to momentarily impede the winding back of retractable belt 704, and the return of reel 726 to its previous rotational position. This can mistakenly appear to CPU 786 as though the user is holding their breath.

Here flex sensor 818, of the second version 703 as well as the third version 900 and embodiment 992, can be used to overcome this problem. Flex sensor 818 is effectively able to measure micro displacements of retractable belt 704, which can manifest as a pressure or force on the flexing elements previously described, causing measurable strains on flex sensor 818 corresponding to the full cycle of respiration. In this way, flex sensor 818 is equivalent to displacement sensor 146 previously discussed. Flex sensor 818 and angle sensor 790 of second version 703 as well as the third version 900 and embodiment 992 also each constitute a type 2 BTD (breath training device), with similar breath training processes applying as previously described for tracking both breathing and posture. In second version 703 as well as the third version 900 and embodiment 992, it is possible to use both rotary sensor 780 and flex sensor 818 to track breathing. For example, if rotary sensor 780 is not detecting a movement of retractable belt 704, data from flex sensor 818 can be used at that time to further analyze or corroborate the respiration state of the user. As an option, a fourth version of breath training device 700 can be provided with the omission of rotary sensor 780 and magnet 760. In this embodiment, the electronic breathing sensor can consist of only the flex sensor 818, which is used to track breathing.

Other Measurement Functions:

The first version 701 and the second version 703 of the breath training device 700 as well as the third version 900 and embodiment 992 can also be used to measure waist and muscle circumferences by utilizing rotary sensor 780. Here, the system processor can execute a formula for calculating the length of a rolled material on a spool for this purpose. For example, the following formula can be used to derive the length, based on measuring the rotation angle of reel 726:

$p = p(phi) = (h/(2*pi))*phi$ $phi0 = (pi*D0)/h$ $phi1 = (pi*D1)/h$

Length of waist or muscle circumference=$L(phi1, phi0)$=Integral(from $phi1$ to $phi0$) of SQRT $(p\hat{}2+(dp/dphi)\hat{}2)dphi$ Where D0 is the diameter of spool 730, and D1 is the diameter of spool 730+the added diameter of retractable belt 704 fully wound onto spool 730, and "h" is the thickness of retractable belt 704. Alternately, a the system processor can use a simple lookup table can to cross-reference the rotation angle of reel 726 with the deployed length of retractable belt 704, with such a lookup table being populated by taking many samples of different angles of reel 726, and noting the deployed length of retractable belt 704 at each angle.

The invention claimed is:

1. A device for tracking respiration and posture from a location on a human user, said device comprising:
 a single case housing comprising an outer surface with a recess, and an interior, and disposed within said interior of said single case housing, a computer processor, and an electronic angle sensor configured to measure user standing or sitting posture across a range of different standing or sitting angles of posture position;
 said recess comprising a housing fastener;
 said interior of said single case housing further comprising a non-elastic retracting belt, and a spring-driven retracting mechanism;
 wherein said device is a unitized device, said retracting mechanism further comprises a single spring tensioned spool, and said belt winds around said single spring tensioned spool;
 wherein said device further comprises an electronic breathing sensor comprising at least one of a housing fastener mounted flex sensor and a housing fastener mounted electronic strain gauge configured to produce an electronic breathing sensor signal measuring force on said retracting belt but not rotation of said single spring tensioned spool;

said retracting belt comprising a first belt end that is connected to said retracting mechanism, and a second belt end configured with a belt fastener configured to reversibly attach to said housing fastener;

said housing and said retracting belt configured so that when said retracting belt is worn around said user's trunk, and said belt fastener is attached to said housing fastener, said retracting belt experiences force in response to user respiration, and said breathing sensor produces a breathing sensor signal reporting on said respiration;

said electronic angle sensor configured so that when said retracting belt is worn around said user's trunk, and said belt fastener is attached to said housing fastener, said angle sensor produces an angle sensor signal reporting on an angle of said user's range of standing or sitting posture angles;

said processor configured to process said breathing sensor signal and said angle sensor signal, and to produce an output reporting on at least one of:
a) angle sensor data reporting on at least one angle of said user's range of standing or sitting posture angles, and breathing sensor data reporting on said user's respiration; and
b) posture adjusted user respiration data.

2. The device of claim 1, wherein said angle sensor is any of an accelerometer, a magnetometer, and a gyroscope, and wherein said angle sensor is configured to determine an orientation of said housing with respect to any of a direction of gravity, a magnetic field, and a prior orientation of said housing.

3. The device of claim 1, wherein said retracting mechanism further comprises a spring-driven tension mechanism for placing one end of said belt under tension during all phases of user respiration, so that one end of belt extends further out of said housing during user inhalation, and one end of said belt retracts further into said housing during user exhalation.

4. The device of claim 1, wherein said breathing sensor is coupled to at least one of said retracting mechanism and said belt, and
wherein said electronic breathing sensor comprises said housing fastener mounted flex sensor, and said flex sensor comprises any of a strain gauge, semiconductor strain gauge, foil strain gauge, force sensitive resistor, piezo-electric sensor, piezo film sensor, variable capacitor, or variable inductance sensor.

5. The device of claim 1, wherein said at least one of a housing fastener mounted flex sensor and a housing fastener mounted electronic strain gauge are configured to report strain type force on said belt to said processor.

6. The device of claim 1, wherein said device further comprises a wireless transceiver, and wherein said device is further configured to use said processor and said wireless transceiver to transmit at least some of said signals or data to an external computing platform.

7. The device of claim 1 wherein any of said processor and an external computing program processor is further configured to correct for effects of different relative user ranges of standing or sitting posture positions by:
a) while said user is in a defined respiratory state, sampling and storing breathing sensor data across a plurality of different relative user ranges of standing or sitting posture positions as defined by said angle sensor data, thereby creating first calibration data;
b) producing said posture adjusted user respiration data by using said first calibration data, said breathing sensor data, and said angle sensor data to correct said breathing sensor data for variations in said user standing or sitting posture position angles; and
wherein said defined respiratory state is any of a defined full exhalation state and a defined full inhalation state.

8. The device of claim 1, further configured to use said angle sensor data and any of said processor and an external computing program processor to reduce impact of varying user standing or sitting posture angles on user respiration measurements.

9. The device of claim 1, wherein any of said processor and an external computing program processor is further configured to use current breathing sensor data and current angle sensor data to determine a user current diaphragm position and a user current standing or sitting angle of posture position.

10. The device of claim 1, wherein said device is further configured for said housing to be worn on said user's back.

11. The device of claim 1, wherein said housing fastener further comprises a clip channel in said single case housing, and said belt fastener is configured to reversibly attach to said clip channel.

12. The device of claim 11, wherein said flex sensor is attached to said clip channel.

13. The device of claim 1, wherein said single case housing is further configured to twist an angle of said belt at 90 degrees from its orientation on said spring-driven retraction mechanism before said belt exits a belt opening on said single case housing.

14. The device of claim 1, wherein said single case housing further comprises a notifier comprising any of a built-in vibrational device, audio output device, or display device, and said computer processor is further configured to evaluate at least said breathing sensor signal as to breathing evaluation states, and activate said notifier in response to at least one said breathing evaluation state.

15. A device for tracking respiration and posture from a location on a human user, said device comprising:
a single case housing comprising an outer surface with a recess, and an interior, and disposed within said interior of said single case housing, a computer processor, and an electronic angle sensor configured to measure user standing or sitting posture across a range of different standing or sitting angles of posture position;
said recess comprising a housing fastener;
said interior of said single case housing further comprising a non-elastic retracting belt, and a spring-driven retracting mechanism;
wherein said device is a unitized device, said retracting mechanism further comprises a single spring tensioned spool, and said belt winds around said single spring tensioned spool;
wherein said device further comprises an electronic breathing sensor comprising at least one of a housing fastener mounted flex sensor and a housing fastener mounted electronic strain gauge configured to produce an electronic breathing sensor signal measuring force on said retracting belt but not rotation of said single spring tensioned spool;
wherein said electronic angle sensor is an accelerometer;
said retracting belt comprising a first belt end that is connected to said retracting mechanism, and a second belt end configured with a belt fastener configured to reversibly attach to said housing fastener;
said housing and said retracting belt configured so that when said retracting belt is worn around said user's trunk, and said belt fastener is attached to said housing fastener, said retracting belt experiences force in response to user respiration, and said breathing sensor produces a breathing sensor signal reporting on said respiration;

wherein said retracting mechanism further comprises a spring-driven tension mechanism for placing one end of said belt under tension during all phases of user respiration, so that said one end of said belt extends further out of said housing during user inhalation, and said one end of said belt retracts further into said housing during user exhalation;

wherein said device further comprises at least one of a rotary encoder and a magnetic rotary encoder for measuring a displacement of said belt;

wherein said single case housing is further configured to create a flat housing by mounting said single spring tensioned spool to rotate within the confines of said flat housing, and to twist an angle of said belt at 90 degrees from its orientation on said spring-driven retraction mechanism before said belt exits a belt opening on said single case housing;

said electronic angle sensor configured so that when said retracting belt is worn around said user's trunk, and said belt fastener is attached to said housing fastener, said angle sensor produces an angle sensor signal reporting on an angle of said user's range of standing or sitting posture angles;

said processor configured to process said breathing sensor signal and said angle sensor signal, and to produce an output reporting on at least one of:

a) angle sensor data reporting on at least one angle of said user's range of standing or sitting posture angles, and breathing sensor data reporting on said user's respiration; and b) posture adjusted user respiration data;

wherein said device further comprises a wireless transceiver, and wherein said device is further configured to use said processor and said wireless transceiver to transmit at least some of said signals or data to an external computing platform;

wherein said device is further configured for said housing to be worn on said user's back.

16. The device of claim 15, wherein said processor is further configured to use said displacement of said belt to compute any of a dimension or change in dimension of a user body part or muscle.

17. A method for tracking respiration and posture from a location on a human user, said method comprising:

Measuring user respiration by using a device comprising a single case housing comprising an outer surface with a recess, and an interior;

wherein disposed within said interior of said single case housing are a computer processor, and an electronic angle sensor configured to measure user standing or sitting posture across a range of different standing or sitting angles of posture position;

said recess comprising a housing fastener;

said interior of said single case housing further comprising a non-elastic retracting belt, and a spring-driven retracting mechanism;

wherein said device is a unitized device, said spring-driven retracting mechanism further comprises a single spring tensioned spool, said belt winds around said single spring tensioned spool;

wherein said device further comprises an electronic breathing sensor comprising at least one of a housing fastener mounted flex sensor and a housing fastener mounted electronic strain gauge to produce an electronic breathing sensor signal measuring force on said non-elastic retracting belt but not rotation of said single spring tensioned spool;

wherein said single case housing is further configured to create a flat housing by mounting said single spring tensioned spool to rotate within the confines of said flat housing, and to twist an angle of said belt at 90 degrees from its orientation on said spring-driven retraction mechanism before said belt exits a belt opening on said single case housing;

said non-elastic retracting belt comprising a first belt end that is connected to said spring-driven retracting mechanism, and a second belt end configured with a belt fastener configured to reversibly attach to said housing fastener;

said housing and said non-elastic retracting belt configured so that when said non-elastic retracting belt is worn around said user's trunk, and said belt fastener is attached to said housing fastener, said non-elastic retracting belt experiences force in response to user respiration, and said breathing sensor produces a breathing sensor signal reporting on said respiration;

using an electronic angle sensor to report on an angle of said user's posture with respect to a direction of gravity, said electronic angle sensor configured so that when said non-elastic retracting belt is worn around said user's trunk, and said belt fastener is attached to said housing fastener, said angle sensor produces an angle sensor signal reporting on an angle of said user's range of standing or sitting posture angles;

processing said breathing sensor signal and said angle sensor signal with said processor, and using said processor to produce an output reporting on at least one of:

a) angle sensor data reporting on at least one angle of said user's range of standing or sitting posture angles, and breathing sensor data reporting on said user's respiration; and b) posture adjusted user respiration data.

18. The method of claim 17, wherein said angle sensor is any of an accelerometer, a magnetometer, and a gyroscope, and wherein said angle sensor is configured to determine an orientation of said housing with respect to any of a direction of gravity, a magnetic field, and a prior orientation of said housing.

19. The method of claim 17, wherein said retracting mechanism further comprises a spring-driven tension mechanism for placing one end of said belt under tension during all phases of user respiration, so that one end of said belt extends further out of said housing during user inhalation, and one end of said belt retracts further into said housing during user exhalation.

20. The method of claim 17, wherein said breathing sensor is coupled to at least one of said retracting mechanism and said belt, and wherein said electronic breathing sensor comprises said housing fastener mounted flex sensor, and said flex sensor comprises any of a strain gauge, semiconductor strain gauge, foil strain gauge, force sensitive resistor, piezo-electric sensor, piezo film sensor, variable capacitor, or variable inductance sensor.

21. The method of claim 17, wherein said device further comprises at least one of a rotary encoder and a magnetic rotary encoder;

further using said single spring tensioned spool and any of said rotary encoder and magnetic rotary encoder to measure a displacement of said belt, and using said displacement to compute any of a dimension or change in dimension of a user body part or muscle.

22. The method of claim 17, wherein said at least one of a housing fastener mounted flex sensor and a housing fastener mounted electronic strain gauge are configured to report strain type force on said belt to said processor.

23. The method of claim 17, wherein said device further comprises a wireless transceiver, further using said processor and said wireless transceiver to transmit at least some of said signals or data to an external computing platform.

24. The method of claim 17, wherein said device is further configured for said housing to be worn on said user's back.

25. The method of claim 17, further using any of a device processor and an external computing platform processor to correct for effects of different relative user posture ranges of standing or sitting positions by:
  a) while said user is in a defined respiratory state, sampling and storing breathing sensor data across a plurality of different relative user ranges of standing or sitting posture positions as defined by said angle sensor data, thereby creating first calibration data;
  b) producing said posture adjusted user respiration data by using said first calibration data, said breathing sensor data, and said angle sensor data to correct said breathing sensor data for variations in said user standing or sitting posture position angles; and
  wherein said defined respiratory state is any of a defined full exhalation state and a defined full inhalation state.

26. The method of claim 17, further using said angle sensor data and any of said processor and an external computing program processor to reduce impact of varying user standing or sitting posture angles on user respiration measurements.

27. The method of claim 17, further using any of a device processor and an external computing platform processor, current breathing sensor data, and current angle sensor data to determine a user current diaphragm position and a user current standing or sitting angle of posture position.

28. A device for tracking respiration and posture from a location on a human user, said device comprising:
  a single case housing comprising an outer surface with a recess, and an interior, and disposed within said interior of said single case housing, a computer processor, and an electronic angle sensor configured to measure user standing or sitting posture across a range of different standing or sitting angles of posture position;
  said recess comprising a housing fastener;
  said interior of said single case housing further comprising a non-elastic retracting belt, a spring-driven retracting mechanism, and an electronic breathing sensor comprising at least one of a housing fastener mounted flex sensor and a housing fastener mounted electronic strain gauge configured to produce an electronic breathing sensor signal measuring force on said retracting belt;
  said retracting belt comprising a first belt end that is connected to said retracting mechanism, and a second belt end configured with a belt fastener configured to reversibly attach to said housing fastener;
  wherein said device is a unitized device, said retracting mechanism further comprises a single spring tensioned spool, and said belt winds around said single spring tensioned spool;
  said housing and said retracting belt configured so that when said retracting belt is worn around said user's trunk, and said belt fastener is attached to said housing fastener, the axis of said single spring tensioned spool is oriented perpendicular to said user's trunk, said retracting belt experiences force in response to user respiration, and said breathing sensor produces a breathing sensor signal reporting on said respiration;
  said electronic angle sensor configured so that when said retracting belt is worn around said user's trunk, and said belt fastener is attached to said housing fastener, said angle sensor produces an angle sensor signal reporting on an angle of said user's range of standing or sitting posture angles;
  said processor configured to process said breathing sensor signal and said angle sensor signal, and to produce an output reporting on at least one of:
  a) angle sensor data reporting on at least one angle of said user's range of standing or sitting posture angles, and breathing sensor data reporting on said user's respiration; and
  b) posture adjusted user respiration data.

* * * * *